(12) United States Patent
Low et al.

(10) Patent No.: US 11,850,262 B2
(45) Date of Patent: Dec. 26, 2023

(54) COMPOSITIONS AND METHODS FOR CAR T CELL THERAPY

(71) Applicants: Purdue Research Foundation, West Lafayette, IN (US); Endocyte, Inc., West Lafayette, IN (US)

(72) Inventors: Philip Stewart Low, West Lafayette, IN (US); Haiyan Chu, West Lafayette, IN (US); Yong Gu Lee, West Lafayette, IN (US); Yingjuan J. Lu, West Lafayette, IN (US); Christopher Paul Leamon, West Lafayette, IN (US); Leroy W. Wheeler, II, West Lafayette, IN (US)

(73) Assignees: Purdue Research Foundation, West Lafayette, IN (US); Endocyte, Inc., West Lafayette, IN (US)

(*) Notice: Subject to any disclaimer, the term of this patent is extended or adjusted under 35 U.S.C. 154(b) by 596 days.

(21) Appl. No.: 16/489,455

(22) PCT Filed: Feb. 28, 2018

(86) PCT No.: PCT/US2018/020095
§ 371 (c)(1),
(2) Date: Aug. 28, 2019

(87) PCT Pub. No.: WO2018/160622
PCT Pub. Date: Sep. 7, 2018

(65) Prior Publication Data
US 2020/0023009 A1    Jan. 23, 2020

Related U.S. Application Data

(60) Provisional application No. 62/634,595, filed on Feb. 23, 2018, provisional application No. 62/620,701, (Continued)

(51) Int. Cl.
*A61K 31/17* (2006.01)
*A61K 35/17* (2015.01)
(Continued)

(52) U.S. Cl.
CPC ........ *A61K 35/17* (2013.01); *C07K 14/70503* (2013.01); *C07K 16/30* (2013.01);
(Continued)

(58) Field of Classification Search
None
See application file for complete search history.

(56) References Cited

U.S. PATENT DOCUMENTS 4,690,915 A   9/1987 Rosenberg
4,946,778 A   8/1990 Ladner et al.
(Continued)

FOREIGN PATENT DOCUMENTS

CN   102775500    11/2012
EP   0340793 A2   11/1989
(Continued)

OTHER PUBLICATIONS

Cianciulli et al., Mediators Inflamm. 2016; 2016: 5240127 (Year: 2016).*

(Continued)

*Primary Examiner* — Karl J Puttlitz
(74) *Attorney, Agent, or Firm* — COOLEY LLP

(57) ABSTRACT

The present disclosure relates to methods of treating a patient with a cancer by administering to the patient a composition comprising CAR T cells and a small molecule linked to a targeting moiety by a linker. The disclosure also relates to compositions for use in such methods.

16 Claims, 98 Drawing Sheets

Specification includes a Sequence Listing.

FR positive (MDA-MB-231 cells)

-O- CAR T cell + PBS
-□- CAR T cell + FITC-Folate (500nmole/kg)_Continue dose
-▽- CAR T cell + FITC-Folate (500nmole/kg)_Break
-△- CAR T cell + FITC-Folate (500nmole/kg)_FA Competitor(100x)

Related U.S. Application Data filed on Jan. 23, 2018, provisional application No. 62/620,384, filed on Jan. 22, 2018, provisional application No. 62/620,423, filed on Jan. 22, 2018, provisional application No. 62/554,421, filed on Sep. 5, 2017, provisional application No. 62/480,627, filed on Apr. 3, 2017, provisional application No. 62/464,792, filed on Feb. 28, 2017.

(51) Int. Cl.
*C07K 14/705* (2006.01)
*C07K 16/30* (2006.01)

(52) U.S. Cl.
CPC .... *C07K 2317/622* (2013.01); *C07K 2319/03* (2013.01); *C07K 2319/033* (2013.01)

(56) References Cited

U.S. PATENT DOCUMENTS

| | | | |
|---|---|---|---|
| 5,087,616 A | 2/1992 | Myers et al. | |
| 5,116,964 A | 5/1992 | Capon et al. | |
| 5,202,238 A | 4/1993 | Fell, Jr. et al. | |
| 5,216,132 A | 6/1993 | Basi | |
| 5,359,046 A | 10/1994 | Capon et al. | |
| 5,372,930 A | 12/1994 | Colton et al. | |
| 5,482,856 A | 1/1996 | Fell, Jr. et al. | |
| 5,514,582 A | 5/1996 | Capon et al. | |
| 5,525,503 A | 6/1996 | Rudd et al. | |
| 5,538,866 A | 7/1996 | Israeli et al. | |
| 5,670,148 A | 9/1997 | Sherwin et al. | |
| 5,686,281 A | 11/1997 | Roberts | |
| 5,712,149 A | 1/1998 | Roberts | |
| 5,714,147 A | 2/1998 | Capon et al. | |
| 5,741,899 A | 4/1998 | Capon et al. | |
| 5,747,292 A | 5/1998 | Greenberg et al. | |
| 5,830,755 A | 11/1998 | Nishimura et al. | |
| 5,834,256 A | 11/1998 | Finer et al. | |
| 5,837,544 A | 11/1998 | Capon et al. | |
| 5,843,728 A | 12/1998 | Seed et al. | |
| 5,851,828 A | 12/1998 | Seed et al. | |
| 5,858,740 A | 1/1999 | Finer et al. | |
| 5,861,156 A | 1/1999 | George et al. | |
| 5,906,936 A | 5/1999 | Eshhar et al. | |
| 5,908,638 A | 6/1999 | Huber et al. | |
| 5,912,170 A | 6/1999 | Seed et al. | |
| 5,912,172 A | 6/1999 | Eshhar et al. | |
| 5,914,109 A | 6/1999 | Zolla-Pazner et al. | |
| 5,935,818 A | 8/1999 | Israeli et al. | |
| 5,969,102 A | 10/1999 | Bram et al. | |
| 6,004,781 A | 12/1999 | Seed | |
| 6,004,811 A | 12/1999 | Seed et al. | |
| 6,005,004 A | 12/1999 | Katz et al. | |
| 6,077,947 A | 6/2000 | Capon et al. | |
| 6,083,751 A | 7/2000 | Feldhaus et al. | |
| 6,103,521 A | 8/2000 | Capon et al. | |
| 6,117,656 A | 9/2000 | Seed | |
| 6,132,718 A | 10/2000 | Hansen et al. | |
| 6,218,187 B1 | 4/2001 | Finer et al. | |
| 6,261,787 B1 | 7/2001 | Davis et al. | |
| 6,319,494 B1 | 11/2001 | Capon et al. | |
| 6,392,013 B1 | 5/2002 | Seed et al. | |
| 6,406,697 B1 | 6/2002 | Capon et al. | |
| 6,407,221 B1 | 6/2002 | Capon et al. | |
| 6,410,014 B1 | 6/2002 | Seed et al. | |
| 6,410,319 B1 | 6/2002 | Raubitschek et al. | |
| 6,432,403 B1 | 8/2002 | Philips | |
| 6,451,995 B1 | 9/2002 | Cheung et al. | |
| 6,521,602 B1 | 2/2003 | Patel et al. | |
| 6,524,572 B1 | 2/2003 | Li | |
| 6,699,972 B1 | 3/2004 | Roffler et al. | |
| 6,753,162 B1 | 6/2004 | Seed et al. | |
| 6,759,243 B2 | 7/2004 | Kranz et al. | |
| 6,770,749 B2 | 8/2004 | Ellenhorn et al. | |
| 6,953,668 B1 | 10/2005 | Israeli et al. | |
| 7,037,647 B1 | 5/2006 | Israeli et al. | |
| 7,049,136 B2 | 5/2006 | Seed et al. | |
| 7,052,906 B1 | 5/2006 | Lawson et al. | |
| 7,070,995 B2 | 7/2006 | Jensen | |
| 7,105,159 B1 | 9/2006 | Israeli et al. | |
| 7,217,421 B1 | 5/2007 | McArthur et al. | |
| 7,265,209 B2 | 9/2007 | Jensen | |
| 7,320,787 B2 | 1/2008 | Seed et al. | |
| 7,348,004 B2 | 3/2008 | Peters et al. | |
| 7,354,587 B1 | 4/2008 | Hansen | |
| 7,354,762 B2 | 4/2008 | Jensen | |
| 7,381,408 B2 | 6/2008 | Mezo et al. | |
| 7,404,956 B2 | 7/2008 | Peters et al. | |
| 7,435,596 B2 | 10/2008 | Campana et al. | |
| 7,446,179 B2 | 11/2008 | Jensen et al. | |
| 7,446,190 B2 | 11/2008 | Sadelain et al. | |
| 7,446,191 B2 | 11/2008 | Jensen | |
| 7,482,005 B2 | 1/2009 | Kim | |
| 7,514,537 B2 | 4/2009 | Jensen | |
| 7,569,663 B2 | 8/2009 | Tykocinski et al. | |
| 7,572,891 B2 | 8/2009 | Belldegrun et al. | |
| 7,618,817 B2 | 11/2009 | Campbell | |
| 7,632,497 B2 | 12/2009 | Stavenhagen | |
| 7,655,461 B2 | 2/2010 | Finn et al. | |
| 7,666,424 B2 | 2/2010 | Cheung et al. | |
| 7,723,111 B2 | 5/2010 | Hwu et al. | |
| 7,741,465 B1 | 6/2010 | Eshhar et al. | |
| 7,871,817 B2 | 1/2011 | Voss et al. | |
| 7,906,620 B2 | 3/2011 | Eisenbach et al. | |
| 7,919,079 B2 | 4/2011 | Simmons et al. | |
| 7,939,059 B2 | 5/2011 | Yang et al. | |
| 7,994,298 B2 | 8/2011 | Zhang et al. | |
| 7,998,736 B2 | 8/2011 | Morgan et al. | |
| 8,105,830 B2 | 1/2012 | Weidanz et al. | |
| 8,148,154 B2 | 4/2012 | Cheung et al. | |
| 8,163,887 B2 | 4/2012 | Hansen | |
| 8,211,422 B2 | 7/2012 | Eshhar et al. | |
| RE43,586 E | 8/2012 | Israeli et al. | |
| 8,252,914 B2 | 8/2012 | Zhang et al. | |
| 8,324,353 B2 | 12/2012 | Jensen | |
| 8,389,282 B2 | 3/2013 | Sadelain et al. | |
| 8,399,645 B2 | 3/2013 | Campana et al. | |
| 8,409,577 B2 | 4/2013 | Thompson et al. | |
| 8,450,112 B2 | 5/2013 | Li et al. | |
| 8,465,743 B2 | 6/2013 | Rosenberg et al. | |
| 8,486,911 B2 | 7/2013 | Okada et al. | |
| 8,497,118 B2 | 7/2013 | Jensen | |
| 8,741,306 B2 | 6/2014 | Belldegrun et al. | |
| 8,802,374 B2 | 8/2014 | Jensen | |
| 8,809,050 B2 | 8/2014 | Vera et al. | |
| 8,822,196 B2 | 9/2014 | Rosenberg et al. | |
| 8,822,647 B2 | 9/2014 | Jensen | |
| 8,859,229 B2 | 10/2014 | Rabinovich et al. | |
| 8,877,199 B2 | 11/2014 | Rader et al. | |
| 8,906,682 B2 | 12/2014 | June et al. | |
| 8,911,993 B2 | 12/2014 | June et al. | |
| 8,932,830 B2 | 1/2015 | Peters et al. | |
| 8,946,385 B2 | 2/2015 | Kawai | |
| 8,956,860 B2 | 2/2015 | Vera et al. | |
| 9,023,621 B2 | 5/2015 | Gurney et al. | |
| 9,040,669 B2 | 5/2015 | Cheung et al. | |
| 9,062,127 B2 | 6/2015 | Voss et al. | |
| 9,074,000 B2 | 7/2015 | Scheinberg et al. | |
| 9,089,520 B2 | 7/2015 | Brenner | |
| 9,101,584 B2 | 8/2015 | June et al. | |
| 9,101,609 B2 | 8/2015 | Tan et al. | |
| 9,102,760 B2 | 8/2015 | June et al. | |
| 9,102,761 B2 | 8/2015 | June et al. | |
| 9,111,061 B2 | 8/2015 | Otsuka et al. | |
| 9,133,436 B2 | 9/2015 | Riley et al. | |
| 9,156,915 B2 | 10/2015 | Waldman et al. | |
| 9,163,258 B2 | 10/2015 | Riddell et al. | |
| 9,175,308 B2 | 11/2015 | Shiku et al. | |
| 9,181,527 B2 | 11/2015 | Sentman | |
| 9,211,321 B2 | 12/2015 | Karlsson-Parra et al. | |
| 9,212,229 B2 | 12/2015 | Schönfeld et al. | |
| 9,220,728 B2 | 12/2015 | Sadelain et al. | |
| 9,226,936 B2 | 1/2016 | Hu et al. | |
| 9,233,125 B2 | 1/2016 | Davila et al. | |

(56) References Cited

U.S. PATENT DOCUMENTS

| | | |
|---|---|---|
| 9,242,014 B2 | 1/2016 | Kipps et al. |
| 9,266,960 B2 | 2/2016 | Morgan et al. |
| 9,272,002 B2 | 3/2016 | Powell, Jr. et al. |
| 9,273,283 B2 | 3/2016 | Sentman |
| 9,279,008 B2 | 3/2016 | Scholler et al. |
| 9,334,330 B2 | 5/2016 | Birkle et al. |
| 9,345,748 B2 | 5/2016 | Morgan et al. |
| 9,352,036 B2 | 5/2016 | McBride et al. |
| 9,359,447 B2 | 6/2016 | Feldman et al. |
| 9,365,641 B2 | 6/2016 | June et al. |
| 9,393,268 B2 | 7/2016 | Waldman et al. |
| 9,393,292 B2 | 7/2016 | Brenner |
| 9,394,364 B2 | 7/2016 | Ho et al. |
| 9,394,368 B2 | 7/2016 | Brogdon et al. |
| 9,402,865 B2 | 8/2016 | Powell et al. |
| 9,402,888 B2 | 8/2016 | Hildegund et al. |
| 9,408,904 B2 | 8/2016 | Wright et al. |
| 9,409,992 B2 | 8/2016 | Ho et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,434,935 B2 | 9/2016 | Spencer et al. |
| 9,446,105 B2 | 9/2016 | Powell et al. |
| 9,447,194 B2 | 9/2016 | Jensen |
| 9,453,075 B2 | 9/2016 | Cheung et al. |
| 9,464,140 B2 | 10/2016 | June et al. |
| 9,469,684 B2 | 10/2016 | Finn et al. |
| 9,476,028 B2 | 10/2016 | Karlsson-Parra et al. |
| 9,481,728 B2 | 11/2016 | June et al. |
| 9,487,800 B2 | 11/2016 | Schonfeld et al. |
| 9,492,499 B2 | 11/2016 | Jaynes et al. |
| 9,492,529 B2 | 11/2016 | Karlsson-Parra et al. |
| 9,493,740 B2 | 11/2016 | Brenner et al. |
| 9,499,629 B2 | 11/2016 | June et al. |
| 9,499,855 B2 | 11/2016 | Hyde et al. |
| 9,511,092 B2 | 12/2016 | Campana et al. |
| 9,518,123 B2 | 12/2016 | June et al. |
| 9,522,955 B2 | 12/2016 | Rosenberg et al. |
| 9,540,445 B2 | 1/2017 | June et al. |
| 9,540,448 B2 | 1/2017 | Scheinberg et al. |
| 9,561,291 B2 | 2/2017 | Kovesdi et al. |
| 9,562,087 B2 | 2/2017 | Ring et al. |
| 9,567,399 B1 | 2/2017 | Campbell et al. |
| 9,572,836 B2 | 2/2017 | June et al. |
| 9,572,837 B2 | 2/2017 | Wu |
| 9,573,988 B2 | 2/2017 | Brogdon et al. |
| 9,574,014 B2 | 2/2017 | Williams et al. |
| 9,587,020 B2 | 3/2017 | Wu et al. |
| 9,587,237 B2 | 3/2017 | Hyde et al. |
| 9,597,357 B2 | 3/2017 | Gregory et al. |
| 9,605,049 B2 | 3/2017 | Campana et al. |
| 9,623,049 B2 | 4/2017 | Eshhar et al. |
| 9,624,292 B2 | 4/2017 | Voss et al. |
| 9,624,306 B2 | 4/2017 | Morgan et al. |
| 9,629,877 B2 | 4/2017 | Cooper et al. |
| 9,636,388 B2 | 5/2017 | Lawman et al. |
| 9,636,416 B2 | 5/2017 | Peters et al. |
| 9,642,906 B2 | 5/2017 | Ramos et al. |
| 9,650,428 B2 | 5/2017 | Sampath et al. |
| 9,657,105 B2 | 5/2017 | Forman et al. |
| 9,662,405 B2 | 5/2017 | Waldman et al. |
| 9,663,756 B1 | 5/2017 | Lipkens et al. |
| 9,663,763 B2 | 5/2017 | Sentman |
| 9,669,058 B2 | 6/2017 | Li et al. |
| 9,670,281 B2 | 6/2017 | Lim et al. |
| 9,676,867 B2 | 6/2017 | Marasco et al. |
| 9,688,740 B2 | 6/2017 | Choi et al. |
| 9,688,760 B2 | 6/2017 | Kufer et al. |
| 9,694,033 B2 | 7/2017 | Yi et al. |
| 9,701,758 B2 | 7/2017 | Cooper et al. |
| 9,708,384 B2 | 7/2017 | Scholler et al. |
| 9,714,278 B2 | 7/2017 | June et al. |
| 9,717,745 B2 | 8/2017 | He |
| 9,725,519 B2 | 8/2017 | Masuko et al. |
| 9,733,245 B2 | 8/2017 | Kawai |
| 9,738,726 B2 | 8/2017 | Dimitrov et al. |
| 9,745,368 B2 | 8/2017 | Milone et al. |
| 9,765,142 B2 | 9/2017 | Dimitrov et al. |
| 9,765,156 B2 | 9/2017 | June et al. |
| 9,765,330 B1 | 9/2017 | Niazi et al. |
| 9,765,342 B2 | 9/2017 | Kochenderfer |
| 9,777,061 B2 | 10/2017 | Ebersbach et al. |
| 9,777,064 B2 | 10/2017 | Wang et al. |
| 9,783,591 B2 | 10/2017 | June et al. |
| 9,789,174 B2 | 10/2017 | Karlsson-Parra et al. |
| 9,790,267 B2 | 10/2017 | Kaplan |
| 9,790,278 B2 | 10/2017 | Sentman et al. |
| 9,790,282 B2 | 10/2017 | Orentas et al. |
| 9,790,467 B2 | 10/2017 | Kevlahan et al. |
| 9,796,783 B2 | 10/2017 | Agerstam et al. |
| 9,802,997 B2 | 10/2017 | Mahr et al. |
| 9,803,022 B2 | 10/2017 | Ho et al. |
| 9,808,486 B2 | 11/2017 | Georgiou et al. |
| 9,809,581 B2 | 11/2017 | Chen et al. |
| 9,815,901 B2 | 11/2017 | Brogdon et al. |
| 9,821,011 B1 | 11/2017 | Sentman |
| 9,821,012 B2 | 11/2017 | Wu et al. |
| 9,822,340 B1 | 11/2017 | Sentman |
| 9,828,399 B2 | 11/2017 | Tremblay et al. |
| 9,828,435 B2 | 11/2017 | Evans et al. |
| 9,833,476 B2 | 12/2017 | Zhang et al. |
| 9,833,480 B2 | 12/2017 | Junghans et al. |
| 9,834,545 B2 | 12/2017 | Chen et al. |
| 9,834,590 B2 | 12/2017 | Campana et al. |
| 9,840,548 B2 | 12/2017 | Mahr et al. |
| 9,845,362 B2 | 12/2017 | Mukherjee |
| 9,849,092 B2 | 12/2017 | Peyman |
| 9,855,297 B2 | 1/2018 | Duchateau et al. |
| 9,855,298 B2 | 1/2018 | Bot et al. |
| 9,856,322 B2 | 1/2018 | Campana et al. |
| 9,856,497 B2 | 1/2018 | Qi et al. |
| 9,856,501 B2 | 1/2018 | O'Keefe et al. |
| 9,862,756 B2 | 1/2018 | Mahr et al. |
| 9,862,775 B2 | 1/2018 | Kwon et al. |
| 9,868,774 B2 | 1/2018 | Orentas et al. |
| 9,868,951 B2 | 1/2018 | Hu et al. |
| 9,873,894 B2 | 1/2018 | Conway et al. |
| 9,879,087 B2 | 1/2018 | DeSander et al. |
| 9,885,021 B2 | 2/2018 | Bollard et al. |
| 9,889,160 B2 | 2/2018 | Jantz et al. |
| 9,889,161 B2 | 2/2018 | Jantz et al. |
| 9,890,393 B2 | 2/2018 | Duchateau et al. |
| 9,914,909 B2 | 3/2018 | Brown et al. |
| 10,117,897 B2 | 11/2018 | Sadelain et al. |
| 11,311,576 B2 | 4/2022 | Jensen et al. |
| 2001/0031252 A1 | 10/2001 | Low et al. |
| 2002/0004052 A1 | 1/2002 | Berd et al. |
| 2002/0018783 A1 | 2/2002 | Sadelain et al. |
| 2002/0111474 A1 | 8/2002 | Capon et al. |
| 2002/0132983 A1 | 9/2002 | Junghans |
| 2003/0077249 A1 | 4/2003 | Bebbington et al. |
| 2003/0170238 A1 | 9/2003 | Gruenberg et al. |
| 2003/0171546 A1 | 9/2003 | Jensen |
| 2003/0175288 A1 | 9/2003 | Itoh |
| 2003/0215427 A1 | 11/2003 | Jensen |
| 2004/0043401 A1 | 3/2004 | Sadelain et al. |
| 2005/0113564 A1 | 5/2005 | Campana |
| 2005/0129671 A1 | 6/2005 | Cooper et al. |
| 2006/0018878 A1 | 1/2006 | Cooper et al. |
| 2006/0067920 A1 | 3/2006 | Jensen |
| 2006/0155115 A1 | 7/2006 | Jakobsen et al. |
| 2007/0031438 A1 | 2/2007 | Junghans |
| 2007/0036773 A1 | 2/2007 | Cooper et al. |
| 2008/0051380 A1 | 2/2008 | Auerbach et al. |
| 2008/0188000 A1 | 8/2008 | Reik et al. |
| 2009/0011984 A1 | 1/2009 | Yla-Herttuala et al. |
| 2009/0191172 A1 | 7/2009 | Cooper et al. |
| 2009/0202501 A1 | 8/2009 | Zhang et al. |
| 2009/0257994 A1 | 10/2009 | Jensen |
| 2009/0324630 A1 | 12/2009 | Jensen |
| 2010/0135974 A1 | 6/2010 | Eshhar et al. |
| 2010/0178276 A1 | 7/2010 | Sadelain et al. |
| 2010/0278830 A1 | 11/2010 | Shoemaker et al. |
| 2011/0172254 A1 | 7/2011 | Leamon |

(56) References Cited

U.S. PATENT DOCUMENTS

| | | |
|---|---|---|
| 2011/0178279 A1 | 7/2011 | Williams et al. |
| 2012/0093842 A1 | 4/2012 | Eshhar et al. |
| 2012/0213783 A1 | 8/2012 | Rosenberg et al. |
| 2012/0302466 A1 | 11/2012 | Sentman |
| 2013/0058936 A1 | 3/2013 | Bruenker et al. |
| 2013/0143895 A1 | 6/2013 | McAllister et al. |
| 2013/0149337 A1 | 6/2013 | Cooper et al. |
| 2013/0156794 A1 | 6/2013 | Eshhar et al. |
| 2013/0287748 A1 | 10/2013 | June et al. |
| 2013/0287752 A1 | 10/2013 | Davila |
| 2013/0309267 A1 | 11/2013 | Simmons et al. |
| 2013/0309258 A1 | 12/2013 | June et al. |
| 2013/0323834 A1 | 12/2013 | Brenner |
| 2013/0344066 A1 | 12/2013 | Faham et al. |
| 2014/0004132 A1 | 1/2014 | Brenner et al. |
| 2014/0004137 A1 | 1/2014 | Ovaa et al. |
| 2014/0017170 A1 | 1/2014 | Irvine et al. |
| 2014/0050708 A1 | 2/2014 | Powell et al. |
| 2014/0099309 A1 | 4/2014 | Powell, Jr. et al. |
| 2014/0120136 A1 | 5/2014 | Katsikis et al. |
| 2014/0134142 A1 | 5/2014 | Smith et al. |
| 2014/0134720 A1 | 5/2014 | Stauss et al. |
| 2014/0227237 A1 | 8/2014 | June et al. |
| 2014/0234348 A1 | 8/2014 | Scholler et al. |
| 2014/0255363 A1 | 9/2014 | Metelitsa et al. |
| 2014/0271582 A1 | 9/2014 | Forman et al. |
| 2014/0271635 A1 | 9/2014 | Brogdon et al. |
| 2014/0274909 A1 | 9/2014 | Orentas et al. |
| 2014/0286973 A1 | 9/2014 | Powell |
| 2014/0286987 A1 | 9/2014 | Spencer et al. |
| 2014/0294861 A1 | 10/2014 | Scholler et al. |
| 2014/0301993 A1 | 10/2014 | Powell, Jr. et al. |
| 2014/0308259 A1 | 10/2014 | Scholler et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0356398 A1 | 12/2014 | Riddell et al. |
| 2014/0378389 A1 | 12/2014 | Robbins et al. |
| 2015/0073154 A1 | 3/2015 | Davis |
| 2015/0110760 A1 | 4/2015 | Zhang et al. |
| 2015/0139943 A1 | 5/2015 | Campana et al. |
| 2015/0152181 A1 | 6/2015 | Sentman et al. |
| 2015/0211023 A1 | 7/2015 | Shiboleth et al. |
| 2015/0225470 A1 | 8/2015 | Zhang et al. |
| 2015/0225480 A1 | 8/2015 | Powell, Jr. |
| 2015/0238631 A1 | 8/2015 | Kim et al. |
| 2015/0283178 A1 | 10/2015 | June et al. |
| 2015/0306141 A1 | 10/2015 | Jensen et al. |
| 2015/0307564 A1 | 10/2015 | Young et al. |
| 2015/0307842 A1 | 10/2015 | Sentman |
| 2015/0314014 A1 | 11/2015 | Lauermann |
| 2015/0320799 A1* | 11/2015 | Low .................. A61P 35/00 435/328 |
| 2015/0328292 A1 | 11/2015 | Spencer et al. |
| 2015/0368342 A1 | 12/2015 | Wu et al. |
| 2016/0008398 A1 | 1/2016 | Sadelain et al. |
| 2016/0046700 A1 | 2/2016 | Foster et al. |
| 2016/0046724 A1 | 2/2016 | Brogdon et al. |
| 2016/0046729 A1 | 2/2016 | Schonfeld et al. |
| 2016/0051651 A1 | 2/2016 | Brogdon et al. |
| 2016/0058857 A1 | 3/2016 | Spencer et al. |
| 2016/0068601 A1 | 3/2016 | Brogdon et al. |
| 2016/0076056 A1 | 3/2016 | Reik et al. |
| 2016/0096892 A1 | 4/2016 | Brogdon et al. |
| 2016/0120907 A1 | 5/2016 | Sentman |
| 2016/0129109 A1 | 5/2016 | Davila et al. |
| 2016/0136190 A1 | 5/2016 | Weichert et al. |
| 2016/0151465 A1 | 6/2016 | Slawin et al. |
| 2016/0166613 A1 | 6/2016 | Spencer et al. |
| 2016/0175359 A1 | 6/2016 | Spencer et al. |
| 2016/0185861 A1 | 6/2016 | Bedoya et al. |
| 2016/0222119 A1 | 8/2016 | Scholler et al. |
| 2016/0243258 A1 | 8/2016 | Scharenberg et al. |
| 2016/0250258 A1 | 9/2016 | Delaney et al. |
| 2016/0340649 A1 | 11/2016 | Brown et al. |
| 2016/0361360 A1 | 12/2016 | Chang et al. |
| 2017/0002017 A1 | 1/2017 | Andrez et al. |
| 2017/0015746 A1 | 1/2017 | Jensen |
| 2017/0029531 A1 | 2/2017 | Crane |
| 2017/0029774 A1 | 2/2017 | Jensen et al. |
| 2017/0044240 A1 | 2/2017 | Wagner et al. |
| 2017/0081411 A1 | 3/2017 | Engels et al. |
| 2017/0087185 A1 | 3/2017 | Crane et al. |
| 2017/0152297 A1 | 6/2017 | Jensen |
| 2017/0166877 A1 | 6/2017 | Bayle et al. |
| 2017/0209543 A9 | 7/2017 | Jensen |
| 2017/0224733 A1 | 8/2017 | Badie et al. |
| 2017/0267742 A1 | 9/2017 | Jensen et al. |
| 2017/0290900 A1 | 10/2017 | Low et al. |
| 2017/0306303 A1 | 10/2017 | Taunton et al. |
| 2017/0340672 A1 | 11/2017 | Wu et al. |
| 2017/0342124 A1 | 11/2017 | Scholler et al. |
| 2017/0356010 A1 | 12/2017 | Frost et al. |
| 2017/0360910 A1 | 12/2017 | Wang et al. |
| 2017/0368098 A1 | 12/2017 | Chen et al. |
| 2018/0009891 A1 | 1/2018 | Jensen |
| 2018/0016539 A1 | 1/2018 | Ding et al. |
| 2018/0022795 A1 | 1/2018 | Milone et al. |
| 2018/0022828 A1 | 1/2018 | Schonfeld et al. |
| 2018/0142198 A1 | 5/2018 | Sharei et al. |
| 2018/0142239 A1 | 5/2018 | Yu et al. |
| 2018/0214527 A1 | 8/2018 | Wang et al. |
| 2018/0282692 A1 | 10/2018 | Rawlings et al. |
| 2018/0320133 A1 | 11/2018 | Forman et al. |
| 2018/0327781 A1 | 11/2018 | Scharenberg et al. |
| 2019/0000881 A1 | 1/2019 | Sadelain et al. |
| 2019/0016776 A1 | 1/2019 | Jensen et al. |
| 2019/0091308 A1 | 3/2019 | Low et al. |
| 2019/0161531 A1 | 5/2019 | Pule et al. |
| 2019/0209611 A1 | 7/2019 | Eckardt et al. |
| 2019/0224237 A1 | 7/2019 | Jensen et al. |
| 2019/0255109 A1 | 8/2019 | Low et al. |
| 2019/0292517 A1 | 9/2019 | Cheung et al. |
| 2019/0388468 A1 | 12/2019 | Lock et al. |
| 2020/0054676 A1 | 2/2020 | Low et al. |
| 2020/0087399 A1 | 3/2020 | Jensen et al. |
| 2020/0123224 A1 | 4/2020 | Scharenberg |
| 2020/0354477 A1 | 11/2020 | Jensen et al. |
| 2020/0405760 A1 | 12/2020 | Low et al. |
| 2021/0147871 A1 | 5/2021 | Scharenberg et al. |
| 2021/0308267 A1 | 10/2021 | Low et al. |
| 2021/0317407 A1 | 10/2021 | Jensen et al. |
| 2021/0340573 A1 | 11/2021 | Scharenberg et al. |
| 2021/0346431 A1 | 11/2021 | Messmann et al. |
| 2022/0000996 A1 | 1/2022 | Low |
| 2022/0017920 A1 | 1/2022 | Scharenberg et al. |
| 2022/0257652 A1 | 8/2022 | Jensen et al. |
| 2022/0280648 A1 | 9/2022 | Low et al. |
| 2022/0409747 A1 | 12/2022 | Low et al. |
| 2023/0068879 A1 | 3/2023 | Jensen et al. |

FOREIGN PATENT DOCUMENTS

| | | |
|---|---|---|
| EP | 2177230 A1 | 4/2010 |
| EP | 10009345 | 9/2010 |
| EP | 2537416 B1 | 11/2014 |
| EP | 2614077 B1 | 8/2016 |
| JP | 2015525765 A | 9/2015 |
| JP | 2016534995 A | 11/2016 |
| WO | WO 86/04356 | 7/1986 |
| WO | WO 92/10591 | 6/1992 |
| WO | WO 92/15671 | 9/1992 |
| WO | WO-9215322 A1 | 9/1992 |
| WO | WO-9530014 A1 | 11/1995 |
| WO | WO-9723613 A2 | 7/1997 |
| WO | WO-9734634 A1 | 9/1997 |
| WO | WO-9958572 A1 | 11/1999 |
| WO | WO-0014257 | 3/2000 |
| WO | WO-0023573 A2 | 4/2000 |
| WO | WO 2001/091625 | 12/2001 |
| WO | WO 02/088334 | 11/2002 |
| WO | WO-02088334 A1 | 11/2002 |
| WO | WO-2005079836 A1 | 9/2005 |
| WO | WO-2005084716 A2 | 9/2005 |

(56) References Cited

FOREIGN PATENT DOCUMENTS

| | | |
|---|---|---|
| WO | WO 2006/029879 | 3/2006 |
| WO | WO-2006036445 A2 | 4/2006 |
| WO | WO-2008031577 A1 | 3/2008 |
| WO | WO-2008045437 A2 | 4/2008 |
| WO | WO 2008/057437 | 5/2008 |
| WO | WO-2008121420 A1 | 10/2008 |
| WO | WO 2009/091826 | 7/2009 |
| WO | WO-2009117117 A1 | 9/2009 |
| WO | WO 2010/025177 | 3/2010 |
| WO | WO-2011041093 A1 | 4/2011 |
| WO | WO-2011059836 A2 | 5/2011 |
| WO | WO-2012028241 A1 | 3/2012 |
| WO | WO-2012031744 A1 | 3/2012 |
| WO | WO 2012/054825 | 4/2012 |
| WO | WO 2012/082841 | 6/2012 |
| WO | WO-2012079000 A1 | 6/2012 |
| WO | WO-2012099973 A2 | 7/2012 |
| WO | WO-2012129514 A1 | 9/2012 |
| WO | WO 2012/138475 | 10/2012 |
| WO | WO-2013019615 A2 | 2/2013 |
| WO | WO 2013/039889 | 3/2013 |
| WO | WO-2013044225 A1 | 3/2013 |
| WO | WO-2013063419 A2 | 5/2013 |
| WO | WO-2013067492 A1 | 5/2013 |
| WO | WO-2013071154 A1 | 5/2013 |
| WO | WO-2013088446 A1 | 6/2013 |
| WO | WO-2013093809 A1 | 6/2013 |
| WO | WO-2013112986 A1 | 8/2013 |
| WO | WO-2013123061 A1 | 8/2013 |
| WO | WO-2013126726 A1 | 8/2013 |
| WO | WO 2013/177247 | 11/2013 |
| WO | WO-2013166321 A1 | 11/2013 |
| WO | WO-2014011984 A1 | 1/2014 |
| WO | WO-2014011987 A1 | 1/2014 |
| WO | WO-2014031687 A1 | 2/2014 |
| WO | WO 2014/043441 | 3/2014 |
| WO | WO-2014039523 A1 | 3/2014 |
| WO | WO 2014/055771 | 4/2014 |
| WO | WO-2014055668 A1 | 4/2014 |
| WO | WO-2014068388 A1 | 5/2014 |
| WO | WO2014/100615 | 6/2014 |
| WO | WO 2014/100615 | 6/2014 |
| WO | WO-2014099671 A1 | 6/2014 |
| WO | WO-2014100385 A1 | 6/2014 |
| WO | WO-2014100615 A1 * | 6/2014 ............ A61K 47/551 |
| WO | WO-2014124143 A1 | 8/2014 |
| WO | WO-2014127261 A1 | 8/2014 |
| WO | WO-2014130635 A1 | 8/2014 |
| WO | WO-2014152177 A1 | 9/2014 |
| WO | WO-2014153002 A1 | 9/2014 |
| WO | WO 2015/057834 | 4/2015 |
| WO | WO 2015/057852 | 4/2015 |
| WO | WO-2015107075 A1 | 7/2015 |
| WO | WO-2015123496 A1 | 8/2015 |
| WO | WO-2015164594 A1 | 10/2015 |
| WO | WO-2015188135 A1 | 12/2015 |
| WO | WO 2016/025322 | 2/2016 |
| WO | WO-2016025454 A2 | 2/2016 |
| WO | WO-2016073755 A2 | 5/2016 |
| WO | WO 2016/102965 | 6/2016 |
| WO | WO-2016098078 A2 | 6/2016 |
| WO | WO 2016/054520 | 7/2016 |
| WO | WO-2016109668 A1 | 7/2016 |
| WO | WO 2016/149665 | 9/2016 |
| WO | WO-2016149665 A1 | 9/2016 |
| WO | WO-2016154621 A1 | 9/2016 |
| WO | WO-2016168766 A1 | 10/2016 |
| WO | WO-2016168769 A1 | 10/2016 |
| WO | WO-2016168773 A2 | 10/2016 |
| WO | WO 2016/201300 | 12/2016 |
| WO | WO2016/201300 | 12/2016 |
| WO | WO 2017/029511 | 2/2017 |
| WO | WO 2017/029512 | 2/2017 |
| WO | WO-2017025638 A1 | 2/2017 |
| WO | WO-2017035362 A1 | 3/2017 |
| WO | WO 2017/068360 | 4/2017 |
| WO | WO 2017/068361 | 4/2017 |
| WO | WO-2017062628 A1 | 4/2017 |
| WO | WO-2017123548 A1 | 7/2017 |
| WO | WO 2017/137758 | 8/2017 |
| WO | WO 2017/137759 | 8/2017 |
| WO | WO-2017136829 A1 | 8/2017 |
| WO | WO-2017143094 A1 | 8/2017 |
| WO | WO-2017143150 A1 | 8/2017 |
| WO | WO 2017/165245 | 9/2017 |
| WO | WO-2017165245 A2 | 9/2017 |
| WO | WO-2017165571 A1 | 9/2017 |
| WO | WO2017/177149 | 10/2017 |
| WO | WO 2017/177149 | 10/2017 |
| WO | WO 2017/180587 | 10/2017 |
| WO | WO 2017/216561 | 12/2017 |
| WO | WO 2017/216562 | 12/2017 |
| WO | WO-2017214167 A1 | 12/2017 |
| WO | WO-2017214170 A2 | 12/2017 |
| WO | WO-2018013797 A1 | 1/2018 |
| WO | WO-2018031694 A1 | 2/2018 |
| WO | WO-2018075794 A1 | 4/2018 |
| WO | WO-2018075807 A1 | 4/2018 |
| WO | WO-2018075813 A1 | 4/2018 |
| WO | WO-2018080541 A1 | 5/2018 |
| WO | WO-2018102761 A1 | 6/2018 |
| WO | WO-2018111763 A1 | 6/2018 |
| WO | WO-2018111834 A1 | 6/2018 |
| WO | WO-2018115146 A1 | 6/2018 |
| WO | WO-2018148224 A1 | 8/2018 |
| WO | WO-2018152451 A1 | 8/2018 |
| WO | WO 2018/160622 | 9/2018 |
| WO | WO-2018165194 A1 | 9/2018 |
| WO | WO-2018165198 A1 | 9/2018 |
| WO | WO-2018170150 A2 | 9/2018 |
| WO | WO-2018175453 A1 | 9/2018 |
| WO | WO-2018213332 A1 | 11/2018 |
| WO | WO-2019028190 A1 | 2/2019 |
| WO | WO-2019033050 A1 | 2/2019 |
| WO | WO-2019144091 A1 | 7/2019 |
| WO | WO-2019144095 A1 | 7/2019 |
| WO | WO-2019156795 A1 | 8/2019 |
| WO | WO-2019165237 A1 | 8/2019 |
| WO | WO-2021007109 A1 | 1/2021 |
| WO | WO-2021055641 A1 | 3/2021 |
| WO | WO-2021076788 A2 | 4/2021 |
| WO | WO-2021154839 A1 | 8/2021 |
| WO | WO-2021158523 A1 | 8/2021 |
| WO | WO-2021158534 A1 | 8/2021 |
| WO | WO-2021178887 A1 | 9/2021 |
| WO | WO-2022015955 A1 | 1/2022 |
| WO | WO-2022109162 A1 | 5/2022 |
| WO | WO-2022164935 A1 | 8/2022 |

OTHER PUBLICATIONS

Zheng et al., Zhongguo Redai Yixue (2015), 15(5), 521-524 (Year: 2015).*

Maude et al., Cancer J Mar.-Apr. 2014;20(2):119-22 (Year: 2014).*

Lu, Y. et al., "Preclinical pharmacokinetics, tissue distribution, and antitumor activity of a folate-hapten conjugate-targeted immunotheraphy in hapten-immunized mice," Molecular Cancer Therapeutics, 2006, 5, 3258-3267.

International Search Report prepared for PCT/US2013/076986, dated Apr. 28, 2014.

Kennedy, M. et al., "Optical imaging of metastatic tumors using a folate-targeted fluorescent probe," J. Biomed. Opt., 2003, 8, 636-641.

Fujita, K. et al., "Prolonged disease-free period in patients with advanced epithelial ovarian cancer after adoptive transfer of tumor-infiltrating lymphocytes." Clin. Cancer Res., 1995, 1, 501-507.

Kandalaft, L. et al., "A phase I clinical trial of adoptive transfer of folate receptor-alpha redirected autologous T cells for recurrent ovarian cancer," Journal of Translational Medicine, 2012, 10:157, 10 pages.

Urbanska, K. et al., "A universal strategy for adoptive immunotherapy of cancer through use of a novel T-cell antigen receptor," Cancer Res., 2012, 72, 1844-1852.

(56) References Cited

OTHER PUBLICATIONS

Kochenderfer, J. et al., "Eradication of B-lineage cells and regression of lymphoma in a patient treated with autologous T cells genetically engineered to recognize CD19," Blood, 2010, 116, 4099-4102.
Rosenberg, S. A. et al., "Adoptive cell therapy for the treatment of patients with metastatic melanoma," Current Opinion in Immunology, 2009, 21, 233-240.
Ertl, H. C. et al., "Considerations for the clinical application of chimeric antigen receptor T cells: observations from a recombinant DNA advisory committee symposium held Jun. 15, 2010," Cancer Res., 2011, 71, 3175-3181.
Zhao, Y. et al., "A herceptin-based chimeric antigen receptor with modified signaling domains leads to enhanced survival of transduced T lymphocytes and antitumor activity," J. Immunol, 2009, 183, 5563-5574.
Sadelain, M. et al., "The basic principles of chimeric antigen receptor design," Cancer Discov., 2013, 3, 388-398.
Cartellieri, M. et al., "Chimeric antigen receptor-engineered T cells for immunotherapy of cancer," J. Biomedicine and Biotechnology, 2010, Article ID 956304, 13 pages.
Urba, W.J. et al., "Redirecting T cells," New Engl. J. Med, 2011, 365, 754-757.
Porter D.L. et al., "Chimeric: antigen receptor-modified T cells in chronic: lymphoid leukemia," N. Engl. J. Med., 2011, 365, 725-733.
Lamers, C. et al., "Treatment of Metastatic Renal Cell Carcinoma With Autologous T-Lymphocytes Genetically Retargeted Against Carbonic Anhydrase IX: First Clinical Experience," J. Clin. Oncol., 2006, 24, e20-22.
Kochenderfer, J. et al., "B-cell depletion and remissions of malignancy along with cytokine-associated toxicity in a clinical trial of anti-CD19 chimeric-antigen-receptor—transduced T cells," Blood, 2012, 119, 2709-2720.
Reichert, J. "Day 1, Emerging Disruptive Technologies and Cutting-Edge AnalyticalTechniques," MAbs, 2009, 1, 190-209.
Kularatne, S.A. et al., "Prostate-specific membrane antigen targeted imaging and therapy of prostate cancer using a PSMA inhibitor as a homing ligand," Mol. Pharm., 2009, 6,780-789.
Wayua, C. et al., "Evaluation of a Cholecystokinin 2 Receptor-Targeted Near-Infrared Dye for Fluorescence-Guided Surgery of Cancer," Molecular Pharmaceutics, 2014, 11, 468-476.
Saga, E. et al., "Tumor detection using folate receptor-targeted imaging agents," Cancer Metastasis Rev., 2008, 27, 655-664.
Alvarez-Vallina, L. et al., "Antigen-specific targeting of CD28-mediated T cell co-stimulation using chimeric single-chain antibody variable fragment-CD28 receptors," Eur. J.Immunol, 1996, 26, 2304-2309.
Imai, C. et al., "Chimeric receptors with 4-1BB signaling capacity provoke potent cytotoxicity against acute lymphoblastic leukemia," Leukemia, 2004, 18, 676-684.
Latza, U. et al., "The human OX40 homolog: cDNA structure, expression and chromosomal assignment of the ACT35 antigen," Eur. J. Immunol., 1994, 24, 677-683.
Hutloff, A. et al., "ICOS is an inducible T-cell costimulator structurally and functionally related to CD28," Nature: 1999, 397, 263-266.
Orr B. et al., "Rapid method for measuring ScFv thermal stability by yeast surface display," Biotechnol Prog., 2003. 19, 631-638.
Kolmar, H. et al., "Alternative binding proteins: biological activity and therapeutic potential of cystine-knot miniproteins," The FEBS Journal, 2008, 275, 26684-26690.
Gross, G. et al., "Expression of immunoguling-T-cell receptor chimeric molecules as functional receptors with antibody-type specificity," Proc. Natl. Acad. Sci., 1989, 86, 10024-10028.
Ma, J. et al., "Versatile strategy for controlling the specificity and activity of engineered T cells," Proc. Natl. Acad. Sci., 2016, 113, E450-458.
Rodgers, D. et al., "Switch-mediated activation and retargeting of CAR-T cells for B-cell malignancies," Proc. Natl. Acad. Sci., 2016, 113, E459-468.

Sambrook et al., "Molecular Cloning: A Laboratory Manual", 3rd Edition, Cold Spring Harbor Laboratory Press, (2001).
Altschul, S. et al., "Basic local alignment search tool," J. Mol. Bio., 1990, 215, 403-410.
Bedzyk, WD et al., "Active site structure and antigen binding properties of idiotypically cross-reactive anti-fluorescein monoclonal antibodies," J Biol Chem., 1990, 265,133-138.
Jung, S. et al., "Selection for improved protein stability by phage display," J. Mol. Biol., 1999, 294, 163-180.
Nieba, L. et al., "Disrupting the hydrophobic patches at the antibody variable/constant domain interface: improved in vivo folding and physical characterization of an engineered scFv fragment," Protein Eng., 1997, 10, 435-444.
UniProtKB-Q07011 (TNR9_Human). Tumor necrosis factor receptor superfamily member 9; 14 pages; retrieved on May 13, 2016 from http://www.uniprot.org/uniprot/Q07011.
UniProtKB-P20963 (CD3Z_Human). T-cell surface glycoprotein CD3 zeta chain; 12 pages; retrieved on May 13, 2016 from http://www.uniprot.org/uniprot/P20963.
UniProtKB-P01732 (CD8A_Human). T-cell surface glycoprotein CD8 alpha chain; 11 pages; retrieved on May 13, 2016 from http://www.uniprot.org/uniprot/P01732.
Wikipedia. "Chimeric antigen receptor"; 9 pages; retrieved on Nov. 13, 2014 from http://en.wikipedia.org/wiki/Chimeric_antigen_receptor.
National Cancer Institute. CAR T-Cell Therapy: Engineering Patients' Immune Cells to Treat Their Cancers, *Cancer Research Updates*, Updated: Oct. 16, 2014; 5 pages; retrieved Nov. 17, 2014 from http://www.cancer.gov/cancertopics/research-updates/2013/CAR-T-Cells.
"Recent patent applications in chimeric antigen receptors," *Nature Biotechnology* 32(3): 239 (2014).
Kim, M. et al, "Redirection of Genetically Engineered CAR-T cells Using Bifunctional Small Molecules," J. Am. Chem. Soc., 2015, 137, 2832-2835.
Product brochure for the Engineered Autologous Cell Therapy (eACT™) Platform, available from Kite Pharma, retrieved Oct. 25, 2015 from http://www.kitepharma.com/c/products/eact.php.
Pameijer, C.R., et al., "Conversion of a tumor-binding peptide identified by phage display to a functional chimeric T cell antigen receptor," Cancer Gene Ther., 2007, 14, 91-07.
Van Dam, G. et al., "Intraoperative tumor-specific fluorescence imaging in ovarian cancer by folate receptor-α targeting: first in-human results," Nature Medicine, 2011, 17, 1315-1319.
Lu, Y. et al., "Folate-targeted dinitrophenyl hapten immunotherapy: effect of linker chemistry on antitumor activity and allergic potential," Mol. Pharm., 2007, 695-706.
Hutchins, B. et al., "Site-specific coupling and sterically controlled formation of multimeric antibody fab fragments with unnatural amino acids," J. Mol. Biol., 2011, 406, 595-603.
Tamada, et al., "Redirecting Gene-Modified T Cells toward Various Cancer Types Using Tagged Antibodies", Clin. Cancer Res., 2012, 18:6436-6445.
Abken, H. et al. "Chemeric T-Cell Receptors: Highly Specific Tools To Target Cytotoxic T-Lymphocytes To Tumour Cells," Cancer Treatment Reviews (1997); 23:97-112.
Altenschmidt, U. et al. "Adoptive transfer of in vitro-targeted, activated T lymphocytes results in total tumor regression," J. Immunol. (1997); 159:5509-15.
Altenschmidt, U., et al., "Specific cytotoxic T lymphocytes in gene therapy," J. Mol. Med. (1997); 75, 259-266.
Becker, M. L. B., et al., "Expression of a hybrid immunoglobulin-T cell receptor protein in transgenic mice," Cell (1989); 58:911-921.
Bluemel, C., et al., Epitope distance to the target cell membrane and antigen size determine the potency of T cell-mediated lysis by BiTE antibodies specific for a large melanoma suiface antigen. Cancer Immunol Immunother (2010); 59(8): 1197-209.
Bolhuis, R. L. et al. "Preparation for a phase I/II study using autologous gene modified T lymphocytes for treatment of metastatic renal cancer patients.," Adv. Exp. Med. Biol. (1998); 451:547-55.
Brentjens, et al., "Eradication of systemic B-cell tumors by genetically targeted human T lymphocytes co-stimulated by CD80 and interleukin-15," Nat. Med. (2003); 9: 279-286.

(56) References Cited

OTHER PUBLICATIONS

Cambier, et al., "Antigen and Fc receptor signaling. The awesome power of the immunoreceptor tyrosine-based activation motif (ITAM)," J Immunol. (Oct. 1, 1995); 155(7):3281-5.
Cameron, B.J., et al., "Identification of a Titin-Derived HLA-A1-Presented Peptide as a Cross-Reactive Target for Engineered MAGE A3-Directed T Cells," Sci Transl Med (Aug. 7, 2013); 5(197): 197ra103 (11 pages).
Chen et al. "Fusion protein linkers: property, design and functionality," Adv Drug Deliv Rev. (2013); 65: 1357-1369 (Epub Sep. 29, 2012).
Colcher, D. et al. "In vivo tumor targeting of a recombinant single-chain antigen-binding protein.," J. Nat. Cancer Inst. (1990); 82:1191-1197.
Cordaro, T. A et al. "Tumor size at the time of adoptive transfer determines whether tumor rejection occurs," Eur. J. Immunol. (2000); 30: 1297-1307.
Dall, Peter et al., "In vivo cervical cancer growth inhibition by genetically engineered cytotoxic T cells." Cancer Immunol. Immunother. (Jan. 2005); 54(1):51-60.
Darcy, P. K. et al. "Expression in cytotoxic T lymphocytes of a single-chain anti-carcinoembryonic antigen antibody. Redirected Fas ligand-mediated lysis of colon carcinoma," Eur. J. Immunol. (1998); 28:1663-72.
Dotti, et al. "Design and development of therapies using chimeric antigen receptor-expressing T cells." Immun Rev (Jan. 2014); 257(1): 107-126.
Dubrovska, A., et al., "A chemically induced vaccine strategy for prostate cancer," ACS Chem Biol (2011); 6(11): 1223-31.
Eshhar, et al., "Design of Cytotoxic T Lymphocytes with Antibody-Type Specificity against Tumor Cells Using Chimeric TcR," Journal of Cellular Biochemistry, Supplement 14B, UCLA Symposia on Molecular & Cellular Biology, Abstracts, 19th Annual Meeting, Jan. 27-Feb. 8, 1990, p. 70.
Eshhar, Z., et al., "Functional expression of chimeric receptor genes in human T cells," J. Immunol. Meth. (2001); 248: 67-76.
Fedorov VD, et al., "PD-1- and CTLA-4-based inhibitory chimeric antigen receptors (iCARs) divert off-target immunotherapy responses," Sci Transl Med. (Dec. 11, 2013); 5(215):215ra172 (12 pages).
Ferrone, S., et al., "How much longer will tumor cells fool the immune system," Immunol. Today (2000); 21: 70-72.
Figini, M, et al., "Conversion of murine antibodies to human antibodies and their optimization for ovarian cancer therapy targeted to the folate receptor," Cancer Immunol Immunother (Apr. 2009); 58(4):531-46 (Epub Aug. 15, 2008).
Gilboa, E., "How tumors escape immune destruction and what we can do about it," Cancer Immunol. Immunother. (1999); 48: 382-385.
Gilham et al., "CAR-T cells and solid tumors: tuning T cells to challenge an inveterate foe," Trends in Molecular Medicine (2012); 18(7): 377-384 (Epub May 19, 2012).
Gilham et al., "Primary polyclonal human T lymphocytes targeted to carcino-embryonic antigens and neural cell adhesion molecule tumor antigens by CD3zeta-based chimeric immune receptors," J. Immunother, (Mar.-Apr. 2002); 25 (2): 139-151.
Gillies, S.D. et al., "Targeting Human Cytotoxic T Lymphocytes to Kill Heterologous Epidermal Growth Factor Receptor-Bearing Tumor Cells," The Journal of Immunology (1991); 146(3): 1067-1071.
Gong, M. C., et al., "Prostate-specific membrane antigen (PSMA)-specific monoclonal antibodies in the treatment of prostate and other cancers," Cancer Metastasis Rev. (1999); 18: 483-490.
Gonzalez et al., "Genetic engineering of cytolytic T lymphocytes for adoptive T-cell therapy of neuroblastoma," J Gene Med (2004); 6:704-711.
Goverman, J. et al., "Chimeric immunoglobulin-T cell receptor proteins form functional receptors: implications for T cell receptor complex formation and activation," Cell (1990); 60:929-939.
Gross et al., "Development and study of chimeric immunoglobulin/T cell receptor molecules as functional receptors that endow T cells with antibody-type specificity," Ph.D. Thesis presented to the Feinberg Graduate School, The Wiezmann Institute of Science, Rehovot, Israel (1990); 1-70.
Gross, G. et al., "Endowing T cells with antibody specific using chimeric T cell receptors," Department of Chemical Immunology, FASEB J. (Dec. 1992); 6(15):3370-8.
Gross, G. et al., "Generation of effector T cells expressing chimeric T cell receptor with antibody type-specificity," Transplant. Proc. (1989); 21 (1 Pt 1): 127-130.
Heuser, et al., "T-cell activation by recombinant immunoreceptors: impact of the intracellular signalling domain on the stability of receptor expression and antigen-specific activation of grafted T-cells," Gene Therapy (2003); 10: 1408-1419.
Hombach, et al., "Adoptive Immunotherapy with Genetically Engineered T Cells: Modification of the IgG1 Fc 'Spacer' Domain in the Extracellular Moiety of Chimeric Antigen Receptors Avoids 'Off-Target' Activation and Unintended Initiation of an Innate Immune Response," Gene Ther. (Oct. 2010); 17(10):1206-13.
Hwu, et al, "The Genetic Modification of T Cells for Cancer Therapy: An Overview of Laboratory and Clinical Trials," Cancer Detection and Prevention (1994); 18(1):43-50.
Irving, B. A., et al., "The cytoplasmic domain of the T cell receptor zeta chain is sufficient to couple to receptor-associated signal transduction pathways'" Cell (1991); 64:891-901.
Jensen, M et al. "CD20 Is A Molecular Target For scFvFc[zeta] Receptor Redirected T Cells: Implications for Cellular Immunotherapy of CD20+ Malignancy," Biology of Blood and Marrow Transplantation (1998); 4:75-83.
Jensen, M. C., et al., Abstract #98: "Targeting Pre-B Acute Lymphoblastic Leukemia With T Cell Clones Engineered To Express A CD19-Specific Chimeric Immunoreceptor," Blood (Nov. 16, 2000); 96(11):26A.
Kim et al., "Protein conjugation with genetically encoded unnatural amino acids," Curr Opin Chem Biol (2013); 17:412-419 (Epub May 9, 2013).
Kochenderfer et al., "Construction and pre-clinical evaluation of an anti-CD19 chimeric antigen receptor," Journal of Immunotherapy (2009); 32(7): 689-702.
Krause, A., et al., "Genetic approaches to sustain the function of tumor-specific T-lymphocytes," Mol. Ther. (2000); 1 (S260): 713.
Kuwana, Y. et al., "Expression of chimeric receptor composed of immunoglobulin-derived V regions and T-cell receptor-derived C regions," Biochem. Biophys. Res. Comm. (1987); 149:960-968.
Lin et al., "Transglutaminase-catalyzed site-specific conjugation of small-molecule probes to proteins in vitro and on the surface of living cells," J. Am. Chem. Soc. (2006); 128:4542-4543.
Lustgarten, J., et al., "Specific Elimination of IgE Production Using T Cell Lines Expressing Chimeric T Cell Receptor Genes," European Journal of Immunology (1995); 25(10):2985-2991.
Ma, Q. et al., "Carcinoembryonic antigen-immunoglobulin Fc fusion protein (CEA-Fc) for identification and activation of anti-CEA immunoglobulin-T-cell receptor-modified T cells, representative of a new class of Ig fusion proteins," Cancer Gene Therapx (2004); 11: 297-306.
Maher, et al., "Human T-lymphocyte cytotoxicity and proliferation directed by a single chimeric TCRzeta/CD28 receptor," Nature Biotechnology (2002); 20: 70-75.
Marincola, F. M., et al., "Escape of human solid tumors from T cell recognition: molecular mechanisms and functional significance," Adv. Immunol. (2000); 74: 181-273.
McGuinness RP, et al., "Anti-tumor activity of human T cells expressing the CC49-zeta chimeric immune receptor," Hum Gene Ther. (Jan. 20, 1999); 10(2):165-73.
Melief, C. J. et al., "Strategies for immunotherapy of cancer," Adv. Immunol. (2000); 75:235-282.
Morgan RA, et al., "Cancer regression in patients after transfer of genetically engineered lymphocytes," Science (Oct. 6, 2006); 314(5796): 126-9.
Morrison, C, "CAR-T Field Booms as Next-Generation Platforms Attract Big Players," Nature Biotechnology (Jun. 2015); 33: 571-72.
Muller T, et al., "Expression of a CD20-specific chimeric antigen receptor enhances cytotoxic activity of NK cells and overcomes

(56) References Cited

OTHER PUBLICATIONS

NK-resistance of lymphoma and leukemia cells," Cancer Immunol. Immunother. (2008); 57: 411-423.
Oelke et al., "Ex vivo induction and expansion of antigen-specific cytotoxic T cells by HLA-Ig-coated artificial antigen-presenting cells," Nature Medicine (2003); 9(5):619-624.
Paillard, F. "Immunotherapy with T cells bearing chimeric antitumor receptors," Hum. Gene Ther. (1999); 10: 151-153.
Pule et al., "Virus-specific T cells engineered to coexpress tumor-specific receptors: persistence and antitumor activity in individuals with neuroblastoma," Nat. Med. (2008); 14: 1264-1270.
Restifo, N.P., et al., "Adoptive immunotherapy for cancer: harnessing the T cell response," Nat Rev Immunol (Mar. 22, 2012); 12(4): 269-81.
Roberts et al., "Chemistry for peptide and protein PEGylation," Advanced Drug Delivery Reviews (2002); 54:459-476.
Romeo, C. at al., "Sequence requirements for induction of cytolysis by the T cell antigen/Fc receptor zeta chain," Cell (1992); 68:889-897.
Romeo, C., et al., "Cellular immunity to HIV activated by CD4 fused to T cell or Fc receptor polypeptides," Cell (1991); 64:1037-1046.
Sadelain et al., "Targeting Tumours with Genetically Enhanced T Lymphocytes," Nat Rev Cancer (Jan. 2003); 3(1): 35-45.
Sadelain, et al., "The promise and potential pitfalls of chimeric antigen receptors," Current Opinion in Immunology (2009); 21: 215-223.
Scholler, J., et al., "Decade-long safety and function of retroviral-modified chimeric antigen receptor T cells," Sci Transl Med (May 2, 2012); 4(132): 132ra53 (7 pages).
Scott, D., et al., "Immunogenicity of biotinylated hapten-avidin complexes," Mol Immunol (1984); 21(11): 1055-60.
Shirasu, N. et al., "Construction and Molecular Characterization of Human Chimeric T-Cell Antigen Receptors Specific for Carcinoernbrxonic Antigen," Anticancer Research (2010); 30:2731-2738.
Stancovski et al., "Targeting of T Lymphocytes t0 Neu/HER2-Expressing Cells Using Chimeric Single Chain Fv Receptors," J. lmmunol. (1993); 151(11):6577-6582.
Stephan et al., "T cell-encoded CD80 and 4-1BBL induce auto- and transcostimulation, resulting in potent tumor rejection," Nature Medicine (Dec. 2007); 13(12): 1440-1449.
Stevens et al., "Generation of Tumor-Specific CTLs from Melanoma Patients by Using Peripheral Blood Stimulated with Allogeneic Melanoma Tumor Cell Lines," J. lmmunol (1995); 154:2762-771.
Themeli, M., et al., "Generation of tumor-targeted human T lymphocytes from induced pluripotent stem cells for cancer therapy," Nat Biotechnol (2013); 31(10):928-33 (Epub Aug. 11, 2013).
Turatti, F., et al., "Redirected activity of human antitumor chimeric immune receptors is governed by antigen and receptor expression levels and affinity of interaction," J Immunother (2007); 30(7): 684-93.
Uherek, C, et al., "Chimeric antigen receptors for the retargeting of cytotoxic effector cells," J. Hematother. Stem Cell Res. (2001); 10: 523-534.
Uttenthal, B.J., et al., Challenges in T cell receptor gene therapy. J Gene Med (Jun. 2012); 14(6): 386-99.
Weijtens, M. E. et al., "Single chain Ig/gamma gene-redirected human T lymphocytes produce cytokines, specifically lyse tumor cells, and recycle lytic capacity," J. Immunol. (Jul. 15, 1996); 157(2):836-43.
Wilson, et al. "DAP12 and KAP10 (DAP10)—novel transmembrane adapter proteins of the CD3zeta family," lmmunol Res. (2000); 22(1):21-42.
Wu, et al., "Remote control of therapeutic T cells through a small molecule-gated chimeric receptor," Science (Oct. 16, 2015); 350(6258): 293 and aab4077-1 through aab4077-10 (epub Sep. 24, 2015) (12 pages).
Wu, et al., "An activating immunoreceptor complex formed by NKGZD and DAP10," Science (1999); 285:730-732.

Xu, X.J., et al., "Efficacy and safety of adoptive immunotherapy using anti-CD 19 chimeric antigen receptor transduced T-cells: a systematic review of phase I clinical trials," Leuk Lymphoma (2013); 54(2): 255-60 (Published online: Sep. 8, 2012).
Yee, C., et al., "Prospects for Adoptive T Cell Therapy," Current Opinion in Immunology (1997); 9(5):702-708.
Zhong, et al., "Integrated CD28 and 4-1BB Signals Strongly Potentiate CD8+ T Cell Mediated Eradication of Metastatic Prostate Cancer," Molecular Therapy (Jan. 1, 2006); 13: p. S103, Abstract.
Herron, J.N., et al., "High resolution structures of the 4-4-20 Fab-fluorescein complex in two solvent systems: effects of solvent on structure and antigen-binding affinity". Biophys J, 1994. 67(6): p. 2167-83.
Jung, S, et al. "Improving in vivo folding and stability of a single-chain Fv antibody fragment by loop grafting." Protein Eng. Aug. 1997; 10(8):959-66.
Vaughan, J,et al. "Human antibodies with sub-nanomolar affinities isolated from a large non-immunized phage display library". Nat Biotechnol. Mar. 1996; 14(3):309-14.
Airenne et al., "Recombinant avidin and avidin-fusion proteins", Biomolecular Engineering 16 (1999) 87-92.
Alcover et al., "A soluble form of the human CD8 alpha chain expressed in the baculovirus system: Biochemical characterization and binding to MHC Class I", Molecular Immunology, vol. 30, No. 1, pp. 55-67, 1993.
Ang et al., "Generating a Chimeric Antigen Receptor To Redirect T-Cell Specificity after Infusion", Molecular Therapy vol. 19, Supplement 1, May 2011, S137-S138.
AVD—Avidin precursor, UniProtKB—P02701 (AVID_Chick).
Baba et al., "N-Linked Carbohydrate on Human Leukocyte Antigen-C and Recognition by Natural Killer Cell Inhibitory Receptors", Human Immunology 61, 1202-1218 (2000).
Chang et al., "A Chimeric Receptor with NKG2D Specificity Enhances Natural Killer Cell Activation and Killing of Tumor Cells", Cancer Res 2013;73:1777-1786. Published online Jan. 9, 2013.
Feng et al., "Convergence on a Distinctive Assembly Mechanism by Unrelated Families of Activating Immune Receptors", Immunity, vol. 22, 427-438, Apr. 2005.
Feng et al., "The Assembly of Diverse Immune Receptors Is Focused on a Polar Membrane-Embedded Interaction Site", 2006. PLoS Biol 4(5):e142.
Hege et al., "Systemic T Cell-independent Tumor Immunity after Transplantation of Universal Receptor-modified Bone Marrow into SCID Mice", J. Exp. Med. vol. 184 Dec. 1996 pp. 2261-2269.
Katz et al., "Recognition of HLA-Cw4 but Not HLA-Cw6 by the NK Cell Receptor Killer Cell Ig-Like Receptor Two-Domain Short Tail No. 4", J Immunol 2001; 166:7260-7267.
Linenberger, "CD33-directed therapy with gemtuzumab ozogamicin in acute myeloid leukemia: progress in understanding cytotoxicity and potential mechanisms of drug resistance", Leukemia (2005) 19, 176-182.
Okazaki et al., "PD-1 immunoreceptor inhibits B cell receptormediated signaling by recruiting src homology 2-domain-containing tyrosine phosphatase 2 to phosphotyrosine", PNAS Nov. 20, 2001, vol. 98, No. 24, 13866-13871.
Wikipedia, Avidin, https://en.wikipedia.org/wiki/Avidin, downloaded Aug. 24, 2018.
Wikipedia, Antibody, https://en.wikipedia.org/w/index.php?title=Antibody&oldid=851456273, downloaded Jul. 22, 2018.
Wikipedia, CD8, https://en.wikipedia.org/w/index.php?title=CD8&oldid=840166968, downloaded May 8, 2018.
Wikipedia, CD28, https://en.wikipedia.org/w/index.php?title=CD28&oldid=831459950, downloaded Mar. 20, 2018.
Wikipedia, CD137, https://en.wikipedia.org/w/index.php?title=CD137&oldid=788581779, downloaded Jul. 2, 2017.
Wikipedia, Cholecystokinin B receptor, https://en.wikipedia.org/w/index.php?title=Cholecystokinin_B_receptor&oldid=837355377, downloaded Apr. 20, 2018.
Wikipedia, Cytokine , https://en.wikipedia.org/w/index.php?title=Cytokine&oldid=847147607, downloaded Jun. 23, 2018.
Wikipedia, Fc receptor, https://en.wikipedia.org/w/index.php?title=Fc_receptor&oldid=845940301, downloaded Jun. 15, 2018.

(56) References Cited

OTHER PUBLICATIONS

Wikipedia, Folate, https://en.wikipedia.org/w/index.php?title=Folate&oldid=851466622, downloaded Jun. 22, 2018.
Wikipedia, Folate receptor, https://en.wikipedia.org/w/index.php?title=Folate_receptor&oldid=834246297, downloaded Apr. 4, 2018.
Wikipedia, Folate receptor 1, https://en.wikipedia.org/w/index.php?title=Folate_receptor_1&oldid=845790606, downloaded Jun. 14, 2018.
Wikipedia, Folate receptor gamma, https://en.wikipedia.org/w/index.php?title=Folate_receptor_gamma&oldid=621589158, downloaded Aug. 17, 2014.
Wikipedia, FOLR2, https://en.wikipedia.org/w/index.php?title=FOLR2&oldid=798129670, downloaded Aug. 31, 2017.
Wikipedia, Glutamate carboxypeptidase II, https://en.wikipedia.org/w/index.php?title=Glutamate_carboxypeptidase_II&oldid=845231234, downloaded Jun. 10, 2018.
Wikipedia, IL-2 receptor, https://en.wikipedia.org/w/index.php?title=IL-2_receptor&oldid=847173411, downloaded Jun. 23, 2018.
Wikipedia, Interferon, https://en.wikipedia.org/w/index.php?title=Interferon&oldid=848844304, downloaded Jul. 4, 2018.
Wikipedia, Interleukin 2, https://en.wikipedia.org/w/index.php?title=Interleukin_2&oldid=838351127, downloaded Apr. 26, 2018.
Wikipedia, Interleukin 10, https://en.wikipedia.org/w/index.php?title=Interleukin_10&oldid=835415026, downloaded Apr. 8, 2018.
Wikipedia, Interleukin-1 family, https://en.wikipedia.org/w/index.php?title=Interleukin-1_family&oldid=847253010, downloaded Jun. 24, 2018.
Wikipedia, Single-chain valiable fragment, https://en.wikipedia.org/w/index.php?title=Single-chain_variable_fragment&oldid=841449115, downloaded May 15, 2018.
Wikipedia, TNF receptor superfamily, https://en.wikipedia.org/w/index.php?title=TNF_receptor_superfamily&oldid=850804991, downloaded Jul. 18, 2018.
Wikipedia, Transforming growth factor beta superfamily, https://en.wikipedia.org/w/index.php?title=Transforming_growth_factor_beta_superfamily&oldid:850390369, downloaded Jul. 15, 2018.
Arch, R, et al., "4-1BB and Ox40 Are Members of a Tumor Necrosis Factor (TNF)-Nerve Growth Factor Receptor Subfamily That Bind TNF Receptor-Associated Factors and Activate Nuclear Factor kB," Molecular And Cellular Biology (1998); 558-565.
Aruffo, A, et al., "Molecular cloning of a CD28 cDNA by a high-efficiency COS cell expression system," Proc. Nati. Acad. Sci. USA (1987); 84: 8573-8577.
Bauer, A, et al., "Differential signal transduction via T-cell receptor CD3'2, CD3C-,v, and CD3'q2 isoforms," Proc. Nati. Acad. Sci. USA (1991); 88: 3842-3846.
Bejcek, B, et al., "Development and Characterization of Three Recombinant Single Chain Antibody Fragments (scFvs) Directed against the CD19 Antigen1," Cancer Research 55, (1995); 2346-2351.
Boomer, J, et al,. "An Enigmatic Tail of CD28 Signaling," Washington University School of Medicine (2010); 1-20.
Camerini, D, et al,. "The T cell activation antigen CD27 is a member of the nerve growth factor/tumor necrosis factor receptor gene family," The Journal of Immunology (1991); 3165-3169.
UniProtKB-P10966 (CD8B_Human).
UniProtKB-P10747 (CD28_Human).
Chalupny, J, et al,."T-cell activation molecule 4-1BB binds to extracellular matrix proteins," Proc. Nat!. Acad. Sci. USA (1992); 89: 10360-10364.
Jang, I, et al., "Human 4-1BB (CD137) Signals Are Mediated by TRAF2 and Activate Nuclear Factor-kB," Biochemical And Biophysical Research Communications (1998); 613-620.
Kwon, B, et al., "cDNA sequences of two inducible T-cell genes," cDNA sequences of two inducible T-cell genes (1989); 86: 1963-1967.
Kwon, B, et al., "Expression Characteristics of Two Potential T Cell Mediator Genes," Cellular Immunology (1989); 414-422.
Lee, D, et al., "4-1BB Signaling Activates the T Cell Factor 1 Effector/b-Catenin Pathway with Delayed Kinetics via ERK Signaling and Delayed PI3K/AKT Activation to Promote the Proliferation of CD8+ T Cells," PLoS One (2013); 8: 1-11.
Melero, I, et al., "Amplification of tumor immunity by gene transfer of the co-stimulatory 4-1BB ligand: synergy with the CD28 co-stimulatory pathway," Bristol-Myers Squibb Pharmaceutical Research Institute (1998); 1116-1121.
Nam, K, et al., "Cross-Linking of 4-1BB Activates TCR-Signaling Pathways in CD8∎ T Lymphocytes1," The Journal of Immunology; 1898-1905.
Paillasse, M, et al., "Insights into the Cholecystokinin 2 Receptor Binding Site and Processes of Activation," The American Society for Pharmacology and Experimental Therapeutics (2006); 70:1935-1945.
Saoulli, C, et al., "CD28-independent, TRAF2-dependent Costimnlation of Resting T Cells by 4-1BB Ligand," Department of Immunology University of Toronto (1998); 1-67.
Stein, P, et al., "The Cytoplasmic Domain of CD28 Is both Necessary and Sufficient for Costimulation of Interleukin-2 Secretion and Association with Phosphatidylinositol 3'-Kinase," American Society for Microbiology (1994); 14: 3392-3402.
"TNF Superfamily Pathway," ThermoFinder Scientific.
"Tumor necrosis factor receptor superfamily," HUGO Gene Nomenclature Committee.
Wen, T, et al., "4-1BB Ligand-Mediated Costimulation of Human T Cells Induces CD4 and CD8 T Cell Expansion, Cytokine Production, and the Development of Cytolytic Effector Function1," 4897-4906.
Ye, H, et al., "The Structural Basis for the Recognition of Diverse Receptor Sequences by TRAF2," The Weill Medical College and Graduate School of Medical Sciences of Cornell University; v: 321-330.
Tam et al., "Functional, Biophysical, and Structural Characterization of Human IgG1 and IgG4 Fc Variants with Ablated Immune Functionality," *Antibodies* 2017, 6, 12.
Reddy et al., "Elimination of Fc Receptor-Dependent Effector Functions of a Modified IgG4 Monoclonal Antibody to Human CD4," J Immunol 2000; 164: 1925-1933.
Alexander et al., "Indoleamine 2,3-Dioxygenase Expression in Transplanted NOD Islets Prolongs Graft Survival After Adoptive Transfer of Diabetogenic Splenocytes," Diabetes 2002, vol. 51 pp. 356-365.
Wikipedia, Amino acid, https://en.wikipedia.org/wiki/Amino_acid, downloaded Jul. 30, 2018.
Bauer et al., "Activation of NK Cells and T Cells by NKG2D, a Receptor for Stress-Inducible MICA," Science 1999, vol. 285 pp. 727-729.
Boursier et al., "Evidence for an Extended Structure of the T-cell Co-receptor CD8α as Deduced from the Hydrodynamic Properties of Soluble Forms of the Extracellular Region," The Journal of Biological Chemistry 1993, vol. 268, No. 3, Issue of Jan. 25, pp. 2013-2020.
Brennan et al., "Carbohydrate Recognition by a Natural Killer Cell Receptor, Ly-49C," The Journal of Biological Chemistry 1995, vol. 270, No. 17, Issue of Apr. 28, pp. 9691-9694.
Bruhns et al., "Differential Roles of N- and C-Terminal Immunoreceptor Tyrosine-Based Inhibition Motifs During Inhibition of Cell Activation by Killer Cell Inhibitory Receptors," The Journal of Immunology 1999; 162:3168-3175.
Canfield et al., "The Binding Affinity of Human IgG for its High Affinity Fc Receptor Is Determined by Multiple Amino Acids in the CH2 Domain and Is Modulated by the Hinge Region," J. Exp. Med. 1991, vol. 173 pp. 1483-1491.
Wikipedia, CD3 (immunology), https://en.wikipedia.org/wiki/CD3_(immunology), downloaded Jul. 24, 2018.
Receptors, NK Cell Lectin-Like MeSH Descriptor Data 2018, NIH U.S. National Library of Medicine, Jul. 25, 2018.
Wikipedia, C-type lectin, https://en.wikipedia.org/wiki/C-type_lectin, downloaded Jul. 25, 2018.
Diefenbach et al., "The innate immune response to tumors and its role in the induction of T-cell immunity," Immunological Reviews 2002, vol. 188: 9-21.
Duncan et al., Localization of the binding site for the human high-affinity Fc receptor on IgG, Nature 1998, vol. 332 pp. 563-564.

(56) References Cited

OTHER PUBLICATIONS

Frost et al., "In Vitro Evaluation of Avidin Antibody Pretargeting Using $^{211}$At-Labeled and Biotinylated Poly-L-Lysine as Effector Molecule," Cancer 2010, Cancer Therapy With Antibodies and Immunoconjugates, Supplement to Cancer, pp. 1101-1110.
Hatakeyama et al., "Transmembrane Signaling of Interleukin 2 Receptor," J. Exp. Med. 1987, vol. 166 pp. 362-375.
Hege et al., "Safety, tumor trafficking and immunogenicity of chimeric antigen receptor (CAR)-T cells specific for TAG-72 in colorectal cancer," Journal for ImmunoTherapy of Cancer 2017, 5:22.
Hombach et al., "T cell activation by recombinant FcεRI γ-chain immune receptors: an extracellular spacer domain impairs antigen-dependent T cell activation but not antigen recognition," Gene Therapy (2000) 7, 1067-1075.
Jena et al., "Redirecting T-cell specificity by introducing a tumor-specific chimeric antigen Receptor," Blood 2010, vol. 116, No. 7, pp. 1035-1044.
Jonnalagadda et al., "Chimeric Antigen Receptors With Mutated IgG4 Fc Spacer Avoid Fc Receptor Binding and Improve T Cell Persistence and Antitumor Efficacy," Molecular Therapy 2015, vol. 23, No. 4, pp. 757-768.
Wikipedia, Killer-cell immunoglobulin-like receptor, https://en.wikipedia.org/wiki/Killer-cell_immunoglobulin-like_receptor, downloaded Jul. 25, 2018.
Wikipedia, KLRA1, https://en.wikipedia.org/wiki/KLRA1, downloaded Jul. 25, 2018.
Laroche et al., "Characterization of a Recombinant Single-chain Molecule Comprising the Variable Domains of a Monoclonal Antibody Specific for Human Fibrin Fragment D-dimer," The Journal of Biological Chemistry 1991, vol. 266, No. 25, Issue of Sep. 5, pp. 16343-16349.
Liou et al., "A chimeric mouse-human antibody that retains specificity for HIV gp 120 and mediates the lysis of HIV-infected cells," J Immunol 1989; 143: 3967-3975.
Lowin-Kropf et al., "Cytoskeletal Polalization of T Cells Is Regulated by an Immunoreceptor Tyrosine-based Activation Motif-dependent Mechanism," The Journal of Cell Biology 1998, vol. 140, No. 4, pp. 861-871.
Moretta et al., "Activating Receptors and Coreceptors Involved in Human Natural Killer Cell-Mediated Cytolysis," Annu. Rev. Immunol. 2001. 19:197-223.
Nelson, Aaron L., "Antibody fragments," mAbs 2010, Landes Bioscience, vol. 2, Issue 1, pp. 77-83.
Wikipedia, NKG2D, https://en.wikipedia.org/wiki/NKG2D, downloaded Jul. 25, 2018.
Wikipedia, Paratope, https://en.wikipedia.org/wiki/Paratope, downloaded Jul. 5, 2018.
PeproTech, Recombinant Human 4-1BB Receptor, https://www.peprotech.com/recombinant-human-4-1bb-receptor, downloaded Jul. 25, 2018.
Pochitaloff et al., "Human CD28 and CTLA-4 Ig superfamily genes are located on chromosome 2 at bands q33-q34," Abstract. Immunogenetics 1990; 31(3): 198-201.
Pollock et al., Inducible T cell antigen 4-1BB. Analysis of expression and function, J Immunol 1993; 150:771-781.
Protein Lounge, 4-1BB Pathway, http://www.proteinlounge.com/Pathway/4-1BB%20Pathway, downloaded Jul. 25, 2018.
Qin et al., "Incorporation of a hinge domain improves the expansion of chimeric antigen receptor T cells," Journal of Hematology & Oncology (2017) 10:68.
Reubi, Jean Claude, "Peptide Receptors as Molecular Targets for Cancer Diagnosis and Therapy," Endocrine Reviews 24(4): 389-427.
Saraswat et al., "DNA as Therapeutics; an Update," Indian J Pharm Sci. Sep.-Oct. 2009; 71(5): 488-498.
Shields et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 2001, vol. 276, No. 9, Issue of Mar. 2, pp. 6591-6604.
Wikipedia, Single-domain antibody, https://en.wikipedia.org/wiki/Single-domain_antibody, downloaded Jul. 27, 2018.
Wikipedia, Small molecule, https://en.wikipedia.org/wiki/Small_molecule, downloaded Jul. 27, 2018.
Sobota et al., "Binding of IgG-Opsonized Particles to FcγR Is an Active Stage of Phagocytosis That Involves Receptor Clustering and PhosEhorxlation," The Journal of Immunology 2005; 175:4450-4457.
The LTR Retroviral Promoter; Long Terminal Repeats: The Retroviral Promoter. https://web.stanford.edu/group/nolan/_OldWebsite/tutorials/retcl_3_ltrs .html retrieved Jul. 26, 2018.
An et al., "IgG2m4, an engineered antibody isotype with reduced Fc function," mAbs 2009, Landes Bioscience, 1:6, 572-579.
Foell et al., "CD137-mediated T cell co-stimulation terminates existing autoimmune disease in SLE-prone NZB/NZW F1 mice.," Ann N Y Acad Sci. Apr. 2003; 987:230-5.
Wikipedia, Glycosylation, https://en.wikipedia.org/wild/Glycosylation, downloaded Jul. 31, 2018.
Kim et al., "Therapeutic Potential of 4-1BB (CD137) As a Regulator for Effector $CD8^+$ T Cells," Journal of Hematotherapy & Stem Cell Research (2001) 10:441-449.
Wang et al., "Current status and perspectives of chimeric antigen receptor modified T cells for cancer treatment," Protein Cell 2017, 8(12):896-925.
Wilkie et al., "Retargeting of Human T Cells to Tumor-Associated MUC1: The Evolution of a Chimeric Antigen Receptor," The Journal of Immunology Apr. 2008, pp. 4901-4909.
Grosenbach et al., "A recombinant vector expressing transgenes for four T-cell costimulatory molecules (OX40L, B7-1, ICAM-1, LFA-3) induces sustained $CD4^+$ and $CD8^+$ T-cell activation, protection from apoptosis, and enhanced cytokine Eroduction," Cellular Immunology 222 (2003) 45-57.
Moore et al., "Characterisation of salmon and, trout CD8α and CD8β," Molecular Immunology 42 (2005) 1225-1234.
Hunter et al., "Inhibition of Fcγ Receptor-Mediated Phagocytosis by a Nonphagocytic Fcγ Receptor," Blood, vol. 91, No. 5 Mar. 1, 1998: pp. 1762-1768.
Swanson et al., "The coordination of signaling during Fc receptor-mediated phagocytosis," Journal of Leukocyte Biology, vol. 76, Dec. 2004, pp. 1093-1103.
Munn et al., "Role of Low-Affinity Fc Receptors in Antibody-dependent Tumor Cell Phagocytosis by Human Monocyte-derived Macrophages," Cancer Research 51, 1117-1123, Feb. 15, 1991.
Cole et al., "The molecular determinants of CD8 co-receptor function", 2012, Immunology, 137, 139-148.
Harper et al., "CTLA-4 and CD28 Activated Lymphocyte Molecules are Closely Related in Both Mouse and Human as to Sequence, Message, Expression, Gene Structure, and Chromosomal Location", The Journal of Immunology, vol. 147, 1037-1044, No. 3, Aug. 1, 1991.
Isakov et al., "PKC-theta-mediated signal delivery from the TCR/CD28 surface receptors", Frontiers in Immunology, T Cell Biology, Aug. 2012, vol. 3, Article 273, pp. 1-12.
Love et al., "ITAM-mediated Signaling by the T-Cell Antigen Receptor", Cold Spring Harb Perspect Biol 2010; 2:a002485.
Medstrand et al., "Long Terminal Repeats Are Used as Alternative Promoters for the Endothelin B Receptor and Apolipoprotein C-I Genes in Humans", The Journal of Biological Chemistry, vol. 276, No. 3, Issue of Jan. 19, pp. 1896-1903, 2001.
Prasad et al., "T-cell antigen CD28 interacts with the lipid kinase phosphatidylinositol 3-kinase by a cytoplasmic Tyr(P)-Met-Xaa-Met motif", Proc. Natl. Acad. Sci. USA, vol. 91, pp. 2834-2838, Mar. 1994.
Definition of "Protein", Concise Dictionary of Biomedicine and Molecular Biology, $2^{nd}$ Edition, Pei-Show Juo, PhD, 2002, p. 903.
Wikipedia, Protein, https://en.wikipedia.org/w/index.php?title=Protein&oldid=861574349, downloaded Oct. 15, 2018.
Riha et al., "CD28 co-Signaling in the adaptive immune response" Self/Nonself 1:3, 231-240; Jul./Aug./Sep. 2010.

(56) References Cited

OTHER PUBLICATIONS

Riley et al., "The CD28 family: a T-cell rheostat for therapeutic control of T-cell activation", Blood, Jan. 1, 2005, vol. 105, No. 1, pp. 13-21.

Cooper et al., Sequence Listing, Compositions and Methods Related to a Human CD19-Specific Chimeric Antigen Receptor (H-CAR), U.S. Appl. No. 61/020,991, filed Jan. 14, 2008, 5 pages.

Maeda et al., "Tumor vascular permeability and the EPR effect in macromolecular therapeutics: a review," Journal of Controlled Release 65 (2000), pp. 271-284 (14 pages).

"Common Terminology Criteria for Adverse Events (CTCAE)" National Cancer Institute Common Toxicity Criteria version 4.03 (NCI-CTCAE v4.03 (2010) (196 pages).

Abken, H., et al., "Tuning tumor-specific T-cell activation: a matter of costimulation?" Trends in Immunology vol. 23 No. 5 May 2002: 240-45.

Abstracts for the 26th Annual Scientific Meeting of the Society for Immunotherapy of Cancer (SITC), J Immunother., vol. 34, No. 9, Nov.-Dec. 2011 (62 pages).

Alonso-Camino et al. "CARbodies: Human Antibodies Against Cell Surface Tumor Antigens Selected From Repertoires Displayed on T Cell Chimeric Antigen Receptors." (2013) Mol Ther Nucl Acids 2, e93 (11 pages).

Altvater, B., et al., "284 (CD244) Signaling by Recombinant Antigen-specific Chimeric Receptors Costimulates Natural Killer Cell Activation to Leukemia and Neuroblastoma Cells", Clin Cancer Res 2009;15(15) Aug. 1, 2009: 4857-66.

Baniyash et al., "The T Cell Antigen Receptor Zeta Chain Is Tyrosine Phosphorylated open Activation" The Journal of Biological Chemistry, vol. 263, No. 34, Issue of Dec. 5, pp. 18225-18230.

Barrett et al., Chimeric Antigen Receptor Therapy for Cancer Annual Review of Medicine vol. 65: 333-347 (2014).

Baum et al. "Retrovirus vectors: toward the plentivirus?" (2006) Molecular Therapy: The Journal of the American Society of Gene Therapy. 13:1050-1063.

Berg et al., "Section 3.2 Primary Structure: Amino Acids Are Linked by Peptide Bonds to Form Polypeptide Chains" Biochemistry. 5th Ed. New York. W.H. Freeman; 2002, pp. 1-16.

Berger, C., et al., Analysis of trans gene-specific immune responses that limit the in vivo persistence of adoptively transferred HSV-TK-modified donor T cells after allogeneic hematopoietic cell transplantation. Blood, 2006. 107(6): p. 2294-302.

Boomer et al., "Cutting Edge: A Double-Mutant Knockin of the CD28 YMNM and PYAP Motifs Reveals a Critical Role for the YMNM Motif in Regulation of T Cell Proliferation and Bcl-x L Expression" The Journal of Immunology. 2014; 192, pp. 3465-3469.

Brentjens et al., "CD19-targeted T cells rapidly induce molecular remissions in adults with chemotherapy-refractory acute lymphoblastic leukemia." Sci Transl Med. 2013 5(177) ra38 (11 pages).

Bukczynski et al., "Costimulatory ligand 4-1 BBL (CD137L) as an efficient adjuvant of human antiviral cytotoxic T cell responses," Proc. Natl. Acad. Sci. USA, 2004, 101: 1291-1296.

Cannons et al., "4-1BB ligand induces cell division, sustains survival, and enhances effector function of CD4 and CD8 T cells with similar efficacy," J Immunol. Aug. 2001, 167(3): 1313-1324.

Carlens et al. "Ex vivo T lymphocyte expansion for retroviral transduction: influence of serum-free media on valiations in cell expansion rates and lymphocyte subset distribution." (2000) Exp Hematol 28(10): 1137-46.

Cavalieri et al. "Human T lymphocytes transduced by lentiviral vectors in the absence of TCR activation maintain an intact immune competence." (2003) Blood. 102(2): 497-505.

Chalupny et al., "T-cell activation molecule 4-1BB binds to extracellular matrix proteins," Proc. Natl. Acad. Sci., USA, 89: 103360-10364 (Nov. 1992).

Cheadle et al, "Chimeric antigen receptors for T-cell based therapy" Methods Mol Biol. 2012; 907:645-66.

Cho C. "Rapid identification of cytokine release syndrome after haploidentical PBSC transplantation and successful therapy with tocilizumab." Bone Marrow Transplant. Dec. 2016;51(12):1620-1621, Epub Sep. 26, 2016.

Cho et al., "Macromolecular versus small-molecule therapeutics: drug discovery, development and clinical considerations" TIBTECH, vol. 14, May 1996, pp. 153-158.

Cohen et al. "Recognition of fresh human tumor by human peripheral blood lymphocytes transduced with a bicistronic retroviral vector encoding a murine anti-p53 TCR" (2005) J Immunol. 175:5799-5808.

Cooper et al. "T-cell Clones can be rendered specific for CD19: toward the selective augmentation of the graft-versus-B-lineage leukemia effec" (2003) Blood. 101(4): 1637-1644.

Croft, M., "The role of TNF superfamily members in T-cell function and diseases" Nature Reviews, Immunology, vol. 9, Apr. 2009, pp. 271-285.

Davila M. L. et al: "Efficacy and toxicity management of 19-28z CAR T cell therapy in B cell acute lymphoblastic leukemia" Sci Transl Med. Feb. 19, 2014;6(224):224-25.

Davila Marco L. et al: "CD19-Targeted T Cells for Hematologic Malignancies—Clinical Experience to Date", Cancer Journal, vol. 21, No. 6, Jan. 1, 2015 (Jan. 1, 2015), pp. 470-474.

Debelouchina et al., "A molecular engineering toolbox for the structural biologist" Quarterly Reviews of Biophysics, 2017, 50, e7, pp. 1-41.

Frecha et al. "Advances in the field of lentivector-based transduction of T and B lymphocytes for gene therapy" (2010) Molecular Therapy: The Journal of the American Society of Gene Therapy. 18:1748-1757.

Gargett, T., et al., GD2-specific CART Cells Undergo Potent Activation and Deletion Following Antigen Encounter but can be Protected From Activation-induced Cell Death by PD-1 Blockade. Mol Ther, 2016. 24(6): p. 1135-49.

Greenfield, E. A, Nguyen, K. A & Kuchroo, V. K. CD28/B7 co-stimulation: a review. Crit. Rev. Immunol. 18, 389-41 8 (1998).

Griffiths et al., "The Nature of DNA" Modern Genetic Analysis. New York: W.H. Freeman; 1999, pp. 1-11.

Grupp Stephan A.: Advances in T-cell therapy for All, Best Practice & Research Clinical Haematology, vol. 27, No. 3-4, Sep. 1, 2014 (Sep. 1, 2014), pp. 222-228.

Gruss et al., "Tumor Necrosis Factor Ligand Superfamily: Involvement in the Pathology of Malignant Lymphomas" Blood, vol. 85, No. 12, Jun. 15, 1995, pp. 3378-3404.

Guinn et al., "4-1BBL Cooperates with B7-1 and B7-2 in Converting a B Cell Lymphoma Cell Line into a Long-Lasting Antitumor Vaccine," The Journal of lmmunology 162:5003-5010 (1999).

Habib-Agahi,H., Phan,T.T. and Searle,P.F. Co-stimulation with 4-1BB ligand allows extended T-cell proliferation, synergizes with CD80/CD86 and can reactivate anergic T cells Int. Immunol. 19 (12), 1383-1394 (2007).

Hackett et al. "A transposon and transposase system for human application" (2010) Molecular Therapy: The Journal of the American Society of Gene Therapy. 18:674-683.

Hanson, H. L. et al. Eradication of established tumors by CD8+ T cell adoptive immunotherapy. Immunity 13, 265-276 (2000).

Haynes, Nicole M., Marie B. Snook, Joseph A. Trapani, Loretta Cerruti, Stephen M. Jane, Mark J. Smyth and Philip K. Darcy "Redirecting Mouse CTL Against Colon Carcinoma: Superior Signaling Efficacy of Single-Chain Variable Domain Chimeras Containing TCR-zeta vs FcepsilonRI-gamma" J Immunol 2001; 166:182-187 (Haynes 2001).

Huang, J., et al., Modulation by IL-2 of CD70 and CD27 expression on CD8+ T cells: importance for the therapeutic effectiveness of cell transfer immunotherapy J. Immunol. 176 (12), 7726-7735 (2006).

Hughes M. S. et al., Transfer of a TCR gene derived from a patient with a marked antitumor response conveys highly active T-cell effector functions. Hum Gene Ther Apr. 2005; 16(4):457-72).

Imai, K., et al., "Comparing Antibody and Small-Molecule Therapies for Cancer"; https://www.medscape.com/viewarticle/550008 (26 pages).

(56) References Cited

OTHER PUBLICATIONS

Janeway et al., "Appendix I. Immunologists' Toolbox" Immunobiology: The Immune System in Health and Disease. 5th ed. New York: Garland Science; 2001 (101 pages).

Janeway et al., "The structure of a typical antibody molecule" Immunobiology: The Immune System in Health and Disease. 5th Ed. New York: Garland Science; 2001, pp. 1-11.

Jensen, M.C., et al., Antitransgene rejection responses contribute to attenuated persistence of adoptively transferred CD20/CD19-specific chimeric antigen receptor redirected T cells in humans. Biol Blood Marrow Transplant, 2010. 16(9): p. 1245-56.

Kagoya, Y., et al., Transient stimulation expands superior antitumor T cells for adoptive therapy. JCI Insight, 2017. 2(2): p. e89580 (13 pages).

Kang, S. et al: "Therapeutic uses of anti-interleukin-6 receptor antibody", International Immunology, vol. 27, No. 1, Aug. 20, 2014 (Aug. 20, 2014), pp. 21-29.

Kariv et al., Analysis of the Site of Interaction of CD28 with Its Counterreceptors CD80 and CD86 and Correlation with Function, 157 J. lmmunol.29-38 (1996).

Kintzing et al., "Emerging Strategies for Developing Next-Generation Protein Therapeutics for Cancer Treatment" Trends in Pharmacological Sciences, vol. 37, No. 12, Dec. 2016, pp. 993-1008.

Klotz et al., "Macromolecule-Small Molecule Interactions. Strong Binding by Intrarnolecularly Cross-Linked Polylysine" Biochemistry. vol. 10, No. 6, Mar. 16, 1971, pp. 923-926.

Kochenderfer et al., "Treating B-cell cancer with T cells expressing anti-CD19 chimeric antigen receptors" 2013, Nature Reviews Clinical Oncology, 10, 267-276 (2013).

Lafage-Pochitaloff M, Costello R, Couez D, Simonetti J, Mannoni P, Mawas C, Olive D. "Human CD28 and CTLA-4 Ig superfamily genes are located on Chromosome 2 at bands q33-q34" Immunogenetics 1190;31(3):198-201.

Lee D. W. et al: "Current concepts in the diagnosis and management of cytokine release syndrome" Blood. Jul. 10, 2014;124(2):188-95. doi: 10.1182/blood-2014-05-552729. Epub May 29, 2014.

Lee, Blood 2015 126:1048. Erratum to Lee D. W. et al: "Current concepts in the diagnosis and management of cytokine release syndrome" Blood. Jul. 10, 2014;124(2):188-95. doi: 10.1182/blood-2014-05-552729. Epub May 29, 2014.

Lee, Blood 2016 128:1533 Erratum to Lee D. W. et al: "Current concepts in the diagnosis and management of cytokine release syndrome" Blood. Jul. 10, 2014;124(2):188-95. doi: 10.1182/blood-2014-05-552729. Epub May 29, 2014.

Liebowitz, D. N., Lee, K. P. & June, C. H. Co-stimulatory approaches to adoptive immunotherapy. Curr. Opin. Oncol. 10, 533-541 (1998).

Lodish et al., "Heirarchical Structure of Proteins" Molecular Cell Biology. 4th Ed. New York: W.H. Freeman; 2000. pp. 1-25.

Long, A.H., et al., 4-1BB costimulation ameliorates T cell exhaustion induced by tonic signaling of chimeric antigen receptors. Nat Med, 2015. 21(6): p. 581-90.

Love et al., "ITAM-mediated Signaling by the T-Cell Antigen Receptor", Cold Spring Harb Perspect Biol 2010;22a002485.

Lueders et al., "The Long Terminal Repeat of an Endogenous Intracisternal A-Particle Gene Functions as a Promoter When Introduced into Eucaryotic Cells by Transfection" Molecular and Cellular Biology, vol. 4, No. 10, Oct. 1984, pp. 2128-2135.

Maude Shannon L. et al. "Chimeric Antigen Receptor T Cells for Sustained Remissions in Leukemia" N Engl J Med. Oct. 16, 2014;371(16):1507-17.

Maude Shannon L. et al. "Managing Cytokine Release Syndrome Associated With Novel T Cell-Engaging Therapies" Cancer J. Mar.-Apr. 2014;20(2):119-22.

Maus et al., "Ex vivo expansion of polyclonal and antigen-specific cytotoxic T lymphocytes by artificial APCs expressing ligands for the T-cell receptor, CD28 and 4-1BB," Nature Biotechnology, Nature Publishing Group, New York, NY, US, vol. 20, No. 2, Feb. 1, 2002, pp. 143-148.

Maus, M.V., et al., T cells expressing chimeric antigen receptors can cause anaphylaxis in humans. Cancer Immunol Res, 2013. 1(1): p. 26-31.

Mooney et al., "Concise Review: Neural Stem Cell-Mediated Targeted Cancer Therapies" Stem Cells Translational Medicine, 2018, pp. 740-747.

Mungra et al., "Targeted human cytolytic fusion proteins at the cutting edge: harnessing the apoptosis-inducing properties of human enzxmes for the selective elimination of tumor cells" Oncotarget, vol. 10, No. 8, 2019, pp. 897-915.

Oelsner, S., et al., "Continuously expanding CAR NK-92 cells display selective cytotoxicity against B-cell leukemia and lymphoma", Cytotherapy, 2017; 19: 235-249.

Pages et al., "Two Distinct Intracytoplasmic Regions of the T-cell Adhesion Molecule CD28 Participate in Phosphatidylinositol 3-Kinase Association" The Journal of Biological Chemistry, vol. 271, No. 16, Apr. 19, 1996, pp. 9403-9409.

Park et al., "Treating cancer with genetically engineered T cells" Trends Biotechnol. Nov. 29, 2011(11): 550-557.

Parkhurst et al. "Characterization of genetically modified T-cell receptors that recognize the CEA:691-699 peptide in the context of HLA-A2.1 on human colorectal cancer cells" (2009) Clin Cancer Res. Jan. 1, 2009;15(1):169-80.

Patel Jaina M et al: "Cancer CARtography: charting out a new approach to cancer immunotherapy", Immunotherapy. 2014;6(6):675-8.

Porter DL, et al. "Chimeric antigen receptor T cells persist and induce sustained remissions in relapsed refractory chronic lymphocytic leukemia". Science translational medicine. 2015;7(303):303-39. doi: 10. 1126/scitranslmed.aac5415. PubMed PMID: 26333935.

Prasad et al., "T-cell antigen CD28 interacts with the lipid kinase phosphatidylinositol 3-kinase by a cytoplasmic Try(P)-Met-Xaa-Met motif", Proc. Natl. Acad. Sci. USA, vol. 91, pp. 2834-2838, Mar. 1994.

Redmond et al., "The role of OX40-mediated co-stimulation in T cell activation and survival," Crit. Rev. Immunol. 2009, 29(3): 187-201.

Riviere, I., Gallardo, H. F., Hagani, A B. & Sadelain, M. Retroviral-mediated gene transfer in primary murine and human T-lymphocytes. Mol. Biotechnol. 15, 133-142 (2000).

Rosenberg "Cell transfer immunotherapy for metastatic solid cancer—what clinicians need to know" (2011) Nat Rev Clin Oncol. 8(10):577-85).

Rosenberg SA, Restifo N P, Yang J C, Morgan RA, Dudley M E. Adoptive cell transfer: a clinical path to effective cancer immunotherapy. Nat Rev Cancer. Apr. 2008; 8(4):299-308.

Rotz Seth J. et al. "Severe cytokine release syndrome in a patient receiving PD-1-directed therapy" Pediatr Blood Cancer. Dec. 2017;64(12). Epub May 24, 2017 (4 pages).

Rueckert S, et al., "A monoclonal antibody as an effective therapeutic agent in breast cancer: trastuzumab" Expert Opin Biol Ther. Jun. 2005;5(6):853-66.

Schonfeld, K, et al., "Selective Inhibition of Tumor Growth by Clonal NK Cells Expressing an Erb82/HER2-Specific Chimeric Antigen Receptor", Mol. Ther., vol. 23 No. 2, 330-338 Feb. 2015.

Schreiber, S.L., "Organic synthesis toward small-molecule probes and drugs" PNAS, vol. 108, No. 17, Apr. 26, 2011, pp. 6699-6702.

Sentman "Challenges of creating effective chimeric antigen receptors for cancer therapy" Immunotherapy. Aug. 2013;5(8):783-5.

Serghides et al., "Evaluation of OX40 Ligand as a Costimulator of Human Antiviral Memory CD8 T Cell Responses: Comparison with B7.1 and 4-1BBL," The Journal of Immunology 175:6368-6377 (2005).

Stein et al., "The Cytoplasmic Domain of CD28 Is both Necessary and Sufficient for Costimulation of Interleukin-2 Secretion and Association with Phosphatidylinositol 3'-Kinase," Molecular And Cellular Biology, (May 1994) 14(5): 3392-3402.

Suhoski, M.M., et al., Engineering artificial antigen-presenting cells to express a diverse array of co-stimulatory molecules. Mol Ther, 2007. 15(5): p. 981-8.

Tamada (2013) Correction: Redirecting Gene-Modified T Cells toward Various Cancer Types Using Tagged Antibodies—Feb. 14, 2013.

(56) References Cited

OTHER PUBLICATIONS

Tamada, K. et al: Redirecting Gene-Modified T Cells toward Various Cancer Types Using Tagged Antibodies, Clinical Cancer Research, vol . 18, No. 23, Oct. 2, 2012 (Oct. 2, 2012), pp. 6436-6445.
Teachey D. T. et al. "Cytokine release syndrome after blinatumomab treatment related to abnormal macrophage activation and ameliorated with cytokine-directed therapy" Blood. Jun. 27, 2013;121(26):5154-7. doi: 10.1182/blood-2013-02-485623. Epub May 15, 2013.
Tsukahara et al. "CD19 target-engineered T-cells accumulate at tumor lesions in human B-Cell lymphoma xenograft mouse models" (2013) Biochem Biophys Res Commun 438(1): 84-9. Epub Jul. 17, 2013.
Turtle et al., "Engineered T cells for anti-cancer therapy" Curr. Opin. Immunol, Oct. 2012; 24(5): 633-39. Epub Jul. 18, 2012.
UniProtKB-O43914, "TYRO protein tyrosine kinase-binding protein", pp. 1-15.
UniProtKB-P02701, AVidin Precursor—Gallus Chicken.
Urbanska, K., et al., "A Universal Immune Receptor Expressed by T Cells for the Targeting of Diverse and Multiple Tumor Associated Antigens" IN Abstracts for the 26th Annual Scientific Meeting of the Society for Immunotherapy of Cancer (SITC), J Immunother, vol. 34, No. 9, Nov.-Dec. 2011 (62 pages), p. 381.
Verdine et al., "The Challenge of Drugging Undruggable Targets in Cancer: Lessons Learned from Targeting BCL-2 Family Members" Clin. Cancer Res. vol. 13, No. 24, Dec. 15, 2007, pp. 7264-7270.
Verhoeyen et al. "Lentiviral vector gene transfer into human T cells" (2009) Methods Mol Biol. 506: 97-114.
Wang et al. "Phenotypic and functional attributes of lentiVirus-modified CD19-specific human CD8+ central memory T cells manufactured at clinical scale" (2012) J Immunother. 35(9):689-701.
Weissman et al., "Molecular cloning and chromosomal localization of the human T-cell receptor zeta chain: Distinction from the molecular CD3 complex" Proc. Natl. Acad. Sci. vol. 85, Dec. 1988, pp. 9709-9713.
Weissman et al., "Role of the zeta chain in the expression of the T cell antigen receptor: genetic reconstitution studies" The EMBO Journal, vol. 8, No. 12, 1989, pp. 3651-3656.
Wesolowski, J, et al., "Single domain antibodies: promising experimental and therapeutic tools in infection and immunity", Med Microbiol Immunol (2009) 198:157-174.
Wikipedia, Avidin, (2018) retrieved from https://en.wikipedia.org/w/index.php?title=Avidin&oldid=849308130.
Wu et al., "Adoptive T-cell therapy using autologous tumor-infiltrating lymphocytes for metastatic melanoma: current status and future outlook" Cancer, Mar. 18, 2012(2): 160-75.
Xu et al., "Cytokine release syndrome in cancer immunotherapy with chimeric antigen receptor engineered T cells" Cancer Lett. Feb. 28, 2014;343(2):172-8. Epub Oct. 16, 2013.
Zhang, H., et al., 4-1BB is superior to CD28 costimulation for generating CD8+ cytotoxic lymphocytes for adoptive immunotherapy. J Immunol, 2007. 179(7): p. 4910-8.
Zheng et al., "Arming Tumor-Reactive T Cells with Costimulator B7-1 Enhances Therapeutic Efficacy of the T Cells," Cancer Research, 2006, vol. 66, No. 13, pp. 6793-6799.
Lamers et al., "Immune responses to transgene and retroviral vector in patients treated with ex vivo-engineered T cells," Blood (2011) 117(1): 72-82.
Barocas et al., "A population-based study of renal cell carcinoma and prostate cancer in the same patients," BJU International, (2006) 97(1): 33-36.
Zhang et al., "Phase I Escalating-Dose Trial of CAR-T Therapy Targeting CEA+ Metastatic Colorectal Cancers," Molecular Therapy (2017), 25(5): 1248-1258.
Gargalionis et al, "The molecular rationale fo Src inhibition in colorectal carcinomas," Int. J. Cancer, 134:2019-2029 (2013).
Karachaliou et al., "Common Co-activation of AXL and CDCP1 in EGFR-mutation-positive Non-smallcell Lung Cancer Associated with Poor Prognosis," EBioMedicine (2017) https://doi.org/10/1016/j.ebiom.2018.02.001.
PCT Search Report and Written Opinion prepared for PCT/US2018/020095, completed Jul. 17, 2018.
Barocas, Daniel A., et al., "A Population-based Study of Renal Cell Carcinoma and Prostate Cancer in the Same Patients," 2006, BJU International, vol. 97, pp. 33-36.
Amers, C. H. J., et al., "Immune Responses to Transgene and Retroviral Vector in Patients Treated with Ex Vivo-Engineered T Cells," 2011, Blood, vol. 117, No. 1, p. 72-82.
FDA Approval Letter dated Apr. 23, 2014, for Biologics License Application for Sylvant™ (siltuximab), 12 pages.
FDA Approval Letter dated Jan. 8, 2010, for Biologics License Application for Acternra (tocilizumab), 9 pages.
Hong; Soon-Sun et al., "A Novel Small-Molecule Inhibitor Targeting the IL-6 Receptor β Subunit, Glycoprotein 130," J Immunol 2015; 195:237-245; Prepublished online May 29, 2015; doi: 10.4049/jimmunol.1402908 http://www.jimmunol.org/content/195/1/237.
Le; Robert Q. et al. "FDA Approval Summary: Tocilizumab for Treatment of ChimericAntigen Receptor T Cell-Induced Severe or Life-Threatening CytokineRelease Syndrome," The Oncologist 23:943-947 (2018).
Abate-Daga, et al., "Abstracts for the 25th Annual Scientific Meeting of the International Society for Biological Therapy of Cancer," Journal of Immunotherapy (2010); 33(8): 859-920.
Altschul et al., "Local Alignment Statistics, [27] Multiple Alignment and Phylogenetic Trees," Methods in Enzymology 266:460-480 (1996).
Amin et al., "The Eighth Edition AJCC Cancer Staging Manual Continuing to Build a Bridge From a Population-Based to a More "Personalized" Approach to Cancer Staging," CA Cancer J Cun 67(2):93-99 (2017).
Barber, et al., "Chimeric NKG2D expressing T cells eliminate immunosuppression and activate immunity within the ovarian tumor microenvironment," J. Immunol. (2009); 183:6939-6947.
Barber, et al., "Immunotherapy with chimeric NKG2D receptors leads to long-term tumor-free survival and development of host antitumor immunity in murine ovarian cancer," J. immunol 180:72-78 (2008).
Barber, et al., J Immunol. (Aug. 1, 2014); 193(3): 1513, pp. 1-2: (Erratum to Barber et al. "Immunotherapy with chimeric NKG2D receptors leads to long-term tumor-free survival and development of host antitumor immunity in murine ovarian cancer," J. Immunol. (2008); 180:72-78.
Barber, et al., Chimeric NKG2D Receptor-Expressing T Cells as an Immunotherapy for Multiple Myeloma, Exp Hematol. (Oct. 2008); 36(10)1318-28.
Berger et al., "Safety of targeting ROR1 in primates with chimeric antigen receptor modified T cells," Cancer Immunology Research, 3(2):206-216 (2015).
Betancur et al., "Nonpeptide antagonists of neuropeptide receptors: tools for research and therapy," Trends Pharmacol Sci. 18(10): 372-386 (1997).
BLAST Search page for "P20334[209-256]" (2 pages), retrieved from http://www. u n iprot. org/bl asV? about=P20334[209-256] &key= Topological %20dom ai n on Oct. 14, 2016.
Boder et al., "Directed evolution of antibody fragments with monovalent femtomolar antigen-binding affinity," Proc Natl Acad Sci U S A 97(20):10701-10705 (2000).
Boulassel et al, "Immunotherapy for B-Cell Neoplasms using T Cells expressing Chimeric Antigen Receptors: From antigen choice to clinical implementation," Sultan Qaboos Univ Med J 12(3):273-285 (2012).
Boursier et al., Evidence for an Extended Structure of the T-cell Co-receptor CD8a as Deduced from the Hydrodynamic Properties of Soluble Forms of the Extracellular Region, The Journal of Biological Chemistry 1993, vol. 268, No. 3, Issue of Jan. 25, pp. 2013-2020.

(56) References Cited

OTHER PUBLICATIONS

Brentjenset al., "Treatment of chronic lymphocytic leukemia with genetically targeted autologous T cells: case report of an unforeseen adverse event in a phase I clinical trialm" Mol Ther 18(4):666-668 (2010).

Bridgeman, J.S., et al., "Structural and biophysical determinants of alpha beta T-cell antigen recognition," Immunology (Jan. 2012); 135(1 ): 9-18 (First published: Dec. 7, 2011 ).

Carpenter, R. O., et al. "B-cell Maturation Antigen is a Promising Target for Adoptive T-cell Therapy of Multiple Myeloma," Clinical Cancer Research, 2013, vol. 19(8), pp. 2048-2060.

"Chain A, 4m5.3 Anti-Fluorescein Single Chain Antibody Fragment (Scfv)" (4 pages), retrieved from https://www.ncbi.nlm.nih.gov/protein/62738392?report=genbank&log$=protalign&blast_rank=I&RID=UWAEY60801 Ron Oct. 12, 2016.

Chen, et al. "Chimeric antigen receptor (CAR)-directed adoptive immunotherapy: a new era m targeted cancer therapy," Stem Cell Investig. (Jan. 18, 2014); 1:2 (2 pages).

Cheng et al., "Hapten-directed targeting to single-chain antibody receptors," Cancer Gene Therapy, 11(5):380-388 (2004).

Chothia, et al., "Conformations of immunoglobulin hypervariable regions," Nature, Dec. 28, 1989, vol. 342, pp. 877-883.

Clay, et al., "Efficient transfer of a tumor antigen-reactive TCR to human peripheral blood lymphocytes confers anti-tumor reactivity," J. Immunol. (1999); 163:507-153.

Cooper et al., "Enhanced antilymphoma efficacy of CD19-redirected influenza MP1-specific CTLs by cotransfer of T cells modified to present influenza MP1," Blood 2005, vol. 105 No. 4 pp. 1622-1631.

Cooper, "Test-driving CARs," Blood (Sep. 15, 2008); 112(6):2172-3.

Dai, et al., "Chimeric Antigen Receptors Modified T-Cells for Cancer Therapy," J Natl Cancer Inst (2016); 108(7): djv439 (14 pages) (First published online Jan. 27, 2016).

Davila et al., "CD19 CAR-targeted T cells induce long-term remission and B Cell Aplasia in an immunocompetent mouse model of B cell acute lymphoblastic leukemia," PLoS One 8(4) e61338 (2013), 14 pages.

Davila ML, et al., "How do CARs work ?: Early insights from recent clinical studies targeting CD19," Oncoimmunology (Dec. 2012 I); 1(9):1577-1583.

Deng et al., "Antitumor activity of NKG2D Car-T cells against human colorectal cancer cells in vitro and in vivo," Am J Cancer Res 9(5)945-958 (2019).

Eshhar et al., Specific activation and targeting of cytotoxic lymphocytes through chimeric single chains consisting of antibody-binding domains and the or subunits of the immunoglobulin and T-cell receptors, Proc. Natl. Acad. Sci. USA 90:720-724 (1993).

Eshhar, Z., et al., "Chimeric T cell receptor which incorporates the anti-tumour specificity of a monoclonal antibody with the cytolytic activity of T cells: a model system for immunotherapeutical approach," Br J Cancer. Suppl. (Jul. 1990); 10: 27-29.

Extended European Search Report issued by the European Patent office for Application No. 18761400.3, dated Sep. 24, 2020, 7 pages.

Extended European Search Report issued by the European Patent Office for Application No. 19204092.1, dated Mar. 16, 2020, 8 pages.

Extended European Search Report issued by the European Patent Office for Application No. 19740881.8, dated Oct. 10, 2021, 9 pages.

Extended European Search report issued by the European Patent Office for Application No. 19741309.9, dated Oct. 5, 2021, 12 pages.

Extended European Search Report issued by the European Patent Office for Application No. 19757681.2, dated Nov. 25, 2021, 9 pages.

Extended European Search Report issued by the European Patent Office for Appliction No. EP17779919, dated Nov. 6, 2019, 7 pages.

Fang et al., "Lipid-insertion enables targeting functionalization of erythrocyte membrane-cloaked nanoparticles," Nanoscale, 5(19):8884-8888 (2013).

Figini, M, et al., "Panning phage antibody libraries on cells: isolation of human Fab fragments against ovarian carcinoma using guided selection," Cancer Res (Mar. 1, 1998); 58(5):991-996.

Finney et al., "Activation of resting human primary T cells with chimeric receptors: costimulation from CD28, inducible costimulator, CD134, and CD137 in series with signals from the TCR zeta chain," J. Immunol., 172(1):104-113, Jan. 2004.

Finney et al., "Chimeric Receptors Providing Both Primary and Costimulatory Signaling in T Cells from a Single Gene Product," J Immunol161, 2791-2797 (1998).

Fitzer-Attas et al., "Harnessing Syk family tyrosine kinases as signaling domains for chimeric single chain of the variable domain receptors: optimal design for T cell activation," J. Immunol., 160(1): 145-54, Jan. 1998.

Friedmann-Morvinski, D., et al., "Redirected primary T cells harboring a chimeric receptor require co stimulation for their antigen-specific activation," Blood (2005); 105(8): 3087-3093.

Gade et al., "Targeted elimination of prostate cancer by genetically directed human T lymphocytes," Cancer Res. (2005); 65:9080-9088.

Gill et al., "Preclinical targeting of human acute myeloid leukemia and myeloablation using chimeric antigen receptor-modified T cells," Blood (2014); 123(15): 2343-54 (pub online Mar. 4, 2014).

Gong, et al., "Cancer Patient T Cells Genetically Targeted to Prostate Specific Membrane Antigen Specifically Lyse Prostate Cancer Cells and Release Cytokines in Response to Prostate-Specific Membrane Antigen," Neoplasia (1999); 1:123-7.

Grada et al., "TanCAR: a novel bispecific chimeric antigen receptor for cancer immunotherapy," Molecular Therapy-Nucleic Acids (2013): 2(7): Article No. e1 05 (internal pp. 1-11) (e-pub. Jul. 9, 2013).

Griffioen, M., et al., "Retroviral transfer of human CD20 as a suicide gene for adoptive T-cell therapy," Haematologica (2009); 94(9): 1316-20.

Gross et al., "Chimaeric T-cell receptors specific to a B-lymphoma idiotype: a model for tumour immunotherapy," Biochem. Soc. Trans. (Nov. 1995); 23(4):1079-82.

Grupp, S.A. et al., "Chimeric antigen receptor-modified T cells for acute lymphoid leukemia", N Engl J Med. (2013); 368(16): 1509-1518.

Gu et al., "Abstract LB-187: New methods for controlling CAR Tcell-mediated cytokine storms : Cancer Research", Proceedings: AACR Annual Meeting 2017, (Jul. 1, 2017), Retrieved from the Internet Sep. 28, 2021: URL:https://cancerres.aacrjournals.org/content/77/13 Supplement/LB-187, 4 pages.

Hansen et al., "Description of an Ectothermic TCR Coreceptor, CD8 a, in Rainbow Trout," J. Immunol., 164, 3132-3139, 2000.

Hekele, A. et al., "Growth retardation of tumors by adoptive transfer of cytotoxic T lymphocytes reprogrammed by CD44v6-specific scFv:zeta-chimera," Int. J. Cancer (1996); 68(2):232-8.

Helen E Heslop: "Safer Cars", Molecular Therapy, vol. 18, No. 4, Apr. 1, 2010, XP55609534.

Hennig I.M., et al., "Substance-p. Receptors in Human Primary Neoplasms: Tumoral and Vascular Localization," International Journal of Cancer, 1995, vol. 61(6), pp. 786-792.

Heslop, "Genetic engineering of T-cell receptors: TCR takes to titin," Blood (Aug. 8, 2013); 122(6):853-4.

Ho, et al., "Adoptive Immunotherapy: Engineering T Cell Responses as Biologic Weapons for Tumor Mass Destruction," Cancer Cell (May 2003); 3:431-7.

Hombach, et al., J Immunol (2004); 173: 695: (Erratum to Hombach, et al., Tumor-specific T cell activation by recombinant immunoreceptors: CD3 zeta signaling and CD28 costimulation are simultaneously required for efficient IL.

Hombach, et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule," J Immunol. (2001); 167:6123-6131.

(56) References Cited

OTHER PUBLICATIONS

Honegger et al., "A mutation designed to alter crystal packing permits structural analysis of a tight-binding fluorescein-scFv complex," Protein Science 14(10): 2537-2549 (2005).

Hudecek et al., "Receptor affinity and extracellular domain modifications affect tumor recognition by ROR1-specific chimeric antigen receptor T-cells," Clin Cancer Res. 19(12):3153-3164 (2013).

Hwu, P., et al., "In Vivo Antitumor Activity of T Cells Redirected with Chimeric Antibody/T-Cell Receptor Genes," Cancer Research (Aug. 1, 1995); 55: 3369-3373.

Hwu, P. et al., "Lysis of Ovarian Cancer Cells by Human Lymphocytes Redirected with a Chimeric Gene Composed of an Antibody Variable Region and the Fc Receptor gamma-Chain," The Journal of Experimental Medicine (1993); 178, 361-366.

Imai, C. et al., "Chimeric receptors with 4-IBB signaling capacity provoke potent cytotoxicity against acute lymphoblastic leukemia," Leukemia, 2004, 18, 676-684.

International Preliminary Report on Patentability issued by the International Searching Authorigy for Application No. PCT/US2017/026618, dated Oct. 9, 2018, 8 pages.

International Search Report and Written Opinion dated Mar. 27, 2019 for PCT/US2019/014478, 8 pages.

International Search Report and Written Opinion issued by the International Searching Authorigy for Application No. PCT/US2017/026618, completed Aug. 30, 2017, 12 pages.

International Search Report and Written Opinion issued by the International Searching Authority for Application No. PCT/US2019/019191, completed Jun. 11, 2021, 11 pages.

International Search Report issued in Appl. No. PCT/US2019/014472 (dated Apr. 26, 2019), 15 pages.

Israeli, R. S., et al., "Expression of the prostate-specific membrane antigen," Cancer Res. (1994); 54, 1807-1811.

Jensen, M. C., et al., "Human T lymphocyte genetic modification with naked DNA," Molecular Therapy (2000); 1:49-55.

Johnson et al., "Kabat database and its applications: 30 years after the first variability plot," Nucleic Acids Res., 28(1): 214-218 (2000).

Johnson, L. A. et al., "Gene therapy with human and mouse T-cell receptors mediates cancer regression and targets normal tissues expressing cognate antigen," Blood , vol. 114, No. 3, pp. 535-546 (Jul. 2009).

Junghans RP, "Is it safer CARs that we need, or safer rules of the road?," Mol Ther. (Oct. 2010); 18(10):1742-3.

Kabat et al., Abstract, Sequence of Proteins of Immunological Interest, US Public Health Services, NIH, Bethesda, MD, Publication No. 91-3242, 3 pages, (1991).

Kalos, et al., "T Cells with Chimeric Antigen Receptors Have Potent AntitumorEffects and Can Establish Memory in Patients with Advanced Leukemia", Sci Transl Med. Aug. 10, 2011; 3(95): 95ra73. doi:10.1126/scitranslmed.3002842.

Kenderian, et al; "CD33-specific chimeric antigen receptor T cells exhibit potent preclinical activity against human acute myeloid leukemia," Leukemia (Aug. 2015); 29(8): 1637-47 (Epub Feb. 27, 2015).

Kershaw et al., "Gene-Engineered T Cells as a Superior Adjuvant Therapy for Metastatic Cancer," The Journal of Immunology 173(3): 2143-2150 (2004).

Kershaw, M. H. et al., "A Phase I Study on Adoptive Immunotherapy Using Gene-Modified T Cells for Ovarian Cancer," Clin Cancer Res, 12(20):6106-6115 (Oct. 2006).

Kim et al., "NMR Structural Studies of Interactions of a Small, Nonpeptidyl Tpo Mimic with the Thrombopoietin Receptor Extracellular Juxtamembrane and Transmembrane Domains," J Biol Chem (2007) 282(19)14253-14261.

Kim et al., "Therapeutic Potential of 4-1BB (CD137) As a Regulator for Effector CDS+ T Cells," Journal of Hematotherapy & Stem Cell Research (2001) 10:441-449.

Kochenderfer, J.N., et al., "Adoptive transfer of syngeneic T cells transduced with a chimeric antigen receptor that recognizes murine CD19 can eradicate lymphoma and normal B cells.," Blood (2010); 116(19):3875-3886.

Kowolik, C. et al., "CD28 costimulation provided through a CD19-specific chimeric antigen receptor enhances in vivo persistence and antitumor efficacy of adoptively transferred T cells", Cancer Res. (2006); 66(22): 10995-11004.

Kowolik, et al., "CD28-costimulation provided through a CD-19-specific chimeric immunoreceptor enhances in vivo persistence and anti-tumor efficacy of adoptively transferred T cells," Blood 106(11): 1278, 4 pages (2005) (Retrieved from http://www.bloodjournal.org/contenU106/11/1278).

Kozak, M. et al., "At least six nucleotides preceding the AUG initiator codon enhance translation in mammalian cells," Journal of Molecular Biology, vol. 196(4):947-950 (1987).

Kranz et al., "Partial elucidation of an anti-hapten repertoire in BALB/c mice comparative characterization of several monoclonal antiFLuorescyl antibodies," Mol Immunol (1981) 18(10), 889-898.

Krause et al., "Antigen-dependent CD28 Signaling Selectively Enhances Survival and Proliferation in Genetically Modified Activated Human Primary T Lymphocytes," J. Exp. Med. 188(4):619-626 (1998).

Kunik et al., "Paratome: an online tool for systematic identification of antigen-binding regions in antibodies based on sequence or structure," Nucl Acids Res. 40:W521-W524 (2012).

Lee et al., Erratum, "Current concepts in the diagnosis and management of cytokine release syndrome," Blood, Sep. 15, 2016, vol. 128, No. 11, 2 pages.

Lee et al., "Use of a Single Car T Cell and Several Bispecific Adapters Facilitates Eradication of Multiple Antigenically Different Solid Tumors," Cancer Res 79:387-396 (2019).

Lefranc, MP. et al., "IMGT unique numbering for immunoglobulin and T cell receptor variable domains and Ig superfamily V-like domains," Developmental & Comparative Immunology, Jan. 2003, 27(1), pp. 55-77.

Letourneur et al. "T-cell and basophil activation through the cytoplasmic tail of T-cell-receptor zeta family proteins" Proc. Natl. Acad. Sci USA (1991); 88:8905-8909.

Li et al., "CAIX-specific CAR-T Cells and Sunitinib Show Synergistic Effects Against Metastatic Renal Cancer Models," Journal of Immunotherapy 4316-4328 (2020).

Linette, G.P., et al., "Cardiovascular toxicity and titin cross-reactivity of affinity-enhanced T cells in myeloma and melanoma," Blood (Aug. 8, 2013); 122(6): 863-71 (Epub Jun. 14, 2013).

Liu H, et al., "Monoclonal antibodies to the extracellular domain of prostate-specific membraneantigen also react with tumor vascular endothelium," Cancer Res. (1997); 57(17): 3629-3634.

Lu et al: "Preclinical Evaluation of Bispecific Adaptor Molecule Controlled Folate Receptor CAR-T Cell Therapy With Special Focus on Pediatric Malignancies", Frontiers in Oncology, vol. 9, pp. 1-20 (2019).

Lu et al., "Strategy to prevent drug-related hypersensitivity in folate-targeted hapten immunotherapy of cancer," AAPS J 11(3):628-638 (2009).

Ma et al., "Targeting of antigens to B lymphocytes via CD19 as a means for tumor vaccine development," Journal of Immunology 190(11):5588-5599 (2013).

Ma, Q., et al., "Genetically engineered T cells as adoptive immunotherapy of cancer," Cancer Chemother Biol Response Modif (2002); 20: 315-41.

Maher, J., Immunotherapy of malignant disease using chimeric antigen receptor engrafted T cells. International Scholarly Research Notices Oncology, 2012:278093 (2012).

Makabe et al., "Thermodynamic consequences of mutations in Vernier zone residues of a humanized anti-human epidermal growth factor receptor murine antibody," Journal of Biological Chemistrv, 283(2):1156-1166 (2008).

Manual pCDH Vectors (System Biosciences) (21 pages), Nov. 18, 2013.

Martin et al., "Modeling antibody hypervariable loops: a combined algorithm," Proc Natl Acad Sci (USA), 86:9268-9272 (1989).

(56) References Cited

OTHER PUBLICATIONS

Maus et al., "Antibody-modified T cells: CARs take the front seat for hematologic malignancies," Blood 123(17):2626-2635 (2014).
Midelfort, KS, et al., "Substantial Energetic Improvement with Minimal Structural Perturbation in a High Affinity Mutant Antibody," J. Mal. Bioi., 343, 685-701, 2004.
Miguel Muñoz, Rafael Coveñas, "Substance P," Encyclopedia of Endocrine Diseases (Second Edition), vol. 1, pp. 571-578 (2018).
Milone et al., "Chimeric receptors containing CD137 signal transduction domains mediate enhanced survival of T cells and increased antileukemic efficacy in vivo," Mol Ther. (2009) 17(8):1453-1464.
Molecular Cloning A Laboraory Manual, 4th Edition, Cold Spring Harbor Laboratory Press, (2012) Green and Sambrook, TOC, 34 pages (2012).
Moore et al., "Application of dual affinity retargeting molecules to achieve optimal redirected T-cell killing of B-cell lymphoma," Blood, The Journal of the American Society of Hematalogy, Apr. 2011, 117(17), pp. 4542-4551.
Morgan RA et al., "Case Report of a Serious Adverse Event Following the Administration of T Cells Transduced With a Chimeric Antigen Receptor Recognizing Erbb2," Molecular Therapy 18(4):843-851 (2010).
Moritz, D. et al., "Cytotoxic T lymphocytes with a grafted recognition specificity for ERBB2-expressing tumor cells," Proc Natl Acad Sci U S A. May 10, 1994; 91(10): 4318-4322.
Nolan K F, et al, "Bypassing immunization: optimized design of 'designer T cells' against carcinoembryonic antigen (CEA)-expressing tumors, and lack of suppression by soluble CEA," Clinical Cancer Research (Dec. 1999); 5(12): 3928-3941.
Patel et al., "T -cell killing of heterogenous tumor or viral targets with bispecific chimeric immune receptors," Cancer Gene Therapy (2000); 7(8): 1127-1134.
Peng-Cheng, "Evaluation of a Carbonic Anhydrase IX-Targeted near-Infrared Dye for Fluorescence-Guided Surgery of Hypoxic Tumors," Mol. Pharmaceutics, 13:1618-1625 (2016).
Pierce, et al., "Computational Design of the Affinity and Specificity of a Therapeutic T Cell Receptor" PLoS Computational Biology (Feb. 13, 2014); 10(2): e1003478 (11 pages).
Pinto et al, "Molecular cloning and characterization of sea bass (Dicentrarchus labrax L.) CD8a," Veterinary Immunology and Immunopathology, 110, 169-177, 2006.
Pizarro, J.C., et al., "Structural and functional characterization of a monoclonal antibody specific for the preSI region of hepatitis B virus," FEBS letters (2001); 509: 463-468.
Rabu et al., "Production of Recombinant Human Trimeric CD137L (4-1BBL), Cross-linking is Essential to its T Cell Co-Stimulation Activity," The Journal of Biological Chemistry vol. 280, No. 50, pp. 41472-41481, Dec. 16, 2005.
Rader, "DARTs take aim at BITEs," Blood (Apr. 28, 2011); 117(17):4403-4.
Rai et al., "Expression systems for production of heterologous proteins," Current Science 2001, vol. 80, No. 9, pp. 1121-1128.
Restifo, N.P. et al., "Adoptive immunotherapy for cancer: harnessing the T cell response", Nat Rev Immunol. (2012); 12(4):269-281.
Roberts, et al., "Antigen-specific cytolysis by neutrophils and NK cells expressing chimeric immune receptors bearing zeta or gamma signaling domains," J. Immunol. (1998); 161:375-84.
Rossi, et al., "2730 Phase 1 Biomarker Analysis of the ZUMA-1 (KTE-CI9-1 01) Study: A Phase 1-2 Multi-Center Study Evaluating the Safety and Efficacy of Anti-CD19 CART Cells (KTEC19) in Subjects with Refractory Aggressive Non-Hodgkin Lymphoma (NHL)," American Society of Hematology (2015) (https://ash confex.com/ash/20 15/webprogramscheduler/Paper80339. html) (2 pages) (presentation date Dec. 6, 2015).
Schutsky, K, et al., "Rigorous optimization and validation of potent RNA CAR T cell therapy for the treatment of common epithelial cancers expressing folate receptor," Oncotarget (Oct. 6, 2015); 6(30):28911-28.

Schwesinger et al., "Unbinding forces of single antibody-antigen complexes correlate with their thermal dissociation rates," PNAS (2000) 97(18), 9972-9977.
Shishkin A.M., Development of a method of adoptive immunotherapy of cancer-embryonic antigen positive human tumors, Moscow, FGBU "Russian Scientific Center of radiology and nuclear medicine," 2015, 23 pages including English Summary.
Song, DG, et al., "A fully human chimeric antigen receptor with potent activity against cancer cells but reduced risk for off-tumor toxicity," Oncotarget (Aug. 28, 2015);6(25):21533-46.
Song, DG, et al., "CD27 costimulation augments the survival and antitumor activity of redirected human T cells in vivo," Blood (Jan. 19, 2012); 119(3):696-706 (Epub Nov. 23, 2011).
Song et al., "In vivo persistence, tumor localization and anti-tumor activity of CAR engineered T cells is enhanced by costimulatory signaling through CD137 (4-IBB)," Cancer Research (2011); 71:4617-27.
Stone, J.D., et al., "A sensitivity scale for targeting T cells with chimeric antigen receptors (CARs) and bispecific T-cell Engagers (BITEs)," Oncoimmunology (Sep. 2012); 1(6): 863-873.
Sun et al., "Immunotherapy with CAR-Modified T cells: toxicities and overcoming strategies," Journal of Immunology Research, 2018:1-10 (2018).
Swanson et al., "The coordination of signaling during Fe receptor-mediated phagocytosis," Journal of Leukocyte Biology, vol. 76, Dec. 2004, pp. 1093-1103.
Tam et al., "Functional, Biophysical, and Structural Characterization of Human IgG1 and lgG4 Fc Variants with Ablated Immune Functionality," Antibodies. Sep. 1, 2017, 6, 12, 34 pages.
Tan, L.K. et al., "Influence of the hinge region on complement activation, C1q binding, and segmental flexibility in chimeric human immunoglobulins," Proc. Natl. Acad. Sci. USA 87:162-166, (1990).
Tanaka, Toshio et al. "Immunotherapeutic implications of IL-6 blockade for cytokine storm." Immunotherapy. Jul. 2016;8(8) :959-70.
Terakura et al., "Generation of CD19-chimeric antigen receptor modified CD8+ T cells derived from virus-specific central memory T cells," Blood 119(1):72-82 (2012) e-pub Oct. 26, 2011.
Till et al., "Adoptive immunotherapy for indolent non-Hodgkin lymphoma and mantle cell lymphoma using genetically modified autologous CD20-specific T cells," Blood 112(6): 2261-2271 (2008).
Traversari et al., "The potential immunogenicity of the TK suicide gene does not prevent full clinical benefit associated with the use of TK-transduced donor lymphocytes in HSCT for hematologic malignancies," Blood 109(11):4708-4715 (2007).
Uherek, C, et al., "Retargeting of natural killer-cell cytolytic activity to ErbB2 expressing cancer cells results in efficient and selective tumor cell destruction," Blood (2002); 100: 1265-1273.
"UniProtKB- P24161 (CD3Z_Mouse)" (12 pages), retrieved from http://www.uniprot.org/uniproVP24161 on Oct. 14, 2016.
Urba et al., "Redirecting T cells," New Engl. J. Med., 2011, 365, 754-757.
Urbanska, K. et al., "Development of a novel universal immune receptor for antigen targeting: To Infinity and beyond," Oncoimmunology (Aug. 2012 I); 1(5): p. 777-779.
U.S. Appl. No. 61/473,409, inventor Morgan; Richard, filed Apr. 8, 2011.
U.S. Appl. No. 61/701,056, inventor Robbins; Paul, filed Sep. 14, 2012.
U.S. Appl. No. 61/891,347, inventor Cao:Yu, filed Oct. 15, 2013.
U.S. Appl. No. 61/895,704, inventor Cao:Yu, filed Oct. 25, 2013.
U.S. Appl. No. 62/009,054, inventor Young:Travis, filed Jun. 6, 2014.
U.S. Appl. No. 62/009,056, inventor Cao:Yu, filed Jun. 6, 2014.
U.S. Appl. No. 62/030,514, inventor Wang; Feng, filed Jul. 29, 2014.
U.S. Appl. No. 62/030,526, inventor Wang; Feng, filed Jul. 29, 2014.
U.S. Appl. No. 62/059,752, inventor Kim:Chanhyuk, filed Oct. 3, 2014.
U.S. Appl. No. 62/108,947, inventor Kim:Chanhyuk, filed Jan. 28, 2015.

(56) References Cited

OTHER PUBLICATIONS

U.S. Appl. No. 62/148,063, inventor Young:Travis, filed Apr. 15, 2015.
U.S. Appl. No. 62/148,070, inventor Kim:Chanhyuk, filed Apr. 15, 2015.
U.S. Appl. No. 62/253,465, inventor Kim:Chanhyuk, filed Nov. 10, 2015.
U.S. Appl. No. 62/253,467, inventor Young:Travis, filed Nov. 10, 2015.
Van Blitterswijk et al., "Anticancer mechanisms and clinical application of alkylphopholipids," Biochimica et Biophysica Acta (2013) 1831(3)663-674.
Van Der Luit et al., "A new class of anticancer alkylphospholipids uses lipid rafts as membrane gateways to induce apoptosis in lymphoma cells," Mol Cancer Ther (2007) 6(8)2337-2345.
Van Der Stegen et al., "The pharmacology of second-generation chimeric antigen receptors." Nature reviews Drug Discovery 14(7):499-509 (2015).
Van Rhijn I. V., et al., "Human Autoreactive T Cells Recognize CD1band Phospholipids," Proceedings of the National Academy of Sciences, Nov. 30, 2015, vol. 113(2), pp. 380-385.
Webpage, COVID-19 Treatment Guidelines—Interleukin-6 Inhibitors, dated Sep. 26, 2022, 5 pages, retrieved online on Oct. 7, 2022 at https://www.covid19treatmentguidelines.nih.gov/therapies/immunomodulators/interleukin-6-inhibitors/.
WO2010025177—Sequence Listing (Mar. 4, 2010), 45 pages.
Zacchetti, A, "Antitumor effects of a human dimeric antibody fragment 131I-AFRA-DFM5.3 in a mouse model for ovarian cancer," J Nucl Med (Dec. 2011); 52(12):1938- 46 (Epub Nov. 8, 2011).
Zarour, "Reversing T-cell dysfunction and exhaustion in cancer," Clinical Cancer Research, 22(8):1856-1864 (2016).
Zhang, et al., "Chimeric NKG2D modified T cells inhibit systemic T-cell lymphoma growth in a manner involving multiple cytokines and cytotoxic pathways," Cancer Res. (2007); 67(22): 11029-36.
Zhang, et al., "Generation of antitumor responses by genetic modification of primary human T cells with a chimeric NKG2D receptor," Cancer Res. (2006); 66(11):5927-33.
Zhang, T. (2005). Chimeric NK-receptor-bearing T cells mediate antitumor immunotherapy. Blood 106, 1544-1551.
Zhong X., et al., "Chimeric Antigen Receptors Combining 4-1BB and CD28 Signaling Domains Augment PI3kinase/AKT/Bcl-XL Activation and CD8+ T Cell-mediated Tumor Eradication," Molecular Therapy, 2010, vol. 18(2), pp. 413-420.

\* cited by examiner

| Percent survival at first week of treatment |||||
|---|---|---|---|---|
| | PBS | FITC-FA (500nmole/kg) |||
| | | Continue | FA competitor (100x) | Break |
| % | 100(5/5) | 40 (2/5) | 100 (5/5) | 100 (5/5) |

*FIG. 1C*

| Final result of tumor response | | | | |
|---|---|---|---|---|
| % | PBS | Break | FA competitor | Continue dose |
| Complete response | – | 100 (5/5) | 75 (3/4) | |
| Stable dieses | – | – | 25 (1/4) | |
| Partial response | – | – | – | 100 (2/2) |
| No response | 100 (5/5) | – | – | – |

| Percent survival at first week of treatment |||||
|---|---|---|---|---|---|
| | PBS | FITC-FA (nmole/kg) ||||
| | | 5 | 50 | 500 | 2500 |
| % | 100 (5/5) | 100 (5/5) | 60 (3/5) | 40 (2/5) | 80 (4/5) |

*FIG. 3C*

| Final result of tumor response ||||||
|---|---|---|---|---|---|
| % | PBS | FITC-FA (nmole/kg) ||||
| | | 5 | 50 | 500 | 2500 |
| Complete response | 0 | 0 | 33.3 (1/3) | 100 (2/2) | 0 |
| Stable dieses | 0 | 0 | 67.7 (2/3) | 0 | 100 (4/5) |
| Partial response | 0 | 100 (5/5) | 0 | 0 | 0 |
| No response | 100 (5/5) | 0 | 0 | 0 | 0 |

*FIG. 3D*

| The Percent of survival at the first week of treatment | | | |
|---|---|---|---|
| | PBS | Continue | Dose escalation |
| % | 100 | 40 (2/5) | 100 (4/4) |

*Note: 1 mouse in dose escalation group was dead during the injection of CAR T cell

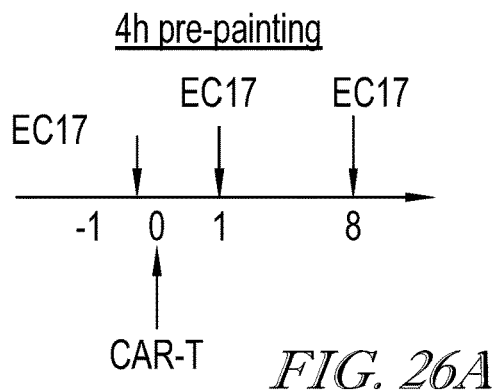
*FIG. 26A*
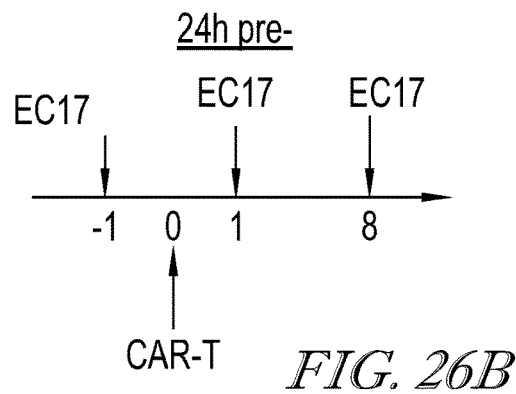
*FIG. 26B*
|  | Mice died due to sCRS | | | Mice survived |
|---|---|---|---|---|
|  | Week 2 | Week 3 | Week 4 | >5 Weeks |
| 4h pre-painting | 33% | 33% | 17% | 17% |
| 24h pre-painting | 17% | 0 | 0 | 83% |
*FIG. 26C*
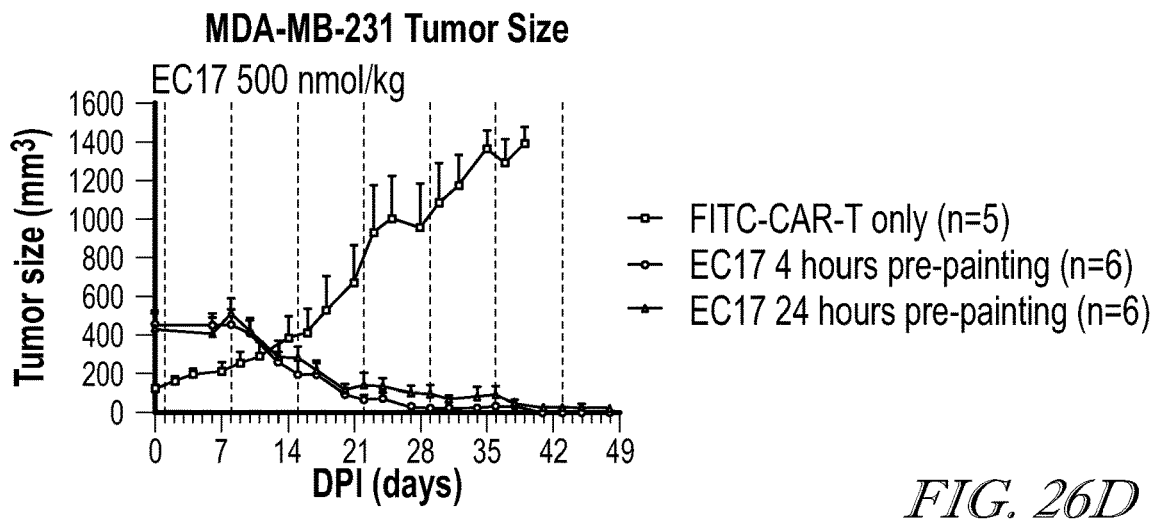
*FIG. 26D*
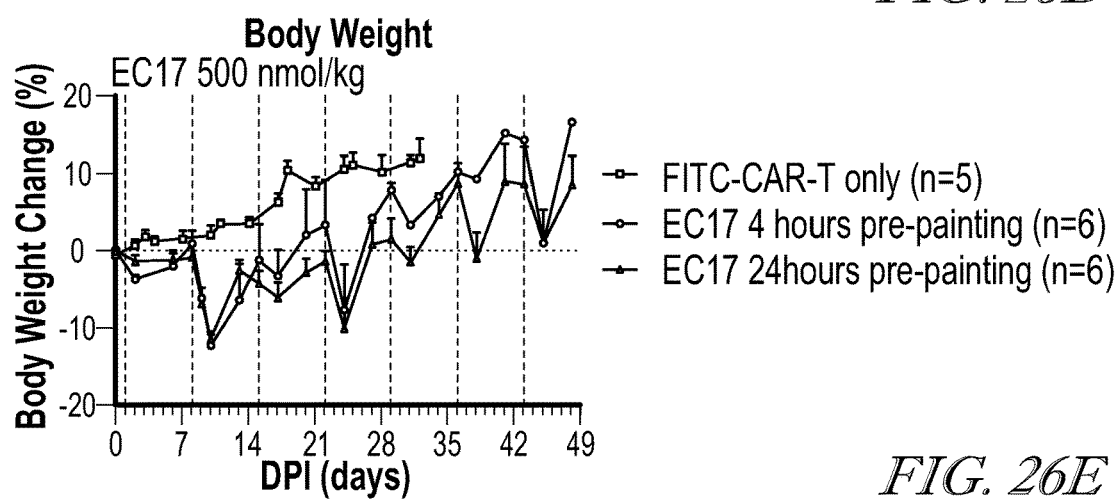
*FIG. 26E*

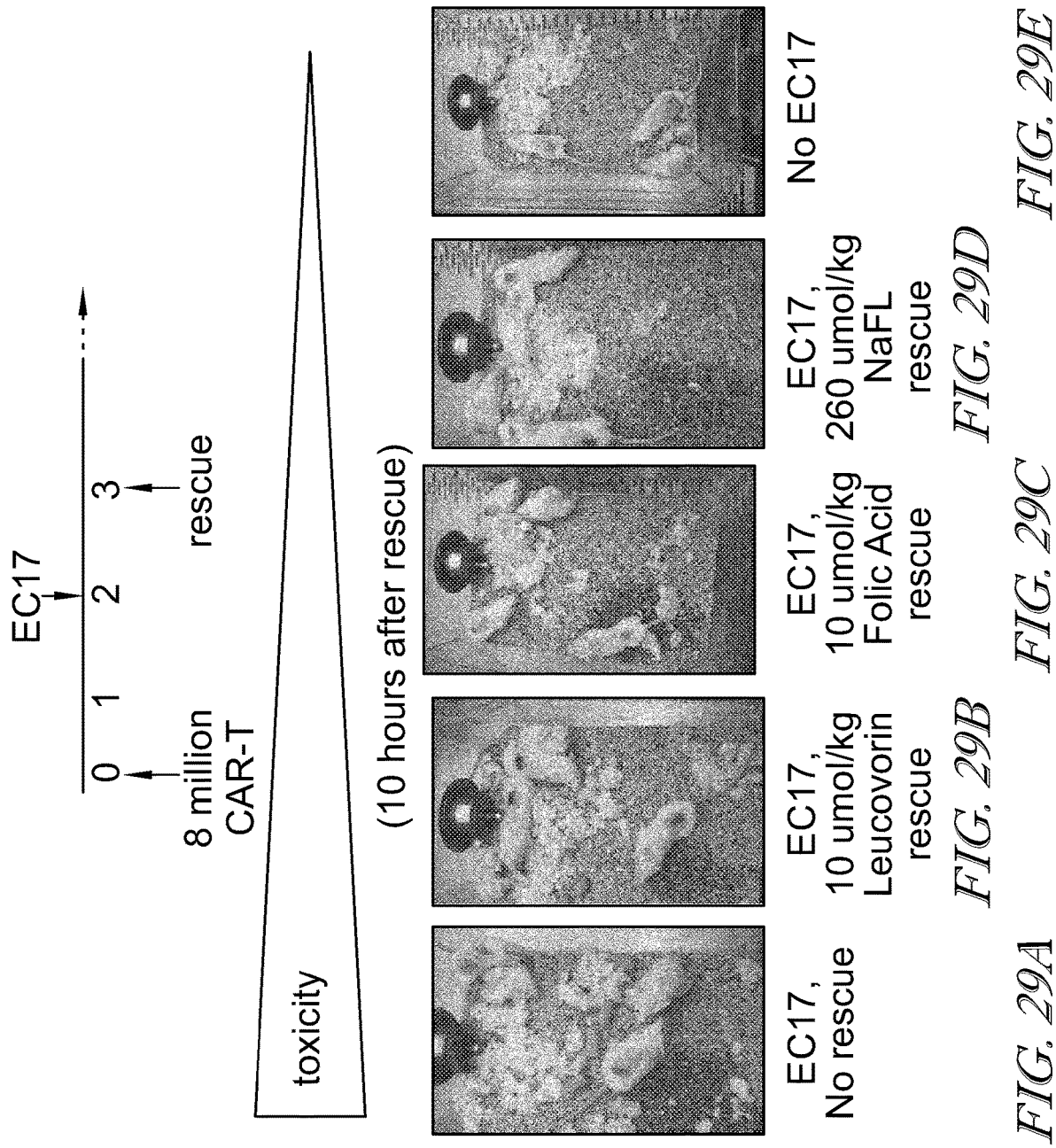

- ○- CAR-T + EC17
- □- CAR-T + EC17 + NaFL rescue
- ○- CAR-T only

EC17 dose dependent CAR-T count in mouse blood

*MDA-MB-231 s.c. model

Universality of anti-FITC CAR T cell therapy: Binding of various adaptors to CAR T cell

- ◨ CAR T cell without staining
- ▨ CAR T cell labeled with FITC-Alexa 647 + FITC-folate (Competition)
- ◱ CAR T cell labeled with FITC-Alexa 647

FITC-folate
Kd: 2nM

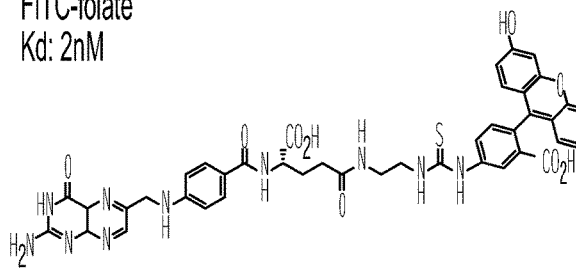

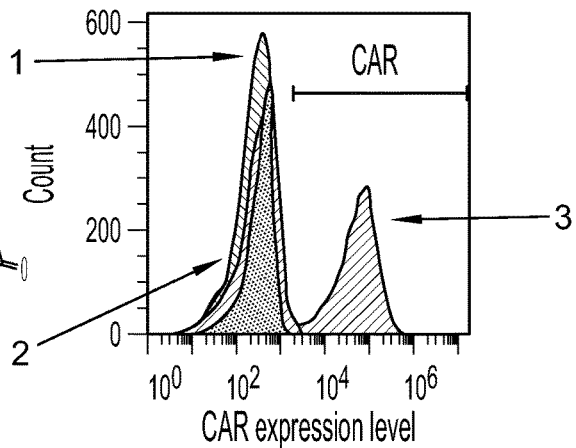

---

- ◨ CAR T cell without staining
- ▨ CAR T cell labeled with FITC-Alexa 647 + FITC-DUPA (Competition)
- ◱ CAR T cell labeled with FITC-Alexa 647

FITC-DUPA
Kd: 8nM

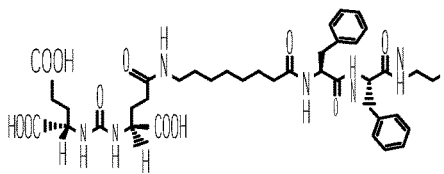

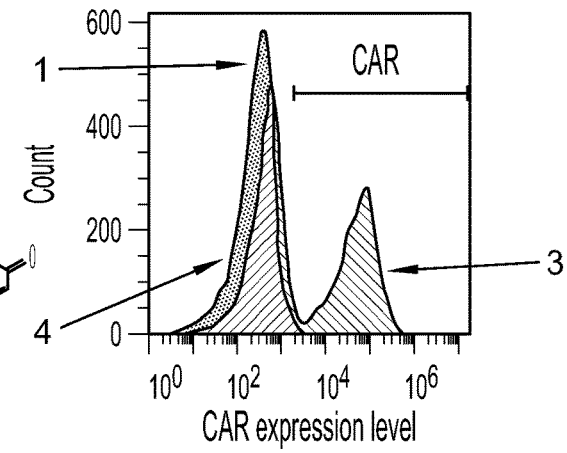

---

FITC-CA9
Kd: 5nM

- ◨ CAR T cell without staining
- ▨ CAR T cell labeled with FITC-Alexa 647 + FITC-CA9 (Competition)
- ◱ CAR T cell labeled with FITC-Alexa 647

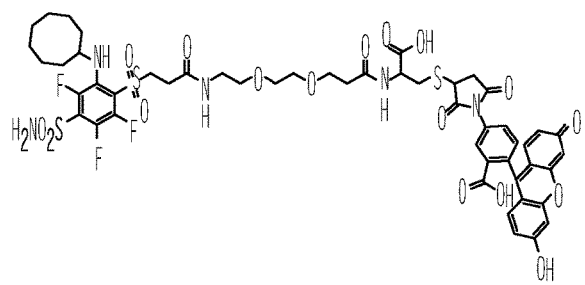

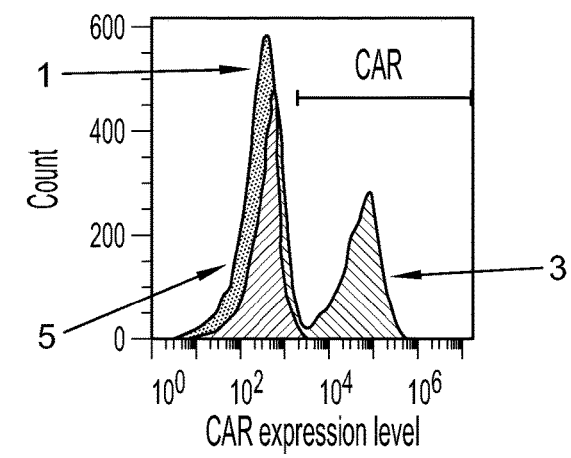

*FIG. 45*

Universality of anti-FITC CAR T cell therapy: All adaptors behave similarly
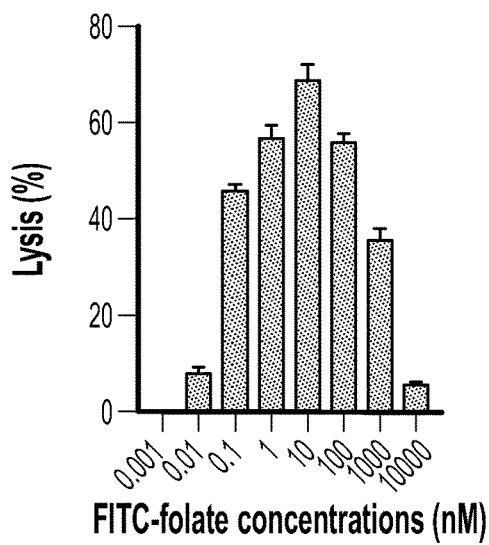
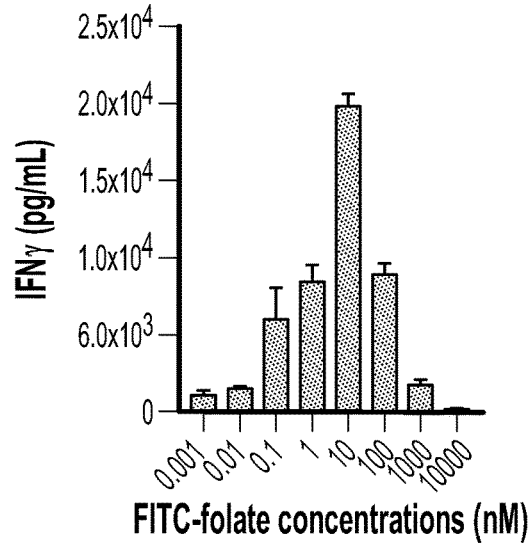
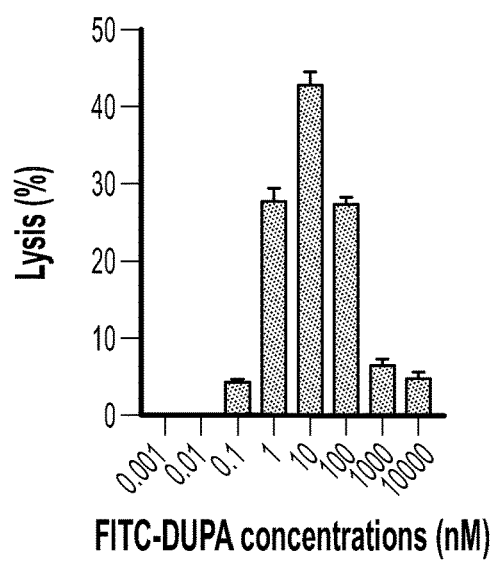
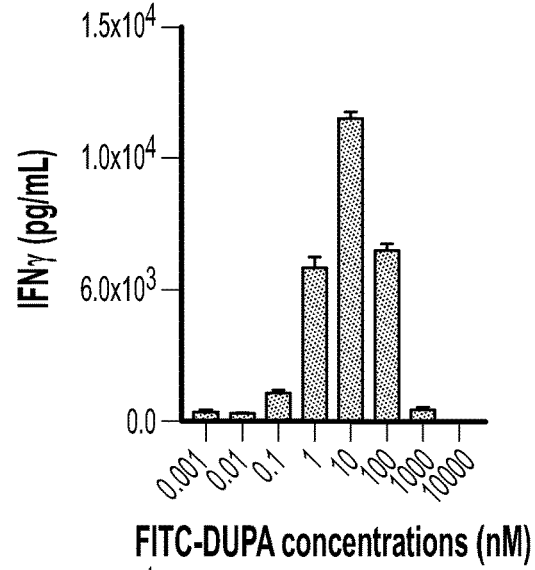
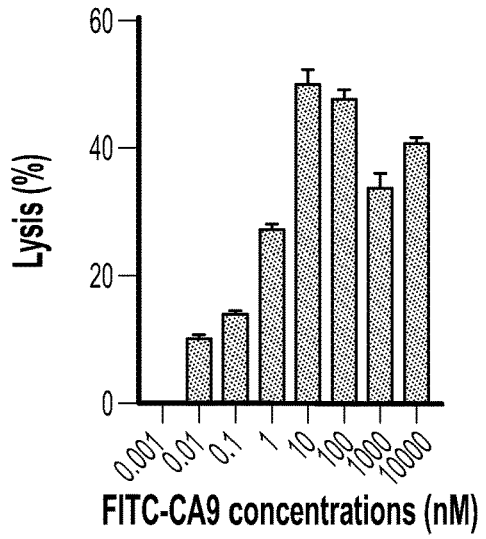
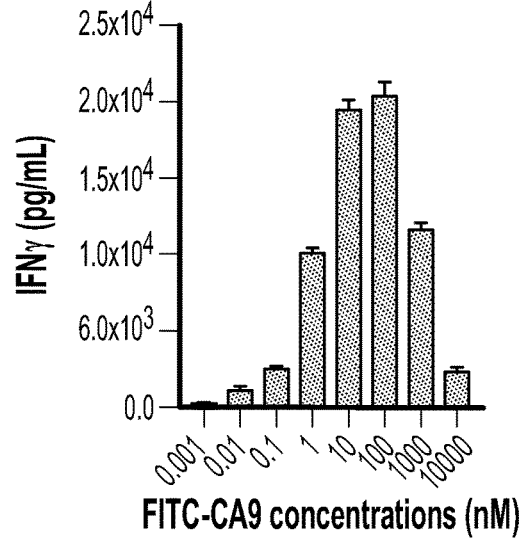
FIG. 47

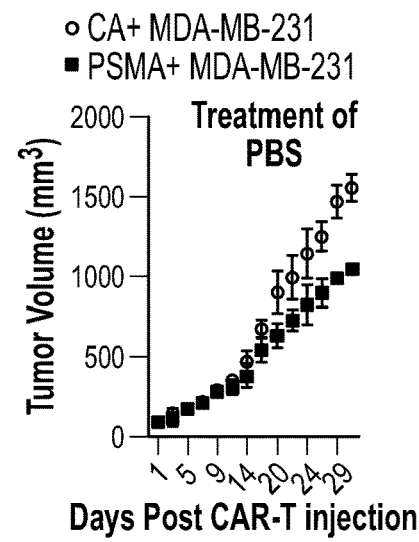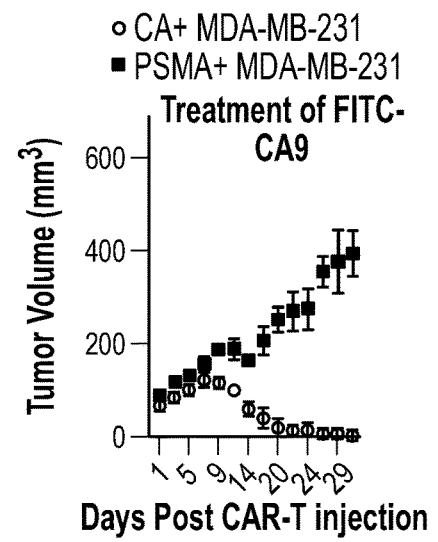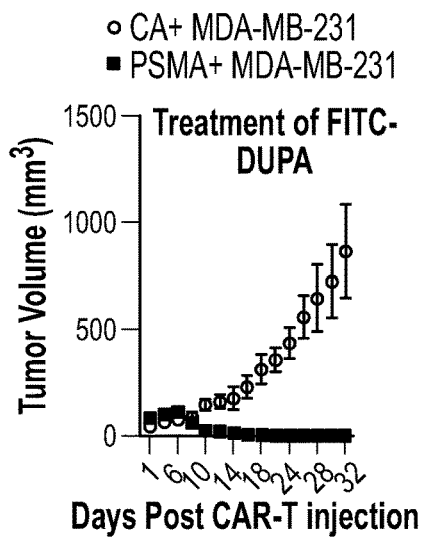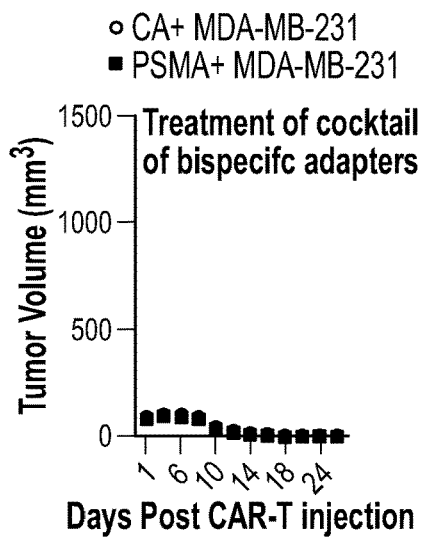
FIG. 49A
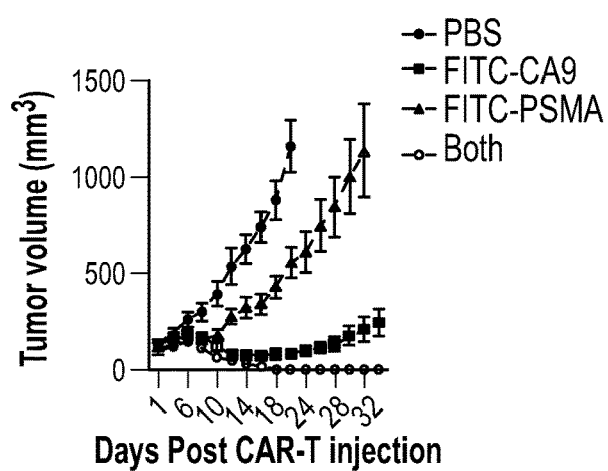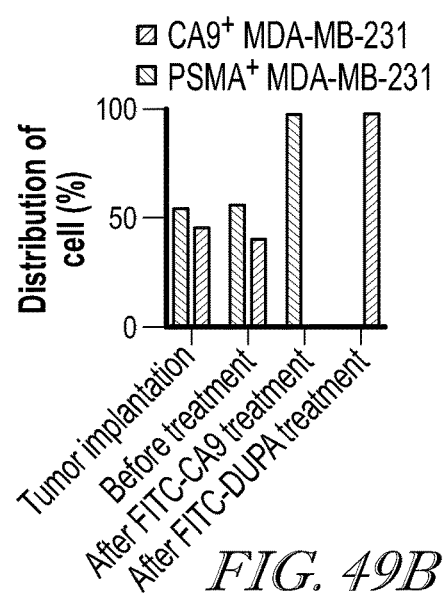
FIG. 49B

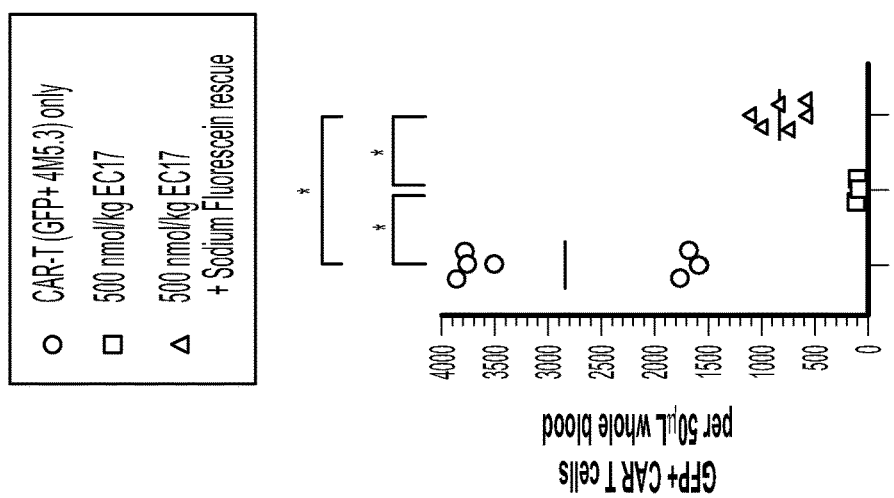
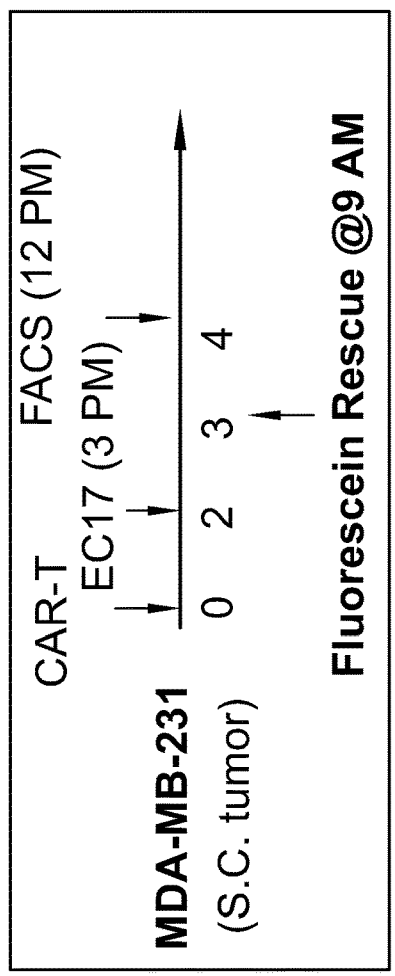
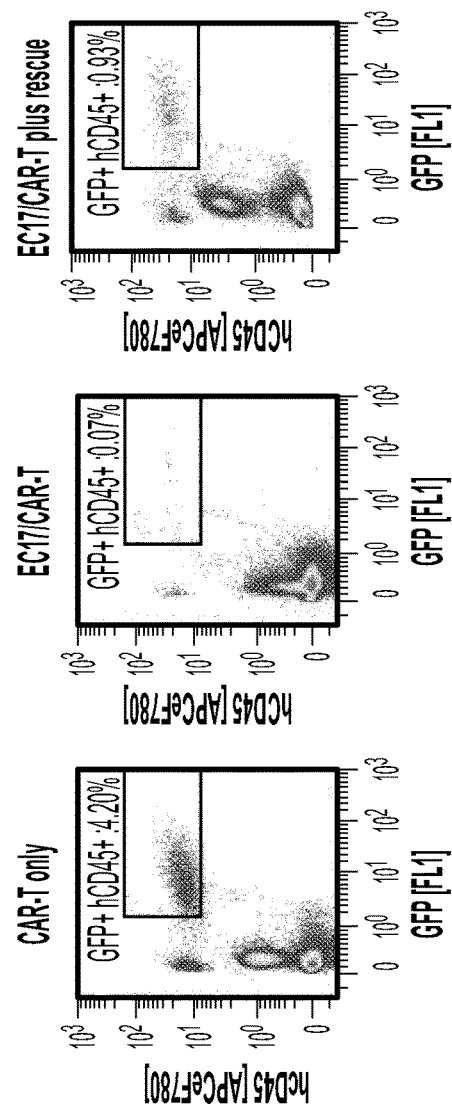
FIG. 53A
FIG. 53B
FIG. 53C

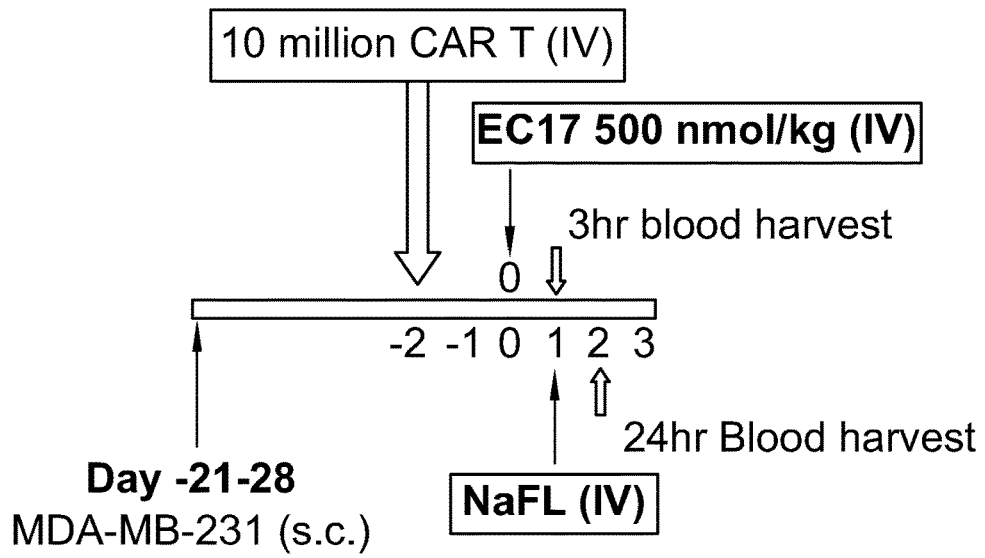
*FIG. 55A*
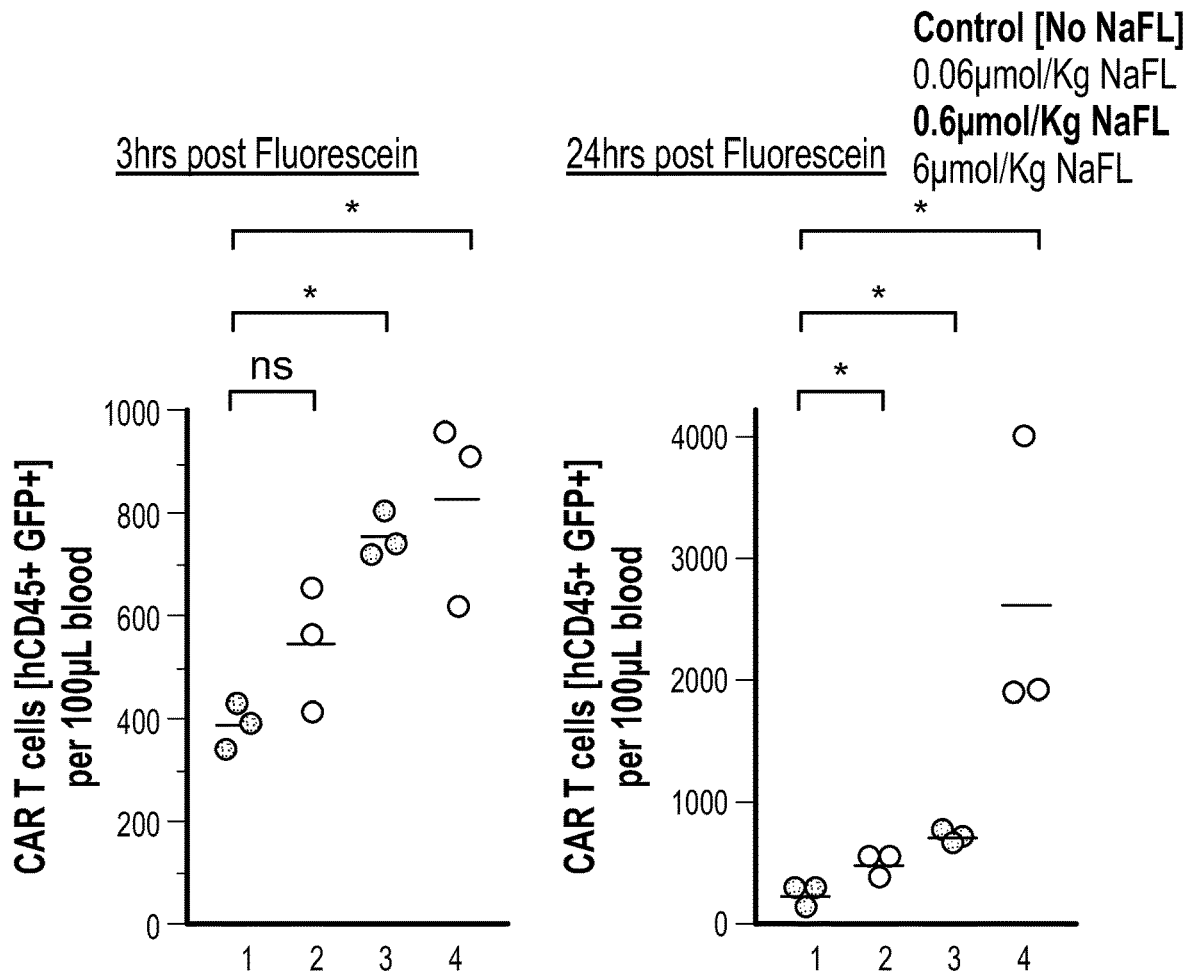
*FIG. 55B*  *FIG. 55C*

Mice with no EC17 treatment had large metastatic tumor burden (not found in the lung!)

1-3
-reproductive track (ovaries, uterine "horns" which are the bilateral sections of the uterus)
-liver
-bone
-mesentery in area caudal area of peritoneal cavity
-mesentery near the intestines
-brain Est. 8-15 visible mets

1 [No EC17]

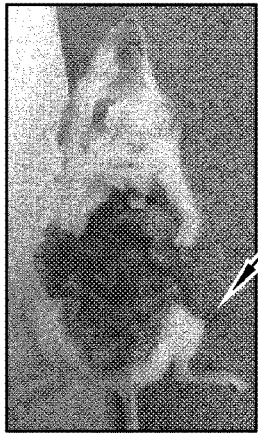

Huge ovary Met.!

5 [+EC17; 5 doses]

5 (small nodules)
- liver
- mesentery in area caudal area of peritoneal cavity
- one near ovary (maybe the oviduct?)

Est. 4-5 visible mets

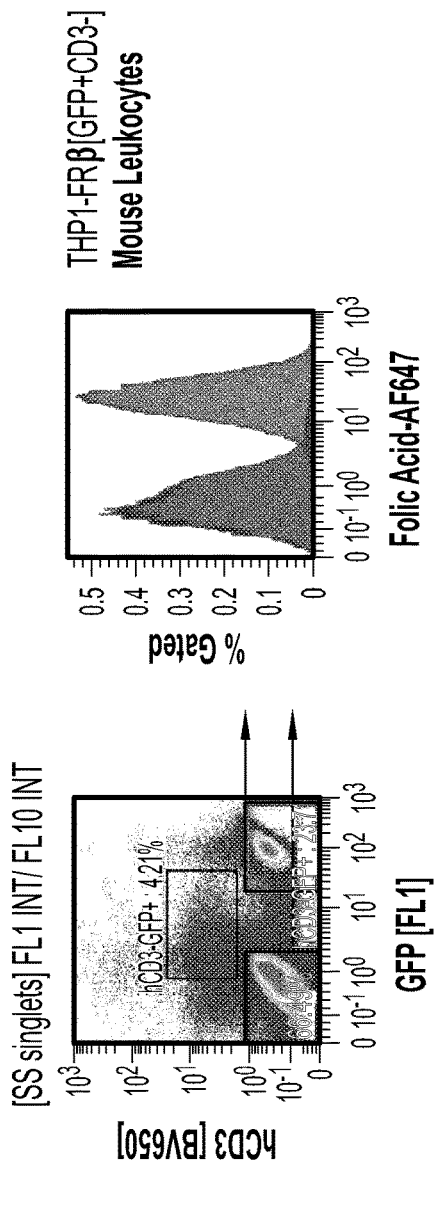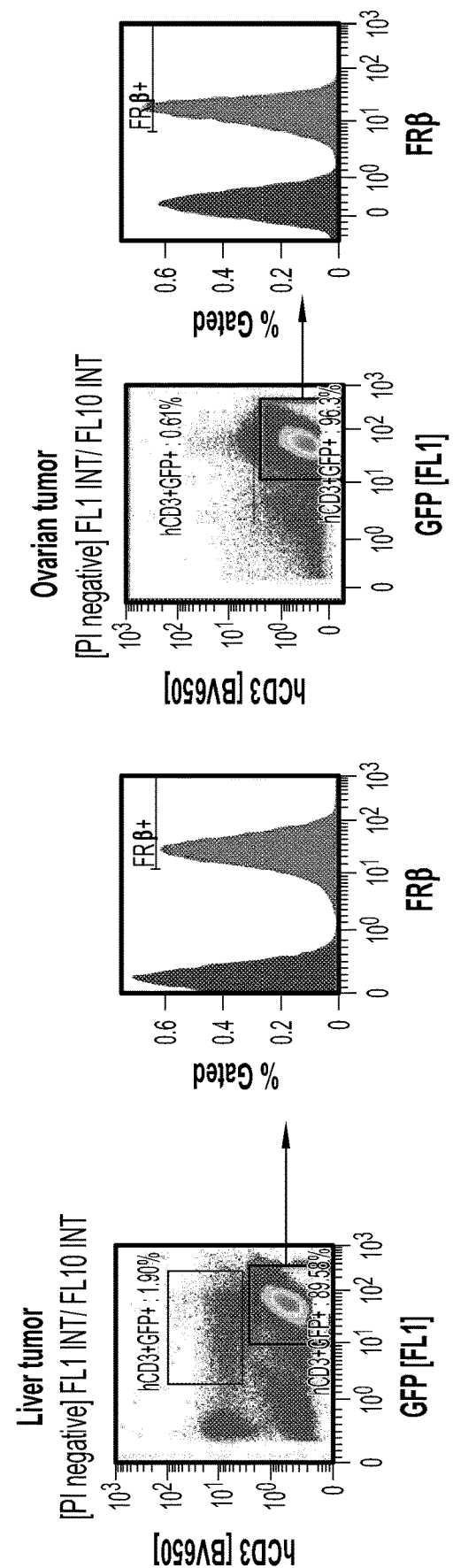
FIG. 59A
FIG. 59B

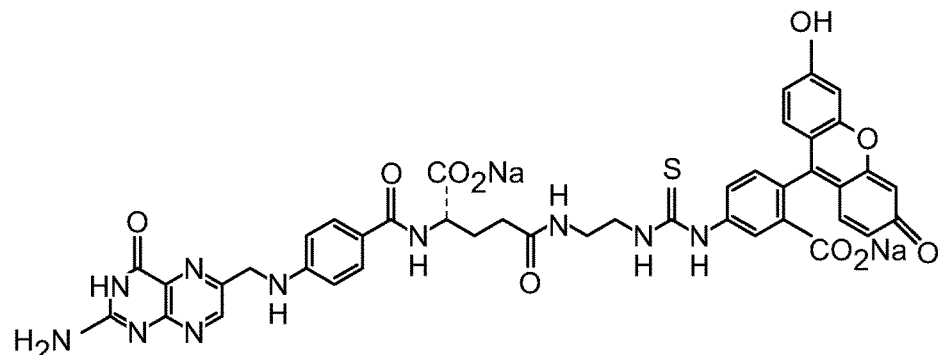
*FIG. 63A*
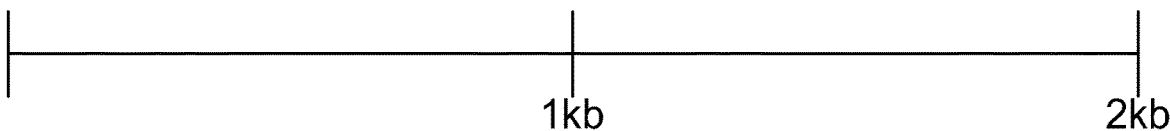
*FIG. 63B*
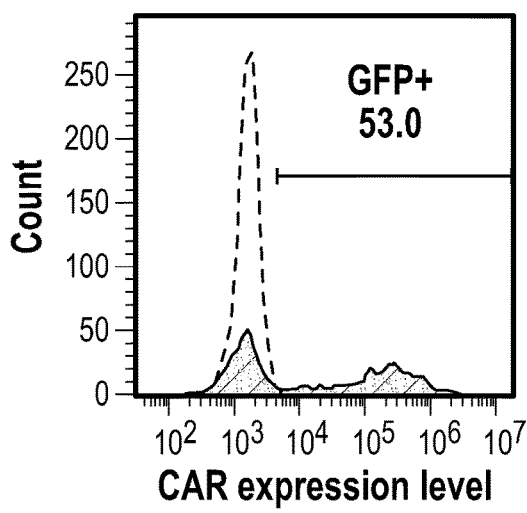 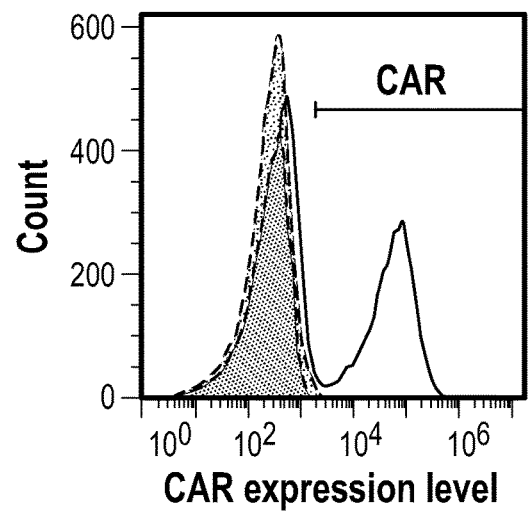
*FIG. 63C*        *FIG. 63D*

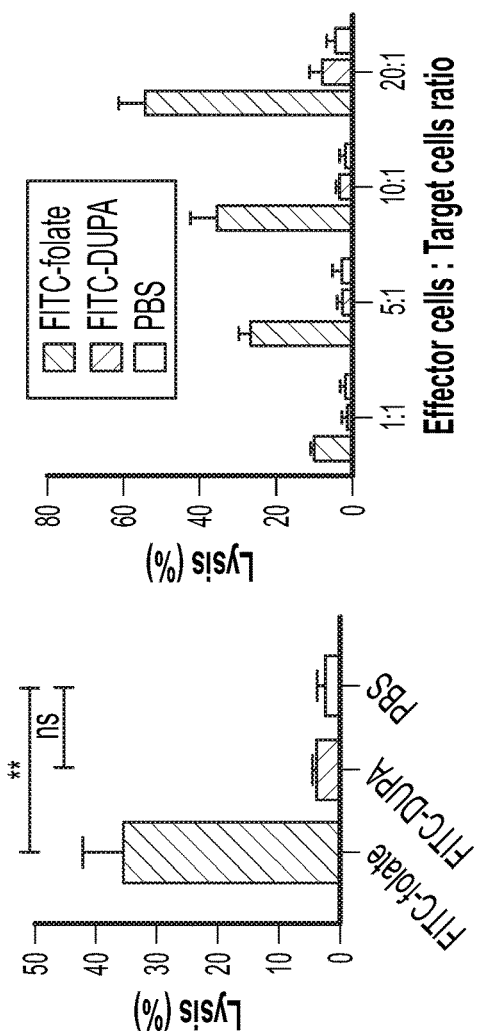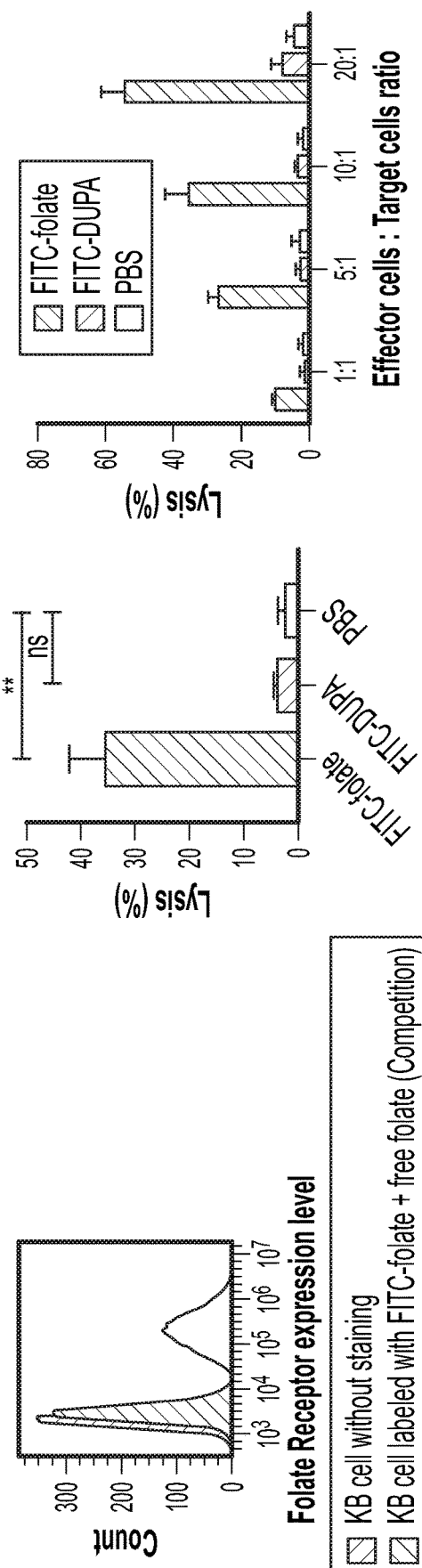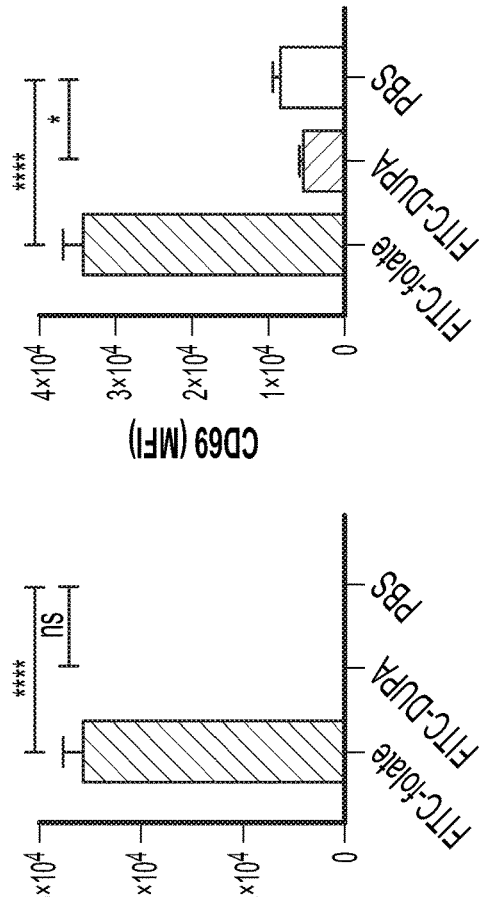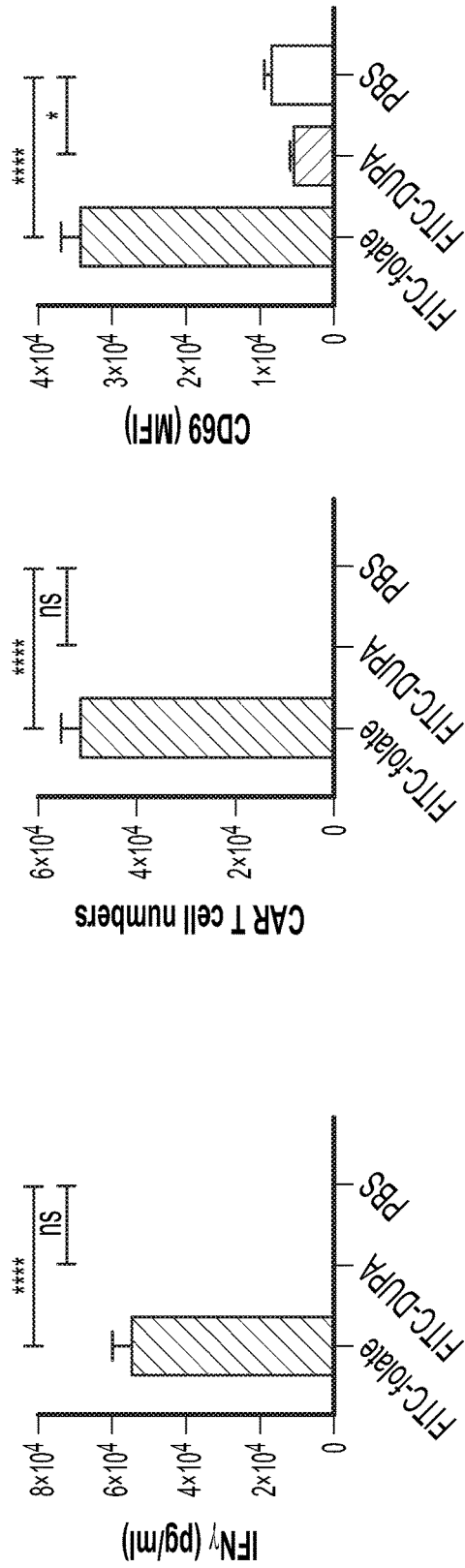

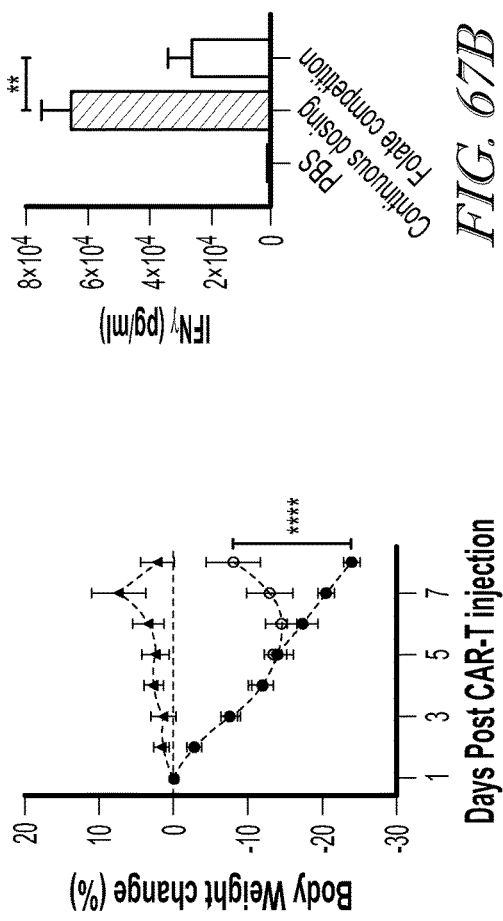
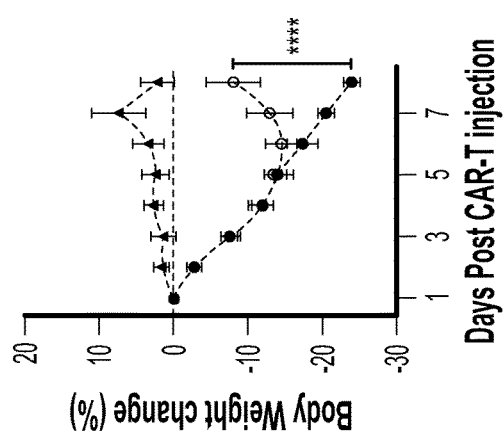
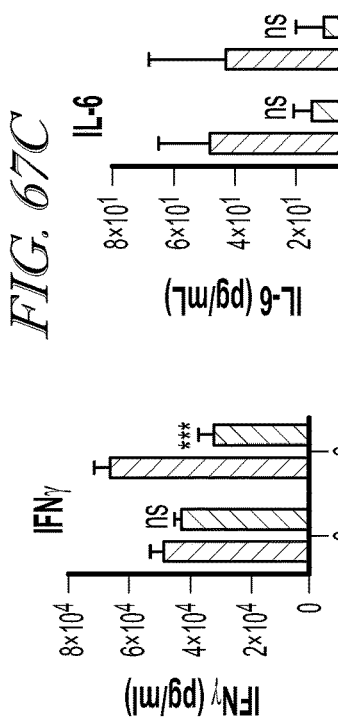
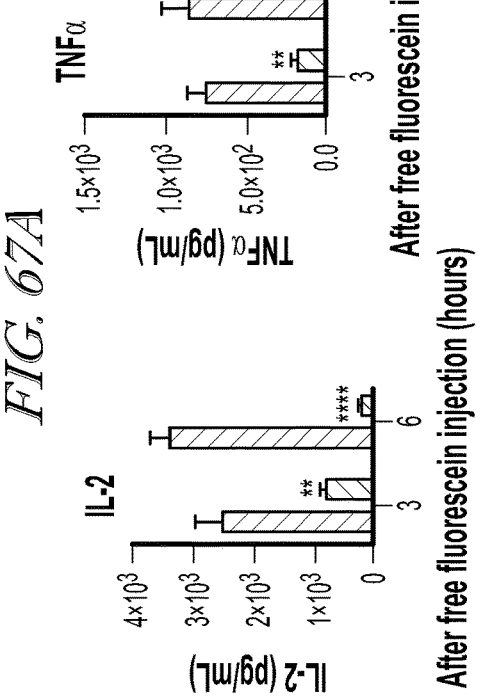
FIG. 67A
FIG. 67B
FIG. 67C
FIG. 67D

- ▲ 15 million CAR-T + PBS
- ☐ 15 million CAR-T + FITC-folate 5 nmoles/kg
- ■ 15 million CAR-T + FITC-folate 50 nmoles/kg
- ○ 15 million CAR-T + FITC-folate 500 nmoles/kg
- △ 15 million CAR-T + FITC-folate 2500 nmoles/kg Day 2: 500 nmol/kg EC17;
Days 10, 24: 5 nmol/kg EC17;
Days 12, 26: 50 nmol/kg EC17;
Days 14, 28: 500 nmol/kg EC17;

HOS143bLVFRa tumor

HOS cancer cells were identified as positive for anti-human FR α [clone LK26] stain

SEQUENCE LISTING

<160> NUMBER OF SEQ ID NOS: 3

<210> SEQ ID NO 1
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atggccttac cagtgaccgc cttgctcctg ccgctggcct tgctgctcca cgccgccagg      60
ccggatgtcg tgatgaccca gacccccctc agcctcccag tgtccctcgg tgaccaggct     120
tctattagtt gcagatccag ccagtccctc gtgcactcta acggtaatac ctacctgaga     180
tggtatctcc agaagcccgg acagagccct aaggtgctga tctacaaagt ctccaaccgg     240
gtgtctggag tccctgaccg cttctcaggg agcggttccg gcaccgactt caccctgaaa     300
atcaaccggg tggaggccga agacctcggc gtctatttct gctctcagag tacacatgtg     360
ccctggacct tcggcggagg gaccaagctg gagatcaaaa gctccgcaga cgatgccaag     420
aaagatgccg ctaagaaaga cgatgctaag aaagacgatg caaagaaaga cggtggcgtg     480
aagctggatg aaaccggagg aggtctcgtc cagccaggag gagccatgaa gctgagttgc     540
gtgaccagcg gattcacctt tgggcactac tggatgaact gggtgcgaca gtccccagag     600
aaggggctcg aatgggtcgc tcagttcagg aacaaaccct acaattatga gacatactat     660
tcagacagcg tgaagggcag gtttactatc agtagagacg attccaaatc tagcgtgtac     720
ctgcagatga acaatctcag ggtcgaagat acaggcatct actattgcac aggggcatcc     780
tatggtatgg agtatctcgg tcagggacag gcgtcacag tcagtttcgt gccggtcttc     840
ctgccagcga agcccaccac gacgccagcg ccgcgaccac caacaccggc gcccaccatc     900
gcgtcgcagc ccctgtccct gcgcccagag gcgtgccggc cagcggcggg gggcgcagtg     960
cacacgaggg ggctggactt cgcctgtgat atctacatct gggcgccctt ggccgggact    1020 tgtgggggtcc ttctcctgtc actggttatc accctttact gcaaccacag gaaccgtttc    1080
tctgttgtta aacggggcag aaagaaactc ctgtatatat tcaaacaacc atttatgaga    1140
ccagtacaaa ctactcaaga ggaagatggc tgtagctgcc gatttccaga agaagaagaa    1200
ggaggatgtg aactgagagt gaagttcagc aggagcgcag acgccccgc gtaccagcag    1260
```

-continued

```
ggccagaacc agctctataa cgagctcaat ctaggacgaa gagaggagta cgatgttttg   1320
gacaagagac gtggccggga ccctgagatg gggggaaagc cgagaaggaa gaaccctcag   1380
gaaggcctgt acaatgaact gcagaaagat aagatggcgg aggcctacag tgagattggg   1440
atgaaaggcg agcgccggag gggcaagggg cacgatggcc tttaccaggg tctcagtaca   1500
gccaccaagg acacctacga cgcccttcac atgcaggccc tgccccctcg ctaa         1554
```

<210> SEQ ID NO 2
<211> LENGTH: 517
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
                20                  25                  30

Pro Val Ser Leu Gly Asp Gln Ala Ser Ile Ser Cys Arg Ser Ser Gln
            35                  40                  45

Ser Leu Val His Ser Asn Gly Asn Thr Tyr Leu Arg Trp Tyr Leu Gln
        50                  55                  60

Lys Pro Gly Gln Ser Pro Lys Val Leu Ile Tyr Lys Val Ser Asn Arg
65                  70                  75                  80

Val Ser Gly Val Pro Asp Arg Phe Ser Gly Ser Gly Ser Gly Thr Asp
                85                  90                  95

Phe Thr Leu Lys Ile Asn Arg Val Glu Ala Glu Asp Leu Gly Val Tyr
            100                 105                 110

Phe Cys Ser Gln Ser Thr His Val Pro Trp Thr Phe Gly Gly Gly Thr
        115                 120                 125

Lys Leu Glu Ile Lys Ser Ala Asp Asp Ala Lys Lys Asp Ala Ala
    130                 135                 140

Lys Lys Asp Asp Ala Lys Lys Asp Asp Ala Lys Lys Asp Gly Gly Val
145                 150                 155                 160

Lys Leu Asp Glu Thr Gly Gly Gly Leu Val Gln Pro Gly Gly Ala Met
                165                 170                 175

Lys Leu Ser Cys Val Thr Ser Gly Phe Thr Phe Gly His Tyr Trp Met
            180                 185                 190

Asn Trp Val Arg Gln Ser Pro Glu Lys Gly Leu Glu Trp Val Ala Gln
        195                 200                 205

Phe Arg Asn Lys Pro Tyr Asn Tyr Glu Thr Tyr Tyr Ser Asp Ser Val
    210                 215                 220

Lys Gly Arg Phe Thr Ile Ser Arg Asp Asp Ser Lys Ser Ser Val Tyr
225                 230                 235                 240

Leu Gln Met Asn Asn Leu Arg Val Glu Asp Thr Gly Ile Tyr Tyr Cys
                245                 250                 255

Thr Gly Ala Ser Tyr Gly Met Glu Tyr Leu Gly Gln Gly Thr Ser Val
            260                 265                 270

Thr Val Ser Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
```

```
                305                 310                 315                 320
His Thr Arg Gly Leu Asp Phe Ala Cys Asp Ile Tyr Ile Trp Ala Pro
                            325                 330                 335
Leu Ala Gly Thr Cys Gly Val Leu Leu Ser Leu Val Ile Thr Leu
                340                 345                 350
Tyr Cys Asn His Arg Asn Arg Phe Ser Val Val Lys Arg Gly Arg Lys
                    355                 360                 365
Lys Leu Leu Tyr Ile Phe Lys Gln Pro Phe Met Arg Pro Val Gln Thr
        370                 375                 380
Thr Gln Glu Glu Asp Gly Cys Ser Cys Arg Phe Pro Glu Glu Glu
385                 390                 395                 400
Gly Gly Cys Glu Leu Arg Val Lys Phe Ser Arg Ser Ala Asp Ala Pro
                405                 410                 415
Ala Tyr Gln Gln Gly Gln Asn Gln Leu Tyr Asn Glu Leu Asn Leu Gly
            420                 425                 430
Arg Arg Glu Glu Tyr Asp Val Leu Asp Lys Arg Arg Gly Arg Asp Pro
                435                 440                 445
Glu Met Gly Gly Lys Pro Arg Arg Lys Asn Pro Gln Glu Gly Leu Tyr
    450                 455                 460
Asn Glu Leu Gln Lys Asp Lys Met Ala Glu Ala Tyr Ser Glu Ile Gly
465                 470                 475                 480
Met Lys Gly Glu Arg Arg Arg Gly Lys Gly His Asp Gly Leu Tyr Gln
                    485                 490                 495
Gly Leu Ser Thr Ala Thr Lys Asp Thr Tyr Asp Ala Leu His Met Gln
                500                 505                 510
Ala Leu Pro Pro Arg
        515

<210> SEQ ID NO 3
<211> LENGTH: 1560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gccaccatgg ccttaccagt gaccgccttg ctcctgccgc tggccttgct gctccacgcc        60
gccaggccgg atgtcgtgat gacccagacc cccctcagcc tcccagtgtc cctcggtgac       120
caggcttcta ttagttgcag atccagccag tccctcgtgc actctaacgg taatacctac       180
ctgagatggt atctccagaa gcccggacag agccctaagg tgctgatcta caaagtctcc       240
aaccgggtgt ctggagtccc tgaccgcttc tcagggagcg gttccggcac cgacttcacc       300
ctgaagatca accgggtgga ggccgaagac ctcggcgtct atttctgctc tcagagtaca       360
catgtgccct ggaccttcgg cggagggacc aagctggaga tcaaaagctc cgcagacgat       420
gccaagaaag atgccgctaa gaaagacgat gctaagaaag acgatgcaaa gaaagacggt       480
ggcgtgaagc tggatgaaac cggaggaggt ctcgtccagc caggaggagc catgaagctg       540
agttgcgtga ccagcggatt caccttcggg cactactgga tgaactgggt gcgacagtcc       600
ccagagaagg ggctcgaatg ggtcgctcag ttcaggaaca aaccctacaa ttatgagaca       660
tactattcag acagcgtgaa gggcaggttt actatcagta gagacgattc caaatctagc       720
gtgtacctgc agatgaacaa tctcagggtc gaagatacag gcatctacta ttgcacaggg       780
gcatcctatg gtatggagta tctcggtcag gggacaagcg tcacagtcag tttcgtgccg       840
```

```
gtcttcctgc cagcgaagcc caccacgacg ccagcgccgc gaccaccaac accggcgccc    900
accatcgcgt cgcagcccct gtccctgcgc ccagaggcgt gccggccagc ggcggggggc    960
gcagtgcaca cgaggggct ggacttcgcc tgtgatatct acatctgggc gcccttggcc   1020
gggacttgtg gggtccttct cctgtcactg gttatcaccc tttactgcaa ccacaggaac   1080
cgtttctctg ttgttaaacg gggcagaaag aaactcctgt atatattcaa acaaccattt   1140
atgagaccag tacaaactac tcaagaggaa gatggctgta gctgccgatt tccagaagaa   1200
gaagaaggag gatgtgaact gagagtgaag ttcagcagga gcgcagacgc ccccgcgtac   1260
cagcagggcc agaaccagct ctataacgag ctcaatctag gacgaagaga ggagtacgat   1320
gttttggaca agagacgtgg ccgggaccct gagatggggg gaaagccgag aaggaagaac   1380
cctcaggaag gcctgtacaa tgaactgcag aaagataaga tggcggaggc ctacagtgag   1440
attgggatga aggcgagcg ccggaggggc aaggggcacg atggccttta ccagggtctc   1500
agtacagcca ccaaggacac ctacgacgcc cttcacatgc aggccctgcc ccctcgctaa   1560
```

COMPOSITIONS AND METHODS FOR CAR T CELL THERAPY

CROSS REFERENCE TO RELATED APPLICATIONS

This application is a U.S. national stage application under 35 U.S.C. § 371(b) of International Application No. PCT/US2018/020095 filed Feb. 28, 2018, which claims priority under 35 U.S.C. § 119(e) to U.S. Provisional Application No. 62/464,792 filed 28 Feb. 2017, U.S. Provisional Application No. 62/480,627 filed 3 Apr. 2017, U.S. Provisional Application No. 62/554,421 filed 5 Sep. 2017, U.S. Provisional Application No. 62/620,701 filed 23 Jan. 2018, U.S. Provisional Application No. 62/620,384 filed 22 Jan. 2018, U.S. Provisional Application No. 62/620,423 filed 22 Jan. 2018, and U.S. Provisional Application No. 62/634,595 filed 23 Feb. 2018, all of which are incorporated herein by reference in their entirety.

TECHNICAL FIELD

The present disclosure relates to methods of treating a patient with a cancer by administering to the patient a composition comprising CAR T cells and administering to the patient a small molecule linked to a targeting moiety by a linker. The disclosure also relates to compositions for use in such methods.

BACKGROUND

Immunotherapy based on adoptive transfer of lymphocytes (e.g., T cells) into a patient is a valuable therapy in the treatment of cancer and other diseases. Important advancements have been made in the development of immunotherapies based on adoptive transfer of lymphocytes. Among the many different types of immunotherapeutic agents, one of the most promising of the immunotherapeutic agents being developed is T cells expressing chimeric antigen receptors (CAR T cells). The chimeric antigen receptor (CAR) is a genetically engineered receptor that is designed to target a specific antigen, for example, a tumor antigen. This targeting can result in cytotoxicity against the tumor, for example, such that CAR T cells expressing CARs can target and kill tumors via the specific tumor antigens.

First generation CARs are composed of a recognition region, e.g., a single chain fragment variable (scFv) region derived from an antibody for recognition and binding to the antigen expressed by the tumor, and an activation signaling domain, e.g., the CD3ζ chain of T cells can serve as a T cell activation signal in CARs. Although CAR T cells have shown positive results in vitro, they have had limited success in eliminating disease (e.g., cancer) in clinical trials. One problem has been the inability to prolong activation and expand the CAR T cell population in vivo.

To address this problem, a co-stimulation domain (e.g., CD137, CD28 or CD134) has been included in second generation CARs to achieve prolonged activation of T cells in vivo. Addition of a co-stimulation domain enhances the in vivo proliferation and survival of T cells containing CARs, and initial clinical data have shown that such constructs are promising therapeutic agents in the treatment of diseases, such as cancer.

Although improvements have been made in CAR T cell therapies, several problems remain. First, 'off-target' toxicity may occur due to normal cells that express the antigen targeted by the CAR T cells (e.g., a tumor-associated antigen). Second, unregulated CAR T cell activation may be found where the rapid and uncontrolled elimination of diseased cells (e.g., cancer cells) by CAR T cells induces a constellation of metabolic disturbances, called tumor lysis syndrome, or cytokine release syndrome (CRS), which can be fatal to patients. Tumor lysis syndrome and CRS can result due to administered CAR T cells that cannot be easily regulated, and are activated uncontrollably. Accordingly, although CAR T cells show great promise as a tool in the treatment of diseases, such as cancer, additional CAR T cell therapies are needed that provide reduced off-target toxicity, and more precise control of CAR T cell activation.

SUMMARY OF THE INVENTION

The present inventors have discovered methods of reducing off-target toxicity, and more precisely controlling CAR T cell activation, providing important advancements in CAR T cell therapy. In the various embodiments described herein, a small molecule ligand linked to a targeting moiety by a linker is used as a bridge between the cancer and the CAR T cells directing the CAR T cells to the cancer for amelioration of the cancer. In one embodiment, the "small molecule ligand" can be, for example, a folate, DUPA, an NK-1R ligand, a CAIX ligand, a ligand of gamma glutamyl transpeptidase, an NKG2D ligand, or a CCK2R ligand, each of which is a small molecule ligand that binds specifically to cancer cells (i.e., the receptor for these ligands is overexpressed on cancers compared to normal tissues).

In one embodiment, the "small molecule ligand" is linked to a "targeting moiety" that binds to the CAR expressed by CAR T cells. In various embodiments, the "targeting moiety" can be selected, for example, from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.

The "targeting moiety" binds to the recognition region of the genetically engineered CAR expressed by CAR T cells. Accordingly, the recognition region of the CAR (e.g., a single chain fragment variable region (scFv) of an antibody, an Fab, Fv, Fc, (Fab')2 fragment, and the like) is directed to the "targeting moiety." Thus, the small molecule ligand linked to a targeting moiety by a linker acts as a bridge between the cancer and the CAR T cells, directing the CAR T cells to the cancer for amelioration of the cancer.

In one embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a first dose of a CAR T cell composition wherein the CAR T cell composition comprises CAR T cells and wherein the CAR T cells comprise the CAR directed to the targeting moiety, and iii) administering to the patient a second dose of the CAR T cell composition wherein the CAR T cell composition comprises CAR T cells and wherein the CAR T cells comprise the CAR directed to the targeting moiety.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition comprising CAR T cells wherein the CAR T cells in the composition comprise the CAR directed to the targeting moiety and wherein the CAR T cell composition comprises a mixture of the CAR T cells and non-transformed T cells.

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a CAR T cell composition wherein the CAR T cell composition comprises CAR T cells and wherein the CAR T cells comprise the CAR directed to the targeting moiety, and iii) administering to the patient a folate, a conjugate comprising a folate wherein the conjugate comprising a folate does not comprise a targeting moiety, or an agent that inhibits activation of the CAR T cells.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and wherein the compound, or the pharmaceutically acceptable salt thereof, is at a dose of about 10 nmoles/kg of body weight of the patient to about 2500 nmoles/kg of body weight of the patient, and ii) administering to the patient a CAR T cell composition comprising CAR T cells wherein the CAR T cells comprise a CAR directed to the targeting moiety, and wherein the CAR T cells are at a dose of about 1 million of the CAR T cells to about 15 million of the CAR T cells.

In still another embodiment, a method of treatment of a cancer is provided. The method comprises i) administering continuously to a patient a compound, or a pharmaceutically acceptable salt thereof, wherein the compound comprises a small molecule ligand linked to a targeting moiety by a linker, ii) administering to the patient a CAR T cell composition comprising CAR T cells wherein the CAR T cells comprise a CAR directed to the targeting moiety, and iii) ending administration of the compound, or the pharmaceutically acceptable salt thereof, to reduce cytokine release syndrome in the patient.

In another illustrative aspect, a method of treatment of a cancer is provided. The method comprises i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof, and ii) administering to the patient a CAR T cell composition comprising CAR T cells wherein the CAR T cells comprise a CAR directed to the targeting moiety.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker and wherein the compound, or the pharmaceutically acceptable salt thereof, is administered once weekly to the patient, and ii) administering to the patient a CAR T cell composition comprising CAR T cells wherein the CAR T cells comprise a CAR directed to the targeting moiety.

In yet another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker, ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof, and iii) administering to the patient a dose of a CAR T cell composition comprising CAR T cells wherein the CAR T cells comprise a CAR directed to the targeting moiety.

In still another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker and wherein the compound, or the pharmaceutically acceptable salt thereof, is administered to the patient at least about one hour prior to the administration of a CAR T cell composition comprising CAR T cells wherein the CAR T cells comprise a CAR directed to the targeting moiety, ii) then administering to the patient a dose of the CAR T cell composition, and iii) then administering to the patient a second dose of the compound, or the pharmaceutically acceptable salt thereof.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR directed to the targeting moiety, and wherein the small molecule ligand is a PSMA ligand and the targeting moiety is FITC. In this embodiment, the small molecule ligand linked to a targeting moiety by a linker can have the formula

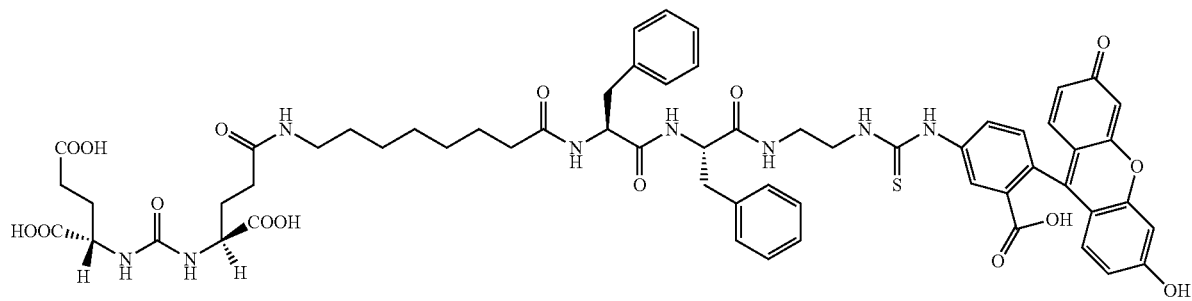 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR directed to the targeting moiety, and wherein the small molecule ligand is a CAIX ligand and the targeting moiety is FITC. In this embodiment, the small molecule ligand linked to a targeting moiety by a linker can have the formula

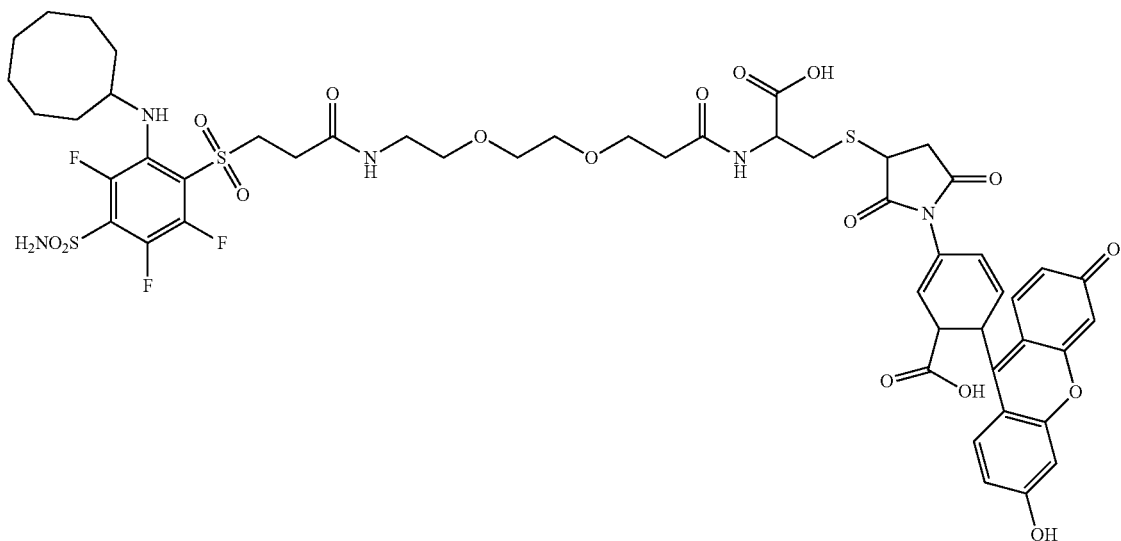 [SMILES: NS(=O)(=O)c1c(F)c(F)c(S(=O)(=O)CCC(=O)NCCOCCOCCC(=O)NC(CSC2CC(=O)N(C3=CC(C(=O)O)C(c4c5ccc(=O)cc-5oc5cc(O)ccc45)C=C3)C2=O)C(=O)O)c(NC2CCCCCCC2)c1F]

In still another embodiment, a method of treatment of a cancer is provided. The method comprises i) administering to a patient a first compound, or a pharmaceutically acceptable salt thereof, wherein the first compound, or the pharmaceutically acceptable salt thereof, comprises a PSMA ligand linked to FITC by a linker, ii) administering to the patient a second compound, or a pharmaceutically acceptable salt thereof, wherein the second compound, or the pharmaceutically acceptable salt thereof, comprises a CAIX ligand linked to FITC by a linker, and iii) administering to the patient a CAR T cell composition wherein the CAR T cell composition comprises CAR T cells and wherein the CAR T cells comprise a CAR directed to the targeting moiety. In this embodiment, the first compound can have the formula

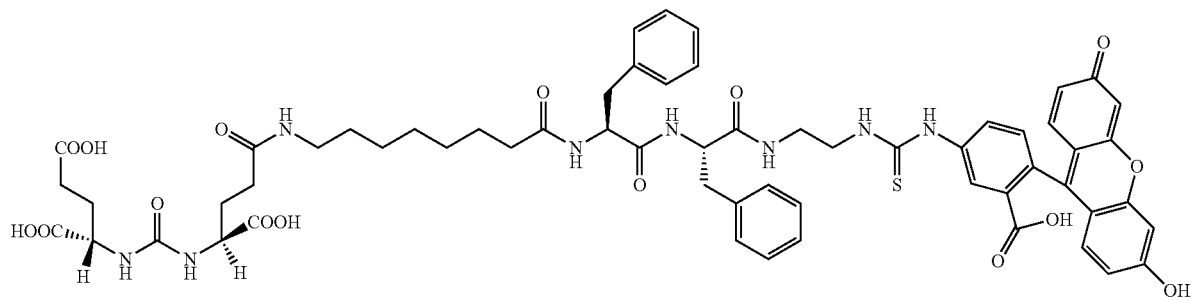 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

and the second compound can have the formula

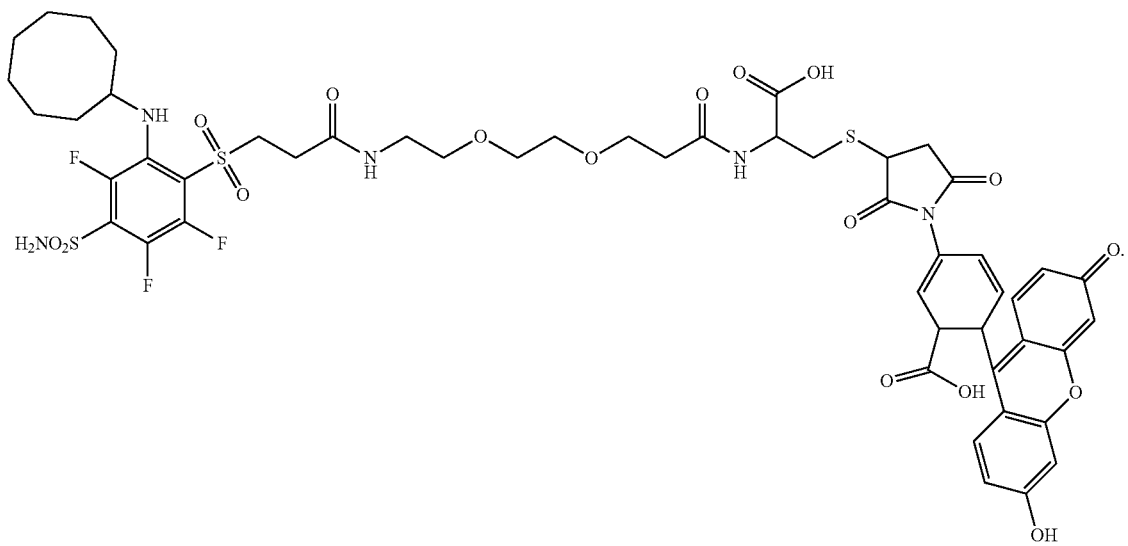 [SMILES: NS(=O)(=O)c1c(F)c(F)c(S(=O)(=O)CCC(=O)NCCOCCOCCC(=O)NC(CSC2CC(=O)N(C3=CC(C(=O)O)C(c4c5ccc(=O)cc-5oc5cc(O)ccc45)C=C3)C2=O)C(=O)O)c(NC2CCCCCCC2)c1F]

Additional embodiments are also described by the following enumerated clauses. Any of the following embodiments in combination with any applicable embodiments described in the Summary section, the Detailed Description of the Illustrative Embodiments section, the Examples section, or the claims of this patent application, are also contemplated.

1. A method of treatment of a cancer, the method comprising
   i) administering to a patient a compound, or a pharmaceutically acceptable salt thereof, wherein the compound comprises a small molecule ligand linked to a targeting moiety by a linker;
   ii) administering to the patient a first dose of a CAR T cell composition comprising CAR T cells wherein the CAR T cells comprise a CAR directed to the targeting moiety; and
   iii) administering to the patient a second dose of a CAR T cell composition comprising CAR T cells wherein the CAR T cells comprise the CAR directed to the targeting moiety.

2. The method of clause 1 wherein the ligand is selected from the group consisting of a folate, DUPA, an NK-1R ligand, a CAIX ligand, a ligand of gamma glutamyl transpeptidase, an NKG2D ligand, and a CCK2R ligand.

3. The method of any one of clauses 1 or 2 wherein the ligand is a folate.

4. The method of any one of clauses 1 or 2 wherein the ligand is an NK-1R ligand.

5. The method of any one of clauses 1 or 2 wherein the ligand is DUPA.

6. The method of any one of clauses 1 or 2 wherein the ligand is a CCK2R ligand.

7. The method of any one of clauses 1 or 2 wherein the ligand is a ligand of gamma glutamyl transpeptidase.

8. The method of any one of clauses 1 to 7 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

9. The method of any one of clauses 1 to 8 wherein the targeting moiety is FITC.

10. The method of any one of clauses 1 to 8 wherein the targeting moiety is DNP.

11. The method of any one of clauses 1 to 8 wherein the targeting moiety is TNP.

12. The method of any one of clauses 1 to 11 wherein the linker comprises polyethylene glycol (PEG), polyproline, a hydrophilic amino acid, a sugar, an unnatural peptidoglycan, a polyvinylpyrrolidone, pluronic F-127, or a combination thereof.

13. The method of any one of clauses 1 to 12 wherein the linker comprises PEG.

14. The method of any one of clauses 1 to 13 wherein the compound, or the pharmaceutically acceptable salt thereof, has the formula

B-L-T, wherein B represents the small molecule ligand, L represents the linker, and T represents the targeting moiety, and wherein L comprises a structure having the formula

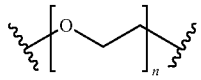

wherein n is an integer from 0 to 200.

15. The method of clause 14 wherein n is an integer from 0 to 150.

16. The method of clause 14 wherein n is an integer from 0 to 110.

17. The method of clause 14 wherein n is an integer from 0 to 20.

18. The method of clause 14 wherein n is an integer from 15 to 20.

19. The method of clause 14 wherein n is an integer from 15 to 110.

20. The method of any one of clauses 1 to 9 or 12 to 19 wherein the linker comprises PEG and the targeting moiety is FITC, or a pharmaceutically acceptable salt thereof.

21. The method of any one of clauses 1 to 20 wherein the compound, or the pharmaceutically acceptable salt thereof, is administered at a dose of about 10 nmoles/kg to about 10000 nmoles/kg of body weight of the patient.

22. The method of any one of clauses 1 to 21 wherein the compound, or the pharmaceutically acceptable salt thereof, is administered at a dose of about 10 nmoles/kg to about 5000 nmoles/kg of body weight of the patient.

23. The method of any one of clauses 1 to 22 wherein the compound, or the pharmaceutically acceptable salt thereof, is administered at a dose of about 10 nmoles/kg to about 1000 nmoles/kg of body weight of the patient.

24. The method of any one of clauses 1 to 23 wherein the compound, or the pharmaceutically acceptable salt thereof, is administered at a dose of about 10 nmoles/kg to about 600 nmoles/kg of body weight of the patient.

25. The method of any one of clauses 1 to 24 wherein the compound, or the pharmaceutically acceptable salt thereof, is administered at a dose of about 200 nmoles/kg to about 600 nmoles/kg of body weight of the patient.

26. The method of any one of clauses 1 to 25 wherein the compound, or the pharmaceutically acceptable salt thereof, is administered at a dose of about 250 nmoles/kg to about 600 nmoles/kg of body weight of the patient.

27. The method of any one of clauses 1 to 26 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

28. The method of any one of clauses 1 to 3 or 8 to 27 wherein the cancer is a folate receptor expressing cancer.

29. The method of clause 28 wherein the cancer is an endometrial cancer.

30. The method of clause 28 wherein the cancer is a non-small cell lung cancer.

31. The method of clause 28 wherein the cancer is an ovarian cancer.

32. The method of clause 28 wherein the cancer is a triple negative breast cancer.

33. The method of any one of clauses 1 to 32 wherein the CAR has a recognition region and the recognition region is a single chain fragment variable (scFv) region of an antibody.

34. The method of any one of clauses 1 to 9 or 12 to 33 wherein the CAR has a recognition region and the recognition region of the CAR is a single chain fragment variable (scFv) region of an anti-FITC antibody.

35. The method of any one of clauses 1 to 34 wherein the CAR has a co-stimulation domain and the co-stimulation domain is selected from the group consisting of CD28, CD137 (4-1BB), CD134 (OX40), and CD278 (ICOS).

36. The method of any one of clauses 1 to 35 wherein the CAR has an activation signaling domain and the activation signaling domain is a T cell CD31 chain or an Fc receptor γ.

37. The method of any one of clauses 1 to 9 or 12 to 36 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

38. The method of any one of clauses 1 to 37 wherein multiple doses of the compound, or the pharmaceutically acceptable salt thereof, and the CAR T cell composition are administered.

39. The method of any one of clauses 1 to 38 wherein the patient is imaged prior to administration of the compound, or the pharmaceutically acceptable salt thereof, or prior to administration of the CAR T cell composition.

40. The method of any one of clauses 1 to 39 wherein the compound, or the pharmaceutically acceptable salt thereof, is not an antibody, and does not comprise a fragment of an antibody.

41. The method of any one of clauses 1 to 40 wherein the targeting moiety does not comprise a peptide epitope.

42. The method of any one of clauses 1 to 41 wherein cytokine release resulting in off-target toxicity in the patient does not occur and wherein CAR T cell toxicity to the cancer occurs.

43. The method of any one of clauses 1 to 41 wherein off-target tissue toxicity does not occur in the patient and wherein CAR T cell toxicity to the cancer occurs.

44. The method of any one of clauses 1 to 41 wherein the cancer comprises a tumor, wherein tumor size is reduced in the patient, and wherein off-target toxicity does not occur.

45. The method of any one of clauses 1 to 44 wherein the CAR T cells comprise a nucleic acid comprising SEQ ID NO:1.

46. The method of any one of clauses 1 to 45 wherein the CAR T cells comprise a polypeptide comprising SEQ ID NO:2.

47. The method of clause 45 wherein the nucleic acid encodes a chimeric antigen receptor.

48. The method of any one of clauses 1 to 47 wherein the CAR comprises humanized amino acid sequences.

49. The method of any one of clauses 1 to 47 wherein the CAR consists of humanized amino acid sequences.

50. The method of any one of clauses 1 to 49 wherein the first dose of the CAR T cell composition comprises a mixture of the CAR T cells and non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

51. The method of any one of clauses 1 to 50 wherein the second dose of the CAR T cell composition comprises a mixture of the CAR T cells and non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

52. The method of any one of clauses 1 to 51 wherein the first dose of the CAR T cell composition comprises a mixture of the CAR T cells and non-transformed T cells in a ratio of from about 1:1 to about 1:5 of the CAR T cells to the non-transformed T cells.

53. The method of any one of clauses 1 to 52 wherein the second dose of the CAR T cell composition comprises a mixture of the CAR T cells and non-transformed T cells in a ratio of from about 1:1 to 1:5 of the CAR T cells to the non-transformed T cells.

54. The method of any one of clauses 1 to 53 wherein the first dose of the CAR T cell composition comprises a mixture of about 10 million of the CAR T cells and about 40 million non-transformed T cells.

55. The method of any one of clauses 1 to 54 wherein the second dose of the CAR T cell composition comprises a mixture of about 10 million of the CAR T cells and about 40 million non-transformed T cells.

56. A method of treatment of a cancer, the method comprising
i) administering to a patient a compound, or a pharmaceutically acceptable salt thereof, wherein the compound comprises a small molecule ligand linked to a targeting moiety by a linker; and
ii) administering to the patient a CAR T cell composition wherein the CAR T cell composition comprises CAR T cells, wherein the CAR T cells comprise a CAR directed to the targeting moiety, and wherein the CAR T cell composition comprises a mixture of the CAR T cells and non-transformed T cells.

57. The method of clause 56 wherein the ligand is selected from the group consisting of a folate, DUPA, an NK-1R ligand, a CAIX ligand, a ligand of gamma glutamyl transpeptidase, an NKG2D ligand, and a CCK2R ligand.

58. The method of any one of clauses 56 or 57 wherein the ligand is a folate.

59. The method of any one of clauses 56 or 57 wherein the ligand is an NK-1R ligand.

60. The method of any one of clauses 56 or 57 wherein the ligand is DUPA.

61. The method of any one of clauses 56 or 57 wherein the ligand is a CCK2R ligand.

62. The method of any one of clauses 56 or 57 wherein the ligand is a ligand of gamma glutamyl transpeptidase.

63. The method of any one of clauses 56 to 62 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

64. The method of any one of clauses 56 to 63 wherein the targeting moiety is FITC.

65. The method of any one of clauses 56 to 63 wherein the targeting moiety is DNP.

66. The method of any one of clauses 56 to 63 wherein the targeting moiety is TNP.

67. The method of any one of clauses 56 to 66 wherein the linker comprises polyethylene glycol (PEG), polyproline, a hydrophilic amino acid, a sugar, an unnatural peptidoglycan, a polyvinylpyrrolidone, pluronic F-127, or a combination thereof.

68. The method of any one of clauses 56 to 67 wherein the linker comprises PEG.

69. The method of any one of clauses 56 to 68 wherein the compound, or the pharmaceutically acceptable salt thereof, has the formula

B-L-T, wherein B represents the small molecule ligand, L represents the linker, and T represents the targeting moiety, and wherein L comprises a structure having the formula

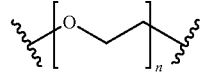

wherein n is an integer from 0 to 200.

70. The method of clause 69 wherein n is an integer from 0 to 150.

71. The method of clause 69 wherein n is an integer from 0 to 110.

72. The method of clause 69 wherein n is an integer from 0 to 20.

73. The method of clause 69 wherein n is an integer from 15 to 20.

74. The method of clause 69 wherein n is an integer from 15 to 110.

75. The method of any one of clauses 56 to 64 or 67 to 74 wherein the linker comprises PEG and the targeting moiety is FITC, or a pharmaceutically acceptable salt thereof.

76. The method of any one of clauses 56 to 75 wherein the compound, or the pharmaceutically acceptable salt thereof, is administered at a dose of about 10 nmoles/kg to about 10000 nmoles/kg of body weight of the patient.

77. The method of any one of clauses 56 to 76 wherein the compound, or the pharmaceutically acceptable salt thereof, is administered at a dose of about 10 nmoles/kg to about 5000 nmoles/kg of body weight of the patient.

78. The method of any one of clauses 56 to 77 wherein the compound, or the pharmaceutically acceptable salt thereof, is administered at a dose of about 10 nmoles/kg to about 1000 nmoles/kg of body weight of the patient.

79. The method of any one of clauses 56 to 78 wherein the compound, or the pharmaceutically acceptable salt thereof, is administered at a dose of about 10 nmoles/kg to about 600 nmoles/kg of body weight of the patient.

80. The method of any one of clauses 56 to 79 wherein the compound, or the pharmaceutically acceptable salt thereof, is administered at a dose of about 200 nmoles/kg to about 600 nmoles/kg of body weight of the patient.

81. The method of any one of clauses 56 to 80 wherein the compound, or the pharmaceutically acceptable salt thereof, is administered at a dose of about 250 nmoles/kg to about 600 nmoles/kg of body weight of the patient.

82. The method of any one of clauses 56 to 81 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

83. The method of any one of clauses 56 to 58 or 63 to 82 wherein the cancer is a folate receptor expressing cancer.

84. The method of clause 83 wherein the cancer is an endometrial cancer.

85. The method of clause 83 wherein the cancer is a non-small cell lung cancer.

86. The method of clause 83 wherein the cancer is an ovarian cancer.

87. The method of clause 83 wherein the cancer is a triple negative breast cancer.

88. The method of any one of clauses 56 to 87 wherein the CAR has a recognition region and the recognition region is a single chain fragment variable (scFv) region of an antibody.

89. The method of any one of clauses 56 to 64 or 67 to 88 wherein the CAR has a recognition region and the recognition region of the CAR is a single chain fragment variable (scFv) region of an anti-FITC antibody.

90. The method of any one of clauses 56 to 89 wherein the CAR has a co-stimulation domain and the co-stimulation domain is selected from the group consisting of CD28, CD137 (4-1BB), CD134 (OX40), and CD278 (ICOS).

91. The method of any one of clauses 56 to 90 wherein the CAR has an activation signaling domain and the activation signaling domain is a T cell CD3ζ chain or an Fc receptor γ.

92. The method of any one of clauses 56 to 64 or 67 to 91 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

93. The method of any one of clauses 56 to 92 wherein multiple doses of the compound, or the pharmaceutically acceptable salt thereof, are administered.

94. The method of any one of clauses 56 to 93 wherein the patient is imaged prior to administration of the compound, or the pharmaceutically acceptable salt thereof, or prior to administration of the CAR T cell composition.

95. The method of any one of clauses 56 to 94 wherein the compound, or the pharmaceutically acceptable salt thereof, is not an antibody, and does not comprise a fragment of an antibody.

96. The method of any one of clauses 56 to 95 wherein the targeting moiety does not comprise a peptide epitope.

97. The method of any one of clauses 56 to 96 wherein cytokine release resulting in off-target toxicity in the patient does not occur and wherein CAR T cell toxicity to the cancer occurs.

98. The method of any one of clauses 56 to 96 wherein off-target tissue toxicity does not occur in the patient and wherein CAR T cell toxicity to the cancer occurs.

99. The method of any one of clauses 56 to 96 wherein the cancer comprises a tumor, wherein tumor size is reduced in the patient, and wherein off-target toxicity does not occur.

100. The method of any one of clauses 56 to 99 wherein the CAR T cells comprise a nucleic acid comprising SEQ ID NO:1.

101. The method of any one of clauses 56 to 100 wherein the CAR T cells comprise a polypeptide comprising SEQ ID NO:2.

102. The method of clause 100 wherein the nucleic acid encodes a chimeric antigen receptor.

103. The method of any one of clauses 56 to 102 wherein the CAR comprises humanized amino acid sequences.

104. The method of any one of clauses 56 to 102 wherein the CAR consists of humanized amino acid sequences.

105. The method of any one of clauses 56 to 104 wherein the mixture of the CAR T cells and the non-transformed T cells is in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

106. The method of any one of clauses 56 to 105 wherein the mixture of the CAR T cells and the non-transformed T cells is in a ratio of from about 1:1 to about 1:5 of the CAR T cells to the non-transformed T cells.

107. The method of any one of clauses 56 to 106 wherein the mixture of the CAR T cells and the non-transformed T cells comprises about 10 million of the CAR T cells and about 40 million of the non-transformed T cells.

108. A method of treatment of a cancer, the method comprising
i) administering to a patient a compound, or a pharmaceutically acceptable salt thereof, wherein the compound comprises a small molecule ligand linked to a targeting moiety by a linker;
ii) administering to the patient a CAR T cell composition wherein the CAR T cell composition comprises CAR T cells and wherein the CAR T cells comprise a CAR directed to the targeting moiety; and
iii) administering to the patient a folate, a conjugate comprising a folate wherein the conjugate comprising a folate does not comprise a targeting moiety, or an agent that inhibits activation of the CAR T cells.

109. The method of clause 108 wherein step iii comprises administering a folate.

110. The method of any one of clauses 108 or 109 wherein step iii comprises administering folic acid or leucovorin.

111. The method of clause 108 wherein step iii comprises administering the conjugate comprising a folate.

112. The method of clause 111 wherein the conjugate comprising a folate comprises a folate linked to one or more amino acids.

113. The method of clause 111 wherein the conjugate comprising a folate has the formula

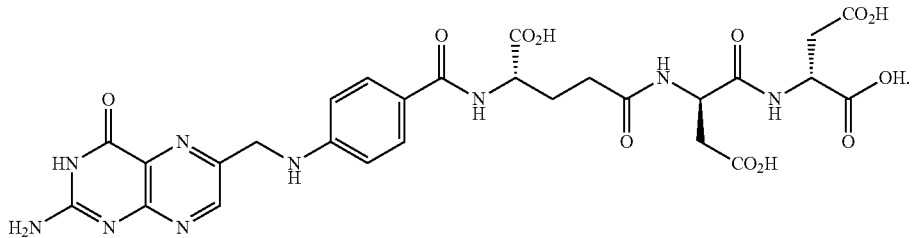 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

114. The method of any one of clauses 109 to 112 wherein the folate has the formula

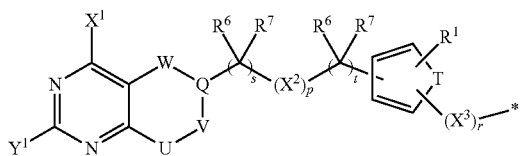

wherein $X^1$ and Y are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$) ($R^{7b}$)—, —N(C≡CH)—, —N(CH$_2$C≡CH)—, C$_1$-C$_{12}$ alkylene, and C$_1$-C$_{12}$ alkyneoxy, where Z is oxygen or sulfur;

$R^1$ is selected-from the group consisting of hydrogen, halo, C$_1$-C$_{12}$ alkyl, and C$_1$-C$_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, C$_1$-C$_{12}$ alkyl, C$_1$-C$_{12}$ alkoxy, C$_1$-C$_{12}$ alkanoyl, C$_1$-C$_{12}$ alkenyl, C$_1$-C$_{12}$ alkynyl, (C$_1$-C$_{12}$ alkoxy)carbonyl, and (C$_1$-C$_{12}$ alkylamino)carbonyl;

$R^6$ and $R^7$ are each independently selected from the group consisting of hydrogen, halo, C$_1$-C$_{12}$ alkyl, and C$_1$-C$_{12}$ alkoxy; or, $R^6$ and $R^7$ are taken together to form a carbonyl group;

$R^{6a}$ and $R^{7a}$ are each independently selected from the group consisting of hydrogen, halo, C$_1$-C$_{12}$ alkyl, and C$_1$-C$_{12}$ alkoxy; or $R^{6a}$ and $R^{7a}$ are taken together to form a carbonyl group;

p, r, s, and t are each independently either 0 or 1; and

* represents an optional covalent bond to the rest of the conjugate, if any additional chemical moieties are part of the folate.

115. The method of any one of clauses 108 to 114 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

116. The method of any one of clauses 108 to 115 wherein the targeting moiety is FITC.

117. The method of any one of clauses 108 to 115 wherein the targeting moiety is DNP.

118. The method of any one of clauses 108 to 115 wherein the targeting moiety is TNP.

119. The method of any one of clauses 108 to 118 wherein the linker comprises polyethylene glycol (PEG), polyproline, a hydrophilic amino acid, a sugar, an unnatural peptidoglycan, a polyvinylpyrrolidone, pluronic F-127, or a combination thereof.

120. The method of any one of clauses 108 to 119 wherein the linker comprises PEG.

121. The method of any one of clauses 108 to 120 wherein the compound, or the pharmaceutically acceptable salt thereof, has the formula

B-L-T, wherein B represents the small molecule ligand, L represents the linker, and T represents the targeting moiety, and wherein L comprises a structure having the formula

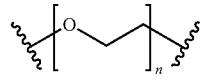

wherein n is an integer from 0 to 200.

122. The method of clause 121 wherein n is an integer from 0 to 12.

123. The method of clause 121 wherein n is an integer from 0 to 150.

124. The method of clause 121 wherein n is an integer from 0 to 110.

125. The method of clause 121 wherein n is an integer from 0 to 20.

126. The method of clause 121 wherein n is an integer from 15 to 20.

127. The method of clause 121 wherein n is an integer from 15 to 110.

128. The method of any one of clauses 108 to 116 or 119 to 127 wherein the linker comprises PEG and the targeting moiety is FITC, or a pharmaceutically acceptable salt thereof.

129. The method of any one of clauses 108 to 128 wherein the compound, or the pharmaceutically acceptable salt thereof, is administered at a dose of about 10 nmoles/kg to about 10000 nmoles/kg of body weight of the patient.

130. The method of any one of clauses 108 to 129 wherein the compound, or the pharmaceutically acceptable salt thereof, is administered at a dose of about 10 nmoles/kg to about 5000 nmoles/kg of body weight of the patient.

131. The method of any one of clauses 108 to 130 wherein the compound, or the pharmaceutically acceptable salt thereof, is administered at a dose of about 10 nmoles/kg to about 1000 nmoles/kg of body weight of the patient.

132. The method of any one of clauses 108 to 131 wherein the compound, or the pharmaceutically acceptable salt thereof, is administered at a dose of about 10 nmoles/kg to about 600 nmoles/kg of body weight of the patient.

133. The method of any one of clauses 108 to 132 wherein the compound, or the pharmaceutically acceptable salt thereof, is administered at a dose of about 200 nmoles/kg to about 600 nmoles/kg of body weight of the patient.

134. The method of any one of clauses 108 to 133 wherein the compound, or the pharmaceutically acceptable salt thereof, is administered at a dose of about 250 nmoles/kg to about 600 nmoles/kg of body weight of the patient.

135. The method of any one of clauses 108 to 134 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

136. The method of any one of clauses 108 to 135 wherein the ligand portion of the small molecule ligand linked to a targeting moiety by a linker is a folate and the cancer is a folate receptor expressing cancer.

137. The method of clause 136 wherein the cancer is an endometrial cancer.

138. The method of clause 136 wherein the cancer is a non-small cell lung cancer.

139. The method of clause 136 wherein the cancer is an ovarian cancer.

140. The method of clause 136 wherein the cancer is a triple negative breast cancer.

141. The method of any one of clauses 108 to 140 wherein the CAR has a recognition region and the recognition region is a single chain fragment variable (scFv) region of an antibody.

142. The method of any one of clauses 108 to 116 or 119 to 141 wherein the CAR has a recognition region and the recognition region of the CAR is a single chain fragment variable (scFv) region of an anti-FITC antibody.

143. The method of any one of clauses 108 to 142 wherein the CAR has a co-stimulation domain and the co-stimulation domain is selected from the group consisting of CD28, CD137 (4-1BB), CD134 (OX40), and CD278 (ICOS).

144. The method of any one of clauses 108 to 143 wherein the CAR has an activation signaling domain and the activation signaling domain is a T cell CD31 chain or an Fc receptor γ.

145. The method of any one of clauses 108 to 116 or 119 to 144 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

146. The method of any one of clauses 108 to 145 wherein multiple doses of the compound, or the pharmaceutically acceptable salt thereof, and/or the CAR T cell composition are administered.

147. The method of any one of clauses 108 to 146 wherein the patient is imaged prior to administration of the compound, or the pharmaceutically acceptable salt thereof, or prior to administration of the CAR T cell composition.

148. The method of any one of clauses 108 to 147 wherein the compound, or the pharmaceutically acceptable salt thereof, is not an antibody, and does not comprise a fragment of an antibody.

149. The method of any one of clauses 108 to 148 wherein the targeting moiety does not comprise a peptide epitope.

150. The method of any one of clauses 108 to 149 wherein cytokine release resulting in off-target toxicity in the patient does not occur and wherein CAR T cell toxicity to the cancer occurs.

151. The method of any one of clauses 108 to 149 wherein off-target tissue toxicity does not occur in the patient and wherein CAR T cell toxicity to the cancer occurs.

152. The method of any one of clauses 108 to 149 wherein the cancer comprises a tumor, wherein tumor size is reduced in the patient, and wherein off-target toxicity does not occur.

153. The method of any one of clauses 108 to 152 wherein the CAR T cells comprise a nucleic acid comprising SEQ ID NO:1.

154. The method of any one of clauses 108 to 153 wherein the CAR T cells comprise a polypeptide comprising SEQ ID NO:2.

155. The method of clause 153 wherein the nucleic acid encodes a chimeric antigen receptor.

156. The method of any one of clauses 108 to 155 wherein the CAR comprises humanized amino acid sequences.

157. The method of any one of clauses 108 to 155 wherein the CAR consists of humanized amino acid sequences.

158. The method of any one of clauses 108 to 157 wherein the CAR T cell composition comprises a mixture of the CAR T cells and non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

159. The method of any one of clauses 108 to 158 wherein the CAR T cell composition comprises a mixture of the CAR T cells and non-transformed T cells in a ratio of from about 1:1 to about 1:5 of the CAR T cells to the non-transformed T cells.

160. The method of any one of clauses 108 to 159 wherein the CAR T cell composition comprises a mixture comprising about 10 million of the CAR T cells and about 40 million of the non-transformed T cells.

161. The method of any one of clauses 108 to 160 wherein the agent that inhibits activation of the CAR T cells is selected from the group consisting of a lymphocyte-specific protein tyrosine kinase inhibitor, a PI3 kinase inhibitor, an inhibitor of an IL-2 inducible T cell kinase, a JAK inhibitor, a BTK inhibitor, EC2319, and an agent that blocks CAR T cell binding to the compound, or the pharmaceutically acceptable salt thereof, but does not bind to the cancer.

162. The method of clause 161 wherein the agent that inhibits activation of the CAR T cells is administered and the agent is a lymphocyte-specific protein tyrosine kinase inhibitor.

163. The method of clause 162 wherein the lymphocyte-specific protein tyrosine kinase inhibitor is Dasatinib.

164. The method of clause 161 wherein the agent that inhibits activation of the CAR T cells is administered and the agent is a PI3 kinase inhibitor.

165. The method of clause 164 wherein the PI3 kinase inhibitor is GDC0980.

166. The method of clause 161 wherein the agent that inhibits activation of the CAR T cells is administered and the agent is an IL-2 inducible T cell kinase inhibitor.

167. The method of clause 166 wherein the IL-2 inducible T cell kinase inhibitor is BMS-509744.

168. The method of any one of clauses 1 to 160 wherein the CAR T cell composition is administered by injection into the patient's bloodstream, and wherein the CAR T cells in the patient's bloodstream are at least 10 percent of the patient's total T cells in the patient's bloodstream by about four weeks after injection of the CAR T cell composition.

169. The method of any one of clauses 1 to 160 wherein the CAR T cell composition is administered by injection into the patient's bloodstream, and wherein the CAR T cells in the patient's bloodstream are at least 12 percent of the patient's total T cells in the patient's bloodstream by about four weeks after injection of the CAR T cell composition.

170. The method of any one of clauses 1 to 160 wherein the CAR T cell composition is administered by injection into the patient's bloodstream, and wherein the CAR T cells in the patient's bloodstream are at least 15 percent of the patient's total T cells in the patient's bloodstream by about four weeks after injection of the CAR T cell composition.

171. The method of any one of clauses 1 to 160 or 168 to 170 wherein the CAR T cells administered to the patient in the CAR T cell composition comprise from about 1 million to about 15 million of the CAR T cells.

172. The method of any one of clauses 1 to 160 or 168 to 171 wherein the dose of the CAR T cells administered to the patient in the CAR T cell composition is selected from the group consisting of about 1 million, about 2 million, about 3 million, about 4 million, about 5 million, about 6 million, about 7 million, about 8 million, about 9 million, about 10 million, about 11 million, about 12 million, about 12.5 million, about 13 million, about 14 million, and about 15 million of the CAR T cells.

173. The method of any one of clauses 1 to 160 or 168 to 170 wherein the CAR T cells administered to the patient in the CAR T cell composition comprise at least about 2 million of the CAR T cells.

174. The method of any one of clauses 1 to 160 or 168 to 170 wherein the CAR T cells administered to the patient in the CAR T cell composition comprise at least about 5 million of the CAR T cells.

175. The method of any one of clauses 1 to 160 or 168 to 170 wherein the CAR T cells administered to the patient in the CAR T cell composition comprise at least about 10 million of the CAR T cells.

176. The method of any one of clauses 1 to 175 wherein the CAR T cells comprise a nucleic acid comprising SEQ ID NO:3.

177. The method of any one of clauses 1 to 176 wherein the CAR T cells comprise a vector comprising SEQ ID NO: 1.

178. The method of any one of clauses 1 to 177 wherein the CAR T cells comprise a vector comprising SEQ ID NO:3.

179. The method of clause 176 wherein the nucleic acid encodes a chimeric antigen receptor.

180. The method of any one of clauses 108 to 160 wherein the agent that inhibits activation of the CAR T cells is administered and is an agent that blocks CAR T cell binding to the compound, or the pharmaceutically acceptable salt thereof, but does not bind to the cancer.

181. The method of clause 180 wherein the agent is fluoresceinamine, FITC, or sodium fluorescein.

182. The method of clause 180 wherein the agent is FITC.

183. A method of treatment of a cancer, the method comprising
i) administering to a patient a compound, or a pharmaceutically acceptable salt thereof, wherein the compound comprises a small molecule ligand linked to a targeting moiety by a linker, and wherein the compound, or the pharmaceutically acceptable salt thereof, is at a dose of about 10 nmoles/kg of body weight of the patient to about 2500 nmoles/kg of body weight of the patient; and
ii) administering to the patient a CAR T cell composition comprising CAR T cells wherein the CAR T cells comprise a CAR directed to the targeting moiety, and wherein the CAR T cells are at a dose of about 1 million of the CAR T cells to about 15 million of the CAR T cells.

184. The method of clause 183 wherein the ligand is selected from the group consisting of a folate, DUPA, an NK-1R ligand, a CAIX ligand, a ligand of gamma glutamyl transpeptidase, an NKG2D ligand, and a CCK2R ligand.

185. The method of any one of clauses 183 or 184 wherein the ligand is a folate.

186. The method of any one of clauses 183 to 185 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

187. The method of any one of clauses 183 to 186 wherein the targeting moiety is FITC.

188. The method of any one of clauses 183 to 187 wherein the linker comprises polyethylene glycol (PEG), polyproline, a hydrophilic amino acid, a sugar, an unnatural peptidoglycan, a polyvinylpyrrolidone, pluronic F-127, or a combination thereof.

189. The method of any one of clauses 183 to 188 wherein the linker comprises PEG.

190. The method of any one of clauses 183 to 189 wherein the compound, or the pharmaceutically acceptable salt thereof, has the formula

B-L-T, wherein B represents the small molecule ligand, L represents the linker, and T represents the targeting moiety, and wherein L comprises a structure having the formula

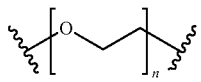

wherein n is an integer from 0 to 200.

191. The method of any one of clauses 183 to 190 wherein the linker comprises PEG and the targeting moiety is FITC, or a pharmaceutically acceptable salt thereof.

192. The method of any one of clauses 183 to 191 wherein the compound, or the pharmaceutically acceptable salt thereof, is administered at a dose of about 10 nmoles/kg to about 100 nmoles/kg of body weight of the patient.

193. The method of any one of clauses 183 to 191 wherein the compound, or the pharmaceutically acceptable salt thereof, is administered at a dose of about 10 nmoles/kg to about 50 nmoles/kg of body weight of the patient.

194. The method of any one of clauses 183 to 191 wherein the compound, or the pharmaceutically acceptable salt thereof, is administered at a dose of about 10 nmoles/kg to about 20 nmoles/kg of body weight of the patient.

195. The method of any one of clauses 183 to 191 wherein the compound, or the pharmaceutically acceptable salt thereof, is administered at a dose of about 10 nmoles/kg to about 600 nmoles/kg of body weight of the patient.

196. The method of any one of clauses 183 to 191 wherein the compound, or the pharmaceutically acceptable salt thereof, is administered at a dose of about 200 nmoles/kg to about 600 nmoles/kg of body weight of the patient.

197. The method of any one of clauses 183 to 191 wherein the compound, or the pharmaceutically acceptable salt thereof, is administered at a dose of about 400 nmoles/kg to about 600 nmoles/kg of body weight of the patient.

198. The method of any one of clauses 183 to 197 wherein the CAR T cells are at a dose of about 1 million of the CAR T cells to about 12.5 million of the CAR T cells.

199. The method of any one of clauses 183 to 197 wherein the CAR T cells are at a dose of about 1 million of the CAR T cells to about 7 million of the CAR T cells.

200. The method of any one of clauses 183 to 197 wherein the CAR T cells are at a dose of about 1 million of the CAR T cells to about 5 million of the CAR T cells.

201. The method of any one of clauses 183 to 197 wherein the CAR T cells are at a dose of about 2 million of the CAR T cells to about 5 million of the CAR T cells.

202. The method of any one of clauses 183 to 201 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

203. The method of any one of clauses 183 to 202 wherein the cancer is a folate receptor expressing cancer.

204. The method of any one of clauses 183 to 203 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

205. The method of any one of clauses 183 to 204 wherein the compound, or the pharmaceutically acceptable salt thereof, is not an antibody, and does not comprise a fragment of an antibody.

206. The method of any one of clauses 183 to 205 wherein the targeting moiety does not comprise a peptide epitope.

207. The method of any one of clauses 183 to 206 wherein cytokine release resulting in off-target toxicity in the patient does not occur and wherein CAR T cell toxicity to the cancer occurs.

208. The method of any one of clauses 183 to 206 wherein off-target tissue toxicity does not occur in the patient and wherein CAR T cell toxicity to the cancer occurs.

209. The method of any one of clauses 183 to 206 wherein the cancer comprises a tumor, wherein tumor size is reduced in the patient, and wherein off-target toxicity does not occur.

210. The method of any one of clauses 183 to 209 wherein the CAR T cells comprise a nucleic acid comprising SEQ ID NO:1.

211. The method of any one of clauses 183 to 209 wherein the CAR T cells comprise a polypeptide comprising SEQ ID NO:2.

212. The method of any one of clauses 183 to 211 wherein the CAR comprises humanized amino acid sequences.

213. The method of any one of clauses 183 to 212 wherein the CAR consists of humanized amino acid sequences.

214. The method of any one of clauses 183 to 213 wherein the CAR T cell composition further comprises non-transformed T cells.

215. A method of treatment of a cancer, the method comprising
  i) administering continuously to a patient a compound, or a pharmaceutically acceptable salt thereof, wherein the compound comprises a small molecule ligand linked to a targeting moiety by a linker;
  ii) administering to the patient a CAR T cell composition comprising CAR T cells wherein the CAR T cells comprise a CAR directed to the targeting moiety; and
  iii) ending the continuous administration of the compound, or the pharmaceutically acceptable salt thereof, to inhibit or prevent cytokine release syndrome in the patient.

216. The method of clause 215 wherein the ligand is selected from the group consisting of a folate, DUPA, an NK-1R ligand, a CAIX ligand, a ligand of gamma glutamyl transpeptidase, an NKG2D ligand, and a CCK2R ligand.

217. The method of any one of clauses 215 or 216 wherein the ligand is a folate.

218. The method of any one of clauses 215 to 217 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

219. The method of any one of clauses 215 to 218 wherein the targeting moiety is FITC.

220. The method of any one of clauses 215 to 219 wherein the linker comprises polyethylene glycol (PEG), polyproline, a hydrophilic amino acid, a sugar, an unnatural peptidoglycan, a polyvinylpyrrolidone, pluronic F-127, or a combination thereof.

221. The method of any one of clauses 215 to 220 wherein the linker comprises PEG.

222. The method of any one of clauses 215 to 221 wherein the compound, or the pharmaceutically acceptable salt thereof, has the formula

B-L-T, wherein B represents the small molecule ligand, L represents the linker, and T represents the targeting moiety, and wherein L comprises a structure having the formula

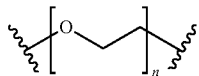

wherein n is an integer from 0 to 200.

223. The method of any one of clauses 215 to 222 wherein the linker comprises PEG and the targeting moiety is FITC, or a pharmaceutically acceptable salt thereof.

224. The method of any one of clauses 215 to 223 wherein the compound, or the pharmaceutically acceptable salt thereof, is administered continuously for at least one hour to the patient.

225. The method of any one of clauses 215 to 223 wherein the compound, or the pharmaceutically acceptable salt thereof, is administered continuously for at least four hours to the patient.

226. The method of any one of clauses 215 to 223 wherein the compound, or the pharmaceutically acceptable salt thereof, is administered continuously for at least six hours to the patient.

227. The method of any one of clauses 215 to 223 wherein the continuous administration of the compound, or the pharmaceutically acceptable salt thereof, is a regimen of administration every other day.

228. The method of any one of clauses 215 to 223 wherein the continuous administration of the compound, or the pharmaceutically acceptable salt thereof, is a regimen of administration three times weekly.

229. The method of any one of clauses 215 to 223 wherein the continuous administration of the compound, or the pharmaceutically acceptable salt thereof, is administration until an unacceptable loss of body weight of the patient, a fever, a drop in blood pressure, or pulmonary edema occurs.

230. The method of any one of clauses 215 to 229 wherein the compound, or the pharmaceutically acceptable salt thereof, is administered at a dose of about 200 nmoles/kg to about 600 nmoles/kg of body weight of the patient.

231. The method of any one of clauses 215 to 229 wherein the compound, or the pharmaceutically acceptable salt thereof, is administered at a dose of about 400 nmoles/kg to about 600 nmoles/kg of body weight of the patient.

232. The method of any one of clauses 215 to 231 wherein about 2 million to about 5 million of the CAR T cells are administered.

233. The method of any one of clauses 215 to 232 wherein the administration is by intravenous administration.

234. The method of any one of clauses 215 to 233 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

235. The method of any one of clauses 215 to 234 wherein the cancer is a folate receptor expressing cancer.

236. The method of any one of clauses 215 to 235 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

237. The method of any one of clauses 215 to 236 wherein the compound, or the pharmaceutically acceptable salt thereof, is not an antibody, and does not comprise a fragment of an antibody.

238. The method of any one of clauses 215 to 237 wherein the targeting moiety does not comprise a peptide epitope.

239. The method of any one of clauses 215 to 238 wherein cytokine release resulting in off-target toxicity in the patient does not occur and wherein CAR T cell toxicity to the cancer occurs.

240. The method of any one of clauses 215 to 238 wherein off-target tissue toxicity does not occur in the patient and wherein CAR T cell toxicity to the cancer occurs.

241. The method of any one of clauses 215 to 238 wherein the cancer comprises a tumor, wherein tumor size is reduced in the patient, and wherein off-target toxicity does not occur.

242. The method of any one of clauses 215 to 241 wherein the CAR T cells comprise a nucleic acid comprising SEQ ID NO:1.

243. The method of any one of clauses 215 to 242 wherein the CAR T cells comprise a polypeptide comprising SEQ ID NO:2.

244. The method of any one of clauses 215 to 243 wherein the CAR comprises humanized amino acid sequences.

245. The method of any one of clauses 215 to 243 wherein the CAR consists of humanized amino acid sequences.

246. The method of any one of clauses 215 to 245 wherein the CAR T cell composition further comprises non-transformed T cells.

247. The method of any one of clauses 215 to 246 wherein the CAR T cell composition further comprises non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

248. The method of any one of clauses 215 to 247 wherein the CAR T cell composition further comprises non-transformed T cells in a ratio of from about 1:1 to about 1:5 of the CAR T cells to the non-transformed T cells.

249. The method of any one of clauses 215 to 248 wherein the CAR T cell composition further comprises non-transformed T cells in a mixture of about 10 million of the CAR T cells and about 40 million non-transformed T cells.

250. The method of any one of clauses 215 to 249 wherein the cancer is a non-small cell lung cancer.

251. The method of any one of clauses 215 to 249 wherein the cancer is an ovarian cancer.

252. A method of treatment of a cancer, the method comprising
i) administering to a patient a compound, or a pharmaceutically acceptable salt thereof, wherein the compound comprises a small molecule ligand linked to a targeting moiety by a linker and wherein the compound, or the pharmaceutically acceptable salt thereof, is administered once weekly to the patient; and
ii) administering to the patient a CAR T cell composition comprising CAR T cells wherein the CAR T cells comprise a CAR directed to the targeting moiety.

253. The method of clause 252 wherein the ligand is selected from the group consisting of a folate, DUPA, an NK-1R ligand, a CAIX ligand, a ligand of gamma glutamyl transpeptidase, an NKG2D ligand, and a CCK2R ligand.

254. The method of any one of clauses 252 or 253 wherein the ligand is a folate.

255. The method of any one of clauses 252 to 254 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

256. The method of any one of clauses 252 to 255 wherein the targeting moiety is FITC.

257. The method of any one of clauses 252 to 256 wherein the linker comprises polyethylene glycol (PEG), polyproline, a hydrophilic amino acid, a sugar, an unnatural peptidoglycan, a polyvinylpyrrolidone, pluronic F-127, or a combination thereof.

258. The method of any one of clauses 252 to 257 wherein the linker comprises PEG.

259. The method of any one of clauses 252 to 258 wherein the compound, or the pharmaceutically acceptable salt thereof, has the formula

B-L-T, wherein B represents the small molecule ligand, L represents the linker, and T represents the targeting moiety, and wherein L comprises a structure having the formula

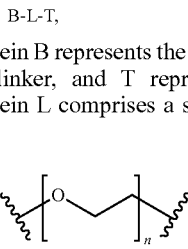

wherein n is an integer from 0 to 200.

260. The method of any one of clauses 252 to 259 wherein the linker comprises PEG and the targeting moiety is FITC, or a pharmaceutically acceptable salt thereof.

261. The method of any one of clauses 252 to 260 wherein the compound, or the pharmaceutically acceptable salt thereof, is administered at a dose of about 10 nmoles/kg to about 100 nmoles/kg of body weight of the patient.

262. The method of any one of clauses 252 to 261 wherein the compound, or the pharmaceutically acceptable salt thereof, is administered at a dose of about 10 nmoles/kg to about 50 nmoles/kg of body weight of the patient.

263. The method of any one of clauses 252 to 262 wherein the compound, or the pharmaceutically acceptable salt thereof, is administered at a dose of about 10 nmoles/kg to about 20 nmoles/kg of body weight of the patient.

264. The method of any one of clauses 252 to 263 wherein the compound, or the pharmaceutically acceptable salt thereof, is administered at a dose of about 10 nmoles/kg to about 600 nmoles/kg of body weight of the patient.

265. The method of any one of clauses 252 to 264 wherein the compound, or the pharmaceutically acceptable salt thereof, is administered at a dose of about 200 nmoles/kg to about 600 nmoles/kg of body weight of the patient.

266. The method of any one of clauses 252 to 265 wherein the compound, or the pharmaceutically acceptable salt thereof, is administered at a dose of about 400 nmoles/kg to about 600 nmoles/kg of body weight of the patient.

267. The method of any one of clauses 252 to 266 wherein the CAR T cells are at a dose of about 1 million of the CAR T cells to about 15 million of the CAR T cells.

268. The method of any one of clauses 252 to 267 wherein the CAR T cells are at a dose of about 1 million of the CAR T cells to about 7 million of the CAR T cells.

269. The method of any one of clauses 252 to 268 wherein the CAR T cells are at a dose of about 1 million of the CAR T cells to about 5 million of the CAR T cells.

270. The method of any one of clauses 252 to 269 wherein the CAR T cells are at a dose of about 2 million of the CAR T cells to about 5 million of the CAR T cells.

271. The method of any one of clauses 252 to 270 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

272. The method of any one of clauses 252 to 271 wherein the cancer is a folate receptor expressing cancer.

273. The method of any one of clauses 252 to 272 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

274. The method of any one of clauses 252 to 273 wherein the compound, or the pharmaceutically acceptable salt thereof, is not an antibody, and does not comprise a fragment of an antibody.

275. The method of any one of clauses 252 to 274 wherein the targeting moiety does not comprise a peptide epitope.

276. The method of any one of clauses 252 to 275 wherein cytokine release resulting in off-target toxicity in the patient does not occur and wherein CAR T cell toxicity to the cancer occurs.

277. The method of any one of clauses 252 to 275 wherein off-target tissue toxicity does not occur in the patient and wherein CAR T cell toxicity to the cancer occurs.

278. The method of any one of clauses 252 to 275 wherein the cancer comprises a tumor, wherein tumor size is reduced in the patient, and wherein off-target toxicity does not occur.

279. The method of any one of clauses 252 to 278 wherein the CAR T cells comprise a nucleic acid comprising SEQ ID NO:1.

280. The method of any one of clauses 252 to 278 wherein the CAR T cells comprise a polypeptide comprising SEQ ID NO:2.

281. The method of any one of clauses 252 to 280 wherein the CAR comprises humanized amino acid sequences.

282. The method of any one of clauses 252 to 280 wherein the CAR consists of humanized amino acid sequences.

283. The method of any one of clauses 252 to 282 wherein the CAR T cell composition further comprises non-transformed T cells.

284. A method of treatment of a cancer, the method comprising
  i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof; and
  ii) administering to the patient a CAR T cell composition comprising CAR T cells wherein the CAR T cells comprise a CAR directed to the targeting moiety.

285. The method of clause 284 wherein at least a first dose, a second dose, and a third dose of the compound, or the pharmaceutically acceptable salt thereof, are administered to the patient, wherein the first dose, the second dose, and the third dose are different, wherein the second dose of the compound, or the pharmaceutically acceptable salt thereof, is about 2-fold to about 750-fold greater in amount than the first dose of the compound, or the pharmaceutically acceptable salt thereof, and wherein the third dose of the compound, or the pharmaceutically acceptable salt thereof, is about 800-fold to about 10000-fold greater in amount than the first dose of the compound, or the pharmaceutically acceptable salt thereof.

286. The method of clause 285 wherein at least a first dose, a second dose, a third dose, and a fourth dose of the compound, or the pharmaceutically acceptable salt thereof, are administered to the patient, wherein the first dose, the second dose, the third dose, and the fourth dose are different, wherein the second dose of the compound, or the pharmaceutically acceptable salt thereof, is about 2-fold to about 750-fold greater in amount than the first dose of the compound, or the pharmaceutically acceptable salt thereof, wherein the third dose of the compound, or the pharmaceutically acceptable salt thereof, is about 800-fold to about 7500-fold greater in amount than the first dose of the compound, or the pharmaceutically acceptable salt thereof, and wherein the fourth dose of the compound, or the pharmaceutically acceptable salt thereof, is about 8000 to about 15000-fold greater in amount than the first dose of the compound, or the pharmaceutically acceptable salt thereof.

287. The method of clause 286 wherein the second dose of the compound, or the pharmaceutically acceptable salt thereof, is about 100-fold greater in amount than the first dose of the compound, or the pharmaceutically acceptable salt thereof, wherein the third dose of the compound, or the pharmaceutically acceptable salt thereof, is about 1000-fold greater in amount than the first dose of the compound, or the pharmaceutically acceptable salt thereof, and wherein the fourth dose of the compound, or the pharmaceutically acceptable salt thereof, is about 10000-fold greater in amount than the first dose of the compound, or the pharmaceutically acceptable salt thereof.

288. The method of any one of clauses 284 to 287 wherein the ligand is selected from the group consisting of a folate, DUPA, an NK-1R ligand, a CAIX ligand, a ligand of gamma glutamyl transpeptidase, an NKG2D ligand, and a CCK2R ligand.

289. The method of any one of clauses 284 to 288 wherein the ligand is a folate.

290. The method of any one of clauses 284 to 289 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

291. The method of any one of clauses 284 to 290 wherein the targeting moiety is FITC.

292. The method of any one of clauses 284 to 291 wherein the linker comprises polyethylene glycol (PEG), polyproline, a hydrophilic amino acid, a sugar, an unnatural peptidoglycan, a polyvinylpyrrolidone, pluronic F-127, or a combination thereof.

293. The method of any one of clauses 284 to 292 wherein the linker comprises PEG.

294. The method of any one of clauses 284 to 293 wherein the compound, or the pharmaceutically acceptable salt thereof, has the formula

wherein B represents the small molecule ligand, L represents the linker, and T represents the targeting moiety, and wherein L comprises a structure having the formula

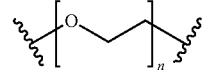

wherein n is an integer from 0 to 200.

295. The method of any one of clauses 284 to 294 wherein the linker comprises PEG and the targeting moiety is FITC, or a pharmaceutically acceptable salt thereof.

296. The method of any one of clauses 284 to 295 wherein the compound, or the pharmaceutically acceptable salt thereof, is administered at a dose of about 10 nmoles/kg to about 100 nmoles/kg of body weight of the patient.

297. The method of any one of clauses 284 to 296 wherein the compound, or the pharmaceutically acceptable salt 297. The method of any one of clauses 284 to 296 wherein the compound, or the pharmaceutically acceptable salt thereof, is administered at a dose of about 10 nmoles/kg to about 50 nmoles/kg of body weight of the patient.

298. The method of any one of clauses 284 to 297 wherein the compound, or the pharmaceutically acceptable salt thereof, is administered at a dose of about 10 nmoles/kg to about 20 nmoles/kg of body weight of the patient.

299. The method of any one of clauses 284 to 298 wherein the compound, or the pharmaceutically acceptable salt thereof, is administered at a dose of about 10 nmoles/kg to about 600 nmoles/kg of body weight of the patient.

300. The method of any one of clauses 284 to 299 wherein the compound, or the pharmaceutically acceptable salt thereof, is administered at a dose of about 200 nmoles/kg to about 600 nmoles/kg of body weight of the patient.

301. The method of any one of clauses 284 to 300 wherein the compound, or the pharmaceutically acceptable salt thereof, is administered at a dose of about 400 nmoles/kg to about 600 nmoles/kg of body weight of the patient.

302. The method of any one of clauses 284 to 301 wherein the CAR T cells are at a dose of about 1 million of the CAR T cells to about 15 million of the CAR T cells.

303. The method of any one of clauses 284 to 302 wherein the CAR T cells are at a dose of about 1 million of the CAR T cells to about 7 million of the CAR T cells.

304. The method of any one of clauses 284 to 303 wherein the CAR T cells are at a dose of about 1 million of the CAR T cells to about 5 million of the CAR T cells.

305. The method of any one of clauses 284 to 304 wherein the CAR T cells are at a dose of about 2 million of the CAR T cells to about 5 million of the CAR T cells.

306. The method of any one of clauses 284 to 305 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

307. The method of any one of clauses 284 to 306 wherein the cancer is a folate receptor expressing cancer.

308. The method of any one of clauses 284 to 307 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

309. The method of any one of clauses 284 to 308 wherein the compound, or the pharmaceutically acceptable salt thereof, is not an antibody, and does not comprise a fragment of an antibody.

310. The method of any one of clauses 284 to 309 wherein the targeting moiety does not comprise a peptide epitope.

311. The method of any one of clauses 284 to 310 wherein cytokine release resulting in off-target toxicity in the patient does not occur and wherein CAR T cell toxicity to the cancer occurs.

312. The method of any one of clauses 284 to 310 wherein off-target tissue toxicity does not occur in the patient and wherein CAR T cell toxicity to the cancer occurs.

313. The method of any one of clauses 284 to 310 wherein the cancer comprises a tumor, wherein tumor size is reduced in the patient, and wherein off-target toxicity does not occur.

314. The method of any one of clauses 284 to 313 wherein the CAR T cells comprise a nucleic acid comprising SEQ ID NO:1.

315. The method of any one of clauses 284 to 313 wherein the CAR T cells comprise a polypeptide comprising SEQ ID NO:2.

316. The method of any one of clauses 284 to 315 wherein the CAR comprises humanized amino acid sequences.

317. The method of any one of clauses 284 to 315 wherein the CAR consists of humanized amino acid sequences.

318. The method of any one of clauses 284 to 317 wherein the CAR T cell composition further comprises non-transformed T cells.

319. The method of any one of clauses 1 to 214 or 252 to 318 wherein the compound, or the pharmaceutically acceptable salt thereof, is administered continuously to the patient and the method further comprises ending the continuous administration of the compound, or the pharmaceutically acceptable salt thereof, to inhibit or prevent cytokine release syndrome in the patient.

320. The method of any one of clauses 1 to 107 or 183 to 318 further comprising administering to the patient a folate, a conjugate comprising a folate wherein the conjugate comprising a folate does not comprise a targeting moiety, or an agent that inhibits activation of the CAR T cells.

321. The method of any one of clauses 1 to 182 or 215 to 318 wherein the compound, or the pharmaceutically acceptable salt thereof, is at a dose of about 10 nmoles/kg of body weight of the patient to about 2500 nmoles/kg of body weight of the patient and the CAR T cells are at a dose of about 1 million of the CAR T cells to about 15 million of the CAR T cells.

322. The method of any one of clauses 1 to 251 or 284 to 318 wherein the compound, or the pharmaceutically acceptable salt thereof, is administered once weekly to the patient.

323. The method of any one of clauses 1 to 283 wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof.

324. The method of any one of clauses 56 to 318 wherein the CAR T cell composition is administered in at least two doses.

325. A method of treatment of a cancer, the method comprising
  i) administering to a patient a first dose of a compound, or a pharmaceutically acceptable salt thereof, wherein the compound comprises a small molecule ligand linked to a targeting moiety by a linker;
  ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof; and iii) administering to the patient a dose of a CAR T cell composition comprising CAR T cells wherein the CAR T cells comprise a CAR directed to the targeting moiety.

326. The method of clause 325 wherein the second dose of the compound, or the pharmaceutically acceptable salt thereof, is at least about 60 percent lower in amount than the first dose of the compound, or the pharmaceutically acceptable salt thereof.

327. The method of clause 325 wherein the second dose of the compound, or the pharmaceutically acceptable salt thereof, is at least about 70 percent lower in amount than the first dose of the compound, or the pharmaceutically acceptable salt thereof.

328. The method of clause 325 wherein the second dose of the compound, or the pharmaceutically acceptable salt thereof, is at least about 80 percent lower in amount than the first dose of the compound, or the pharmaceutically acceptable salt thereof.

329. The method of clause 325 wherein the second dose of the compound, or the pharmaceutically acceptable salt thereof, is at least about 90 percent lower in amount than the first dose of the compound, or the pharmaceutically acceptable salt thereof.

330. The method of clause 325 wherein the second dose of the compound, or the pharmaceutically acceptable salt thereof, is at least about 95 percent lower in amount than the first dose of the compound, or the pharmaceutically acceptable salt thereof.

331. The method of clause 325 wherein the second dose of the compound, or the pharmaceutically acceptable salt thereof, is at least about 96 percent lower in amount than the first dose of the compound, or the pharmaceutically acceptable salt thereof.

332. The method of clause 325 wherein the second dose of the compound, or the pharmaceutically acceptable salt thereof, is at least about 97 percent lower in amount than the first dose of the compound, or the pharmaceutically acceptable salt thereof.

333. The method of clause 325 wherein the second dose of the compound, or the pharmaceutically acceptable salt thereof, is at least about 98 percent lower in amount than the first dose of the compound, or the pharmaceutically acceptable salt thereof.

334. The method of clause 325 wherein the second dose of the compound, or the pharmaceutically acceptable salt thereof, is at least about 99 percent lower in amount than the first dose of the compound, or the pharmaceutically acceptable salt thereof.

335. The method of clause 325 wherein the second dose of the compound, or the pharmaceutically acceptable salt thereof, is at least about 99.5 percent lower in amount than the first dose of the compound, or the pharmaceutically acceptable salt thereof.

336. The method of any one of clauses 325 to 335 wherein the first dose of the compound, or the pharmaceutically acceptable salt thereof, is about 100 nmoles/kg to about 1000 nmoles/kg of body weight of the patient.

337. The method of any one of clauses 325 to 335 wherein the first dose of the compound, or the pharmaceutically acceptable salt thereof, is about 100 nmoles/kg to about 900 nmoles/kg of body weight of the patient.

338. The method of any one of clauses 325 to 335 wherein the first dose of the compound, or the pharmaceutically acceptable salt thereof, is about 100 nmoles/kg to about 800 nmoles/kg of body weight of the patient.

339. The method of any one of clauses 325 to 335 wherein the first dose of the compound, or the pharmaceutically acceptable salt thereof, is about 100 nmoles/kg to about 700 nmoles/kg of body weight of the patient.

340. The method of any one of clauses 325 to 335 wherein the first dose of the compound, or the pharmaceutically acceptable salt thereof, is about 100 nmoles/kg to about 600 nmoles/kg of body weight of the patient.

341. The method of any one of clauses 325 to 335 wherein the first dose of the compound, or the pharmaceutically acceptable salt thereof, is about 200 nmoles/kg to about 600 nmoles/kg of body weight of the patient.

342. The method of any one of clauses 325 to 335 wherein the first dose of the compound, or the pharmaceutically acceptable salt thereof, is about 400 nmoles/kg to about 600 nmoles/kg of body weight of the patient.

343. The method of any one of clauses 325 to 335 wherein the first dose of the compound, or the pharmaceutically acceptable salt thereof, is about 500 nmoles/kg of body weight of the patient.

344. The method of clause 336 wherein the second dose of the compound, or the pharmaceutically acceptable salt thereof, is about 0.5 nmoles/kg to about 500 nmoles/kg of body weight of the patient.

345. The method of clause 337 wherein the second dose of the compound, or the pharmaceutically acceptable salt thereof, is about 0.5 nmoles/kg to about 450 nmoles/kg of body weight of the patient.

346. The method of clause 338 wherein the second dose of the compound, or the pharmaceutically acceptable salt thereof, is about 0.5 nmoles/kg to about 400 nmoles/kg of body weight of the patient.

347. The method of clause 339 wherein the second dose of the compound, or the pharmaceutically acceptable salt thereof, is about 0.5 nmoles/kg to about 350 nmoles/kg of body weight of the patient.

348. The method of clause 340 wherein the second dose of the compound, or the pharmaceutically acceptable salt thereof, is about 0.5 nmoles/kg to about 300 nmoles/kg of body weight of the patient.

349. The method of clause 341 wherein the second dose of the compound, or the pharmaceutically acceptable salt thereof, is about 1 nmole/kg to about 300 nmoles/kg of body weight of the patient.

350. The method of clause 342 wherein the second dose of the compound, or the pharmaceutically acceptable salt thereof, is about 2 nmoles/kg to about 300 nmoles/kg of body weight of the patient.

351. The method of clause 343 wherein the second dose of the compound, or the pharmaceutically acceptable salt thereof, is about 2 nmoles/kg to about 250 nmoles/kg of body weight of the patient.

352. The method of any one of clauses 336 to 343 wherein the second dose of the compound, or the pharmaceutically acceptable salt thereof, is about 5 nmoles/kg to about 40 nmoles/kg of body weight of the patient.

353. The method of any one of clauses 336 to 343 wherein the second dose of the compound, or the pharmaceutically acceptable salt thereof, is about 40 nmoles/kg to about 150 nmoles/kg of body weight of the patient.

354. The method of any one of clauses 325 to 353 further comprising administering a third dose of the compound, or the pharmaceutically acceptable salt thereof, wherein the third dose of the compound, or the pharmaceutically acceptable salt thereof, is the same as the second dose of the compound, or the pharmaceutically acceptable salt thereof.

355. The method of clause 354 further comprising administering a fourth dose of the compound, or the pharmaceutically acceptable salt thereof, wherein the fourth dose of the compound, or the pharmaceutically acceptable salt thereof, is the same as the second dose, or the pharmaceutically acceptable salt thereof, and the third dose of the compound, or the pharmaceutically acceptable salt thereof.

356. The method of any one of clauses 325 to 355 wherein the dose(s) of the compound, or the pharmaceutically acceptable salt thereof, administered after the first dose of the compound, or the pharmaceutically acceptable salt thereof, maintain inhibition of growth of the cancer relative to the first dose of the compound, or the pharmaceutically acceptable salt thereof.

357. The method of any one of clauses 325 to 356 wherein the CAR T cells are administered at a dose of about 1 million of the CAR T cells to about 40 million of the CAR T cells.

358. The method of any one of clauses 325 to 357 wherein the dose(s) of the compound, or the pharmaceutically acceptable salt thereof, administered after the first dose of the compound, or the pharmaceutically acceptable salt thereof, are administered once weekly.

359. The method of any one of clauses 325 to 357 wherein the dose(s) of the compound, or the pharmaceutically acceptable salt thereof, are administered twice weekly.

360. The method of any one of clauses 325 to 359 wherein the ligand is selected from the group consisting of a folate, DUPA, an NK-1R ligand, a CAIX ligand, a ligand of gamma glutamyl transpeptidase, an NKG2D ligand, and a CCK2R ligand.

361. The method of any one of clauses 325 to 360 wherein the ligand is a folate.

362. The method of any one of clauses 325 to 360 wherein the ligand is an NK-1R ligand.

363. The method of any one of clauses 325 to 360 wherein the ligand is DUPA.

364. The method of any one of clauses 325 to 360 wherein the ligand is a CCK2R ligand.

365. The method of any one of clauses 325 to 360 wherein the ligand is a ligand of gamma glutamyl transpeptidase.

366. The method of any one of clauses 325 to 365 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

367. The method of any one of clauses 325 to 366 wherein the targeting moiety is FITC.

368. The method of any one of clauses 325 to 366 wherein the targeting moiety is DNP.

369. The method of any one of clauses 325 to 366 wherein the targeting moiety is TNP.

370. The method of any one of clauses 325 to 369 wherein the linker comprises polyethylene glycol (PEG), polyproline, a hydrophilic amino acid, a sugar, an unnatural peptidoglycan, a polyvinylpyrrolidone, pluronic F-127, or a combination thereof.

371. The method of any one of clauses 325 to 370 wherein the linker comprises PEG.

372. The method of any one of clauses 325 to 371 wherein the compound, or the pharmaceutically acceptable salt thereof, has the formula

B-L-T, wherein B represents the small molecule ligand, L represents the linker, and T represents the targeting moiety, and wherein L comprises a structure having the formula

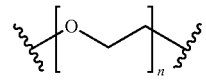

wherein n is an integer from 0 to 200.

373. The method of clause 372 wherein n is an integer from 0 to 150.

374. The method of clause 372 wherein n is an integer from 0 to 110.

375. The method of clause 372 wherein n is an integer from 0 to 20.

376. The method of clause 372 wherein n is an integer from 15 to 20.

377. The method of clause 372 wherein n is an integer from 15 to 110.

378. The method of any one of clauses 325 to 367 or 370 to 377 wherein the linker comprises PEG and the targeting moiety is FITC, or a pharmaceutically acceptable salt thereof.

379. The method of any one of clauses 325 to 378 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

380. The method of any one of clauses 325 to 361 or 366 to 379 wherein the cancer is a folate receptor expressing cancer.

381. The method of clause 380 wherein the cancer is an endometrial cancer.

382. The method of clause 380 wherein the cancer is a non-small cell lung cancer.

383. The method of clause 380 wherein the cancer is an ovarian cancer.

384. The method of clause 380 wherein the cancer is a triple negative breast cancer.

385. The method of any one of clauses 325 to 384 wherein the CAR has a recognition region and the recognition region is a single chain fragment variable (scFv) region of an antibody.

386. The method of any one of clauses 325 to 367 or 370 to 385 wherein the CAR has a recognition region and the recognition region of the CAR is a single chain fragment variable (scFv) region of an anti-FITC antibody.

387. The method of any one of clauses 325 to 386 wherein the CAR has a co-stimulation domain and the co-stimulation domain is selected from the group consisting of CD28, CD137 (4-1BB), CD134 (OX40), and CD278 (ICOS).

388. The method of any one of clauses 325 to 387 wherein the CAR has an activation signaling domain and the activation signaling domain is a T cell CD3ζ chain or an Fc receptor γ.

389. The method of any one of clauses 325 to 367 or 370 to 388 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

390. The method of any one of clauses 325 to 389 wherein multiple doses of the CAR T cell composition are administered.

391. The method of any one of clauses 325 to 390 wherein the patient is imaged prior to administration of the compound, or the pharmaceutically acceptable salt thereof, or prior to administration of the CAR T cell composition.

392. The method of any one of clauses 325 to 391 wherein the compound, or the pharmaceutically acceptable salt thereof, is not an antibody, and does not comprise a fragment of an antibody.

393. The method of any one of clauses 325 to 392 wherein the targeting moiety does not comprise a peptide epitope.

394. The method of any one of clauses 325 to 393 wherein cytokine release resulting in off-target toxicity in the patient does not occur and wherein CAR T cell toxicity to the cancer occurs.

395. The method of any one of clauses 325 to 393 wherein off-target tissue toxicity does not occur in the patient and wherein CAR T cell toxicity to the cancer occurs.

396. The method of any one of clauses 325 to 393 wherein the cancer comprises a tumor, wherein tumor size is reduced in the patient, and wherein off-target toxicity does not occur.

397. The method of any one of clauses 325 to 398 wherein the CAR T cells comprise a nucleic acid comprising SEQ ID NO:1.

398. The method of any one of clauses 325 to 397 wherein the CAR T cells comprise a polypeptide comprising SEQ ID NO:2.

399. The method of clause 397 wherein the nucleic acid encodes a chimeric antigen receptor.

400. The method of any one of clauses 325 to 399 wherein the CAR comprises humanized amino acid sequences.

401. The method of any one of clauses 325 to 399 wherein the CAR consists of humanized amino acid sequences.

402. The method of any one of clauses 325 to 401 further comprising the step of administering to the patient a folate, a conjugate comprising a folate wherein the conjugate comprising a folate does not comprise a targeting moiety, or an agent that inhibits activation of the CAR T cells.

403. The method of clause 402 wherein the agent that inhibits activation of the CAR T cells is administered to the patient and the agent is an agent that blocks CAR T cell binding to the compound, or the pharmaceutically acceptable salt thereof, but does not bind to the cancer.

404 The method of clause 403 wherein the agent is fluoresceinamine, sodium fluorescein, or fluorescein.

405. The method of clause 404 wherein the agent is sodium fluorescein.

406. A method of treatment of a cancer, the method comprising i) administering to a patient a first dose of a compound, or a pharmaceutically acceptable salt thereof, wherein the compound comprises a small molecule ligand linked to a targeting moiety by a linker and wherein the compound, or the pharmaceutically acceptable salt thereof, is administered to the patient at least about one hour prior to the administration of a CAR T cell composition comprising CAR T cells wherein the CAR T cells comprise a CAR directed to the targeting moiety;

ii) then administering to the patient a dose of the CAR T cell composition; and iii) then administering to the patient a second dose of the compound, or the pharmaceutically acceptable salt thereof.

407. The method of clause 406 wherein the first dose of the compound, or the pharmaceutically acceptable salt thereof, is administered to the patient at least about two hours prior to the administration of the CAR T cell composition.

408. The method of clause 406 wherein the first dose of the compound, or the pharmaceutically acceptable salt thereof, is administered to the patient at least about four hours prior to the administration of the CAR T cell composition.

409. The method of clause 406 wherein the first dose of the compound, or the pharmaceutically acceptable salt thereof, is administered to the patient at least about eight hours prior to the administration of the CAR T cell composition.

410. The method of clause 406 wherein the first dose of the compound, or the pharmaceutically acceptable salt thereof, is administered to the patient at least about twelve hours prior to the administration of the CAR T cell composition.

411. The method of clause 406 wherein the first dose of the compound, or the pharmaceutically acceptable salt thereof, is administered to the patient at least about sixteen hours prior to the administration of the CAR T cell composition.

412. The method of clause 406 wherein the first dose of the compound, or the pharmaceutically acceptable salt thereof, is administered to the patient at least about twenty hours prior to the administration of the CAR T cell composition.

413. The method of clause 406 wherein the first dose of the compound, or the pharmaceutically acceptable salt thereof, is administered to the patient at least about twenty-four hours prior to the administration of the CAR T cell composition.

414. The method of any one of clauses 406 to 413 wherein the second dose of the compound, or the pharmaceutically acceptable salt thereof, is administered to the patient by at least about twenty-four hours after the administration of the CAR T cell composition.

415. The method of any one of clauses 406 to 413 wherein the second dose of the compound, or the pharmaceutically acceptable salt thereof, is administered to the patient by at least about sixteen hours after the administration of the CAR T cell composition.

416. The method of any one of clauses 406 to 413 wherein the second dose of the compound, or the pharmaceutically acceptable salt thereof, is administered to the patient by at least about twelve hours after the administration of the CAR T cell composition.

417. The method of any one of clauses 406 to 413 wherein the second dose of the compound, or the pharmaceutically acceptable salt thereof, is administered to the patient by at least about eight hours after the administration of the CAR T cell composition.

418. The method of any one of clauses 406 to 413 wherein the second dose of the compound, or the pharmaceutically acceptable salt thereof, is administered to the patient by at least about four hours after the administration of the CAR T cell composition.

419. The method of any one of clauses 406 to 418 wherein cytokine release resulting in off-target toxicity in the patient does not occur and wherein CAR T cell toxicity to the cancer occurs.

420. The method of any one of clauses 406 to 418 wherein off-target tissue toxicity does not occur in the patient and wherein CAR T cell toxicity to the cancer occurs.

421. The method of any one of clauses 406 to 418 wherein the cancer comprises a tumor, wherein tumor size is reduced in the patient, and wherein off-target toxicity does not occur.

422. The method of any one of clauses 406 to 418 wherein the cancer comprises a tumor, and wherein reduction in tumor size in the patient is greater than in a patient not pre-treated with the compound, or the pharmaceutically acceptable salt thereof, prior to administration of the CAR T cell composition.

423. The method of any one of clauses 406 to 422 wherein the ligand is selected from the group consisting of a folate, DUPA, an NK-1R ligand, a CAIX ligand, a ligand of gamma glutamyl transpeptidase, an NKG2D ligand, and a CCK2R ligand.

424. The method of any one of clauses 406 to 423 wherein the ligand is a folate.

425. The method of any one of clauses 406 to 423 wherein the ligand is an NK-1R ligand.

426. The method of any one of clauses 406 to 423 wherein the ligand is DUPA.

427. The method of any one of clauses 406 to 423 wherein the ligand is a CCK2R ligand.

428. The method of any one of clauses 406 to 423 wherein the ligand is a ligand of gamma glutamyl transpeptidase.

429. The method of any one of clauses 406 to 428 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

430. The method of any one of clauses 406 to 429 wherein the targeting moiety is FITC.

431. The method of any one of clauses 406 to 429 wherein the targeting moiety is DNP.

432. The method of any one of clauses 406 to 429 wherein the targeting moiety is TNP.

433. The method of any one of clauses 406 to 432 wherein the linker comprises polyethylene glycol (PEG), polyproline, a hydrophilic amino acid, a sugar, an unnatural peptidoglycan, a polyvinylpyrrolidone, pluronic F-127, or a combination thereof.

434. The method of any one of clauses 406 to 433 wherein the linker comprises PEG.

435. The method of any one of clauses 406 to 434 wherein the compound, or the pharmaceutically acceptable salt thereof, has the formula

B-L-T, wherein B represents the small molecule ligand, L represents the linker, and T represents the targeting moiety, and wherein L comprises a structure having the formula

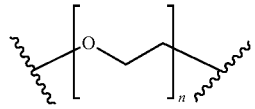

wherein n is an integer from 0 to 200.

436. The method of clause 435 wherein n is an integer from 0 to 150.

437. The method of clause 435 wherein n is an integer from 0 to 110.

438. The method of clause 435 wherein n is an integer from 0 to 20.

439. The method of clause 435 wherein n is an integer from 15 to 20.

440. The method of clause 435 wherein n is an integer from 15 to 110.

441. The method of any one of clauses 406 to 430 or 433 to 440 wherein the linker comprises PEG and the targeting moiety is FITC, or a pharmaceutically acceptable salt thereof.

442. The method of any one of clauses 406 to 441 wherein the compound, or the pharmaceutically acceptable salt thereof, is administered at a dose of about 10 nmoles/kg to about 10000 nmoles/kg of body weight of the patient.

443. The method of any one of clauses 406 to 441 wherein the compound, or the pharmaceutically acceptable salt thereof, is administered at a dose of about 10 nmoles/kg to about 5000 nmoles/kg of body weight of the patient.

444. The method of any one of clauses 406 to 441 wherein the compound, or the pharmaceutically acceptable salt thereof, is administered at a dose of about 10 nmoles/kg to about 1000 nmoles/kg of body weight of the patient.

445. The method of any one of clauses 406 to 441 wherein the compound, or the pharmaceutically acceptable salt thereof, is administered at a dose of about 10 nmoles/kg to about 600 nmoles/kg of body weight of the patient.

446. The method of any one of clauses 406 to 441 wherein the compound, or the pharmaceutically acceptable salt thereof, is administered at a dose of about 200 nmoles/kg to about 600 nmoles/kg of body weight of the patient.

447. The method of any one of clauses 406 to 441 wherein the compound, or the pharmaceutically acceptable salt thereof, is administered at a dose of about 250 nmoles/kg to about 600 nmoles/kg of body weight of the patient.

448. The method of any one of clauses 406 to 447 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

449. The method of any one of clauses 406 to 424 or 429 to 448 wherein the cancer is a β expressing cancer.

450. The method of clause 448 wherein the cancer is an endometrial cancer.

451. The method of clause 448 wherein the cancer is a non-small cell lung cancer.

452. The method of clause 448 wherein the cancer is an ovarian cancer.

453. The method of clause 448 wherein the cancer is a triple negative breast cancer.

454. The method of any one of clauses 406 to 453 wherein the CAR has a recognition region and the recognition region is a single chain fragment variable (scFv) region of an antibody.

455. The method of any one of clauses 406 to 430 or 433 to 454 wherein the CAR has a recognition region and the recognition region of the CAR is a single chain fragment variable (scFv) region of an anti-FITC antibody.

456. The method of any one of clauses 406 to 455 wherein the CAR has a co-stimulation domain and the co-stimulation domain is selected from the group consisting of CD28, CD137 (4-1BB), CD134 (OX40), and CD278 (ICOS).

457. The method of any one of clauses 406 to 456 wherein the CAR has an activation signaling domain and the activation signaling domain is a T cell CD3ζ chain or an Fc receptor γ.

458. The method of any one of clauses 406 to 430 or 433 to 457 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

459. The method of any one of clauses 406 to 458 wherein multiple doses of the CAR T cell composition are administered.

460. The method of any one of clauses 406 to 459 wherein the patient is imaged prior to administration of the compound, or the pharmaceutically acceptable salt thereof.

461. The method of any one of clauses 406 to 460 wherein the compound, or the pharmaceutically acceptable salt thereof, is not an antibody, and does not comprise a fragment of an antibody.

462. The method of any one of clauses 406 to 461 wherein the targeting moiety does not comprise a peptide epitope.

463. The method of any one of clauses 406 to 462 wherein the CAR T cells comprise a nucleic acid comprising SEQ ID NO:1.

464. The method of any one of clauses 406 to 463 wherein the CAR T cells comprise a polypeptide comprising SEQ ID NO:2.

465. The method of clause 463 wherein the nucleic acid encodes a chimeric antigen receptor.

466. The method of any one of clauses 406 to 465 wherein the CAR comprises humanized amino acid sequences.

467. The method of any one of clauses 406 to 465 wherein the CAR consists of humanized amino acid sequences.

468. The method of any one of clauses 108 to 182 wherein more than one dose is administered to the patient of the folate, the conjugate comprising a folate wherein the conjugate comprising a folate does not comprise a targeting moiety, or the agent that inhibits activation of the CAR T cells.

469. The method of any one of clauses 108 to 182 wherein the folate, the conjugate comprising a folate wherein the conjugate comprising a folate does not comprise a targeting moiety, or the agent that inhibits activation of the CAR T cells is administered to the patient before and/or after the compound, or the pharmaceutically acceptable salt thereof.

470. The method of any one of clauses 108 to 182 wherein administration of the folate, the conjugate comprising a folate wherein the conjugate comprising a folate does not comprise a targeting moiety, or the agent that inhibits activation of the CAR T cells causes reduction in cytokine levels in the patient.

471. The method of clause 470 wherein the reduction in cytokine levels occurs by about 3 hours after administration to the patient of the folate, the conjugate comprising a folate wherein the conjugate comprising a folate does not comprise a targeting moiety, or the agent that inhibits activation of the CAR T cells.

472. The method of clause 470 wherein the reduction in cytokine levels occurs by about 6 hours after administration to the patient of the folate, the conjugate comprising a folate wherein the conjugate comprising a folate does not comprise a targeting moiety, or the agent that inhibits activation of the CAR T cells.

473. The method of clause 470 wherein the reduction in cytokine levels is a reduction to about the cytokine levels in an untreated patient.

474. The method of any one of clauses 108 to 182 wherein the compound, or the pharmaceutically acceptable salt thereof, is administered before and subsequent to administration of the folate, the conjugate comprising a folate wherein the conjugate comprising a folate does not comprise a targeting moiety, or the agent that inhibits activation of the CAR T cells.

475. The method of any one of clauses 108 to 182 wherein CAR T cell number increases in the blood of the patient after administration of the folate, the conjugate comprising a folate wherein the conjugate comprising a folate does not comprise a targeting moiety, or the agent that inhibits activation of the CAR T cells, even though cytokine levels in the patient are reduced.

476. The method of any one of clauses 108 to 182 wherein CAR T cell activation is enhanced or maintained, relative to a patient not treated with a rescue agent, after administration of the folate, the conjugate comprising a folate wherein the conjugate comprising a folate does not comprise a targeting moiety, or the agent that inhibits activation of the CAR T cells, even though cytokine levels in the treated patient are reduced.

477. The method of any one of clauses 108 to 182 wherein the cancer comprises a tumor and tumor size in the patient is not increased when the folate, the conjugate comprising a folate wherein the conjugate comprising a folate does not comprise a targeting moiety, or the agent that inhibits activation of the CAR T cells is administered to the patient.

478. The method of clause 477 wherein a complete response for the tumor is obtained.

479. The method of any one of clauses 108, 115-160, 168-182, and 468-478 wherein the agent that inhibits activation of the CAR T cells is administered to the patient when the CRS grade reaches 1, 2, 3, or 4.

480. The method of any one of clauses 108, 115-160, 168-182, and 468-478 wherein the agent that inhibits activation of the CAR T cells is administered to the patient when the CRS grade reaches 3 or 4.

481. The method of any one of clauses 108 to 182 and 468 to 480 wherein lung edema is reduced.

482. The method of any one of clauses 108, 115-160, 168-182, and 468-481 wherein the agent that inhibits activation of the CAR T cells is administered at a dose of about 0.01 to about 300 umoles/kg of body weight of the patient.

483. The method of any one of clauses 108, 115-160, 168-182, and 468-481 wherein the agent that inhibits activation of the CAR T cells is administered at a dose of about 0.06 to about 100 umoles/kg of body weight of the patient.

484. The method of any one of clauses 108, 115-160, 168-182, and 468-481 wherein the agent that inhibits activation of the CAR T cells is administered at a dose of about 0.06 to about 90 umoles/kg of body weight of the patient.

485. The method of any one of clauses 108, 115-160, 168-182, and 468-481 wherein the agent that inhibits activation of the CAR T cells is administered at a dose of about 0.06 to about 80 umoles/kg of body weight of the patient.

486. The method of any one of clauses 108, 115-160, 168-182, and 468-481 wherein the agent that inhibits activation of the CAR T cells is administered at a dose of about 0.06 to about 70 umoles/kg of body weight of the patient.

487. The method of any one of clauses 108, 115-160, 168-182, and 468-481 wherein the agent that inhibits activation of the CAR T cells is administered at a dose of about 0.06 to about 60 umoles/kg of body weight of the patient.

488. The method of any one of clauses 108, 115-160, 168-182, and 468-481 wherein the agent that inhibits activation of the CAR T cells is administered at a dose of about 0.06 to about 50 umoles/kg of body weight of the patient.

489. The method of any one of clauses 108, 115-160, 168-182, and 468-481 wherein the agent that inhibits activation of the CAR T cells is administered at a dose of about 0.06 to about 40 umoles/kg of body weight of the patient.

490. The method of any one of clauses 108, 115-160, 168-182, and 468-481 wherein the agent that inhibits activation of the CAR T cells is administered at a dose of about 0.06 to about 30 umoles/kg of body weight of the patient.

491. The method of any one of clauses 108, 115-160, 168-182, and 468-481 wherein the agent that inhibits activation of the CAR T cells is administered at a dose of about 0.06 to about 20 umoles/kg of body weight of the patient.

492. The method of any one of clauses 108, 115-160, 168-182, and 468-481 wherein the agent that inhibits activation of the CAR T cells is administered at a dose of about 0.06 to about 10 umoles/kg of body weight of the patient.

493. The method of any one of clauses 108, 115-160, 168-182, and 468-481 wherein the agent that inhibits activation of the CAR T cells is administered at a dose of about 0.06 to about 8 umoles/kg of body weight of the patient.

494. The method of any one of clauses 108, 115-160, 168-182, and 468-481 wherein the agent that inhibits activation of the CAR T cells is administered at a dose of about 0.06 to about 6 umoles/kg of body weight of the patient.

495. The method of any one of clauses 108, 115-160, 168-181, and 468-494 wherein the agent that inhibits activation of the CAR T cells is administered to the patient and the agent is sodium fluorescein.

496. The method of any one of clauses 1 to 495 wherein CRS is reduced or prevented and the method results in a decrease in tumor volume in the patient.

497. The method of any one of clauses 1 to 496 wherein body weight loss due to CRS is reduced or prevented.

498. The method of any one of clauses 1-3, 8-28, 33-58, 63-83, 88-136, 141-249, 252-361, 366-380, 385-424, 429-449, and 454 to 497 wherein the cancer is acute myelocytic leukemia.

499. The method of clause 498 wherein the cancer expresses the folate receptor-3.

500. The method of clause 498 or 499 wherein the CAR-T cells have a central memory/effector memory phenotype.

501. The method of any one of clauses 1 to 500 wherein the CD8:CD4 ratio of the CAR T cells is about 1:1.

502. The method of any one of clauses 215 to 251 further comprising step iv) of re-administering the compound, or the pharmaceutically acceptable salt thereof, to the patient.

503. The method of clause 474 wherein the subsequent administration of the compound, or the pharmaceutically acceptable salt thereof, causes CAR T cell activation and an increase in cytokine levels in the patient.

504. The method of any one of clauses 1 to 107, 183 to 476, or 479 to 503 wherein the cancer comprises a tumor and wherein a complete response for the tumor is obtained.

505. A method of treatment of a cancer, the method comprising
  i) administering to a patient a compound, or a pharmaceutically acceptable salt thereof, wherein the compound comprises a small molecule ligand linked to a targeting moiety by a linker; and
  ii) administering to the patient a CAR T cell composition wherein the CAR T cell composition comprises CAR T cells and wherein the CAR T cells comprise a CAR directed to the targeting moiety; and wherein the small molecule ligand is a PSMA ligand and the targeting moiety is FITC.

506. The method of clause 505 wherein the small molecule ligand linked to a targeting moiety by a linker has the formula

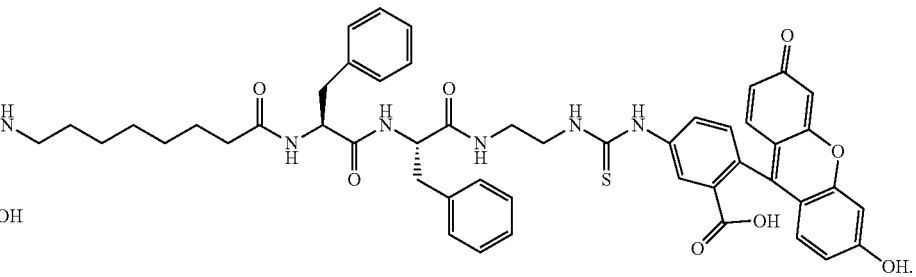

507. A method of treatment of a cancer, the method comprising
  i) administering to a patient a compound, or a pharmaceutically acceptable salt thereof, wherein the compound comprises a small molecule ligand linked to a targeting moiety by a linker; and
  ii) administering to the patient a CAR T cell composition wherein the CAR T cell composition comprises CAR T cells and wherein the CAR T cells comprise a CAR directed to the targeting moiety; and wherein the small molecule ligand is a CAIX ligand and the targeting moiety is FITC.

508. The method of clause 507 wherein the small molecule ligand linked to a targeting moiety by a linker has the formula

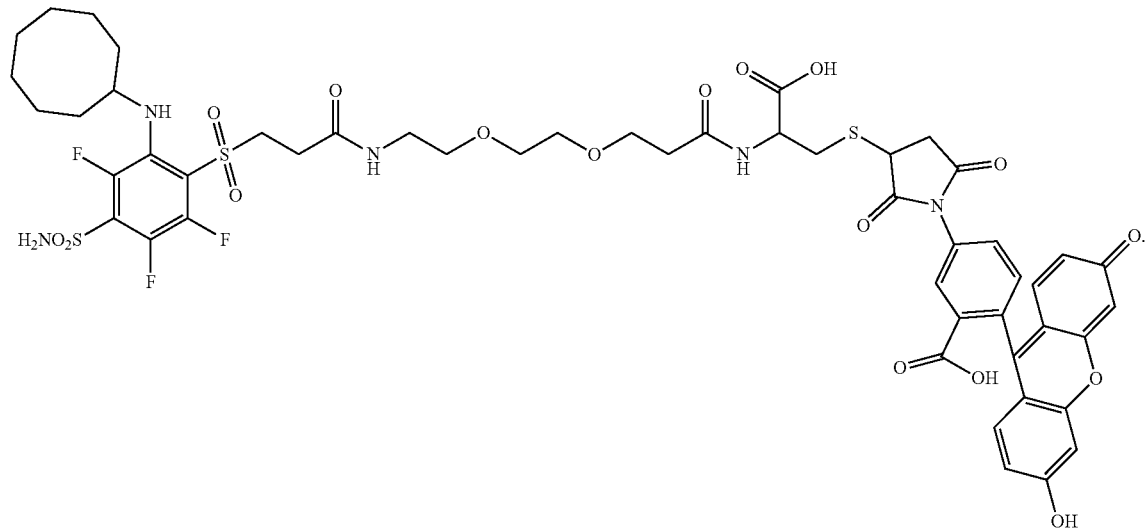 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

509. A method of treatment of a cancer, the method comprising
  i) administering to a patient a first compound, or a pharmaceutically acceptable salt thereof, wherein the first compound, or the pharmaceutically acceptable salt thereof, comprises a PSMA ligand linked to FITC by a linker;
  ii) administering to the patient a second compound, or a pharmaceutically acceptable salt thereof, wherein the second compound, or the pharmaceutically acceptable salt thereof, comprises a CAIX ligand linked to FITC by a linker; and
  iii) administering to the patient a CAR T cell composition wherein the CAR T cell composition comprises CAR T cells and wherein the CAR T cells comprise a CAR directed to the targeting moiety.

510. The method of clause 509 wherein the first compound has the formula

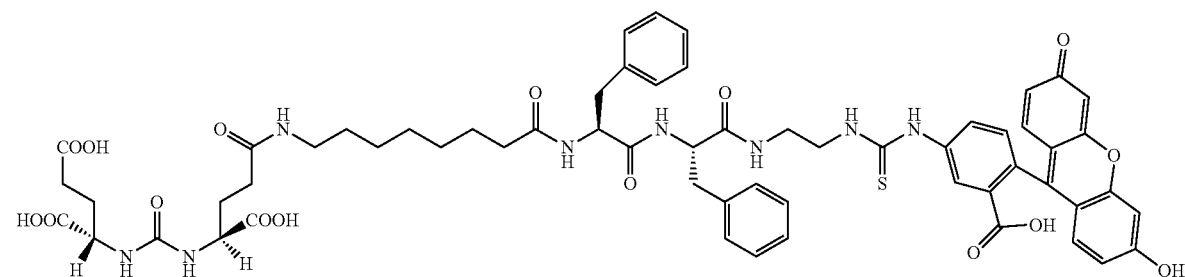 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

and the second compound has the formula

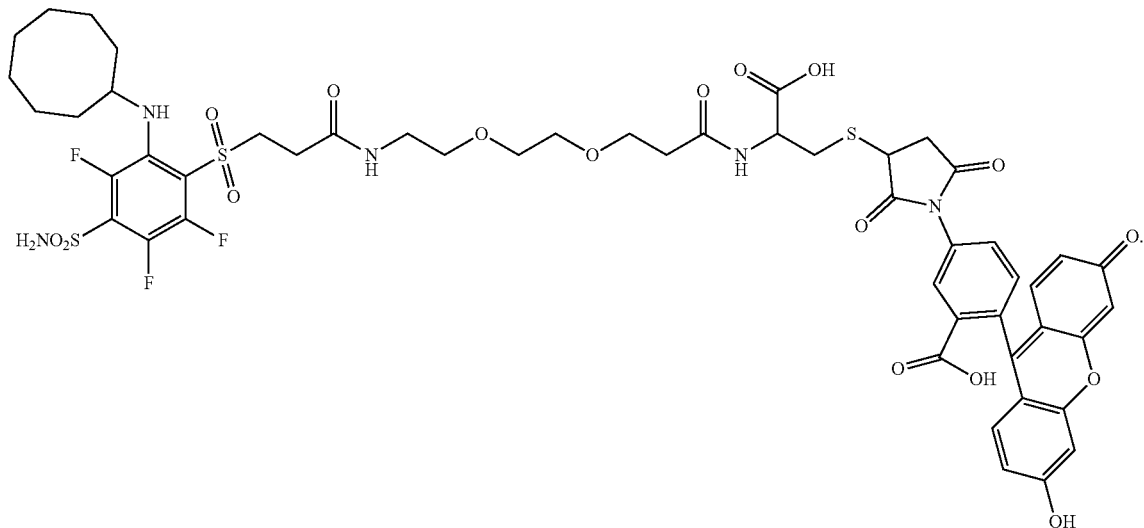 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

BRIEF DESCRIPTION OF THE DRAWINGS

FIG. 1A shows the changes in bodyweight for the mice of different treatment groups. FIG. 1B shows the detected concentration of IFN-gamma for the different treatment groups. FIG. 1C shows the first-week survival (%) of the mice in the different treatment groups.

FIG. 2A shows tumor growth for mice that are treated with either CAR T cells and PBS or CAR T cells and FITC-Folate. FIG. 2B shows a summary of the tumor response results for mice used in the study.

FIGS. 3A-D show the effect of FITC-Folate concentration on the tumor response. FIG. 3A shows the detected concentration of IFN-gamma at the different FITC-folate concentrations. FIG. 3B shows post CAR T cell injection tumor growth in the presence of different FITC-folate concentrations. FIG. 3C shows the first-week survival (%) of the mice. FIG. 3D shows a summary of the tumor response results for the mice used in the study.

FIG. 4A shows the changes in IFN-gamma concentration as a function of agent concentration. FIG. 4B shows the changes in CD69 expression as a function of agent concentration.

FIG. 6A shows tumor volume over time. FIG. 6B shows body weight changes over time. FIG. 6C shows the maximal percentage body weight loss for each EC17 dose. FIG. 6D shows the percentage of mice showing sCRS (cytokine release syndrome) for each EC17 dose. (1) no CAR-T+EC17 500 nmoles/kg; (2) 12.5 million CAR-T+EC17 10000 nmoles/kg; (3) 12.5 million CAR-T+EC17 1500 nmoles/kg; (4) 12.5 million CAR-T+EC17 500 nmoles/kg; (5) 10 million CAR-T+EC17 100 nmoles/kg; (6) 10 million CAR-T+EC17 20 nmoles/kg.

FIG. 8A shows tumor volume over time. FIG. 8B shows body weight changes over time. FIG. 8C shows the maximal percentage of body weight loss for each CAR T dose. FIG. 8D shows the percentage of mice showing sCRS for each CAR T dose.

FIG. 9A shows tumor volume over time. FIG. 9B shows body weight change over time.

FIG. 10A shows tumor volume over time; (●) no CAR-T, (○) CAR-T on Day 0, (■) CAR-T on Day 0, unmodified T on Day 52, (▼) CAR-T on Day 0, Day 46 and Day 52. FIG. 10B shows body weight change over time; (●) no CAR-T, (○) CAR-T on Day 0, (■) CAR-T on Day 0, unmodified T on Day 52, (▼) CAR-T on Day 0, Day 46 and Day 52. FIG. 10C shows the amount of CAR T cells in blood and tumor volume for different CAR T cell and non-transformed T cell mixtures.

FIG. 11A shows tumor volume over time. FIG. 11B shows body weight change over time.

FIG. 13A shows the percent body weight change over time after administration of the bridge and the CAR T cells. FIG. 13B shows the change in tumor volume over time after injection of CAR T cells and the bridge. FIG. 13C shows the percent of survival after the first week of treatment with the bridge and the CAR T cells.

FIG. 14A shows the number of CAR T cells 6 days after the introduction of the CAR T cells into mice. FIG. 14B shows the concentration of the serum cytokines IL-2, IFN-γ, and TNF-α 6 days after the introduction of CAR T cells into mice.

FIG. 18A shows body weight change in mice (with no tumors) injected with CAR-T cells, but no EC17 or with 500 nmoles/kg of EC17 three times weekly. FIGS. 18B and C show CAR-T cell number and spleen size in these mice versus mice with HEK (folate-receptor positive) tumors. For FIGS. 18B and C, the left-hand bar in each group of three bars is mice without tumors injected with no EC17 but with CAR-T cells, the middle bar is mice without tumors injected with CAR-T cells and EC17, and the right-hand bar is mice with tumors injected with CAR-T cells and EC17. In FIG. 18B, N.D. is not determined and the y-axis is logarithmic for FIG. 18.

FIG. 26, Panels C and E, show toxicity studies in mice with EC17 prep-painting. Panels A and B show the protocol for treatment. Panel D shows the effect of EC17 pre-painting on tumor size.

FIG. 29, Panels A-E, show comparison studies of three rescue agents (folic acid, sodium fluorescein (NAFL), and leucovorin).

FIG. 45 shows the universality of anti-FITC CAR T cell therapy: binding of various adaptors to CAR T cells. (1) CAR T cell without staining; (2) CAR T cell labeled with FITC-Alexa 647+FITC-folate (Competition); (3) CAR T cell labeled with FITC-Alexa 647; (4) CAR T cell labeled with FITC-Alexa 647+FITC-DUPA (Competition); (5) CAR T cell labeled with FITX-Alexa 647+FITC-CA9 (Competition).

FIG. 47 shows the relationship between concentration of bridges and the universal CAR T cell's anti-tumor activity in vitro.

FIG. 49 shows that the universal CAR T cell can eliminate two tumors via cocktail of bridges in vivo.

FIG. 53, Panel A shows a rescue schema. Panels B and C show enumeration of FITC CAR T cells in the blood after rescue.

FIG. 55A shows a rescue schema. Panels B and C show enumeration of CAR T cells in the blood after rescue. (1) Control [No NaFL]; (2) 0.06 umol/kg NaFL; (3) 0.6 umol/kg NAFL; (4) 6 umol·kg NaFL.

FIG. 56 shows tumor burden in EC17 treated and non-treated animals.

FIGS. 59A and 59B show the characterization of circulating tumor cells.

FIG. 63 shows the design and characterization of an anti-fluorescein CAR T cell and fluorescein-folate bridge. (A) Structure of fluorescein-folate (FITC-folate). (B) Diagram showing construction of anti-fluorescein CAR, where SP=signal peptide, scFv=single chain variable fragment that recognizes fluorescein with a KD=270 fM, TM=transmembrane domain, 4-1BB=cytoplasmic activation domain from CD137, and CD3ζ=the cytoplasmic activation domain of CD3 zeta. (C) Transduction efficiency of CAR T cells evaluated by flow cytometry. Open histogram: Non-transduced T cells; filled histogram: T cells transduced with lentivirus expressing GFP and the CAR construct shown in (B). (D) Demonstration that FITC-folate binds to anti-fluorescein CAR T cell. Filled histogram (grey): anti-fluorescein CAR T cell without staining; open histogram: anti-fluorescein CAR T cell labeled with FITC-Alexa647 (10 nM); filled histogram (black): anti-fluorescein CAR T cell labeled with FITC-Alexa647 (10 nM) in the presence of competing 100-fold excess FITC-folate (1 μM)).

FIG. 64 shows the demonstration that FITC-folate bridge mediates anti-fluorescein CAR T cell engagement with folate receptor-expressing cancer cells (KB cells). (A) Demonstration that FR is expressed on KB cells. Grey histogram: KB cells without staining; Black histogram: KB cells labeled with 100 nM FITC-folate in the presence of excess (10 μM) free folate as competitor; Open histogram: KB cells labeled with 100 nM FITC-folate. (B) Cytotoxicity of CAR T cells towards KB cells upon addition of correct FITC-folate (100 nM) but not mismatched FITC-DUPA (100 nM) or no (PBS) bridge. (C) Impact of effector:target cell ratio on CAR T cell lysis of KB cells in presence of FITC-folate, FITC-DUPA, or no bridge. (D) IFNγ production is induced by addition of FITC-folate (100 nM) but not FITC-DUPA (100 nM). (E) Proliferation of anti-fluorescein CAR T cells is induced by FITC-folate but not FITC-DUPA. (F) Expression of activation marker (CD69) on anti-fluorescein CAR T cells occurs only upon addition of correct bridge. For panels B, D, E and F, the ratio of anti-fluorescein CAR T cells to KB cells was 10 to 1. Bar graphs represent mean±s.d. n=3. One-way ANOVA performed for all comparisons (**P<0.0001, P<0.005, *P<0.01, ns (not significant)).

FIG. 67 shows the effect of blockade of bridge via competition with free folate or free fluorescein on CAR T cell-mediated cytotoxicity. (A) Measurement of body weight change (%) after administration of anti-fluorescein CAR T cells (15×106) in the absence (PBS) or presence of FITC-folate (500 nmole/kg administered on days 1, and 2, and alternate days thereafter). For competition studies, 100-fold excess folate was co-injected on days 4 and 6. ** P<0.0001. (B) Analysis on day 6 of IFNγ levels in plasma of above treatment groups.  P<0.005. (C) Measurement of tumor volume in same treatment groups. n=5 mice per group. Error bars represent mean±s.e.m. (D) Analysis of time dependence of cytokine levels in plasma of CAR T cell after administration of 12-fold excess free fluorescein to suppress CRS. CRS was induced in all mice by injection of 10×106 anti-fluorescein CAR T cells plus FITC-folate (500 nmole/kg on day 3). On day 4, to suppress a potent CRS, 6 mole/kg free fluorescein was injected, and the indicated cytokines were measured in plasma at 3 and 6 hours after administration of fluorescein. n=3 mice/group. Data represent mean±s.e.m.  P<0.01, * P<0.001, **** P<0.0001 by two-way ANOVA test.

DEFINITIONS

Figure 1A:
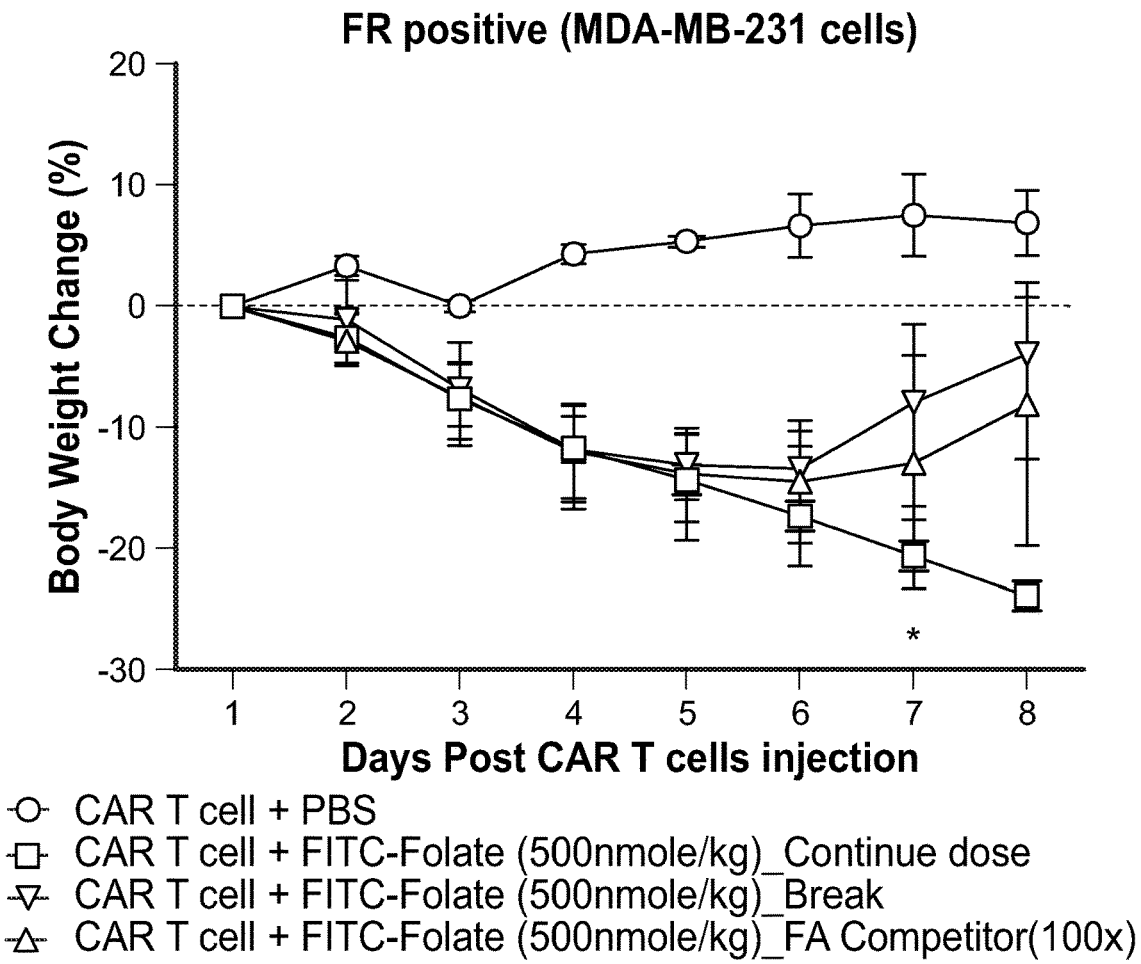
FIGS. 1A-B show anti-FITC CAR T cell mediated toxicity.

As used herein, "a" or "an" may mean one or more. As used herein, "about" in reference to a numeric value, including, for example, whole numbers, fractions, and percentages, generally refers to a range of numerical values (e.g., +/−5% to 10% of the recited value) that one of ordinary skill in the art would consider equivalent to the recited value (e.g., having the same function or result).

As used herein, the terms "treat," "treating," "treated," or "treatment" refer to both therapeutic treatment and prophylactic or preventative treatment.

As used herein, the terms "ameliorate," "ameliorating," "amelioration," or "ameliorated" in reference to cancer can mean reducing the symptoms of the cancer, reducing the size of a tumor, completely or partially removing the tumor (e.g., a complete or partial response), causing stable disease, preventing progression of the cancer (e.g., progression free survival), or any other effect on the cancer that would be considered by a physician to be a therapeutic, prophylactic, or preventative treatment of the cancer.

As used herein, the terms "administer," "administering," or "administered" mean all means of introducing the compound, or pharmaceutically acceptable salt thereof, or CAR T cell composition described herein to the patient, including, but not limited to, oral, intravenous, intramuscular, subcutaneous, and transdermal.

As used herein, the term "off-target toxicity" means organ damage or a reduction in the patient's weight that is unacceptable to the physician treating the patient, or any other effect on the patient that is unacceptable to the physician treating the patient, for example, B cell aplasia, a fever, a drop in blood pressure, or pulmonary edema.

As used herein, the terms "transduction" and "transfection" are used equivalently and the terms mean introducing a nucleic acid into a cell by any artificial method, including viral and non-viral methods.

DETAILED DESCRIPTION OF THE ILLUSTRATIVE EMBODIMENTS

In the various embodiments described herein, a small molecule ligand linked to a targeting moiety by a linker is used as a bridge between a cancer and CAR T cells (i.e, T cells expressing a chimeric antigen receptor). The bridge directs the CAR T cells to the cancer for amelioration of the cancer. In one embodiment, the "small molecule ligand" can be a folate, a CAIX ligand, DUPA, an NK-1R ligand, a ligand of gamma glutamyl transpeptidase, an NKG2D ligand, or a CCK2R ligand, each of which is a small molecule ligand that binds specifically to a cancer cell type (i.e., the receptor for each of these ligands is overexpressed on cancers compared to normal tissues).

The "targeting moiety" linked to the small molecule ligand binds to the recognition region of the genetically engineered CAR expressed by CAR T cells. Accordingly, the recognition region of the CAR (e.g., a single chain fragment variable region (scFv) of an antibody, an Fab, Fv, Fc, or (Fab')2 fragment, and the like) is directed to the "targeting moiety." Thus, the small molecule ligand linked to a targeting moiety by a linker acts as a bridge between the cancer and the CAR T cells directing the CAR T cells to the cancer for amelioration of the cancer. In various embodiments, the bridge between the cancer and the CAR T cells can be any of the conjugates shown in the Examples.

The bridge is a small organic molecule so clearance from the bloodstream can be rapidly achieved (e.g., about 20 minutes or less). In one aspect, the CAR T cell response can be targeted to only those cancer cells expressing a receptor for the small molecule ligand portion of the 'bridge,' thereby reducing off-target toxicity to normal tissues. Additionally, this system can be 'universal' because one type of CAR T cell construct can be used to target a wide variety of cancers using different 'bridges'. Illustratively, the targeting moiety recognized by the CAR T cell may remain constant so that one type of CAR T cell construct can be used, while the small molecule ligand that binds to the cancer can be altered to allow targeting of a wide variety of cancers.

In various embodiments described in the clause list below and in the claims and throughout the application, the small molecule ligand linked to a targeting moiety by a linker is referred to as a "compound."

Several embodiments are described by the following enumerated clauses. Any of the following embodiments in combination with any applicable embodiments described in the Summary section of this patent application, in the Detailed Description of the Illustrative Embodiments section, the Examples section, or the claims of this patent application, are also contemplated.

1. A method of treatment of a cancer, the method comprising
   i) administering to a patient a compound, or a pharmaceutically acceptable salt thereof, wherein the compound comprises a small molecule ligand linked to a targeting moiety by a linker;
   ii) administering to the patient a first dose of a CAR T cell composition comprising CAR T cells wherein the CAR T cells comprise a CAR directed to the targeting moiety; and
   iii) administering to the patient a second dose of a CAR T cell composition comprising CAR T cells wherein the CAR T cells comprise the CAR directed to the targeting moiety.

2. The method of clause 1 wherein the ligand is selected from the group consisting of a folate, DUPA, an NK-1R ligand, a CAIX ligand, a ligand of gamma glutamyl transpeptidase, an NKG2D ligand, and a CCK2R ligand.

3. The method of any one of clauses 1 or 2 wherein the ligand is a folate.

4. The method of any one of clauses 1 or 2 wherein the ligand is an NK-1R ligand.

5. The method of any one of clauses 1 or 2 wherein the ligand is DUPA.

6. The method of any one of clauses 1 or 2 wherein the ligand is a CCK2R ligand.

7. The method of any one of clauses 1 or 2 wherein the ligand is a ligand of gamma glutamyl transpeptidase.

8. The method of any one of clauses 1 to 7 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

9. The method of any one of clauses 1 to 8 wherein the targeting moiety is FITC.

10. The method of any one of clauses 1 to 8 wherein the targeting moiety is DNP.

11. The method of any one of clauses 1 to 8 wherein the targeting moiety is TNP.

12. The method of any one of clauses 1 to 11 wherein the linker comprises polyethylene glycol (PEG), polyproline, a hydrophilic amino acid, a sugar, an unnatural peptidoglycan, a polyvinylpyrrolidone, pluronic F-127, or a combination thereof.

13. The method of any one of clauses 1 to 12 wherein the linker comprises PEG.

14. The method of any one of clauses 1 to 13 wherein the compound, or the pharmaceutically acceptable salt thereof, has the formula

B-L-T, wherein B represents the small molecule ligand, L represents the linker, and T represents the targeting moiety, and wherein L comprises a structure having the formula

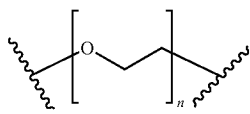

wherein n is an integer from 0 to 200.

15. The method of clause 14 wherein n is an integer from 0 to 150.

16. The method of clause 14 wherein n is an integer from 0 to 110.

17. The method of clause 14 wherein n is an integer from 0 to 20.

18. The method of clause 14 wherein n is an integer from 15 to 20.

19. The method of clause 14 wherein n is an integer from 15 to 110.

20. The method of any one of clauses 1 to 9 or 12 to 19 wherein the linker comprises PEG and the targeting moiety is FITC, or a pharmaceutically acceptable salt thereof.

21. The method of any one of clauses 1 to 20 wherein the compound, or the pharmaceutically acceptable salt thereof, is administered at a dose of about 10 nmoles/kg to about 10000 nmoles/kg of body weight of the patient.

22. The method of any one of clauses 1 to 21 wherein the compound, or the pharmaceutically acceptable salt thereof, is administered at a dose of about 10 nmoles/kg to about 5000 nmoles/kg of body weight of the patient.

23. The method of any one of clauses 1 to 22 wherein the compound, or the pharmaceutically acceptable salt thereof, is administered at a dose of about 10 nmoles/kg to about 1000 nmoles/kg of body weight of the patient.

24. The method of any one of clauses 1 to 23 wherein the compound, or the pharmaceutically acceptable salt thereof, is administered at a dose of about 10 nmoles/kg to about 600 nmoles/kg of body weight of the patient.

25. The method of any one of clauses 1 to 24 wherein the compound, or the pharmaceutically acceptable salt thereof, is administered at a dose of about 200 nmoles/kg to about 600 nmoles/kg of body weight of the patient.

26. The method of any one of clauses 1 to 25 wherein the compound, or the pharmaceutically acceptable salt thereof, is administered at a dose of about 250 nmoles/kg to about 600 nmoles/kg of body weight of the patient.

27. The method of any one of clauses 1 to 26 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

28. The method of any one of clauses 1 to 3 or 8 to 27 wherein the cancer is a folate receptor expressing cancer.

29. The method of clause 28 wherein the cancer is an endometrial cancer.

30. The method of clause 28 wherein the cancer is a non-small cell lung cancer.

31. The method of clause 28 wherein the cancer is an ovarian cancer.

32. The method of clause 28 wherein the cancer is a triple negative breast cancer.

33. The method of any one of clauses 1 to 32 wherein the CAR has a recognition region and the recognition region is a single chain fragment variable (scFv) region of an antibody.

34. The method of any one of clauses 1 to 9 or 12 to 33 wherein the CAR has a recognition region and the recognition region of the CAR is a single chain fragment variable (scFv) region of an anti-FITC antibody.

35. The method of any one of clauses 1 to 34 wherein the CAR has a co-stimulation domain and the co-stimulation domain is selected from the group consisting of CD28, CD137 (4-1BB), CD134 (OX40), and CD278 (ICOS).

36. The method of any one of clauses 1 to 35 wherein the CAR has an activation signaling domain and the activation signaling domain is a T cell CD31 chain or an Fc receptor γ.

37. The method of any one of clauses 1 to 9 or 12 to 36 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

38. The method of any one of clauses 1 to 37 wherein multiple doses of the compound, or the pharmaceutically acceptable salt thereof, and the CAR T cell composition are administered.

39. The method of any one of clauses 1 to 38 wherein the patient is imaged prior to administration of the compound, or the pharmaceutically acceptable salt thereof, or prior to administration of the CAR T cell composition.

40. The method of any one of clauses 1 to 39 wherein the compound, or the pharmaceutically acceptable salt thereof, is not an antibody, and does not comprise a fragment of an antibody.

41. The method of any one of clauses 1 to 40 wherein the targeting moiety does not comprise a peptide epitope.

42. The method of any one of clauses 1 to 41 wherein cytokine release resulting in off-target toxicity in the patient does not occur and wherein CAR T cell toxicity to the cancer occurs.

43. The method of any one of clauses 1 to 41 wherein off-target tissue toxicity does not occur in the patient and wherein CAR T cell toxicity to the cancer occurs.

44. The method of any one of clauses 1 to 41 wherein the cancer comprises a tumor, wherein tumor size is reduced in the patient, and wherein off-target toxicity does not occur.

45. The method of any one of clauses 1 to 44 wherein the CAR T cells comprise a nucleic acid comprising SEQ ID NO:1.

46. The method of any one of clauses 1 to 45 wherein the CAR T cells comprise a polypeptide comprising SEQ ID NO:2.

47. The method of clause 45 wherein the nucleic acid encodes a chimeric antigen receptor.

48. The method of any one of clauses 1 to 47 wherein the CAR comprises humanized amino acid sequences.

49. The method of any one of clauses 1 to 47 wherein the CAR consists of humanized amino acid sequences.

50. The method of any one of clauses 1 to 49 wherein the first dose of the CAR T cell composition comprises a mixture of the CAR T cells and non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

51. The method of any one of clauses 1 to 50 wherein the second dose of the CAR T cell composition comprises a mixture of the CAR T cells and non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

52. The method of any one of clauses 1 to 51 wherein the first dose of the CAR T cell composition comprises a mixture of the CAR T cells and non-transformed T cells in a ratio of from about 1:1 to about 1:5 of the CAR T cells to the non-transformed T cells.

53. The method of any one of clauses 1 to 52 wherein the second dose of the CAR T cell composition comprises a mixture of the CAR T cells and non-transformed T cells in a ratio of from about 1:1 to 1:5 of the CAR T cells to the non-transformed T cells.

54. The method of any one of clauses 1 to 53 wherein the first dose of the CAR T cell composition comprises a mixture of about 10 million of the CAR T cells and about 40 million non-transformed T cells.

55. The method of any one of clauses 1 to 54 wherein the second dose of the CAR T cell composition comprises a mixture of about 10 million of the CAR T cells and about 40 million non-transformed T cells.

56. A method of treatment of a cancer, the method comprising
  i) administering to a patient a compound, or a pharmaceutically acceptable salt thereof, wherein the compound comprises a small molecule ligand linked to a targeting moiety by a linker; and
  ii) administering to the patient a CAR T cell composition wherein the CAR T cell composition comprises CAR T cells, wherein the CAR T cells comprise a CAR directed to the targeting moiety, and wherein the CAR T cell composition comprises a mixture of the CAR T cells and non-transformed T cells.

57. The method of clause 56 wherein the ligand is selected from the group consisting of a folate, DUPA, an NK-1R ligand, a CAIX ligand, a ligand of gamma glutamyl transpeptidase, an NKG2D ligand, and a CCK2R ligand.

58. The method of any one of clauses 56 or 57 wherein the ligand is a folate.

59. The method of any one of clauses 56 or 57 wherein the ligand is an NK-1R ligand.

60. The method of any one of clauses 56 or 57 wherein the ligand is DUPA.

61. The method of any one of clauses 56 or 57 wherein the ligand is a CCK2R ligand.

62. The method of any one of clauses 56 or 57 wherein the ligand is a ligand of gamma glutamyl transpeptidase.

63. The method of any one of clauses 56 to 62 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

64. The method of any one of clauses 56 to 63 wherein the targeting moiety is FITC.

65. The method of any one of clauses 56 to 63 wherein the targeting moiety is DNP.

66. The method of any one of clauses 56 to 63 wherein the targeting moiety is TNP.

67. The method of any one of clauses 56 to 66 wherein the linker comprises polyethylene glycol (PEG), polyproline, a hydrophilic amino acid, a sugar, an unnatural peptidoglycan, a polyvinylpyrrolidone, pluronic F-127, or a combination thereof.

68. The method of any one of clauses 56 to 67 wherein the linker comprises PEG.

69. The method of any one of clauses 56 to 68 wherein the compound, or the pharmaceutically acceptable salt thereof, has the formula

B-L-T, wherein B represents the small molecule ligand, L represents the linker, and T represents the targeting moiety, and wherein L comprises a structure having the formula

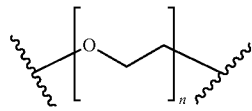

wherein n is an integer from 0 to 200.

70. The method of clause 69 wherein n is an integer from 0 to 150.

71. The method of clause 69 wherein n is an integer from 0 to 110.

72. The method of clause 69 wherein n is an integer from 0 to 20.

73. The method of clause 69 wherein n is an integer from 15 to 20.

74. The method of clause 69 wherein n is an integer from 15 to 110.

75. The method of any one of clauses 56 to 64 or 67 to 74 wherein the linker comprises PEG and the targeting moiety is FITC, or a pharmaceutically acceptable salt thereof.

76. The method of any one of clauses 56 to 75 wherein the compound, or the pharmaceutically acceptable salt thereof, is administered at a dose of about 10 nmoles/kg to about 10000 nmoles/kg of body weight of the patient.

77. The method of any one of clauses 56 to 76 wherein the compound, or the pharmaceutically acceptable salt thereof, is administered at a dose of about 10 nmoles/kg to about 5000 nmoles/kg of body weight of the patient.

78. The method of any one of clauses 56 to 77 wherein the compound, or the pharmaceutically acceptable salt thereof, is administered at a dose of about 10 nmoles/kg to about 1000 nmoles/kg of body weight of the patient.

79. The method of any one of clauses 56 to 78 wherein the compound, or the pharmaceutically acceptable salt thereof, is administered at a dose of about 10 nmoles/kg to about 600 nmoles/kg of body weight of the patient.

80. The method of any one of clauses 56 to 79 wherein the compound, or the pharmaceutically acceptable salt thereof, is administered at a dose of about 200 nmoles/kg to about 600 nmoles/kg of body weight of the patient.

81. The method of any one of clauses 56 to 80 wherein the compound, or the pharmaceutically acceptable salt thereof, is administered at a dose of about 250 nmoles/kg to about 600 nmoles/kg of body weight of the patient.

82. The method of any one of clauses 56 to 81 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

83. The method of any one of clauses 56 to 58 or 63 to 82 wherein the cancer is a folate receptor expressing cancer.

84. The method of clause 83 wherein the cancer is an endometrial cancer.

85. The method of clause 83 wherein the cancer is a non-small cell lung cancer.

86. The method of clause 83 wherein the cancer is an ovarian cancer.

87. The method of clause 83 wherein the cancer is a triple negative breast cancer.

88. The method of any one of clauses 56 to 87 wherein the CAR has a recognition region and the recognition region is a single chain fragment variable (scFv) region of an antibody.

89. The method of any one of clauses 56 to 64 or 67 to 88 wherein the CAR has a recognition region and the recognition region of the CAR is a single chain fragment variable (scFv) region of an anti-FITC antibody.

90. The method of any one of clauses 56 to 89 wherein the CAR has a co-stimulation domain and the co-stimulation domain is selected from the group consisting of CD28, CD137 (4-1BB), CD134 (OX40), and CD278 (ICOS).

91. The method of any one of clauses 56 to 90 wherein the CAR has an activation signaling domain and the activation signaling domain is a T cell CD3ζ chain or an Fc receptor γ.

92. The method of any one of clauses 56 to 64 or 67 to 91 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

93. The method of any one of clauses 56 to 92 wherein multiple doses of the compound, or the pharmaceutically acceptable salt thereof, are administered.

94. The method of any one of clauses 56 to 93 wherein the patient is imaged prior to administration of the compound, or the pharmaceutically acceptable salt thereof, or prior to administration of the CAR T cell composition.

95. The method of any one of clauses 56 to 94 wherein the compound, or the pharmaceutically acceptable salt thereof, is not an antibody, and does not comprise a fragment of an antibody.

96. The method of any one of clauses 56 to 95 wherein the targeting moiety does not comprise a peptide epitope.

97. The method of any one of clauses 56 to 96 wherein cytokine release resulting in off-target toxicity in the patient does not occur and wherein CAR T cell toxicity to the cancer occurs.

98. The method of any one of clauses 56 to 96 wherein off-target tissue toxicity does not occur in the patient and wherein CAR T cell toxicity to the cancer occurs.

99. The method of any one of clauses 56 to 96 wherein the cancer comprises a tumor, wherein tumor size is reduced in the patient, and wherein off-target toxicity does not occur.

100. The method of any one of clauses 56 to 99 wherein the CAR T cells comprise a nucleic acid comprising SEQ ID NO:1.

101. The method of any one of clauses 56 to 100 wherein the CAR T cells comprise a polypeptide comprising SEQ ID NO:2.

102. The method of clause 100 wherein the nucleic acid encodes a chimeric antigen receptor.

103. The method of any one of clauses 56 to 102 wherein the CAR comprises humanized amino acid sequences.

104. The method of any one of clauses 56 to 102 wherein the CAR consists of humanized amino acid sequences.

105. The method of any one of clauses 56 to 104 wherein the mixture of the CAR T cells and the non-transformed T cells is in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

106. The method of any one of clauses 56 to 105 wherein the mixture of the CAR T cells and the non-transformed T cells is in a ratio of from about 1:1 to about 1:5 of the CAR T cells to the non-transformed T cells.

107. The method of any one of clauses 56 to 106 wherein the mixture of the CAR T cells and the non-transformed T cells comprises about 10 million of the CAR T cells and about 40 million of the non-transformed T cells.

108. A method of treatment of a cancer, the method comprising
i) administering to a patient a compound, or a pharmaceutically acceptable salt thereof, wherein the compound comprises a small molecule ligand linked to a targeting moiety by a linker;
ii) administering to the patient a CAR T cell composition wherein the CAR T cell composition comprises CAR T cells and wherein the CAR T cells comprise a CAR directed to the targeting moiety; and
iii) administering to the patient a folate, a conjugate comprising a folate wherein the conjugate comprising a folate does not comprise a targeting moiety, or an agent that inhibits activation of the CAR T cells.

109. The method of clause 108 wherein step iii comprises administering a folate.

110. The method of any one of clauses 108 or 109 wherein step iii comprises administering folic acid or leucovorin.

111. The method of clause 108 wherein step iii comprises administering the conjugate comprising a folate.

112. The method of clause 111 wherein the conjugate comprising a folate comprises a folate linked to one or more amino acids.

113. The method of clause 111 wherein the conjugate comprising a folate has the formula

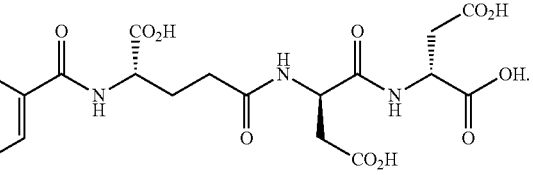

114. The method of any one of clauses 109 to 112 wherein the folate has the formula

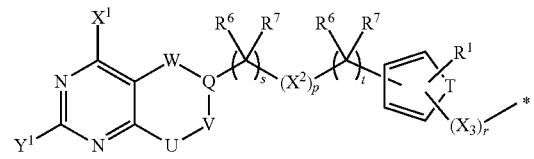

wherein $X^1$ and Y are each-independently selected from the group consisting of halo, $R^2$, $OR^2$, $SR^3$, and $NR^4R^5$;
U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;
$X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$) ($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;
$R^1$ is selected from the group consisting of hydrogen, halo, $C_1$-$C_{12}$ alkyl, and $C_1$-$C_{12}$ alkoxy;
$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;
$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;
$R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

p, r, s, and t are each independently either 0 or 1; and

* represents an optional covalent bond to the rest of the conjugate, if any additional chemical moieties are part of the folate.

115. The method of any one of clauses 108 to 114 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

116. The method of any one of clauses 108 to 115 wherein the targeting moiety is FITC.

117. The method of any one of clauses 108 to 115 wherein the targeting moiety is DNP.

118. The method of any one of clauses 108 to 115 wherein the targeting moiety is TNP.

119. The method of any one of clauses 108 to 118 wherein the linker comprises polyethylene glycol (PEG), polyproline, a hydrophilic amino acid, a sugar, an unnatural peptidoglycan, a polyvinylpyrrolidone, pluronic F-127, or a combination thereof.

120. The method of any one of clauses 108 to 119 wherein the linker comprises PEG.

121. The method of any one of clauses 108 to 120 wherein the compound, or the pharmaceutically acceptable salt thereof, has the formula

B-L-T, wherein B represents the small molecule ligand, L represents the linker, and T represents the targeting moiety, and wherein L comprises a structure having the formula

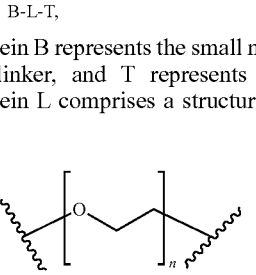

wherein n is an integer from 0 to 200.

122. The method of clause 121 wherein n is an integer from 0 to 12.

123. The method of clause 121 wherein n is an integer from 0 to 150.

124. The method of clause 121 wherein n is an integer from 0 to 110.

125. The method of clause 121 wherein n is an integer from 0 to 20.

126. The method of clause 121 wherein n is an integer from 15 to 20.

127. The method of clause 121 wherein n is an integer from 15 to 110.

128. The method of any one of clauses 108 to 116 or 119 to 127 wherein the linker comprises PEG and the targeting moiety is FITC, or a pharmaceutically acceptable salt thereof.

129. The method of any one of clauses 108 to 128 wherein the compound, or the pharmaceutically acceptable salt thereof, is administered at a dose of about 10 nmoles/kg to about 10000 nmoles/kg of body weight of the patient.

130. The method of any one of clauses 108 to 129 wherein the compound, or the pharmaceutically acceptable salt thereof, is administered at a dose of about 10 nmoles/kg to about 5000 nmoles/kg of body weight of the patient.

131. The method of any one of clauses 108 to 130 wherein the compound, or the pharmaceutically acceptable salt thereof, is administered at a dose of about 10 nmoles/kg to about 1000 nmoles/kg of body weight of the patient.

132. The method of any one of clauses 108 to 131 wherein the compound, or the pharmaceutically acceptable salt thereof, is administered at a dose of about 10 nmoles/kg to about 600 nmoles/kg of body weight of the patient.

133. The method of any one of clauses 108 to 132 wherein the compound, or the pharmaceutically acceptable salt thereof, is administered at a dose of about 200 nmoles/kg to about 600 nmoles/kg of body weight of the patient.

134. The method of any one of clauses 108 to 133 wherein the compound, or the pharmaceutically acceptable salt thereof, is administered at a dose of about 250 nmoles/kg to about 600 nmoles/kg of body weight of the patient.

135. The method of any one of clauses 108 to 134 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

136. The method of any one of clauses 108 to 135 wherein the ligand portion of the small molecule ligand linked to a targeting moiety by a linker is a folate and the cancer is a folate receptor expressing cancer.

137. The method of clause 136 wherein the cancer is an endometrial cancer.

138. The method of clause 136 wherein the cancer is a non-small cell lung cancer.

139. The method of clause 136 wherein the cancer is an ovarian cancer.

140. The method of clause 136 wherein the cancer is a triple negative breast cancer.

141. The method of any one of clauses 108 to 140 wherein the CAR has a recognition region and the recognition region is a single chain fragment variable (scFv) region of an antibody.

142. The method of any one of clauses 108 to 116 or 119 to 141 wherein the CAR has a recognition region and the recognition region of the CAR is a single chain fragment variable (scFv) region of an anti-FITC antibody.

143. The method of any one of clauses 108 to 142 wherein the CAR has a co-stimulation domain and the co-stimulation domain is selected from the group consisting of CD28, CD137 (4-1BB), CD134 (OX40), and CD278 (ICOS).

144. The method of any one of clauses 108 to 143 wherein the CAR has an activation signaling domain and the activation signaling domain is a T cell CD31 chain or an Fc receptor γ.

145. The method of any one of clauses 108 to 116 or 119 to 144 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

146. The method of any one of clauses 108 to 145 wherein multiple doses of the compound, or the pharmaceutically acceptable salt thereof, and/or the CAR T cell composition are administered.

147. The method of any one of clauses 108 to 146 wherein the patient is imaged prior to administration of the compound, or the pharmaceutically acceptable salt thereof, or prior to administration of the CAR T cell composition.

148. The method of any one of clauses 108 to 147 wherein the compound, or the pharmaceutically acceptable salt thereof, is not an antibody, and does not comprise a fragment of an antibody.

149. The method of any one of clauses 108 to 148 wherein the targeting moiety does not comprise a peptide epitope.

150. The method of any one of clauses 108 to 149 wherein cytokine release resulting in off-target toxicity in the patient does not occur and wherein CAR T cell toxicity to the cancer occurs.

151. The method of any one of clauses 108 to 149 wherein off-target tissue toxicity does not occur in the patient and wherein CAR T cell toxicity to the cancer occurs.

152. The method of any one of clauses 108 to 149 wherein the cancer comprises a tumor, wherein tumor size is reduced in the patient, and wherein off-target toxicity does not occur.

153. The method of any one of clauses 108 to 152 wherein the CAR T cells comprise a nucleic acid comprising SEQ ID NO:1.

154. The method of any one of clauses 108 to 153 wherein the CAR T cells comprise a polypeptide comprising SEQ ID NO:2.

155. The method of clause 153 wherein the nucleic acid encodes a chimeric antigen receptor.

156. The method of any one of clauses 108 to 155 wherein the CAR comprises humanized amino acid sequences.

157. The method of any one of clauses 108 to 155 wherein the CAR consists of humanized amino acid sequences.

158. The method of any one of clauses 108 to 157 wherein the CAR T cell composition comprises a mixture of the CAR T cells and non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

159. The method of any one of clauses 108 to 158 wherein the CAR T cell composition comprises a mixture of the CAR T cells and non-transformed T cells in a ratio of from about 1:1 to about 1:5 of the CAR T cells to the non-transformed T cells.

160. The method of any one of clauses 108 to 159 wherein the CAR T cell composition comprises a mixture comprising about 10 million of the CAR T cells and about 40 million of the non-transformed T cells.

161. The method of any one of clauses 108 to 160 wherein the agent that inhibits activation of the CAR T cells is selected from the group consisting of a lymphocyte-specific protein tyrosine kinase inhibitor, a PI3 kinase inhibitor, an inhibitor of an IL-2 inducible T cell kinase, a JAK inhibitor, a BTK inhibitor, EC2319, and an agent that blocks CAR T cell binding to the compound, or the pharmaceutically acceptable salt thereof, but does not bind to the cancer.

162. The method of clause 161 wherein the agent that inhibits activation of the CAR T cells is administered and the agent is a lymphocyte-specific protein tyrosine kinase inhibitor.

163. The method of clause 162 wherein the lymphocyte-specific protein tyrosine kinase inhibitor is Dasatinib.

164. The method of clause 161 wherein the agent that inhibits activation of the CAR T cells is administered and the agent is a PI3 kinase inhibitor.

165. The method of clause 164 wherein the PI3 kinase inhibitor is GDC0980.

166. The method of clause 161 wherein the agent that inhibits activation of the CAR T cells is administered and the agent is an IL-2 inducible T cell kinase inhibitor.

167. The method of clause 166 wherein the IL-2 inducible T cell kinase inhibitor is BMS-509744.

168. The method of any one of clauses 1 to 160 wherein the CAR T cell composition is administered by injection into the patient's bloodstream, and wherein the CAR T cells in the patient's bloodstream are at least 10 percent of the patient's total T cells in the patient's bloodstream by about four weeks after injection of the CAR T cell composition.

169. The method of any one of clauses 1 to 160 wherein the CAR T cell composition is administered by injection into the patient's bloodstream, and wherein the CAR T cells in the patient's bloodstream are at least 12 percent of the patient's total T cells in the patient's bloodstream by about four weeks after injection of the CAR T cell composition.

170. The method of any one of clauses 1 to 160 wherein the CAR T cell composition is administered by injection into the patient's bloodstream, and wherein the CAR T cells in the patient's bloodstream are at least 15 percent of the patient's total T cells in the patient's bloodstream by about four weeks after injection of the CAR T cell composition.

171. The method of any one of clauses 1 to 160 or 168 to 170 wherein the CAR T cells administered to the patient in the CAR T cell composition comprise from about 1 million to about 15 million of the CAR T cells.

172. The method of any one of clauses 1 to 160 or 168 to 171 wherein the dose of the CAR T cells administered to the patient in the CAR T cell composition is selected from the group consisting of about 1 million, about 2 million, about 3 million, about 4 million, about 5 million, about 6 million, about 7 million, about 8 million, about 9 million, about 10 million, about 11 million, about 12 million, about 12.5 million, about 13 million, about 14 million, and about 15 million of the CAR T cells.

173. The method of any one of clauses 1 to 160 or 168 to 170 wherein the CAR T cells administered to the patient in the CAR T cell composition comprise at least about 2 million of the CAR T cells.

174. The method of any one of clauses 1 to 160 or 168 to 170 wherein the CAR T cells administered to the patient in the CAR T cell composition comprise at least about 5 million of the CAR T cells.

175. The method of any one of clauses 1 to 160 or 168 to 170 wherein the CAR T cells administered to the patient in the CAR T cell composition comprise at least about 10 million of the CAR T cells.

176. The method of any one of clauses 1 to 175 wherein the CAR T cells comprise a nucleic acid comprising SEQ ID NO:3.

177. The method of any one of clauses 1 to 176 wherein the CAR T cells comprise a vector comprising SEQ ID NO: 1.

178. The method of any one of clauses 1 to 177 wherein the CAR T cells comprise a vector comprising SEQ ID NO:3.

179. The method of clause 176 wherein the nucleic acid encodes a chimeric antigen receptor.

180. The method of any one of clauses 108 to 160 wherein the agent that inhibits activation of the CAR T cells is administered and is an agent that blocks CAR T cell binding to the compound, or the pharmaceutically acceptable salt thereof, but does not bind to the cancer.

181. The method of clause 180 wherein the agent is fluoresceinamine, FITC, or sodium fluorescein.

182. The method of clause 180 wherein the agent is FITC.

183. A method of treatment of a cancer, the method comprising
   i) administering to a patient a compound, or a pharmaceutically acceptable salt thereof, wherein the compound comprises a small molecule ligand linked to a targeting moiety by a linker, and wherein the compound, or the pharmaceutically acceptable salt thereof, is at a dose of about 10 nmoles/kg of body weight of the patient to about 2500 nmoles/kg of body weight of the patient; and
   ii) administering to the patient a CAR T cell composition comprising CAR T cells wherein the CAR T cells comprise a CAR directed to the targeting moiety, and wherein the CAR T cells are at a dose of about 1 million of the CAR T cells to about 15 million of the CAR T cells.

184. The method of clause 183 wherein the ligand is selected from the group consisting of a folate, DUPA, an NK-1R ligand, a CAIX ligand, a ligand of gamma glutamyl transpeptidase, an NKG2D ligand, and a CCK2R ligand.

185. The method of any one of clauses 183 or 184 wherein the ligand is a folate.

186. The method of any one of clauses 183 to 185 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

187. The method of any one of clauses 183 to 186 wherein the targeting moiety is FITC.

188. The method of any one of clauses 183 to 187 wherein the linker comprises polyethylene glycol (PEG), polyproline, a hydrophilic amino acid, a sugar, an unnatural peptidoglycan, a polyvinylpyrrolidone, pluronic F-127, or a combination thereof.

189. The method of any one of clauses 183 to 188 wherein the linker comprises PEG.

190. The method of any one of clauses 183 to 189 wherein the compound, or the pharmaceutically acceptable salt thereof, has the formula

B-L-T, wherein B represents the small molecule ligand, L represents the linker, and T represents the targeting moiety, and wherein L comprises a structure having the formula

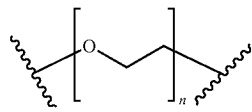

wherein n is an integer from 0 to 200.

191. The method of any one of clauses 183 to 190 wherein the linker comprises PEG and the targeting moiety is FITC, or a pharmaceutically acceptable salt thereof.

192. The method of any one of clauses 183 to 191 wherein the compound, or the pharmaceutically acceptable salt thereof, is administered at a dose of about 10 nmoles/kg to about 100 nmoles/kg of body weight of the patient.

193. The method of any one of clauses 183 to 191 wherein the compound, or the pharmaceutically acceptable salt thereof, is administered at a dose of about 10 nmoles/kg to about 50 nmoles/kg of body weight of the patient.

194. The method of any one of clauses 183 to 191 wherein the compound, or the pharmaceutically acceptable salt thereof, is administered at a dose of about 10 nmoles/kg to about 20 nmoles/kg of body weight of the patient.

195. The method of any one of clauses 183 to 191 wherein the compound, or the pharmaceutically acceptable salt thereof, is administered at a dose of about 10 nmoles/kg to about 600 nmoles/kg of body weight of the patient.

196. The method of any one of clauses 183 to 191 wherein the compound, or the pharmaceutically acceptable salt thereof, is administered at a dose of about 200 nmoles/kg to about 600 nmoles/kg of body weight of the patient.

197. The method of any one of clauses 183 to 191 wherein the compound, or the pharmaceutically acceptable salt thereof, is administered at a dose of about 400 nmoles/kg to about 600 nmoles/kg of body weight of the patient.

198. The method of any one of clauses 183 to 197 wherein the CAR T cells are at a dose of about 1 million of the CAR T cells to about 12.5 million of the CAR T cells.

199. The method of any one of clauses 183 to 197 wherein the CAR T cells are at a dose of about 1 million of the CAR T cells to about 7 million of the CAR T cells.

200. The method of any one of clauses 183 to 197 wherein the CAR T cells are at a dose of about 1 million of the CAR T cells to about 5 million of the CAR T cells.

201. The method of any one of clauses 183 to 197 wherein the CAR T cells are at a dose of about 2 million of the CAR T cells to about 5 million of the CAR T cells.

202. The method of any one of clauses 183 to 201 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

203. The method of any one of clauses 183 to 202 wherein the cancer is a folate receptor expressing cancer.

204. The method of any one of clauses 183 to 203 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

205. The method of any one of clauses 183 to 204 wherein the compound, or the pharmaceutically acceptable salt thereof, is not an antibody, and does not comprise a fragment of an antibody.

206. The method of any one of clauses 183 to 205 wherein the targeting moiety does not comprise a peptide epitope.

207. The method of any one of clauses 183 to 206 wherein cytokine release resulting in off-target toxicity in the patient does not occur and wherein CAR T cell toxicity to the cancer occurs.

208. The method of any one of clauses 183 to 206 wherein off-target tissue toxicity does not occur in the patient and wherein CAR T cell toxicity to the cancer occurs.

209. The method of any one of clauses 183 to 206 wherein the cancer comprises a tumor, wherein tumor size is reduced in the patient, and wherein off-target toxicity does not occur.

210. The method of any one of clauses 183 to 209 wherein the CAR T cells comprise a nucleic acid comprising SEQ ID NO:1.

211. The method of any one of clauses 183 to 209 wherein the CAR T cells comprise a polypeptide comprising SEQ ID NO:2.

212. The method of any one of clauses 183 to 211 wherein the CAR comprises humanized amino acid sequences.

213. The method of any one of clauses 183 to 212 wherein the CAR consists of humanized amino acid sequences.

214. The method of any one of clauses 183 to 213 wherein the CAR T cell composition further comprises non-transformed T cells.

215. A method of treatment of a cancer, the method comprising
   i) administering continuously to a patient a compound, or a pharmaceutically acceptable salt thereof, wherein the compound comprises a small molecule ligand linked to a targeting moiety by a linker;
   ii) administering to the patient a CAR T cell composition comprising CAR T cells wherein the CAR T cells comprise a CAR directed to the targeting moiety; and
   iii) ending the continuous administration of the compound, or the pharmaceutically acceptable salt thereof, to inhibit or prevent cytokine release syndrome in the patient.

216. The method of clause 215 wherein the ligand is selected from the group consisting of a folate, DUPA, an NK-1R ligand, a CAIX ligand, a ligand of gamma glutamyl transpeptidase, an NKG2D ligand, and a CCK2R ligand.

217. The method of any one of clauses 215 or 216 wherein the ligand is a folate.

218. The method of any one of clauses 215 to 217 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

219. The method of any one of clauses 215 to 218 wherein the targeting moiety is FITC.

220. The method of any one of clauses 215 to 219 wherein the linker comprises polyethylene glycol (PEG), polyproline, a hydrophilic amino acid, a sugar, an unnatural peptidoglycan, a polyvinylpyrrolidone, pluronic F-127, or a combination thereof.

221. The method of any one of clauses 215 to 220 wherein the linker comprises PEG.

222. The method of any one of clauses 215 to 221 wherein the compound, or the pharmaceutically acceptable salt thereof, has the formula

B-L-T, wherein B represents the small molecule ligand, L represents the linker, and T represents the targeting moiety, and wherein L comprises a structure having the formula

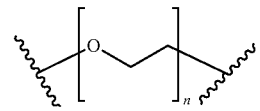

wherein n is an integer from 0 to 200.

223. The method of any one of clauses 215 to 222 wherein the linker comprises PEG and the targeting moiety is FITC, or a pharmaceutically acceptable salt thereof.

224. The method of any one of clauses 215 to 223 wherein the compound, or the pharmaceutically acceptable salt thereof, is administered continuously for at least one hour to the patient.

225. The method of any one of clauses 215 to 223 wherein the compound, or the pharmaceutically acceptable salt thereof, is administered continuously for at least four hours to the patient.

226. The method of any one of clauses 215 to 223 wherein the compound, or the pharmaceutically acceptable salt thereof, is administered continuously for at least six hours to the patient.

227. The method of any one of clauses 215 to 223 wherein the continuous administration of the compound, or the pharmaceutically acceptable salt thereof, is a regimen of administration every other day.

228. The method of any one of clauses 215 to 223 wherein the continuous administration of the compound, or the pharmaceutically acceptable salt thereof, is a regimen of administration three times weekly.

229. The method of any one of clauses 215 to 223 wherein the continuous administration of the compound, or the pharmaceutically acceptable salt thereof, is administration until an unacceptable loss of body weight of the patient, a fever, a drop in blood pressure, or pulmonary edema occurs.

230. The method of any one of clauses 215 to 229 wherein the compound, or the pharmaceutically acceptable salt thereof, is administered at a dose of about 200 nmoles/kg to about 600 nmoles/kg of body weight of the patient.

231. The method of any one of clauses 215 to 229 wherein the compound, or the pharmaceutically acceptable salt thereof, is administered at a dose of about 400 nmoles/kg to about 600 nmoles/kg of body weight of the patient.

232. The method of any one of clauses 215 to 231 wherein about 2 million to about 5 million of the CAR T cells are administered.

233. The method of any one of clauses 215 to 232 wherein the administration is by intravenous administration.

234. The method of any one of clauses 215 to 233 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

235. The method of any one of clauses 215 to 234 wherein the cancer is a folate receptor expressing cancer.

236. The method of any one of clauses 215 to 235 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

237. The method of any one of clauses 215 to 236 wherein the compound, or the pharmaceutically acceptable salt thereof, is not an antibody, and does not comprise a fragment of an antibody.

238. The method of any one of clauses 215 to 237 wherein the targeting moiety does not comprise a peptide epitope.

239. The method of any one of clauses 215 to 238 wherein cytokine release resulting in off-target toxicity in the patient does not occur and wherein CAR T cell toxicity to the cancer occurs.

240. The method of any one of clauses 215 to 238 wherein off-target tissue toxicity does not occur in the patient and wherein CAR T cell toxicity to the cancer occurs.

241. The method of any one of clauses 215 to 238 wherein the cancer comprises a tumor, wherein tumor size is reduced in the patient, and wherein off-target toxicity does not occur.

242. The method of any one of clauses 215 to 241 wherein the CAR T cells comprise a nucleic acid comprising SEQ ID NO:1.

243. The method of any one of clauses 215 to 242 wherein the CAR T cells comprise a polypeptide comprising SEQ ID NO:2.

244. The method of any one of clauses 215 to 243 wherein the CAR comprises humanized amino acid sequences.

245. The method of any one of clauses 215 to 243 wherein the CAR consists of humanized amino acid sequences.

246. The method of any one of clauses 215 to 245 wherein the CAR T cell composition further comprises non-transformed T cells.

247. The method of any one of clauses 215 to 246 wherein the CAR T cell composition further comprises non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

248. The method of any one of clauses 215 to 247 wherein the CAR T cell composition further comprises non-transformed T cells in a ratio of from about 1:1 to about 1:5 of the CAR T cells to the non-transformed T cells.

249. The method of any one of clauses 215 to 248 wherein the CAR T cell composition further comprises non-transformed T cells in a mixture of about 10 million of the CAR T cells and about 40 million non-transformed T cells.

250. The method of any one of clauses 215 to 249 wherein the cancer is a non-small cell lung cancer.

251. The method of any one of clauses 215 to 249 wherein the cancer is an ovarian cancer.

252. A method of treatment of a cancer, the method comprising
  i) administering to a patient a compound, or a pharmaceutically acceptable salt thereof, wherein the compound comprises a small molecule ligand linked to a targeting moiety by a linker and wherein the compound, or the pharmaceutically acceptable salt thereof, is administered once weekly to the patient; and
  ii) administering to the patient a CAR T cell composition comprising CAR T cells wherein the CAR T cells comprise a CAR directed to the targeting moiety.

253. The method of clause 252 wherein the ligand is selected from the group consisting of a folate, DUPA, an NK-1R ligand, a CAIX ligand, a ligand of gamma glutamyl transpeptidase, an NKG2D ligand, and a CCK2R ligand.

254. The method of any one of clauses 252 or 253 wherein the ligand is a folate.

255. The method of any one of clauses 252 to 254 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

256. The method of any one of clauses 252 to 255 wherein the targeting moiety is FITC.

257. The method of any one of clauses 252 to 256 wherein the linker comprises polyethylene glycol (PEG), polyproline, a hydrophilic amino acid, a sugar, an unnatural peptidoglycan, a polyvinylpyrrolidone, pluronic F-127, or a combination thereof.

258. The method of any one of clauses 252 to 257 wherein the linker comprises PEG.

259. The method of any one of clauses 252 to 258 wherein the compound, or the pharmaceutically acceptable salt thereof, has the formula

B-L-T, wherein B represents the small molecule ligand, L represents the linker, and T represents the targeting moiety, and wherein L comprises a structure having the formula

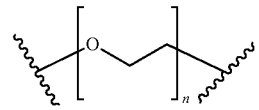

wherein n is an integer from 0 to 200.

260. The method of any one of clauses 252 to 259 wherein the linker comprises PEG and the targeting moiety is FITC, or a pharmaceutically acceptable salt thereof.

261. The method of any one of clauses 252 to 260 wherein the compound, or the pharmaceutically acceptable salt thereof, is administered at a dose of about 10 nmoles/kg to about 100 nmoles/kg of body weight of the patient.

262. The method of any one of clauses 252 to 261 wherein the compound, or the pharmaceutically acceptable salt thereof, is administered at a dose of about 10 nmoles/kg to about 50 nmoles/kg of body weight of the patient.

263. The method of any one of clauses 252 to 262 wherein the compound, or the pharmaceutically acceptable salt thereof, is administered at a dose of about 10 nmoles/kg to about 20 nmoles/kg of body weight of the patient.

264. The method of any one of clauses 252 to 263 wherein the compound, or the pharmaceutically acceptable salt thereof, is administered at a dose of about 10 nmoles/kg to about 600 nmoles/kg of body weight of the patient.

265. The method of any one of clauses 252 to 264 wherein the compound, or the pharmaceutically acceptable salt thereof, is administered at a dose of about 200 nmoles/kg to about 600 nmoles/kg of body weight of the patient.

266. The method of any one of clauses 252 to 265 wherein the compound, or the pharmaceutically acceptable salt thereof, is administered at a dose of about 400 nmoles/kg to about 600 nmoles/kg of body weight of the patient.

267. The method of any one of clauses 252 to 266 wherein the CAR T cells are at a dose of about 1 million of the CAR T cells to about 15 million of the CAR T cells.

268. The method of any one of clauses 252 to 267 wherein the CAR T cells are at a dose of about 1 million of the CAR T cells to about 7 million of the CAR T cells.

269. The method of any one of clauses 252 to 268 wherein the CAR T cells are at a dose of about 1 million of the CAR T cells to about 5 million of the CAR T cells.

270. The method of any one of clauses 252 to 269 wherein the CAR T cells are at a dose of about 2 million of the CAR T cells to about 5 million of the CAR T cells.

271. The method of any one of clauses 252 to 270 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

272. The method of any one of clauses 252 to 271 wherein the cancer is a folate receptor expressing cancer.

273. The method of any one of clauses 252 to 272 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

274. The method of any one of clauses 252 to 273 wherein the compound, or the pharmaceutically acceptable salt thereof, is not an antibody, and does not comprise a fragment of an antibody.

275. The method of any one of clauses 252 to 274 wherein the targeting moiety does not comprise a peptide epitope.

276. The method of any one of clauses 252 to 275 wherein cytokine release resulting in off-target toxicity in the patient does not occur and wherein CAR T cell toxicity to the cancer occurs.

277. The method of any one of clauses 252 to 275 wherein off-target tissue toxicity does not occur in the patient and wherein CAR T cell toxicity to the cancer occurs.

278. The method of any one of clauses 252 to 275 wherein the cancer comprises a tumor, wherein tumor size is reduced in the patient, and wherein off-target toxicity does not occur.

279. The method of any one of clauses 252 to 278 wherein the CAR T cells comprise a nucleic acid comprising SEQ ID NO:1.

280. The method of any one of clauses 252 to 278 wherein the CAR T cells comprise a polypeptide comprising SEQ ID NO:2.

281. The method of any one of clauses 252 to 280 wherein the CAR comprises humanized amino acid sequences.

282. The method of any one of clauses 252 to 280 wherein the CAR consists of humanized amino acid sequences.

283. The method of any one of clauses 252 to 282 wherein the CAR T cell composition further comprises non-transformed T cells.

284. A method of treatment of a cancer, the method comprising
  i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof; and
  ii) administering to the patient a CAR T cell composition comprising CAR T cells wherein the CAR T cells comprise a CAR directed to the targeting moiety.

285. The method of clause 284 wherein at least a first dose, a second dose, and a third dose of the compound, or the pharmaceutically acceptable salt thereof, are administered to the patient, wherein the first dose, the second dose, and the third dose are different, wherein the second dose of the compound, or the pharmaceutically acceptable salt thereof, is about 2-fold to about 750-fold greater in amount than the first dose of the compound, or the pharmaceutically acceptable salt thereof, and wherein the third dose of the compound, or the pharmaceutically acceptable salt thereof, is about 800-fold to about 10000-fold greater in amount than the first dose of the compound, or the pharmaceutically acceptable salt thereof.

286. The method of clause 285 wherein at least a first dose, a second dose, a third dose, and a fourth dose of the compound, or the pharmaceutically acceptable salt thereof, are administered to the patient, wherein the first dose, the second dose, the third dose, and the fourth dose are different, wherein the second dose of the compound, or the pharmaceutically acceptable salt thereof, is about 2-fold to about 750-fold greater in amount than the first dose of the compound, or the pharmaceutically acceptable salt thereof, wherein the third dose of the compound, or the pharmaceutically acceptable salt thereof, is about 800-fold to about 7500-fold greater in amount than the first dose of the compound, or the pharmaceutically acceptable salt thereof, and wherein the fourth dose of the compound, or the pharmaceutically acceptable salt thereof, is about 8000 to about 15000-fold greater in amount than the first dose of the compound, or the pharmaceutically acceptable salt thereof.

287. The method of clause 286 wherein the second dose of the compound, or the pharmaceutically acceptable salt thereof, is about 100-fold greater in amount than the first dose of the compound, or the pharmaceutically acceptable salt thereof, wherein the third dose of the compound, or the pharmaceutically acceptable salt thereof, is about 1000-fold greater in amount than the first dose of the compound, or the pharmaceutically acceptable salt thereof, and wherein the fourth dose of the compound, or the pharmaceutically acceptable salt thereof, is about 10000-fold greater in amount than the first dose of the compound, or the pharmaceutically acceptable salt thereof.

288. The method of any one of clauses 284 to 287 wherein the ligand is selected from the group consisting of a folate, DUPA, an NK-1R ligand, a CAIX ligand, a ligand of gamma glutamyl transpeptidase, an NKG2D ligand, and a CCK2R ligand.

289. The method of any one of clauses 284 to 288 wherein the ligand is a folate.

290. The method of any one of clauses 284 to 289 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

291. The method of any one of clauses 284 to 290 wherein the targeting moiety is FITC.

292. The method of any one of clauses 284 to 291 wherein the linker comprises polyethylene glycol (PEG), polyproline, a hydrophilic amino acid, a sugar, an unnatural peptidoglycan, a polyvinylpyrrolidone, pluronic F-127, or a combination thereof.

293. The method of any one of clauses 284 to 292 wherein the linker comprises PEG.

294. The method of any one of clauses 284 to 293 wherein the compound, or the pharmaceutically acceptable salt thereof, has the formula

B-L-T, wherein B represents the small molecule ligand, L represents the linker, and T represents the targeting moiety, and wherein L comprises a structure having the formula

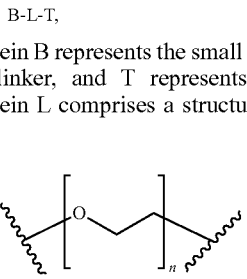

wherein n is an integer from 0 to 200.

295. The method of any one of clauses 284 to 294 wherein the linker comprises PEG and the targeting moiety is FITC, or a pharmaceutically acceptable salt thereof.

296. The method of any one of clauses 284 to 295 wherein the compound, or the pharmaceutically acceptable salt thereof, is administered at a dose of about 10 nmoles/kg to about 100 nmoles/kg of body weight of the patient.

297. The method of any one of clauses 284 to 296 wherein the compound, or the pharmaceutically acceptable salt thereof, is administered at a dose of about 10 nmoles/kg to about 50 nmoles/kg of body weight of the patient.

298. The method of any one of clauses 284 to 297 wherein the compound, or the pharmaceutically acceptable salt thereof, is administered at a dose of about 10 nmoles/kg to about 20 nmoles/kg of body weight of the patient.

299. The method of any one of clauses 284 to 298 wherein the compound, or the pharmaceutically acceptable salt thereof, is administered at a dose of about 10 nmoles/kg to about 600 nmoles/kg of body weight of the patient.

300. The method of any one of clauses 284 to 299 wherein the compound, or the pharmaceutically acceptable salt thereof, is administered at a dose of about 200 nmoles/kg to about 600 nmoles/kg of body weight of the patient.

301. The method of any one of clauses 284 to 300 wherein the compound, or the pharmaceutically acceptable salt thereof, is administered at a dose of about 400 nmoles/kg to about 600 nmoles/kg of body weight of the patient.

302. The method of any one of clauses 284 to 301 wherein the CAR T cells are at a dose of about 1 million of the CAR T cells to about 15 million of the CAR T cells.

303. The method of any one of clauses 284 to 302 wherein the CAR T cells are at a dose of about 1 million of the CAR T cells to about 7 million of the CAR T cells.

304. The method of any one of clauses 284 to 303 wherein the CAR T cells are at a dose of about 1 million of the CAR T cells to about 5 million of the CAR T cells.

305. The method of any one of clauses 284 to 304 wherein the CAR T cells are at a dose of about 2 million of the CAR T cells to about 5 million of the CAR T cells.

306. The method of any one of clauses 284 to 305 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

307. The method of any one of clauses 284 to 306 wherein the cancer is a folate receptor expressing cancer.

308. The method of any one of clauses 284 to 307 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

309. The method of any one of clauses 284 to 308 wherein the compound, or the pharmaceutically acceptable salt thereof, is not an antibody, and does not comprise a fragment of an antibody.

310. The method of any one of clauses 284 to 309 wherein the targeting moiety does not comprise a peptide epitope.

311. The method of any one of clauses 284 to 310 wherein cytokine release resulting in off-target toxicity in the patient does not occur and wherein CAR T cell toxicity to the cancer occurs.

312. The method of any one of clauses 284 to 310 wherein off-target tissue toxicity does not occur in the patient and wherein CAR T cell toxicity to the cancer occurs.

313. The method of any one of clauses 284 to 310 wherein the cancer comprises a tumor, wherein tumor size is reduced in the patient, and wherein off-target toxicity does not occur.

314. The method of any one of clauses 284 to 313 wherein the CAR T cells comprise a nucleic acid comprising SEQ ID NO:1.

315. The method of any one of clauses 284 to 313 wherein the CAR T cells comprise a polypeptide comprising SEQ ID NO:2.

316. The method of any one of clauses 284 to 315 wherein the CAR comprises humanized amino acid sequences.

317. The method of any one of clauses 284 to 315 wherein the CAR consists of humanized amino acid sequences.

318. The method of any one of clauses 284 to 317 wherein the CAR T cell composition further comprises non-transformed T cells.

319. The method of any one of clauses 1 to 214 or 252 to 318 wherein the compound, or the pharmaceutically acceptable salt thereof, is administered continuously to the patient and the method further comprises ending the continuous administration of the compound, or the pharmaceutically acceptable salt thereof, to inhibit or prevent cytokine release syndrome in the patient.

320. The method of any one of clauses 1 to 107 or 183 to 318 further comprising administering to the patient a folate, a conjugate comprising a folate wherein the conjugate comprising a folate does not comprise a targeting moiety, or an agent that inhibits activation of the CAR T cells.

321. The method of any one of clauses 1 to 182 or 215 to 318 wherein the compound, or the pharmaceutically acceptable salt thereof, is at a dose of about 10 nmoles/kg of body weight of the patient to about 2500 nmoles/kg of body weight of the patient and the CAR T cells are at a dose of about 1 million of the CAR T cells to about 15 million of the CAR T cells.

322. The method of any one of clauses 1 to 251 or 284 to 318 wherein the compound, or the pharmaceutically acceptable salt thereof, is administered once weekly to the patient.

323. The method of any one of clauses 1 to 283 wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof.

324. The method of any one of clauses 56 to 318 wherein the CAR T cell composition is administered in at least two doses.

325. A method of treatment of a cancer, the method comprising
i) administering to a patient a first dose of a compound, or a pharmaceutically acceptable salt thereof, wherein the compound comprises a small molecule ligand linked to a targeting moiety by a linker;
ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof; and
iii) administering to the patient a dose of a CAR T cell composition comprising CAR T cells wherein the CAR T cells comprise a CAR directed to the targeting moiety.

326. The method of clause 325 wherein the second dose of the compound, or the pharmaceutically acceptable salt thereof, is at least about 60 percent lower in amount than the first dose of the compound, or the pharmaceutically acceptable salt thereof.

327. The method of clause 325 wherein the second dose of the compound, or the pharmaceutically acceptable salt thereof, is at least about 70 percent lower in amount than the first dose of the compound, or the pharmaceutically acceptable salt thereof.

328. The method of clause 325 wherein the second dose of the compound, or the pharmaceutically acceptable salt thereof, is at least about 80 percent lower in amount than the first dose of the compound, or the pharmaceutically acceptable salt thereof.

329. The method of clause 325 wherein the second dose of the compound, or the pharmaceutically acceptable salt thereof, is at least about 90 percent lower in amount than the first dose of the compound, or the pharmaceutically acceptable salt thereof.

330. The method of clause 325 wherein the second dose of the compound, or the pharmaceutically acceptable salt thereof, is at least about 95 percent lower in amount than the first dose of the compound, or the pharmaceutically acceptable salt thereof.

331. The method of clause 325 wherein the second dose of the compound, or the pharmaceutically acceptable salt thereof, is at least about 96 percent lower in amount than the first dose of the compound, or the pharmaceutically acceptable salt thereof.

332. The method of clause 325 wherein the second dose of the compound, or the pharmaceutically acceptable salt thereof, is at least about 97 percent lower in amount than the first dose of the compound, or the pharmaceutically acceptable salt thereof.

333. The method of clause 325 wherein the second dose of the compound, or the pharmaceutically acceptable salt thereof, is at least about 98 percent lower in amount than the first dose of the compound, or the pharmaceutically acceptable salt thereof.

334. The method of clause 325 wherein the second dose of the compound, or the pharmaceutically acceptable salt thereof, is at least about 99 percent lower in amount than the first dose of the compound, or the pharmaceutically acceptable salt thereof.

335. The method of clause 325 wherein the second dose of the compound, or the pharmaceutically acceptable salt thereof, is at least about 99.5 percent lower in amount than the first dose of the compound, or the pharmaceutically acceptable salt thereof.

336. The method of any one of clauses 325 to 335 wherein the first dose of the compound, or the pharmaceutically acceptable salt thereof, is about 100 nmoles/kg to about 1000 nmoles/kg of body weight of the patient.

337. The method of any one of clauses 325 to 335 wherein the first dose of the compound, or the pharmaceutically acceptable salt thereof, is about 100 nmoles/kg to about 900 nmoles/kg of body weight of the patient.

338. The method of any one of clauses 325 to 335 wherein the first dose of the compound, or the pharmaceutically acceptable salt thereof, is about 100 nmoles/kg to about 800 nmoles/kg of body weight of the patient.

339. The method of any one of clauses 325 to 335 wherein the first dose of the compound, or the pharmaceutically acceptable salt thereof, is about 100 nmoles/kg to about 700 nmoles/kg of body weight of the patient.

340. The method of any one of clauses 325 to 335 wherein the first dose of the compound, or the pharmaceutically acceptable salt thereof, is about 100 nmoles/kg to about 600 nmoles/kg of body weight of the patient.

341. The method of any one of clauses 325 to 335 wherein the first dose of the compound, or the pharmaceutically acceptable salt thereof, is about 200 nmoles/kg to about 600 nmoles/kg of body weight of the patient.

342. The method of any one of clauses 325 to 335 wherein the first dose of the compound, or the pharmaceutically acceptable salt thereof, is about 400 nmoles/kg to about 600 nmoles/kg of body weight of the patient.

343. The method of any one of clauses 325 to 335 wherein the first dose of the compound, or the pharmaceutically acceptable salt thereof, is about 500 nmoles/kg of body weight of the patient.

344. The method of clause 336 wherein the second dose of the compound, or the pharmaceutically acceptable salt thereof, is about 0.5 nmoles/kg to about 500 nmoles/kg of body weight of the patient.

345. The method of clause 337 wherein the second dose of the compound, or the pharmaceutically acceptable salt thereof, is about 0.5 nmoles/kg to about 450 nmoles/kg of body weight of the patient.

346. The method of clause 338 wherein the second dose of the compound, or the pharmaceutically acceptable salt thereof, is about 0.5 nmoles/kg to about 400 nmoles/kg of body weight of the patient.

347. The method of clause 339 wherein the second dose of the compound, or the pharmaceutically acceptable salt thereof, is about 0.5 nmoles/kg to about 350 nmoles/kg of body weight of the patient.

348. The method of clause 340 wherein the second dose of the compound, or the pharmaceutically acceptable salt thereof, is about 0.5 nmoles/kg to about 300 nmoles/kg of body weight of the patient.

349. The method of clause 341 wherein the second dose of the compound, or the pharmaceutically acceptable salt thereof, is about 1 nmole/kg to about 300 nmoles/kg of body weight of the patient.

350. The method of clause 342 wherein the second dose of the compound, or the pharmaceutically acceptable salt thereof, is about 2 nmoles/kg to about 300 nmoles/kg of body weight of the patient.

351. The method of clause 343 wherein the second dose of the compound, or the pharmaceutically acceptable salt thereof, is about 2 nmoles/kg to about 250 nmoles/kg of body weight of the patient.

352. The method of any one of clauses 336 to 343 wherein the second dose of the compound, or the pharmaceutically acceptable salt thereof, is about 5 nmoles/kg to about 40 nmoles/kg of body weight of the patient.

353. The method of any one of clauses 336 to 343 wherein the second dose of the compound, or the pharmaceutically acceptable salt thereof, is about 40 nmoles/kg to about 150 nmoles/kg of body weight of the patient.

354. The method of any one of clauses 325 to 353 further comprising administering a third dose of the compound, or the pharmaceutically acceptable salt thereof, wherein the third dose of the compound, or the pharmaceutically acceptable salt thereof, is the same as the second dose of the compound, or the pharmaceutically acceptable salt thereof.

355. The method of clause 354 further comprising administering a fourth dose of the compound, or the pharmaceutically acceptable salt thereof, wherein the fourth dose of the compound, or the pharmaceutically acceptable salt thereof, is the same as the second dose, or the pharmaceutically acceptable salt thereof, and the third dose of the compound, or the pharmaceutically acceptable salt thereof.

356. The method of any one of clauses 325 to 355 wherein the dose(s) of the compound, or the pharmaceutically acceptable salt thereof, administered after the first dose of the compound, or the pharmaceutically acceptable salt thereof, maintain inhibition of growth of the cancer relative to the first dose of the compound, or the pharmaceutically acceptable salt thereof.

357. The method of any one of clauses 325 to 356 wherein the CAR T cells are administered at a dose of about 1 million of the CAR T cells to about 40 million of the CAR T cells.

358. The method of any one of clauses 325 to 357 wherein the dose(s) of the compound, or the pharmaceutically acceptable salt thereof, administered after the first dose of the compound, or the pharmaceutically acceptable salt thereof, are administered once weekly.

359. The method of any one of clauses 325 to 357 wherein the dose(s) of the compound, or the pharmaceutically acceptable salt thereof, are administered twice weekly.

360. The method of any one of clauses 325 to 359 wherein the ligand is selected from the group consisting of a folate, DUPA, an NK-1R ligand, a CAIX ligand, a ligand of gamma glutamyl transpeptidase, an NKG2D ligand, and a CCK2R ligand.

361. The method of any one of clauses 325 to 360 wherein the ligand is a folate.

362. The method of any one of clauses 325 to 360 wherein the ligand is an NK-1R ligand.

363. The method of any one of clauses 325 to 360 wherein the ligand is DUPA.

364. The method of any one of clauses 325 to 360 wherein the ligand is a CCK2R ligand.

365. The method of any one of clauses 325 to 360 wherein the ligand is a ligand of gamma glutamyl transpeptidase.

366. The method of any one of clauses 325 to 365 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

367. The method of any one of clauses 325 to 366 wherein the targeting moiety is FITC.

368. The method of any one of clauses 325 to 366 wherein the targeting moiety is DNP.

369. The method of any one of clauses 325 to 366 wherein the targeting moiety is TNP.

370. The method of any one of clauses 325 to 369 wherein the linker comprises polyethylene glycol (PEG), polyproline, a hydrophilic amino acid, a sugar, an unnatural peptidoglycan, a polyvinylpyrrolidone, pluronic F-127, or a combination thereof.

371. The method of any one of clauses 325 to 370 wherein the linker comprises PEG.

372. The method of any one of clauses 325 to 371 wherein the compound, or the pharmaceutically acceptable salt thereof, has the formula

B-L-T, wherein B represents the small molecule ligand, L represents the linker, and T represents the targeting moiety, and wherein L comprises a structure having the formula

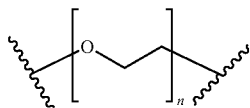

wherein n is an integer from 0 to 200.

373. The method of clause 372 wherein n is an integer from 0 to 150.

374. The method of clause 372 wherein n is an integer from 0 to 110.

375. The method of clause 372 wherein n is an integer from 0 to 20.

376. The method of clause 372 wherein n is an integer from 15 to 20.

377. The method of clause 372 wherein n is an integer from 15 to 110.

378. The method of any one of clauses 325 to 367 or 370 to 377 wherein the linker comprises PEG and the targeting moiety is FITC, or a pharmaceutically acceptable salt thereof.

379. The method of any one of clauses 325 to 378 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

380. The method of any one of clauses 325 to 361 or 366 to 379 wherein the cancer is a folate receptor expressing cancer.

381. The method of clause 380 wherein the cancer is an endometrial cancer.

382. The method of clause 380 wherein the cancer is a non-small cell lung cancer.

383. The method of clause 380 wherein the cancer is an ovarian cancer.

384. The method of clause 380 wherein the cancer is a triple negative breast cancer.

385. The method of any one of clauses 325 to 384 wherein the CAR has a recognition region and the recognition region is a single chain fragment variable (scFv) region of an antibody.

386. The method of any one of clauses 325 to 367 or 370 to 385 wherein the CAR has a recognition region and the recognition region of the CAR is a single chain fragment variable (scFv) region of an anti-FITC antibody.

387. The method of any one of clauses 325 to 386 wherein the CAR has a co-stimulation domain and the co-stimulation domain is selected from the group consisting of CD28, CD137 (4-1BB), CD134 (OX40), and CD278 (ICOS).

388. The method of any one of clauses 325 to 387 wherein the CAR has an activation signaling domain and the activation signaling domain is a T cell CD3ζ chain or an Fc receptor γ.

389. The method of any one of clauses 325 to 367 or 370 to 388 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

390. The method of any one of clauses 325 to 389 wherein multiple doses of the CAR T cell composition are administered.

391. The method of any one of clauses 325 to 390 wherein the patient is imaged prior to administration of the compound, or the pharmaceutically acceptable salt thereof, or prior to administration of the CAR T cell composition.

392. The method of any one of clauses 325 to 391 wherein the compound, or the pharmaceutically acceptable salt thereof, is not an antibody, and does not comprise a fragment of an antibody.

393. The method of any one of clauses 325 to 392 wherein the targeting moiety does not comprise a peptide epitope.

394. The method of any one of clauses 325 to 393 wherein cytokine release resulting in off-target toxicity in the patient does not occur and wherein CAR T cell toxicity to the cancer occurs.

395. The method of any one of clauses 325 to 393 wherein off-target tissue toxicity does not occur in the patient and wherein CAR T cell toxicity to the cancer occurs.

396. The method of any one of clauses 325 to 393 wherein the cancer comprises a tumor, wherein tumor size is reduced in the patient, and wherein off-target toxicity does not occur.

397. The method of any one of clauses 325 to 398 wherein the CAR T cells comprise a nucleic acid comprising SEQ ID NO:1.

398. The method of any one of clauses 325 to 397 wherein the CAR T cells comprise a polypeptide comprising SEQ ID NO:2.

399. The method of clause 397 wherein the nucleic acid encodes a chimeric antigen receptor.

400. The method of any one of clauses 325 to 399 wherein the CAR comprises humanized amino acid sequences.

401. The method of any one of clauses 325 to 399 wherein the CAR consists of humanized amino acid sequences.

402. The method of any one of clauses 325 to 401 further comprising the step of administering to the patient a folate, a conjugate comprising a folate wherein the conjugate comprising a folate does not comprise a targeting moiety, or an agent that inhibits activation of the CAR T cells.

403. The method of clause 402 wherein the agent that inhibits activation of the CAR T cells is administered to the patient and the agent is an agent that blocks CAR T cell binding to the compound, or the pharmaceutically acceptable salt thereof, but does not bind to the cancer.

404. The method of clause 403 wherein the agent is fluoresceinamine, sodium fluorescein, or fluorescein.

405. The method of clause 404 wherein the agent is sodium fluorescein.

406. A method of treatment of a cancer, the method comprising
  i) administering to a patient a first dose of a compound, or a pharmaceutically acceptable salt thereof, wherein the compound comprises a small molecule ligand linked to a targeting moiety by a linker and wherein the compound, or the pharmaceutically acceptable salt thereof, is administered to the patient at least about one hour prior to the administration of a CAR T cell composition comprising CAR T cells wherein the CAR T cells comprise a CAR directed to the targeting moiety;
  ii) then administering to the patient a dose of the CAR T cell composition; and
  iii) then administering to the patient a second dose of the compound, or the pharmaceutically acceptable salt thereof.

407. The method of clause 406 wherein the first dose of the compound, or the pharmaceutically acceptable salt thereof, is administered to the patient at least about two hours prior to the administration of the CAR T cell composition.

408. The method of clause 406 wherein the first dose of the compound, or the pharmaceutically acceptable salt thereof, is administered to the patient at least about four hours prior to the administration of the CAR T cell composition.

409. The method of clause 406 wherein the first dose of the compound, or the pharmaceutically acceptable salt thereof, is administered to the patient at least about eight hours prior to the administration of the CAR T cell composition.

410. The method of clause 406 wherein the first dose of the compound, or the pharmaceutically acceptable salt thereof, is administered to the patient at least about twelve hours prior to the administration of the CAR T cell composition.

411. The method of clause 406 wherein the first dose of the compound, or the pharmaceutically acceptable salt thereof, is administered to the patient at least about sixteen hours prior to the administration of the CAR T cell composition.

412. The method of clause 406 wherein the first dose of the compound, or the pharmaceutically acceptable salt thereof, is administered to the patient at least about twenty hours prior to the administration of the CAR T cell composition.

413. The method of clause 406 wherein the first dose of the compound, or the pharmaceutically acceptable salt thereof, is administered to the patient at least about twenty-four hours prior to the administration of the CAR T cell composition.

414. The method of any one of clauses 406 to 413 wherein the second dose of the compound, or the pharmaceutically acceptable salt thereof, is administered to the patient by at least about twenty-four hours after the administration of the CAR T cell composition.

415. The method of any one of clauses 406 to 413 wherein the second dose of the compound, or the pharmaceutically acceptable salt thereof, is administered to the patient by at least about sixteen hours after the administration of the CAR T cell composition.

416. The method of any one of clauses 406 to 413 wherein the second dose of the compound, or the pharmaceutically acceptable salt thereof, is administered to the patient by at least about twelve hours after the administration of the CAR T cell composition.

417. The method of any one of clauses 406 to 413 wherein the second dose of the compound, or the pharmaceutically acceptable salt thereof, is administered to the patient by at least about eight hours after the administration of the CAR T cell composition.

418. The method of any one of clauses 406 to 413 wherein the second dose of the compound, or the pharmaceutically acceptable salt thereof, is administered to the patient by at least about four hours after the administration of the CAR T cell composition.

419. The method of any one of clauses 406 to 418 wherein cytokine release resulting in off-target toxicity in the patient does not occur and wherein CAR T cell toxicity to the cancer occurs.

420. The method of any one of clauses 406 to 418 wherein off-target tissue toxicity does not occur in the patient and wherein CAR T cell toxicity to the cancer occurs.

421. The method of any one of clauses 406 to 418 wherein the cancer comprises a tumor, wherein tumor size is reduced in the patient, and wherein off-target toxicity does not occur.

422. The method of any one of clauses 406 to 418 wherein the cancer comprises a tumor, and wherein reduction in tumor size in the patient is greater than in a patient not pre-treated with the compound, or the pharmaceutically acceptable salt thereof, prior to administration of the CAR T cell composition.

423. The method of any one of clauses 406 to 422 wherein the ligand is selected from the group consisting of a folate, DUPA, an NK-1R ligand, a CAIX ligand, a ligand of gamma glutamyl transpeptidase, an NKG2D ligand, and a CCK2R ligand.

424. The method of any one of clauses 406 to 423 wherein the ligand is a folate.

425. The method of any one of clauses 406 to 423 wherein the ligand is an NK-1R ligand.

426. The method of any one of clauses 406 to 423 wherein the ligand is DUPA.

427. The method of any one of clauses 406 to 423 wherein the ligand is a CCK2R ligand.

428. The method of any one of clauses 406 to 423 wherein the ligand is a ligand of gamma glutamyl transpeptidase.

429. The method of any one of clauses 406 to 428 wherein the targeting moiety is selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, and a DARPin.

430. The method of any one of clauses 406 to 429 wherein the targeting moiety is FITC.

431. The method of any one of clauses 406 to 429 wherein the targeting moiety is DNP.

432. The method of any one of clauses 406 to 429 wherein the targeting moiety is TNP.

433. The method of any one of clauses 406 to 432 wherein the linker comprises polyethylene glycol (PEG), polyproline, a hydrophilic amino acid, a sugar, an unnatural peptidoglycan, a polyvinylpyrrolidone, pluronic F-127, or a combination thereof.

434. The method of any one of clauses 406 to 433 wherein the linker comprises PEG.

435. The method of any one of clauses 406 to 434 wherein the compound, or the pharmaceutically acceptable salt thereof, has the formula

B-L-T, wherein B represents the small molecule ligand, L represents the linker, and T represents the targeting moiety, and wherein L comprises a structure having the formula

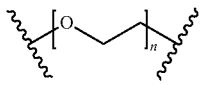

wherein n is an integer from 0 to 200.

436. The method of clause 435 wherein n is an integer from 0 to 150.

437. The method of clause 435 wherein n is an integer from 0 to 110.

438. The method of clause 435 wherein n is an integer from 0 to 20.

439. The method of clause 435 wherein n is an integer from 15 to 20.

440. The method of clause 435 wherein n is an integer from 15 to 110.

441. The method of any one of clauses 406 to 430 or 433 to 440 wherein the linker comprises PEG and the targeting moiety is FITC, or a pharmaceutically acceptable salt thereof.

442. The method of any one of clauses 406 to 441 wherein the compound, or the pharmaceutically acceptable salt thereof, is administered at a dose of about 10 nmoles/kg to about 10000 nmoles/kg of body weight of the patient.

443. The method of any one of clauses 406 to 441 wherein the compound, or the pharmaceutically acceptable salt thereof, is administered at a dose of about 10 nmoles/kg to about 5000 nmoles/kg of body weight of the patient.

444. The method of any one of clauses 406 to 441 wherein the compound, or the pharmaceutically acceptable salt thereof, is administered at a dose of about 10 nmoles/kg to about 1000 nmoles/kg of body weight of the patient.

445. The method of any one of clauses 406 to 441 wherein the compound, or the pharmaceutically acceptable salt thereof, is administered at a dose of about 10 nmoles/kg to about 600 nmoles/kg of body weight of the patient.

446. The method of any one of clauses 406 to 441 wherein the compound, or the pharmaceutically acceptable salt thereof, is administered at a dose of about 200 nmoles/kg to about 600 nmoles/kg of body weight of the patient.

447. The method of any one of clauses 406 to 441 wherein the compound, or the pharmaceutically acceptable salt thereof, is administered at a dose of about 250 nmoles/kg to about 600 nmoles/kg of body weight of the patient.

448. The method of any one of clauses 406 to 447 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

449. The method of any one of clauses 406 to 424 or 429 to 448 wherein the cancer is a folate receptor expressing cancer.

450. The method of clause 448 wherein the cancer is an endometrial cancer.

451. The method of clause 448 wherein the cancer is a non-small cell lung cancer.

452. The method of clause 448 wherein the cancer is an ovarian cancer.

453. The method of clause 448 wherein the cancer is a triple negative breast cancer.

454. The method of any one of clauses 406 to 453 wherein the CAR has a recognition region and the recognition region is a single chain fragment variable (scFv) region of an antibody.

455. The method of any one of clauses 406 to 430 or 433 to 454 wherein the CAR has a recognition region and the recognition region of the CAR is a single chain fragment variable (scFv) region of an anti-FITC antibody.

456. The method of any one of clauses 406 to 455 wherein the CAR has a co-stimulation domain and the co-stimulation domain is selected from the group consisting of CD28, CD137 (4-1BB), CD134 (OX40), and CD278 (ICOS).

457. The method of any one of clauses 406 to 456 wherein the CAR has an activation signaling domain and the activation signaling domain is a T cell CD3ζ chain or an Fc receptor γ.

458. The method of any one of clauses 406 to 430 or 433 to 457 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

459. The method of any one of clauses 406 to 458 wherein multiple doses of the CAR T cell composition are administered.

460. The method of any one of clauses 406 to 459 wherein the patient is imaged prior to administration of the compound, or the pharmaceutically acceptable salt thereof.

461. The method of any one of clauses 406 to 460 wherein the compound, or the pharmaceutically acceptable salt thereof, is not an antibody, and does not comprise a fragment of an antibody.

462. The method of any one of clauses 406 to 461 wherein the targeting moiety does not comprise a peptide epitope.

463. The method of any one of clauses 406 to 462 wherein the CAR T cells comprise a nucleic acid comprising SEQ ID NO:1.

464. The method of any one of clauses 406 to 463 wherein the CAR T cells comprise a polypeptide comprising SEQ ID NO:2.

465. The method of clause 463 wherein the nucleic acid encodes a chimeric antigen receptor.

466. The method of any one of clauses 406 to 465 wherein the CAR comprises humanized amino acid sequences.

467. The method of any one of clauses 406 to 465 wherein the CAR consists of humanized amino acid sequences.

468. The method of any one of clauses 108 to 182 wherein more than one dose is administered to the patient of the folate, the conjugate comprising a folate wherein the conjugate comprising a folate does not comprise a targeting moiety, or the agent that inhibits activation of the CAR T cells.

469. The method of any one of clauses 108 to 182 wherein the folate, the conjugate comprising a folate wherein the conjugate comprising a folate does not comprise a targeting moiety, or the agent that inhibits activation of the CAR T cells is administered to the patient before and/or after the compound, or the pharmaceutically acceptable salt thereof.

470. The method of any one of clauses 108 to 182 wherein administration of the folate, the conjugate comprising a folate wherein the conjugate comprising a folate does not comprise a targeting moiety, or the agent that inhibits activation of the CAR T cells causes reduction in cytokine levels in the patient.

471. The method of clause 470 wherein the reduction in cytokine levels occurs by about 3 hours after administration to the patient of the folate, the conjugate comprising a folate wherein the conjugate comprising a folate does not comprise a targeting moiety, or the agent that inhibits activation of the CAR T cells.

472. The method of clause 470 wherein the reduction in cytokine levels occurs by about 6 hours after administration to the patient of the folate, the conjugate comprising a folate wherein the conjugate comprising a folate does not comprise a targeting moiety, or the agent that inhibits activation of the CAR T cells.

473. The method of clause 470 wherein the reduction in cytokine levels is a reduction to about the cytokine levels in an untreated patient.

474. The method of any one of clauses 108 to 182 wherein the compound, or the pharmaceutically acceptable salt thereof, is administered before and subsequent to administration of the folate, the conjugate comprising a folate wherein the conjugate comprising a folate does not comprise a targeting moiety, or the agent that inhibits activation of the CAR T cells.

475. The method of any one of clauses 108 to 182 wherein CAR T cell number increases in the blood of the patient after administration of the folate, the conjugate comprising a folate wherein the conjugate comprising a folate does not comprise a targeting moiety, or the agent that inhibits activation of the CAR T cells, even though cytokine levels in the patient are reduced.

476. The method of any one of clauses 108 to 182 wherein CAR T cell activation is enhanced or maintained, relative to a patient not treated with a rescue agent, after administration of the folate, the conjugate comprising a folate wherein the conjugate comprising a folate does not comprise a targeting moiety, or the agent that inhibits activation of the CAR T cells, even though cytokine levels in the treated patient are reduced.

477. The method of any one of clauses 108 to 182 wherein the cancer comprises a tumor and tumor size in the patient is not increased when the folate, the conjugate comprising a folate wherein the conjugate comprising a folate does not comprise a targeting moiety, or the agent that inhibits activation of the CAR T cells is administered to the patient.

478. The method of clause 477 wherein a complete response for the tumor is obtained.

479. The method of any one of clauses 108, 115-160, 168-182, and 468-478 wherein the agent that inhibits activation of the CAR T cells is administered to the patient when the CRS grade reaches 1, 2, 3, or 4.

480. The method of any one of clauses 108, 115-160, 168-182, and 468-478 wherein the agent that inhibits acti-vation of the CAR T cells is administered to the patient when the CRS grade reaches 3 or 4.

481. The method of any one of clauses 108 to 182 and 468 to 480 wherein lung edema is reduced.

482. The method of any one of clauses 108, 115-160, 168-182, and 468-481 wherein the agent that inhibits activation of the CAR T cells is administered at a dose of about 0.01 to about 300 umoles/kg of body weight of the patient.

483. The method of any one of clauses 108, 115-160, 168-182, and 468-481 wherein the agent that inhibits activation of the CAR T cells is administered at a dose of about 0.06 to about 100 umoles/kg of body weight of the patient.

484. The method of any one of clauses 108, 115-160, 168-182, and 468-481 wherein the agent that inhibits activation of the CAR T cells is administered at a dose of about 0.06 to about 90 umoles/kg of body weight of the patient.

485. The method of any one of clauses 108, 115-160, 168-182, and 468-481 wherein the agent that inhibits activation of the CAR T cells is administered at a dose of about 0.06 to about 80 umoles/kg of body weight of the patient.

486. The method of any one of clauses 108, 115-160, 168-182, and 468-481 wherein the agent that inhibits activation of the CAR T cells is administered at a dose of about 0.06 to about 70 umoles/kg of body weight of the patient.

487. The method of any one of clauses 108, 115-160, 168-182, and 468-481 wherein the agent that inhibits activation of the CAR T cells is administered at a dose of about 0.06 to about 60 umoles/kg of body weight of the patient.

488. The method of any one of clauses 108, 115-160, 168-182, and 468-481 wherein the agent that inhibits activation of the CAR T cells is administered at a dose of about 0.06 to about 50 umoles/kg of body weight of the patient.

489. The method of any one of clauses 108, 115-160, 168-182, and 468-481 wherein the agent that inhibits activation of the CAR T cells is administered at a dose of about 0.06 to about 40 umoles/kg of body weight of the patient.

490. The method of any one of clauses 108, 115-160, 168-182, and 468-481 wherein the agent that inhibits activation of the CAR T cells is administered at a dose of about 0.06 to about 30 umoles/kg of body weight of the patient.

491. The method of any one of clauses 108, 115-160, 168-182, and 468-481 wherein the agent that inhibits activation of the CAR T cells is administered at a dose of about 0.06 to about 20 umoles/kg of body weight of the patient.

492. The method of any one of clauses 108, 115-160, 168-182, and 468-481 wherein the agent that inhibits activation of the CAR T cells is administered at a dose of about 0.06 to about 10 umoles/kg of body weight of the patient.

493. The method of any one of clauses 108, 115-160, 168-182, and 468-481 wherein the agent that inhibits activation of the CAR T cells is administered at a dose of about 0.06 to about 8 umoles/kg of body weight of the patient.

494. The method of any one of clauses 108, 115-160, 168-182, and 468-481 wherein the agent that inhibits activation of the CAR T cells is administered at a dose of about 0.06 to about 6 umoles/kg of body weight of the patient.

495. The method of any one of clauses 108, 115-160, 168-181, and 468-494 wherein the agent that inhibits activation of the CAR T cells is administered to the patient and the agent is sodium fluorescein.

496. The method of any one of clauses 1 to 495 wherein CRS is reduced or prevented and the method results in a decrease in tumor volume in the patient.

497. The method of any one of clauses 1 to 496 wherein body weight loss due to CRS is reduced or prevented.

498. The method of any one of clauses 1-3, 8-28, 33-58, 63-83, 88-136, 141-249, 252-361, 366-380, 385-424, 429-449, and 454 to 497 wherein the cancer is acute myelocytic leukemia.

499. The method of clause 498 wherein the cancer expresses the folate receptor-3.

500. The method of clause 498 or 499 wherein the CAR-T cells have a central memory/effector memory phenotype.

501. The method of any one of clauses 1 to 500 wherein the CD8:CD4 ratio of the CAR T cells is about 1:1.

502. The method of any one of clauses 215 to 251 further comprising step iv) of re-administering the compound, or the pharmaceutically acceptable salt thereof, to the patient.

503. The method of clause 474 wherein the subsequent administration of the compound, or the pharmaceutically acceptable salt thereof, causes CAR T cell activation and an increase in cytokine levels in the patient.

504. The method of any one of clauses 1 to 107, 183 to 476, or 479 to 503 wherein the cancer comprises a tumor and wherein a complete response for the tumor is obtained.

505. A method of treatment of a cancer, the method comprising
i) administering to a patient a compound, or a pharmaceutically acceptable salt thereof, wherein the compound comprises a small molecule ligand linked to a targeting moiety by a linker; and
ii) administering to the patient a CAR T cell composition wherein the CAR T cell composition comprises CAR T cells and wherein the CAR T cells comprise a CAR directed to the targeting moiety; and wherein the small molecule ligand is a PSMA ligand and the targeting moiety is FITC.

506. The method of clause 505 wherein the small molecule ligand linked to a targeting moiety by a linker has the formula

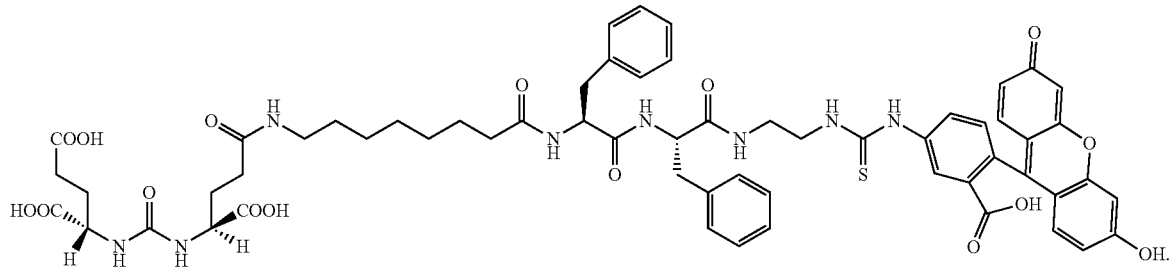 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

507. A method of treatment of a cancer, the method comprising
i) administering to a patient a compound, or a pharmaceutically acceptable salt thereof, wherein the compound comprises a small molecule ligand linked to a targeting moiety by a linker; and
ii) administering to the patient a CAR T cell composition wherein the CAR T cell composition comprises CAR T cells and wherein the CAR T cells comprise a CAR directed to the targeting moiety; and wherein the small molecule ligand is a CAIX ligand and the targeting moiety is FITC.

508. The method of clause 507 wherein the small molecule ligand linked to a targeting moiety by a linker has the formula

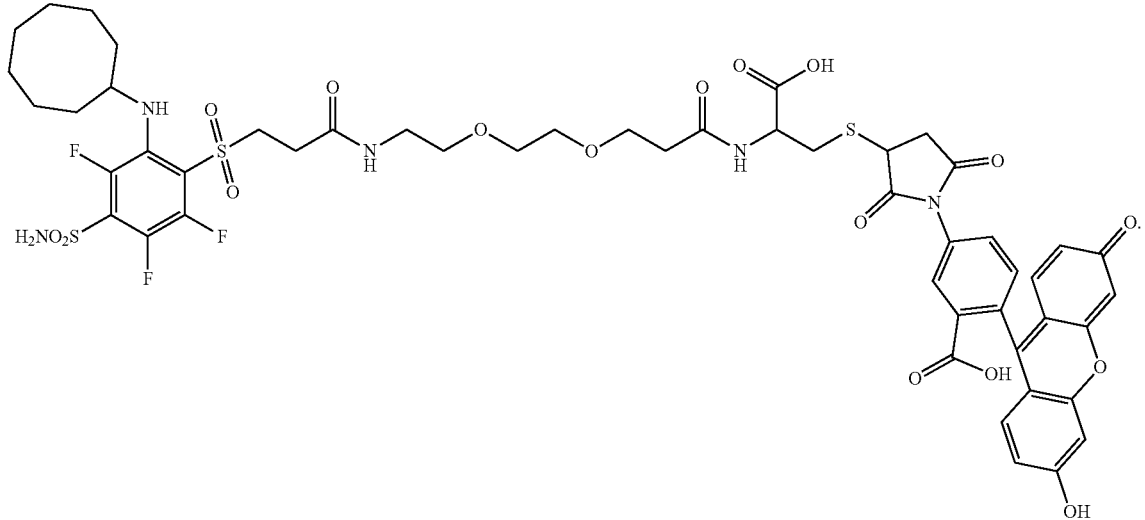 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

509. A method of treatment of a cancer, the method comprising
  i) administering to a patient a first compound, or a pharmaceutically acceptable salt thereof, wherein the first compound, or the pharmaceutically acceptable salt thereof, comprises a PSMA ligand linked to FITC by a linker;
  ii) administering to the patient a second compound, or a pharmaceutically acceptable salt thereof, wherein the second compound, or the pharmaceutically acceptable salt thereof, comprises a CAIX ligand linked to FITC by a linker; and
  iii) administering to the patient a CAR T cell composition wherein the CAR T cell composition comprises CAR T cells and wherein the CAR T cells comprise a CAR directed to the targeting moiety.

510. The method of clause 509 wherein the first compound has the formula

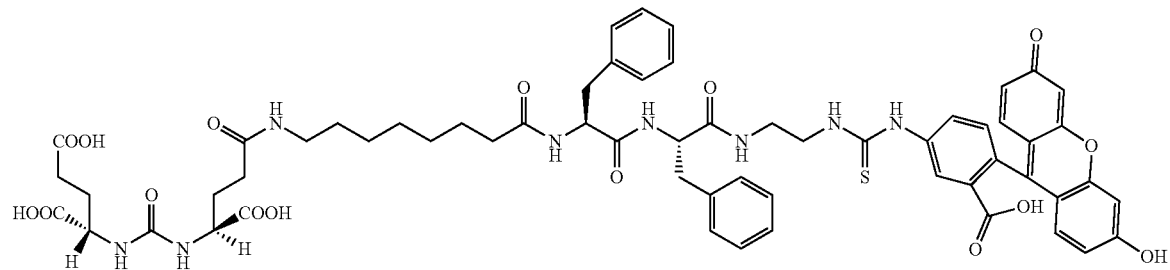 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

and the second compound has the formula

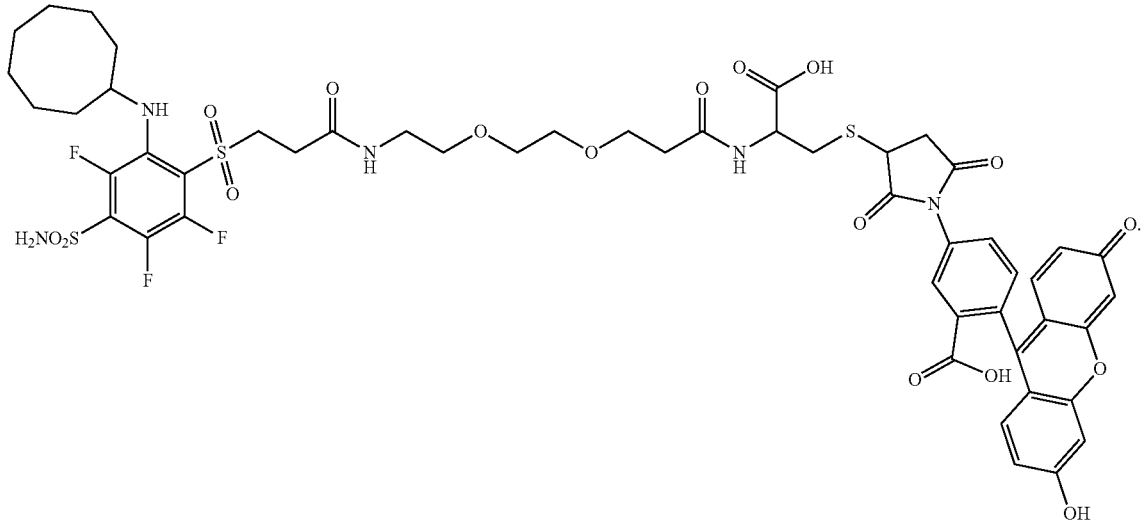 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

Thus, in one embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a first dose of a CAR T cell composition wherein the CAR T cell composition comprises CAR T cells and wherein the CAR T cells comprise the CAR directed to the targeting moiety, and iii) administering to the patient a second dose of the CAR T cell composition wherein the CAR T cell composition comprises CAR T cells and wherein the CAR T cells comprise the CAR directed to the targeting moiety.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition comprising CAR T cells wherein the CAR T cells in the composition comprise the CAR directed to the targeting moiety and wherein the CAR T cell composition comprises a mixture of the CAR T cells and non-transformed T cells.

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a CAR T cell composition wherein the CAR T cell composition comprises CAR T cells and wherein the CAR T cells comprise the CAR directed to the targeting moiety, and iii) administering to the patient a folate, a conjugate comprising a folate wherein the conjugate comprising a folate does not comprise a targeting moiety, or a drug that inhibits activation of the CAR T cells.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and wherein the compound, or the pharmaceutically acceptable salt thereof, is at a dose of about 10 nmoles/kg of body weight of the patient to about 2500 nmoles/kg of body weight of the patient, and ii) administering to the patient a CAR T cell composition comprising CAR T cells wherein the CAR T cells comprise a CAR directed to the targeting moiety, and wherein the CAR T cells are at a dose of about 1 million of the CAR T cells to about 15 million of the CAR T cells.

In still another embodiment, a method of treatment of a cancer is provided. The method comprises i) administering continuously to a patient a compound, or a pharmaceutically acceptable salt thereof, wherein the compound comprises a small molecule ligand linked to a targeting moiety by a linker, ii) administering to the patient a CAR T cell composition comprising CAR T cells wherein the CAR T cells comprise a CAR directed to the targeting moiety, and iii) ending the continuous administration of the compound, or the pharmaceutically acceptable salt thereof, to inhibit or prevent cytokine release syndrome in the patient.

In another illustrative aspect, a method of treatment of a cancer is provided. The method comprises i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof, and ii) administering to the patient a CAR T cell composition comprising CAR T cells wherein the CAR T cells comprise a CAR directed to the targeting moiety.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof, and iii) administering to the patient a dose of a CAR T cell composition comprising CAR T cells wherein the CAR T cells comprise a CAR directed to the targeting moiety.

In still another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker and wherein the compound, or the pharmaceutically acceptable salt thereof, is administered to the patient at least about one hour prior to the administration of a CAR T cell composition comprising CAR T cells wherein the CAR T cells comprise a CAR directed to the targeting moiety, ii) then administering to the patient a dose of the CAR T cell composition, and iii) then administering to the patient a second dose of the compound, or the pharmaceutically acceptable salt thereof.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR directed to the targeting moiety, and wherein the small molecule ligand is a PSMA ligand and the targeting moiety is FITC. In this embodiment, the small molecule ligand linked to a targeting moiety by a linker can have the formula

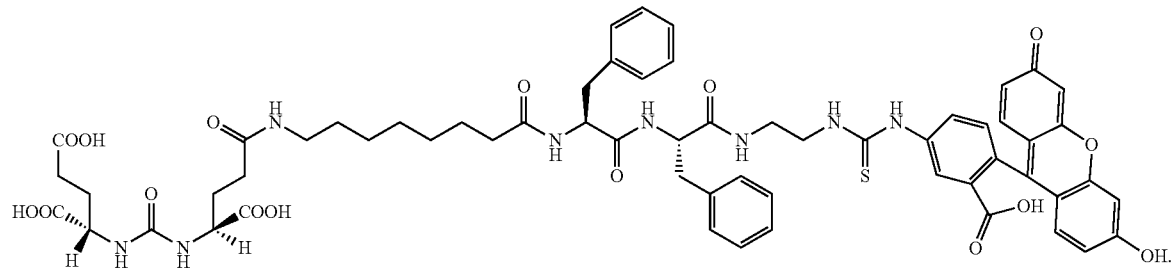 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

patient a compound, or a pharmaceutically acceptable salt thereof, wherein the compound comprises a small molecule ligand linked to a targeting moiety by a linker and wherein the compound, or the pharmaceutically acceptable salt thereof, is administered once weekly to the patient, and ii) administering to the patient a CAR T cell composition comprising CAR T cells wherein the CAR T cells comprise a CAR directed to the targeting moiety.

In yet another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR directed to the targeting moiety, and wherein the small molecule ligand is a CAIX ligand and the targeting moiety is FITC. In this embodiment, the small molecule ligand linked to a targeting moiety by a linker can have the formula

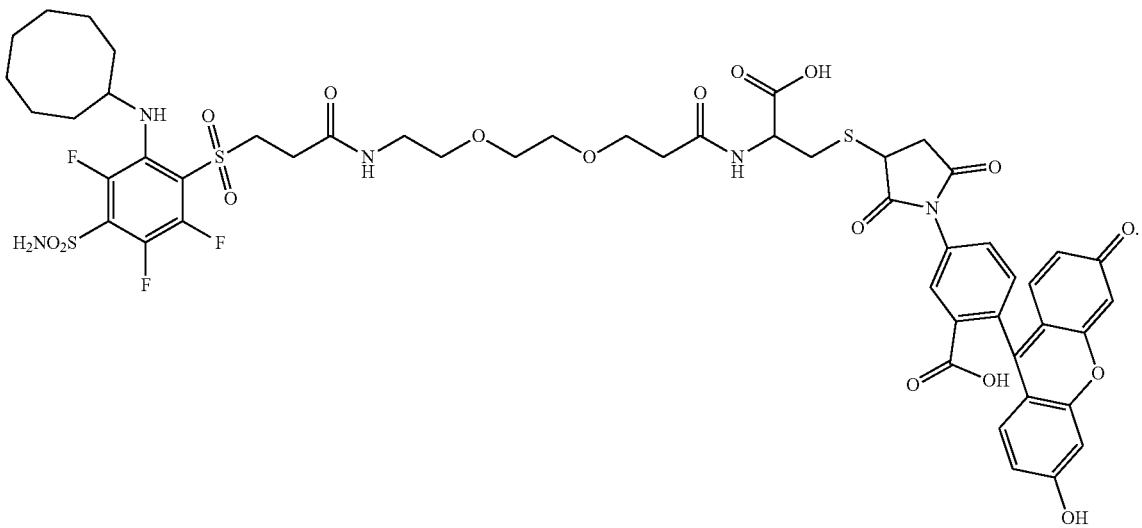 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

In still another embodiment, a method of treatment of a cancer is provided. The method comprises i) administering to a patient a first compound, or a pharmaceutically acceptable salt thereof, wherein the first compound, or the pharmaceutically acceptable salt thereof, comprises a PSMA ligand linked to FITC by a linker, ii) administering to the patient a second compound, or a pharmaceutically acceptable salt thereof, wherein the second compound, or the pharmaceutically acceptable salt thereof, comprises a CAIX ligand linked to FITC by a linker, and iii) administering to the patient a CAR T cell composition wherein the CAR T cell composition comprises CAR T cells and wherein the CAR T cells comprise a CAR directed to the targeting moiety. In this embodiment, the first compound can have the formula

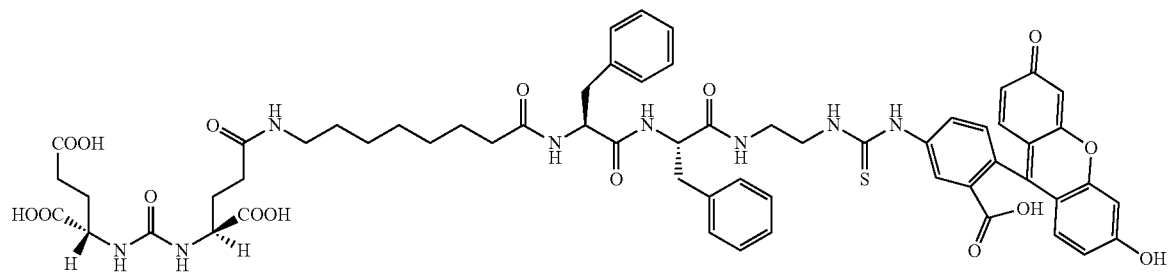 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

and the second compound can have the formula

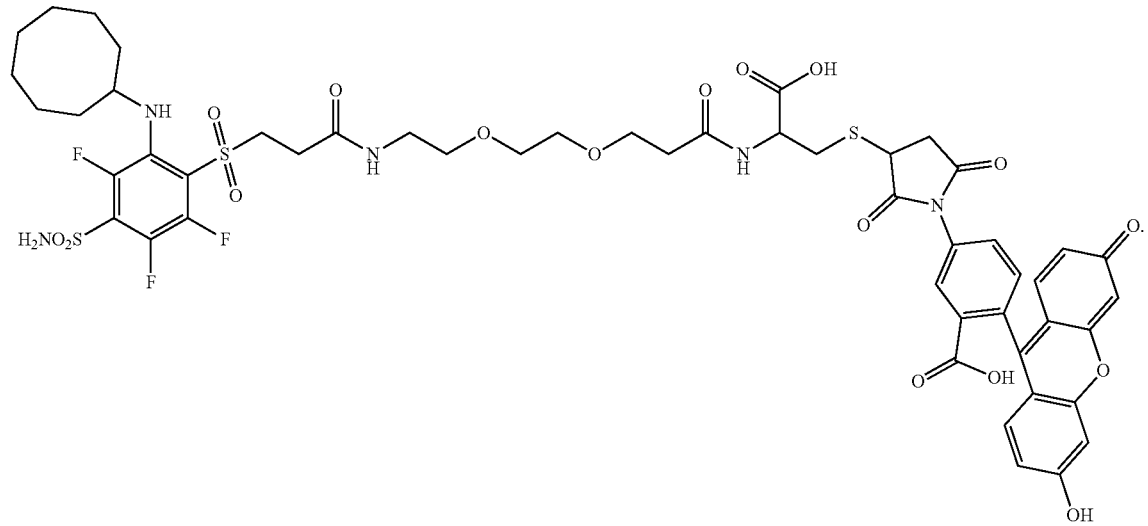 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

Accordingly, various embodiments are provided in the twelve preceding paragraphs and in the clause list above, and all applicable embodiments described in this "Detailed Description of Illustrative Embodiments," the Summary section, the Examples, and the claims apply to these embodiments.

As described herein, a "patient" can be a human or, in the case of veterinary applications, the patient can be a laboratory, an agricultural, a domestic, or a wild animal. In various aspects, the patient can be a laboratory animal such as a rodent (e.g., mouse, rat, hamster, etc.), a rabbit, a monkey, a chimpanzee, a domestic animal such as a dog, a cat, or a rabbit, an agricultural animal such as a cow, a horse, a pig, a sheep, a goat, or a wild animal in captivity such as a bear, a panda, a lion, a tiger, a leopard, an elephant, a zebra, a giraffe, a gorilla, a dolphin, or a whale.

In various embodiments, the cancer to be treated can be selected from a carcinoma, a sarcoma, an osteosarcoma, a lymphoma, a melanoma, a mesothelioma, a nasopharyngeal carcinoma, a leukemia, an adenocarcinoma, or a myeloma. In other embodiments, the cancer may be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, including acute myelocytic leukemia, a lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, a neoplasm of the central nervous system (CNS), primary CNS lymphoma, a spinal axis tumor, a brain stem glioma, a pituitary adenoma, and an adenocarcinoma of the gastroesophageal junction.

In some aspects of these embodiments, the cancer is a folate receptor expressing cancer. In another embodiment, the cancer is a folate receptor α-expressing cancer. In yet another embodiment, the cancer is a folate receptor β-expressing cancer. In some aspects of these embodiments, the cancer is an endometrial cancer, a non-small cell lung cancer, an ovarian cancer, or a triple-negative breast cancer. In another embodiment, the cancer being treated is a tumor. In another embodiment, the cancer is malignant. In another embodiment, the cancer is acute myelocytic leukemia. In yet another embodiment, the cancer is acute myelocytic leukemia and the cancer expresses the folate receptor-β. In still another embodiment, the cancer is acute myelocytic leukemia and the CAR-T cells have a central memory/effector memory phenotype. In yet another embodiment, the CD8:CD4 ratio of the CAR T cells is about a 1:1 ratio. In another embodiment, the CD8:CD4 ratio is about a 1.2 to 1 ratio, about a 1 to 1.2 ratio, about a 1.3 to 1 ratio, about a 1 to 1.3 ratio, about a 1.4 to 1 ratio, about a 1 to 1.4 ratio, about a 1.5 to 1 ratio, or about a 1 to 1.5 ratio. In still other embodiments where the cancer is acute myelocytic leukemia and a rescue agent is used, the CAR T cells can remain present in the patient for at least about 40 days, at least about 45 days, at least about 50 days, at least about 55 days, at least about 60 days, at least about 70 days, at least about 80 days, at least about 90 days, or at least about 100 days after administration of the CAR T cells, even after a rescue agent is used to inhibit or prevent CRS. In another embodiment where the cancer is acute myelocytic leukemia or another cancer, the CAR T cells associated with the tumor can have increased CD25 expression relative to the CAR T cells not associated with the tumor.

In one embodiment, the "small molecule ligand" can be a folate, DUPA (a ligand bound by PSMA-positive human prostate cancer cells and other cancer cell types), an NK-1R ligand (receptors for the NK-1R ligand are found, for example, on cancers of the colon and pancreas), a CAIX ligand (receptors for the CAIX ligand are found, for example, on renal, ovarian, vulvar, and breast cancers), a ligand of gamma glutamyl transpeptidase (the transpeptidase is overexpressed, for example, in ovarian cancer, colon cancer, liver cancer, astrocytic gliomas, melanomas, and leukemias), an NKG2D ligand (receptors for the NKG2D ligand are found, for example, on cancers of the lung, colon, kidney, prostate, and on T and B cell lymphomas), or a CCK2R ligand (receptors for the CCK2R ligand are found on cancers of the thyroid, lung, pancreas, ovary, brain, stomach, gastrointestinal stroma, and colon, among others), each of which is a small molecule ligand that binds specifically to a cancer cell type (i.e., the receptor for each of these ligands can be overexpressed on cancers compared to normal tissues).

In one embodiment, the small molecule ligand may have a mass of less than about 10,000 Daltons, less than about 9000 Daltons, less than about 8,000 Daltons, less than about 7000 Daltons, less than about 6000 Daltons, less than about 5000 Daltons, less than about 4500 Daltons, less than about 4000 Daltons, less than about 3500 Daltons, less than about 3000 Daltons, less than about 2500 Daltons, less than about 2000 Daltons, less than about 1500 Daltons, less than about 1000 Daltons, or less than about 500 Daltons. In another embodiment, the small molecule ligand may have a mass of about 1 to about 10,000 Daltons, about 1 to about 9000 Daltons, about 1 to about 8,000 Daltons, about 1 to about 7000 Daltons, about 1 to about 6000 Daltons, about 1 to about 5000 Daltons, about 1 to about 4500 Daltons, about 1 to about 4000 Daltons, about 1 to about 3500 Daltons, about 1 to about 3000 Daltons, about 1 to about 2500 Daltons, about 1 to about 2000 Daltons, about 1 to about 1500 Daltons, about 1 to about 1000 Daltons, or about 1 to about 500 Daltons.

In one embodiment, a DUPA derivative can be the ligand of the small molecule ligand linked to a targeting moiety, and DUPA derivatives are described in WO 2015/057852, incorporated herein by reference.

In one embodiment, the small molecule ligand in the context of the "small molecule ligand linked to a linker" is a folate. In various embodiments, the folate can be folic acid, a folic acid analog, or another folate receptor-binding molecule. In various embodiments, analogs of folate that can be used include folinic acid (e.g., leucovorin), pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), N10-methylfolate, 2-deamino-hydroxyfolate, deaza analogs such as 1-deazamethopterin or 3-deazamethopterin, and 3',5'-dichloro-4-amino-4-deoxy-N10-methylpteroylglutamic acid (dichloromethotrexate).

In another embodiment, the small molecule ligand in the context of the "small molecule ligand linked to a linker" can have the formula

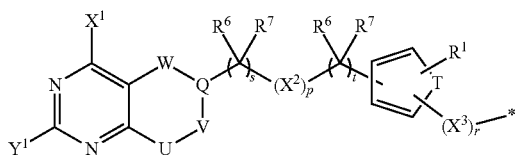

wherein $X^1$ and $Y^1$ are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyleneoxy, where Z is oxygen or sulfur;

$R^1$ is selected from the group consisting of hydrogen, halo, $C_1$-$C_{12}$ alkyl, and $C_1$-$C_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;

$R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

p, r, s, and t are each independently either 0 or 1; and

* represents an optional covalent bond to the rest of the conjugate, if any additional chemical moieties are part of the folate.

In one aspect, the "targeting moiety" that binds to the CAR expressed by CAR T cells can be selected, for example, from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester, tetrafluorophenyl ester, a knottin, a centyrin, a DARPin, an affibody, an affilin, an anticalin, an atrimer, an avimer, a bicyclic peptide, an FN3 scaffold, a cys-knot, a fynomer, a Kunitz domain, or an Obody. The identity of the targeting moiety is limited only in that it should be recognized and bound by the CAR, preferably with specificity, and that it have a relatively low molecular weight. In various aspects, exemplary targeting moieties are haptens, including small molecular weight organic molecules.

In one illustrative embodiment, the targeting moiety can have the following illustrative structure:

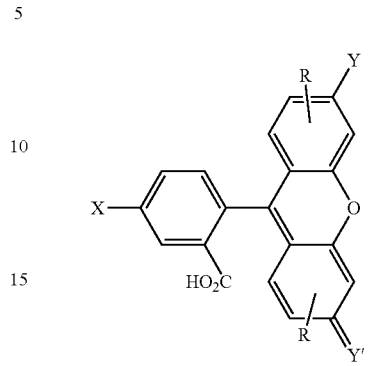

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from H, fluoro, sulfonic acid, sulfonate, and salts thereof, and the like; and $R^a$ is hydrogen or alkyl.

In one illustrative aspect, the linker can comprise polyethylene glycol (PEG), polyproline, a hydrophilic amino acid, a sugar, an unnatural peptidoglycan, a polyvinylpyrrolidone, pluronic F-127, or a combination thereof.

In another illustrative aspect, the linker in the compound, or pharmaceutically acceptable salt thereof, described herein can comprise a direct linkage (e.g., a reaction between the isothiocyanate group of FITC and a free amine group of a small molecule ligand) or the linkage can be through an intermediary linker. In one embodiment, if present, an intermediary linker can be any biocompatible linker known in the art, such as a divalent linker. In one illustrative embodiment, the divalent linker can comprise about 1 to about 30 carbon atoms. In another illustrative embodiment, the divalent linker can comprise about 2 to about 20 carbon atoms. In other embodiments, lower molecular weight divalent linkers (i.e., those having an approximate molecular weight of about 30 to about 300 Daltons) are employed. In another embodiment, linker lengths that are suitable include, but are not limited to, linkers having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, or more atoms.

In various embodiments, the small molecule ligand linked to a targeting moiety can be of the formula

B-L-T, wherein B represents the small molecule ligand, L represents the linker, and T represents the targeting moiety, and wherein L comprises a structure having the formula

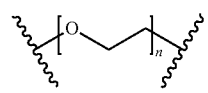

wherein n is an integer from 0 to 200. In another embodiment, n can be an integer from 0 to 150, 0 to 110, 0 to 100, 0 to 90, 0 to 80, 0 to 70, 0 to 60, 0 to 50, 0 to 40, 0 to 30, 0 to 20, 0 to 15, 0 to 14, 0 to 13, 0 to 12, 0 to 11, 0 to 10, 0 to 9, 0 to 8, 0 to 7, 0 to 6, 0 to 5, 0 to 4, 0 to 3, 0 to 2, 0 to 1, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 15 to 31, 15 to 32, 15 to 33, 15 to 34, 15 to 35, 15 to 36, 15 to 37, 15 to 38, 15 to 39, 15 to 40, 15 to 50, 15 to 60, 15 to 70, 15 to 80, 15 to 90, 15 to 100, 15 to 110, 15 to 120, 15 to 130, 15 to 140, 15 to 150, or n can be 1,2,3,4,5,6,7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 108, 110, 120, 130, 140, or 150.

In another embodiment, the linker may be a divalent linker that may include one or more spacers. Illustrative spacers are shown in the following table. The following non-limiting, illustrative spacers are described where * indicates the point of attachment to the small molecule ligand or to the targeting moiety, or to other divalent linker portions.

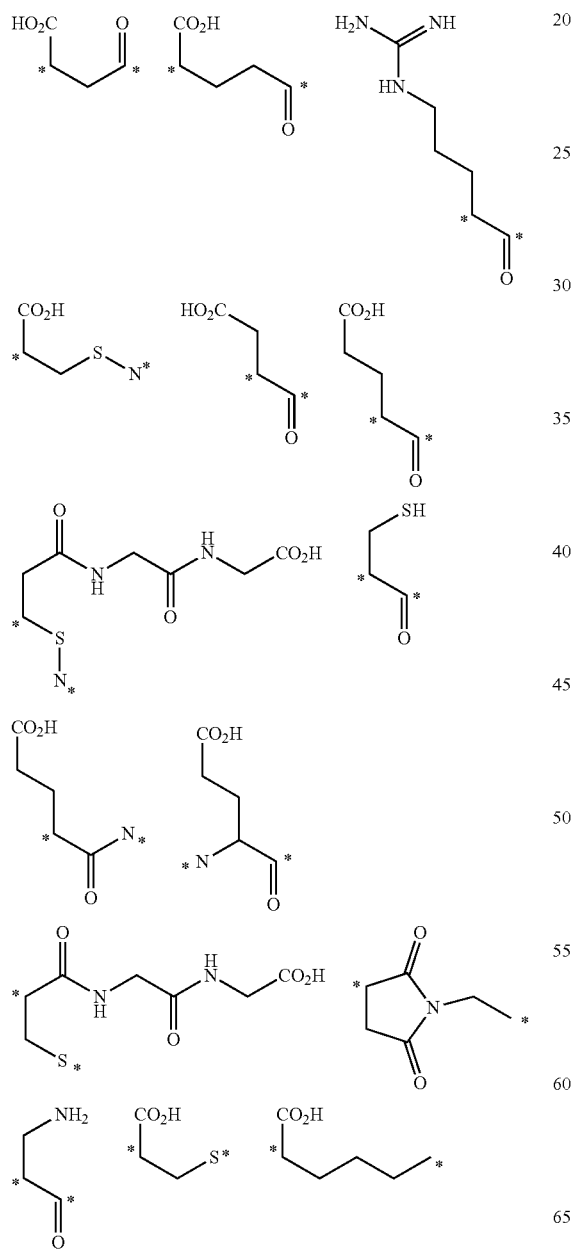
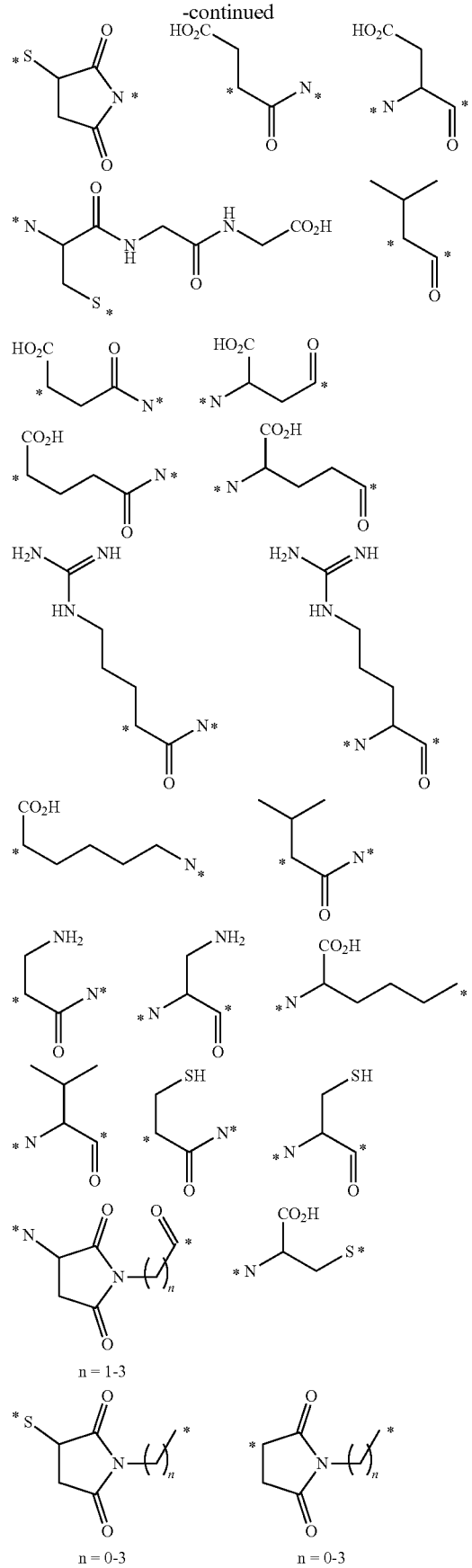

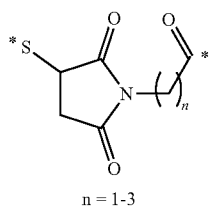
n = 1-3
In other embodiments, the small molecule ligand linked to a targeting moiety (bridge) can have any of the following structures.
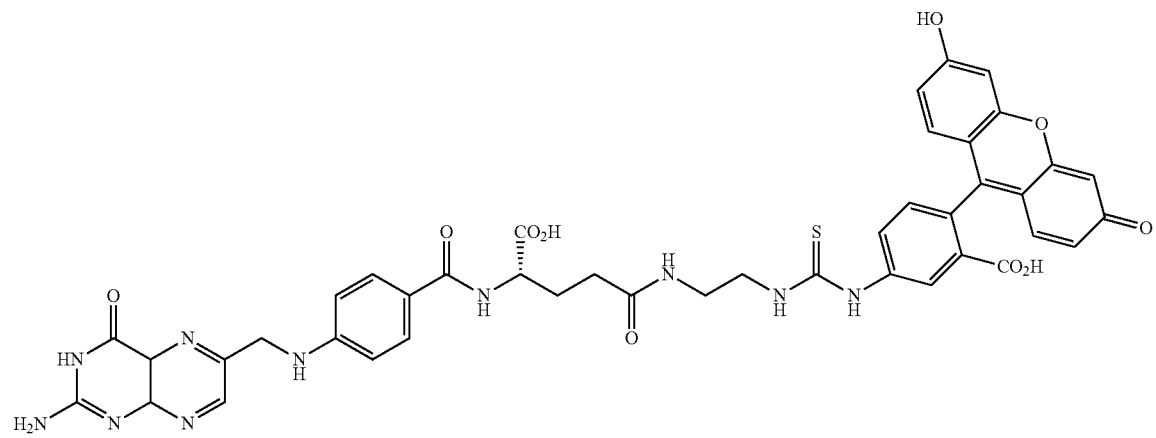
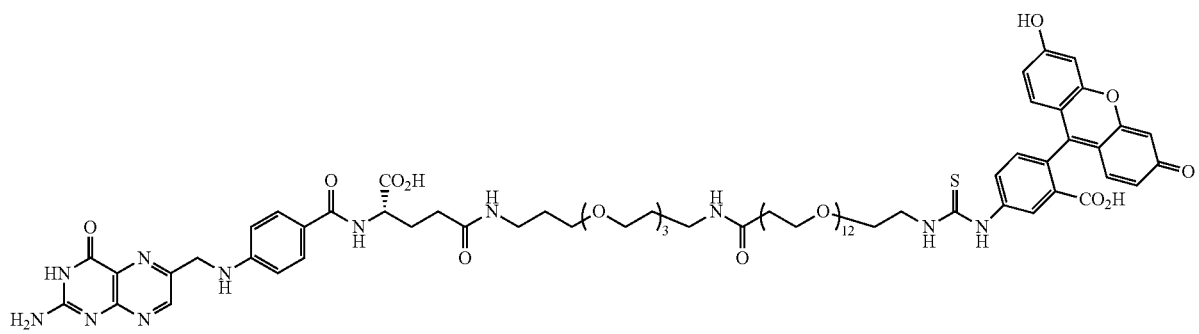
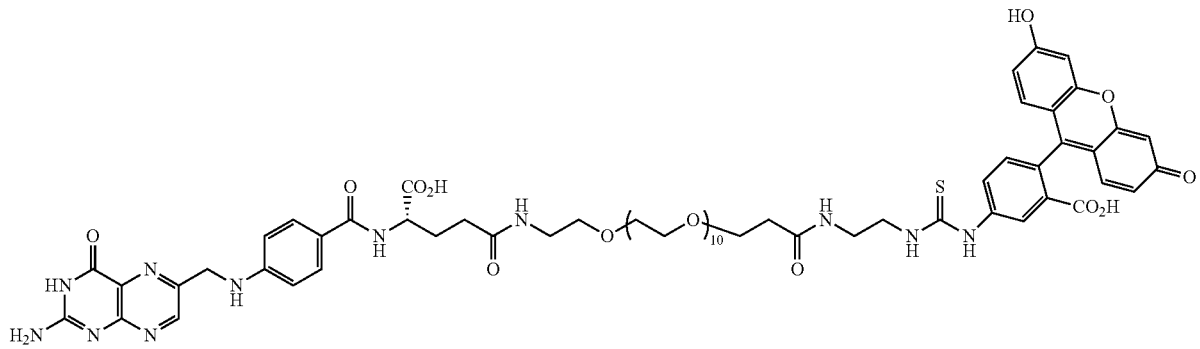

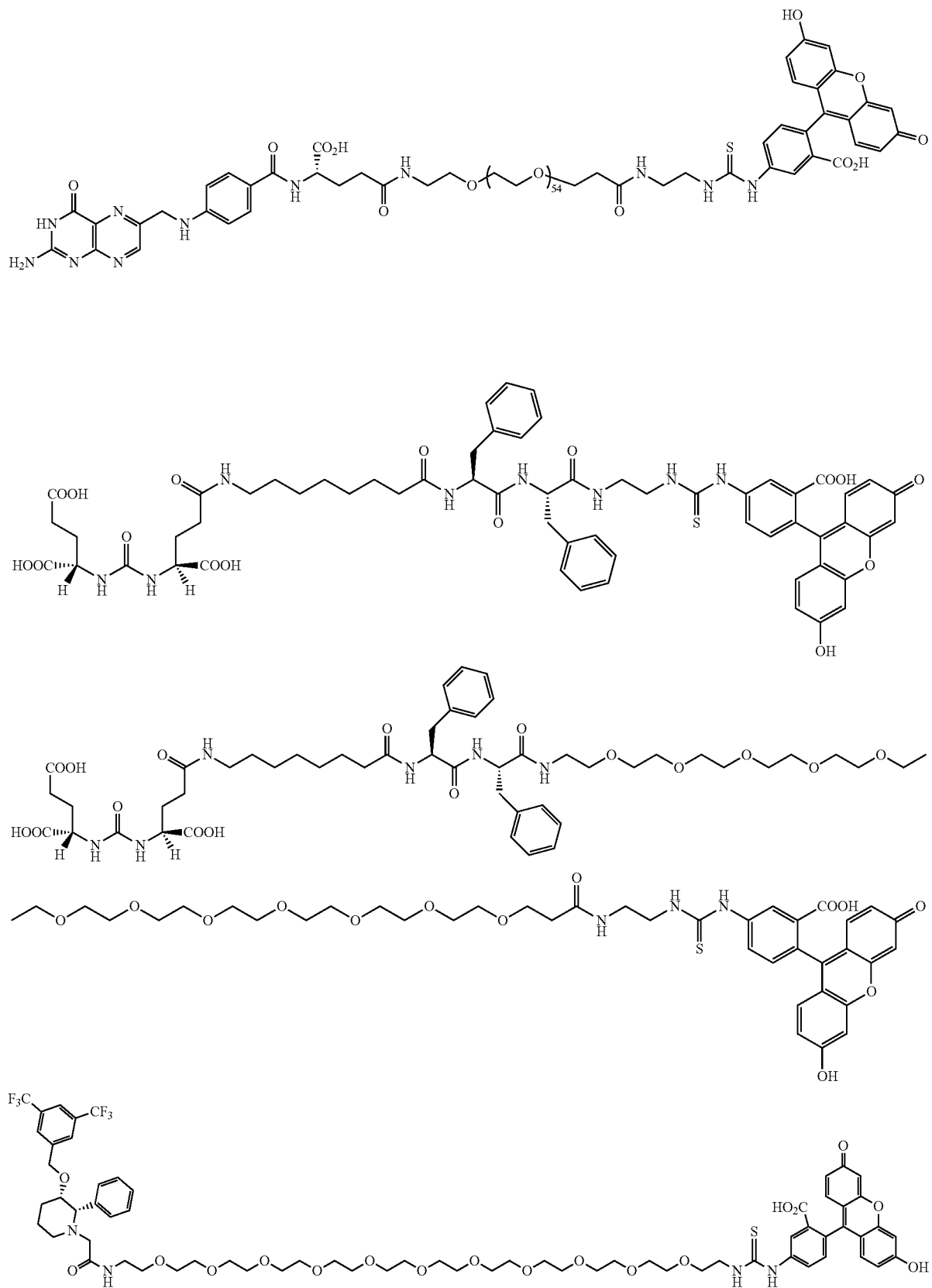

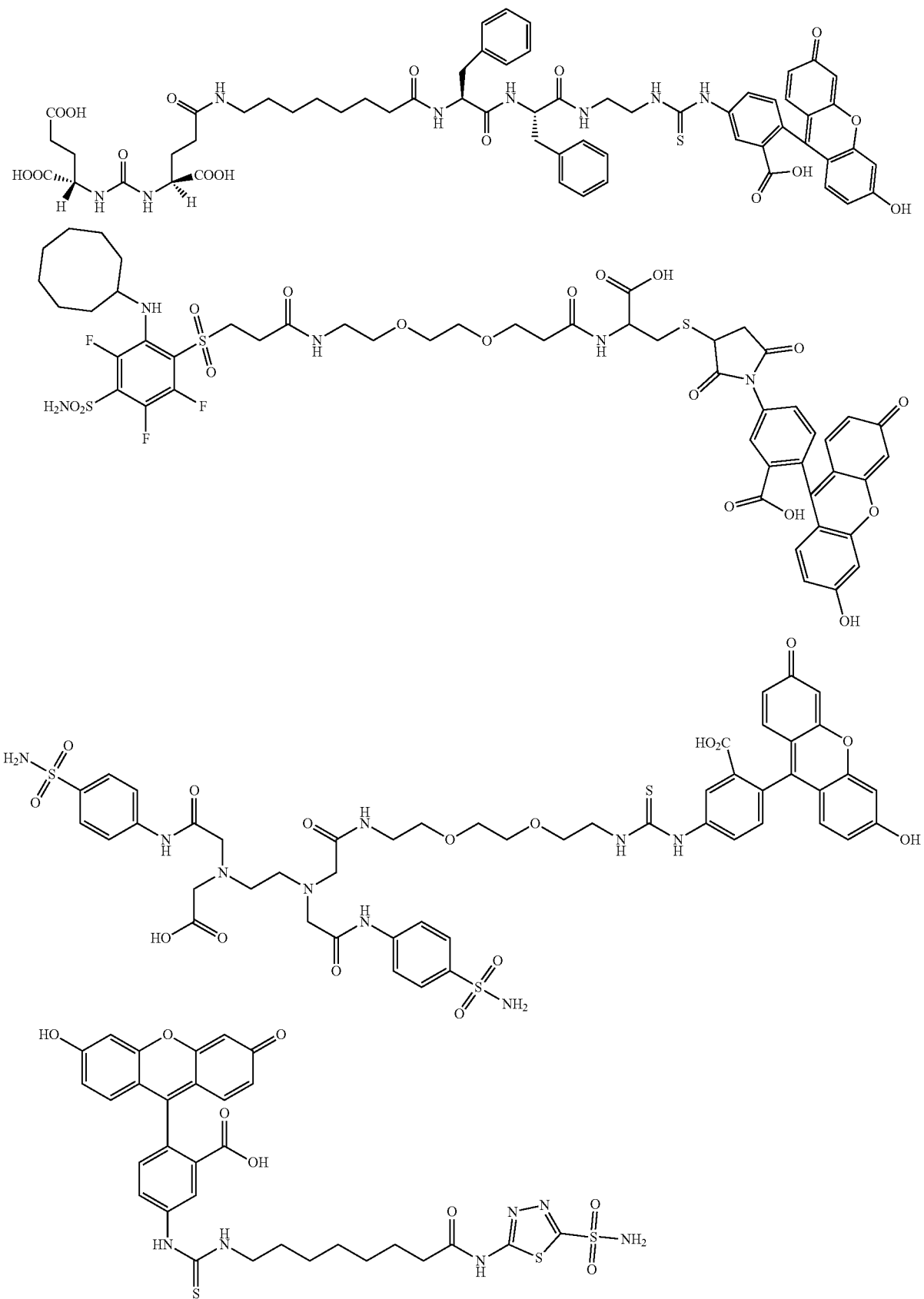

-continued

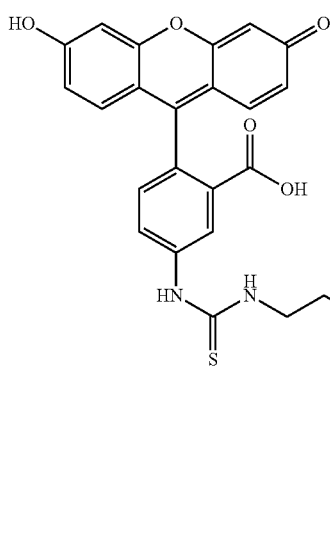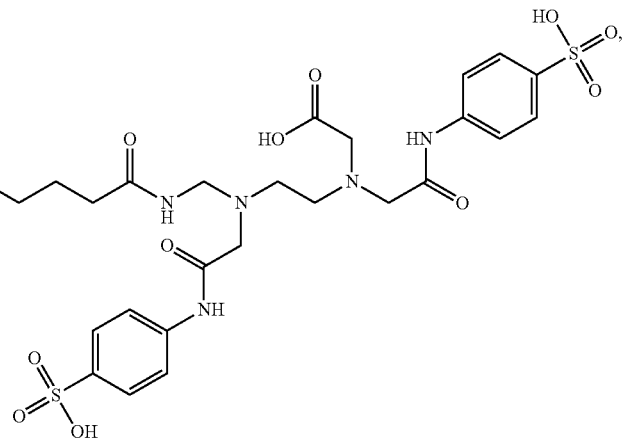

In other embodiments the compound or the pharmaceutically acceptable salt thereof, is not an antibody, and does not comprise a fragment of an antibody. In yet another embodiment, the targeting moiety does not comprise a peptide epitope.

In one illustrative embodiment, the small molecule ligand linked to a targeting moiety by a linker (the bridge) comprises fluorescein isothiocyanate (FITC) linked to the small molecule ligand. In one aspect, the cancer may overexpress a receptor for the small molecule ligand. In another aspect, for example, cytotoxic T cells, or another type of T cell, can be transformed to express a CAR that comprises anti-FITC scFv. In this aspect, the CAR may target FITC decorating the cancer with FITC molecules as a result of binding of the small molecule ligand to the cancer. Thus, toxicity to normal, non-target cells can be avoided. In this embodiment, when the anti-FITC CAR-expressing T cells bind FITC, the CAR T cells are activated and the cancer is ameliorated.

A "pharmaceutically acceptable salt" of a small molecule ligand linked to a targeting moiety by a linker is contemplated. As used herein, the term "pharmaceutically acceptable salt" refers to those salts whose counter ions may be used in pharmaceuticals. In various embodiments, such salts include, but are not limited to 1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or 2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like. Pharmaceutically acceptable salts are well-known to those skilled in the art, and any such pharmaceutically acceptable salt is contemplated in connection with the embodiments described herein.

In various embodiments, suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

In various embodiments, suitable base salts are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one illustrative aspect, the compound, or a pharmaceutically salt thereof, described herein may contain one or more chiral centers, or may otherwise be capable of existing as multiple stereoisomers. Accordingly, various embodiments may include pure stereoisomers as well as mixtures of stereoisomers, such as enantiomers, diastereomers, and enantiomerically or diastereomerically enriched mixtures. In one aspect, the compound, or pharmaceutically acceptable salt thereof, described herein may be capable of existing as geometric isomers. Accordingly, various embodiments may include pure geometric isomers or mixtures of geometric isomers.

In some aspects, the compound, or pharmaceutically acceptable salt thereof, described herein may exist in unsolvated forms as well as solvated forms, including hydrated forms. In general, the solvated forms are equivalent to unsolvated forms and are encompassed within the scope of the present invention.

The methods described herein also utilize T lymphocytes (e.g., cytotoxic T lymphocytes) engineered to express a chimeric antigen receptor (CAR) that recognizes and binds to the targeting moiety (e.g., FITC, DNP, or TNP) of the bridge. In one embodiment, the CARs described herein comprise three domains including 1) a recognition region (e.g., a single chain fragment variable (scFv) region of an antibody, a Fab fragment, and the like) which recognizes and binds to the targeting moiety with specificity, 2) a co-stimulation domain which enhances the proliferation and survival of the T lymphocytes, and 3) an activation signaling domain which generates a T lymphocyte activation signal.

In various aspects, as non-limiting examples, scFv regions of antibodies that bind a folate, DUPA, a CAIX ligand, an NK-1R ligand, a ligand of gamma glutamyl transpeptidase, an NKG2D ligand, or a CCK2R ligand can be used. In illustrative non-limiting embodiments, the scFv regions can be prepared from (i) an antibody known in the art that binds a targeting moiety, (ii) an antibody newly prepared using a selected targeting moiety, such as a hapten, and (iii) sequence variants derived from the scFv regions of such antibodies, e.g., scFv regions having at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity with the amino acid sequence of the scFv region from which they are derived.

In one aspect, the co-stimulation domain serves to enhance the proliferation and survival of the cytotoxic T lymphocytes upon binding of the CAR to a targeting moiety.

Suitable co-stimulation domains include, but are not limited to, CD28, CD137 (4-1BB), a member of the tumor necrosis factor (TNF) receptor family, CD134 (OX40), a member of the TNFR-superfamily of receptors, CD27, CD30, CD150, DAP10, NKG2D, and CD278 (ICOS), a CD28-superfamily co-stimulatory molecule expressed on activated T cells, or combinations thereof. A skilled artisan will understand that sequence variants of these co-stimulation domains can be used without adversely impacting the invention, where the variants have the same or similar activity as the domain upon which they are modeled. In various embodiments, such variants can have at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the domain from which they are derived.

In an illustrative embodiment, the activation signaling domain serves to activate T lymphocytes (e.g., cytotoxic T lymphocytes) upon binding of the CAR to a targeting moiety. In various embodiments, suitable activation signaling domains include the T cell CD3ζ chain, CD3 delta receptor protein, mb1 receptor protein, B29 receptor protein, and Fc receptor γ. The skilled artisan will understand that sequence variants of these activation signaling domains can be used where the variants have the same or similar activity as the domain upon which they are modeled. In various embodiments, the variants have at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity with the amino acid sequence of the domain from which they are derived.

In one aspect, constructs encoding the CARs are prepared using genetic engineering techniques. Such techniques are described in detail in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference.

As examples, a plasmid or viral expression vector (e.g., a lentiviral vector, a retrovirus vector, sleeping beauty, and piggyback (transposon/transposase systems that include a non-viral mediated CAR gene delivery system)) can be prepared that encodes a fusion protein comprising a recognition region, one or more co-stimulation domains, and an activation signaling domain, in frame and linked in a 5' to 3' direction. In other embodiments, other arrangements are acceptable and include a recognition region, an activation signaling domain, and one or more co-stimulation domains. In one embodiment, the placement of the recognition region in the fusion protein will generally be such that display of the region on the exterior of the cell is achieved. In one embodiment, the CARs may include additional elements, such as a signal peptide (e.g., CD8α signal peptide) to ensure proper export of the fusion protein to the cell surface, a transmembrane domain to ensure the fusion protein is maintained as an integral membrane protein (e.g., CD8α transmembrane domain, CD28 transmembrane domain, or CD3ζ transmembrane domain), and a hinge domain (e.g., CD8α hinge) that imparts flexibility to the recognition region and allows strong binding to the targeting moiety.

Figure 5:
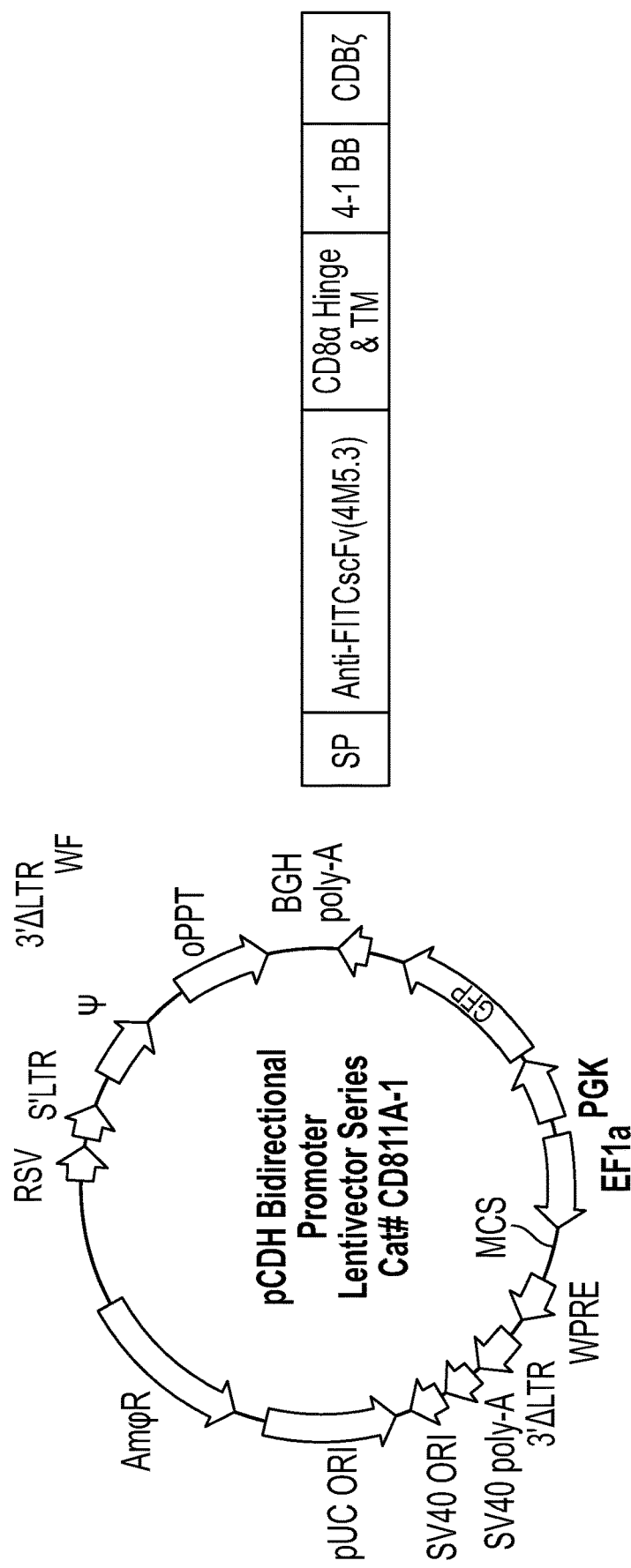
FIG. 5 shows a general diagram of the constructs used for CAR T transduction.

A diagram of an exemplary CAR is shown in FIG. 5 where the fusion protein sequence is incorporated into a lentivirus expression vector and where "SP" is a signal peptide, the CAR is an anti-FITC CAR, a CD8α hinge and a CD8α transmembrane domain are present, the co-stimulation domain is 4-1BB, and the activation signaling domain is CD3ζ. Exemplary nucleic acid sequences of a CAR insert are provided as SEQ ID NOS: 1 and 3 and the encoded amino acid sequence is provided as SEQ ID NO:2. In yet another embodiment, SEQ ID NO:2 can comprise or consist of humanized, or human amino acid sequences.

In one embodiment, the CAR has a recognition region and the recognition region is a single chain fragment variable (scFv) region of an anti-FITC antibody, a co-stimulation domain and the co-stimulation domain is CD137 (4-1BB), and an activation signaling domain and the activation signaling domain is a T cell CD3ζ chain. It is well-known to the skilled artisan that an anti-FITC scFv and an anti-fluorescein scFv are equivalent terms.

In one embodiment, T lymphocytes (e.g., cytotoxic T lymphocytes) can be genetically engineered to express CAR constructs by transfecting a population of the T lymphocytes with an expression vector encoding the CAR construct. Suitable methods for preparing a transduced population of T lymphocytes expressing a selected CAR construct are well-known to the skilled artisan, and are described in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference.

In one embodiment, CAR T cells comprising a nucleic acid of SEQ ID NO: 1 or 3 are provided. In another embodiment, CAR T cells comprising a polypeptide of SEQ ID NO:2 is provided. In another illustrative aspect, a nucleic acid (e.g., an isolated nucleic acid) comprising SEQ ID NO: 1 or 3 and encoding a chimeric antigen receptor is provided. In yet another embodiment, a chimeric antigen receptor polypeptide comprising SEQ ID NO:2 is provided. In another embodiment, a vector is provided comprising SEQ ID NO: 1 or 3. In another aspect, a lentiviral vector is provided comprising SEQ ID NO: 1 or 3. In yet another embodiment, SEQ ID NO:2 can comprise or consist of humanized, or human amino acid sequences.

In each of these embodiments, variant nucleic acid sequences or amino acid sequences having at least about 80%, at least about 90%, at least about 95%, at least about 97%, at least about 98%, at least about 99%, or at least about 99.5% sequence identity to SEQ ID NOS:1 to 3 are contemplated. In another embodiment, the nucleic acid sequence can be a variant nucleic acid sequence having at least about 80%, at least about 90%, at least about 95%, at least about 97%, at least about 98%, at least about 99%, or at least about 99.5% sequence identity to SEQ ID NO: 1 or 2 as long as the variant sequence encodes a polypeptide of SEQ ID NO:2. In another embodiment, the nucleic acid sequence or the amino acid sequence can be a variant nucleic acid or amino acid sequence having at least about 80%, at least about 90%, at least about 95%, at least about 97%, at least about 98%, at least about 99%, or at least about 99.5% sequence identity to SEQ ID NO:1 or 3 along a stretch of 200 nucleic acids or, for SEQ ID NO:2, along a stretch of 200 amino acids. In one embodiment, determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid or amino acid sequence of interest. Algorithms for database searching are typically based on the BLAST software (Altschul et al., 1990). In some embodiments, the percent identity can be determined along the full-length of the nucleic acid or amino acid sequence.

Also within the scope of the invention are nucleic acids complementary to the nucleic acids represented by SEQ ID NO: 1 and 3, and those that hybridize to the nucleic acids represented by SEQ ID NO:1 and 3, or those that hybridize to their complements under highly stringent conditions. In accordance with the invention "highly stringent conditions" means hybridization at 65° C. in 5×SSPE and 50% formamide, and washing at 65° C. in 0.5×SSPE. Conditions for high stringency, low stringency and moderately stringent hybridization are described in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference. In some illustrative aspects, hybridization occurs along the full-length of the nucleic acid.

In one embodiment, the T lymphocytes (e.g., cytotoxic T lymphocytes used to prepare CAR T cells or non-transformed T cells), used in the methods described herein, can be autologous cells, although heterologous cells can also be used, such as when the patient being treated has received high-dose chemotherapy or radiation treatment to destroy the patient's immune system. In one embodiment, allogenic cells can be used.

In one aspect, the T lymphocytes can be obtained from a patient by means well-known in the art. For example, T cells (e.g., cytotoxic T cells or non-transformed T cells) can be obtained by collecting peripheral blood from the patient, subjecting the blood to Ficoll density gradient centrifugation, and then using a negative T cell isolation kit (such as EasySep™ T Cell Isolation Kit) to isolate a population of T cells from the peripheral blood. In one illustrative embodiment, the population of T lymphocytes (e.g., cytotoxic T cells or non-transformed T cells) need not be pure and may contain other cells such as other types of T cells (in the case of cytotoxic T cells, for example), monocytes, macrophages, natural killer cells, and B cells. In one aspect, the population being collected can comprise at least about 90% of the selected cell type, at least about 91%, 92%, 93%, 94%, 95%, 96%, 97%, 98%, 99%, or 100% of the selected cell type.

In one embodiment, after the T lymphocytes (e.g., cytotoxic T cells used to prepare CAR T cells) are obtained, the cells are cultured under conditions that promote the activation of the cells. In this embodiment, the culture conditions may be such that the cells can be administered to a patient without concern for reactivity against components of the culture medium. For example, the culture conditions may not include bovine serum products, such as bovine serum albumin. In one illustrative aspect, the activation can be achieved by introducing known activators into the culture medium, such as anti-CD3 antibodies in the case of cytotoxic T cells. Other suitable activators include anti-CD28 antibodies. In one aspect, the population of lymphocytes can be cultured under conditions promoting activation for about 1 to about 4 days. In one embodiment, the appropriate level of activation can be determined by cell size, proliferation rate, or activation markers determined by flow cytometry.

In one illustrative embodiment, after the population of T lymphocytes (e.g., cytotoxic T lymphocytes used to prepare CAR T cells) has been cultured under conditions promoting activation, the cells can be transfected with an expression vector encoding a CAR. Suitable vectors and transfection methods for use in various embodiments are described above. In one aspect, after transfection, the cells can be immediately administered to the patient or the cells can be cultured for at least about 1, 2, 3, 4, 5, 6, 7, 8, 9, 10, 11, 12, 13, 14, 15, 16, 17, 18 or more days, or between about 5 and about 12 days, between about 6 and about 13 days, between about 7 and about 14 days, or between about 8 and about 15 days, for example, to allow time for the cells to recover from the transfection. In one aspect, suitable culture conditions can be similar to the conditions under which the cells were cultured for activation either with or without the agent that was used to promote activation.

Thus, as described above, in one illustrative aspect, the methods of treatment described herein can further comprise 1) obtaining a population of autologous or heterologous T lymphocytes (e.g., cytotoxic T lymphocytes used to prepare CAR T cells), 2) culturing the T lymphocytes under conditions that promote the activation of the cells, and 3) transfecting the lymphocytes with an expression vector encoding a CAR to form CAR T cells.

In one illustrative embodiment, when the cells have been transfected and activated, a composition comprising the CAR T cells can be prepared and administered to the patient, with or without non-transformed T cells. In one embodiment, culture media that lacks any animal products, such as bovine serum, can be used to culture the CAR T cells and/or the non-transformed T cells. In another embodiment, tissue culture conditions typically used by the skilled artisan to avoid contamination with bacteria, fungi and *Mycoplasma* can be used. In an exemplary embodiment, prior to being administered to a patient, the cells (e.g., CAR T cells and/or non-transformed T cells are pelleted, washed, and are resuspended in a pharmaceutically acceptable carrier or diluent. Exemplary compositions comprising CAR-expressing T lymphocytes (e.g., cytotoxic T lymphocytes) or non-transformed T cells include compositions comprising the cells in sterile 290 mOsm saline, in infusible cryomedia (containing Plasma-Lyte A, dextrose, sodium chloride injection, human serum albumin and DMSO), in 0.9% NaCl with 2% human serum albumin, or in any other sterile 290 mOsm infusible materials. Alternatively, in another embodiment, depending on the identity of the culture medium, the CAR T cells or non-transformed T cells can be administered in the culture media as the composition, or concentrated and resuspended in the culture medium before administration. In various embodiments, the CAR T cell composition, with or without non-transformed T cells, can be administered to the patient via any suitable means, such as parenteral administration, e.g., intradermally, subcutaneously, intramuscularly, intraperitoneally, intravenously, or intrathecally.

In one aspect, the total number of CAR T cells and the concentration of the cells in the composition administered to the patient will vary depending on a number of factors including the type of T lymphocytes (e.g., cytotoxic T lymphocytes) being used, the binding specificity of the CAR, the identity of the targeting moiety and the small molecule ligand, the identity of the cancer, the location of the cancer in the patient, the means used to administer the compositions to the patient, and the health, age and weight of the patient being treated. In various embodiments, suitable compositions comprising transduced CAR T cells include those having a volume of about 0.1 ml to about 200 ml and about 0.1 ml to about 125 ml.

In various embodiments, the transduced CAR T cells administered to the patient can comprise from about $1 \times 10^5$ to about $1 \times 10^{15}$ or $1 \times 10^6$ to about $1 \times 10^{15}$ transduced CAR T cells. In various embodiments about $1 \times 10^5$ to about $1 \times 10^{10}$, about $1 \times 10^6$ to about $1 \times 10^{10}$, about $1 \times 10^6$ to about $1 \times 10^9$, about $1 \times 10^6$ to about $1 \times 10^8$, about $1 \times 10^6$ to about $2 \times 10^7$, about $1 \times 10^6$ to about $3 \times 10^7$, about $1 \times 10^6$ to about $1.5 \times 10^7$, about $1 \times 10^6$ to about $1 \times 10^7$, about $1 \times 10^6$ to about $9 \times 10^6$, about $1 \times 10^6$ to about $8 \times 10^6$, about $1 \times 10^6$ to about $7 \times 10^6$, about $1 \times 10^6$ to about $6 \times 10^6$, about $1 \times 10^6$ to about $5 \times 10^6$, about $1 \times 10^6$ to about $4 \times 10^6$, about $1 \times 10^6$ to about $3 \times 10^6$, about $1 \times 10^6$ to about $2 \times 10^6$, about $2 \times 10^6$ to about $6 \times 10^6$, about $2 \times 10^6$ to about $5 \times 10^6$, about $3 \times 10^6$ to about $6 \times 10^6$, about $4 \times 10^6$ to about $6 \times 10^6$, about $4 \times 10^6$ to about $1 \times 10^7$, about $1 \times 10^6$ to about $1 \times 10^7$, about $1 \times 10^6$ to about $1.5 \times 10^7$, about $1 \times 10^6$ to about $2 \times 10^7$, about $0.2 \times 10^6$ to about $1 \times 10^7$, about $0.2 \times 10^6$ to about $1.5 \times 10^7$, about $0.2 \times 10^6$ to about $2 \times 10^7$, or about $5 \times 10^6$ CAR T cells can be administered to the patient. In one aspect, in any embodiment described herein, a single dose or multiple doses of the CAR T cells can be administered to the patient. In any of the embodiments described in this paragraph, the CAR T cell dose can be in numbers of CAR T cells per kg of patient body weight. In any embodiment described herein, the CAR T cells can be administered before the compound, or the pharmaceutically acceptable salt thereof. As would be understood, the designations i), ii), and iii), etc. for steps of any method described herein do not indicate an order unless otherwise stated.

In the various embodiments described herein, non-transformed T cells can also be administered with the CAR T cells and can be administered in amounts described herein for the CAR T cells and the non-transformed T cells. In one aspect, a mixture of CAR T cells and non-transformed T cells can be administered a single time or multiple times, or combinations of doses of pure CAR T cells and mixtures of CAR T cells and non-transformed T cells can be administered (e.g., a dose of CAR T cells followed by one or more doses of a mixture of CAR T cells and non-transformed T cells). As is clear to the skilled artisan from the disclosure herein, a mixture of CAR T cells and non-transformed T cells as described herein, means that CAR T cells are mixed with non-transformed T cells that have not been exposed to a construct used for expression of a chimeric antigen receptor.

In other embodiments, the dose of the CAR T cells administered to the patient in the CAR T cell composition is selected from the group consisting of about 1 million, about 2 million, about 3 million, about 4 million, about 5 million, about 6 million, about 7 million, about 8 million, about 9 million, about 10 million, about 11 million, about 12 million, about 12.5 million, about 13 million, about 14 million, and about 15 million of the CAR T cells. In these embodiments, the CAR T cell dose can be in numbers of CAR T cells per kg of patient body weight.

In still other illustrative embodiments, the CAR T cell composition is administered by injection into the patient's bloodstream, and the CAR T cells in the patient's bloodstream are at least 5 percent, at least 7 percent, at least 10 percent, at least 11 percent, at least 12 percent, at least 13 percent, at least 14 percent, or at least 15 percent of the patient's total T cells in the patient's bloodstream by about four weeks after injection of the CAR T cell composition, at least 20 percent, 25 percent, 30 percent, 35 percent, 40 percent, or 50 percent by about 3 weeks after injection of the CAR T cell composition, at least 60 percent, 65 percent, 70 percent, 75 percent, or 80 percent by about 2 weeks after injection of the CAR T cell composition, or at least 85 percent, 90 percent, or 95 by about 1 week after injection of the CAR T cell composition.

In embodiments described herein, the CAR T cell composition can comprise CAR T cells without any other cell type, or non-transformed T cells can be administered to the patient in combination with CAR T cells. For embodiments where multiple doses of the CAR T cell composition are administered, any dose can comprise CAR T cells or a mixture of CAR T cells and non-transformed T cells. In various embodiments, the non-transformed T cells can be administered in amounts described herein for the CAR T cells.

In another embodiment, any dose of the CAR T cell composition can comprise a mixture of the CAR T cells and non-transformed T cells in a ratio selected from about 1:5 of the CAR T cells to the non-transformed T cells, about 1:4 of the CAR T cells to the non-transformed T cells, about 1:3 of the CAR T cells to the non-transformed T cells, about 1:2 of the CAR T cells to the non-transformed T cells, and about 1:1 of the CAR T cells to the non-transformed T cells.

In still other embodiments, any dose of the CAR T cell composition can comprise a mixture of the CAR T cells and non-transformed T cells in a ratio of from about 1:1 to about 1:5 of the CAR T cells to the non-transformed T cells, or the CAR T cell composition can comprise a mixture of about 10 million of the CAR T cells and about 40 million non-transformed T cells, about 15 million of the CAR T cells and about 35 million of the non-transformed T cells, about 20 million of the CAR T cells and about 30 million of the non-transformed T cells, or about 25 million of the CAR T cells and about 25 million of the non-transformed T cells.

The compound, or pharmaceutically acceptable salt thereof, or CAR T cell composition described herein can be administered to the patient using any suitable method known in the art. As described herein, the term "administering" or "administered" includes all means of introducing the compound, or pharmaceutically acceptable salt thereof, or CAR T cell composition to the patient, including, but not limited to, oral, intravenous, intramuscular, subcutaneous, transdermal, and the like. In one aspect, the compound, or pharmaceutically acceptable salt thereof, described herein may be administered in unit dosage forms and/or formulations containing conventional nontoxic pharmaceutically-acceptable carriers, adjuvants, and vehicles.

In one aspect, the compound, or pharmaceutically acceptable salt thereof, or CAR T cell composition as described herein may be administered directly into the blood stream, into muscle, or into an internal organ. In various embodiments, suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but they may be more suitably formulated as a sterile non-aqueous solution or as a dried form to be used in conjunction with a suitable vehicle such as sterile, pyrogen-free water or sterile saline. In other embodiments, any of the liquid formulations described herein may be adapted for parenteral administration as described herein. The preparation under sterile conditions, by lyophilization to produce a sterile lyophilized powder for a parenteral formulation, may readily be accomplished using standard pharmaceutical techniques well-known to those skilled in the art. In one embodiment, the solubility of the compound, or pharmaceutically acceptable salt thereof, used in the preparation of a parenteral formulation may be increased by the use of appropriate formulation techniques, such as the incorporation of solubility-enhancing agents.

The amount of the compound, or pharmaceutically acceptable salt thereof, to be administered to the patient can vary significantly depending on the cancer being treated, the route of administration of the compound, or pharmaceutically acceptable salt thereof, and the tissue distribution. The amount to be administered to a patient can be based on body surface area, mass, and physician assessment. In various embodiments, amounts to be administered can range, for example, from about 0.05 mg to about 30 mg, 0.05 mg to about 25.0 mg, about 0.05 mg to about 20.0 mg, about 0.05 mg to about 15.0 mg, about 0.05 mg to about 10.0 mg, about 0.05 mg to about 9.0 mg, about 0.05 mg to about 8.0 mg, about 0.05 mg to about 7.0 mg, about 0.05 mg to about 6.0 mg, about 0.05 mg to about 5.0 mg, about 0.05 mg to about 4.0 mg, about 0.05 mg to about 3.0 mg, about 0.05 mg to about 2.0 mg, about 0.05 mg to about 1.0 mg, about 0.05 mg to about 0.5 mg, about 0.05 mg to about 0.4 mg, about 0.05 mg to about 0.3 mg, about 0.05 mg to about 0.2 mg, about 0.05 mg to about 0.1 mg, about 0.01 mg to about 2 mg, about 0.3 mg to about 10 mg, about 0.1 mg to about 20 mg, or about 0.8 to about 3 mg. One of skill in the art will readily appreciate that the dose may vary within the various ranges provided above based on the factors noted above, and may be at the physician's discretion.

In other embodiments, the dose of the compound, or pharmaceutically acceptable salt thereof, can range, for example, from about 50 nmoles/kg to about 3000 nmoles/kg of patient body weight, about 50 nmoles/kg to about 2000 nmoles/kg, about 50 nmoles/kg to about 1000 nmoles/kg, about 50 nmoles/kg to about 900 nmoles/kg, about 50 nmoles/kg to about 800 nmoles/kg, about 50 nmoles/kg to about 700 nmoles/kg, about 50 nmoles/kg to about 600 nmoles/kg, about 50 nmoles/kg to about 500 nmoles/kg, about 50 nmoles/kg to about 400 nmoles/kg, about 50 nmoles/kg to about 300 nmoles/kg, about 50 nmoles/kg to about 200 nmoles/kg, about 50 nmoles/kg to about 100 nmoles/kg, about 100 nmoles/kg to about 300 nmoles/kg, about 100 nmoles/kg to about 500 nmoles/kg, about 100 nmoles/kg to about 1000 nmoles/kg, about 100 nmoles/kg to about 2000 nmoles/kg of patient body weight. In other embodiments, the dose may be about 1 nmoles/kg, about 5 nmoles/kg, about 10 nmoles/kg, about 20 nmoles kg, about 25 nmoles/kg, about 30 nmoles/kg, about 40 nmoles/kg, about 50 nmoles/kg, about 60 nmoles/kg, about 70 nmoles/kg, about 80 nmoles/kg, about 90 nmoles/kg, about 100 nmoles/kg, about 150 nmoles/kg, about 200 nmoles/kg, about 250 nmoles/kg, about 300 nmoles/kg, about 350 nmoles/kg, about 400 nmoles/kg, about 450 nmoles/kg, about 500 nmoles/kg, about 600 nmoles/kg, about 700 nmoles/kg, about 800 nmoles/kg, about 900 nmoles/kg, about 1000 nmoles/kg, about 2000 nmoles/kg, about 2500 nmoles/kg or about 3000 nmoles/kg of body weight of the patient. In yet other embodiments, the dose may be about 0.1 nmoles/kg, about 0.2 nmoles/kg, about 0.3 nmoles/kg, about 0.4 nmoles kg, or about 0.5 nmoles/kg, about 0.1 nmoles/kg to about 1000 nmoles/kg, about 0.1 nmoles/kg to about 900 nmoles/kg, about 0.1 nmoles/kg to about 850 nmoles/kg, about 0.1 nmoles/kg to about 800 nmoles/kg, about 0.1 nmoles/kg to about 700 nmoles/kg, about 0.1 nmoles/kg to about 600 nmoles/kg, about 0.1 nmoles/kg to about 500 nmoles/kg, about 0.1 nmoles/kg to about 400 nmoles/kg, about 0.1 nmoles/kg to about 300 nmoles/kg, about 0.1 nmoles/kg to about 200 nmoles/kg, about 0.1 nmoles/kg to about 100 nmoles/kg, about 0.1 nmoles/kg to about 50 nmoles/kg, about 0.1 nmoles/kg to about 10 nmoles/kg, or about 0.1 nmoles/kg to about 1 nmoles/kg of body weight of the patient. In other embodiments, the dose may be about 0.3 nmoles/kg to about 1000 nmoles/kg, about 0.3 nmoles/kg to about 900 nmoles/kg, about 0.3 nmoles/kg to about 850 nmoles/kg, about 0.3 nmoles/kg to about 800 nmoles/kg, about 0.3 nmoles/kg to about 700 nmoles/kg, about 0.3 nmoles/kg to about 600 nmoles/kg, about 0.3 nmoles/kg to about 500 nmoles/kg, about 0.3 nmoles/kg to about 400 nmoles/kg, about 0.3 nmoles/kg to about 300 nmoles/kg, about 0.3 nmoles/kg to about 200 nmoles/kg, about 0.3 nmoles/kg to about 100 nmoles/kg, about 0.3 nmoles/kg to about 50 nmoles/kg, about 0.3 nmoles/kg to about 10 nmoles/kg, or about 0.3 nmoles/kg to about 1 nmoles/kg of body weight of the patient. In these embodiments, "kg" is kilograms of body weight of the patient. In one aspect, a single dose or multiple doses of the compound, or pharmaceutically acceptable salt thereof, may be administered to the patient.

In various other embodiments, the dose of the compound, or the pharmaceutically acceptable salt thereof, may range from, for example, about 10 nmoles/kg to about 10000 nmoles/kg, from about 10 nmoles/kg to about 5000 nmoles/kg, from about 10 nmoles/kg to about 3000 nmoles/kg, about 10 nmoles/kg to about 2500 nmoles/kg, about 10 nmoles/kg to about 2000 nmoles/kg, about 10 nmoles/kg to about 1000 nmoles/kg, about 10 nmoles/kg to about 900 nmoles/kg, about 10 nmoles/kg to about 800 nmoles/kg, about 10 nmoles/kg to about 700 nmoles/kg, about 10 nmoles/kg to about 600 nmoles/kg, about 10 nmoles/kg to about 500 nmoles/kg, about 10 nmoles/kg to about 400 nmoles/kg, about 10 nmoles/kg to about 300 nmoles/kg, about 10 nmoles/kg to about 200 nmoles/kg, about 10 nmoles/kg to about 150 nmoles/kg, about 10 nmoles/kg to about 100 nmoles/kg, about 10 nmoles/kg to about 90 nmoles/kg, about 10 nmoles/kg to about 80 nmoles/kg, about 10 nmoles/kg to about 70 nmoles/kg, about 10 nmoles/kg to about 60 nmoles/kg, about 10 nmoles/kg to about 50 nmoles/kg, about 10 nmoles/kg to about 40 nmoles/kg, about 10 nmoles/kg to about 30 nmoles/kg, about 10 nmoles/kg to about 20 nmoles/kg, about 200 nmoles/kg to about 900 nmoles/kg, about 200 nmoles/kg to about 800 nmoles/kg, about 200 nmoles/kg to about 700 nmoles/kg, about 200 nmoles/kg to about 600 nmoles/kg, about 200 nmoles/kg to about 500 nmoles/kg, about 250 nmoles/kg to about 600 nmoles/kg, about 300 nmoles/kg to about 600 nmoles/kg, about 300 nmoles/kg to about 500 nmoles/kg, or about 400 nmoles/kg to about 600 nmoles/kg, of body weight of the patient. In various other embodiments, the dose of the compound, or the pharmaceutically acceptable salt thereof, may range from, for example, about 1 nmoles/kg to about 10000 nmoles/kg, from about 1 nmoles/kg to about 5000 nmoles/kg, from about 1 nmoles/kg to about 3000 nmoles/kg, about 1 nmoles/kg to about 2500 nmoles/kg, about 1 nmoles/kg to about 2000 nmoles/kg, about 1 nmoles/kg to about 1000 nmoles/kg, about 1 nmoles/kg to about 900 nmoles/kg, about 1 nmoles/kg to about 800 nmoles/kg, about 1 nmoles/kg to about 700 nmoles/kg, about 1 nmoles/kg to about 600 nmoles/kg, about 1 nmoles/kg to about 500 nmoles/kg, about 1 nmoles/kg to about 400 nmoles/kg, about 1 nmoles/kg to about 300 nmoles/kg, about 1 nmoles/kg to about 200 nmoles/kg, about 1 nmoles/kg to about 150 nmoles/kg, about 1 nmoles/kg to about 100 nmoles/kg, about 1 nmoles/kg to about 90 nmoles/kg, about 1 nmoles/kg to about 80 nmoles/kg, about 1 nmoles/kg to about 70 nmoles/kg, about 1 nmoles/kg to about 60 nmoles/kg, about 1 nmoles/kg to about 50 nmoles/kg, about 1 nmoles/kg to about 40 nmoles/kg, about 1 nmoles/kg to about 30 nmoles/kg, or about 1 nmoles/kg to about 20 nmoles/kg, In these embodiments, "kg" is kilograms of body weight of the patient. In one aspect, a single dose or multiple doses of the compound, or pharmaceutically acceptable salt thereof, may be administered to the patient.

In another embodiment, from about 20 ug/kg of body weight of the patient to about 3 mg/kg of body weight of the patient of the compound, or the pharmaceutically acceptable salt thereof, can be administered to the patient. In another aspect, amounts can be from about 0.2 mg/kg of body weight of the patient to about 0.4 mg/kg of body weight of the patient, or can be about 50 ug/kg of body weight of the patient. In one aspect, a single dose or multiple doses of the compound, or the pharmaceutically acceptable salt thereof, may be administered to the patient.

In one embodiment, the small molecule ligand linked to the targeting moiety can be administered to the patient before the CAR T cell composition. In another embodiment, the small molecule ligand linked to the targeting moiety can be administered to the patient at the same time as the CAR T cell composition, but in different formulations, or in the same formulation. In yet another embodiment, the small molecule ligand linked to the targeting moiety can be administered to the patient after the CAR T cell composition.

In one illustrative aspect, the timing between the administration of CAR T cells and the small molecule linked to the targeting moiety may vary widely depending on factors that include the type of CAR T cells being used, the binding specificity of the CAR, the identity of the targeting moiety and the small molecule ligand, the identity of the cancer, the location in the patient of the cancer, the means used to administer to the patient the CAR T cells and the small molecule ligand linked to the targeting moiety, and the health, age, and weight of the patient. In one aspect, the small molecule ligand linked to the targeting moiety can be administered before or after the CAR T cells, such as within about 3, 6, 9, 12, 15, 18, 21, 24, 27, 30, 33, 36, 39, 42, 45, 48, or 51 hours, or within about 0.5, 1, 1.5, 2, 2.5, 3, 4 5, 6, 7, 8, 9, 10 or more days.

In one embodiment, any applicable dosing schedule known in the art can be used for administration of the compound, or the pharmaceutically acceptable salt thereof, or for the CAR T cell composition. For example, once per day dosing (a.k.a qd), twice per day dosing (a.k.a. bid), three times per day dosing (a.k.a. tid), twice per week dosing (a.k.a. BIW), three times per week dosing (a.k.a. TIW), once weekly dosing, and the like, can be used. In one aspect, the dosing schedule selected for the compound, or the pharmaceutically acceptable salt thereof, and the CAR T cell composition can take into consideration the concentration of the compound, or the pharmaceutically acceptable salt thereof, and the number of CAR T cells administered, to regulate the cytotoxicity of the CAR T cell composition and to control CRS.

In one embodiment, to prevent or inhibit cytokine release syndrome (CRS) in the patient, a method of treatment of a cancer is provided, and the method comprises i) administering to a patient a compound, or a pharmaceutically acceptable salt thereof, wherein the compound comprises a small molecule ligand linked to a targeting moiety by a linker, ii) administering to the patient a CAR T cell composition wherein the CAR T cell composition comprises CAR T cells and wherein the CAR T cells comprise a CAR directed to the targeting moiety, and iii) administering to the patient a folate, a conjugate comprising a folate wherein the conjugate comprising a folate does not comprise a targeting moiety, or a drug that inhibits activation of the CAR T cells.

In this method embodiment, the step of administering to the patient a folate, a conjugate comprising a folate wherein the conjugate comprising a folate does not comprise a targeting moiety, or a drug that inhibits activation of the CAR T cells can be used to prevent or inhibit CRS in the patient. In this embodiment, any of a folate, a conjugate comprising a folate wherein the conjugate comprising a folate does not comprise a targeting moiety, or a drug that inhibits activation of the CAR T cells can be referred to herein as "a rescue agent". In one embodiment, a folate, such as folic acid, can be administered to prevent or inhibit CRS in the patient. In this embodiment, the folate inhibits interaction of the bridge (i.e., the small molecule ligand linked to the targeting moiety by a linker) with the receptors for the bridge on the tumor inhibiting tumor lysis and preventing or inhibiting CRS in the patient.

In one embodiment, the folate administered as an inhibitor of binding of the bridge to the tumor can be, for example, folic acid, a folic acid analog, or another folate receptor-binding molecule. In various embodiments, analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), N10-methylfolate, 2-deamino-hydroxyfolate, deaza analogs such as 1-deazamethopterin or 3-deazamethopterin, and 3',5'-dichloro-4-amino-4-deoxy-N10-methylpteroylglutamic acid (dichloromethotrexate).

In another embodiment, the folate administered as an inhibitor of binding of the bridge to the tumor has the formula

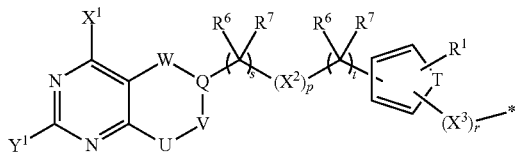

wherein $X^1$ and $Y^1$ are each-independently selected from the group consisting of halo, $R^2$, $OR^2$, $SR^3$, and $NR^4R^5$;

U, V, and W represent divalent moieties each independently selected from the group consisting of —($R^{6a}$) $C$=, —N=, —($R^{6a}$)$C(R^{7a})$—, and —$N(R^{4a})$—; Q is selected from the group consisting of C and CH; T is selected from the group consisting of S, O, N, and —C=C—;

$X^2$ and $X^3$ are each independently selected from the group consisting of oxygen, sulfur, —C(Z)—, —C(Z)O—, —OC(Z)—, —$N(R^{4b})$—, —$C(Z)N(R^{4b})$—, —$N(R^{4b})C(Z)$—, —$OC(Z)N(R^{4b})$—, —$N(R^{4b})C(Z)O$—, —$N(R^{4b})C(Z)N(R^{5b})$—, —S(O)—, —$S(O)_2$—, —$N(R^{4a})S(O)_2$—, —$C(R^{6b})$ $(R^{7b})$—, —N(C≡CH)—, —N(CH$_2$C≡CH)—, $C_1$-$C_{12}$ alkylene, and $C_1$-$C_{12}$ alkyneoxy, where Z is oxygen or sulfur;

$R^1$ is selected-from the group consisting of hydrogen, halo, $C_1$-$C_{12}$ alkyl, and $C_1$-$C_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;

$R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

* p, r, s, and t are each independently either 0 or 1; and represents an optional covalent bond to the rest of the conjugate, if any additional chemical moieties are part of the folate.

In yet another embodiment, a conjugate comprising a folate can be administered to prevent or inhibit cytokine release syndrome (CRS) in the patient. CRS is a term well-known in the art and this syndrome can cause detrimental effects to the patient, including, but not limited to weight loss, high fever, pulmonary edema, and a dangerous drop in blood pressure.

In this embodiment, the conjugate comprising a folate does not comprise a targeting moiety, and, thus, the conjugate inhibits interaction of the bridge with the tumor to prevent tumor lysis and reduce CRS in the patient. In this embodiment, the folate moiety in the conjugate comprising a folate can comprise any of the folates described in the preceding paragraphs linked to a chemical moiety that does not comprise a targeting moiety. In one aspect, the conjugate comprising a folate can comprise a folate linked to one or more amino acids that do not comprise a targeting moiety. Illustratively, the conjugate comprising a folate can have the formula

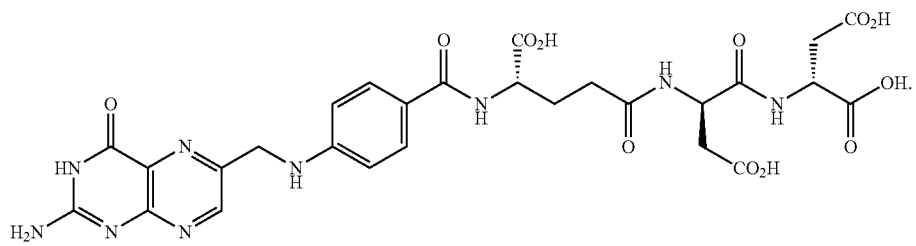 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

This compound can also be referred to as "EC923". In these embodiments, the folate or the conjugate comprising a folate can be administered to the patient in molar excess relative to the bridge (i.e., the small molecule ligand linked to a targeting moiety by a linker), such as a 10-fold excess, a 100-fold excess, a 200-fold excess a 300-fold excess a 400-fold excess a 500-fold excess a 600-fold excess a 700-fold excess a 800-fold excess a 900-fold excess, a 1000-fold excess, or a 10,000-fold excess of the folate or the conjugate comprising a folate relative to the small molecule ligand linked to a targeting moiety by a linker. The amount of the folate or the conjugate comprising a folate relative to the amount of the small molecule ligand linked to a targeting moiety by a linker needed to inhibit interaction of the bridge with the tumor can be determined by the skilled artisan.

In another embodiment, an agent that inhibits activation of the CAR T cells can be administered to the patient to inhibit CAR T cell activation and to inhibit or prevent CRS in the patient. In one aspect the agent can be selected from the group consisting of a lymphocyte-specific protein tyrosine kinase inhibitor (e.g., Dasatinib), a PI3 kinase inhibitor (e.g., GDC0980), Tociluzumab, an inhibitor of an IL-2 inducible T cell kinase (e.g., BMS-509744), JAK inhibitors, BTK inhibitors, SIP agonists (e.g. Siponimod and Ozanimod), and an agent that blocks CAR T cell binding to the bridge, but does not bind to the cancer (e.g., fluoresceinamine, FITC, or sodium fluorescein). It is understood by the skilled artisan that FITC (i.e., fluorescein) can be in the form of a salt (e.g., sodium fluorescein), or in its unsalted form, under physiological conditions or, for example, in a buffer at physiological pH. Accordingly, in one embodiment, when fluorescein is administered to a patient it may be in equilibrium between its salted form (e.g., sodium fluorescein) and its unsalted form. In another embodiment, a rescue agent that inhibits activation of CAR T cells can be a compound of the formula

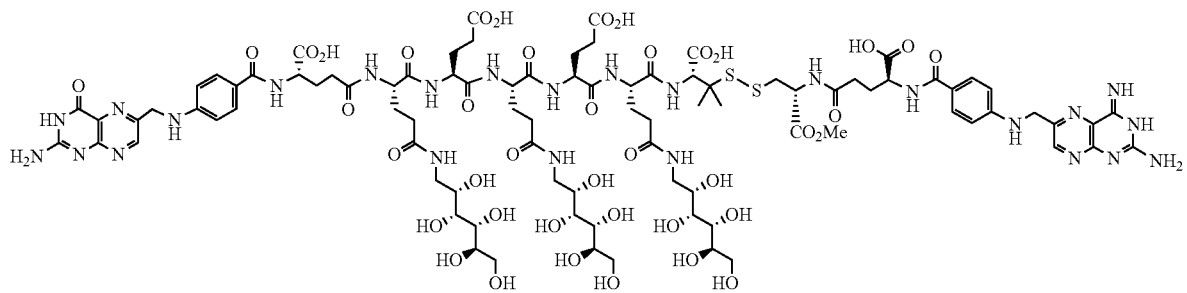 [SMILES: COC(=O)[C@H](CSSC(C)(C)[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c1ccc(NCc2cnc3nc(N)[nH]c(=O)c3n2)cc1)C(=O)O)C(=O)O)NC(=O)CC[C@H](NC(=O)c1ccc(NCc2cnc3nc(N)[nH]c(=N)c3n2)cc1)C(=O)O]

In various embodiments, the rescue agent can be administered at a concentration of from about 0.001 nM to about 100 mM, about 0.01 nM to about 100 mM, about 1 nM to about 100 mM, about 10 nM to about 100 mM, about 50 nM to about 100 mM, or from about 100 nM to about 100 mM in any appropriate volume, including, for example, 0.1 ml, 0.2 ml, 0.3 ml, 0.4 ml, 0.5 ml, 0.6 ml, 0.7 ml, 0.8 ml, 0.9 ml, 1 ml, 2 ml, 3 ml, 4 ml, 5 ml, 10 ml, 100 ml, or 1000 ml. In other embodiments, the rescue agent can be administered at a dose of about 0.01 to about 300 umoles/kg of body weight of the patient, about 0.06 to about 100 umoles/kg of body weight of the patient, about 0.06 to about 90 umoles/kg of body weight of the patient, about 0.06 to about 80 umoles/kg of body weight of the patient, about 0.06 to about 70 umoles/kg of body weight of the patient, about 0.06 to about 60 umoles/kg of body weight of the patient, about 0.06 to about 50 umoles/kg of body weight of the patient, about 0.06 to about 40 umoles/kg of body weight of the patient, about 0.06 to about 30 umoles/kg of body weight of the patient, about 0.06 to about 20 umoles/kg of body weight of the patient, about 0.06 to about 10 umoles/kg of body weight of the patient, about 0.06 to about 8 umoles/kg of body weight of the patient, or about 0.06 to about 6 umoles/kg of body weight of the patient.

In these embodiments, the rescue agent can be administered to the patient in molar excess relative to the compound, or its pharmaceutically acceptable salt (i.e., the small molecule ligand linked to a targeting moiety by a linker), such as about a 10-fold excess, about a 20-fold excess, about a 30-fold excess, about a 40-fold excess, about a 50-fold excess, about a 60-fold excess, about a 70-fold excess, about a 80-fold excess, about a 90-fold excess, about a 100-fold excess, about a 200-fold excess, about a 300-fold excess, about a 400-fold excess, about a 500-fold excess, about a 600-fold excess, about a 700-fold excess, about a 800-fold excess, about a 900-fold excess, about a 1000-fold excess, or about a 10,000-fold excess of the rescue agent relative to the small molecule ligand linked to a targeting moiety by a linker. The amount of the rescue agent relative to the amount of the small molecule ligand linked to a targeting moiety by a linker needed to inhibit interaction of the compound, or its pharmaceutically acceptable salt, with the tumor and/or the CAR T cells can be determined by the skilled artisan.

In another embodiment, more than one dose can be administered to the patient of the folate, the conjugate comprising a folate wherein the conjugate comprising a folate does not comprise a targeting moiety, or the agent that inhibits activation of the CAR T cells.

In the 'rescue agent' embodiments described herein, the folate, the conjugate comprising a folate wherein the conjugate comprising a folate does not comprise a targeting moiety, or the agent that inhibits activation of the CAR T cells can be administered to the patient before and/or after the compound, or the pharmaceutically acceptable salt thereof. In another aspect, the compound, or the pharmaceutically acceptable salt thereof, can be administered before and subsequent to administration of the folate, the conjugate comprising a folate wherein the conjugate comprising a folate does not comprise a targeting moiety, or the agent that inhibits activation of the CAR T cells. In this embodiment, the subsequent administration of the compound, or the pharmaceutically acceptable salt thereof, can cause CAR T cell activation and an increase in cytokine levels in the patient.

In another embodiment, administration of the folate, the conjugate comprising a folate wherein the conjugate comprising a folate does not comprise a targeting moiety, or the agent that inhibits activation of the CAR T cells can cause reduction in cytokine levels in the patient. In yet another embodiment, the reduction in cytokine levels can occur by about 1 hour, by about 2 hours, by about 3 hours, by about 4 hours, by about 5 hours, by about 6 hours, by about 7 hours, or by about 8 hours after administration to the patient of the folate, the conjugate comprising a folate wherein the conjugate comprising a folate does not comprise a targeting moiety, or the agent that inhibits activation of the CAR T cells. In another embodiment, the reduction in cytokine levels is a reduction to about the cytokine levels in an untreated patient. In another illustrative embodiment, CAR T cell number can increase in the blood of the patient after administration of the folate, the conjugate comprising a folate wherein the conjugate comprising a folate does not comprise a targeting moiety, or the agent that inhibits activation of the CAR T cells, even though cytokine levels in the patient are reduced. In another illustrative aspect, CAR T cell activation can be enhanced or maintained, relative to a patient not treated with a rescue agent, after administration of the folate, the conjugate comprising a folate wherein the conjugate comprising a folate does not comprise a targeting moiety, or the agent that inhibits activation of the CAR T cells, even though cytokine levels in the treated patient are reduced. In still another embodiment, the cancer comprises a tumor and tumor size in the patient is not increased when the folate, the conjugate comprising a folate wherein the conjugate comprising a folate does not comprise a targeting moiety, or the agent that inhibits activation of the CAR T cells is administered to the patient. In this embodiment, a complete response for the tumor can be obtained.

In other embodiments, the agent that inhibits activation of the CAR T cells is administered to the patient when the CRS grade reaches 1, 2, 3, or 4 or when the CRS grade reaches 3 or 4. In another aspect, lung edema is reduced in the patient when the rescue agent is administered.

In one embodiment described herein a method of treatment of a cancer is provided, and the method comprises i) administering continuously to a patient a compound, or a pharmaceutically acceptable salt thereof, wherein the compound comprises a small molecule ligand linked to a targeting moiety by a linker, ii) administering to the patient a CAR T cell composition comprising CAR T cells wherein the CAR T cells comprise a CAR directed to the targeting moiety, and iii) ending the continuous administration of the compound, or the pharmaceutically acceptable salt thereof, to inhibit or prevent cytokine release syndrome in the patient.

In accordance with this embodiment, the term "continuously" can mean administering the compound, or the pharmaceutically acceptable salt thereof, to the patient, for example, at least one hour, at least four hours, at least six hours, at least eight hours, at least ten hours, at least twelve hours, or at least twenty-four hours, or can mean a regimen of daily or weekly administration, such as once a day, two times a day, three times a day, every day, every other day, one time weekly, two times weekly, three times weekly, or any other suitable regimen that would be considered continuous administration by a person skilled in the art. In another aspect, the term "continuously" can mean any combination of the embodiments described in this paragraph.

In this method embodiment, the step of "ending the continuous administration" of the compound, or the pharmaceutically acceptable salt thereof, to inhibit or prevent cytokine release syndrome in the patient, can mean, for example, discontinuing administration after administration for a continuous period of time, such as hours or days, or discontinuing a treatment regimen, such as the daily or weekly regimens described above. In another embodiment, the step of "ending the continuous administration" can mean, for example, administration until an unacceptable loss of body weight for the patient occurs, or until any other unacceptable side effect occurs such as a high fever, a drop in blood pressure, or pulmonary edema. In this embodiment, the step of "ending the continuous administration" of the compound, or the pharmaceutically acceptable salt thereof, does not mean a single treatment with the compound, or the pharmaceutically acceptable salt thereof, with no subsequent treatment with the compound, or the pharmaceutically acceptable salt thereof. In this method embodiment "to inhibit or prevent" cytokine release syndrome (CRS) means eliminating CRS or reducing or ameliorating the symptoms of CRS.

In one embodiment of the embodiment involving ending the continuous administration" of the compound, or the pharmaceutically acceptable salt thereof, the method can further comprise step iv) of re-administering the compound, or the pharmaceutically acceptable salt thereof, to the patient. In one embodiment, the compound, or the pharmaceutically acceptable salt thereof, can be administered, for example, once weekly and one dose can be omitted. In another embodiment, the compound, or the pharmaceutically acceptable salt thereof, can be administered on alternate days (i.e., every other day) and one or more (e.g., two, three, four, etc.) doses can be omitted. In another embodiment, the compound, or the pharmaceutically acceptable salt thereof, can be administered twice weekly and one or more (e.g., two, three, four, etc.) doses can be omitted. In another embodiment, the compound, or the pharmaceutically acceptable salt thereof, can be administered Monday, Tuesday, and the following Monday, and then dosing can be stopped for two weeks and the cycle repeated. In another embodiment, any of the regimen embodiments described above can be used and one or more (e.g., two, three, four, etc.) doses can be omitted. In another embodiment, combinations of these embodiments can be used. In these embodiments, the omitted doses can prevent or reduce CRS in the patient.

In yet another illustrative aspect, a method of treatment of a cancer is provided. The method comprises i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof, and ii) administering to the patient a CAR T cell composition comprising CAR T cells wherein the CAR T cells comprise a CAR directed to the targeting moiety.

In this embodiment, the dose of the compound, or the pharmaceutically acceptable salt thereof, can be escalated gradually to inhibit or prevent cytokine release syndrome in the patient. For example, at least a first dose and a second dose of the compound, or the pharmaceutically acceptable salt thereof, can be administered to the patient, wherein the first dose and the second dose are different, wherein the second dose of the compound, or the pharmaceutically acceptable salt thereof, is about 20-fold to about 15000-fold greater, about 2-fold to about 15000-fold greater in amount than the first dose of the compound, or the pharmaceutically acceptable salt thereof. In other embodiments, the second dose, or a subsequent dose, can be about 2-fold to about 5-fold, about 2-fold to about 10-fold, about 2-fold to about 20-fold, about 2-fold to about 30-fold, about 2-fold to about 40-fold, about 2-fold to about 50-fold, about 2-fold to about 60-fold, about 2-fold to about 70-fold, about 2-fold to about 80-fold, about 2-fold to about 90-fold, about 2-fold to about 100-fold, about 2-fold to about 15000-fold, about 2-fold to about 10000-fold, about 5-fold to about 9000-fold, about 5-fold to about 8000-fold, about 5-fold to about 7000-fold, about 5-fold to about 6000-fold, about 5-fold to about 5000-fold, about 5-fold to about 4000-fold, about 5-fold to about 3000-fold, about 5-fold to about 4000-fold, about 5-fold to about 3000-fold, about 5-fold to about 2000-fold, about 5-fold to about 1000-fold, about 5-fold to about 750-fold, about 2-fold to about 750-fold, about 5-fold to about 500-fold, about 5-fold to about 100-fold, about 800-fold to about 15000-fold, about 800-fold to about 10000-fold, about 800-fold to about 9000-fold, about 800-fold to about 8000-fold, about 800-fold to about 7000-fold, about 800-fold to about 6000-fold, about 800-fold to about 5000-fold, about 800-fold to about 4000-fold, about 800-fold to about 3000-fold, about 800-fold to about 2000-fold, about 800-fold to about 1000-fold, about 8000-fold to about 15000-fold, about 8000-fold to about 10000-fold, about 8000-fold to about 9000-fold, about 15000-fold, about 10000-fold, about 9000-fold, about 8000-fold, about 7000-fold, about 6000-fold, about 5000-fold, about 4000-fold, about 3000-fold, about 2000-fold, about 1000-fold, about 500-fold, about 400-fold, about 300-fold, about 200-fold, about 100-fold, about 90-fold, about 80-fold, about 70-fold, about 60-fold, about 50-fold, about 40-fold, about 30-fold, about 20-fold, about 10-fold, about 5-fold, or about 2-fold greater in amount than the first dose of the compound, or the pharmaceutically acceptable salt thereof.

In another illustrative embodiment of the dose escalation method, at least a first dose, a second dose, and a third dose of the compound, or the pharmaceutically acceptable salt thereof, can be administered to the patient, wherein the first dose, the second dose, and the third dose are different, wherein the second dose of the compound, or the pharmaceutically acceptable salt thereof, is about 2-fold to about 750-fold greater in amount than the first dose of the compound, or the pharmaceutically acceptable salt thereof, and wherein the third dose of the compound, or the pharmaceutically acceptable salt thereof, is about 800-fold to about 10000-fold greater in amount than the first dose of the compound, or the pharmaceutically acceptable salt thereof.

In another aspect of the dose escalation method, at least a first dose, a second dose, a third dose, and a fourth dose of the compound, or the pharmaceutically acceptable salt thereof, can be administered to the patient, wherein the first dose, the second dose, the third dose, and the fourth dose are different, wherein the second dose of the compound, or the pharmaceutically acceptable salt thereof, is about 2-fold to about 750-fold greater in amount than the first dose of the compound, or the pharmaceutically acceptable salt thereof, wherein the third dose of the compound, or the pharmaceutically acceptable salt thereof, is about 800-fold to about 7500-fold greater in amount than the first dose of the compound, or the pharmaceutically acceptable salt thereof, and wherein the fourth dose of the compound, or the pharmaceutically acceptable salt thereof, is about 8000 to about 15000-fold greater in amount than the first dose of the compound, or the pharmaceutically acceptable salt thereof.

In still another embodiment, the second dose of the compound, or the pharmaceutically acceptable salt thereof, can be about 100-fold greater in amount than the first dose of the compound, or the pharmaceutically acceptable salt thereof, the third dose of the compound, or the pharmaceutically acceptable salt thereof, can be about 1000-fold greater in amount than the first dose of the compound, or the pharmaceutically acceptable salt thereof, and the fourth dose of the compound, or the pharmaceutically acceptable salt thereof, can be about 10000-fold greater in amount than the first dose of the compound, or the pharmaceutically acceptable salt thereof. In an exemplary embodiment, the first dose of the compound, or the pharmaceutically acceptable salt thereof, is 0.05 nmoles/kg, the second dose is 5 nmoles/kg, the third dose is 50 nmoles/kg, and the fourth dose is 500 nmoles/kg. In the dose escalation embodiments described herein, the first, second, third, fourth, and any subsequent doses of the compound, or the pharmaceutically acceptable salt thereof, can be administered multiple times (e.g., the first dose at 0.05 nmoles/kg can be administered several times before the subsequent escalated doses are administered).

In another embodiment described herein, a method of treatment of a cancer is provided. The method comprises i) administering to a patient a first dose of a compound, or a pharmaceutically acceptable salt thereof, wherein the compound comprises a small molecule ligand linked to a targeting moiety by a linker, ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof, and iii) administering to the patient a dose of a CAR T cell composition comprising CAR T cells wherein the CAR T cells comprise a CAR directed to the targeting moiety.

In various embodiments of this dose de-escalation embodiment, the second dose of the compound, or the pharmaceutically acceptable salt thereof, can be at least about 60 percent lower in amount than the first dose of the compound, or the pharmaceutically acceptable salt thereof, at least about 70 percent lower in amount than the first dose of the compound, or the pharmaceutically acceptable salt thereof. at least about 80 percent lower in amount than the first dose of the compound, or the pharmaceutically acceptable salt thereof, at least about 90 percent lower in amount than the first dose of the compound, or the pharmaceutically acceptable salt thereof, at least about 95 percent lower in amount than the first dose of the compound, or the pharmaceutically acceptable salt thereof, at least about 96 percent lower in amount than the first dose of the compound, or the pharmaceutically acceptable salt thereof, at least about 97 percent lower in amount than the first dose of the compound, or the pharmaceutically acceptable salt thereof, at least about 98 percent lower in amount than the first dose of the compound, or the pharmaceutically acceptable salt thereof, at least about 99 percent lower in amount than the first dose of the compound, or the pharmaceutically acceptable salt thereof, or at least about 99.5 percent lower in amount than the first dose of the compound, or the pharmaceutically acceptable salt thereof.

In various embodiments of the dose de-escalation embodiment described herein, the first dose of the compound, or the pharmaceutically acceptable salt thereof, can be about 100 nmoles/kg to about 1000 nmoles/kg of body weight of the patient, about 100 nmoles/kg to about 900 nmoles/kg of body weight of the patient, about 100 nmoles/kg to about 800 nmoles/kg of body weight of the patient, about 100 nmoles/kg to about 700 nmoles/kg of body weight of the patient, about 100 nmoles/kg to about 600 nmoles/kg of body weight of the patient, about 200 nmoles/kg to about 600 nmoles/kg of body weight of the patient, about 400 nmoles/kg to about 600 nmoles/kg of body weight of the patient, or about 500 nmoles/kg of body weight of the patient.

In various embodiments of the dose de-escalation embodiment described herein, the second dose of the compound, or the pharmaceutically acceptable salt thereof, can be about 0.5 nmoles/kg to about 500 nmoles/kg of body weight of the patient, about 0.5 nmoles/kg to about 450 nmoles/kg of body weight of the patient, about 0.5 nmoles/kg to about 400 nmoles/kg of body weight of the patient, about 0.5 nmoles/kg to about 350 nmoles/kg of body weight of the patient, about 0.5 nmoles/kg to about 300 nmoles/kg of body weight of the patient, about 1 nmole/kg to about 300 nmoles/kg of body weight of the patient, about 2 nmoles/kg to about 300 nmoles/kg of body weight of the patient, about 2 nmoles/kg to about 250 nmoles/kg of body weight of the patient, about 5 nmoles/kg to about 40 nmoles/kg of body weight of the patient, or about 40 nmoles/kg to about 150 nmoles/kg of body weight of the patient.

In additional embodiments of the dose de-escalation embodiment described herein, the method can further comprise administering a third dose of the compound, or the pharmaceutically acceptable salt thereof, wherein the third dose of the compound, or the pharmaceutically acceptable salt thereof, is the same as the second dose of the compound, or the pharmaceutically acceptable salt thereof. In another embodiment, the method can further comprise administering a fourth dose of the compound, or the pharmaceutically acceptable salt thereof, wherein the fourth dose of the compound, or the pharmaceutically acceptable salt thereof, is the same as the second dose, or the pharmaceutically acceptable salt thereof, and the third dose of the compound, or the pharmaceutically acceptable salt thereof. In yet another embodiment, the dose(s) of the compound, or the pharmaceutically acceptable salt thereof, administered after the first dose of the compound, or the pharmaceutically acceptable salt thereof, can maintain inhibition of growth of the cancer relative to the first dose of the compound, or the pharmaceutically acceptable salt thereof.

In other embodiments of the dose de-escalation embodiment described herein, the CAR T cells can be administered at a dose of about 1 million of the CAR T cells to about 40 million of the CAR T cells. In still other embodiments, the dose(s) of the compound or the pharmaceutically acceptable salt thereof, administered after the first dose of the compound, or the pharmaceutically acceptable salt thereof, can be administered once or twice weekly.

In still other embodiments of the dose de-escalation embodiment described herein, the method can further comprise the step of administering to the patient a folate, a conjugate comprising a folate wherein the conjugate comprising a folate does not comprise a targeting moiety, or an agent that inhibits activation of the CAR T cells. In another embodiment, the agent that inhibits activation of the CAR T cells is administered to the patient and the agent is an agent that blocks CAR T cell binding to the compound, or the pharmaceutically acceptable salt thereof, but does not bind to the cancer, and the agent is fluoresceinamine, sodium fluorescein, or fluorescein. In yet another embodiment, the agent is sodium fluorescein.

In another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker and wherein the compound, or the pharmaceutically acceptable salt thereof, is administered to the patient at least about one hour prior to the administration of a CAR T cell composition comprising CAR T cells wherein the CAR T cells comprise a CAR directed to the targeting moiety, ii) then administering to the patient a dose of the CAR T cell composition, and iii) then administering to the patient a second dose of the compound, or the pharmaceutically acceptable salt thereof. In various embodiments of this pre-treatment embodiment, the first dose of the compound, or the pharmaceutically acceptable salt thereof, can be administered to the patient at least about two hours prior to the administration of the CAR T cell composition, at least about four hours prior to the administration of the CAR T cell composition, at least about eight hours prior to the administration of the CAR T cell composition, at least about twelve hours prior to the administration of the CAR T cell composition, at least about sixteen hours prior to the administration of the CAR T cell composition, at least about twenty hours prior to the administration of the CAR T cell composition, or at least about twenty-four hours prior to the administration of the CAR T cell composition.

In various embodiments of this pre-treatment embodiment, the second dose of the compound, or the pharmaceutically acceptable salt thereof, can be administered to the patient by at least about twenty-four hours after the administration of the CAR T cell composition, by at least about twenty hours after the administration of the CAR T cell composition, by at least about eighteen hours after the administration of the CAR T cell composition, by at least about sixteen hours after the administration of the CAR T cell composition, by at least about fourteen hours after the administration of the CAR T cell composition, by at least about twelve hours after the administration of the CAR T cell composition, by at least about ten hours after the administration of the CAR T cell composition, by at least about eight hours after the administration of the CAR T cell composition, by at least about six hours after the administration of the CAR T cell composition, by at least about four hours after the administration of the CAR T cell composition, or by at least about two hours after the administration of the CAR T cell composition.

In various additional embodiments of this pre-treatment embodiment, cytokine release resulting in off-target toxicity in the patient does not occur, but CAR T cell toxicity to the cancer occurs or off-target tissue toxicity does not occur in the patient, but CAR T cell toxicity to the cancer occurs, or the cancer comprises a tumor, and tumor size is reduced in the patient, but off-target toxicity does not occur, or reduction in tumor size in the patient is greater than in a patient not pre-treated with the compound, or the pharmaceutically acceptable salt thereof, prior to administration of the CAR T cell composition. As would be understood by a skilled artisan, the "target" can be the cancer (for example a tumor).

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR directed to the targeting moiety, and wherein the small molecule ligand is a PSMA ligand and the targeting moiety is FITC. In this embodiment, the small molecule ligand linked to a targeting moiety by a linker can have the formula

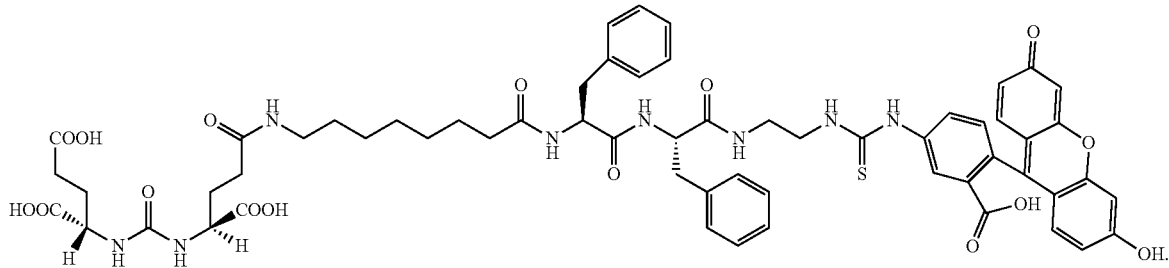 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR directed to the targeting moiety, and wherein the small molecule ligand is a CAIX ligand and the targeting moiety is FITC. In this embodiment, the small molecule ligand linked to a targeting moiety by a linker can have the formula

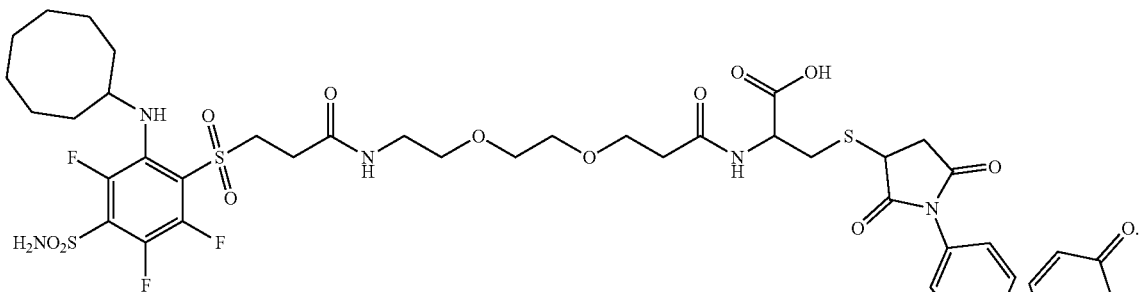

In still another embodiment, a method of treatment of a cancer is provided. The method comprises i) administering to a patient a first compound, or a pharmaceutically acceptable salt thereof, wherein the first compound, or the pharmaceutically acceptable salt thereof, comprises a PSMA ligand linked to FITC by a linker, ii) administering to the patient a second compound, or a pharmaceutically acceptable salt thereof, wherein the second compound, or the pharmaceutically acceptable salt thereof, comprises a CAIX ligand linked to FITC by a linker, and iii) administering to the patient a CAR T cell composition wherein the CAR T cell composition comprises CAR T cells and wherein the CAR T cells comprise a CAR directed to the targeting moiety. In this embodiment, the first compound can have the formula

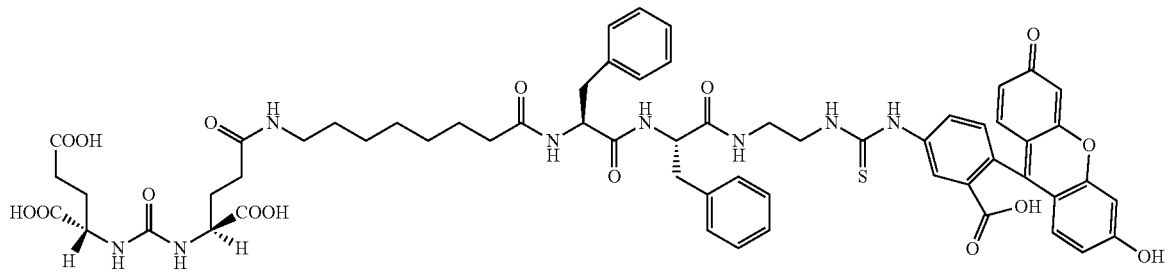 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

and the second compound can have the formula

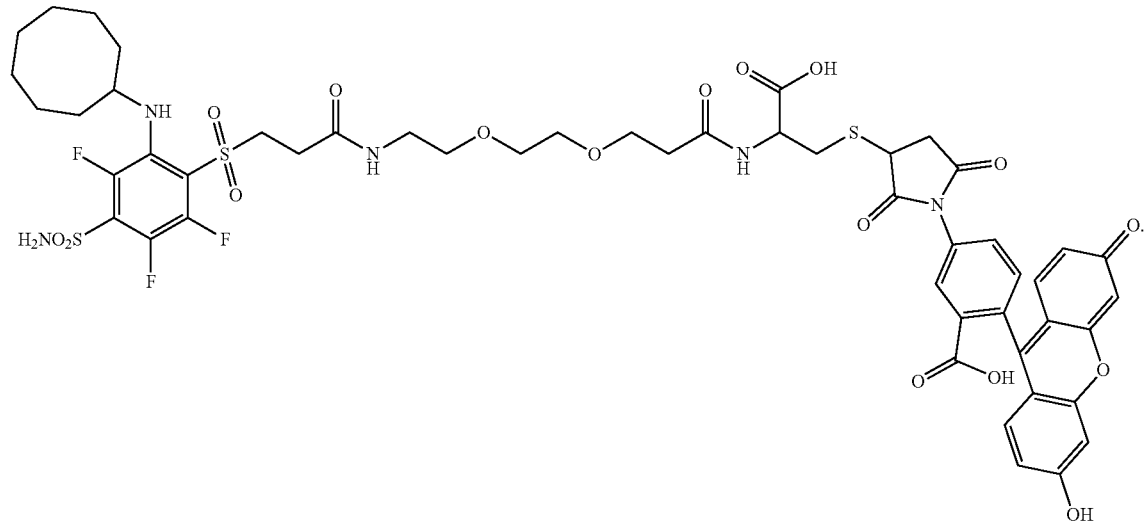 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

In one embodiment of the methods described herein, the cancer is imaged prior to administration to the patient of the compound, or the pharmaceutically acceptable salt thereof, or prior to administration of the CAR T cell composition to the patient. In one illustrative embodiment, imaging occurs by PET imaging. In other illustrative embodiments imaging occurs by MRI imaging or SPECT/CT imaging. The imaging method can be any suitable imaging method known in the art. In one embodiment, the imaging method can involve the use of the small molecule ligand described herein, but linked to an imaging agent suitable for the types of imaging described herein.

In any of the embodiments described herein, cytokine release resulting in off-target toxicity in the patient may not occur even though CAR T cell toxicity to the cancer occurs. In any embodiment described herein, off-target tissue toxicity may not occur in the patient even though CAR T cell toxicity to the cancer occurs. In any embodiment described herein, the cancer may comprise a tumor, and tumor size may be reduced in the patient, even though off-target toxicity does not occur. In any of the embodiments described herein, CRS can be reduced or prevented and the method can result in a decrease in tumor volume in the patient. In any embodiment described herein, body weight loss due to CRS can be reduced or prevented. In any embodiment described herein, the cancer can comprise a tumor and a complete response for the tumor can be obtained.

In another embodiment of the methods described herein, any of the methods described herein can be used alone, or any of the methods described herein can be used in combination with any other method or methods described herein.

EXAMPLES

Example 1

Synthesis of FITC-Folate

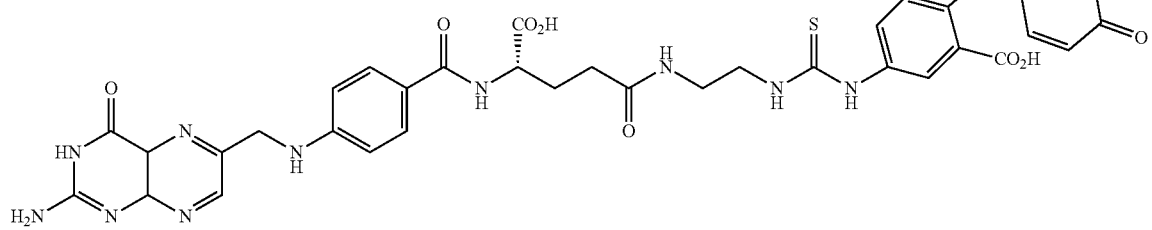

Folate-γ-ethylenediamine was coupled to fluorescein isothiocyanate (FITC) isomer I (Sigma-Aldrich) in anhydrous dimethylsulfoxide (DMF) in the presence of tetramethylguanidine and diisopropylamine. The crude product was loaded onto an Xterra RP18 preparative HPLC column (Waters) and eluted with gradient conditions starting with 99% 5 mM sodium phosphate (mobile phase A, pH 7.4) and 1% acetonitrile (mobile phase B) and reaching 90% A and 10% B in 10 min at a flow rate of 20 mL/min. Under these conditions, the FITC-folate main peak typically eluted at 27-50 min. The quality of the FITC-folate fraction was monitored by analytical reverse-phase HPLC with a UV detector. Fractions with greater than 98.0% purity (LCMS) were lyophilized to obtain the final FITC-folate product. As known in the art, the compound with this structure is also referred to as EC17.

Example 2

Synthesis of FITC-PEG12-Folate

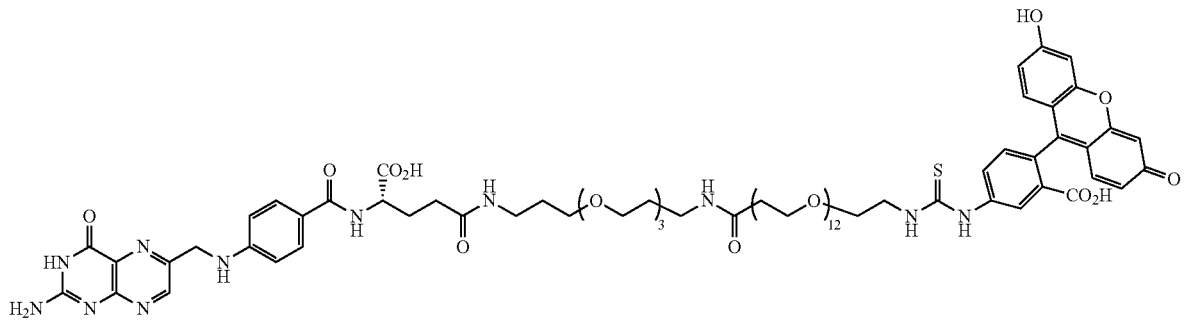

Universal polyethylene glycol (PEG) Nova Tag™ resin (0.2 g) was loaded into a peptide synthesis vessel and washed with isopropyl alcohol (i-PrOH) (3×10 mL) and dimethylformamide (DMF, 3×10 mL). 9-fluorenylmethoxycarbonyl (Fmoc) deprotection was carried out using 20% piperidine in DMF (3×10 mL). Kaiser tests were performed to assess reaction progress. To the vessel was then introduced a solution of Fmoc-L-glutamic acid 5-tert-butyl ester (Fmoc-Glu-(O-t-Bu)—OH) (23.5 mg) in DMF, N,N-diisopropylethylamine (i-Pr$_2$NEt) (4 equiv), and benzotriazol-1-yl-oxytripyrrolidinophosphonium hexafluorophosphate (PyBOP) (2 equiv). Fmoc deprotection was carried out using 20% piperidine in DMF (3×10 mL). To the vessel was then introduced a solution of N10-TFA-Pte-OH (22.5 mg), DMF, i-Pr$_2$NEt (4 equiv), and PyBOP (2 equiv). Argon was bubbled for 2 h, and the resin was washed with DMF (3×3 mL) and i-PrOH (3×3 mL). After swelling the resin in dichloromethane (DCM), a solution of 1M hydroxybenzotriazole (HOBT) in DCM/trifluoroethane (TFE) (1:1) (2×3 mL) was added. Argon was bubbled for 1 h, the solvent was removed, and the resin was washed with DMF (3×3 mL) and i-PrOH (3×3 mL). After swelling the resin in DMF, a solution of Fmoc-NH-(PEG)$_{12}$-COOH (46.3 mg) in DMF, i-Pr$_2$NEt (4 equiv), and PyBOP (2 equiv) was added. Argon was bubbled for 2 h, and the resin was washed with DMF (3×3 mL) and i-PrOH (3×3 mL). Fmoc deprotection was carried out using 20% piperidine in DMF (3×10 mL). Kaiser tests were performed to assess reaction progress. To the vessel was then introduced a solution of FITC (Life Technologies 21.4 mg) in DMF and i-Pr$_2$NEt (4 equiv), then Argon was bubbled for 2 h, and the resin was washed with DMF (3×3 mL) and i-PrOH (3×3 mL). Then to the vessel was added 2% NH$_2$NH$_2$ in DMF (2×2 mL). The final compound was cleaved from the resin using a TFA:H$_2$O:triisopropylsilane (TIS) (95:2.5:2.5) (Cleavage Solution) and concentrated under vacuum. The concentrated product was precipitated in Et$_2$O and dried under vacuum. The crude product was purified using preparative RP-HPLC (mobile phase: A=10 mM ammonium acetate pH=7, B=ACN; method: 0% B to 30% B in 30 min at 13 mL/min). The pure fractions were pooled and freeze-dried, providing the FITC-PEG12-Folate.

Example 3

Synthesis of FITC-PEG20-Folate

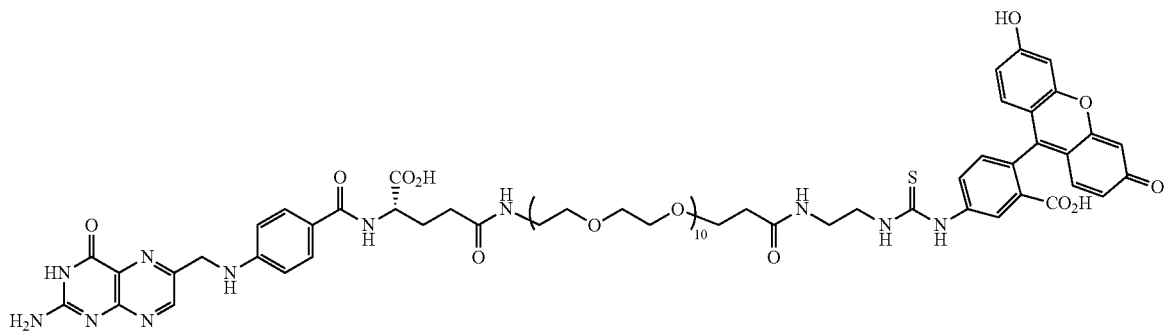

Ethylenediamine, polymer-bound (200-400 mesh)-resin (50 mg) was loaded into a peptide synthesis vessel and swollen with DCM (3 mL). To the vessel was then introduced the Fmoc-PEG$_{20}$-COOH solution (131 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete the reaction with Fmoc-Glu-OtBu (72 mg, 2.0 equiv) and Tfa.Pteroic-acid (41 mg, 1.2 equiv) coupling steps. The resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. The folate-peptide was cleaved from the resin using the Cleavage Solution. 10 mL of the cleavage mixture was introduced and argon was bubbled for 1.5 h. The cleavage mixture was drained into a clean flask. The resin was washed 3 times with more cleavage mixture. The combined mixture was concentrated under reduced pressure to a smaller volume (~5 mL) and precipitated in ethyl ether.

The precipitate was collected by centrifugation, washed with ethyl ether (3 times) and dried under high vacuum. The dried Folate-PEG$_{20}$-EDA (1.0 equiv) was treated with FITC (50 mg, 1.5 equiv) in DMSO and DIPEA at room temperature. Progress of the reaction monitored by LCMS. After 8 h the starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG20-Folate in 60% yield.

Example 4

Synthesis of FITC-PEG108-Folate

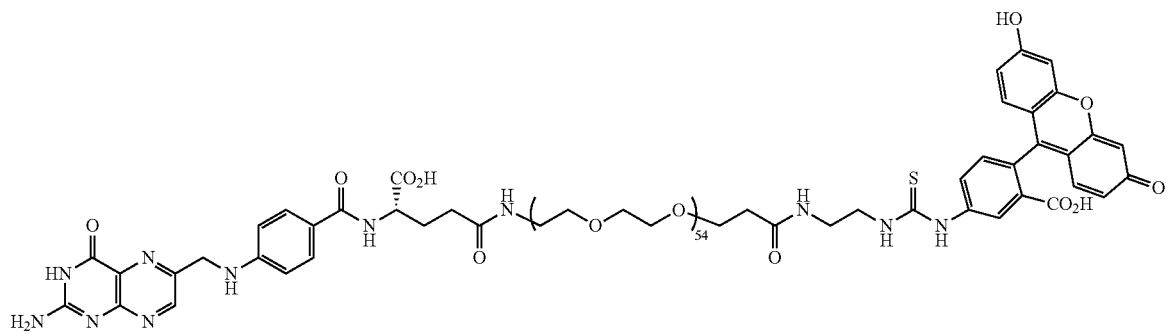

Ethylenediamine, polymer-bound (200-400 mesh)-resin (50 mg) was loaded in a peptide synthesis vessel and swollen with DCM (3 mL) followed by DMF (3 mL). To the vessel was then introduced the Fmoc-PEG$_{36}$-COOH solution (161 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete reaction with 2× Fmoc-PEG$_{36}$-COOH (161 mg, 1.0 equiv), Fmoc-Glu-OtBu (72 mg, 2.0 equiv) and Tfa.Pteroic-acid (41.0 mg, 1.2 equiv) coupling steps. At the end the resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. Folate-peptide was cleaved from the resin using the Cleavage Solution. 10 mL of the cleavage mixture was introduced and argon was bubbled for 1.5 h. The cleavage mixture was drained into a clean flask. The resin was washed 3× with more Cleavage Solution. The combined mixture was concentrated under reduced pressure to a smaller volume (~5 mL) and precipitated in ethyl ether.

The precipitate was collected by centrifugation, washed with ethyl ether (3×) and dried under high vacuum. The dried Folate-PEG$_{108}$-EDA (1.0 equiv) was treated with FITC (50 mg, 1.5 equiv) in DMSO and DIPEA at room temperature. Reaction progress was monitored by LCMS. After 10 h starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG108-Folate in 64% yield.

Example 5

Synthesis of FITC-DUPA

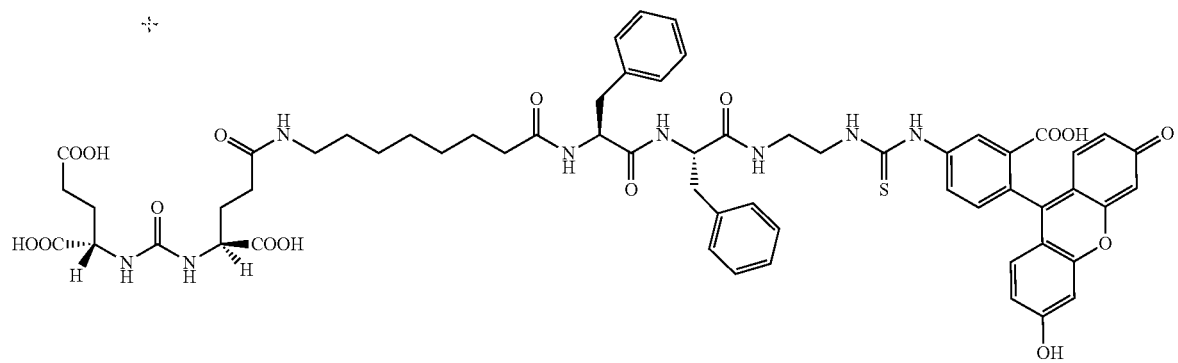 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

DUPA-FITC was synthesized by solid phase methodology as follows. Universal Nova Tag™ resin (50 mg, 0.53 mM) was swollen with DCM (3 mL) followed by DMF 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). After swelling the resin in DMF, a solution of DUPA-(OtBu)—OH (1.5 equiv), HATU (2.5 equiv), and i-Pr$_2$NEt (4.0 equiv) in DMF was added. Argon was bubbled for 2 h, and resin was washed with DMF (3×3 mL) and i-PrOH (3×3 mL). After swelling the resin in DCM, a solution of 1 M HOBt in DCM/TFE (1:1) (2×3 mL) was added. Argon was bubbled for 1 h, the solvent was removed and resin was washed with DMF (3×3 mL) and i-PrOH (3×3 mL). After swelling the resin in DMF, a solution of Fmoc-Phe-OH (2.5 equiv), HATU (2.5 equiv) and DIPEA (4.0 equiv) in DMF was added. Argon was bubbled for 2 h, and the resin was washed with DMF (3×3 mL) and i-PrOH (3×3 mL). The above sequence was repeated for 2 more coupling steps for addition of 8-aminooctanoic acid and fluorescein isothiocyanate or rhodamine B isothiocyanate. The final compound was cleaved from the resin using the Cleavage Solution and concentrated under vacuum. The concentrated product was precipitated in diethyl ether and dried under vacuum. The crude product was purified using preparative RP-HPLC [λ=488 nm; solvent gradient: 1% B to 80% B in 25 min, 80% B wash 30 min run; A=10 mM NH$_4$OAc, pH=7; B=acetonitrile (ACN)]. ACN was removed under vacuum, and purified fractions were freeze-dried to yield FITC-DUPA as a brownish-orange solid. RP-HPLC: tR=8.0 min (A=10 mM NH$_4$OAc, pH=7.0; B=ACN, solvent gradient: 1% B to 50% B in 10 min, 80% B wash 15 min run). $^1$H NMR (DMSO-d6/D$_2$O): δ 0.98-1.27 (ms, 9H); 1.45 (b, 3H); 1.68-1.85 (ms, 11H); 2.03 (m, 8H); 2.6-3.44 (ms, 12H); 3.82 (b, 2H); 4.35 (m, 1H); 6.53 (d, J=8.1 Hz, 2H); 6.61 (dd, J=5.3, 3.5 Hz, 2H); 6.64 (s, 2H); 7.05 (d, J=8.2 Hz, 2H); 7.19 (m, 5H); 7.76 (d, J=8.0 Hz, 1H); 8.38 (s, 1H). HRMS (ESI) (m/z): (M+H)$^+$ calcd for C$_{51}$H$_{59}$N$_7$O$_{15}$S, 1040.3712, found, 1040.3702. UV/vis: λ max=491 nm.

Example 6

Synthesis of FITC-PEG12-DUPA 1,2-Diaminoethane trityl-resin (0.025 g) was loaded into a peptide synthesis vessel and washed with i-PrOH (3×10 mL), followed by DMF (3×10 mL). To the vessel was then introduced a solution of Fmoc-NH-(PEG)$_{12}$-COOH (42.8 mg) in DMF, i-Pr$_2$NEt (2.5 equiv), and PyBOP (2.5 equiv). The resulting solution was bubbled with Ar for 1 h, the coupling solution was drained, and the resin washed with DMF (3×10 mL) and i-PrOH (3×10 mL). Kaiser tests were performed to assess reaction progress. Fmoc deprotection was carried out using 20% piperidine in DMF (3×10 mL). This procedure was repeated to complete the all coupling steps (2×1.5 equiv of Fmoc-Phe-OH and 1.5 equiv of 8-aminooctanoic acid and 1.2 equiv of DUPA were used on each of their respective coupling steps). After the DUPA coupling, the resin was washed with DMF (3×10 mL) and i-PrOH (3×10 mL) and dried under reduced pressure. The peptide was cleaved from the resin in the peptide synthesis vessel using the Cleavage Solution. 15 mL of the Cleavage Solution was added to the peptide synthesis vessel, and the reaction was bubbled under Ar for 15 min. The resin was treated with two additional 10 mL quantities of the Cleavage Solution for 5 min each. The cleavage mixture was concentrated to about 5 mL and precipitated with ethyl ether. The precipitate was collected by centrifugation, washed with ethyl ether (3×), and dried under high vacuum, resulting in the recovery of crude material. To a stirred solution of the crude DUPA-(PEG)$_{12}$-EDA (10 mg) and FITC (5.6 mg) in dimethylsulfoxide (DMSO, 1 mL) was added i-Pr$_2$NEt (5 equiv) at room temperature and stirred for 6 h under argon. The reaction was monitored by LCMS and purified by preparative HPLC (mobile phase: A=10 mM ammonium acetate pH=7, B=ACN; method: 0% B to 50% B in 30 min at 13 mL/min). The purified fractions were pooled and freeze-dried, providing the FITC-PEG12-DUPA.

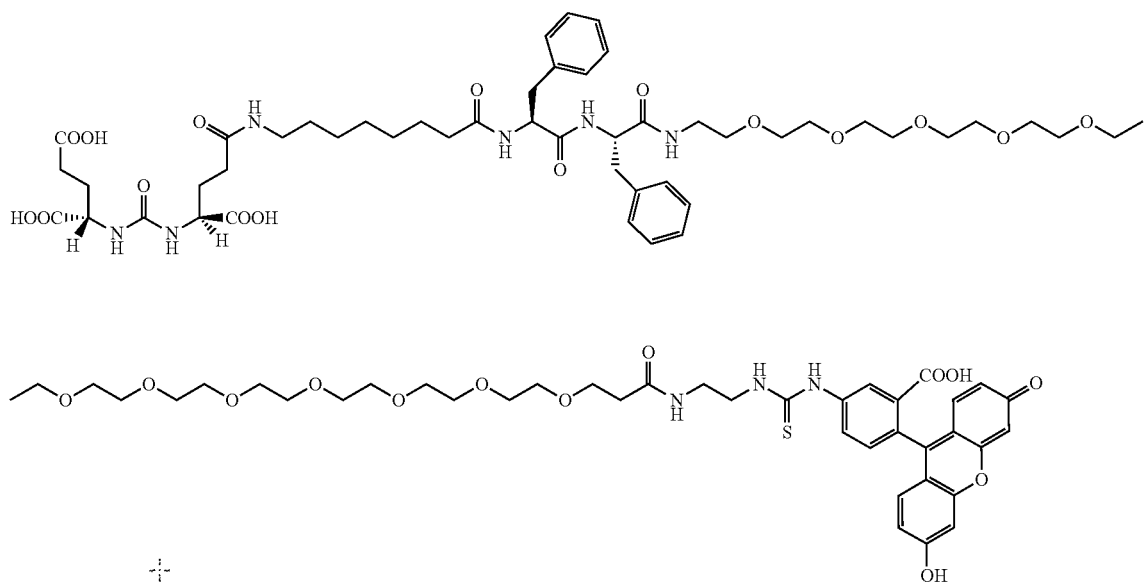

Example 7

Synthesis of FITC-PEG11-NK1

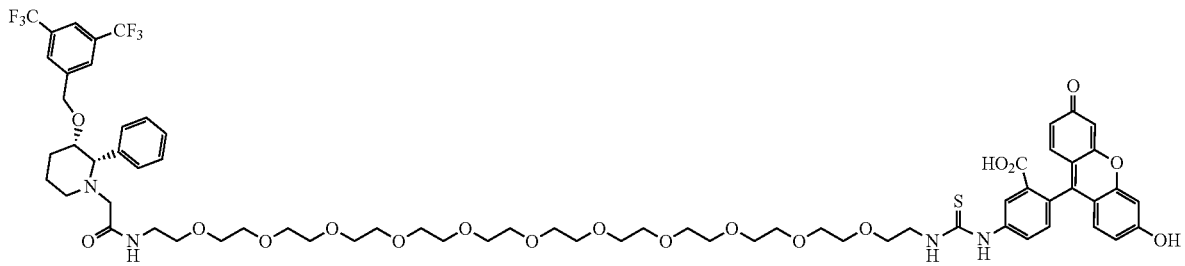 [SMILES: O=C(CN1CCC[C@H](OCc2cc(C(F)(F)F)cc(C(F)(F)F)c2)[C@@H]1c1ccccc1)NCCOCCOCCOCCOCCOCCOCCOCCOCCOCCOCCOCCNC(=S)Nc1ccc(-c2c3ccc(=O)cc-3oc3cc(O)ccc23)c(C(=O)O)c1]

To a stirred solution of NK-1 (0.02 g, 0.0433 mmol, 1.0 eq.), O-(2-Aminoethyl)-O'-[2-(Boc-amino)ethyl]decaethylene glycol (BocNH-PEG$_{11}$-NH$_2$) (Sigma, 0.0336 g, 0.0521 mmol, 1.2 eq.), Benzotriazol-1-yl-oxytripyrrolidinophosphonium hexafluorophosphate (PyBOP) (0.027 g, 0.0521 mmol, 1.2 eq.) in dry CH$_2$Cl$_2$ was added N,N-Diisopropylethylamine (DIPEA) (0.076 mL, 0.4338 mmol, 10 eq.) under argon at room temperature. The reaction progress was monitored by LCMS and purified by preparative RP-HPLC (Waters, XBridge™ Prep C18, 5 µm; 19×100 mm column, mobile phase A=20 mM ammonium acetate buffer, pH 7, B=acetonitrile, gradient 10-100% B in 30 min, 13 mL/min, λ=220 nm, 254 nm). The pure fractions were collected, all organic solvents were evaporated and the sample was lyophilized for 48 h to provide the NK1-PEG$_{11}$-NHBoc. Yield: 40.13 mg (97%). To the NK1-PEG$_{11}$-NHBoc (0.0165 g, 0.015 mmol) in dry DCM was added trifluoroacetic acid (TFA, 20 eq.) and the reaction mixture was stirred for 4 h at r.t. The excess TFA was removed, and the remaining solution was diluted with water and extracted using CH$_2$Cl$_2$ (3×5 mL). The combined organic layers were washed with brine, dried (Na$_2$SO$_4$) and concentrated. The residue obtained was dried under vacuum and used for the next-step without further purification. A stirred solution of NK1-PEG$_{11}$-NH$_2$ (0.008 g, 0.0081 mmol, 1.0 eq.), Fluorescein isothiocyanate (FITC) (Sigma, 0.0037 g, 0.0097 mmol, 1.2 eq.) in dry dimethylsulfoxide (DMSO, 0.3 mL) was added to diisopropylethyl amine (0.0028 mL, 0.0162 mmol, 2.0 eq.) at room temperature under argon. The reaction progress was monitored by LCMS and the product was purified by preparative RP-HPLC (Waters, XBridge™ Prep C18, 5 µm; 19×100 mm column, mobile phase A=20 mM ammonium acetate buffer, pH 7, B=acetonitrile, gradient 10-100% B in 30 min, 13 mL/min, λ=280 nm). The pure fractions were collected, all organic solvents were evaporated and the sample was lyophilized for 48 h to provide the FITC-PEG11-NK1 in a yield of 8.54 mg (77%).

*Note: The NK-1 compound was synthesized by a two-step procedure starting from the base ligand, which was prepared by using a procedure in the literature. (Ref: DESIGN AND DEVELOPMENT OF NEUROKININ-1 RECEPTOR-BINDING AGENT DELIVERY CONJUGATES, Application Number: PCT/US2015/44229; incorporated herein by reference.

Example 8

Synthesis of FITC-PEG2-CA9

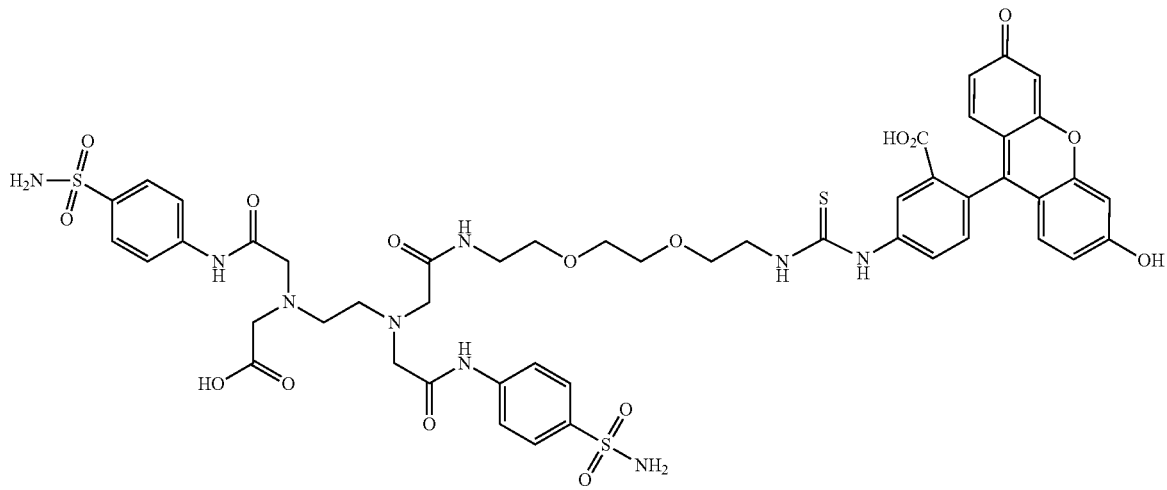 [SMILES: NS(=O)(=O)c1ccc(NC(=O)CN(CCN(CC(=O)NCCOCCOCCNC(=S)Nc2ccc(-c3c4ccc(=O)cc-4oc4cc(O)ccc34)c(C(=O)O)c2)CC(=O)Nc2ccc(S(N)(=O)=O)cc2)CC(=O)O)cc1]

CA9 ligand (53.6 mg) was dissolved in DMF (2-3 mL) in a 50 mL round bottom flask using a Teflon magnetic stir bar. Ambient air was removed using a vacuum and replaced with nitrogen gas, this was done in three cycles. The round bottom flask was kept under constant nitrogen gas. To the flask, 28.9 mg of N-(3-Dimethylaminopropyl)-N'-ethylcarbodiimide hydrochloride (EDC) was added followed by 21.6 mg 1-Hydroxybenzotriazole hydrate (HOBt) and 18.9 µL of Boc-$PEG_2$-$NH_2$ (Sigma Aldrich). 5.4 µL of triethylamine (TEA) was added and the reaction was stirred overnight. The reaction mixture was purified using HPLC and confirmed with UHPLC-MS (target m/z of 831). Acetonitrile was removed using high vacuum rotary evaporation and the product lyopholized. The compound was mixed with 1:1 TFA:DCM for 30 minutes. The TFA/DCM was removed using high vacuum rotary evaporation followed by 30 minutes on high vacuum. The compound was then dissolved in DMF and combined with 5 molar equivalents of i-$Pr_2$NEt, 16 mg of fluorescein isothiocyanate (Life Technologies) and stirred for 1 h. The reaction mixture was purified by HPLC and the target compound was confirmed with UHPLC-MS (target m/z of 1120). The samples were lyophilized and stored at −20 OC.

Example 9

Anti-FITC CAR T Cell Activation can be Controlled by Either Discontinuation of FITC-Ligands Administration or Introduction of Excess Amount of Competitor Small Molecule MDA-MB-231 cells were subcutaneously injected into the shoulders of NSG mice (Jackson Laboratory) to establish solid tumor xenografts. When tumor volume reached around 50-100 $mm^3$, anti-FITC CAR T cells ($15 \times 10^6$ cells) were intravenously introduced into tumor-bearing mice. Twenty NSG mice were divided into four study groups (5 animals in each group). The first group was treated with anti-FITC CAR T cells with phosphate-buffered saline (PBS) as a negative control. The second, third, and fourth groups were treated with anti-FITC CAR T cells with FITC-Folate (500 nmole/kg) every other day. Once a significant toxicity (e.g. serious loss of body weight) was detected, these groups were treated with either: continued FITC-Folate administration (second group); discontinuation of FITC-Folate administration until the mice recovered (third group); or a mixture of 100-fold excess of EC0923 (i.e. free folate) and FITC-Folate until the mice recovered (fourth group). The body weight was measured regularly to monitor toxicity. In addition, the blood concentration of interferon (IFN)-gamma for each treatment group was measured to monitor the degree of anti-FITC CAR T activation. Finally, tumor volume was measured to identify anti-tumor efficacy in each treatment group.

Figure 1B:
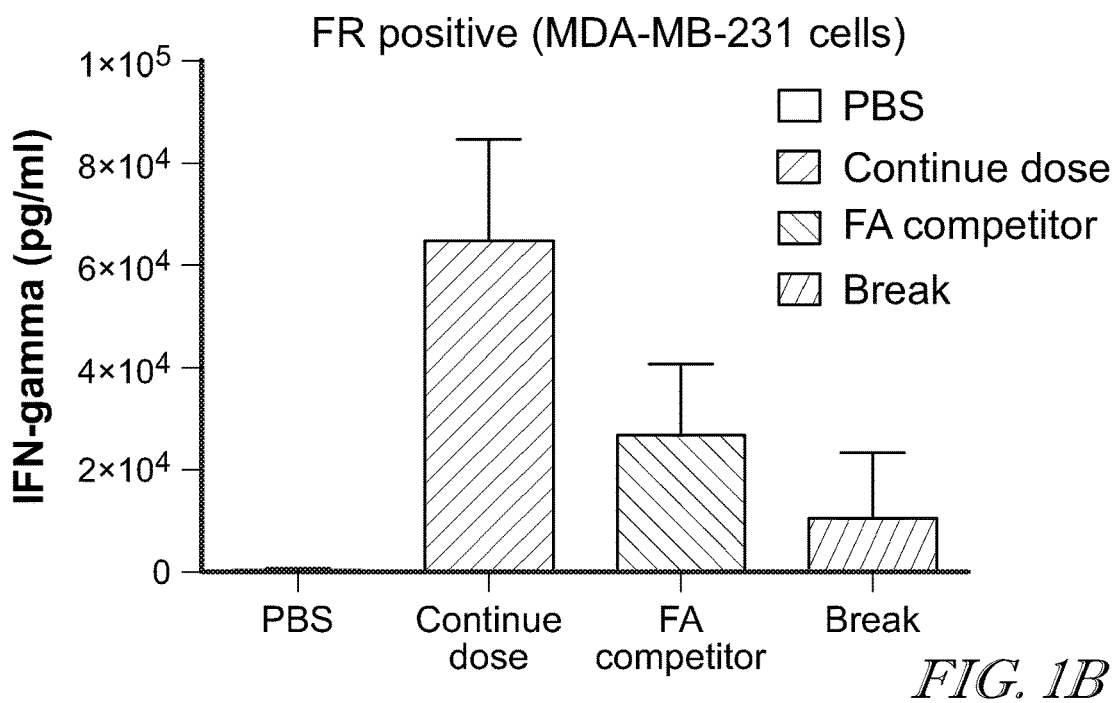

FIG. 1A shows body weight changes in each treatment group. Each treatment group, except the PBS-treated group, showed a decrease in body weight due to anti-FITC CAR T cell mediated toxicity after the second dose of FITC-Folate (Day 1 and Day 2). Since toxicity was detected in each group of mice, treatments to each group were separated as described above into: (1) continued dose of FITC-Folate (continued group); (2) discontinue FITC-Folate injection (break group) at day 4 and day 6; and (3) a mixture of 100-fold excess of free folate and FITC-Folate (competitor group) at day 4 and day 6. As shown in FIG. 1A, groups treated with either discontinued FITC-Folate injection or administration of a mixture of a competitor molecule and FITC-Folate recovered from serious anti-FITC CAR T cell mediated toxicity (i.e. gain of body weight). However, the group that was continuously treated with FITC-Folate at day 4 and day 6, kept losing body weight to reach a lethargic condition (i.e. loss of body weight >20% of original). As shown in FIG. 1B, a significant amount IFN-gamma was detected in the continued dose group. Unlike the continued dose group, the IFN-gamma concentration decreased in both the break and competitor groups. These results indicate that anti-FITC CAR T cell activation can be controlled by methods resulting in alleviation of CAR T cell mediated toxicity. FIG. 1C summarizes the survival of mice in each treatment group at the first week of treatment (%). As toxicity caused by anti-FITC CAR T cell was detected in the continued dose group, only 40% of mice in the continued dose group (i.e. 2 of 5 mice) were able to survive the treatment. However, as shown in FIG. 1C, all of the mice in both the break and competitor groups survived the CAR T cell mediated toxicity due to the reduction of CAR T cell activation.

Figures 2A, 2B:
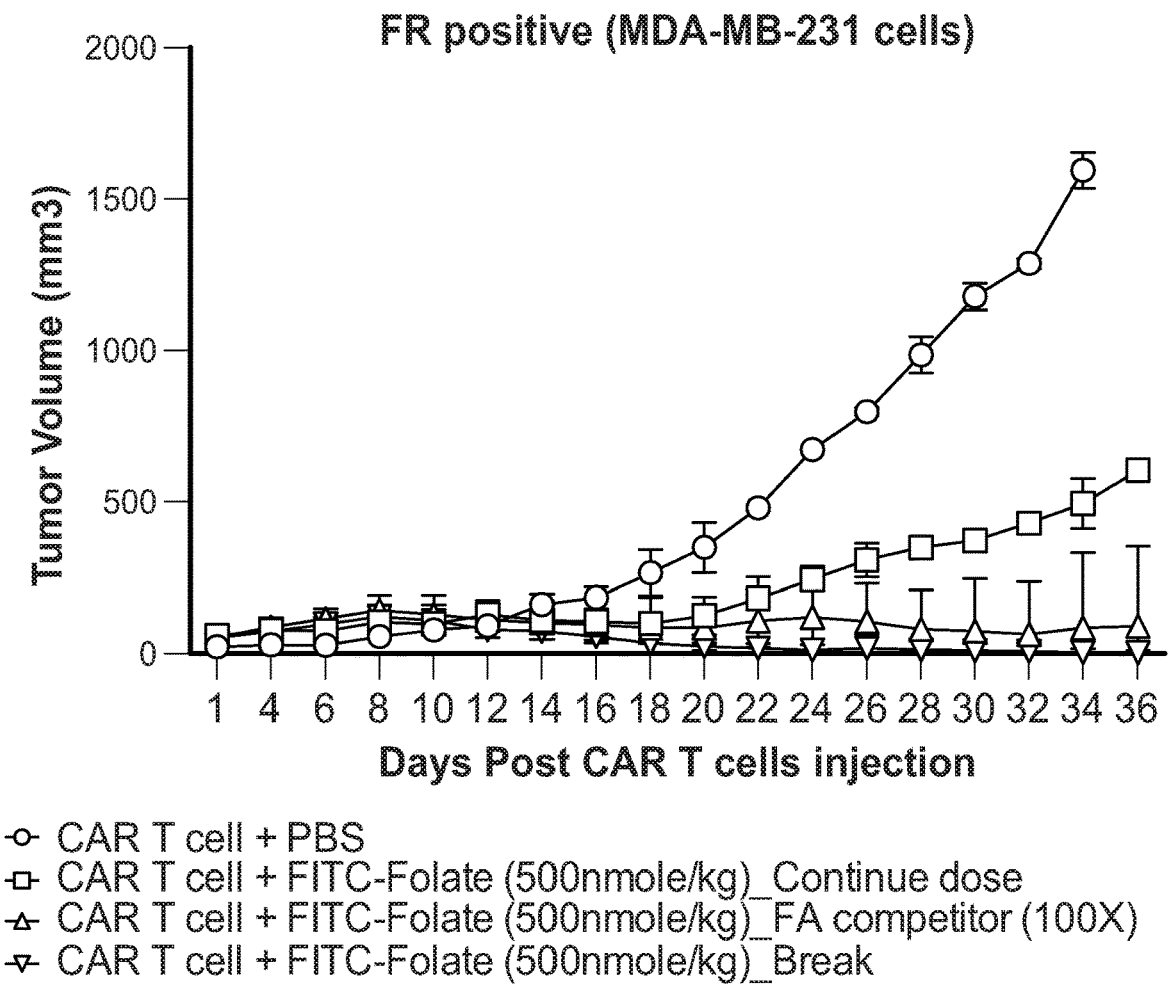
FIGS. 2A-B show the effect of anti-FITC CAR T cell regulation on the tumor response.

Although anti-FITC CAR T cell mediated toxicity can be managed by controlling anti-FITC CAR T cell activation, it was determined whether the regulation of anti-FITC CAR T cell activation causes any reduction in tumor response. Therefore, tumor volume was measured every other day. As shown in FIGS. 2A and 2B, the control group treated with anti-FITC CAR T cells with PBS showed no tumor response, as expected. Interestingly, the break (100% complete response) and competitor groups (75% complete response) showed more potent tumor response compared to the continued dose group (delay of tumor growth). The lack of complete response in the continued dose group may be due to: (1) too frequent dosing with FITC-Folate causing a saturation of both target receptors (i.e. CAR T cells and folate receptors in the cancer cells) resulting in a reduction of anti-FITC CAR T cell activation; (2) anti-FITC CAR T cells may have become hyper-activated due to repeatable engagement of the cancer cells via continuously injected FITC-Folate. This hyper-activation may have caused a significant induction of an inhibitor mechanism as a feedback response preventing activation. In summary, monitoring the toxicity (Example 9) and the tumor response demonstrate that control of anti-FITC CAR T cell activation can be achieved by managing CAR T cell mediated toxicity (e.g. cytokine storm) without a loss of CAR T cell's anti-tumor efficacy.

Example 10

The Effect of Anti-FITC CAR T Cell Regulation on Tumor Response

Five experimental groups: (1) anti-FITC CAR T cell with PBS; (2) anti-FITC CAR T cell with FITC-Folate (5 nmoles/kg); (3) anti-FITC CAR T cell with FITC-Folate (50 nmoles/kg); (4) anti-FITC CAR T cell with FITC-Folate (500 nmoles/kg); (5) anti-FITC CAR T cell with FITC-Folate (2500 nmoles/kg) were designed to identify the relationship between anti-FITC CAR T cell response and the dose of FITC-ligands. MDA-MB-231 cells were subcutaneously injected into the shoulders of NSG mice (Jackson Laboratory) to establish solid tumor xenografts. When tumor volume reached around 50-100 $mm^3$, anti-FITC CAR T cells ($15 \times 10^6$ cells) and different doses of FITC-Folate were intravenously introduced into the mice.

To monitor anti-FITC CAR T cell activation with the different doses of FITC-Folate, IFN-gamma concentration was measured in mouse blood by a bead-based immunoassay (Legendplex kit from Biolegend). Tumor volume was also measured. General toxicity for each treatment group was monitored by measuring weight loss.

Figure 3A:
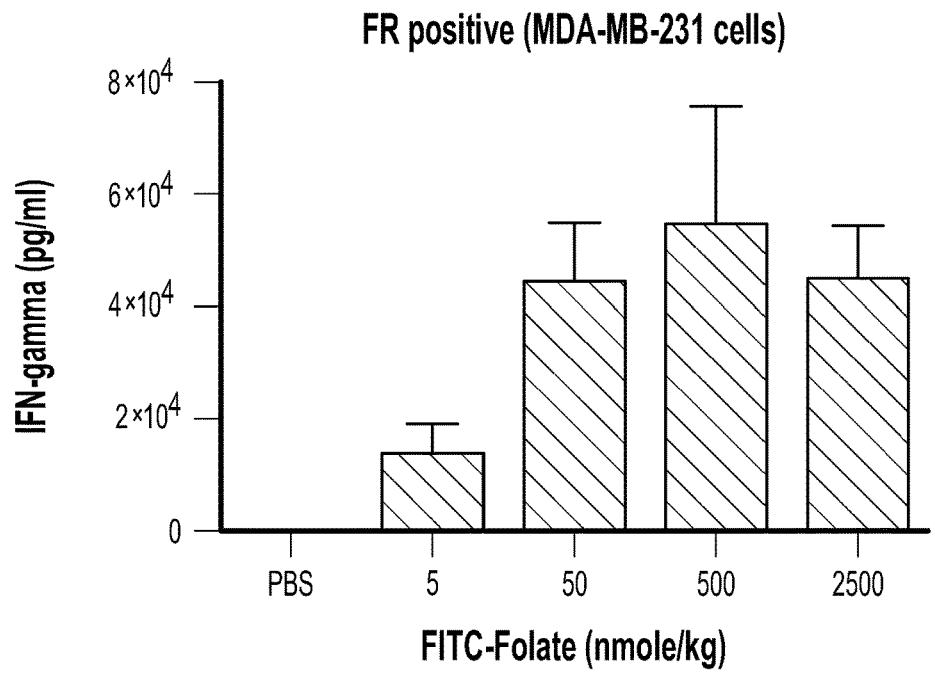
Figure 3B:
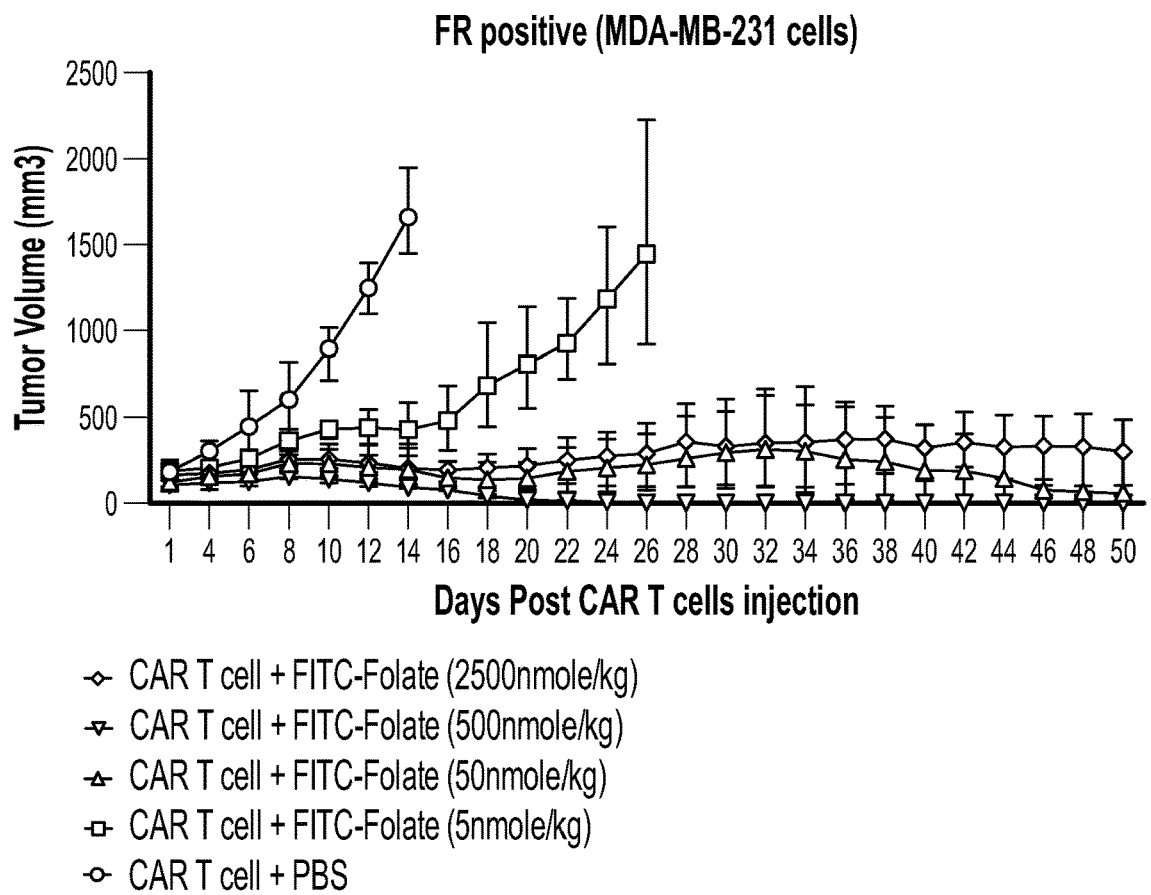

FIGS. 3A-D show that anti-FITC CAR T cell activation is dependent on the concentration of FITC-Folate. The concentrations of INF-gamma in each treatment group showed a bell-shaped dose-response curve (FIG. 3A). Anti-FITC CAR T cell activation was positively correlated with an increase in FITC-Folate dose. However, if the dose of FITC-Folate (2500 nmole/kg) was over 500 nmole/kg, the CAR T cell activation started to decrease. This may be due to the fact that target receptors in both the CAR T cell (e.g. anti-FITC) and the cancer cell (e.g. folate receptor) may be separately saturated at the higher doses of the FITC-ligands. This may decrease the functionality of the FITC-ligands as a bridge between CAR T cells and cancer cells. As shown in FIG. 3B, the bell-shaped dose-response was also confirmed with tumor response. The CAR T cell's anti-tumor efficacy was induced by increasing concentrations of FITC-Folate (from 5 nmoles/kg to 500 nmoles/kg). Similar to the levels of the pro-inflammatory cytokine, anti-tumor efficacy of CAR T cells also started to decrease at higher concentration of FITC-Folate (2500 nmole/kg). As shown in FIG. 3C, the maximum toxicity (i.e. lowest survival rate of mice) was observed in the group treated with 500 nmoles/kg, which also showed the highest anti-tumor efficacy. Moreover, via either a decrease or an increase of the FITC-Folate dose, CAR T cell mediated toxicity was gradually alleviated. Therefore, since anti-FITC CAR T cell activation is dependent on the FITC-ligand dose, management of CAR T cell mediated toxicity can be achieved through altering the FITC-ligand dose.

Example 11

Administration of Drug that can Turn Off Anti-FITC CAR T Cell Activation Signal

To test whether anti-FITC CAR T cell activation can be suppressed by agents that inhibit a mediator of the T cell activation signal, the following agents were selected: (1) dasatinib, which is FDA approved for use in the treatment of adult CML (Dasatinib is known to suppress natural T cell activation through inhibiting LCK activation.), (2) PI3K inhibitor (GDC0980), which is under a phase 2 clinical trial (PI3K is known to play a critical role in activation of T cells), (3) Inducible T cell kinase (ITK, BMS-509744), which is also involved in the T cell activation signal and is in a preclinical stage. To study the efficacy of each agent in suppressing CAR T cell activation, an in vitro CAR T cell functional study (e.g. pro-inflammatory cytokine production assay and evaluation of the degree of CAR T cell activation via surface activation markers) was done in the presence several concentrations of each agent.

CAR T Cell Functional Study 1: Pro-Inflammatory Cytokine (e.g. IFN-Gamma) Production Assay An ELISA assay was performed to quantify the level of IFN-gamma production by anti-FITC CAR T cells in the presence of each agent using a Human IFN-gamma detection ELISA kit from Biolegend. To perform the ELISA assay, each sample was obtained from the co-incubation of anti-FITC CAR T cells, MDA-MB-231 cells, FITC-ligands, and each agent. MDA-MB-231 cells were pre-seeded at a density of $10^4$ cells/100 µl of media in each well of a 96-well plate and grown overnight. The following day, CAR T cells were introduced into each well where the MDA-MB-231 cells were seeded. 100 nM FITC-Folate was introduced to activate the anti-FITC CAR T cell. 0.01 nM to 100 µM of each agent was added to each well and the cells were cultured 24 hours. After co-incubation, the supernatants were harvested and centrifuged to remove cell debris at 1000 g and 4° C. for 10 min. The cleared supernatants from each sample were either used to detect IFN-gamma by ELISA directly or stored at −80 OC. The ELISA assay was performed according to manufacturer's instructions.

CAR T Cell Functional Study 2: Evaluation of Degree of CAR T Cell Activation

To identify the degree of CAR T cell activation in the presence of each agent, the surface of the CAR T cells was stained with an anti-CD69 antibody (CD69 is a T cell activation surface marker). Specifically, CAR T cells were co-incubated with pre-seeded MDA-MB-231 cells in the presence FITC-Folate (100 nM) and each agent (0.01 nM to 100 µM) for 24 hours. After co-incubation, CAR T cells were harvested and stained with an anti-CD69 antibody for 15 min on ice. The CAR T cells were washed 2 times with staining buffer (2% FBS in PBS). After washing, the CAR T cells were analyzed by flow cytometry.

Figure 4A:
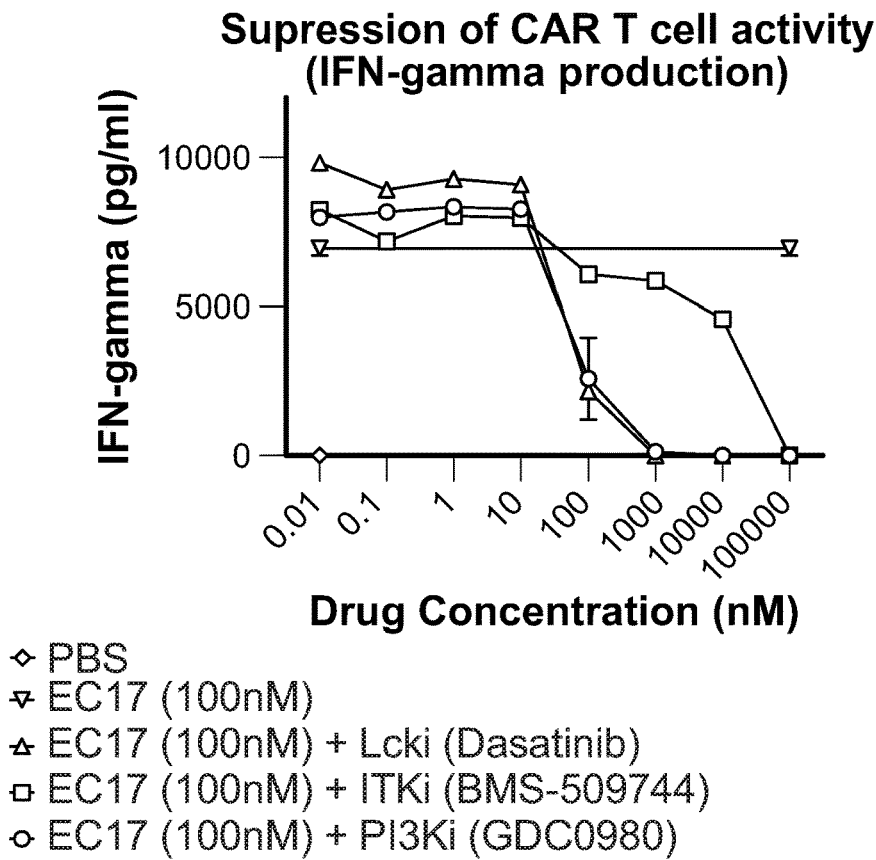
FIGS. 4A-B show suppressing FITC CAR T cell activation with agents that inhibit a mediator of T cell activation signal.
Figure 4B:
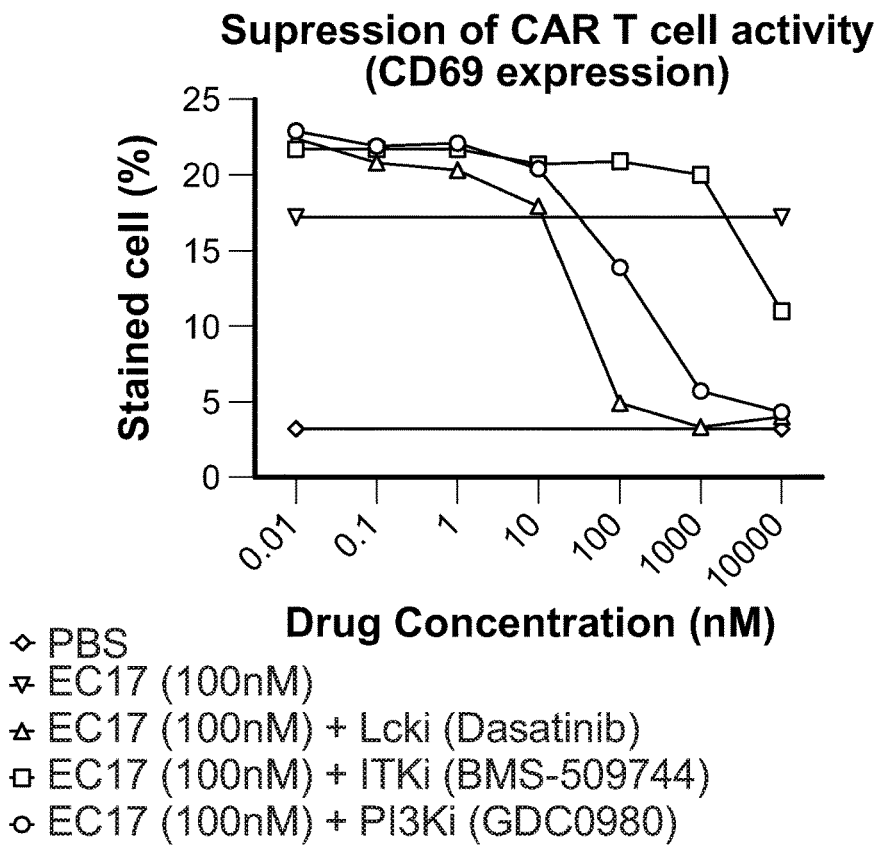

FIGS. 4A-B show that the activation of anti-FITC CAR T cells can be regulated by targeting a key mediator of T cell activation signal. As shown in FIGS. 4A and 4B, dasatinib and GDC0980 showed efficacy in suppressing anti-FITC CAR T cell activation. In the presence of each agent (>10 nM), IFN-gamma production was significantly inhibited and anti-FITC CAR T cells still targeted cancer cells via FITC-Folate (FIG. 4A). Inhibiting CAR T cell activation using each agent was also confirmed by checking a standard T cell activation marker, CD69. As shown in FIG. 4B, activated CAR T cells (CD69 positive cell) were decreased in the presence of each agent at a concentration >10 nM. Although PI3K inhibitor and dasatinib showed similar efficacy in suppressing CAR T cell activation in vitro, dasatinib may be preferred.

Example 12

T Cell Preparation

Human peripheral blood mononuclear cells (PBMCs) were isolated from whole blood of healthy donors by using Ficoll density gradient centrifugation (GE Healthcare Lifesciences). T cells were then isolated from PBMCs by using an EasySep™ Human T Cell Isolation Kit (STEM CELL technologies). T cells were cultured in TexMACS medium (Miltenyi Biotech Inc) with 40-100 IU/mL human IL-2 (Miltenyi Biotech), 2% human AB type serum, and 1% penicillin/streptomycin sulfate. Dynabeads Human T-Activator CD3/CD28 (ThermoFisher Scientific) were added to T cells at 1:1 ratio to activate T cells. 12-24 hours after activation, T cells were transduced with FITC-CAR lentiviral particles in the presence of 8 µg/mL polybrine (Santa Cruz Biotech) by spinfection at 1,200 g for 90 minutes at 22-32° C. T cell mixture containing those with CAR modification (CAR-Ts) and those without CAR modification (non-transformed Ts) was cultured in the presence of activation beads for 6 days before the removal of activation beads. Fluorescence-Activated Cell Sorting was used to sort out CAR-T cells (GFP positive) and non-transformed T cells (GFP negative) based on their GFP expression. The sorted T cells were cultured for 7-15 days before injection into mice. When a T cell mixture was used, CAR-T cells and non-transformed T cells were mixed at the desired ratio before mouse injection. The data shown in FIGS. 6-11 was obtained with T cells prepared with these procedures.

Example 13

Generation of Lentiviral Vector Encoding CAR Gene

An overlap PCR method was used to generate CAR constructs comprising scFv against fluorescein. scFV against fluorescein, 4M5.3 (Kd=270 fM, 762 bp) derived from anti-fluorescein (4-4-20) antibody was synthesized. Sequence encoding the human CD8α signal peptide (SP, 63 bp), the hinge, and transmembrane region (249 bp), the cytoplasmic domain of 4-1BB (CD137, 141 bp) and the CD3ζ chain (336 bp), as shown in FIG. 5, were fused with the anti-fluorescein scFV by overlapping PCR. The resulting CAR construct (1551 bp) was inserted into EcoRI/NotI cleaved lentiviral expression vector pCDH-EF1-MCS-(PGK-GFP) (FIG. 5, System Biosciences). The sequence of the CAR construct in lentiviral vector was confirmed by DNA sequencing. Unless otherwise specified herein, the CAR construct used to generate the data for the Examples, has the nucleic acid sequence of SEQ ID NO:1 and the amino acid sequence of SEQ ID NO:2.

An exemplary CAR nucleic acid coding sequence may comprise:

```
                                          (SEQ ID NO: 1)
ATGGCCTTACCAGTGACCGCCTTGCTCCTGCCGCTGGCCTTGCTGCTCCA

CGCCGCCAGGCCGGATGTCGTGATGACCCAGACCCCCCTCAGCCTCCCAG

TGTCCCTCGGTGACCAGGCTTCTATTAGTTGCAGATCCAGCCAGTCCCTC

GTGCACTCTAACGGTAATACCTACCTGAGATGGTATCTCCAGAAGCCCGG

ACAGAGCCCTAAGGTGCTGATCTACAAAGTCTCCAACCGGGTGTCTGGAG

TCCCTGACCGCTTCTCAGGGAGCGGTTCCGGCACCGACTTCACCCTGAAG

ATCAACCGGGTGGAGGCCGAAGACCTCGGCGTCTATTTCTGCTCTCAGAG

TACACATGTGCCCTGGACCTTCGGCGGAGGGACCAAGCTGGAGATCAAAA

GCTCCGCAGACGATGCCAAGAAAGATGCCGCTAAGAAAGACGATGCTAAG

AAAGACGATGCAAAGAAAGACGGTGGCGTGAAGCTGGATGAAACCGGAGG

AGGTCTCGTCCAGCCAGGAGGAGCCATGAAGCTGAGTTGCGTGACCAGCG

GATTCACCTTTGGGCACTACTGGATGAACTGGGTGCGACAGTCCCCAGAG

AAGGGGCTCGAATGGGTCGCTCAGTTCAGGAACAAACCCTACAATTATGA

GACATACTATTCAGACAGCGTGAAGGGCAGGTTTACTATCAGTAGAGACG

ATTCCAAATCTAGCGTGTACCTGCAGATGAACAATCTCAGGGTCGAAGAT

ACAGGCATCTACTATTGCACAGGGGCATCCTATGGTATGGAGTATCTCGG

TCAGGGGACAAGCGTCACAGTCAGTTTCGTGCCGGTCTTCCTGCCAGCGA

AGCCCACCACGACGCCAGCGCCGCGACCACCAACACCGGCGCCCACCATC

GCGTCGCAGCCCCTGTCCCTGCGCCCAGAGGCGTGCCGGCCAGCGGCGGG

GGGCGCAGTGCACACGAGGGGGCTGGACTTCGCCTGTGATATCTACATCT

GGGCGCCCTTGGCCGGGACTTGTGGGGTCCTTCTCCTGTCACTGGTTATC

```

-continued

```
ACCCTTTACTGCAACCACAGGAACCGTTTCTCTGTTGTTAAACGGGGCAG

AAAGAAACTCCTGTATATATTCAAACAACCATTTATGAGACCAGTACAAA

CTACTCAAGAGGAAGATGGCTGTAGCTGCCGATTTCCAGAAGAAGAAGAA

GGAGGATGTGAACTGAGAGTGAAGTTCAGCAGGAGCGCAGACGCCCCCGC

GTACCAGCAGGGCCAGAACCAGCTCTATAACGAGCTCAATCTAGGACGAA

GAGAGGAGTACGATGTTTTGGACAAGAGACGTGGCCGGGACCCTGAGATG

GGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCG

AGCGCCGGAGGGGCAAGGGGCACGATGGCCTTTACCAGGGTCTCAGTACA

GCCACCAAGGACACCTACGACGCCCTTCACATGCAGGCCCTGCCCCCTCG

CTAA.
```

In the exemplary nucleic acid sequence shown above (SEQ ID NO: 1) the first ATG is the start codon. An exemplary CAR amino acid sequence may comprise:

```
                                          (SEQ ID NO: 2)
MALPVTALLLPLALLLHAARPDVVMTQTPLSLPVSLGDQASISCRSSQSL

VHSNGNTYLRWYLQKPGQSPKVLIYKVSNRVSGVPDRFSGSGSGTDFTLK

INRVEAEDLGVYFCSQSTHVPWTFGGGTKLEIKSSADDAKKDAAKKDDAK

KDDAKKDGGVKLDETGGGLVQPGGAMKLSCVTSGFTFGHYWMNWVRQSPE

KGLEWVAQFRNKPYNYETYYSDSVKGRFTISRDDSKSSVYLQMNNLRVED

TGIYYCTGASYGMEYLGQGTSVTVSFVPVFLPAKPTTTPAPRPPTPAPTI

ASQPLSLRPEACRPAAGGAVHTRGLDFACDIYIWAPLAGTCGVLLLSLVI

TLYCNHRNRFSVVKRGRKKLLYIFKQPFMRPVQTTQEEDGCSCRFPEEEE

GGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR
```

An exemplary insert may comprise:

```
                                          (SEQ ID NO: 3)
GCCACCATGGCCTTACCAGTGACCGCCTTGCTCCTGCCGCTGGCCTTGCT

GCTCCACGCCGCCAGGCCGGATGTCGTGATGACCCAGACCCCCCTCAGCC

TCCCAGTGTCCCTCGGTGACCAGGCTTCTATTAGTTGCAGATCCAGCCAG

TCCCTCGTGCACTCTAACGGTAATACCTACCTGAGATGGTATCTCCAGAA

GCCCGGACAGAGCCCTAAGGTGCTGATCTACAAAGTCTCCAACCGGGTGT

CTGGAGTCCCTGACCGCTTCTCAGGGAGCGGTTCCGGCACCGACTTCACC

CTGAAGATCAACCGGGTGGAGGCCGAAGACCTCGGCGTCTATTTCTGCTC

TCAGAGTACACATGTGCCCTGGACCTTCGGCGGAGGGACCAAGCTGGAGA

TCAAAAGCTCCGCAGACGATGCCAAGAAAGATGCCGCTAAGAAAGACGAT

GCTAAGAAAGACGATGCAAAGAAAGACGGTGGCGTGAAGCTGGATGAAAC

CGGAGGAGGTCTCGTCCAGCCAGGAGGAGCCATGAAGCTGAGTTGCGTGA

CCAGCGGATTCACCTTTGGGCACTACTGGATGAACTGGGTGCGACAGTCC
```

-continued

```
CCAGAGAAGGGGCTCGAATGGGTCGCTCAGTTCAGGAACAAACCCTACAA

TTATGAGACATACTATTCAGACAGCGTGAAGGGCAGGTTTACTATCAGTA

GAGACGATTCCAAATCTAGCGTGTACCTGCAGATGAACAATCTCAGGGTC

GAAGATACAGGCATCTACTATTGCACAGGGGCATCCTATGGTATGGAGTA

TCTCGGTCAGGGGACAAGCGTCACAGTCAGTTTCGTGCCGGTCTTCCTGC

CAGCGAAGCCCACCACGACGCCAGCGCCGCGACCACCAACACCGGCGCCC

ACCATCGCGTCGCAGCCCCTGTCCCTGCGCCCAGAGGCGTGCCGGCCAGC

GGCGGGGGCGCAGTGCACACGAGGGGGCTGGACTTCGCCTGTGATATCT

ACATCTGGGCGCCCTTGGCCGGGACTTGTGGGGTCCTTCTCCTGTCACTG

GTTATCACCCTTTACTGCAACCACAGGAACCGTTTCTCTGTTGTTAAACG

GGGCAGAAAGAAACTCCTGTATATATTCAAACAACCATTTATGAGACCAG

TACAAACTACTCAAGAGGAAGATGGCTGTAGCTGCCGATTTCCAGAAGAA

GAAGAAGGAGGATGTGAACTGAGAGTGAAGTTCAGCAGGAGCGCAGACGC

CCCCGCGTACCAGCAGGGCCAGAACCAGCTCTATAACGAGCTCAATCTAG

GACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAA

TGAACTGCAGAAAGATAAGATGGCGGAGGCCTACAGTGAGATTGGGATGA

AAGGCGAGCGCCGGAGGGGCAAGGGGCACGATGGCCTTTACCAGGGTCTC

AGTACAGCCACCAAGGACACCTACGACGCCCTTCACATGCAGGCCCTGCC

CCCTCGCTAA
```

In the exemplary insert described above (SEQ ID NO:3), the first GCCACC sequence may comprise a restriction enzyme cleavage site, followed by the ATG start codon. The encoded amino acid sequence may comprise:

(SEQ ID NO: 2)
```
MALPVTALLLPLALLLHAARPDVVMTQTPLSLPVSLGDQASISCRSSQSL

VHSNGNTYLRWYLQKPGQSPKVLIYKVSNRVSGVPDRFSGSGSGTDFTLK

INRVEAEDLGVYFCSQSTHVPWTFGGGTKLEIKSSADDAKKDAAKKDDAK

KDDAKKDGGVKLDETGGGLVQPGGAMKLSCVTSGFTFGHYWMNWVRQSPE

KGLEWVAQFRNKPYNYETYYSDSVKGRFTISRDDSKSSVYLQMNNLRVED

TGIYYCTGASYGMEYLGQGTSVTVSFVPVFLPAKPTTTPAPRPPTPAPTI

ASQPLSLRPEACRPAAGGAVHTRGLDFACDIYIWAPLAGTCGVLLLSLVI

TLYCNHRNRFSVVKRGRKKLLYIFKQPFMRPVQTTQEEDGCSCRFPEEEE

GGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR
```

Example 14

Production of Lentivirus Containing CAR Gene for Human T Cell Transduction

To prepare lentiviral virus containing an anti-fluorescein (i.e., anti-FITC) single chain fragment variable (scFv) CAR, a HEK-293TN packaging cell line was co-transfected with the lentiviral vector encoding anti-fluorescein scFv CAR and a 2nd generation of a lentiviral packaging plasmid mix (Cellecta) or ViraPower Lentivrial Packaging Mix (ThermoFisher). After 24 and 48 hours of transfection, supernatants containing the lentivirus with the CAR gene were harvested and virus particles were concentrated by the standard polyethylene glycol virus concentration method (Clontech) for future transduction with human T cells.

Example 15

Isolation of Human T Cells from Human PBMC

T cells were isolated from human peripheral blood mononuclear cells (PBMC) by Ficoll density gradient centrifugation (GE Healthcare Lifesciences). After washing away remaining Ficoll solution, T cells were isolated by using an EasySep™ Human T Cell Isolation Kit (STEM CELL technologies). Purified T cells were cultured in TexMACS™ medium (Miltenyi Biotech Inc) with 1% penicillin and streptomycin sulfate in the presence of human IL-2 (100 IU/mL, Miltenyi Biotech Inc). T cells were cultured at density of $1\times10^6$ cells/mL in multi-well plates. T cells were split and re-feed every 2-3 days.

Example 16

Transduction of Human T Cells

Isolated T cells were activated with Dynabeads coupled with anti-CD3/CD28 antibodies (Life Technologies) for 12-24 hours in the presence of human IL-2 (100 IU/mL), then transduced with lentivirus encoding an anti-fluorescein CAR gene. Cells were harvested after 72 hours and the expression of CAR on transduced T cells was identified by measuring GFP fluorescent cells using flow cytometry.

Example 17

Test Anti-Tumor Efficacy of CAR T Cells In Vivo

Immunodeficient NSG mice (Jackson Laboratory) were used to identify the efficacy of CAR T cell anti-tumor activity in vivo. A folate receptor expressing MDA-MB-231 cancer cell line was subcutaneously injected into the back of NSG mice to establish solid tumor xenografts. When tumor volume of around 100-300 mm³ was reached, a desired concentration of EC17 (as shown in the figure legends) was introduced 4 hours before the administration of a desired number of CAR T cell (as shown in the figure legends) into the mice bearing tumors. After initial administration of EC17 and CAR T cells, desired concentrations of EC17 (as shown in the figure legends) were also introduced (i.v.) three times per week. Control mice were administered T cells without CAR modification. Other control mice were administrated CAR-Ts, but PBS was dosed instead of EC17. Anti-tumor efficacy was monitored by tumor volume. General toxicity of the therapy was monitored by weight loss, gross animal morphology and behavior.

Figure 6A:
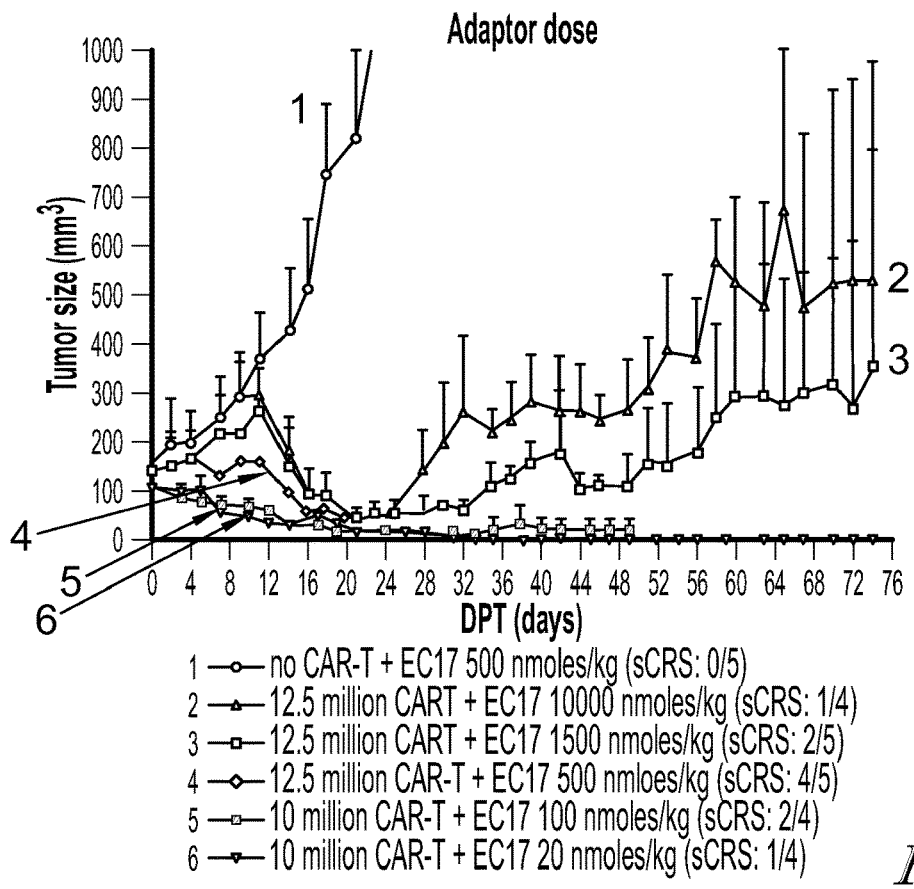
FIGS. 6A-D show anti-tumor efficacy and toxicity at different EC17 doses and numbers of CART cells.
Figure 6B:
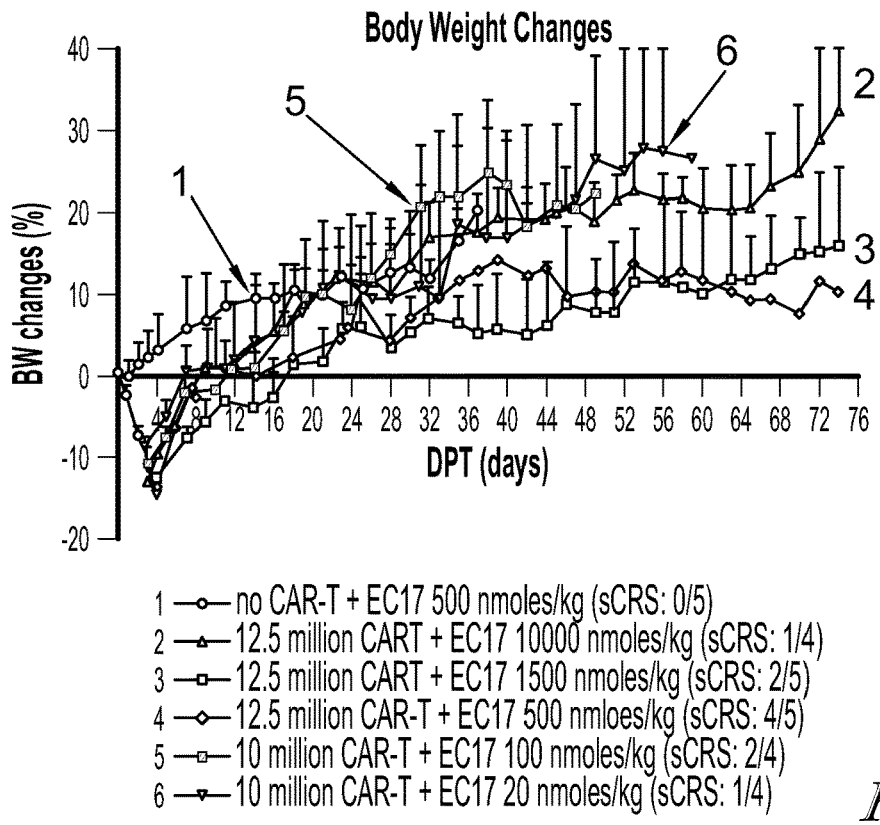
Figure 6C:
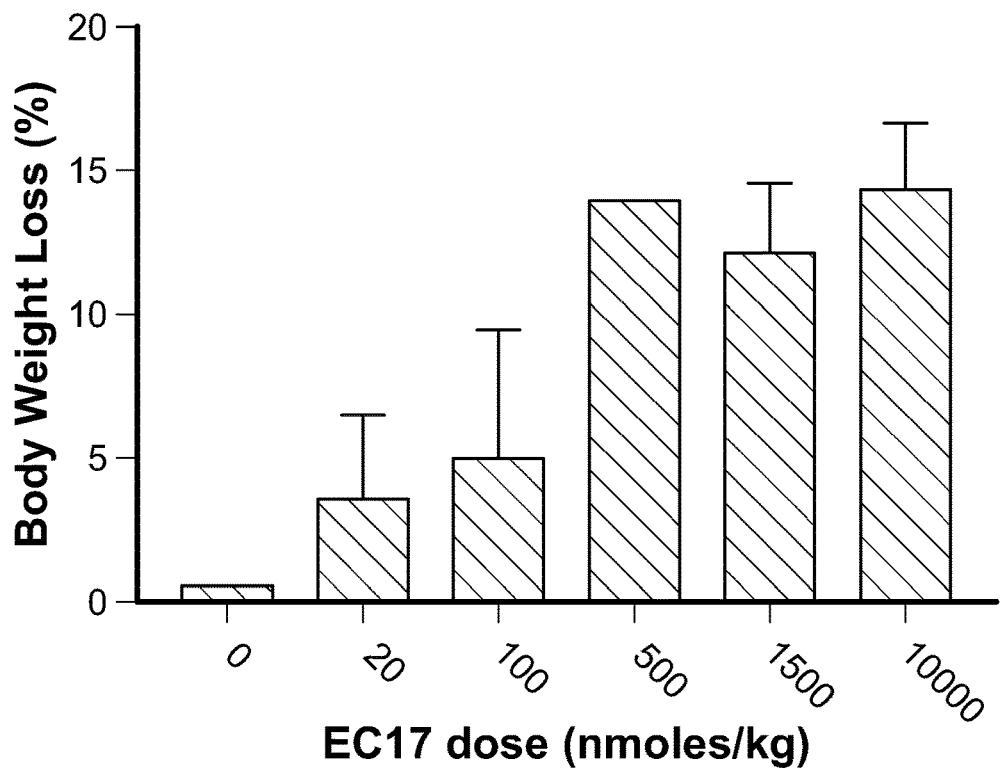
Figure 6D:
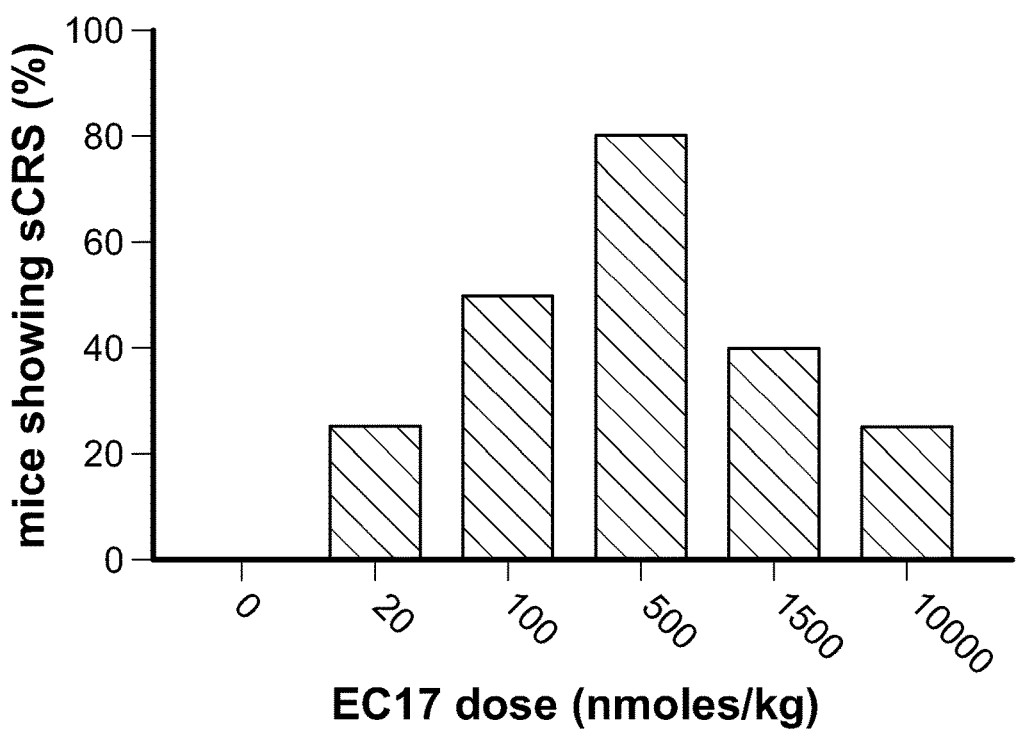

Adjusting the bridge dose can reduce cytokine release and toxicity while maintaining the anti-tumor effect. As shown in the legends of FIGS. 6A-D, either T cells or CAR T cells were administered to mice along with 0, 20 nmoles/kg, 100 nmoles/kg, 500 nmoles/kg, 1500 nmoles/kg, or 10000 nmoles/kg of EC17. Tumor volume (FIG. 6A) and body weight changes (FIG. 6B) were measured over 74 days. The maximal percentage body weight loss for each EC17 dose is shown in FIG. 6C. The number of mice exhibiting severe cytokine release syndrome and the number of total mice in each group are shown in parentheses. The percentage of mice showing sCRS for each EC17 dose is shown in FIG. 6D. Compared to mice in a cohort with a higher EC17 dose (500 nmoles/kg), mice in a cohort with 20 and 100 nmoles/kg EC17 doses had a lower percentage of sCRS and less body weight loss, while they all reached complete cures. With over-saturated bridge EC17 doses (1500 and 10000 nmoles/kg), less mice showed sCRS but less mice reached cures.

Figure 8A:
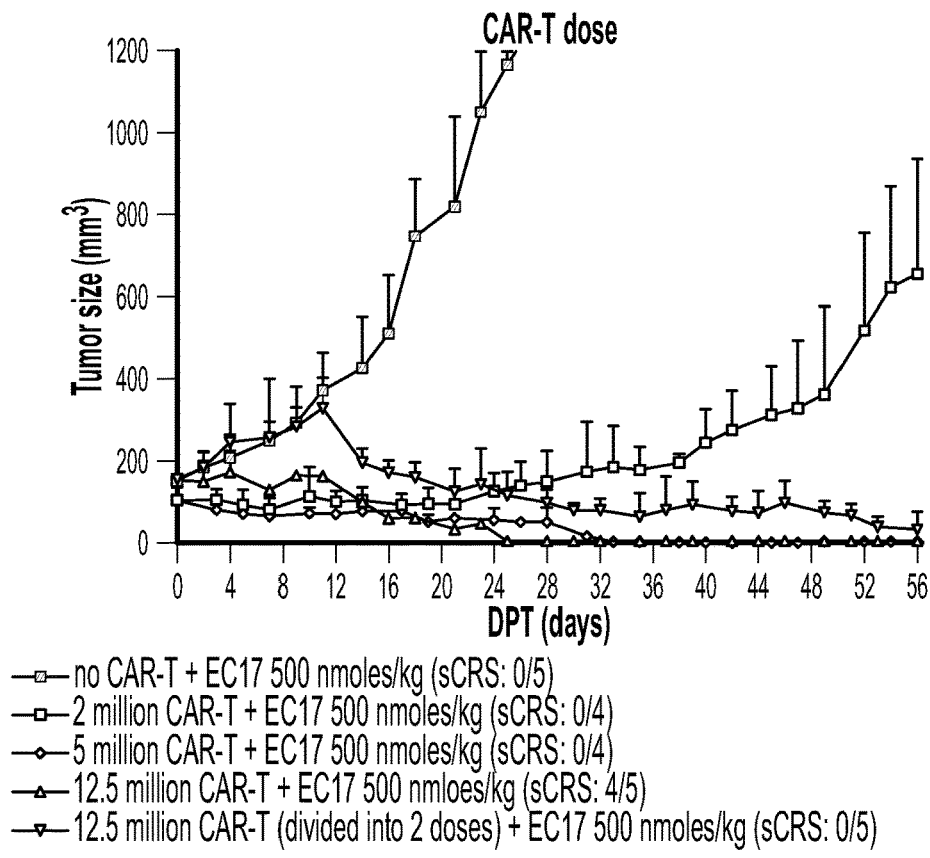
FIGS. 8A-D show anti-tumor efficacy and toxicity of different CAR T doses.
Figure 8B:
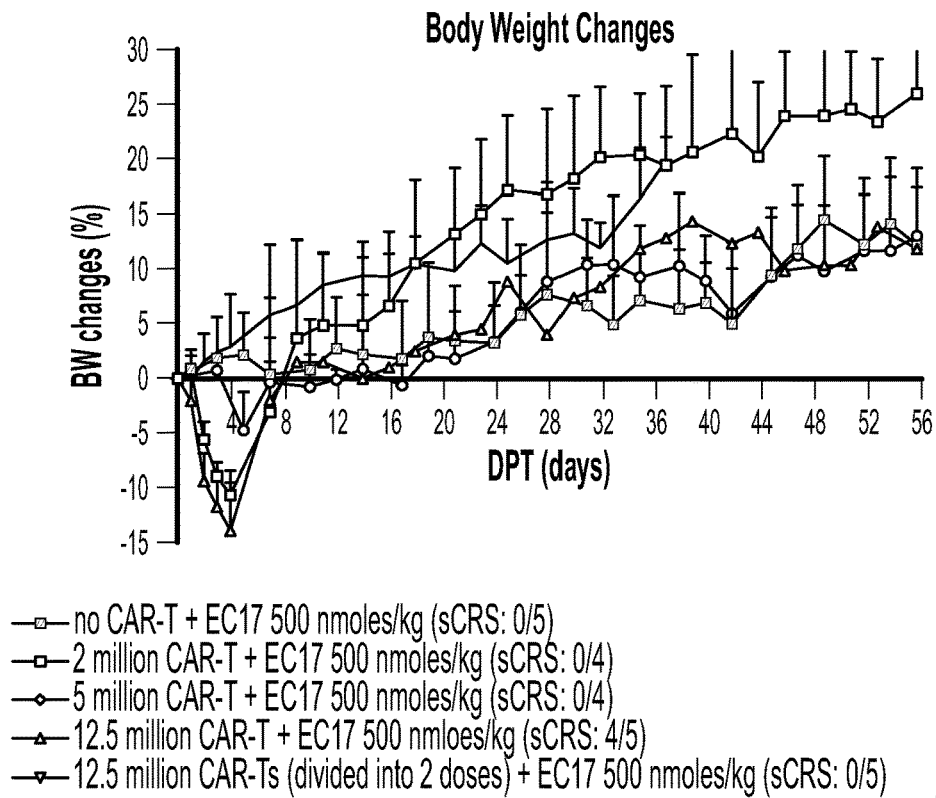
Figure 8C:
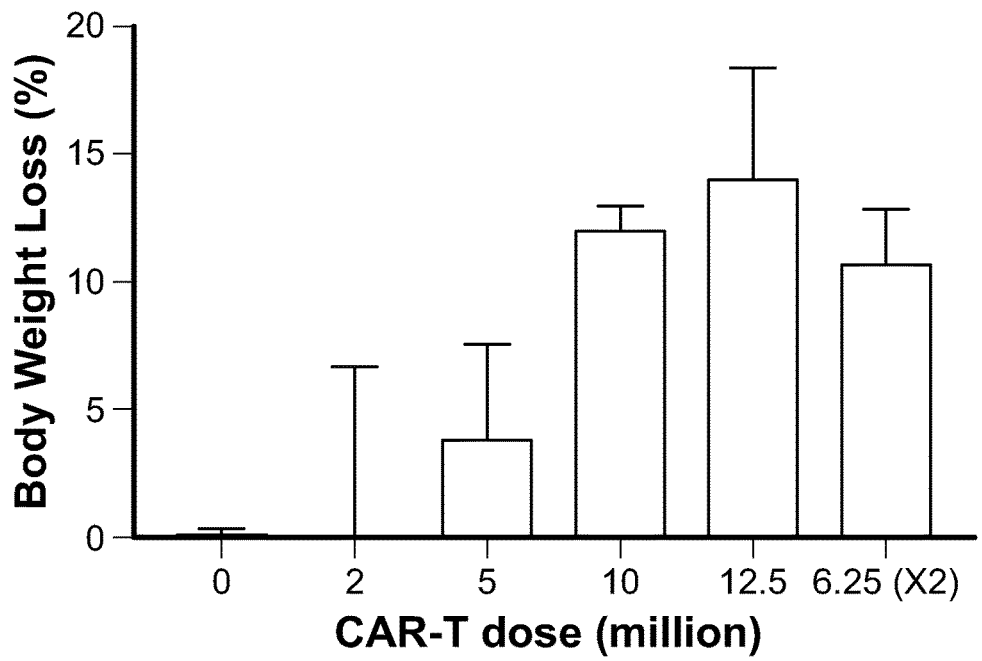
Figure 8D:
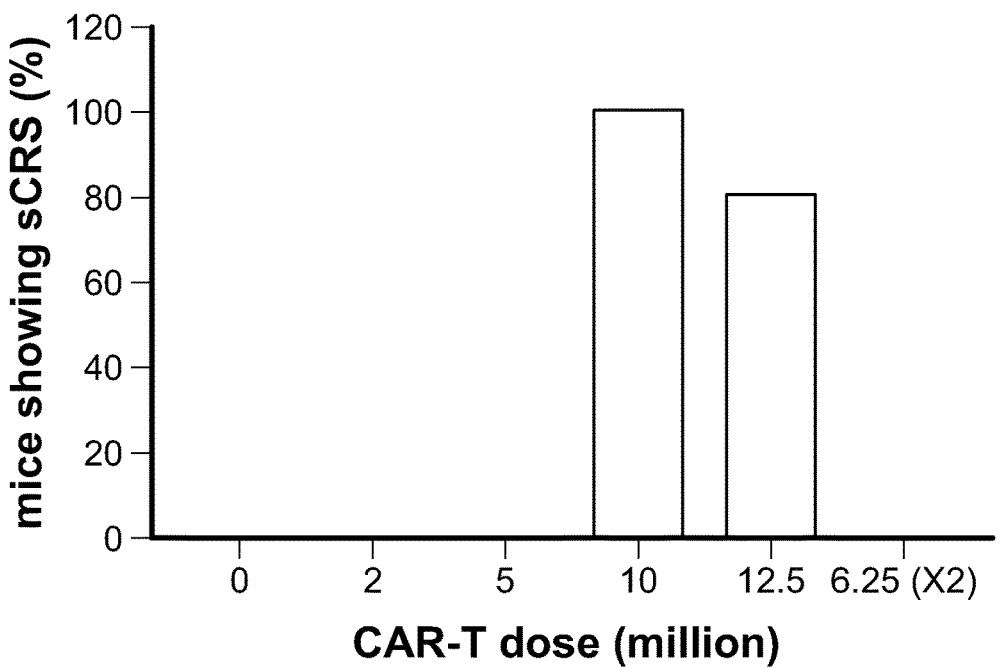

Reducing the CAR-T dose or dividing the CAR-T dose into 2 doses can avoid severe cytokine release syndrome while maintaining anti-tumor efficacy. The EC17 dose was fixed at 500 nmoles/kg. As shown in the legends of FIGS. 8A-D different CAR T doses were introduced into the mice. Tumor volume (FIG. 8A) and body weight (FIG. 8B) were measured over 56 days. The number of mice exhibiting severe cytokine release syndrome and the number of total mice in each group are shown in parentheses. The maximal percentage body weight loss for each CAR T dose is shown in FIG. 8C. The percentage of mice showing sCRS for each CAR T dose is shown in FIG. 8D.

Figure 9A:
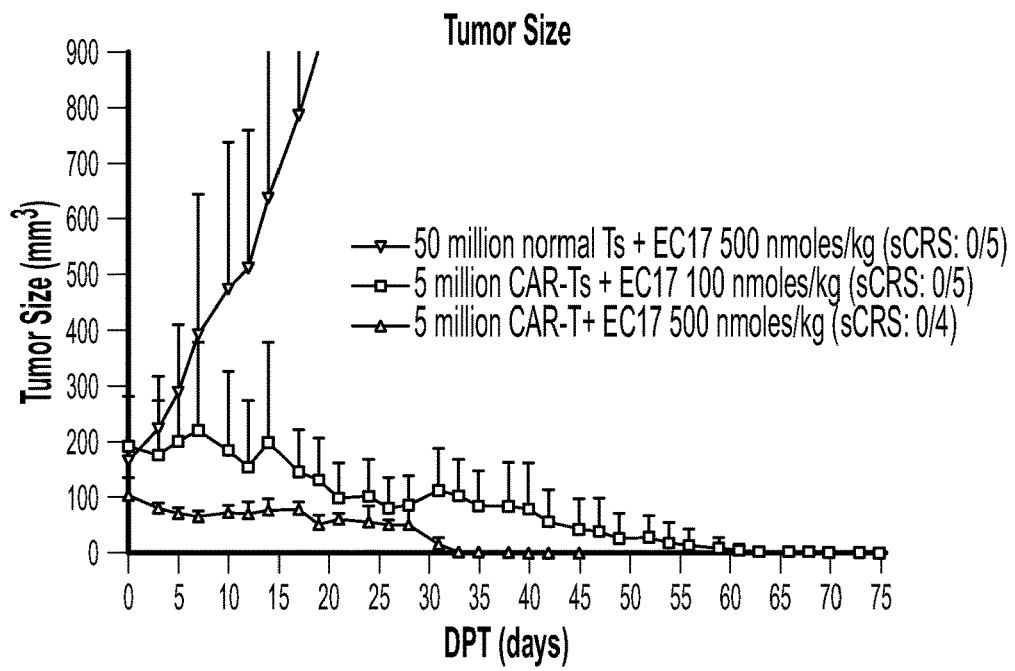
FIGS. 9A-B show anti-tumor efficacy and body weight change for different EC17 doses.
Figure 9B:
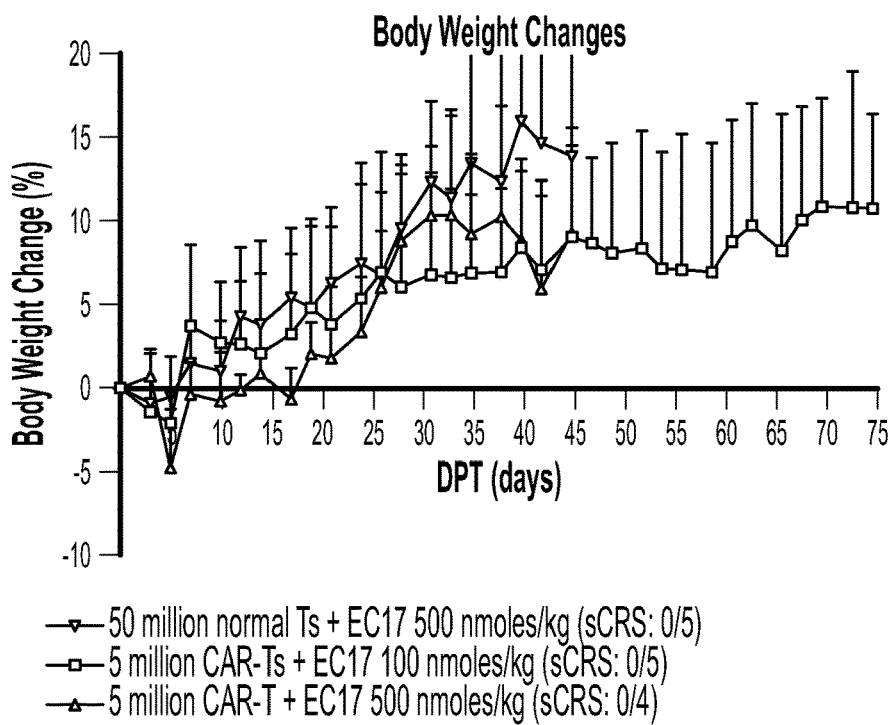

Adjusting the CAR T cell dose and the EC17 dose can affect tumor size. Either T cells or CAR T cells were administered to mice along with 100 nmoles/kg or 500 nmoles/kg of EC17. As shown in the legends of FIGS. 9A-B, control or CAR T cells were administered with different concentrations of EC17. Tumor volume (FIG. 9A) and body weight (FIG. 9B) were measured for 75 days. The number of mice exhibiting severe cytokine release syndrome and the number of total mice in each group are shown in parentheses. With optimized EC17 amount and CAR T numbers, mice only had 2% body weight loss while reaching complete cures.

Figure 10A:
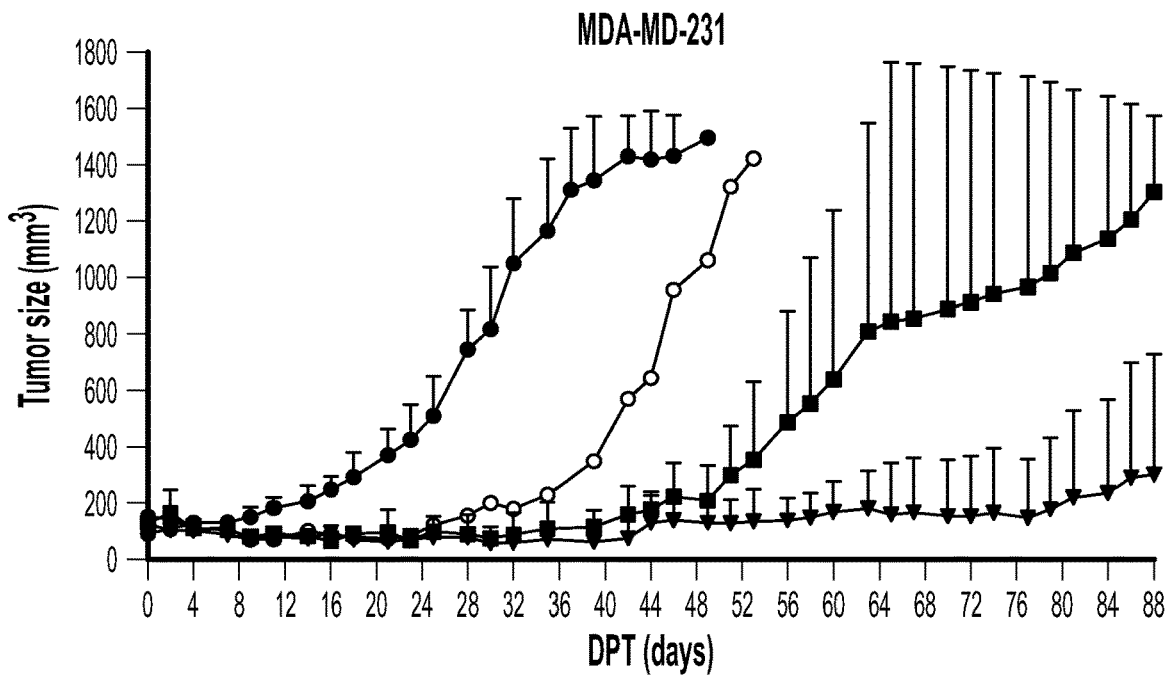
FIGS. 10A-C show anti-tumor efficacy of different CAR T cell and non-transformed T cell mixtures.
Figure 10B:
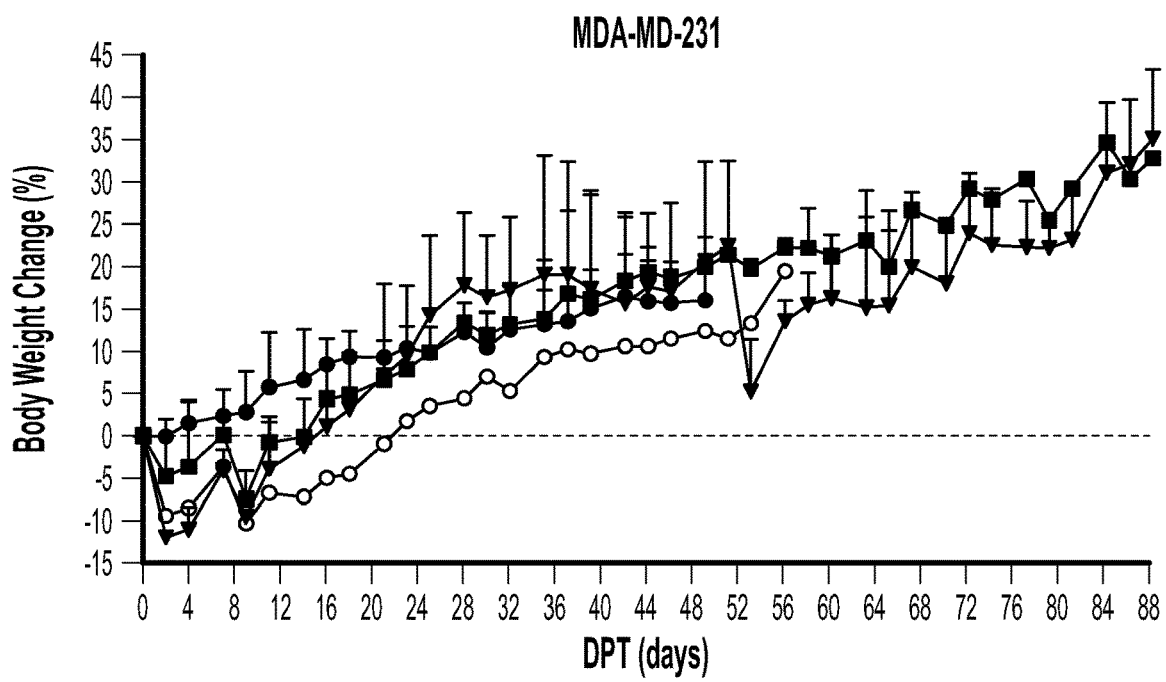
Figure 10C:
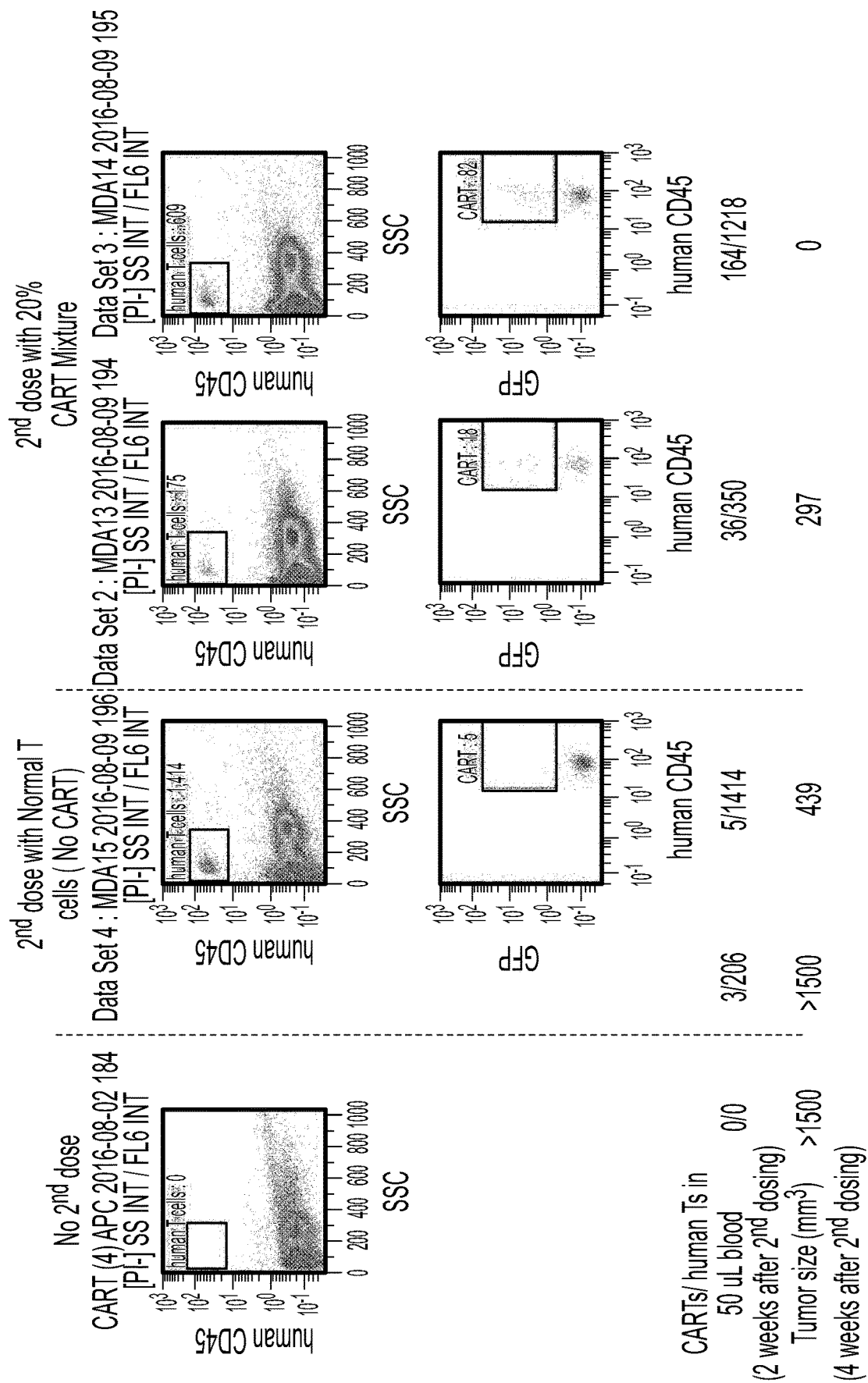

The presence of CAR T cells in a second dose of T cells can affect tumor size. As shown in the legends of FIGS. 10A-C, no second dose of T cells, a second dose with 20 million non-transformed T cells, or a second dose with a mixture of non-transformed T cells and CAR T cells was administered to the mice. Tumor volume (FIG. 10A) and body weight (FIG. 10B) were measured over time. The measured amounts of CAR T cells/normal T cells in 50 yl of the patient's blood 2 weeks after injection of the CAR T cell mixture are shown in FIG. 10C for one mouse for the treatment with no second dose of T cells, and for two mice each for the treatment groups of a second dose with 20 million non-transformed T cells, or a second dose with a mixture of non-transformed T cells and CAR T cells. FIG. 10C also shows corresponding flow cytometry plots of the measured amounts of normal T cells and CAR T cells, and corresponding tumor volumes 4 weeks after injection of the CAR T cell mixture.

Figure 11A:
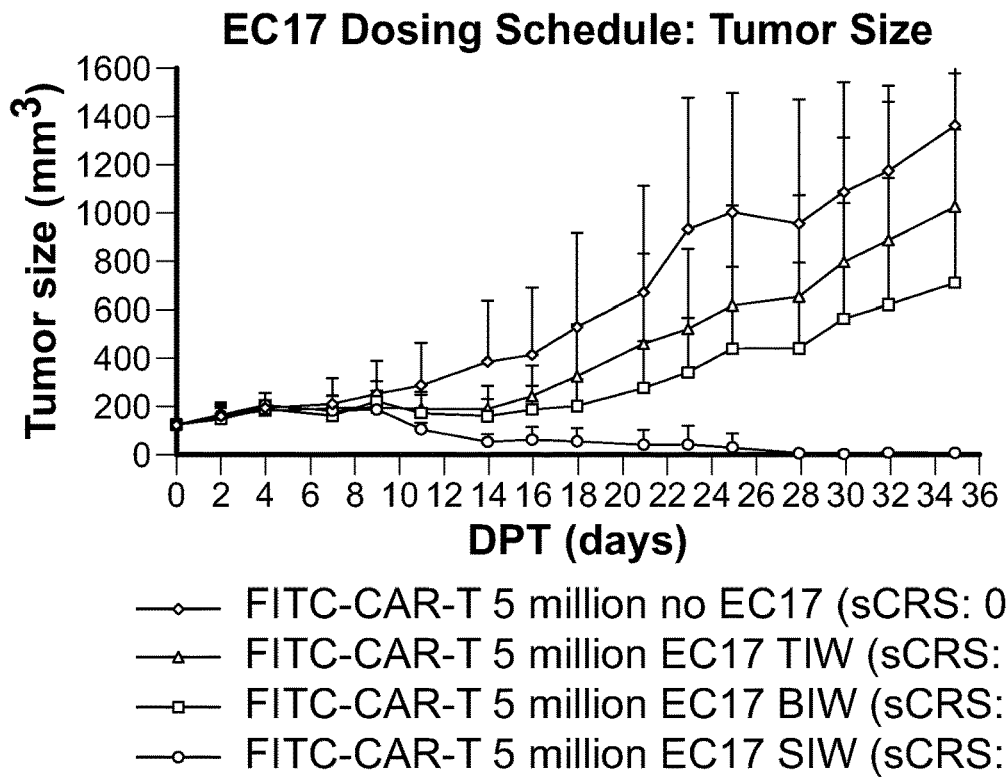
FIGS. 11A-B show anti-tumor efficacy and toxicity of 5 million CAR T cells and different EC17 dosing schedules.
Figure 11B:
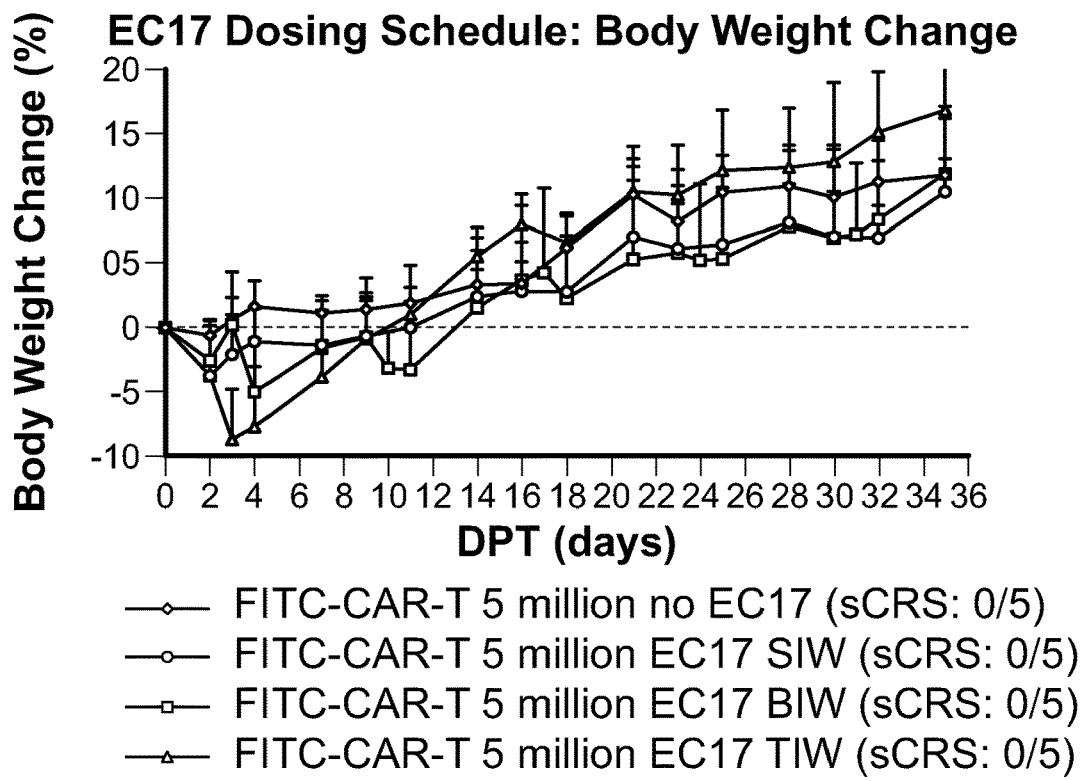

Adjusting the EC17 dose schedule can lower toxicity and can affect tumor size. As shown in the legends of FIGS. 11A-B, CAR T cells and EC17 were administered to mice using different dosing schedules. Tumor volume (FIG. 11A) and body weight (FIG. 11B) were measured over time. The number of mice exhibiting severe cytokine release syndrome and the number of total mice in each group are shown in parentheses. Adjusting bridge dosing frequency (from three times per week (TIW) to once per week (SIW)) can reduce the toxicity and achieve better anti-tumor potency.

Example 18

Test Rescue Ability of EC0923 During CAR T Cell Treatment In Vivo

Figure 7:
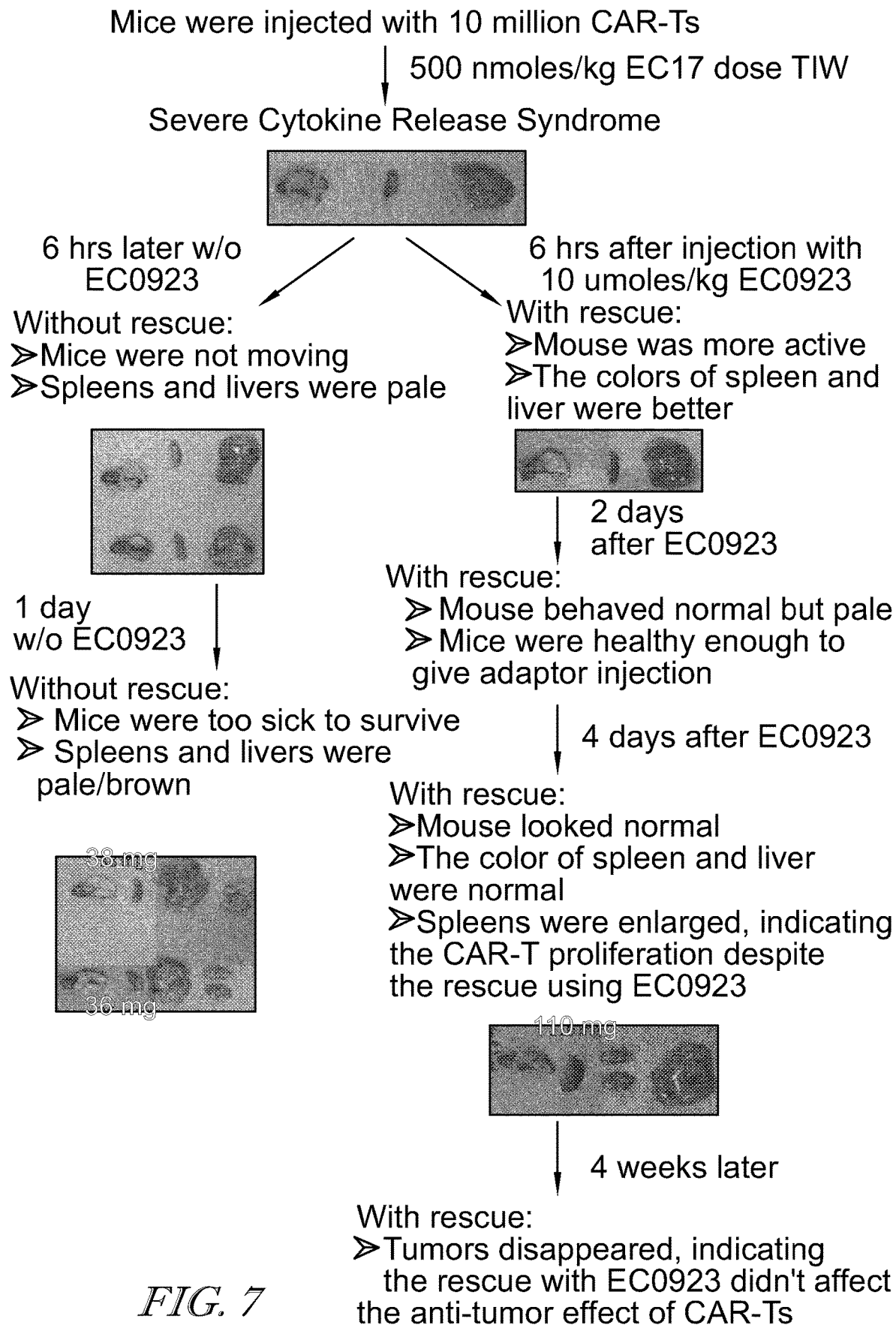
FIG. 7 shows the rescue with EC0923 of mice having sCRS and observed responses of mice treated with or without EC0923, and harvested organs from mice treated with or without EC0923.

CAR T cells were introduced into mice bearing tumors and EC17 was also introduced (i.v.) three times per week. When severe cytokine release syndrome was observed, one dose of EC0923 at 10 μmoles/kg was introduced to rescue mice. Mice were monitored for 4 more days, and some were euthanized to evaluate organs. Organs from mice treated with or without EC0923 6 hours, 1 day, and 4 days after treatment are shown in FIG. 7. Mice with one dose of EC0923 started to move and look for food after 4 hours, and their spleens and livers were red. Control mice without EC0923 didn't move after 6 hours, and their spleens and livers were pale. Mice with EC0923 treatment were active again in 24 hours and expected to survive, and were put back to a normal EC17 dosing schedule. Control mice without EC0923 started to move a little in 24 hours, but had to be euthanized to prevent animal suffering. Mice with EC0923 looked normal in 4 days. One of the mice was euthanized and found to have normal colored spleen and liver. The spleen of the rescued mouse was enlarged, which indicates that CAR-Ts were still proliferating despite the single dose of EC0923 for rescue. Other remaining mice with EC0923 were given routine EC17 dosing three times per week, and their tumors disappeared in 4 weeks.

Example 19

Control of CAR T Cell Activation In Vivo

Anti-FITC CAR T cell activation can be controlled by discontinuation of FITC-ligands administration, introduction of excess amounts of competitor small molecules (e.g. folic acid (FA)), or a combination of these two approaches.

In order to show control of CART T cell activation, a human breast cancer cell line (e.g. MDA-MB-231) was subcutaneously injected into the shoulder of NSG mice (Jackson Laboratory) to establish solid tumor xenografts. When tumor volume reached around 50-100 mm$^3$, about $15 \times 10^6$ anti-FITC CAR T cells were introduced into mice with tumors intravenously. Five study groups were designed to test whether anti-FITC CAR T cell activation can be controlled via temporal termination of FITC-ligands, by administering a competitor small molecule, or a combination approach of both discontinuing of FITC-ligands and/or administering an FA competitor. The first group was treated by administering anti-FITC CAR T cell with phosphate-buffered saline (PBS) as a negative control. Every other day over the course of the study, the second, third, fourth and fifth groups were treated with anti-FITC CAR T cell mixed with FITC-Folate (500 nmole/kg). Once a significant toxicity event was detected (e.g. serious loss of body weight), the treatment regimen was altered for the four groups as follows: (1) group 2 continued with FITC-Folate injections (Continued); (2) group 3 received combination treatment including termination of FITC-Folate and receiving an excess amount of free folate (Break+FA Competitor); (3) group 4 received a discontinuation of FITC-Folate until mice recovered (Break); and (4) group 5 received a mixture containing a 100-fold excess of free folic acid (i.e. EC0923) relative to FITC-Folate until mice recovered (FITC-Folate+ FA Competitor). Mouse bodyweight was measured regularly to test for toxicity.

Figure 12:
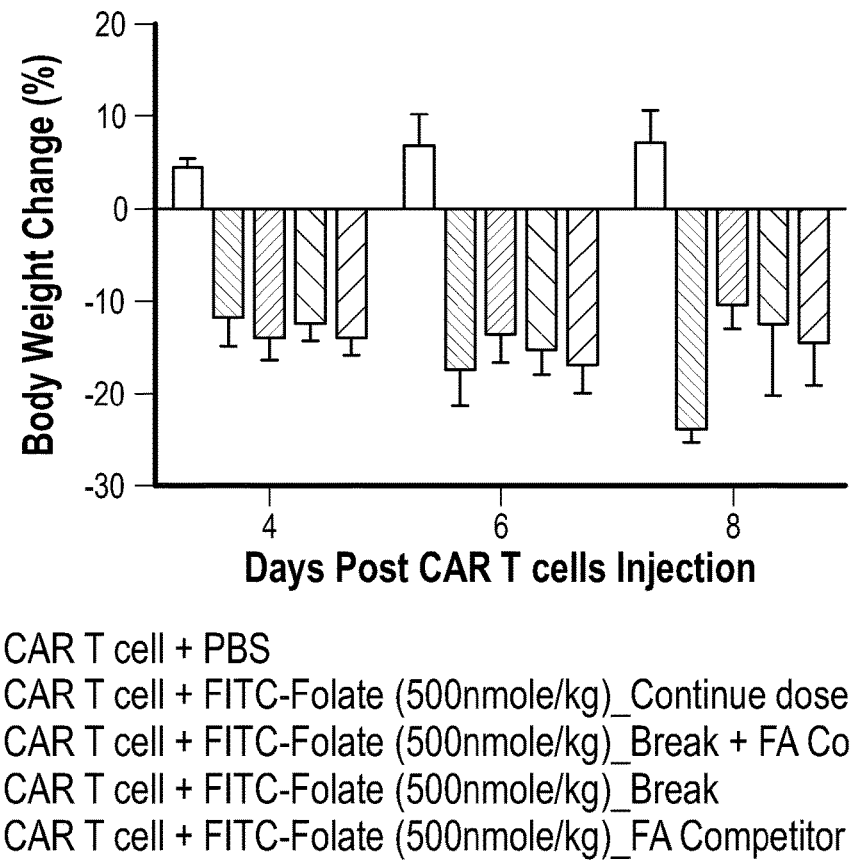
FIG. 12 shows control of CAR T cell mediated toxicity via regulation of CAR T cell activation by the use of competitors to inhibit CAR T cell activation and by ending administration of the bridge.

Results. FIG. 12 (bars about the 0 line=PBS control; first bar in each group below the 0 line=continuous; second bar in each group below the 0 line=break+FA competitor; third bar in each group below the 0 line=break; fourth bar in each group below the 0 line=FA competitor) shows that anti-FITC CAR T cell mediated toxicity can be managed by controlling anti-FITC CAR T cell activation via discontinuation of FITC-Folate injection, administration of an excess amount of a competitor molecule, or a combination of both. The FIG. 12 graph and table show that CAR T cell mediated toxicity (e.g. cytokine storm) can be managed by controlling CAR T cell activation either by discontinuation of FITC-ligands (Break); administration of an excess amount of free folic acid as a competitor with FITC-Folate (500 nmole/kg) (FITC-Folate+FA Competitor); or a combination of these two approaches (Break+FA Competitor). FIG. 12 further shows groups treated with CAR T cells+FITC-Folate demonstrated body weight loss due to hyper-activation of CAR T cells. When serious CAR T cell mediated toxicity was detected (i.e. >10% weight loss), three different methods were tested (mentioned above) to find out whether the degree of CAR T cell activation can be decreased and CAR T cell mediated toxicity can be managed. Based on the data, the three methods are able to control the degree of CAR T cell activation to alleviate CAR T cell mediated toxicity. Furthermore, the combination of discontinuing FITC-Folate and administering an excess amount of free folic acid showed better efficacy in decreasing CAR T cell mediated toxicity compared to each approach alone. As expected, the degree of CAR T cell activation was decreased when the FITC-Folate amount is limited. Simultaneously, administration of an excess amount of free folic acid may compete with FITC-Folate by interfering with the interaction between FITC-Folate and the folate receptor. Therefore, a combination treatment including termination of FITC-Folate and administering a folate competitor may promote the rapid decrease of CAR T cell mediated toxicity.

Example 20

FITC-Folate Dose Escalation Study In Vivo

To test whether gradual escalation of FITC-Folate dose can minimize CAR T cell mediated toxicity without compromising anti-tumor efficacy of CAR T cells, an experiment was designed. A dose of FITC-Folate (0.05 nmole/kg) was introduced first into NSG mice bearing MDA-MB-231 (tumor volume about 50-100 mm$^3$) along with anti-FITC CAR T cell injections (using about 15×10$^6$ cells). An additional two doses of about 0.05 nmole/kg FITC-Folate was administered to the mice. Then doses of FITC-Folate were gradually increased from 5 nmole/kg (single dose) to 50 nmole/kg (two doses). After a gradual increase of FITC-Folate dose, mice were treated with a 500 nmole/kg dose of FITC-Folate. This concentration showed good tumor efficacy, but also caused toxicity if mice were initially treated with the 500 nmole/kg dose. General toxicity of each treatment group was monitored by measuring body weight loss. Tumor volume was measured to monitor anti-FITC CAR T cells' anti-tumor efficacy.

Figure 13A:
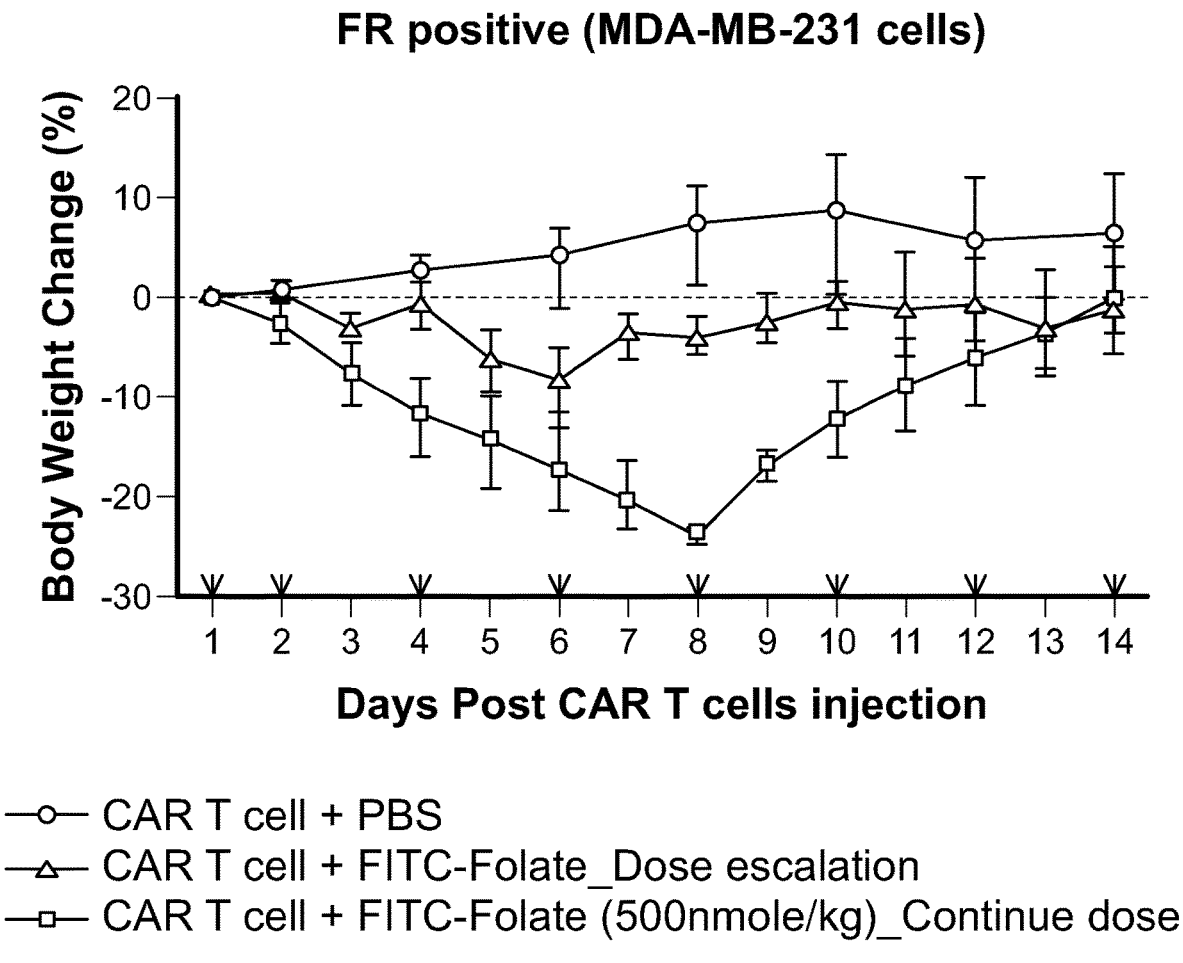
FIGS. 13A-C show the results of a FITC-Folate dose escalation study.
Figures 13B, 13C:
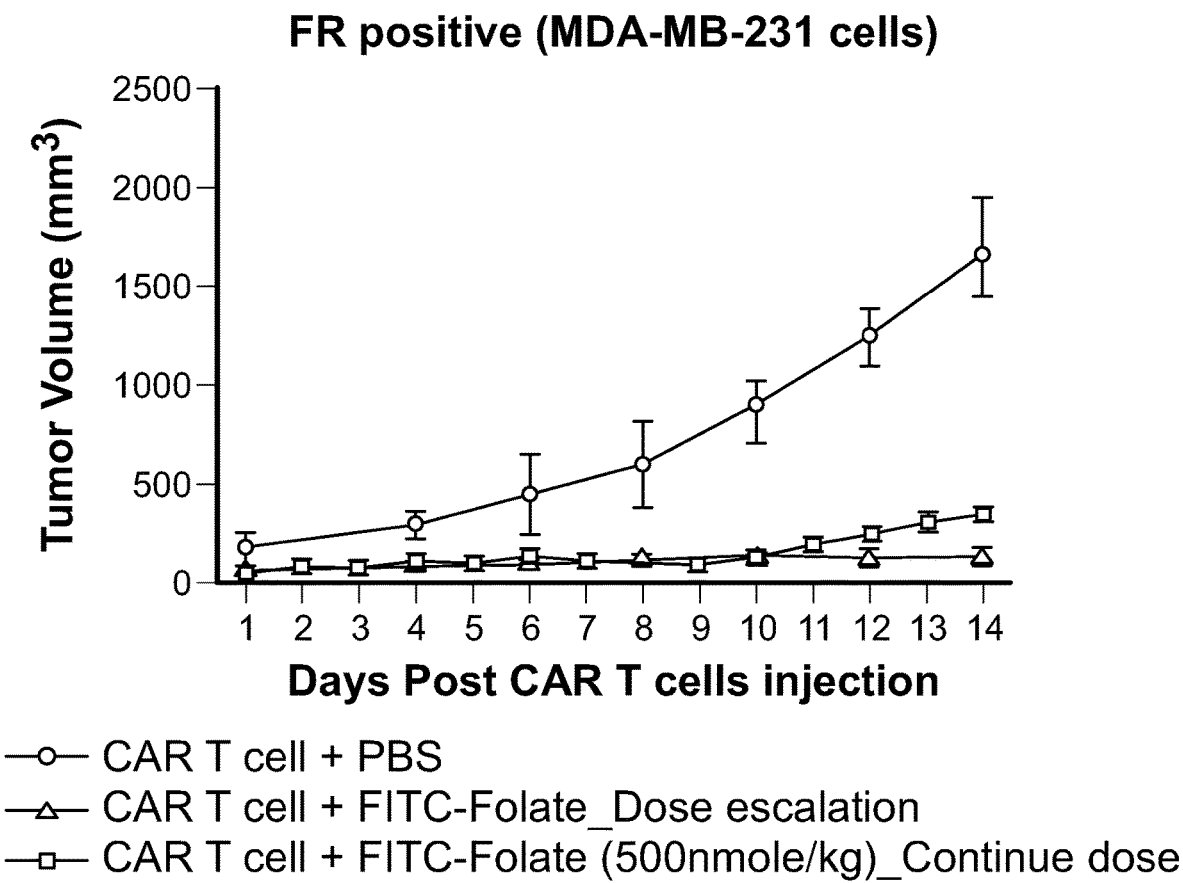

FIG. 13 shows that a gradual dose increase of FITC-Folate can minimize anti-FITC CAR T cell mediated toxicity without compromising anti-tumor efficacy of CAR T cells. Specifically, FIGS. 13A and 13C demonstrate no serious toxicity (i.e. >10% weight loss) was detected using the gradual treatment protocols compared to the group that was continuously treated with 500 nmole/kg of FITC-Folate. FIG. 13B shows that gradual activation of CAR T cells by a gradual increase in FITC-Folate dose, did not negatively affect the CAR T cells' anti-tumor efficacy. Therefore, a gradual dose increase of FITC-Folate could be used to treat tumors using a FITC-Folate bridge while avoiding substantial serious toxicity side effects.

Example 21

Effect of Folate-FITC on CAR-T Cell Number and on Serum Cytokines

The triple negative human breast cancer cell line (i.e. MDA-MB-231) was subcutaneously implanted into the shoulders of immunodeficient (e.g. NSG) mice. When tumor volume reached around 50-100 mm$^3$, anti-FITC CAR T cells (10$^7$ cells) were intravenously introduced with either FITC-folate (500 nmole/kg) or PBS. To monitor CAR T cell proliferation and pro-inflammatory cytokine production, mice blood was collected at Day 6. CAR T cell proliferation was evaluated by staining a whole blood sample with anti-human CD3 antibody (Biolegend) and detecting GFP expression on the CD3 positive T cell population. Pro-inflammatory cytokine production was measured by a bead-based immunoassay (Legendplex kit from biolegend).

Figure 14A:
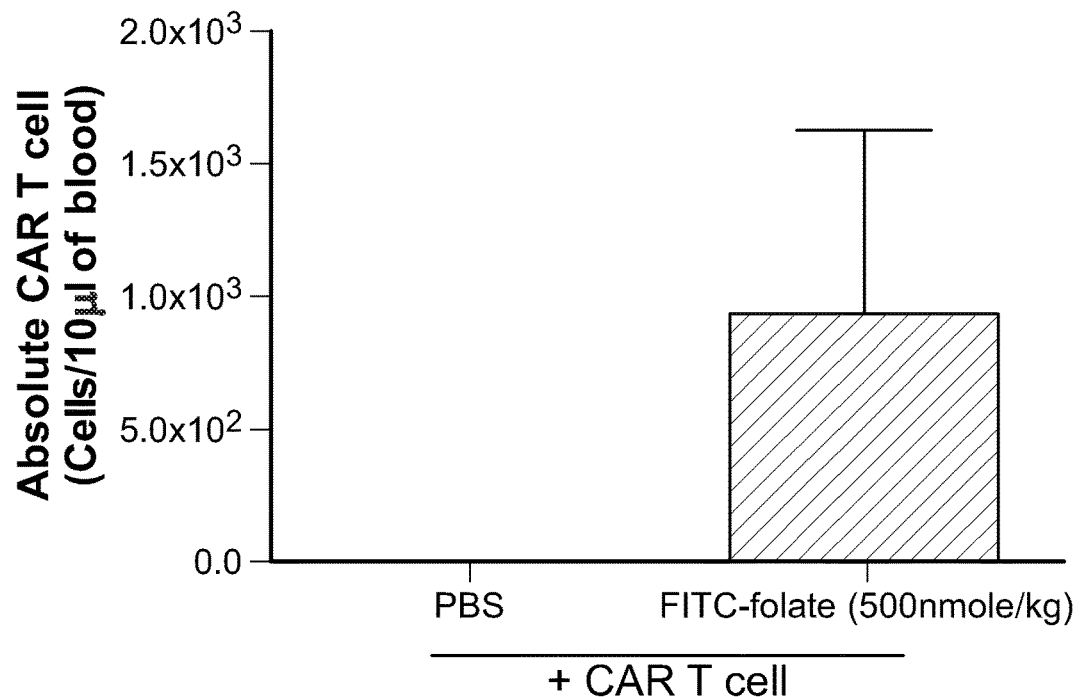
FIGS. 14A-B show the effect of the FITC-ligand bridge molecule on CAR T cell proliferation and cytokine production.
Figure 14B:
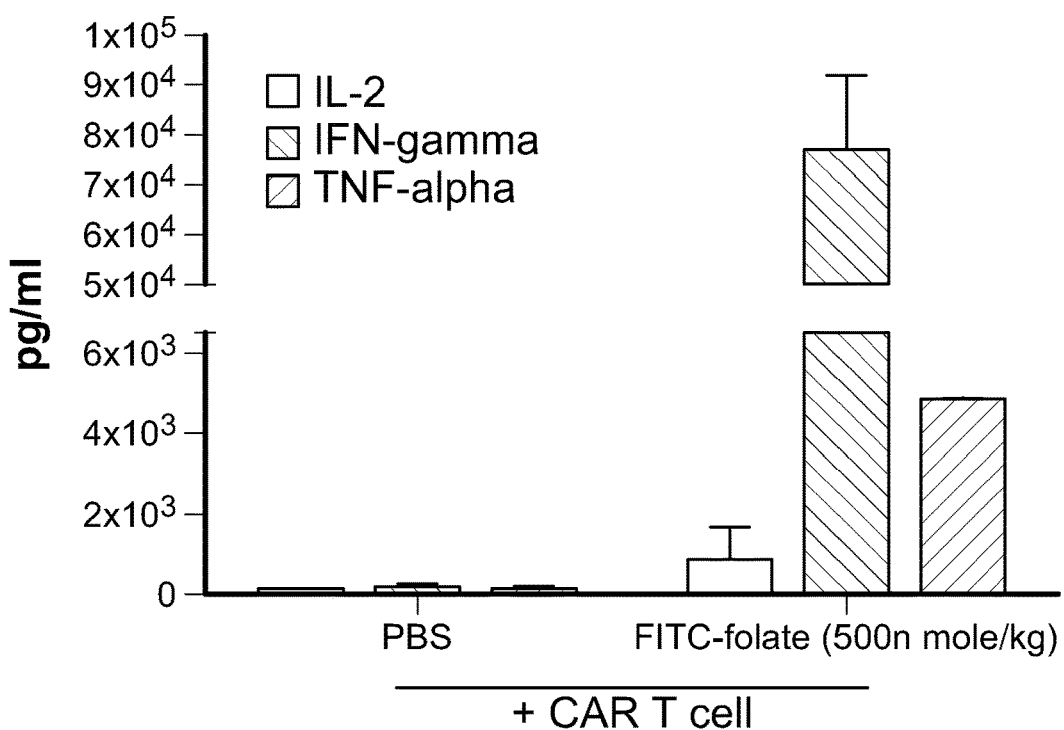

FIG. 14A shows that anti-FITC CAR T cells only proliferated significantly when the bridge molecule was introduced into tumor bearing mice. However, in the absence of the antigen matched bridge molecule, anti-FITC CAR T cells did not proliferate significantly. Furthermore, pro-inflammatory cytokines (e.g. IL-2, TNF-α and IFN-γ) were significantly produced when tumor-bearing mice were treated with both anti-FITC CAR T cells and the antigen matched bridge molecule. Taken together FIGS. 14A and 14B, show that anti-FITC CAR T cells can be specifically proliferated and activated to produce pro-inflammatory cytokines by targeting cancer cells via the antigen matched bridge molecule Folate-FITC.

Example 22

In Vitro Interferon-γ Assay

In order to study the relationship between bridge dose and anti-FITC CAR T cell activation, a folate receptor positive cancer cell line (MDA-MB-231) was seeded at a density of 10$^4$ cells/100 ul of media in each well of a 96-well plate and the cells were grown overnight. Anti-FITC CAR T cells (5×10$^4$ cells) were then added into each well containing cancer cells with various concentrations of Folate-FITC (from 0.001 nM to 100 µM) for 6-24 hours. After co-incubation, the plates containing anti-FITC CAR T cells and cancer cells were centrifuged for 10 min at 350×g to remove cells and cellular debris, and 50 ul of supernatant was assayed by ELISA (Human IFN-γ ELISA kit from Biolegend) to detect IFN-γ production by anti-FITC CAR T cells.

Figure 15:
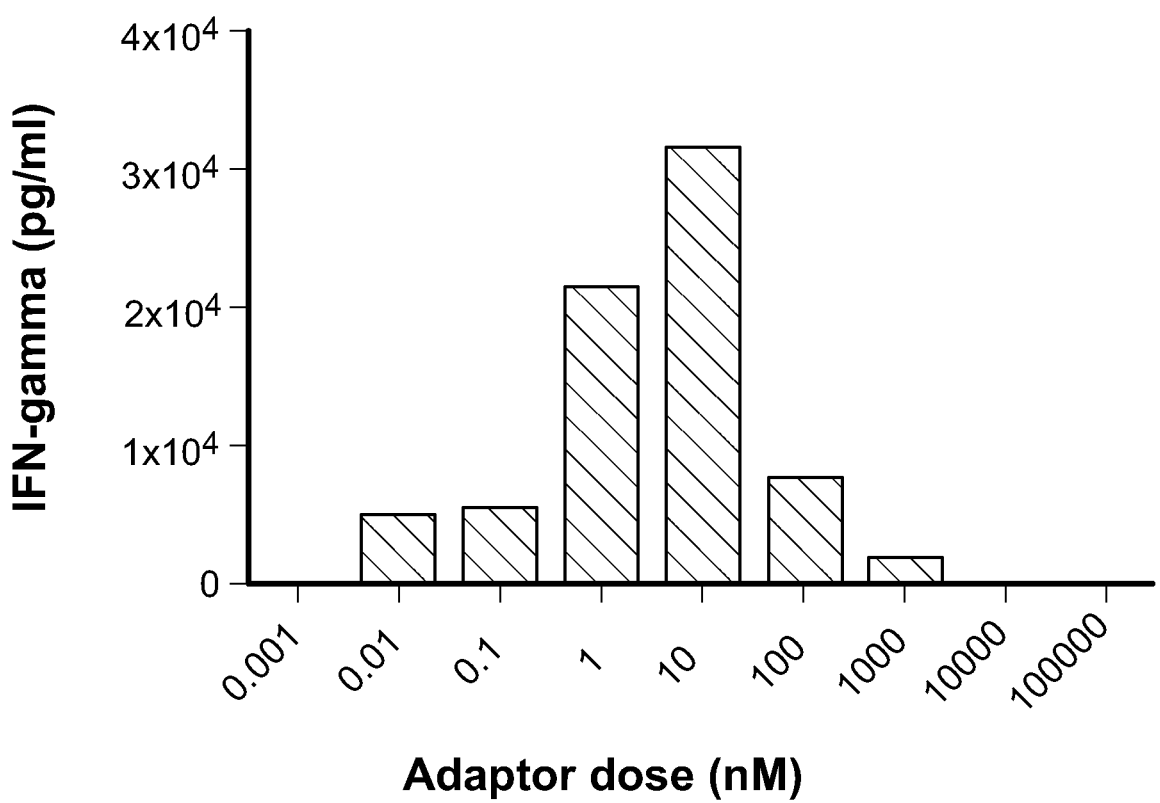
FIG. 15 shows the concentration of IFN-γ as a function of the concentration of FITC-folate in an in vitro assay.

To evaluate the relationship between bridge dose and anti-FITC CAR T cell activation, the level of IFN-γ produced by anti-FITC CAR T cells was measured after CAR T cells were co-incubated with cancer cells at various concentrations of FITC-folate in vitro as described above. As shown in FIG. 15, the level of IFN-γ production was increased as bridge dose was increased. However, if the dose of the bridge was higher than the optimal dose (i.e. highest IFN-γ level [10 nM]), IFN-γ production decreased and eventually was not detected when very high doses (e.g. 10 µM and 100 µM) of the bridge were introduced (i.e. bell-shaped bridge dose-response). This result in vitro may be because the high dose of the bridge can saturate all of target receptors on both cancer cells and CAR T cells in vitro. These results show that CAR T cell mediated toxicity can be controlled by manipulating the dose of the bridge. In FIG. 15, "Adaptor Dose" on the X-axis is the Folate-FITC dose.

Example 23

Rescue Ability of Competitors During CAR T Cell Treatment In Vivo

Figure 16:
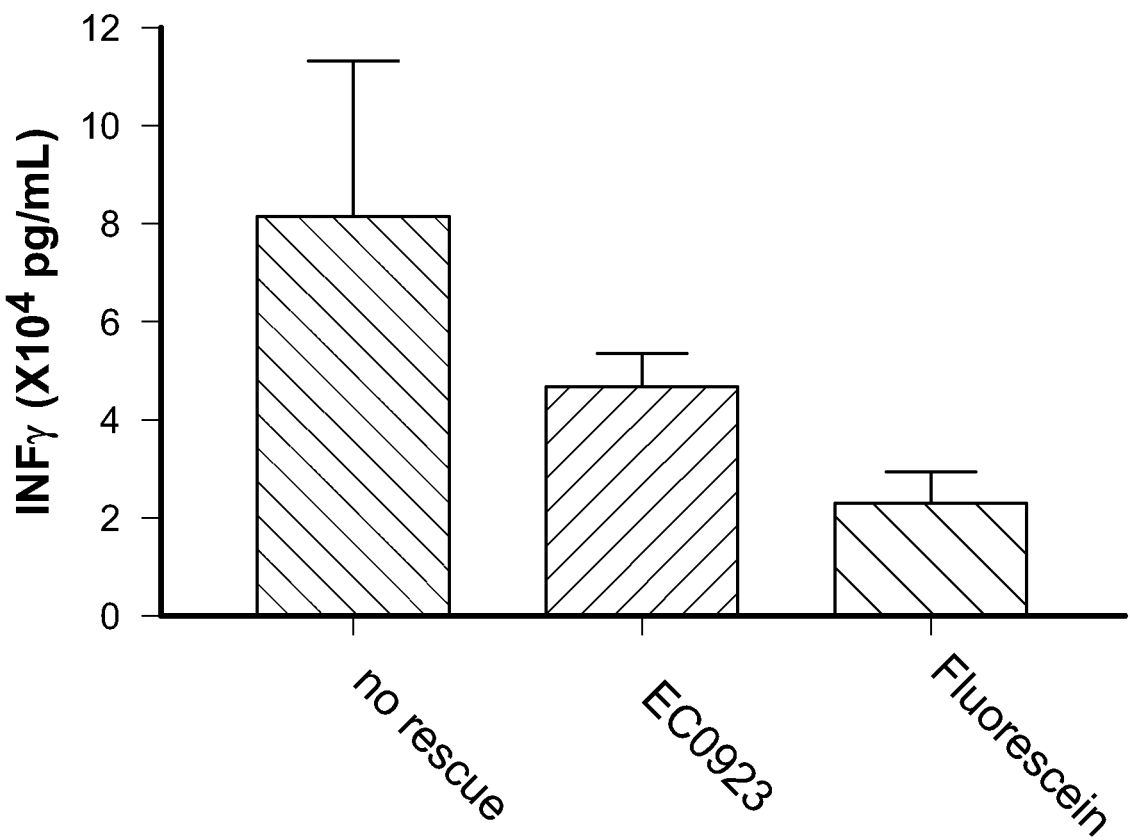
FIG. 16 shows the rescue (based on a measurement of cytokine production) with EC0923 or fluorescein or mice having cytokine release syndrome.

Excess CAR T cells (8 to 10 million in each study) were introduced into mice bearing MDA-MB-231 tumors, and 500 nmol/kg of EC17 was also introduced (i.v.) three times per week. When severe cytokine release syndrome was observed, one dose of EC0923 (folate) or untethered fluorescein (both at 10 μmoles/kg) was introduced intravenously to rescue mice (FIG. 16). Mice with one dose of EC0923 or fluorescein started to move and look for food after 4 hours, were active again in 24 hours, and looked normal in 4 days. EC17 administration was then continued. Control mice without EC0923 or fluorescein didn't move after 4 hours, and had to be euthanized because of the sickness. Blood samples were collected 6 hours after the administration of competitors, and cytokine levels were measured (see FIG. 16). Four weeks later, tumors were eliminated from the mice with rescue treatment. All mice tested for cytokine production were injected with 8 million CAR-T cells.

Example 24

Figure 17:
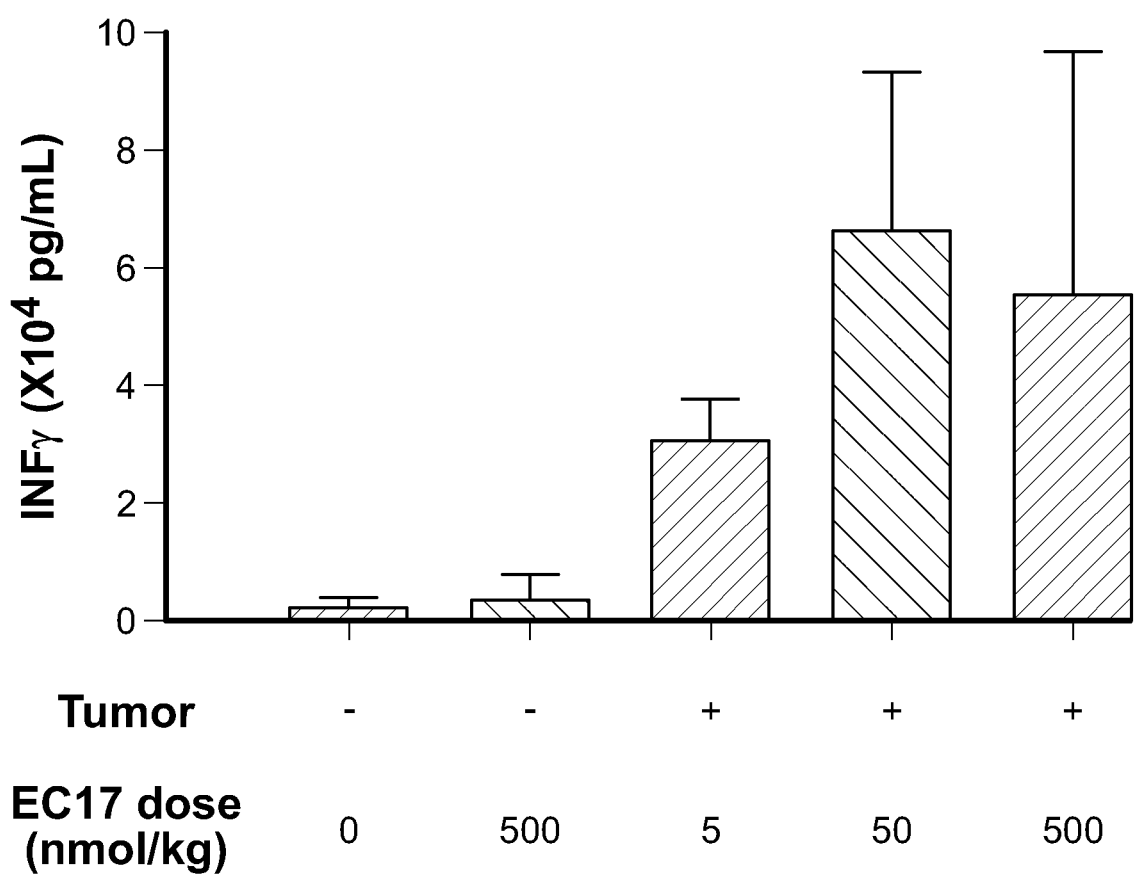
FIG. 17 shows that CAR-T cell activity (based on a measurement of cytokine production) is dependent on the presence of the tumor and on EC17 dose level.

CAR-T Activity is Dependent on Both the Bridge Dose Level and the Presence of the Tumor CAR-T cells were injected into naïve mice (8 million per mouse) and mice bearing MDA-MB-231 tumors (5 million per mouse). Various levels of EC17 were administrated three times per week. IFN-γ in blood was measured 10 days after CAR-T cell injection. As shown in FIG. 17, cytokine production (CAR-T activity) is dependent on both the bridge (EC17) dose level and the presence of the tumor.

Example 25

CAR-T Cells do not Proliferate in Naïve Mice without Tumors

Figure 18A:
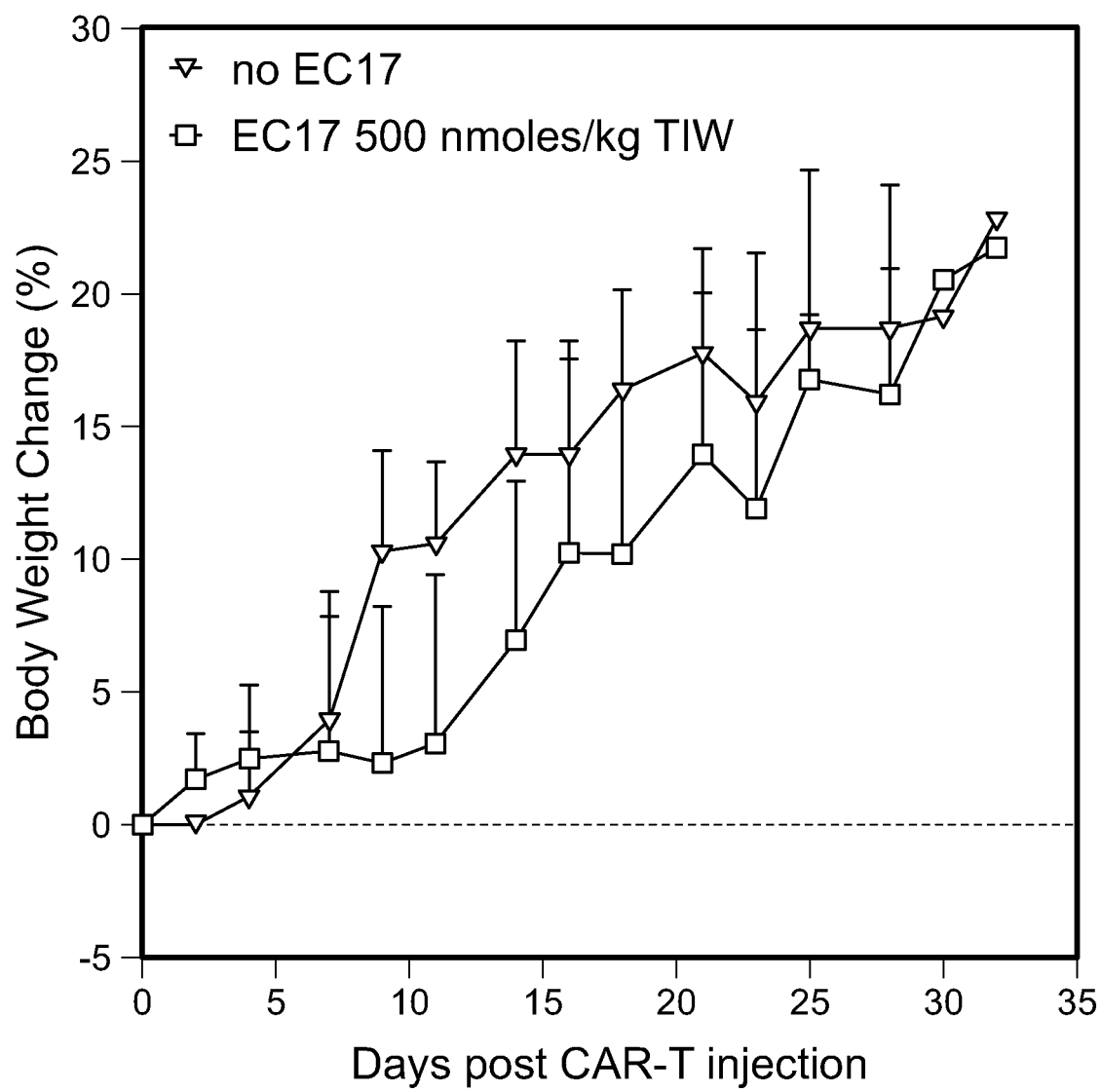
FIGS. 18A-C show that CAR-T cells do not proliferate in naïve mice with no tumors.
Figure 18B:
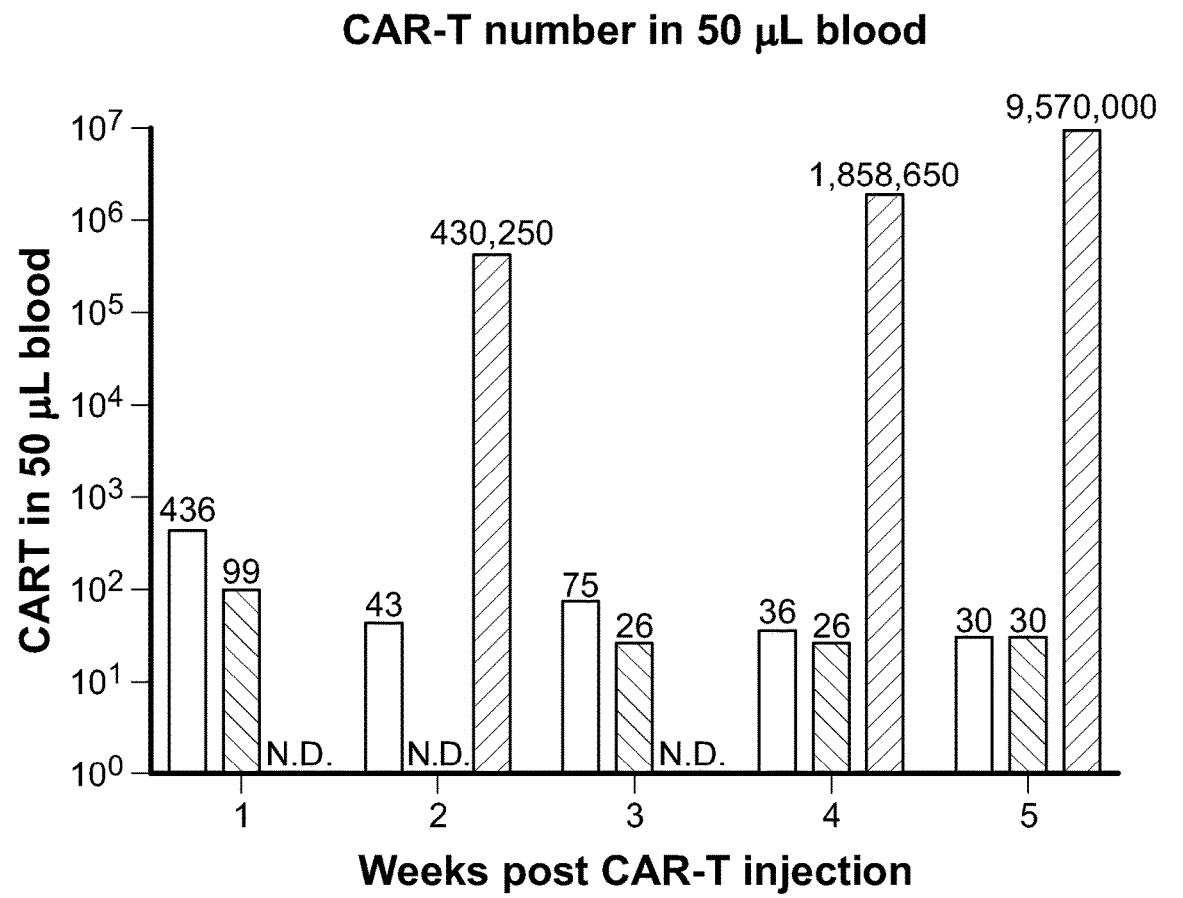
Figure 18C:
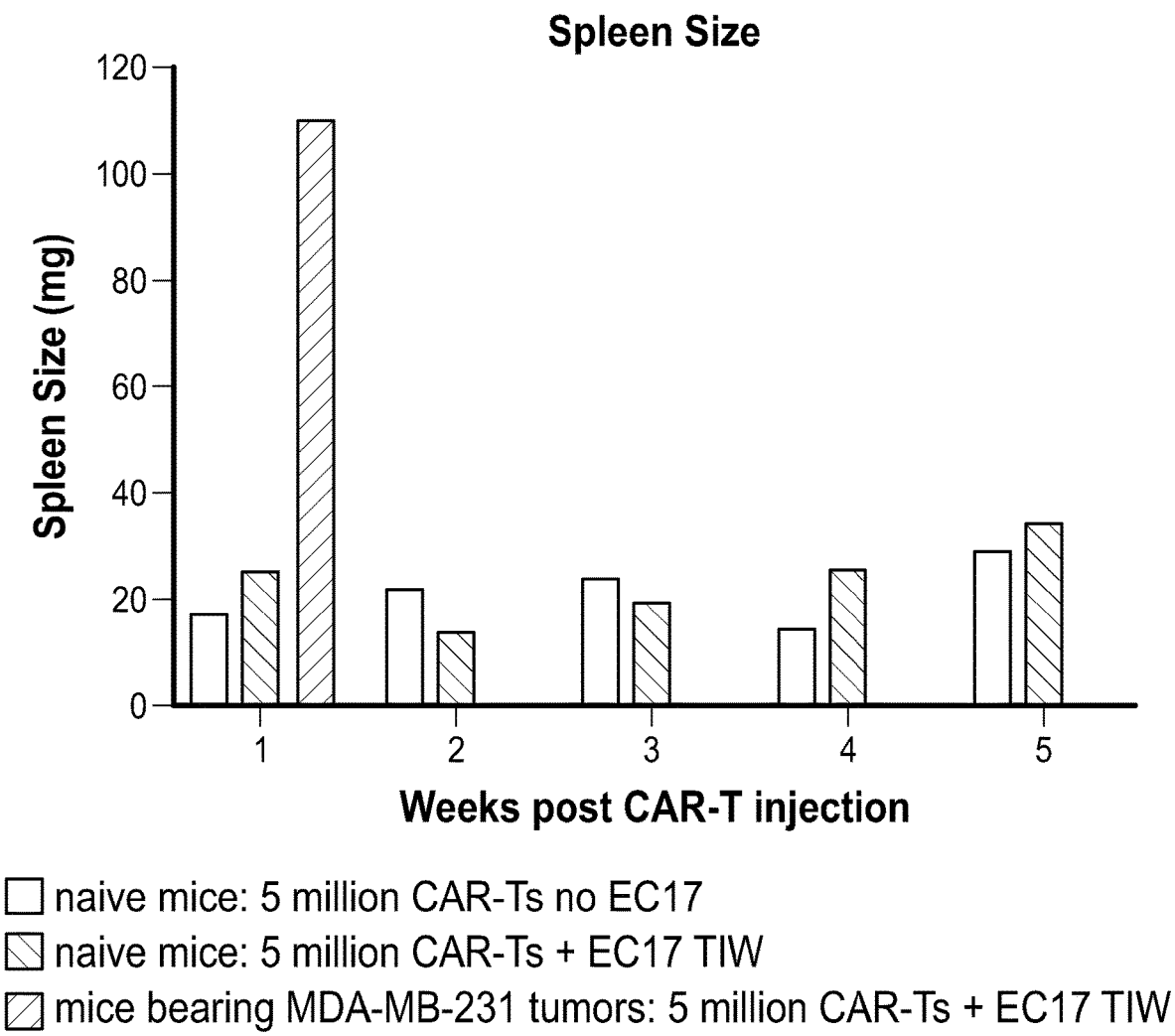

Five million CAR-T cells were injected (i.v.) into naïve mice without tumors. 500 nmoles/kg EC17 was administrated three times per week. Mice were monitored for 5 weeks, and some were euthanized every week to evaluate organs. No apparent body weight loss (toxicity) was observed for any mice, whether EC17 was administrated or not (FIG. 18A). CAR-T cells did not proliferate in naïve mice with or without EC17 administration, as indicated by CAR-T cell number in blood (FIG. 18B) and spleen size (FIG. 18C).

Example 26

EC17 Dependent Anti-Tumor Activity of FITC-CAR-T in Different Folate Receptor-Positive Tumor Xenograft Models Immunodeficient NSG mice (Jackson Laboratory) were used to show the efficacy of CAR T cell anti-tumor activity with a single dose of EC17 per week. Two folate receptor expressing cancer cell lines were used to establish subcutaneous solid tumor xenografts: MDA-MB-231 has high folate receptor expression, while OV90 has low folate receptor expression. When tumor volume of around 100-250 $mm^3$ was reached, mice were divided into two groups. Mice in the "EC17 500 nmol/kg" group (nmol/kg is equivalent to nmoles/kg as used in this patent application for the bridge) were injected with 500 nmoles/kg of body weight of EC17, while mice in the "no EC17" group were not injected with EC17. Four hours later, mice in both groups were administered 5 million anti-FITC CAR-T cells. After initial administration of EC17 and CAR-T cells, only mice in the "EC17 500 nmol/kg" group were injected (i.v.) with 500 nmoles/kg of EC17 once per week. Anti-tumor efficacy was monitored by tumor volume.

Figure 19A:
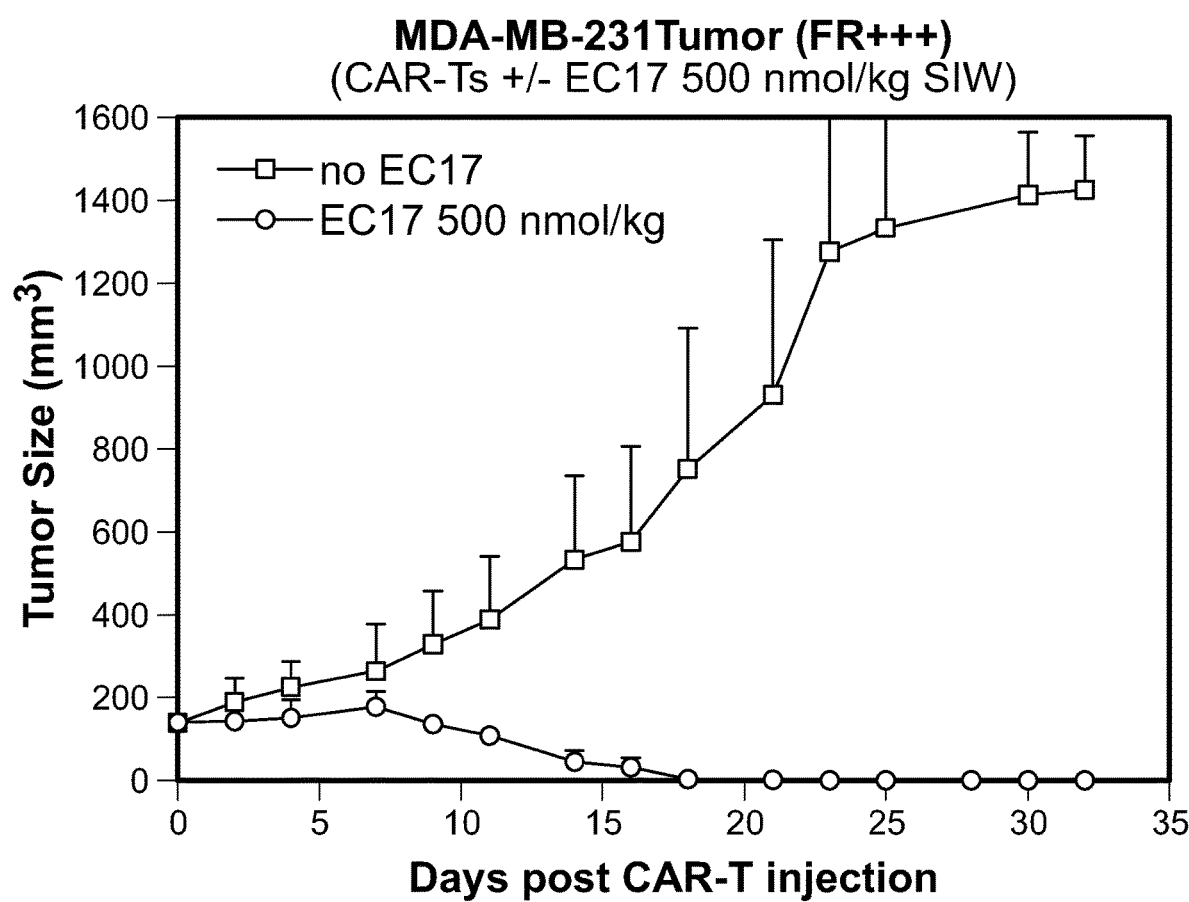
FIGS. 19A-B show effects on tumor size of CAR-T cells and EC17 injected into mice using an MDA-MB-231 model (high folate receptor expression levels—FIG. 19A) or an OV90 tumor model (low folate receptor expression levels—FIG. 19B).
Figure 19B:
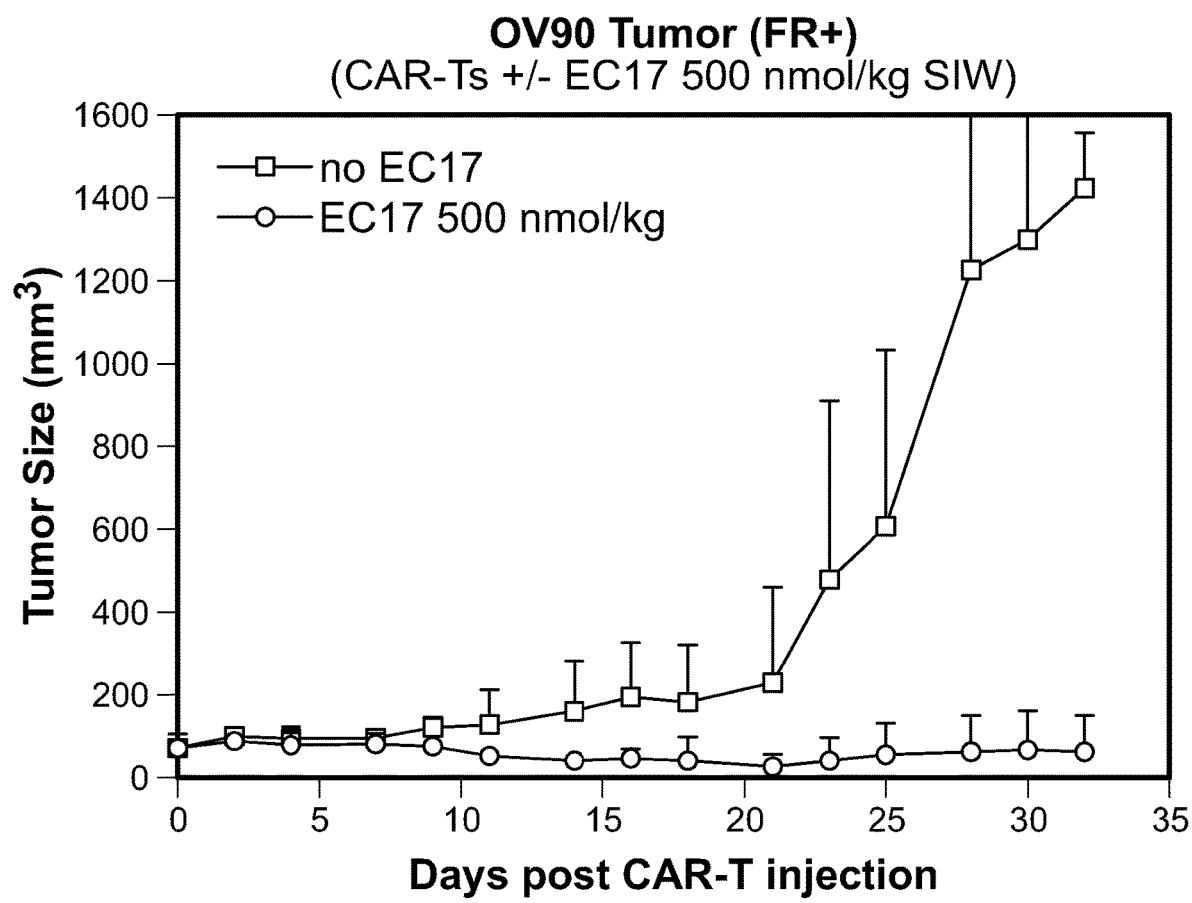

FIG. 19A shows that anti-FITC CAR-T cells by themselves don't have anti-tumor activity in MDA-MB-231 tumor models with high folate receptor expression. Only with the administration of EC17 (single dose per week), do the anti-FITC CAR-T cells eliminate MDA-MB-231 tumors. Therefore, a single dose per week of EC17 is sufficient in activating and bridging anti-FITC CAR-T cells to tumor cells to eliminate the tumors. FIG. 19B shows that anti-FITC CAR-T cells also show EC17 dependent anti-tumor activity in an OV90 xenograft model which has a low expression level of folate receptors on tumor cells.

Example 27

Maintenance of CAR-T Anti-Tumor Activity by Adjusting Bridge Dose Level

Figure 20A:
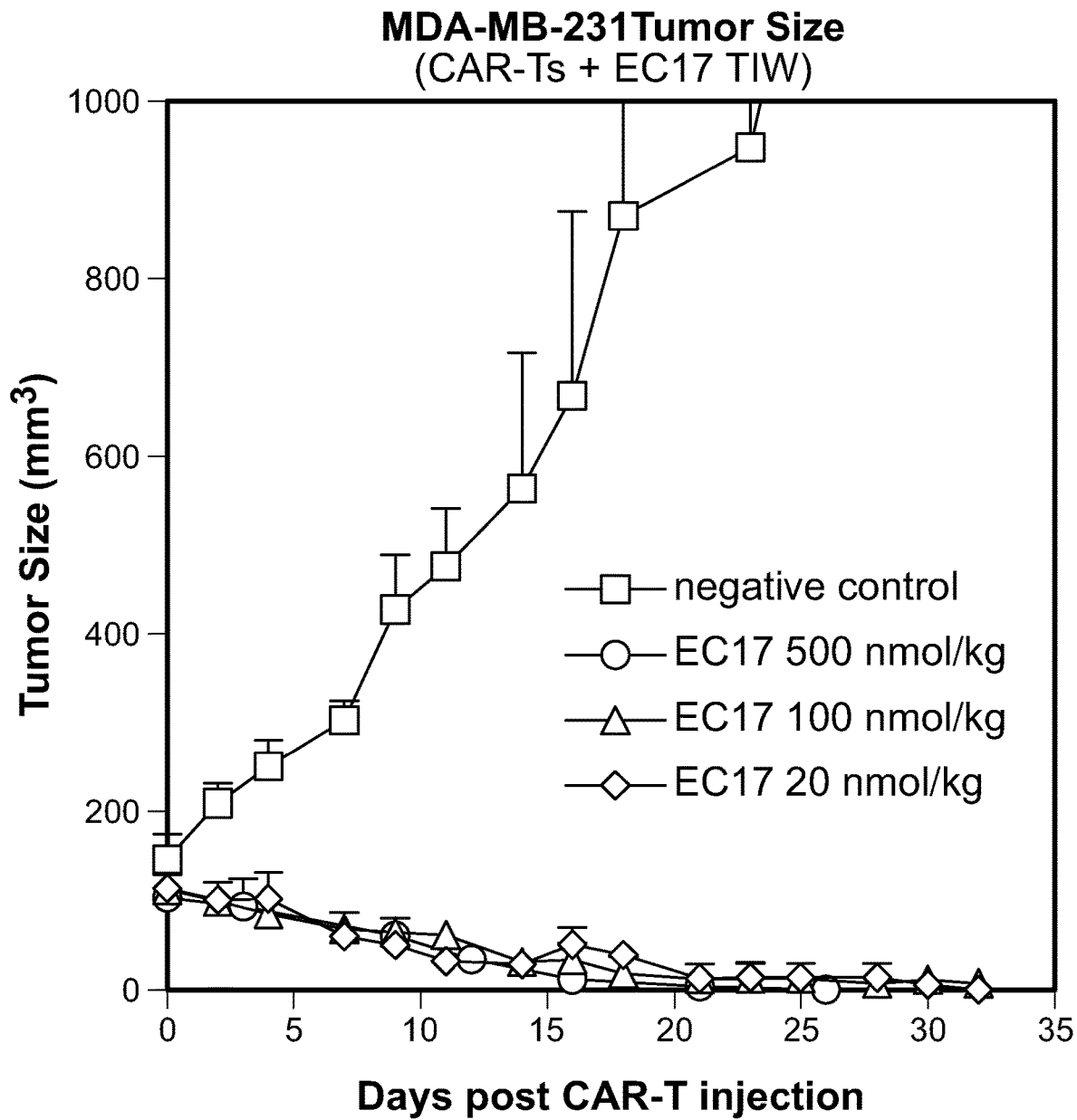
FIGS. 20A-B show effects on tumor size (FIG. 20A) and body weight loss (FIG. 20B) of CAR-T cells and various doses of EC17 injected into mice using an MDA-MB-231 model.
Figure 20B:
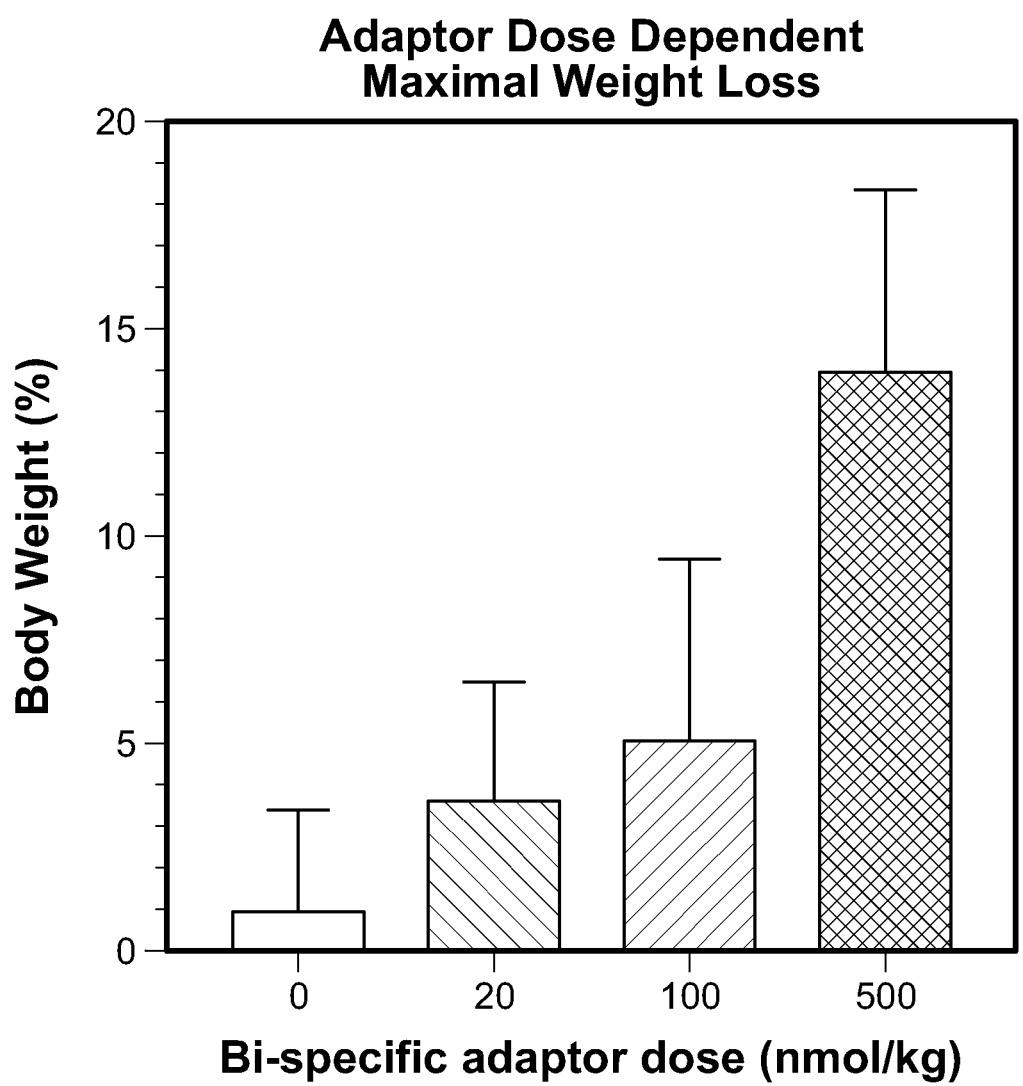

Immunodeficient NSG mice (Jackson Laboratory) were used to study CAR T cell anti-tumor activity and its toxicity in the presence of different EC17 dose levels. MDA-MB-231 tumor cells were used to establish subcutaneous solid tumor xenografts. When tumor volume of around 100-150 $mm^3$ was reached, various concentrations of EC17 were pre-injected 4 hours before i.v. injection of 10 million CAR-T cells. Various concentrations of EC17 were then administrated three times per week after the initial EC17 and CAR-T cell injections. The negative control group was injected with 500 nmol/kg EC17 (4 hour in advance) and 50 million unmodified T cells. 500 nmol/kg EC17 was then administrated three times per week after initial injection. Tumor size and body weight were measured to monitor the anti-tumor activity and the toxicity. As shown in FIG. 20A, tumors in mice treated with 10 million CAR-T cells and EC17 500 nmol/kg, 100 nmol/kg or 20 nmol/kg were all eliminated, but tumors in the negative control group were not eliminated. When comparing the body weight loss due to treatment in mice administrated 10 million CAR-T cells but different EC17 dose levels, the group administrated 500 nmol/kg EC17 TIW was found to show the strongest toxicity (body weight loss (FIG. 20B)). 20 nmol/kg EC17 TIW showed the least toxicity (indicated by body weight loss) among three EC17 dose groups, but still maintained sufficient anti-tumor activity. By adjusting the EC17 dose level, CAR-T anti-tumor activity can be maintained while the resulting body weight loss (toxicity) can be reduced. In FIGS. 20A and 20B, EC17 is also referred to as "adaptor" or "bi-specific adaptor".

Example 28

FITC-CAR-T/EC17 Therapy Shows Anti-Tumor Activity in Various FR+ Tumor Models

To test whether FITC-CAR-T/EC17 therapy has anti-tumor activity in various FR+ tumor models, NSG mice were subcutaneously implanted with MDA-MB-231 (triple negative breast cancer cell line), OV90 (human ovarian cancer cell line), KB (human cervical adenocarcinoma cell line), SKOV-3 (human ovarian carcinoma cell line), or HEK293-FRa (HEK293 stably-transfected with human FRa). When tumor size reached 100-300 nm3, one dose of EC17 at 500 nmol/kg of body weight was injected by tail vein followed with administering of 5 million FITC-CAR-T cells 4 hours later. 500 nmol/kg EC17 was dosed once every week after the initial EC17/CAR-T administration (about day 7), tumor size and body weights of mice were monitored three times per week. The EC17 dosing days were labeled as green dashed vertical lines in the graph. As shown in FIG. 21 to 25, FITC-CAR-T treatment did not show any anti-tumor activity in the absence of EC17, whereas the FITC-CAR-T/EC17 therapy showed EC17 dependent anti-tumor activity in various FR+ tumor xenograft models. The therapy achieved 100% cures in MDA-MB-231 xenograft mice, 50% cures and 50% stable disease in OV90 mice, stable disease in all KB xenograft mice and SKOV3 xenograft mice, and progressive disease in the HEK293-FRa model. EC17 dose-dependent temporary body weight loss was also observed in all tumor bearing mice, indicating the activation of CAR-Ts is EC17-dependent in these mice.

Figure 21A:
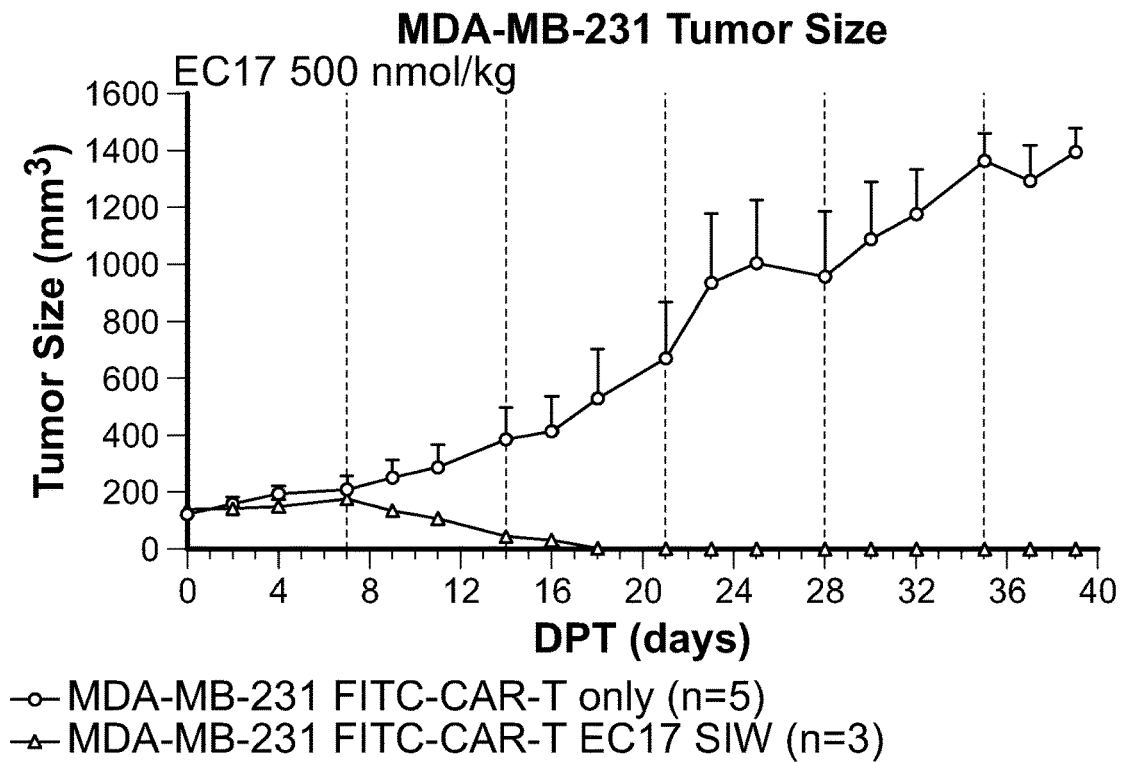
FIGS. 21A and 21B show FITC-CAR-T anti-tumor activity in a MDA-MB-231 model.
Figure 21B:
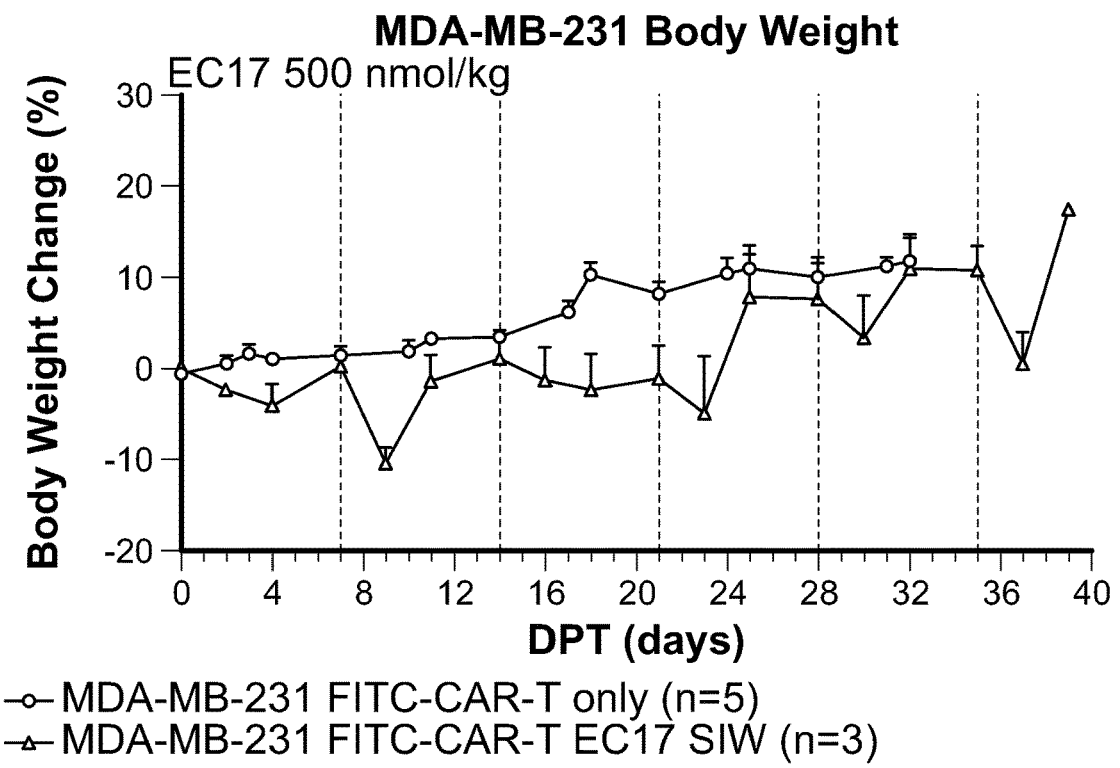
Figure 22A:
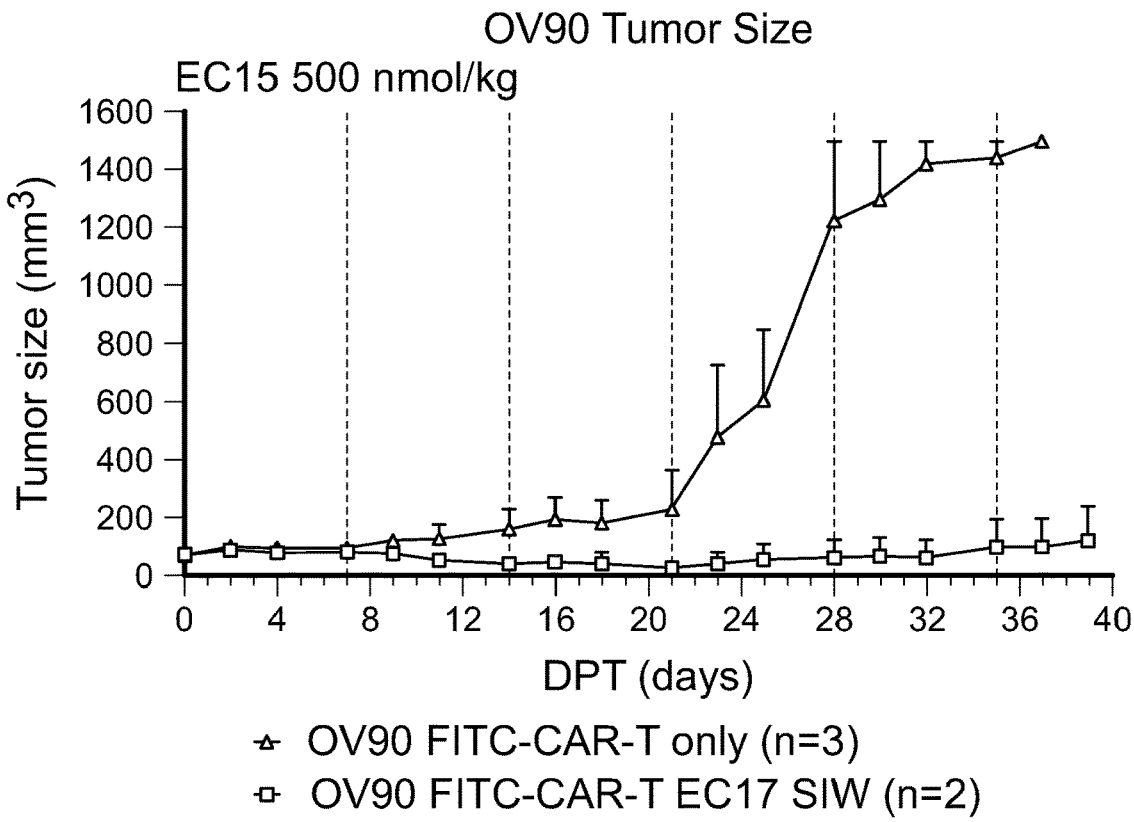
FIGS. 22A and 22B show FITC-CAR-T anti-tumor activity in an OV-90 model.
Figure 22B:
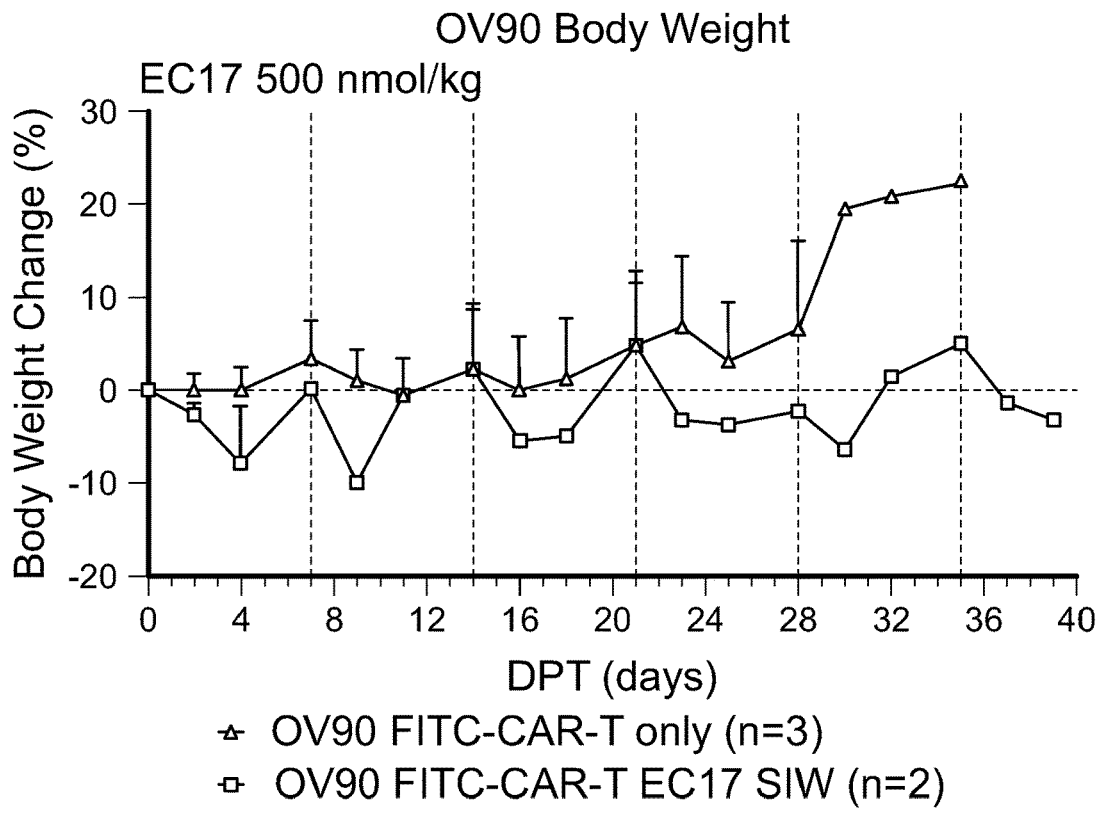
Figure 23A:
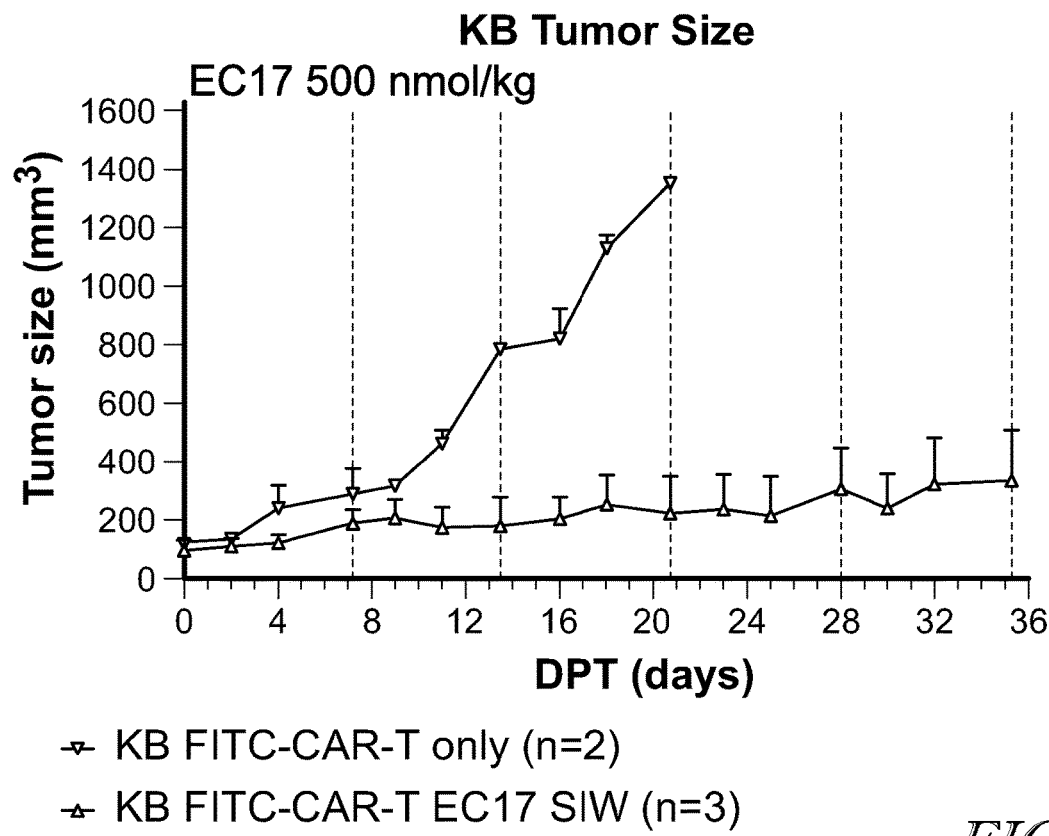
FIGS. 23A and 23B show FITC-CAR-T anti-tumor activity in a KB model. For the EC17 group, ⅔ had sCRS on day 23 and ⅓ had sCRS on day 37.
Figure 23B:
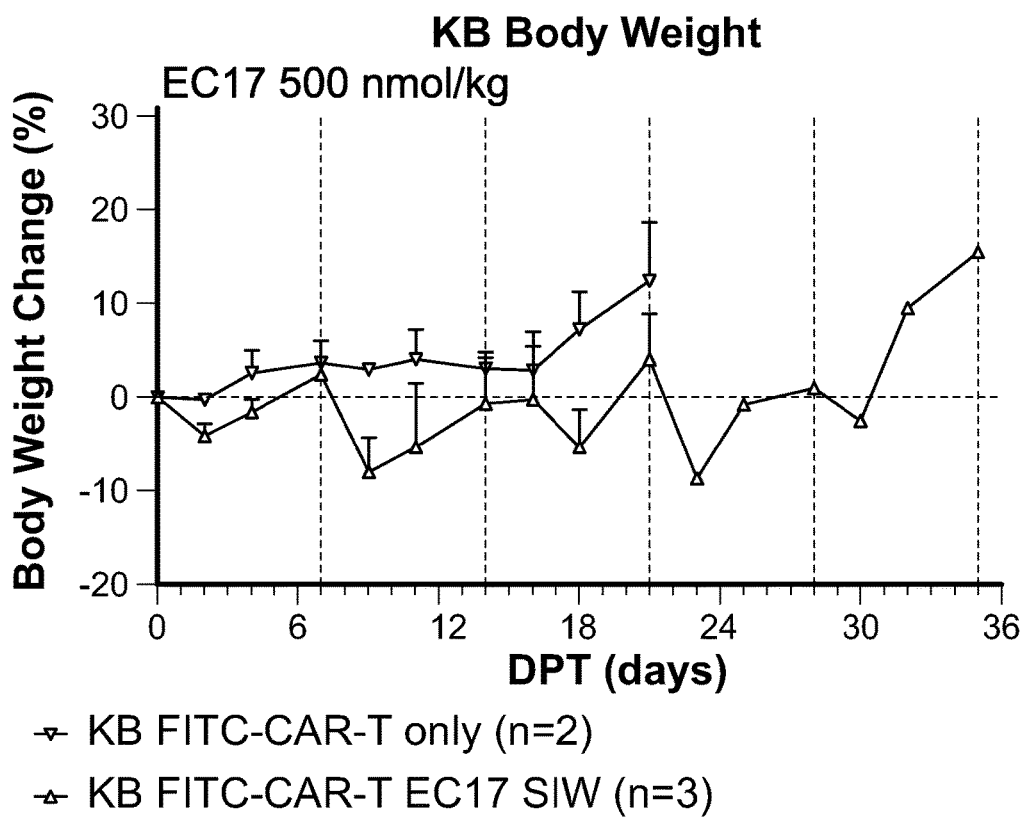
Figure 24A:
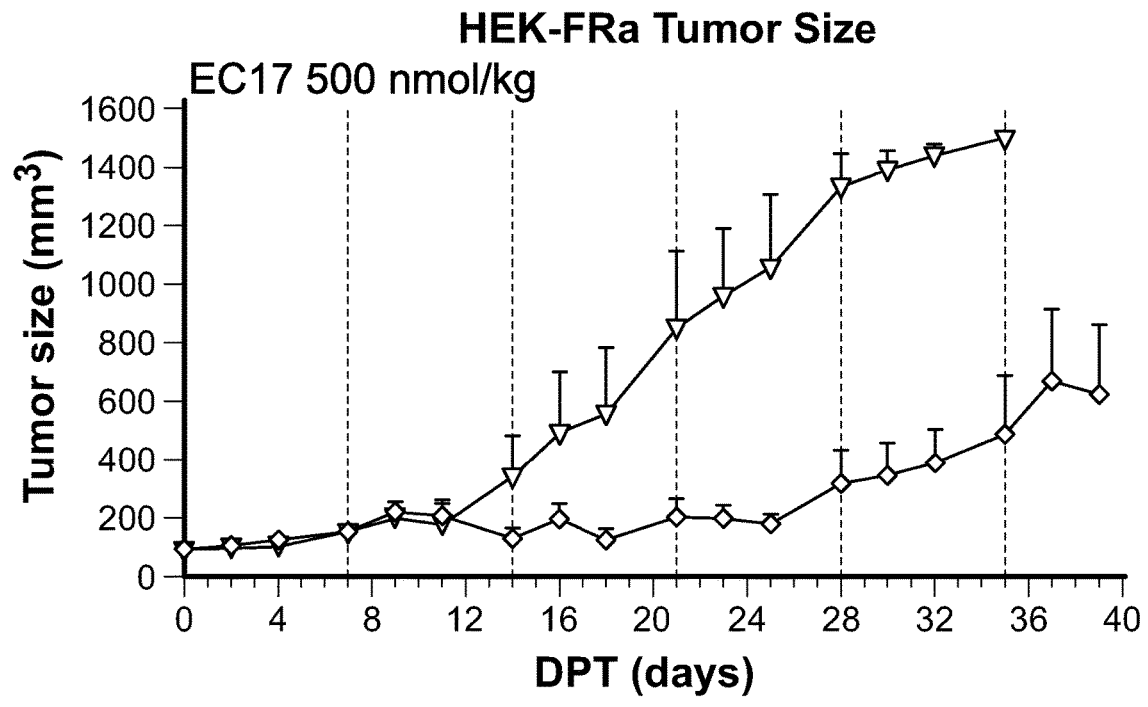
FIGS. 24A and 24B show FITC-CAR-T anti-tumor activity in a HEK-FRa model.
Figure 24B:
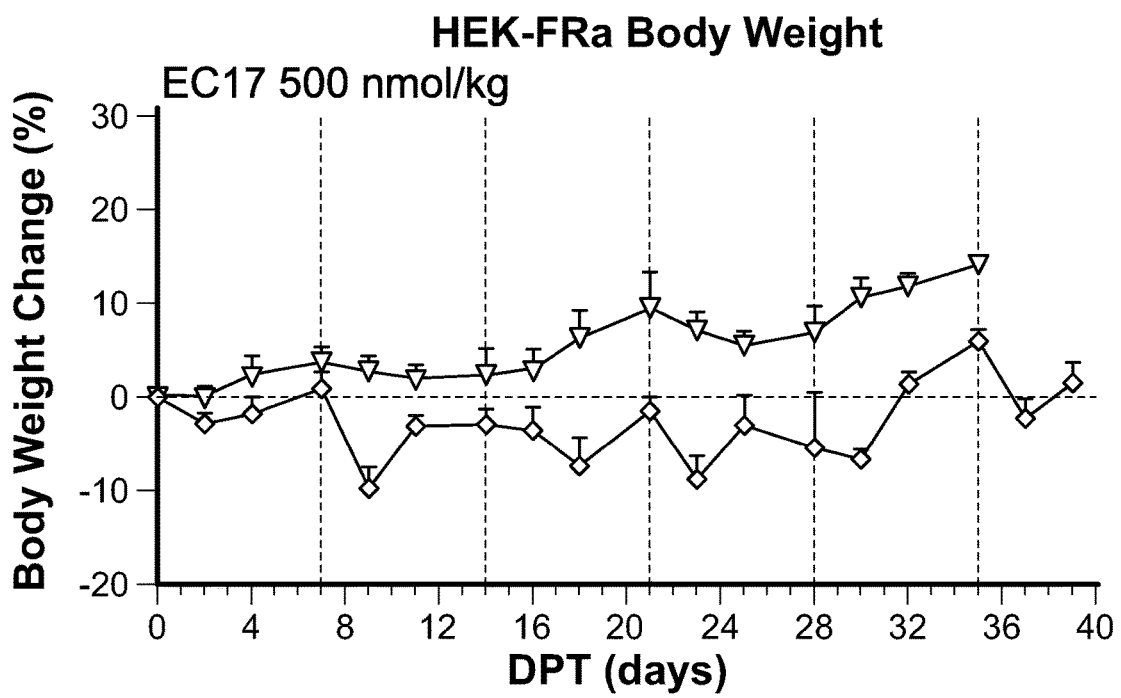
Figure 25A:
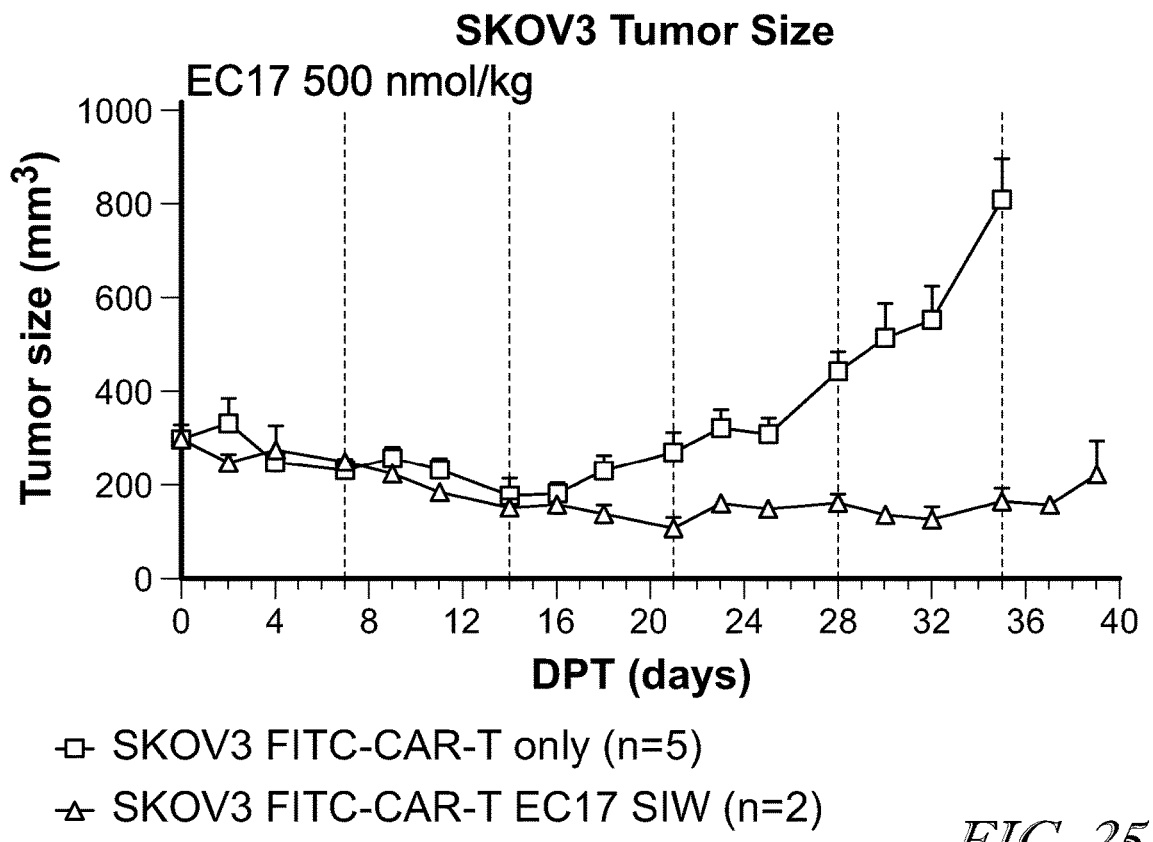
FIGS. 25A and 25B show FITC-CAR-T anti-tumor activity in a SKOV-3 model.
Figure 25B:
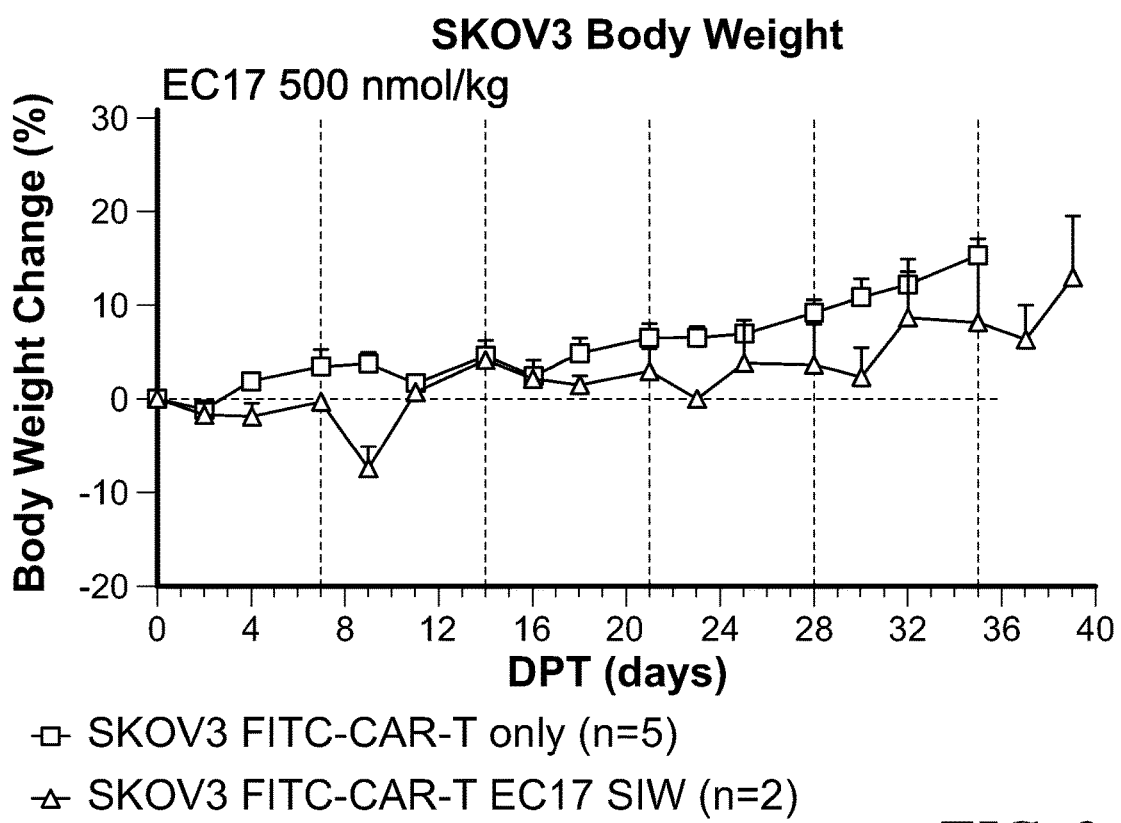

FITC-CAR-T anti-tumor activity in a MDA-MB-231 model is shown in FIGS. 21A and 21B. FITC-CAR-T anti-tumor activity in an OV-90 model is shown in FIGS. 22A and 22B. FITC-CAR-T anti-tumor activity in a KB model is shown in FIGS. 23A and 23B. FITC-CAR-T anti-tumor activity in a HEK-FRa model is shown in FIGS. 24A and 24B. FITC-CAR-T anti-tumor activity in a SKOV-3 model is shown in FIGS. 25A and 25B.

Example 29

FITC-CAR-T Related Toxicity (e.g. sCRS) can be Reduced by Pre-Painting Tumors with EC17

To evaluate whether pre-painting tumors with EC17 can reduce the therapy-related toxicity (e.g. sCRS), NSG mice were implanted with MDA-MB-231. Since larger tumor burden is correlated with more severe CRS, the treatment was started when tumor size reached 400-500 nm3. Mice were divided into two groups and predosed with 500 nmol/kg EC17 at different time points before CAR-T administration (FIGS. 26A and 26B). Group #1 was pre-dosed 4 hours before the administration of 8 million CAR-T cells, while group #2 was pre-dosed 24 hours before the administration of 8 million CAR-T cells. 500 nmol/kg EC17 was then i.v. dosed once per week (at days 1, 8, 15 etc.) post CAR-T administration (FIGS. 26D and 26E). Although mice in two groups showed similar EC17-dependent body weight loss, mice in the group with 4 hour pre-painting of EC17 showed worse sCRS than mice in the group painted with EC17 24 hours before CAR-T administration. As shown in FIG. 26C, in the 4-hour pre-painting group, 33% of mice died (or were euthanized due to sCRS) in Week 2, 33% died in Week 3, 17% died in week 4, and only 17% survived over 5 weeks; in the 24-hour pre-painting group, only 17% mice died (or were euthanized due to sCRS) in Week 2, and 83% survived over 5 weeks. No difference in anti-tumor activity was found in these two groups, and all surviving mice became tumor free eventually. Thus, toxicity was less in mice with 24 hour pre-painting than in mice with 4 hour pre-painting with EC17.

Example 30

Pre-Painting Tumors with EC17 Reduces Toxicity (sCRS)

Figure 27A:
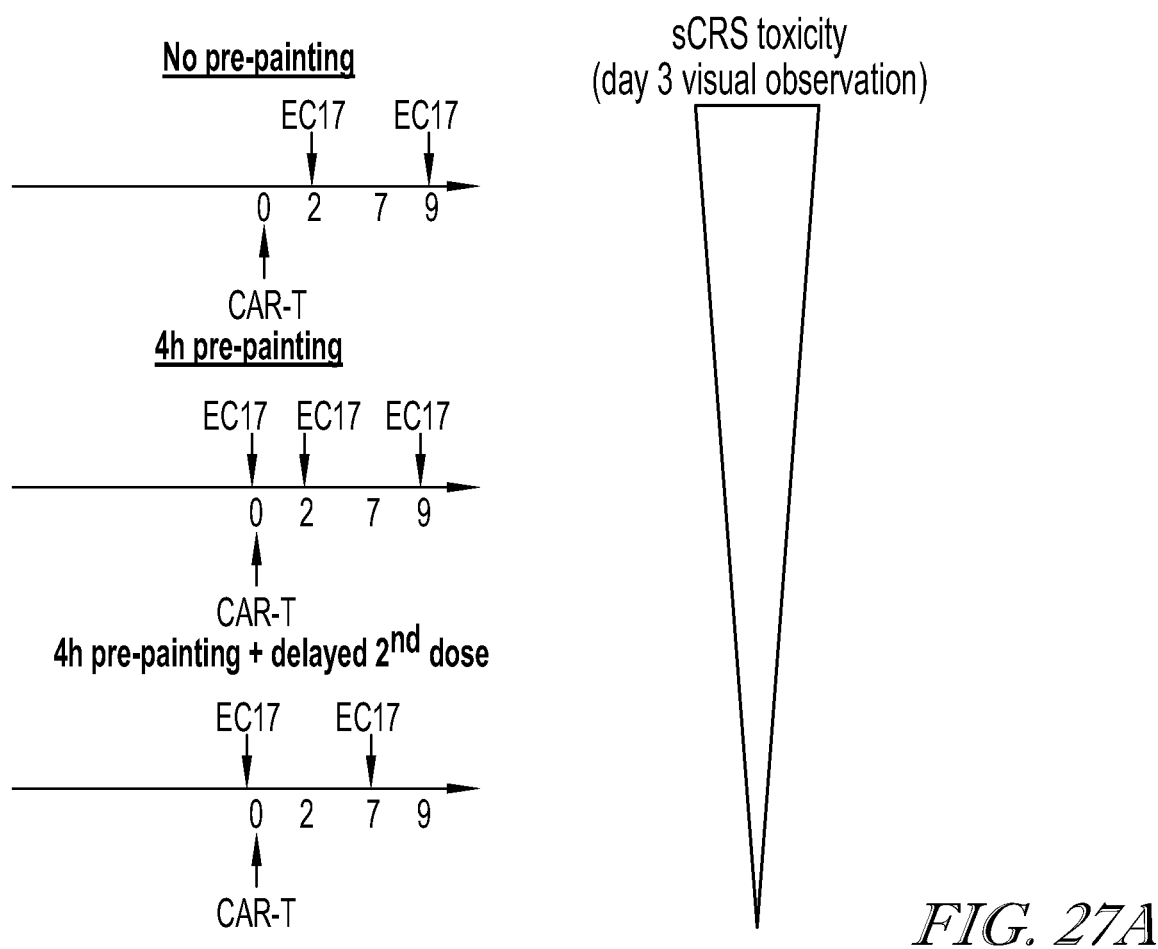
FIG. 27, Panel A shows the protocols for treatment. Panel B shows toxicity studies. Panel C shows the effect of EC17 pre-painting on tumor toxicity. Line1: no EC17. Line 2: EC17 4 h pre-done. Line 3: EC17 4 h pre-dose then 24 h post-CARTs. Line 4: EC17 48 h post CAR-Ts.
Figure 27B:
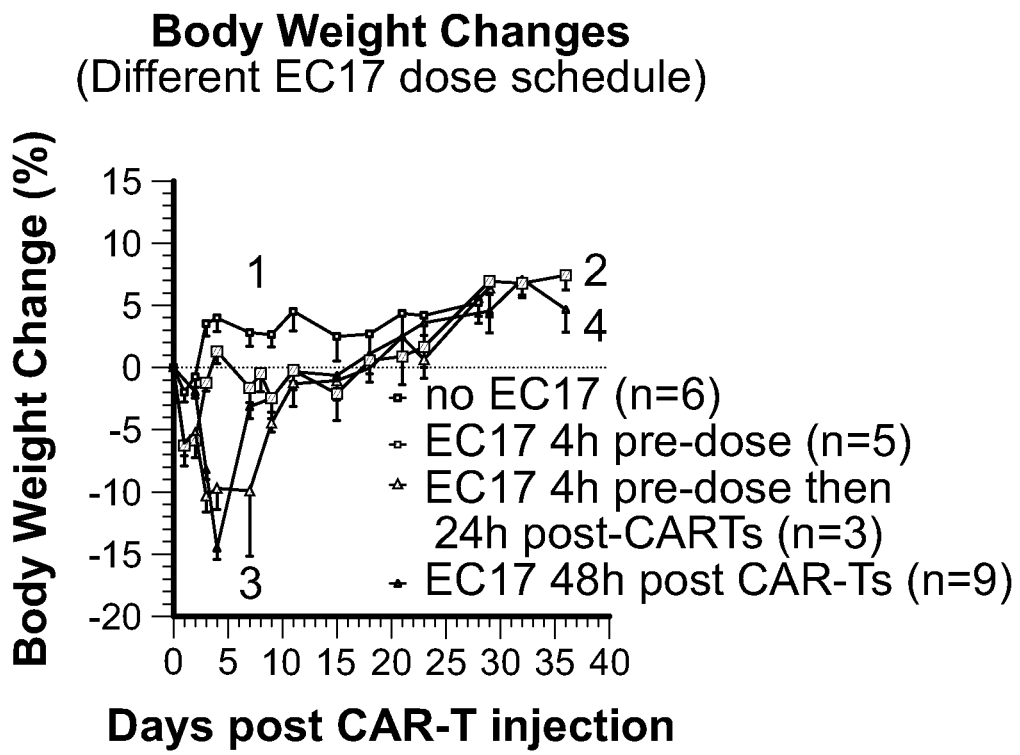
Figure 27C:
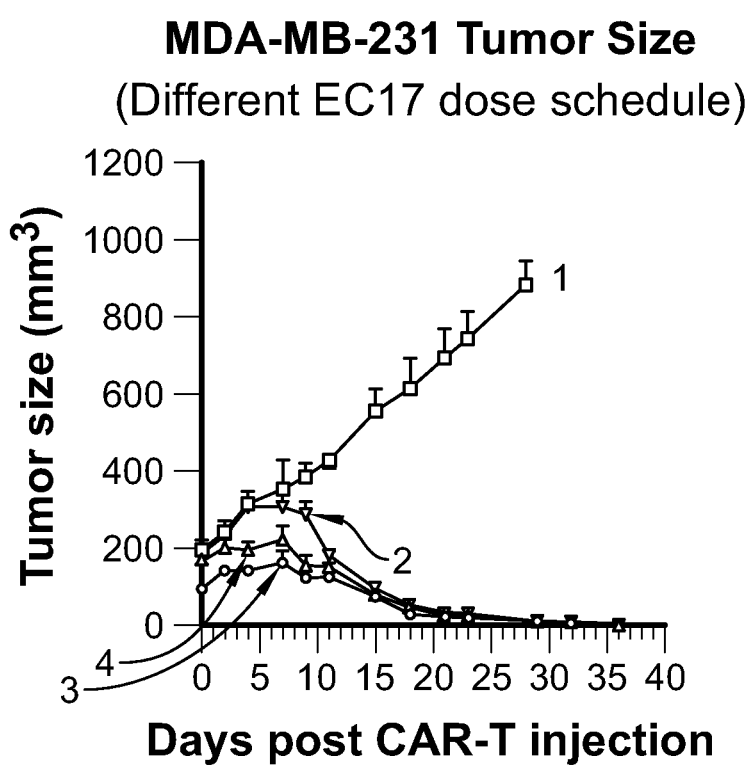
Figure 28A:
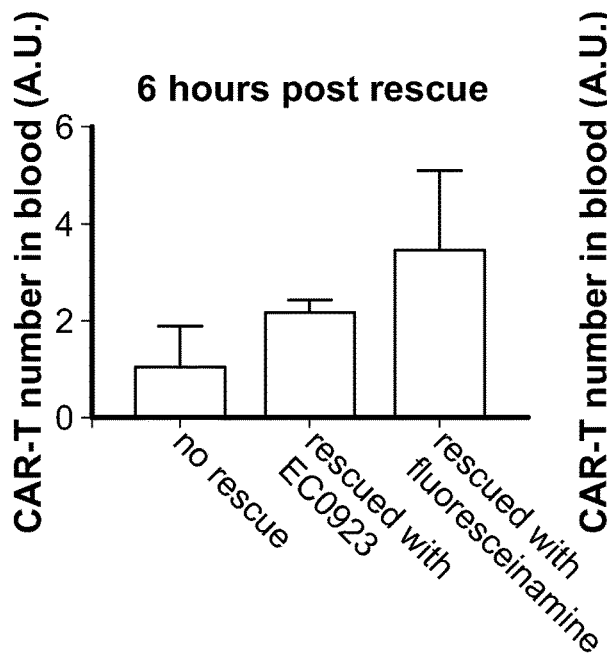
FIG. 28, Panels A-D, show CAR-T cell number in blood. CAR-T number in mice without rescue was considered as 1.
Figure 28B:
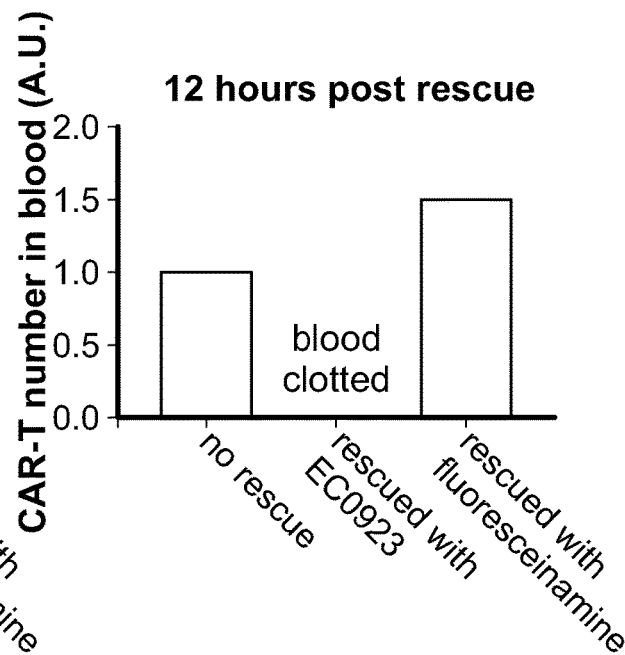
Figure 28C:
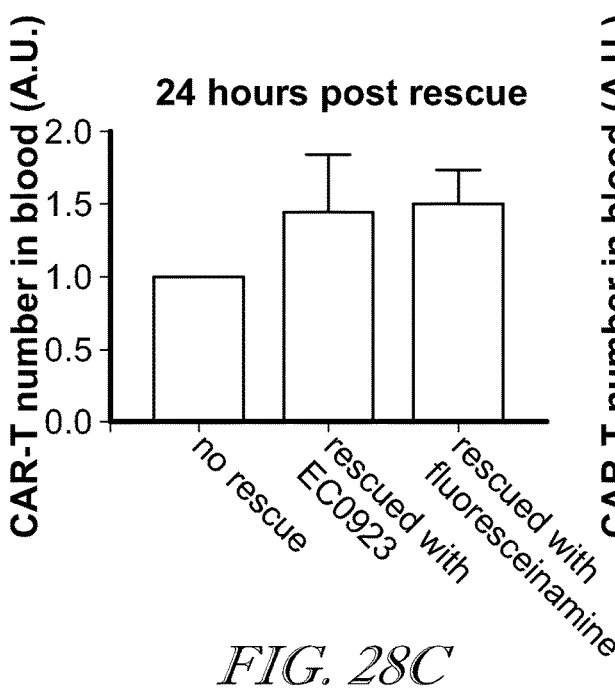
Figure 28D:
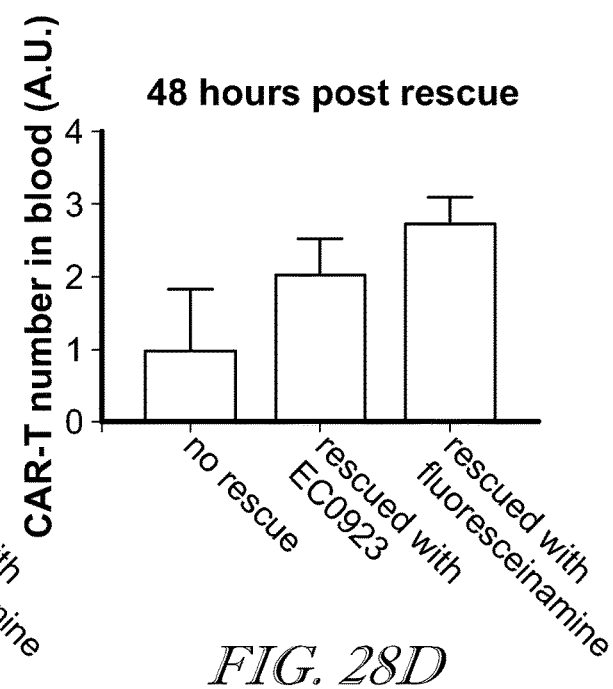

FITC-CAR-T related toxicity (e.g. sCRS) can be reduced by the combination of EC17 pre-painting and the delay of EC17 dosing post CAR-T administration. To explore strategies to control therapy-related toxicity, the combination of the EC17 pre-painting and EC17 dosing schedule optimization was evaluated. Mice bearing MDA-MB-231 tumors (100-200 mm3) were divided into three groups. Mice in group #1 (no EC17 pre-painting) were administered with 8 million FITC-CAR-T cells through the tail vein, and 500 nmol/kg EC17 was then dosed as a single dose per week (at days 2, 9, 16, etc.) post CAR-T administration. Mice in group #2 (EC17 4 hour pre-painting) were pre-painted with 500 nmol/kg EC17 4 hours before the administration of 8 million CAR-T cells, and 500 nmol/kg EC17 was then dosed as a single dose per week post CAR-T administration. Mice in group #3 (EC17 4 hour pre-painting+delayed second EC17 dose) were also pre-painted with 500 nmol/kg EC17 4 hours before the administration of 8 million CAR-T cells, but the second dose of 500 nmol/kg EC17 was postponed until 7 days after CAR-T administration, and the single dose per week schedule of EC17 dosing was then followed. Three days after CAR-T administration, mice in the three groups were evaluated by visual observation. As shown in FIG. 27A, mice in group #1 (no pre-painting) showed the worst sCRS, mice in group #2 ((EC17 4 hour pre-painting) showed sCRS but less severe than those in group #1. More importantly, mice in group #3 (EC17 4 hour pre-painting+delayed second EC17 dose) didn't show sCRS. As shown in FIG. 27B, mice in group #3 with the combined treatment with EC17 4-hour pre-painting and the delayed second EC17 dose showed the least body weight loss. The variations of the EC17 dosing schedule did not affect CAR-T anti-tumor activity, and mice in all three groups reached complete responses (FIG. 27C).

Example 31

CAR-T Number in Blood is Increased after Rescue

EC17/CAR-T therapy strategy is controllable through bridge displacement by either free folate or free fluorescein. To evaluate whether FITC-CAR-T therapy strategy is controllable through bridge (e.g. EC17) dose/displacement, NSG mice bearing MDA-MB-231 tumors (100-250 mm3) were administered with excess FITC-CAR-T cells (8 million) and dosed with 500 nmol/kg EC17 three times per week (at days 1, 3, 5, etc. post CAR-T administration). Those mice showed sCRS after one week, and were divided into three groups. One group of mice was i.v. injected with 10 umol/kg of unconjugated folate (EC0923), the second group was i.v. injected with 10 umol/kg of fluoresceinamine for "rescue", whereas the third group was not treated as a control group. Mice from three groups were then euthanized at 8, 12, 24 and 48 hours post injection of EC0923 or fluoresceinamine, and their blood samples were analyzed for CAR-T cell number and cytokine levels. CAR-T cells in blood were stained with anti-human CD45 antibody labeled with APCeF780 (Biolegend) and counted by FACS. Count-Bright™ Absolute Counting Beads (ThermoFisher Scientific) were mixed into the samples and used as a reference for cell counting. As shown in FIG. 28A-D, treatments with both 10 umol/kg EC0923 (unconjugated folate) and 10 umol/kg fluoresceinamine (unconjugated fluorescein) caused an increase of CAR-T number in blood circulation, indicating that some CAR-T cells were dissociated from their target tumor cells and returned back to the blood circulation when the bridge (EC17) was displaced by excess unconjugated folate or fluorescein. The increase of CAR-T cell count in blood circulation of rescued mice was found as early as 6 hours post EC0923/fluorescein injection, indicating that the mice responded to the displacement "rescue" quickly. Furthermore, fluorescein seemed to cause more CAR-T displacement than folate (EC0923), which is correlated with previously described findings that rescue with fluoresceinamine reduced cytokine production in blood more strongly than folate did.

Example 32

Comparison of Three Rescue Reagents (Folic Acid, Sodium Fluorescein (NAFL) And Leucovorin)

Figure 30A:
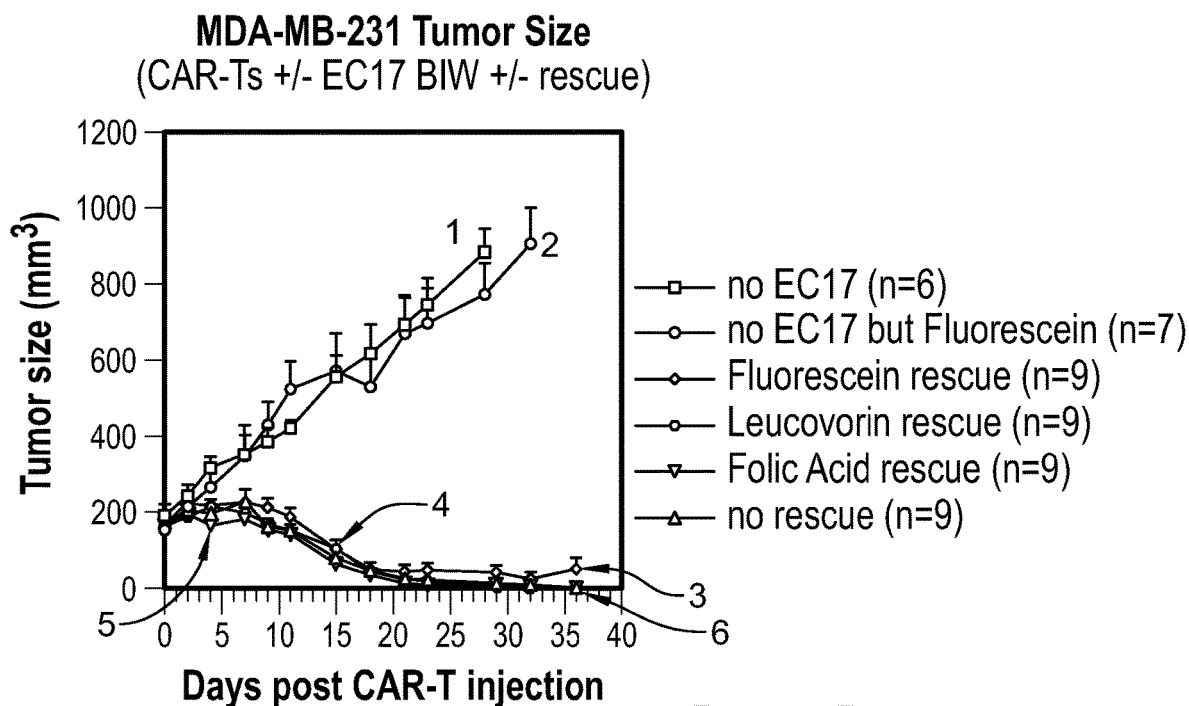
FIGS. 30A and 30B show rescue assays. Mice with fluorescein rescue had the least body weight loss. All mice with rescue reached complete response, except ⅖ in the fluorescein rescue group. Line 1 no EC17. Line 2: no EC17 but Fluorescein. Line 3: Fluorescein rescue. Line 4: Leucovorin rescue. Line 5: Folic acid rescue. Line 6: no rescue.
Figure 30B:
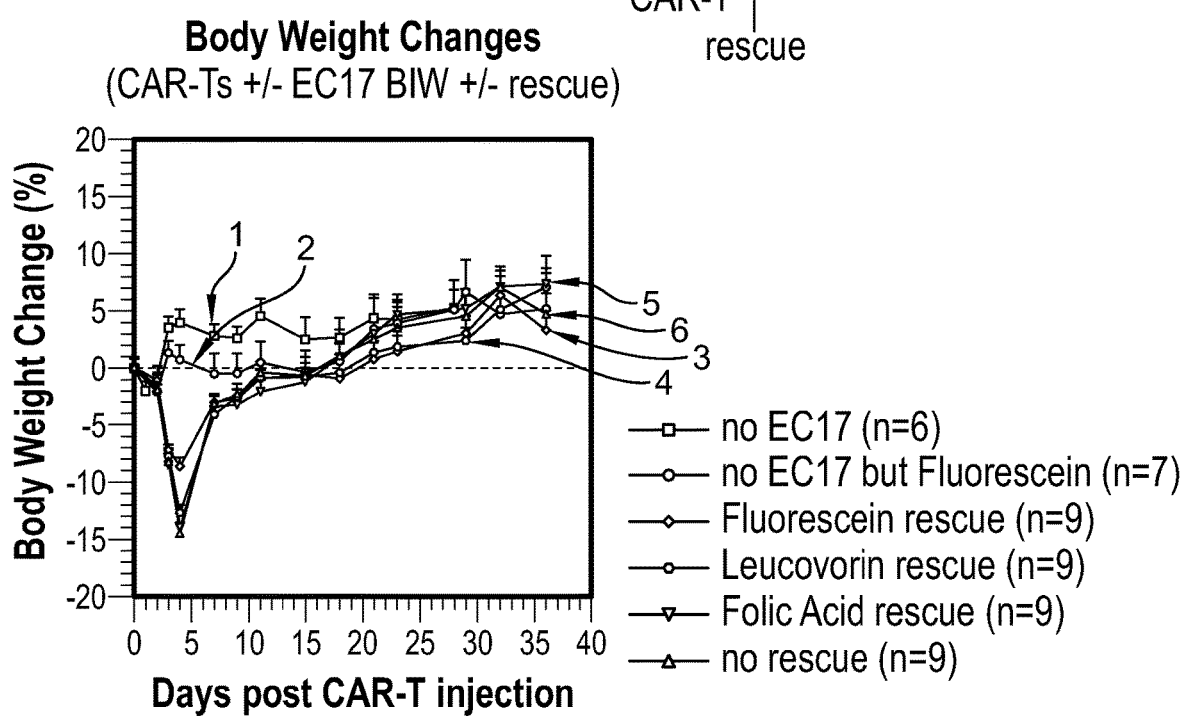

One dose of folate, sodium fluorescein, or leucovorin can "rescue" mice under sCRS by displacing the bridge EC17 between CART and tumor cells. To evaluate whether mice with FITC-CAR-T therapy related sCRS can be rescued by using competitors which may displace EC17 from either FITC-CAR-T or FR+ tumor cells, 49 NSG mice bearing MDA-MB-231 tumors (150-250 mm3) were administered with excess FITC-CAR-T cells (8 million), 36 of them were then dosed with 500 nmol/kg EC17 48 hours post CAR-T administration, 6 of them were not dosed with EC17 and were used as "No EC17" control, and 7 of them were dosed with 260 umol/kg sodium fluorescein (no EC17 but Fluorescein) to test its toxicity. One day later, while the mice in the "No EC17" control group and "no EC17 but Fluorescein" were healthy, mice dosed with EC17 started to show sCRS and were divided into four groups. Each group was i.v. injected with 10 umol/kg of Leucovorin, or 10 umol/kg folic acid, or 260 umol/kg sodium fluorescein, or nothing as an un-rescued control. Those mice were evaluated 10 hours after the rescue injection, and were found to have different levels of severity of sCRS. Although all three rescued groups showed better recovery from sCRS compared to the un-rescued control group, the levels of recovery in these rescue groups were different. The orders of sCRS severity were (from worst to least): no rescue group >leucovorin rescue group >folic acid rescue group >sodium fluorescein rescue group >no EC17 group. Mouse body weight changes were also monitored as the indication of toxicity. As shown in FIG. 29A-E, mice rescued with fluorescein had the least body weight loss comparing to the other two rescue groups. To evaluate whether the rescue injections affect the anti-tumor activity of FITC-CAR-T cells, these mice were dosed with 500 nmol/kg EC17 twice per week (days 9, 11, 15, 18, 22, 25, etc.) and the tumor size was monitored. As shown in FIG. 30A and FIG. 30B, almost all mice were cured except 2 out of 9 mice in the fluorescein rescue group still had a tiny tumor left at day 36 post CART injection, indicating that a single dose of rescue reagents had little effect on the anti-tumor activity of FITC-CAR-Ts.

Example 33

Sodium Fluorescein Rescue

Sodium fluorescein as a rescue agent for mitigation of cytokine release syndrome in EC17/CAR-T antitumor therapy is shown.

Materials:

EC17 (folate-FITC, m.w. 873) was synthesized in house. Sodium fluorescein (AK-FLUOR®, fluorescein injection, USP) was purchased from Purdue Pharmacy.

In-Vivo Methods:

Cell Line

MDA-MB-231 is a human triple-negative breast cancer (TNBC) cell line that expresses a high level of the human FRα. THP1-FRβ is a CD33+CD123+ human acute myeloid leukemia cell line stably expressing human FRβ. The cells were grown respectively in a folate-free RPMI1640 medium (Gibco BRL) (FFRPMI) containing 5-10% heat-inactivated fetal calf serum (HIFCS) and maintained under a 5% $CO_2$ atmosphere using standard cell culture techniques.

Mice

Female NSG™ (NOD.Cg-Prkdc$^{scid}$ Il2rg$^{tm1Wjl}$/SzJ, stock #005557) mice were purchased from The Jackson Laboratory (Bar Harbor, ME) and used when they reached ~4 weeks of age. The mice were fed a folate-deficient diet (TestDiet, St. Louis, MO) on the day of arrival.

Tumor Implantation

MDA-MB-231 tumors were generated by subcutaneous implantation of cultured cells at $2\times10^6$ in NSG mice.

CAR-T Cell Preparation

FITC-CAR-T cells were prepared as described previously. After culturing in-vitro for 12-20 days, they were frozen and stored at −80° C. in a freezing reagent containing 50% heat-inactivated AB+ human serum, 40% T cell culture media, and 10% DMSO. Frozen CAR-T cells were quickly thawed at 37° C., washed twice with PBS, and used for animal injection.

EC17/CAR-T Therapy of Tumor-Bearing Mice

Figure 31:
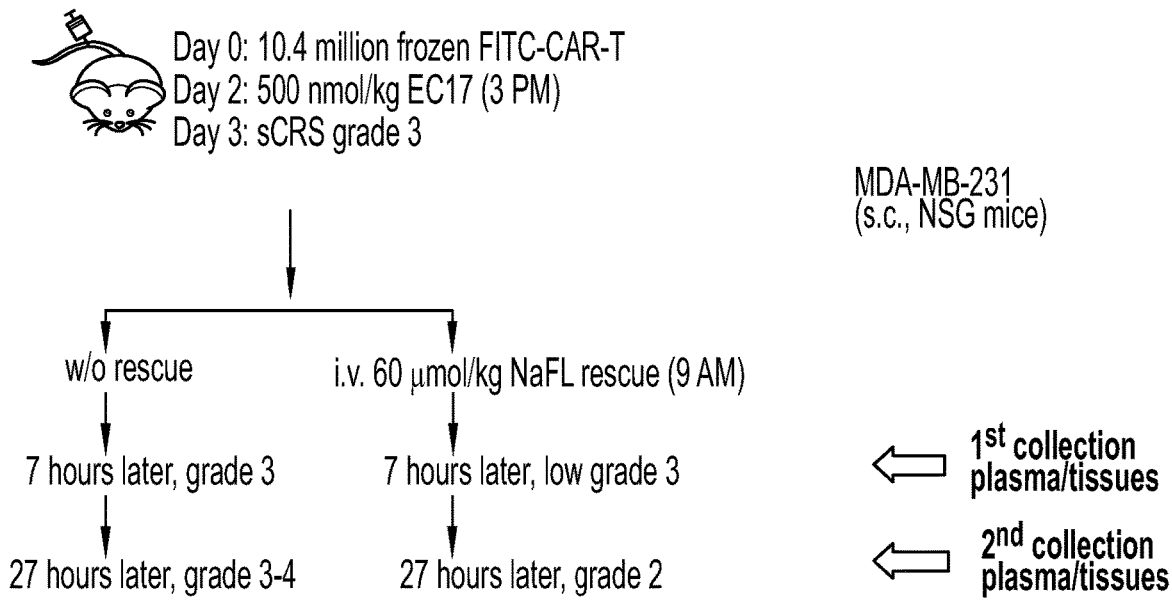
FIG. 31 shows a sodium fluorescein (60 umol/kg) rescue study schema.

In general, EC17/CAR-T therapy initiated when mouse tumors reached ~200-250 mm$^3$ and weekly EC17 doses at 500 nmol/kg started 2 days after the CAR-T administration. All EC17 doses were given towards the end of day (~3-4 PM) to allow cytokine release syndrome (CRS) to develop overnight. Sodium fluorescein rescue at various doses (0.06-60 μmol/kg) was administrated after the first dose of EC17, when the animals experienced a severe CRS of grade 3-4 on a 0-5 grading scale (FIG. 31). Plasma samples at various time points (3-27 hours) post sodium fluorescein rescue were collected for multiplex cytokine analysis.

Whole Blood Cell Analysis by Flow Cytometry

Plasma was removed from predetermined volumes of whole EDTA treated blood with a 10-minute 4° C. spin at 3000 g and the resulting cell pellets were incubated with a 10-fold volume of room temperature 1×RBC lysis solution [prepared from 10× stock; Biolegend, catalog #420301] for 5 minutes, centrifuged at 400 g for 5 min, and the cell pellet was washed in a 10-fold volume of ice cold phosphate buffered saline pH=7.4 and filtered with a 40 m nylon filter and then pelleted again. The leukocyte pellets were then resuspended in flow cytometry staining solution [1% bovine serum albumin, 50 mg/mL human IgG (Equitech Bio, cat #SLH56-0001), 0.9% sodium azide in a phosphate buffered saline, pH=7.4] supplemented with both anti-mouse FcγIII/II receptor (CD16/CD32) block [clone 2.4G2; BD Bioscience, catalog #553142 at 1:100 (v/v) dilution] and anti-human Fc Block [BD Biosciences, catalog #564220 at 1:50 (v/v) dilution]. Leukocyte surface marker staining was performed with the addition of the following fluorochrome conjugated monoclonal antibodies added to each sample for 20 minutes on ice in the dark: anti-human CD45-APCeF780 [clone HI30, eBioscience #47-0459-42 at 1:20 (v/v) dilution], anti-human CD137-BV650 [clone 4B4-1, BD Bioscience #564092 at 1:20 (v/v) dilution], anti-human CD8α-

PECy7 [clone RPA-T8, BD Bioscience, catalog #557746 at 1:20 (v/v) dilution], anti-human CD4-Percpe710 [clone SK3, eBioscience catalog #46-0047-42 at 1:20 (v/v) dilution]. After leukocyte staining, cells were washed with PBS and resuspended in cold PBS containing 53,000 CountBright™ beads [Invitrogen catalog #C36950] and transferred to flow cytometry collection tubes. Flow cytometry data was collected on the Gallios flow cytometer (Beckman Coulter, Brea, CA), where a minimum of 15,000 CountBright™ bead events were collected in an attempt to collect enough leukocyte events for an accurate count of infused CAR T cells in each mouse blood sample. Determination of the concentration of CAR T cells in each blood sample was calculated according to Invitrogen's instructions. Briefly, CAR T cells were identified as human CD45+ GFP+ events and were easily distinguished and counted using the Kaluza™ flow cytometry software. CountBright™ beads were uniformly labeled with a fluorochrome not utilized in the antibody panel used to identify the CAR T cells and were easily distinguished from the leukocytes and bead events were counted. Because 53,000 CountBright™ beads were added to each sample tube, we calculated the ratio of 53,000 total beads to bead events collected per sample and set the bead ratio equivalent to the unknown number of CAR T cells in each sample divided by the known number of CAR T cell events collected. Solving for the unknown gave us the number of CAR T cells isolated from each blood sample of known volumes. The number of CAR T cells in the circulation of each infused mouse was then represented on the graphs as the total number of CAR T cells per 50 μL of whole blood analyzed. Statistical significance was determined by utilizing an unpaired, two-tailed, students t-test with significance set at $p<0.05$ for comparisons between each of the three groups of mice.

Preparation of Single Cell Suspension of Tumor and Normal Tissues

Solid tumors (100-1000 mm$^3$) were harvested, weighed, and minced into small pieces and then transferred into 50 mL tubes containing 20 mL of a tumor digestion cocktail. The enzymatic tumor digestion cocktail consisted of 0.5 mg/mL Collagenase IV (Sigma-Aldrich, Catalog #C5138), 0.5 mg/mL Hyaluronidase (Sigma-Aldrich, Catalog #H3506) and 0.1 mg/mL DNase I (Sigma-Aldrich, Catalog #DN25) in serum-free and folate-deficient RPMI1640 medium supplemented with antibiotics. The tumor fragments were digested for one hour at 37° C. at 300 rpm on a horizontal shaker. Afterwards, the tumor digest was centrifuged at 400×g for 5 minutes and tumor cell pellet underwent a red blood cell lysis step, was then washed with cold phosphate-buffered saline (PBS, pH 7.4) and finally filtered through a 40 m nylon cell strainer.

Data and Results:

As shown in FIG. 31, effects of one-time sodium fluorescein rescue at 60 μmol/kg on both cytokine production and CAR-T anti-tumor activity in-vivo were evaluated. On day 0, ~10.4 million FITC-CAR-T cells were administered intravenously into MDA-MB-231 tumor bearing NSG mice. Approximately 48 hours after CAR-T cell infusion, mice were separated into 3 groups. The first group (#1) was not dosed with EC17 and served as the CAR-T cell control, the second (#2) and the third (#3) groups were intravenously injected with a single dose of EC17 (500 nmol/kg). At 17 hours post the EC17 dose, mice in groups #2 and #3 that received EC17 (500 nmol/kg) showed sCRS while mice in the CAR-T cell control group #1 did not show any related toxicity. Group #2 then received a single intravenous sodium fluorescein (60 μmol/kg) while group #3 was left un-rescued. Seven hours after sodium fluorescein rescue, mice in group #2 rescued with 60 μmol/kg sodium fluorescein were recovering and scored at a low grade 3 sCRS while mice without rescue in group #3 still had a grade 3 sCRS. Three satellite animals from each group were euthanized to collect blood and organs for cytokine analysis and organ toxicity evaluation. Whole blood was obtained via cardiac puncture and collected into EDTA containing tubes. Twenty-seven hours after sodium fluorescein rescue, mice rescued with 60 μmol/kg sodium fluorescein in group #2 were recovering and sCRS scale decreased to grade 2, while mice without rescue in group #3 had worse sCRS (grade 3-4). At this time, 6 satellite mice from each group were euthanized for blood collection and organ evaluation. The remaining mice were dosed with a single dose of 500 nmol/kg EC17 every week if desired, and the EC17 dosing dates were labeled in FIG. 36 as dashed vertical lines occurring after the notation "EC17". Tumor volume and body weight changes were monitored 2-3 times per week.

Figure 36A:
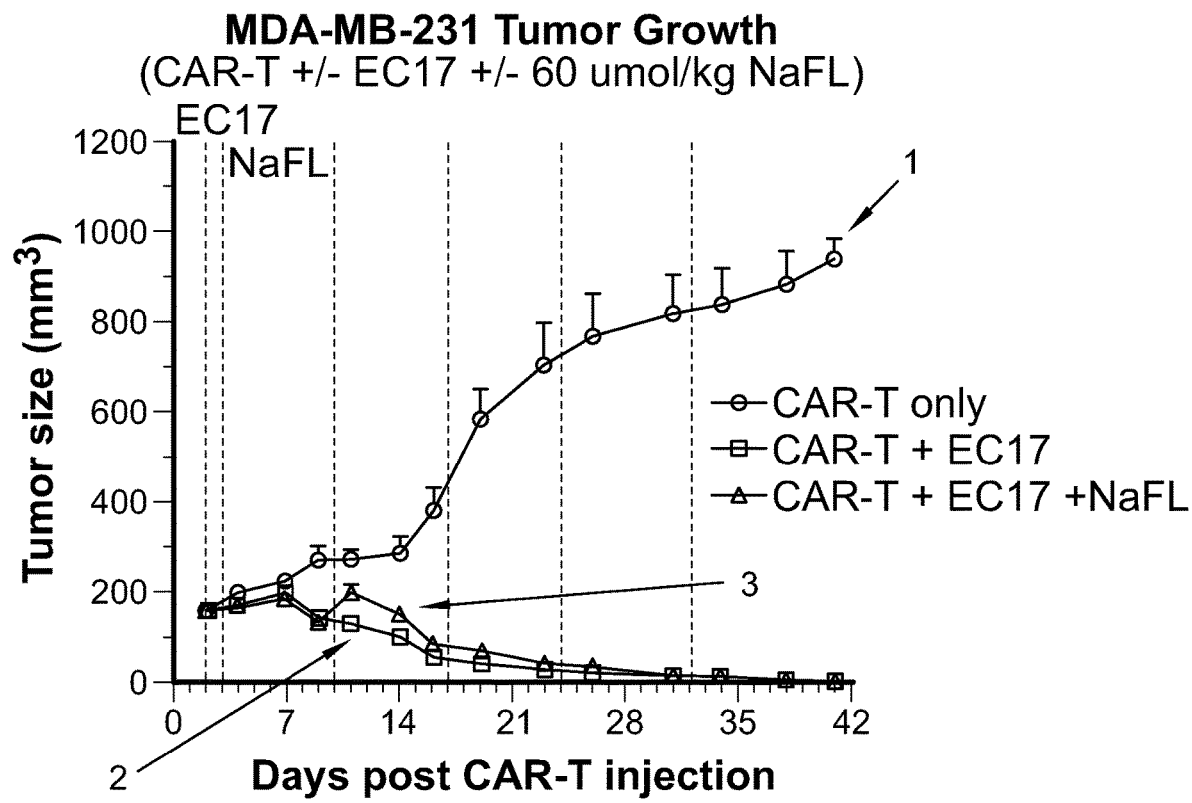
FIGS. 36A and 36B show NaFL rescue effect on FITC CAR-T anti-tumor activity and body weight change. (1) CAR-T only; (2) CAR-T+EC17; (3) CAR-T+EC17+NaFL.
Figure 36B:
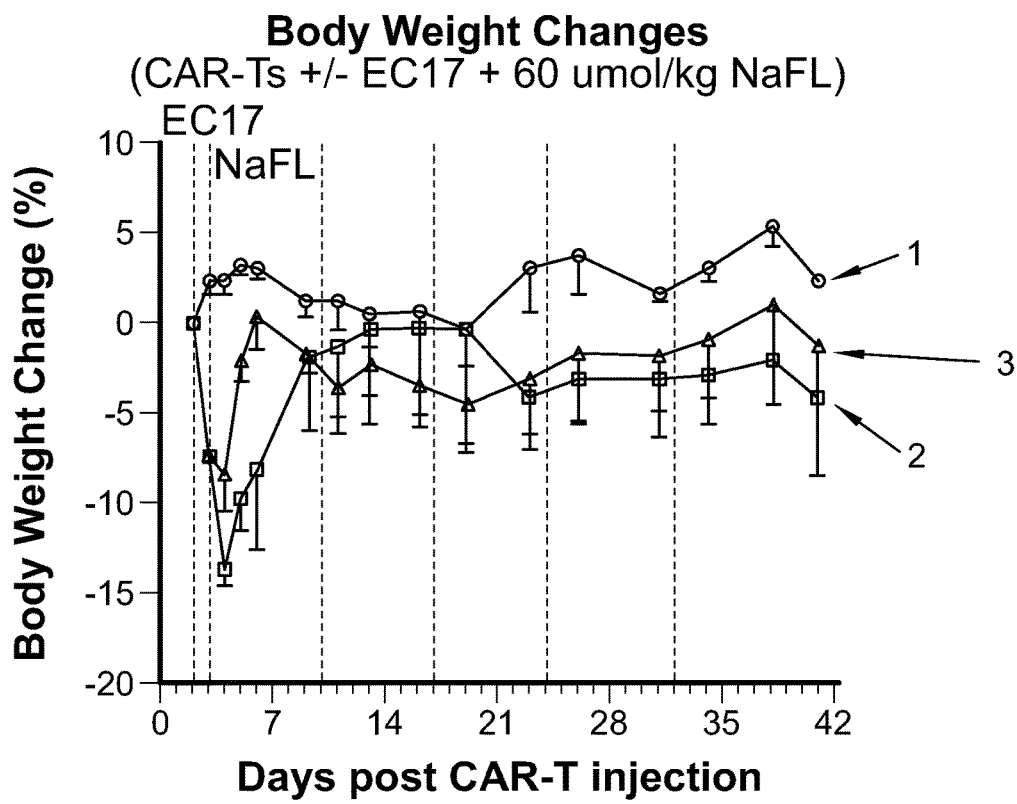

As shown in FIG. 36, although tumors in the CAR-T only group grew rapidly, tumors in mice dosed with 500 nmol/kg EC17 SIW kept growing slowly for about one week, and then started to shrink and disappeared eventually. Although it took a few more days for tumors in the rescued groups to start to shrink, no significant difference in tumor growth between the rescued group and non-rescued group was found. This finding suggested that one dose of 60 μmol/kg sodium fluorescein did not interfere with CAR-T anti-tumor activity in vivo. As shown in FIG. 36B, mice in the rescued group seemed to have less body weight loss compared to those in the un-rescued group, indicating that 60 μmol/kg sodium fluorescein rescue can reduce the CAR-T therapy related toxicity (shown as less body weight loss).

Figure 32A:
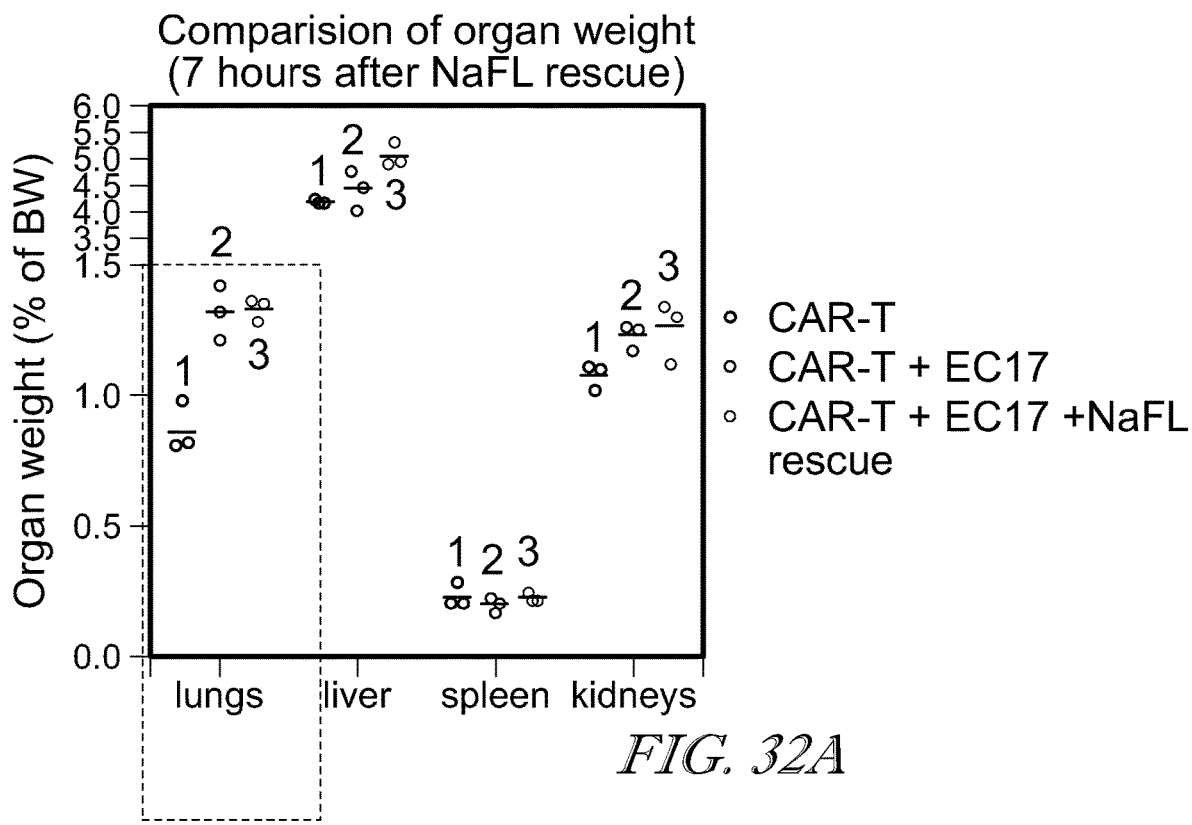
FIGS. 32A and 32B show NaFL rescue related organ weight changes. (1) CAR-T; (2) CAR-T+EC17; (3) CAR-T+EC17+NaFL rescue.
Figure 32B:
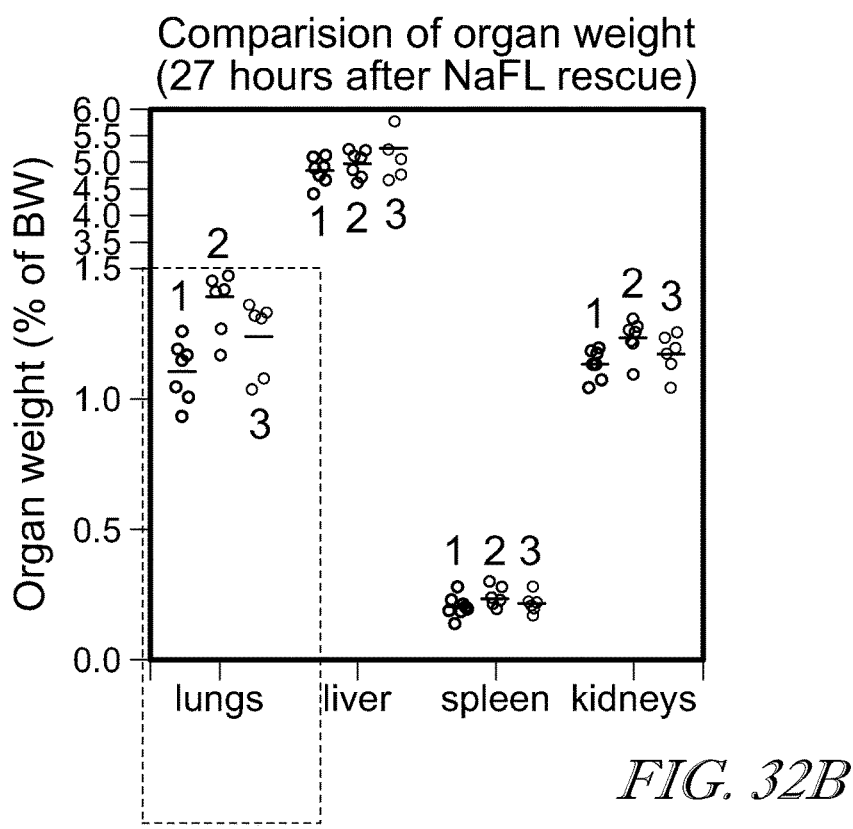
Figures 33A, 33B:
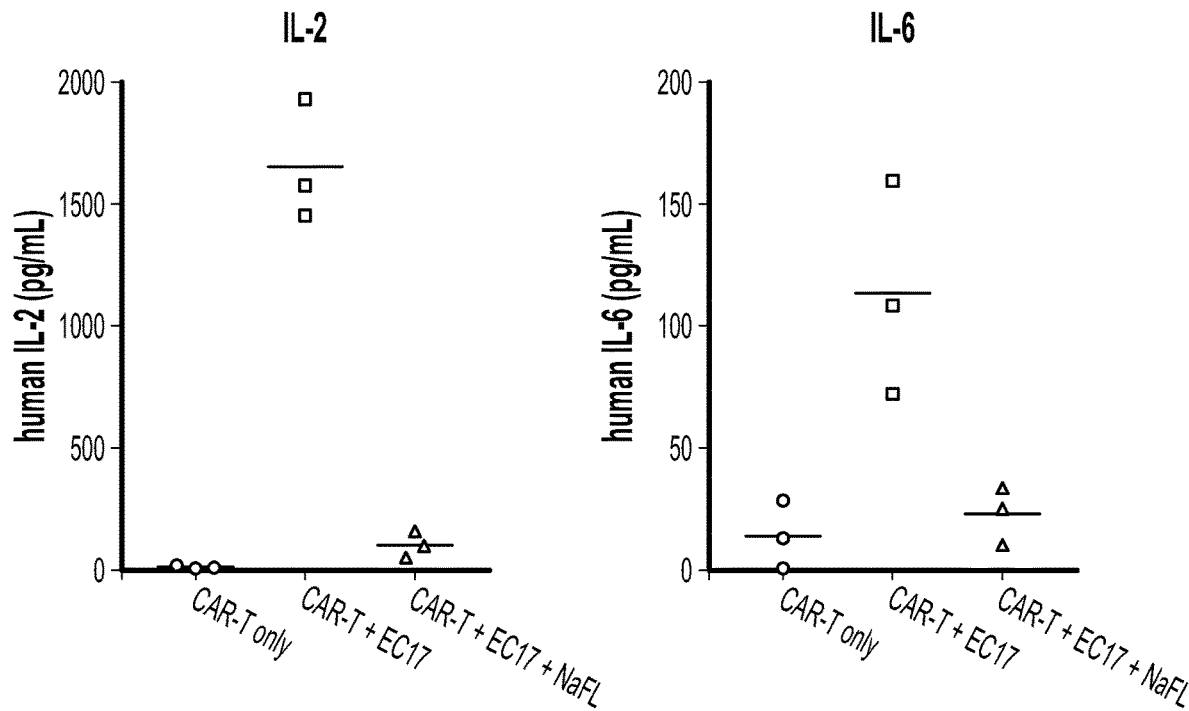
FIG. 33, Panels A-G, show cytokine production in mouse blood 7 hours after NaFL rescue.
Figures 33C, 33D:
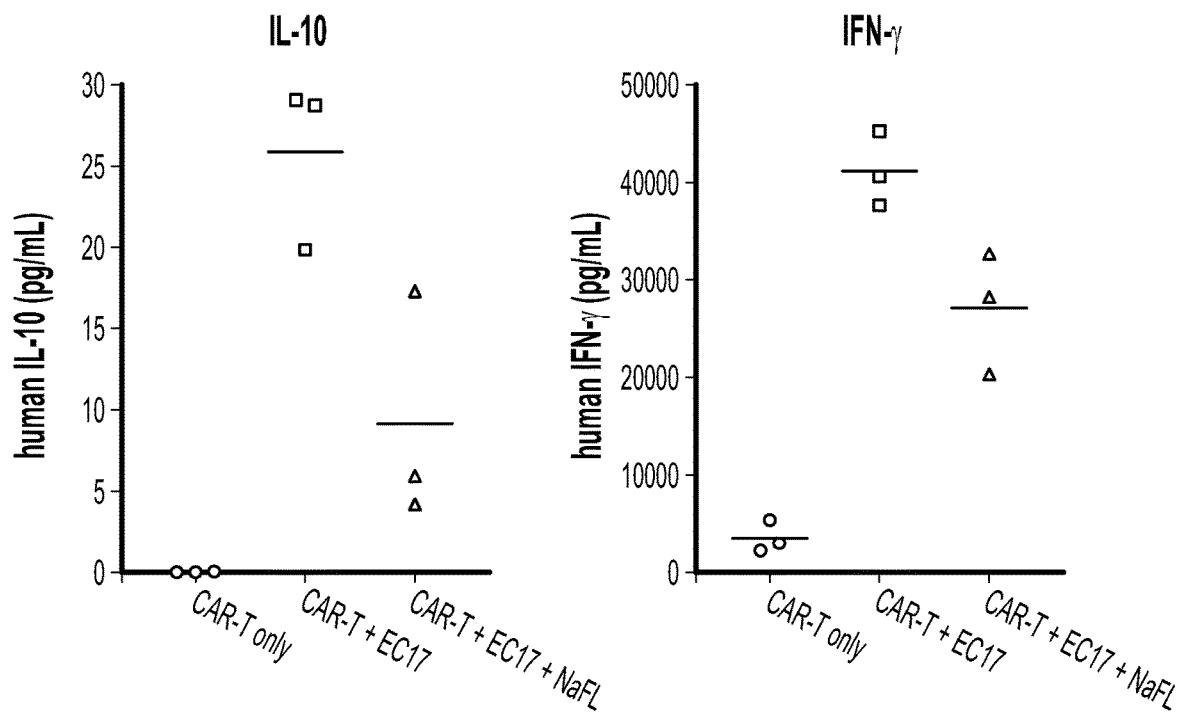
Figure 33E:
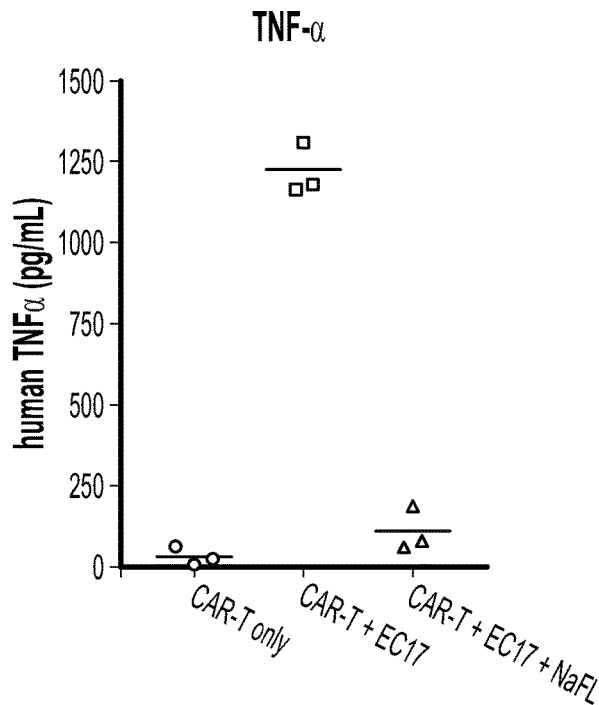
Figure 33F:
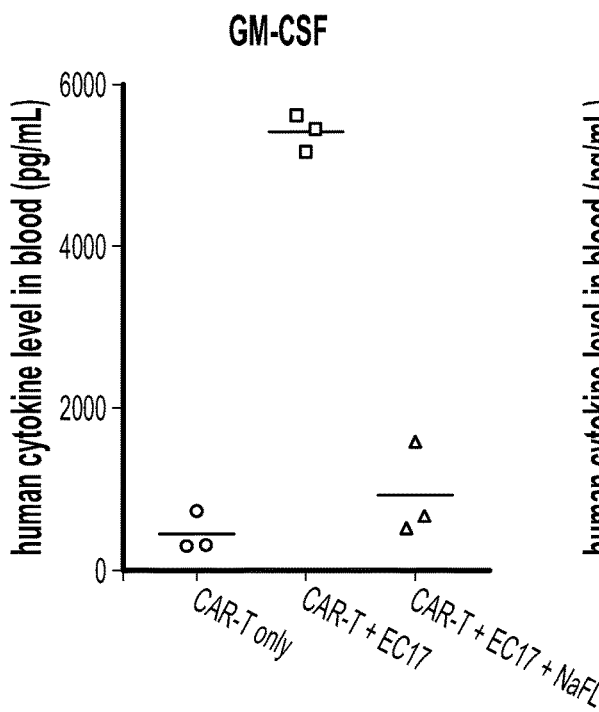
Figure 33G:
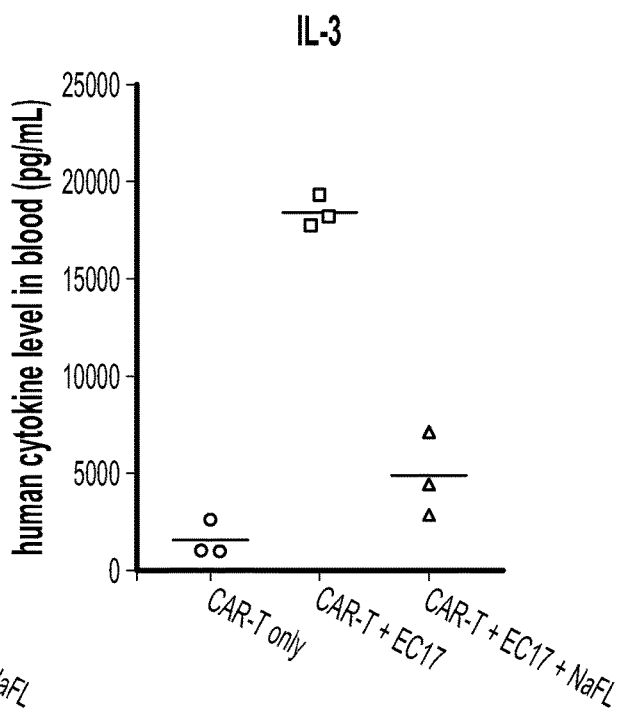
Figures 34A, 34B:
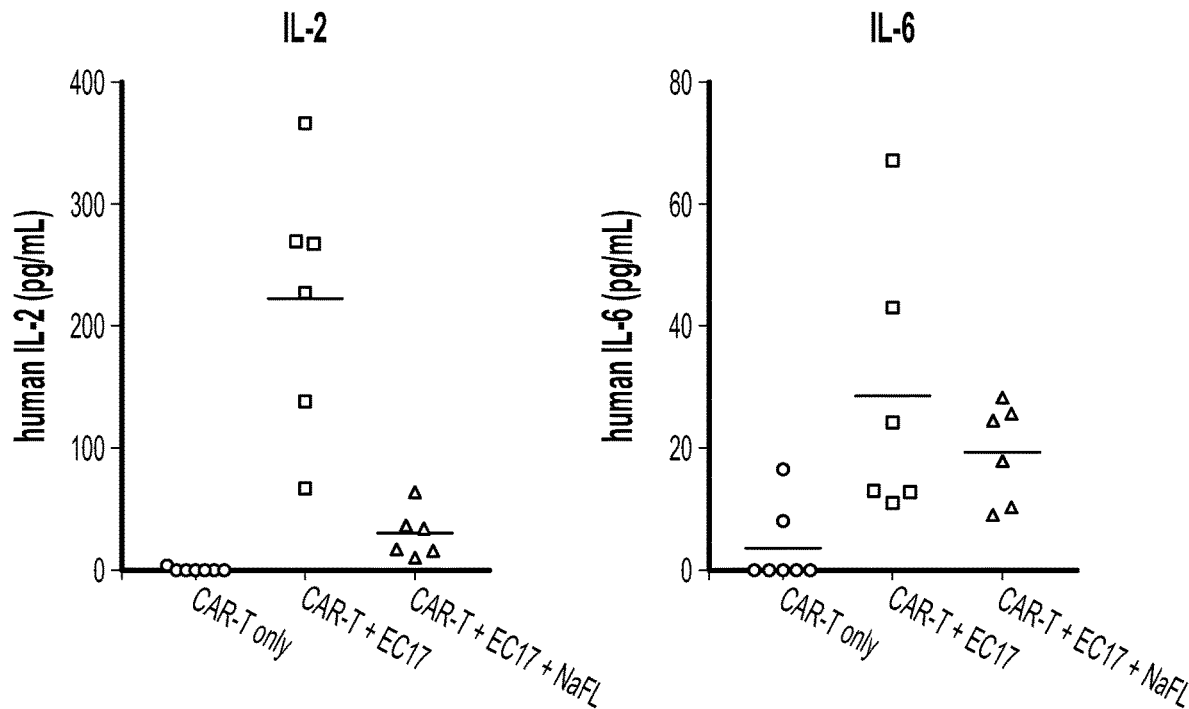
FIG. 34, Panels A-G, show cytokine production in mice (27 hours after NaFL rescue).
Figures 34C, 34D:
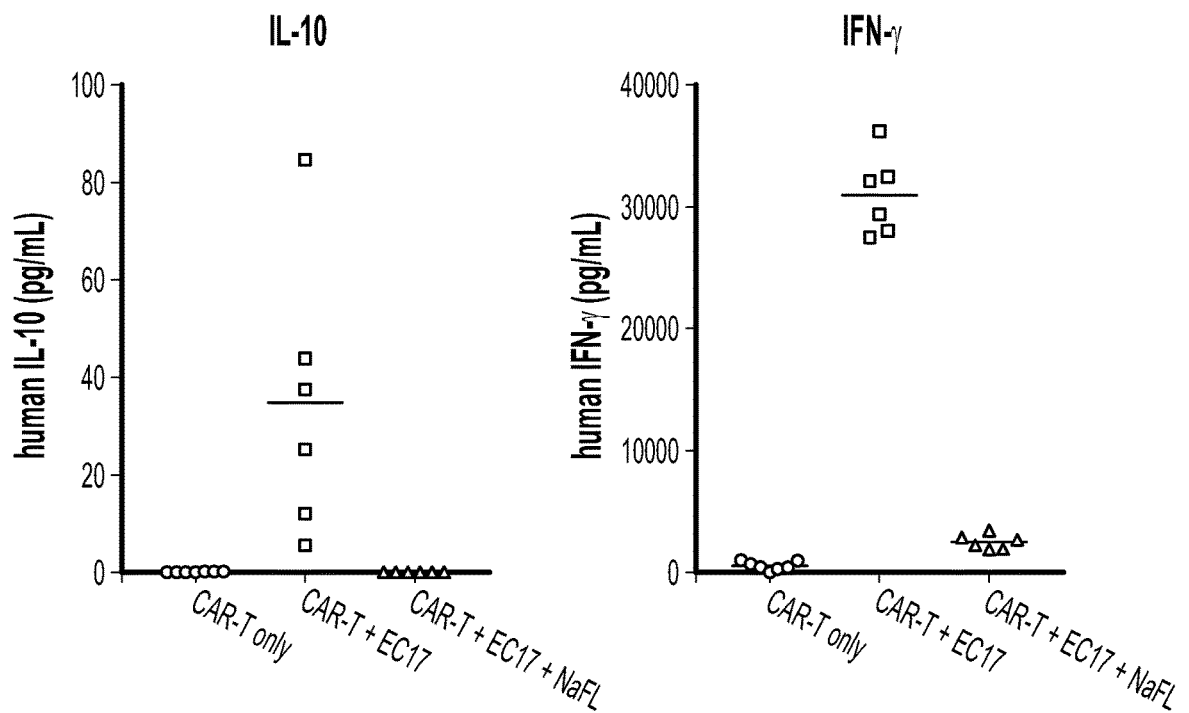
Figure 34E:
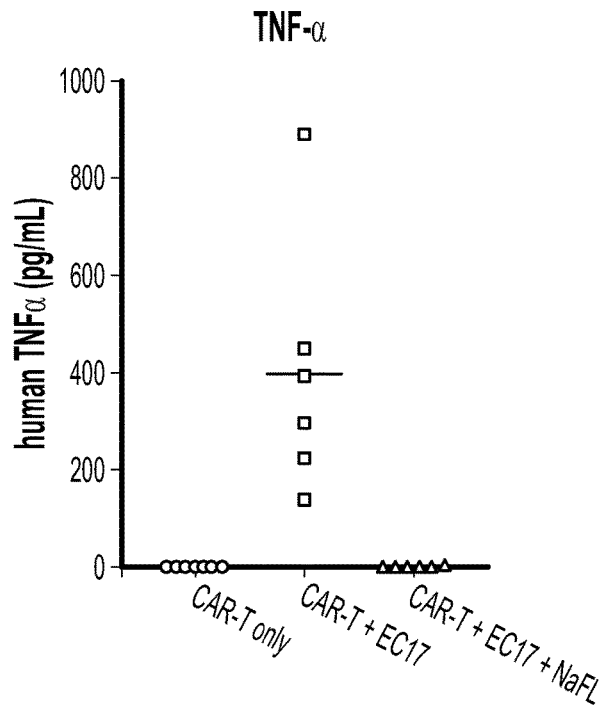
Figure 34F:
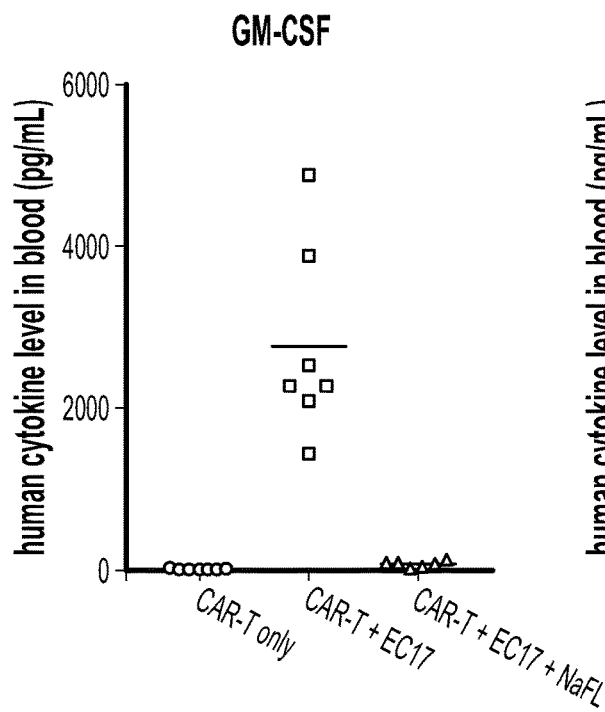
Figure 34G:
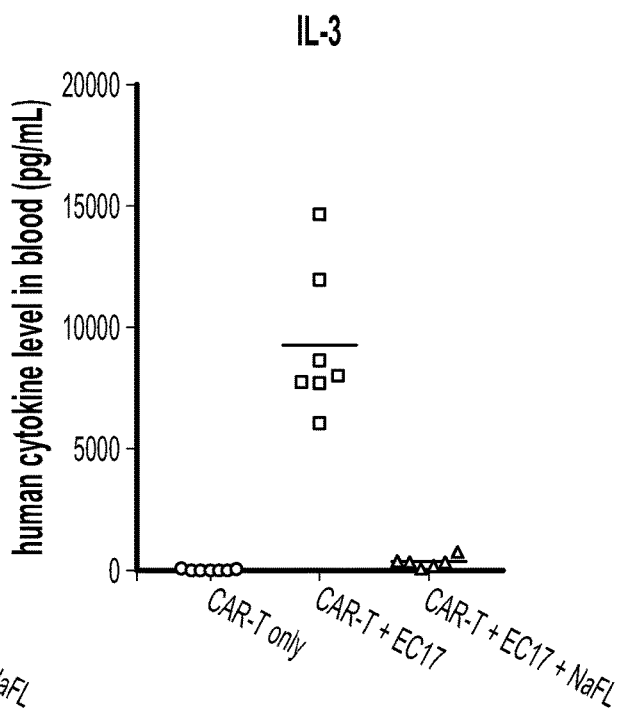
Figure 35A:
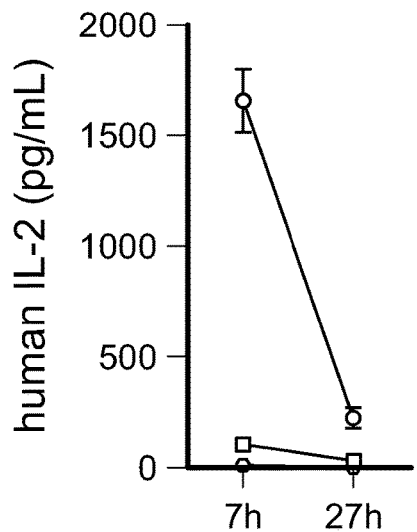
FIG. 35, Panels A-E, show cytokine production reduced in mouse blood (<7 hours after NaFL rescue).
Figure 35B:
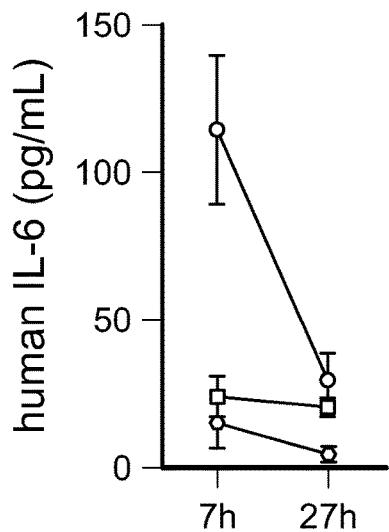
Figure 35C:
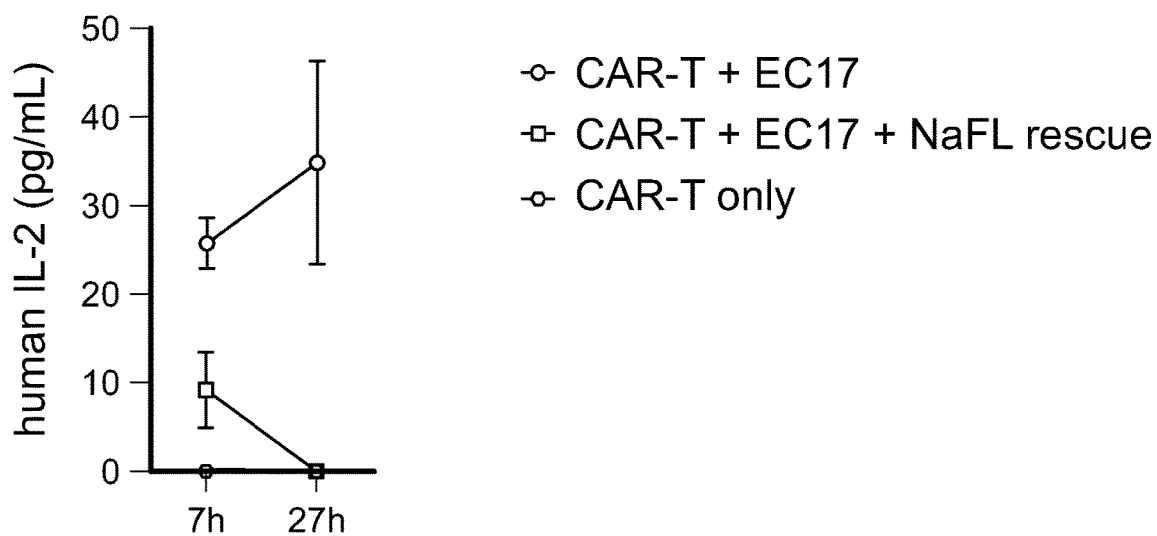
Figure 35D:
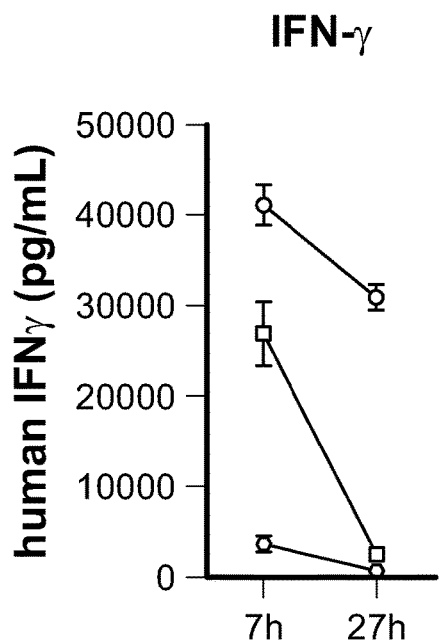
Figure 35E:
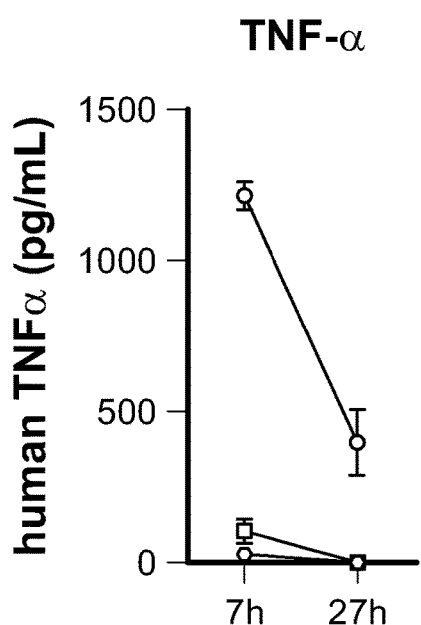

Organs from all three groups were also evaluated at 7 hours and 27 hours post sodium fluorescein rescue and their weights were compared as shown in FIG. 32. As shown in FIG. 32A, 7 hours after rescue, lungs from mice treated with CAR-T and EC17 were swollen and heavier than lungs collected from mice in the CAR-T cell only group. As shown in FIG. 32B, 27 hours after rescue, lung weights from the rescued group decreased more than that of the un-rescued group. Although no obvious weight differences in liver or kidneys were found between the rescued group and un-rescued group, organs in the rescued group looked healthier by visual examination (less discoloring of liver and kidney, and less lung edema). For FIG. 32, lung edema was improved 27 hours after NaFL rescue.

CRS-associated cytokine levels were also measured to determine whether rescue inactivates CAR-T cells and reduces cytokine production. Human cytokine levels in mouse plasma samples were measured using FACS-based Multi-Analyte Flow Assay Kits (BioLegend) and ELISA-based cytokine detection kits (ThermoFisher Scientific) by following the manufacturer's instructions. FIG. 33A-G showed cytokine levels 7 hours post rescue. For FIG. 33, cytokine production in mouse blood was reduced in <7 hours after NaFL rescue. FIG. 34A-G show cytokine levels 27 hours post rescue. For FIG. 34, cytokine production in mouse blood was reduced in <7 hours after NaFL rescue. FIG. 35A-E show time dependent changes in cytokine levels. For FIG. 35, there was a delay between cytokine levels in blood and mouse overall condition (CRS scores). In summary, mice administered with CAR-T cells but without EC17 had a very low level of cytokines in their blood, while mice dosed with EC17 had increased cytokine levels in their blood, including IL-2, IFN-γ, TNF-α, IL-6, IL-10, GM-CSF, and IL-3. More importantly, cytokine levels in the mice rescued with 60 µmol/kg sodium fluorescein were much lower than those in un-rescued mice (both 7 hours and 27 hours post rescue). The levels of some cytokines (e.g. IL-2, TNF-α, IL-3, GM-CSF, and IL-6) were decreased to normal range 7 hours post rescue, while other cytokines (e.g. IFN-γ) decreased to near normal range at 27 hours post rescue.

Figure 50:
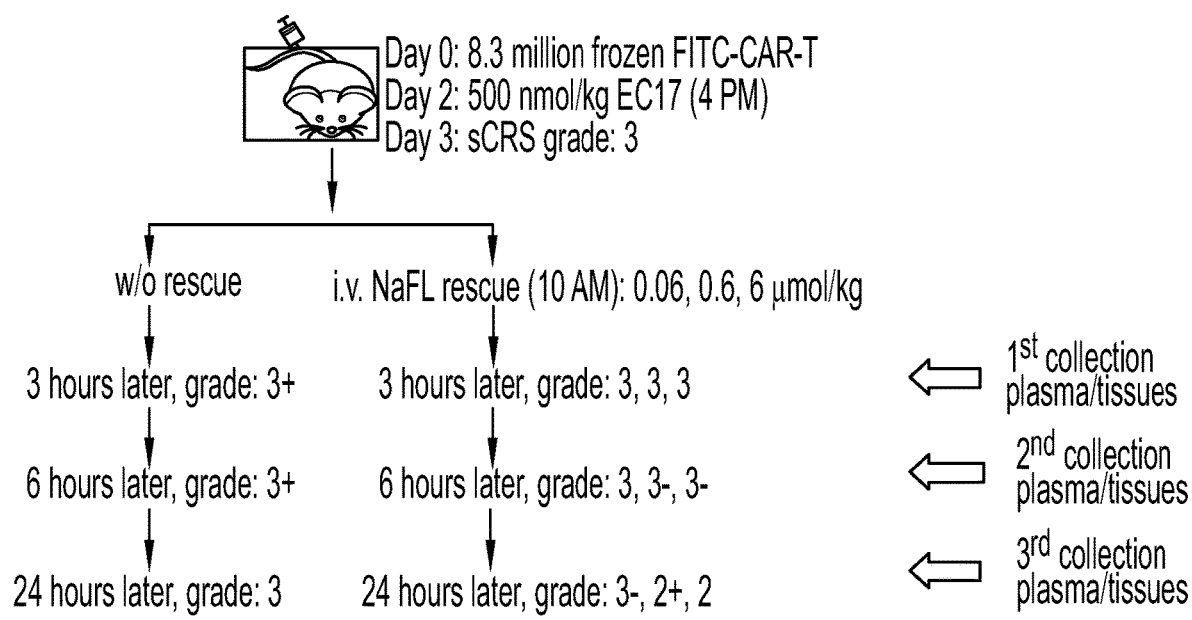
FIG. 50 shows a sodium fluorescein (0.06, 0.6, 6 umol/kg) rescue study schema.

To evaluate whether a lower level of sodium fluorescein can also rescue mice under sCRS, the same rescue study was performed except that sodium fluorescein was dosed at 0.06, 0.6, and 6 µmol/kg. As shown in FIG. 50, ~8.3 million frozen CAR-T cells were administered and sCRS was induced with a 500 nmol/kg EC17 dose. While mice without rescue showed increased severity of sCRS, mice rescued with sodium fluorescein showed a dose-dependent reduction of sCRS severity (FIG. 50). In summary, mice rescued with 6 µmol/kg sodium fluorescein recovered the fastest, while mice rescued with 0.06 µmol/kg sodium fluorescein showed the slowest recovery.

Figure 51A:
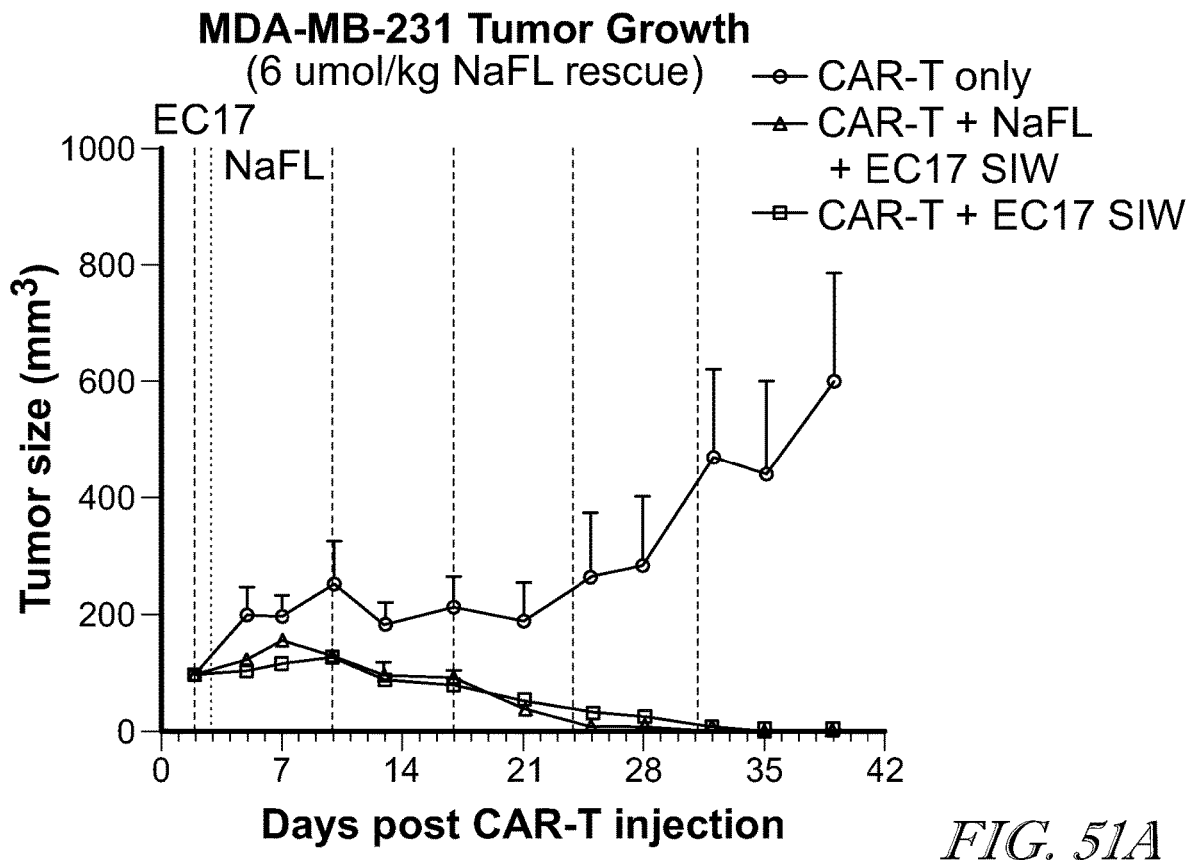
FIG. 51A shows anti-tumor activity (6 umol/kg NaFL rescue).
Figure 51B:
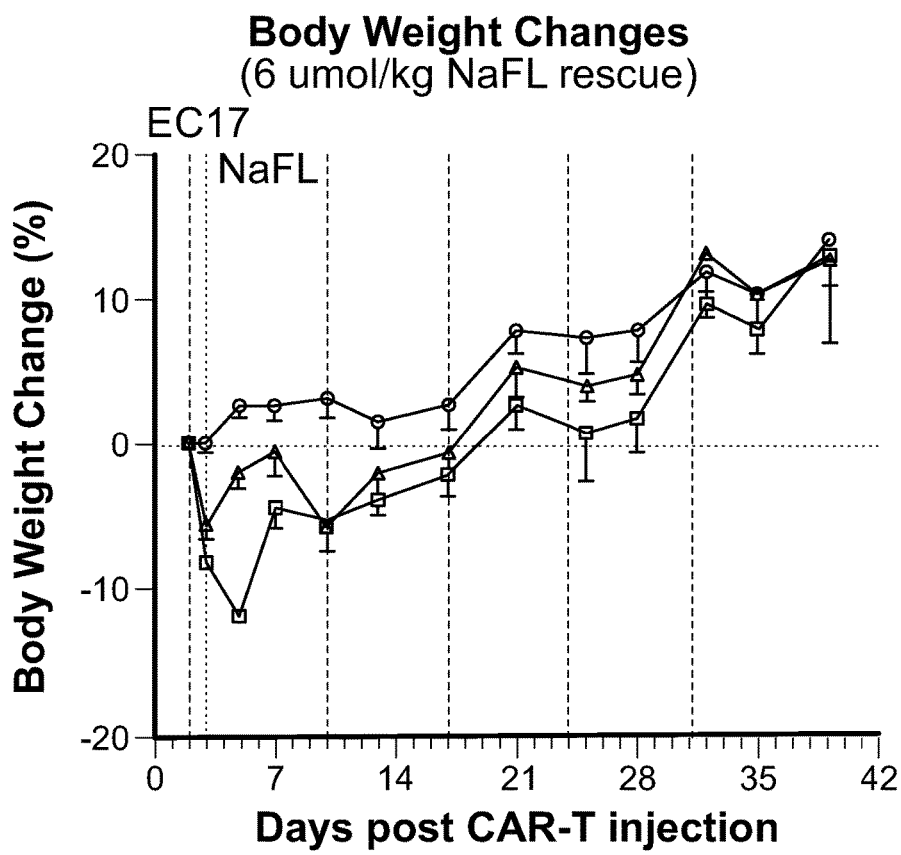
FIG. 51B shows the corresponding body weight changes.
Figure 52A:
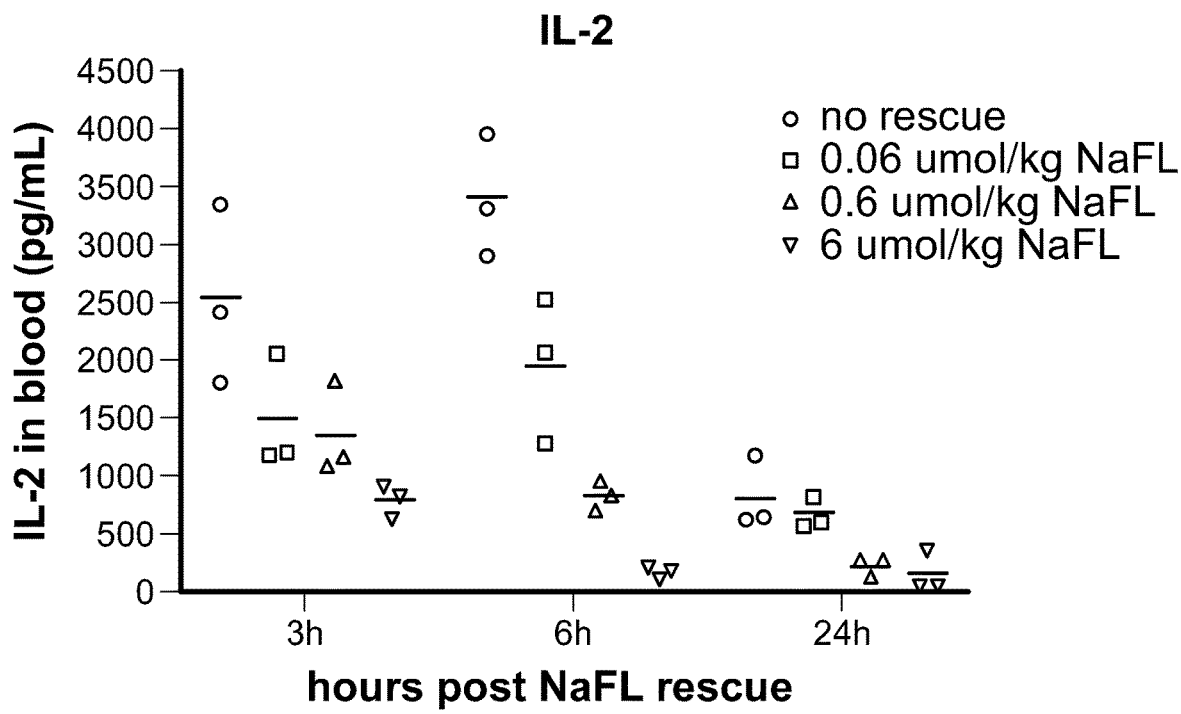
FIG. 52, Panels A-E, show cytokine levels in mouse blood following sodium fluorescein rescue.
Figure 52B:
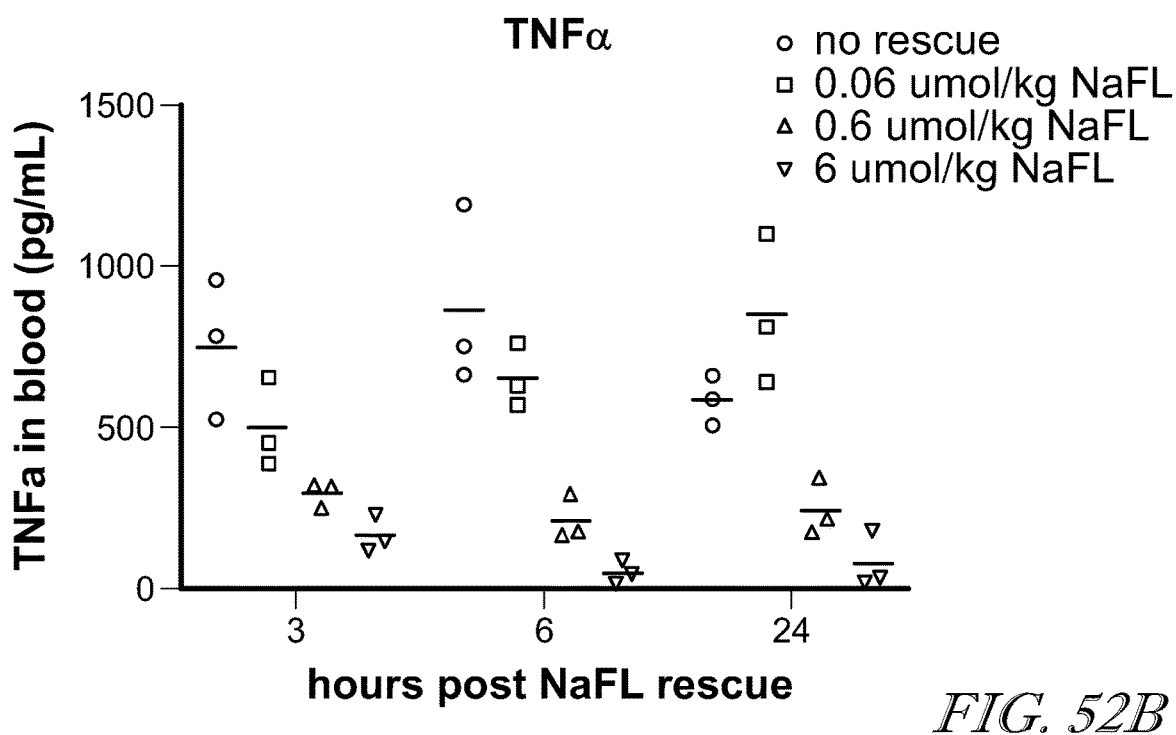
Figure 52C:
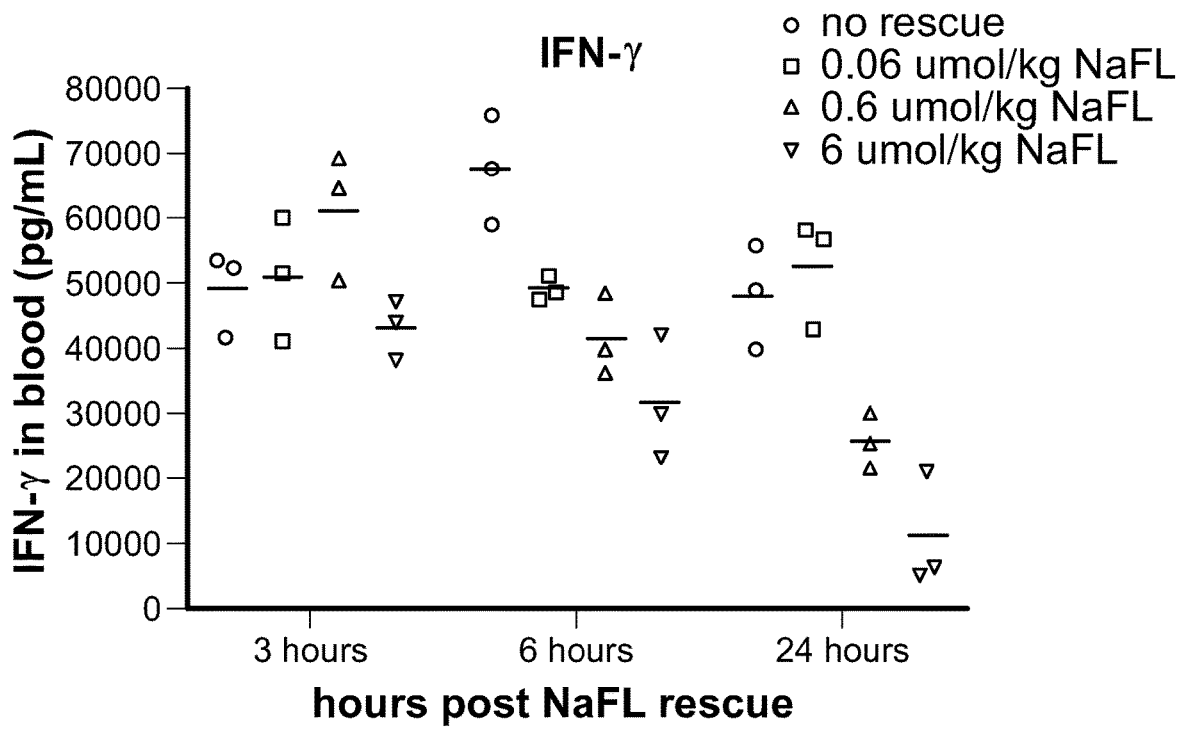
Figure 52D:
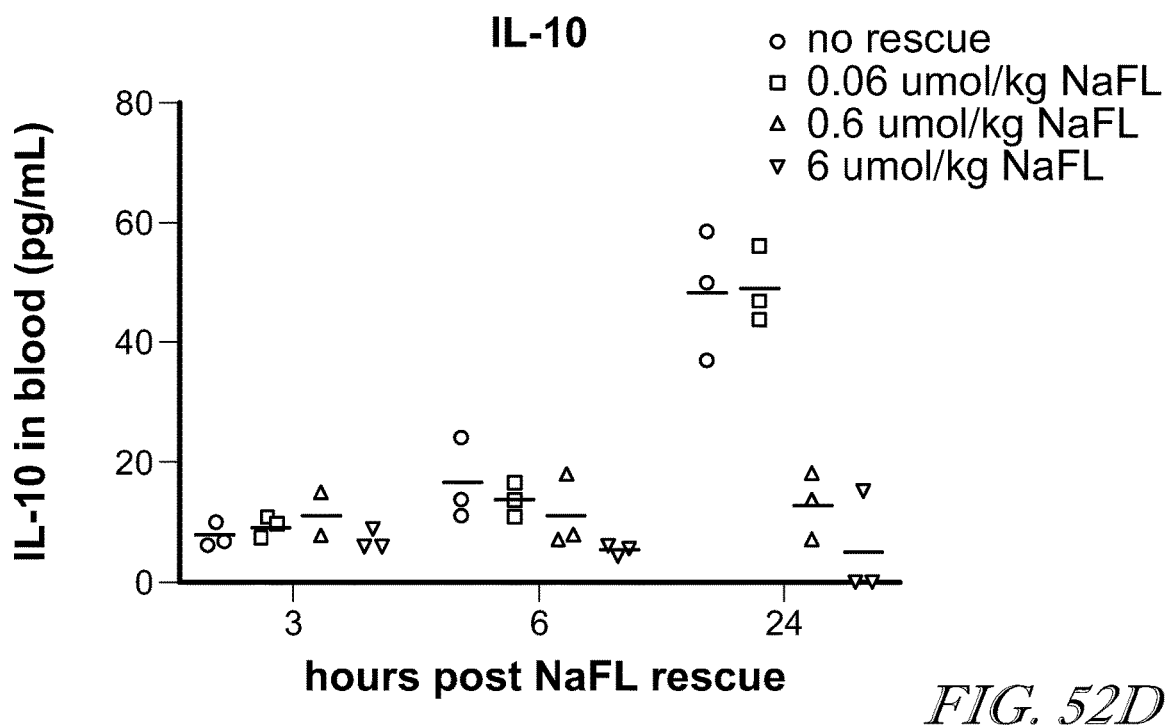
Figure 52E:
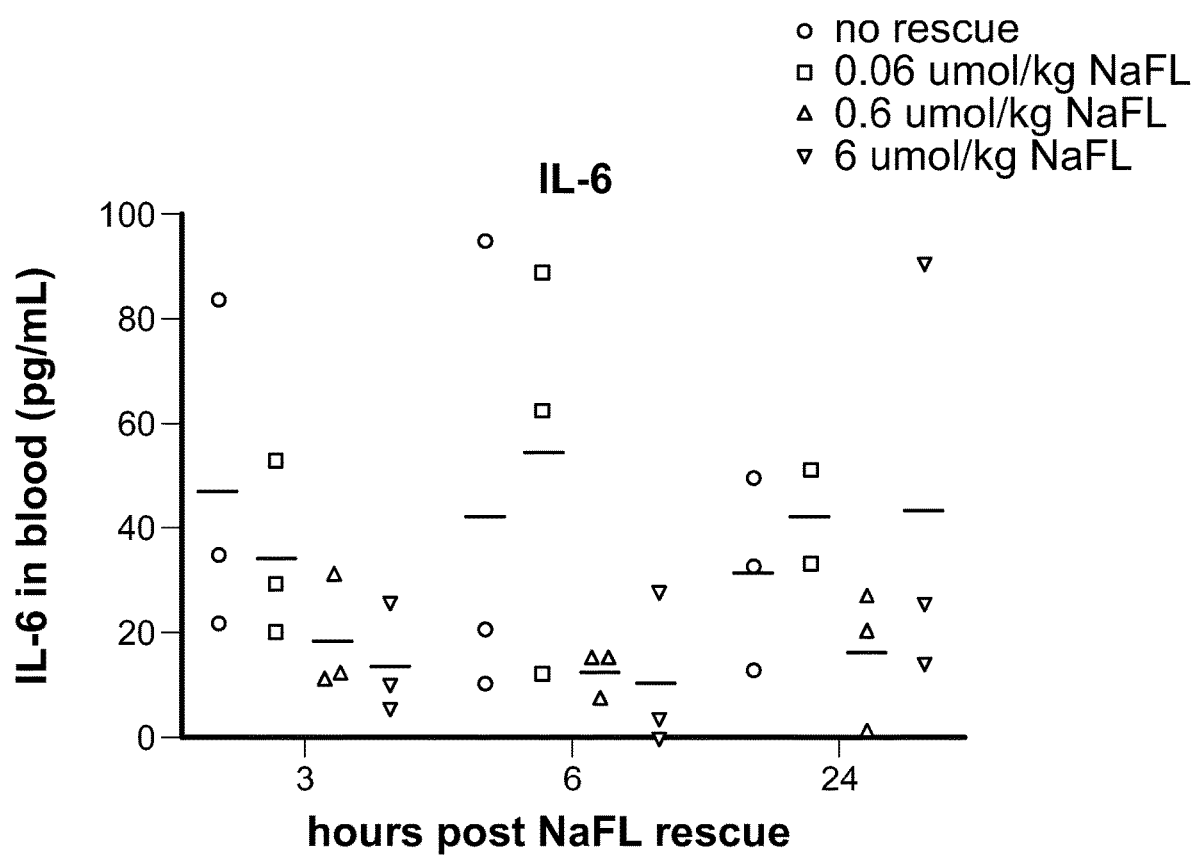

As shown in FIG. 51, rescue with one dose of 6 µmol/kg sodium fluorescein didn't affect the anti-tumor activity of the EC17/CAR-T cell therapy (FIG. 51A, tumor growth curve), but the rescue reduced the EC17-dependent CAR-T toxicity (less initial body weight loss) (FIG. 51B). As shown in FIG. 52, cytokine levels in mouse blood were also dependent on the concentrations of sodium fluorescein used for rescue, and the median effective dose is about 0.6 µmol/kg with key cytokines (e.g. IL-2, TNF-α, IFN-γ, etc.) starting to respond as early as 3 hours post rescue.

Enumeration of FITC CAR T Cells in the Blood

The experimental timeline is represented in FIG. 53A. On day 0, GFP+FITC-CAR T cells [clone 4M5.3] were removed from cryopreservation, thawed and then infused intravenously into MDA-MB-231 tumor bearing NSG mice at 10 million per mouse [tumors ~250 mm$^3$]. Approximately 48 hours after infusion, mice were separated into three groups to test the effects of sodium fluorescein on the behavior of CAR T cells, in vivo, specifically in the circulation. The first group served as a no EC17/no fluorescein control (FIG. 53B-C). The second group was intravenously injected with a single dose of EC17 [500 nmol/kg] to generate severe cytokine release syndrome (sCRS) (FIG. 53B-C, red). The third group (FIG. 53B-C) received EC17 [500 nmol/kg] to generate sCRS but also received a single intravenous sodium fluorescein [60 µmol/kg] approximately 18 hours later to inhibit CAR T cell interaction with folate receptor positive tumor cells. Twenty-seven hours after sodium fluorescein rescue, mice were euthanized and whole blood was obtained via cardiac puncture and collected into EDTA containing tubes and then blood leukocytes were prepared for analysis, according to the protocol detailed in the methods section. Monoclonal antibodies specific for human surface markers, which do not cross react with mouse markers, were utilized for flow cytometry analysis. Staining for anti-human CD45 allows clear identification of human T cells circulating in the blood of CAR T cell infused mice (FIG. 53B, y-axis, dot plots). Additionally, infused human T cells which were successfully transduced with the CAR lentivirus construct were visualized by green fluorescence enabled by the co-expression of cDNA also present in the CAR lentiviral construct that codes for green fluorescent protein (FIG. 53B, x-axis, dot plot). Thus, by gating on human CD45+ GFP+ double positive events, we are able to reliably distinguish and count the number of FITC-CAR expressing human T cells from either un-transduced human T cells or mouse leukocytes (FIG. 53B).

Human CAR T cells are present at high levels in the mouse circulation four days after infusion into the control group of mice which have not received the CAR bridge molecule, EC17 (FIG. 53B, left dot plot). Interestingly in the group of mice which received one dose of EC17, very few CAR T cells are detected in the circulation, presumably because EC17 has directed the CAR T cells to localize to the sites of antigen on the surface of the tumor cells (FIG. 53B, middle dot plot). The shrinkage of tumors by CAR T cells that we routinely observe under this treatment condition, results in the production of elevated levels of the human inflammatory cytokines, including TNFα and IFNγ, causing severe CRS in these animals. Importantly when we dose these sick animals with 60 µmol/kg sodium fluorescein, we not only reduce symptoms of sCRS, we also observe that the CAR T cells reappear in the circulation (FIG. 53B, right dot plot). Thus, excess fluorescein may mediate release of the CAR T cells from the EC17 CAR bridge molecule that labels folate receptor positive tumor cells. Upon release of CAR T cells from tumor cells, production of inflammatory cytokines which drive sCRS will cease, thus leading to rescue of the tumor bearing mice from death.

Figure 54:
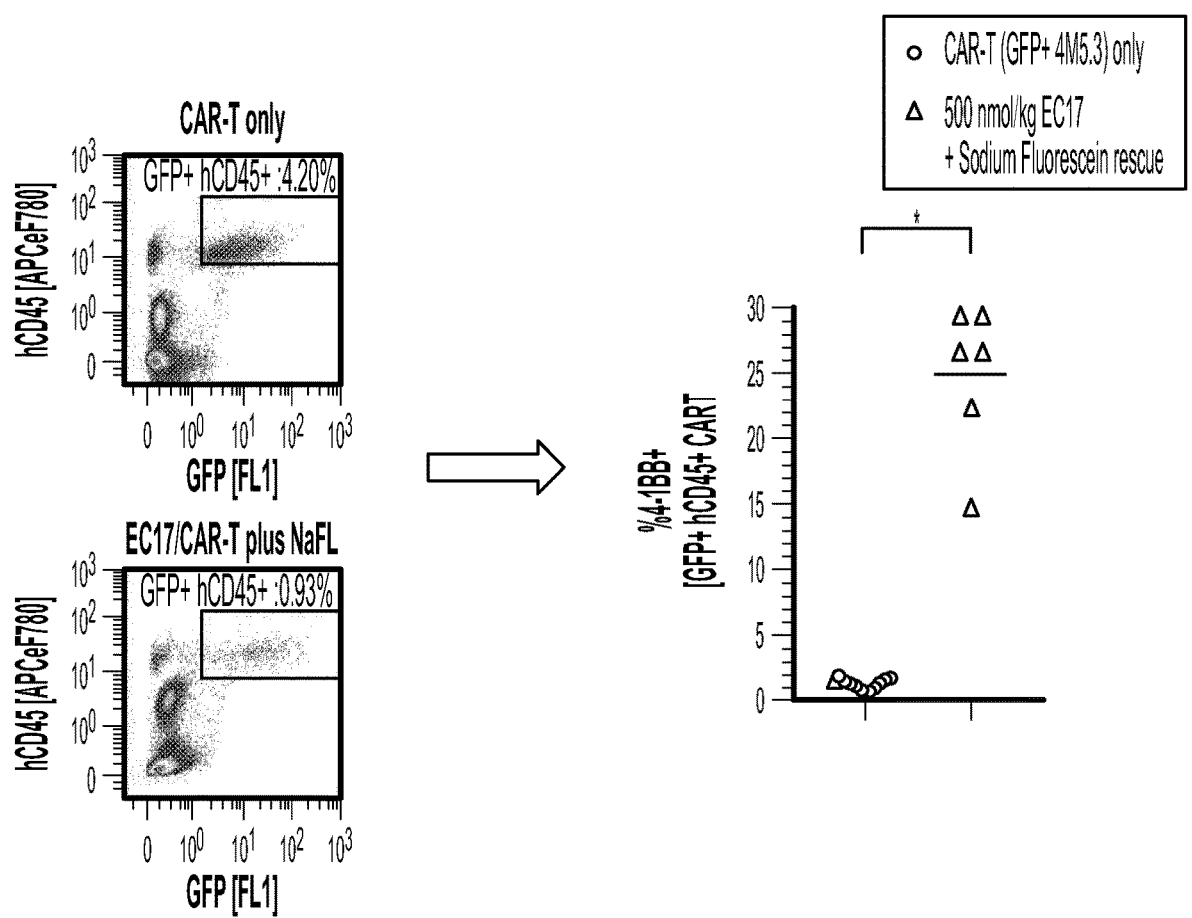
FIG. 54 shows the characterization of circulating CAR T cells in mouse blood after rescue.

Activation of T cells through either a T cell receptor or chimeric antigen receptor, is visualized by increased expression of co-stimulatory surface receptors, including 4-1BB (CD137). This increased expression of 4-1BB will last for several days after initial antigen activation of the T cell receptor or chimeric antigen receptor. Not surprisingly, upon characterization of circulating CAR T cells from the blood of mice infused with CAR T cells only, we observed very little expression of the surface activation marker, 4-1BB, on the surface of less than 2% of the infused CAR T cells isolated from animals which did not receive EC17 (FIG. 54). Interestingly, when we measured the activation state of the circulating CAR T cells from animals which received the CAR T cell infusion plus both EC17 and sodium fluorescein treatments, the circulating CAR T cells express significant amounts of 4-1BB consistent with their recent activation by EC17 within the tumor, two days prior to harvest (FIG. 54). Circulating CAR T cells from the second group of tumor-bearing mice which received the CAR T infusion plus EC17 treatment could not be reliably analyzed for 4-1BB expression due to their very low numbers in circulation (FIG. 53A-C).

Although sodium fluorescein at 60 µmol/kg is well below the established tolerated dose in human patients, knowledge of the minimum effective dose of sodium fluorescein that rescues patients from sCRS infused with FITC CAR T cells and EC17, would be useful. As shown in FIG. 50 and FIG. 55A, CAR-T infused animals were dosed with EC17 to induce sCRS and then separated into four different groups one day later. Three groups received low doses of sodium fluorescein rescue at 0.06, 0.6 and 6 µmol/kg. Notably, the highest sodium fluorescein dose used in this study was 10-fold less than the dose given to the mice in FIG. 31. Animals from the above dose groups were euthanized at 3 and 24 hours post sodium fluorescein rescue so that circulating CAR-T cells in the blood could be enumerated (FIG. 55B-C). Interestingly, the number of circulating CAR T cells in animals that received 0.06-6 µmol/kg sodium fluorescein treatment increased as early as 3 hours post rescue (FIG. 55B). This suggests that injection of sodium fluorescein likely displaced CAR T cells from their targets on FR+ tumor cells. Importantly, at 24 hours post rescue, CAR T cell extravasation into the blood was increased in a sodium fluorescein dose-dependent manner (FIG. 55C). These observations shown in FIGS. 53-55 suggest that the behavior and localization of the FITC CAR-T cells can be modified to different degrees in animals experiencing severe CRS by giving low doses of sodium fluorescein.

Example 34

Previous Rescue Did not Affect EC17-Induced FITC-CAR-T Re-Activation

Figure 37A:
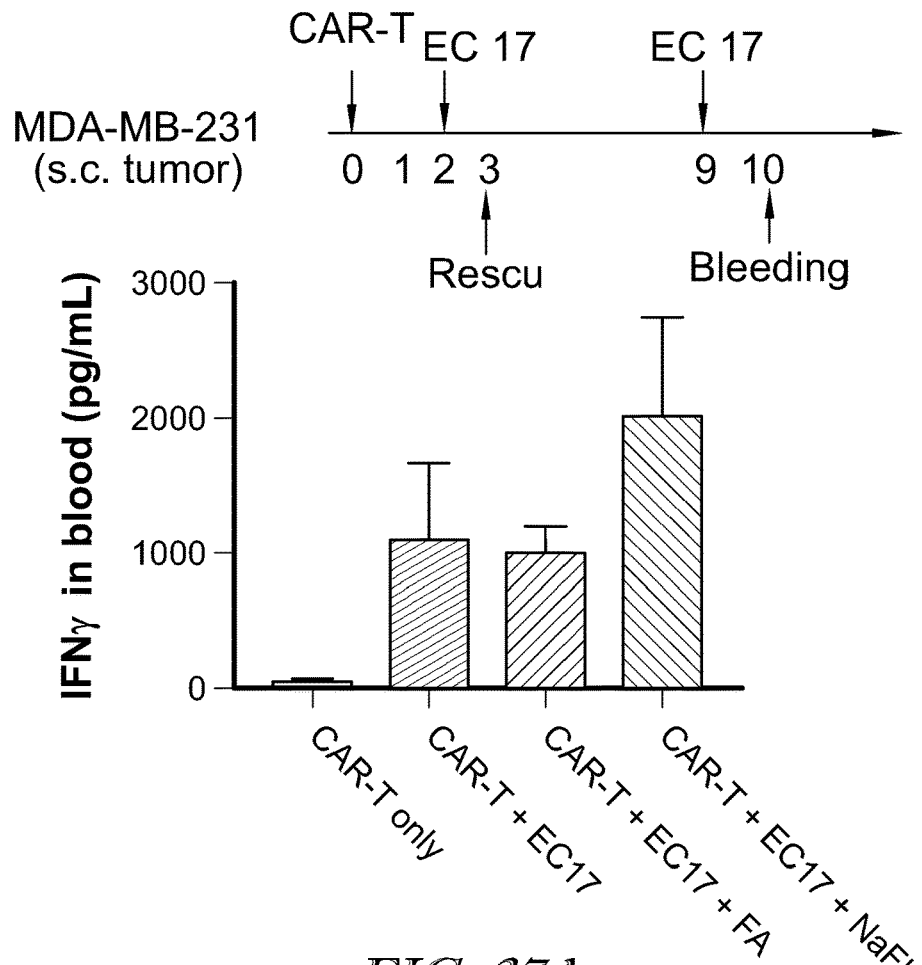
FIGS. 37A and 37B show the effect of rescue on cytokine levels.
Figure 37B:
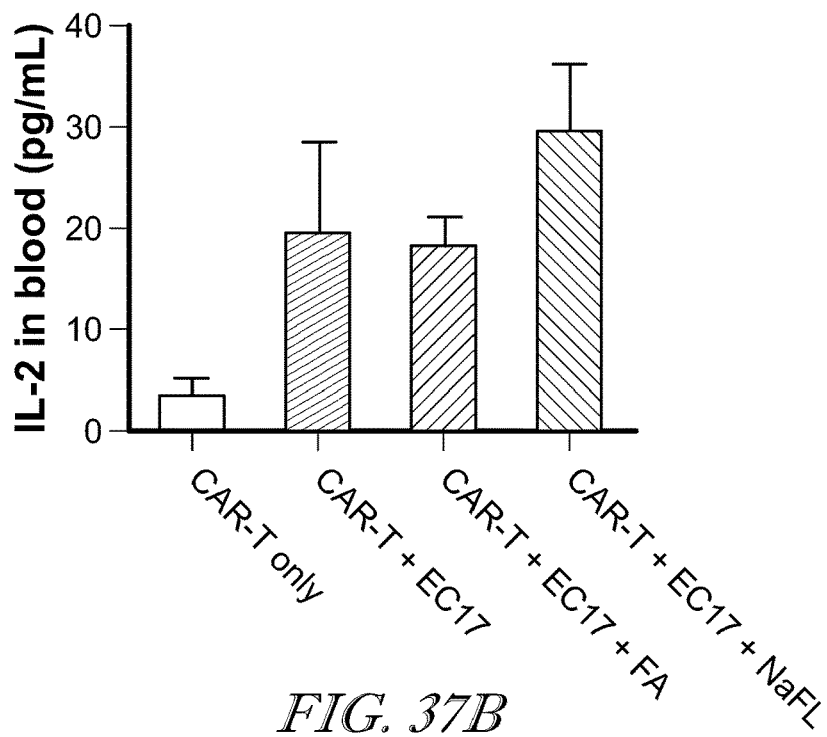

To evaluate whether the rescue affects FITC-CAR-T function, 12 NSG mice bearing MDA-MB-231 tumors (150-250 mm3) were administered with excess FITC-CAR-T cells (8 million). Nine mice were then dosed with 500 nmol/kg EC17 48 hours post CAR-T administration, and 3 mice were not dosed with EC17 and used as "CAR-T only" controls. While the mice in the "CAR-T only" control group were healthy, mice dosed with EC17 showed sCRS one day later and were divided into three groups. One group of mice (CAR-T+EC17+FA) was i.v. injected with 10 umol/kg of folic acid, the second group of mice (CAR-T+EC17+NaFL) was i.v. injected with 260 umol/kg of sodium fluorescein, while the third group (CAR-T+EC17) was not rescued. All mice were re-boosted with 500 nmol/kg EC17 six days later for FITC-CAR-T re-activation, and their blood samples were collected 18 hours after EC17 re-boost for blood cytokine analysis. Human cytokine production is an indication of CAR-T activation. As shown in FIG. 37A-B the levels of human cytokines (e.g. IFN gamma, IL-2) in rescued mice ("CAR-T+EC17+FA" group and "CAR-T+EC17+NaFL" group) are similar to those in mice without rescue ("CAR-T+EC17" group). The data indicate that the rescues did not affect EC17-induced CAR-T re-activation.

Example 35

Cytokine Production in Blood and Body Weight Loss are CAR-T Dose Dependent

Figure 38A:
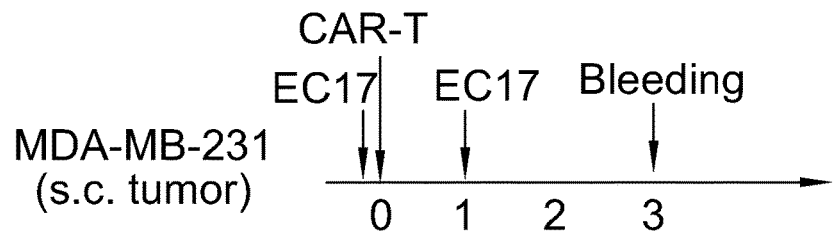
FIG. 38A shows a CAR-T administration schedule.
Figure 38B:
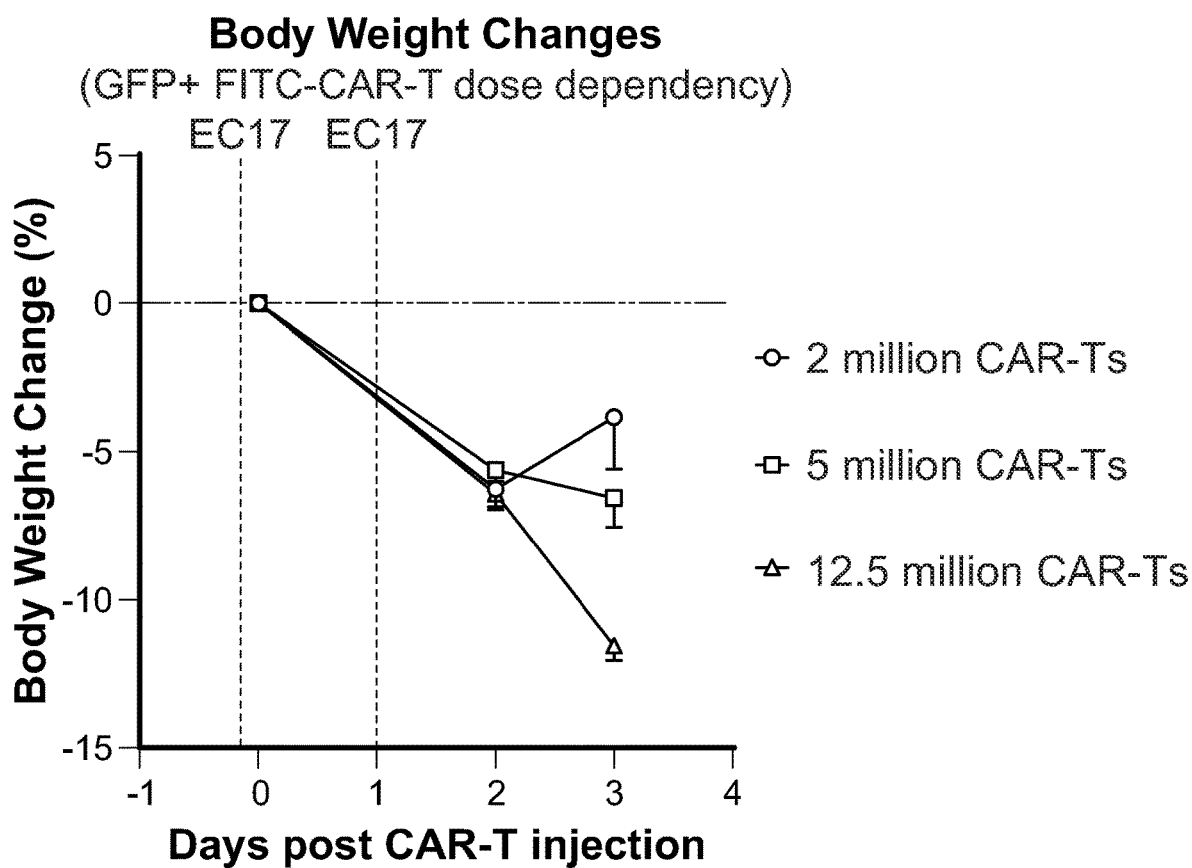
FIG. 38B shows body weight changes.
Figure 39A:
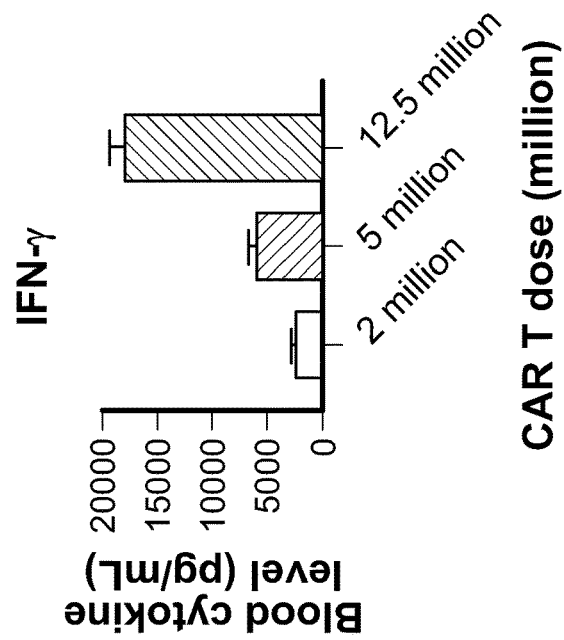
FIG. 39, Panels A-D, show that cytokine production in blood is CAR-T dose dependent.
Figure 39B:
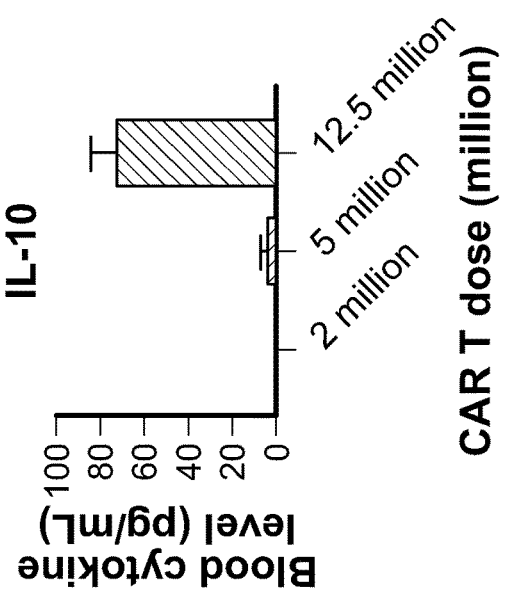
Figure 39C:
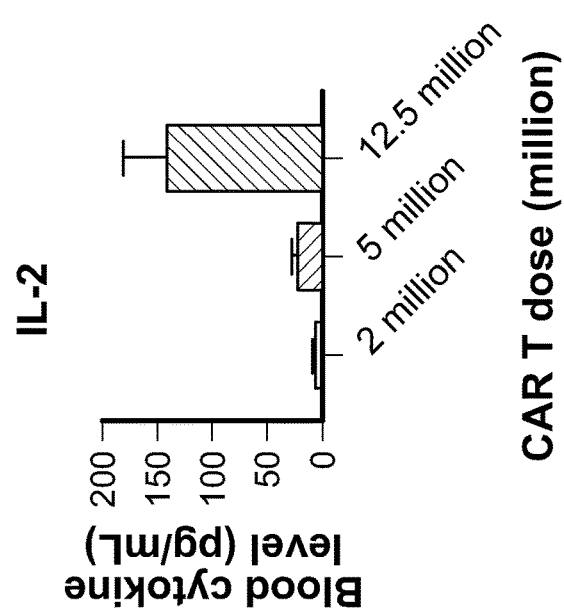
Figure 39D:
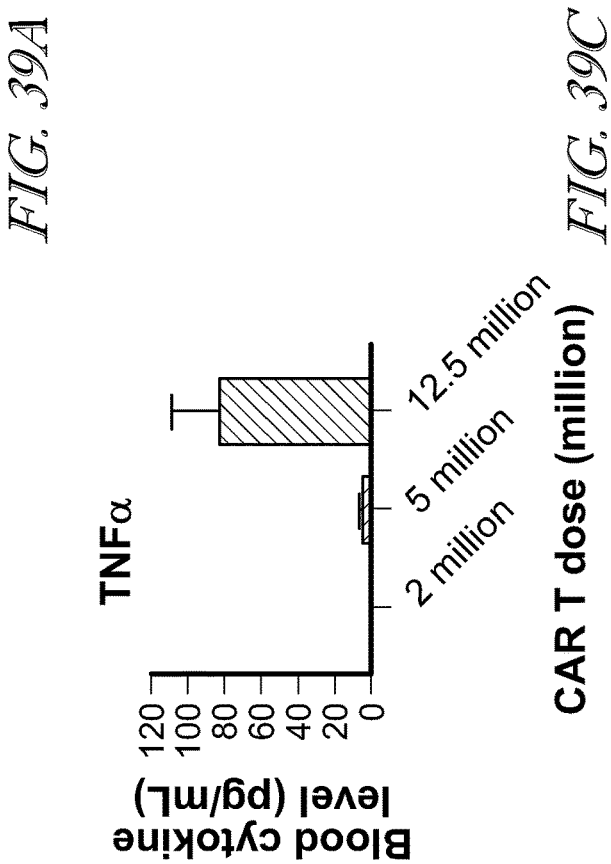

To evaluate whether the cytokine production in mouse blood is correlated with CAR-T number in mice, 15 NSG mice bearing MDA-MB-231 tumors (250-500 mm3) were dosed with 500 nmol/kg of body weight of EC17 and then divided into three groups. Four hours later, each group was administered with 2, 5 or 12.5 million FITC-CAR-T cells respectively. Mice in the three groups were then dosed with a second dose of 500 nmol/kg EC17 24 hours post CAR-T administration, and their blood samples were collected 48 hours later (administration schedule is shown in FIG. 38A). As shown in FIG. 38B, mice administered with 12.5 million CAR-T cells showed the most body weight loss while the mice with 2.5 million CAR-T administration showed the least body weight loss. The production of cytokines (e.g. human IL-2, human IFN gamma, human TNF alpha and human IL-10) is correlated with the number of CAR-T cells administered (FIG. 39A-D). With the increase of CAR-T cells in mice, the production of cytokines increases and the body weight loss also increases.

Example 36

FITC-CAR-T Cell Proliferation In Vivo is EC17 Dose Dependent

Figure 40A:
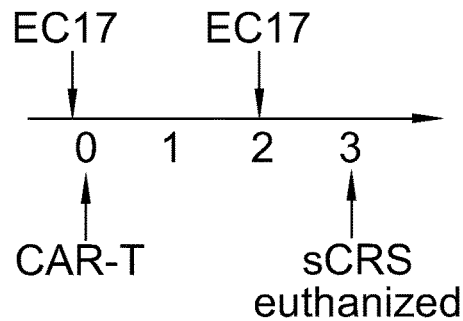
FIG. 40A shows the dosing schedule and FIG. 40B shows that CAR-T number in blood is EC17 dose dependent (day 3 in vivo).
Figure 40B:
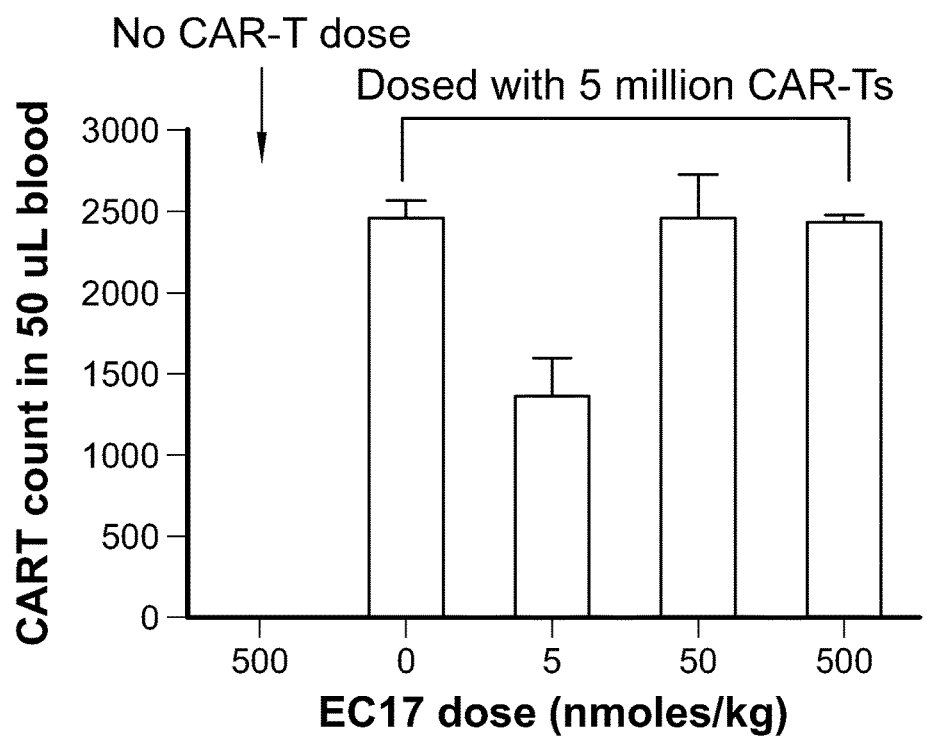

To evaluate whether the bridge dose can control CAR-T proliferation in vivo, NSG mice bearing MDA-MB-231 tumors (250-500 mm3) were divided into 4 groups and dosed with 0, 5, 50, or 500 nmol/kg of body weight of EC17 respectively (as shown in FIG. 40A). Four hours later, the four groups were administered with 5 million FITC-CAR-T cells which were cultured in vitro for 11 days, while one group of mice pre-dosed with 500 nmol/kg EC17 was not dosed with CAR-T cells and was used as a "No CAR-T control". Two days later, mice in all five groups were dosed with various levels of EC17 as indicated in FIG. 40B. While mice in the "No CAR-T dose" group showed little CRS related syndrome, mice dosed with 5 million CAR-T cells showed EC17 dose-dependent CRS 3 days post CAR-T administration. Blood samples were then collected 16 hours post the second EC17 dose and analyzed for CAR-T numbers in blood circulation (FIG. 40B). As shown in FIG. 40B, in comparison to mice dosed with 0 nmol/kg EC17, mice dosed with 5 nmol/kg EC17 had less CAR-T cells in their blood circulation, probably due to the EC17-dependent CAR-T cell trafficking to tumor tissues which removed CAR-T cells from the blood circulation. Importantly, mice administered with the same amount of CAR-T cells but dosed with 50 or 500 nmol/kg EC17 had more CAR-T cells in their blood circulation. The interpretation of this finding is that CAR-T cells proliferated more in mice dosed with 50 or 500 nmol/kg EC17 than in mice dosed with 5 nmol/kg EC17, so that the CAR-T counts in blood circulation were higher.

Figure 41A:
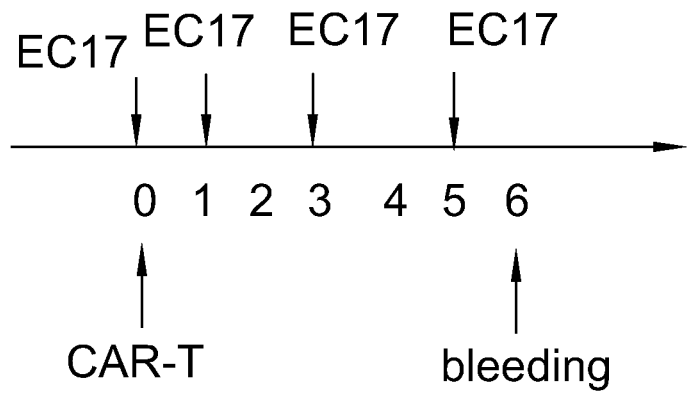
FIG. 41A shows the dosing schedule and FIG. 41B shows that CAR-T count in blood is EC17 dose dependent although the difference is smaller (day 6 in vivo).
Figure 41B:
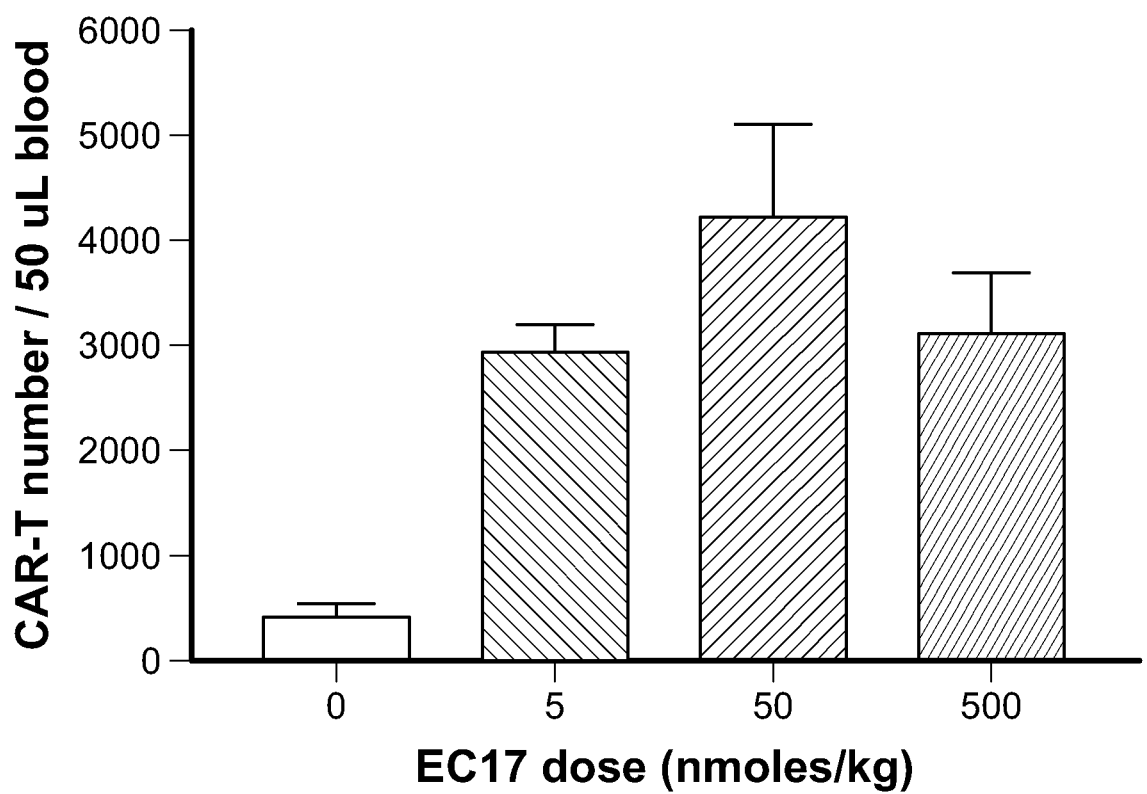

To further confirm that FITC-CAR-T proliferation is EC17 dose-dependent, we also evaluated CAR-T proliferation in vivo when CAR-Ts were given more time to settle down and proliferate. For this purpose, we examined CAR-T cell number in mice which were administered with CAR-T cells six days earlier and four doses of EC17 had been given to boost CAR-T proliferation in vivo. NSG mice bearing MDA-MB-231 tumors (250-500 mm3) were divided into 4 groups and dosed with 0, 5, 50, or 500 nmol/kg of body weight of EC17 respectively (as shown in FIG. 41A). Four hours later, all mice were administered with 5 million FITC-CAR-T cells which were cultured in vitro for 18 days. Various levels of EC17 were then dosed at days 1, 3, 5 post CAR-T administering to boost CAR-T proliferation. Mouse blood samples were collected 24 hours post the last EC17 dose, CAR-T cells in blood were stained with anti-human CD45 antibody and counted by FACS. As shown in FIG. 41B, CAR-T count was the lowest in mice without EC17 dose, increased in mice with the 5 nmol/kg EC17 dose, reached the highest in mice dosed with 50 nmol/kg EC17, and started to decrease when the EC17 dose was 500 nmol/kg probably due to the oversaturation of EC17 and consequent dissociation of CAR-T cells from tumor cell. In summary, EC17 dose-dependent FITC-CAR-T proliferation in mice bearing MDA-MB-231 tumors has been observed at two different time points, indicating that control of EC17 dose level can control FITC-CAR-T proliferation in vivo.

Example 37

FITC-CAR-T does not Proliferate and Cause Toxicity in Naïve Mice

Figure 42:
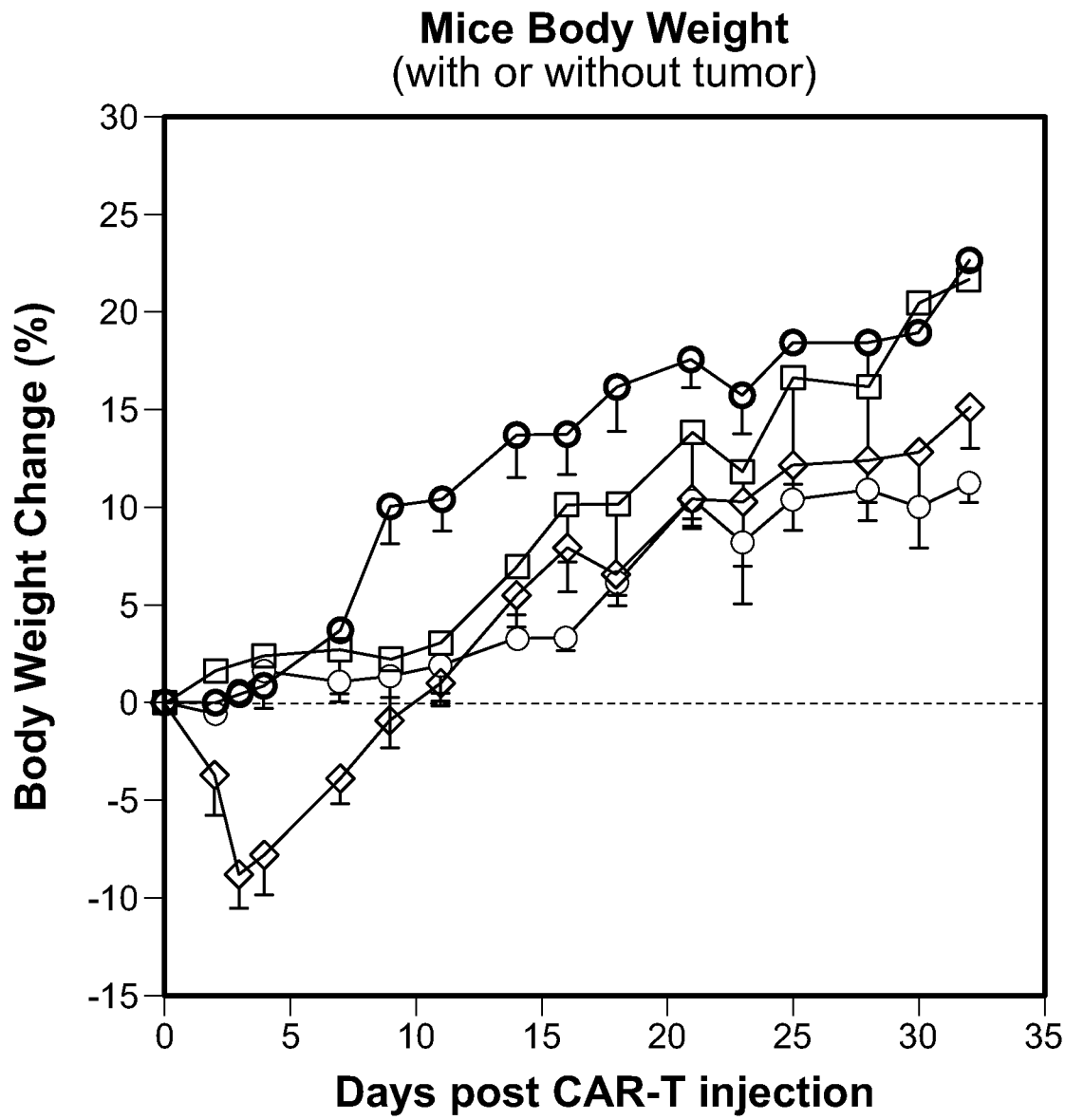
FIG. 42 shows mouse body weight changes following CAR-T and EC17 injection.
Figure 43A:
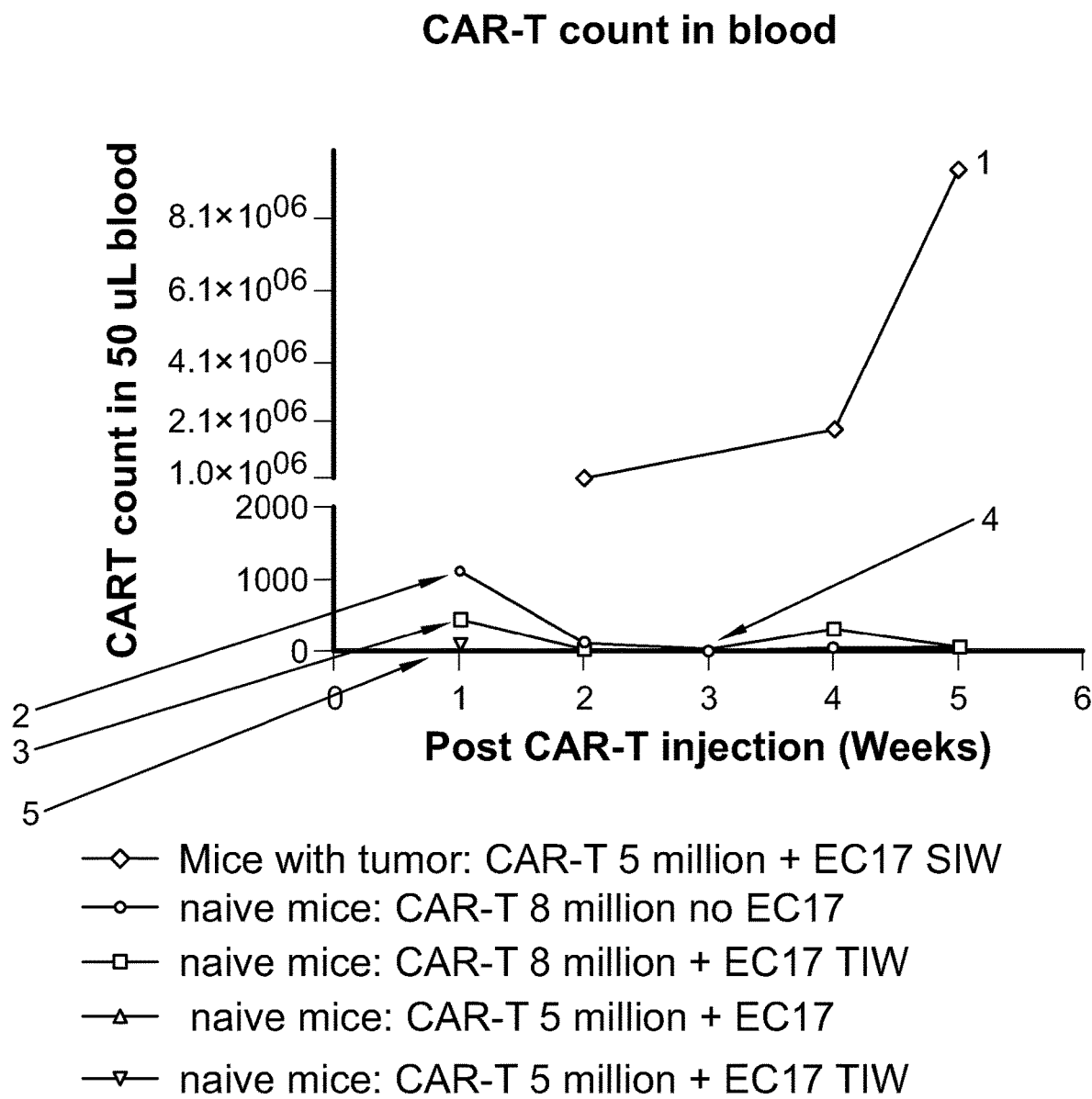
FIGS. 43A and 43B show CAR-T cell count and spleen size in mice post CAR-T cell and EC17 injection. (1) Mice with tumor: CAR-T 5 million+EC17 SIW; (2) naïve mice: CAR-T 8 million no EC17; (3) naïve mice: CAR-T 8 million+EC17 TIW; (4) naïve mice: CAR-T 5 million no EC17; (5) naïve mice: CAR-T 5 million+EC17 TIW.
Figure 43B:
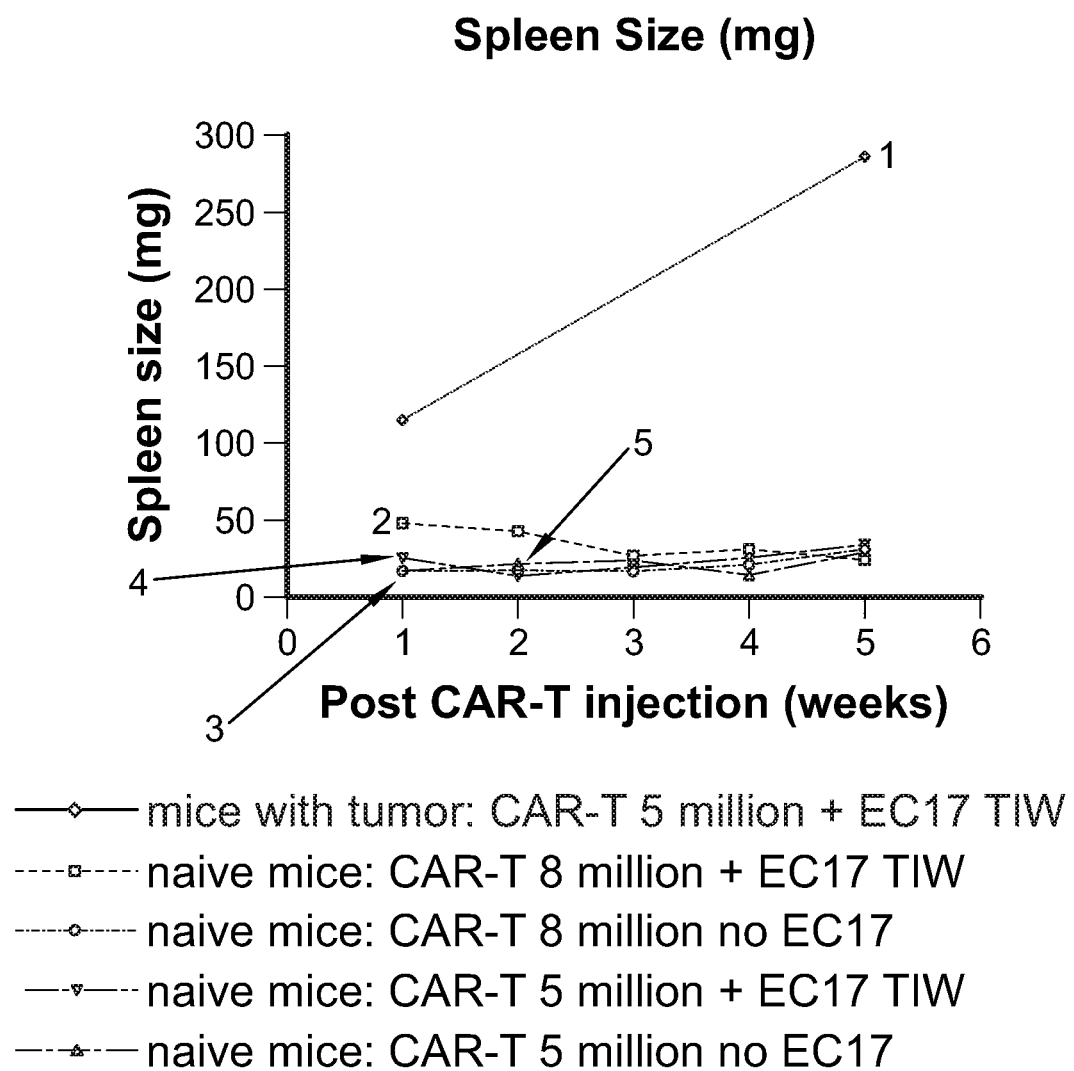

The evaluation of FITC-CAR-T proliferation and related toxicity in both naïve mice and mice bearing FR+ tumor xenografts was tested. To evaluate whether FITC-CAR-T proliferation in vivo is dependent on the co-existence of the bridge (e.g. EC17) and the tumor antigen (e.g. folate receptor), FITC-CAR-T proliferation in vivo was compared in naïve mice and mice bearing FR+ tumor xenografts, either with or without EC17. 5-8 million CAR-T cells (as indicated in FIGS. 42 and 43) were administered (i.v.) into naïve mice without tumors and mice bearing FR+ tumor xenografts (80-200 mm3). 500 nmol/kg EC17 was dosed 4 hours before and three times per week post CAR-T administration, if desired. Mice were monitored for body weight changes and CAR-T cell count in blood circulation; some mice were also euthanized weekly to evaluate organs. As shown in FIG. 42, naïve mice without tumor burden did not show any apparent body weight loss (toxicity), no matter whether EC17 was dosed or not. On the other hand, mice bearing FR+ MDA-MB-231 tumors showed EC17-dependent body weight loss: the mice dosed with EC17 three times per week had body weight loss in the first 10 days, whereas mice without EC17 dose did not have body weight loss (FIG. 42). CAR-T cell count in blood samples was also compared to evaluate CAR-T proliferation. As shown in FIG. 43A, FITC-CAR-T did not proliferate in naïve mice dosed with either 5 or 8 million FITC-CAR-T cells, no matter whether EC17 was dosed or not. On the contrary, FITC-CAR-T cells in the mice implanted with FR+ HEK-FRa xenografts had rapid proliferation when 500 nmol/kg EC17 was given three times per week. Since the enlargement of spleen size is another indicator for CAR-T proliferation in vivo, spleen size was also measured as shown in FIG. 43B. Naïve mice without tumor burden did not show much spleen enlargement (indication of no CAR-T proliferation), no matter whether EC17 was dosed or not. On the other hand, mice bearing FR+ MDA-MB-231 tumors had enlarged spleens when they were dosed with 500 nmol/kg EC17 three times per week. In conclusion, FITC-CAR-T cells do not proliferate or cause toxicity in naïve mice even in the presence of EC17, but proliferate quickly in FR+ tumor bearing mice when EC17 is also administered.

For FIG. 42, the MDA-MB-231 s.c. model was used. For FIG. 43A, the HEK-FRa s.c. xenograft model was used. For FIG. 43B, the MDA-MB-231 s.c. model was used.

Results show that FITC-CAR-T is not active in naïve mice without a tumor burden. CAR-T cells were i.v. injected into naïve mice (8 million per mouse) and mice bearing MDA-MB-231 tumors (5 million per mouse). 500 nmol/kg EC17 was administered three times per week when desired (shown in figure label). After one week, mouse blood samples were collected in EDTA coated tubes and centrifugated at 3000 g for 15 min at 4° C., and the plasma was isolated and stored at −20° C. until analysis.

Cytokine levels including IFN were measured using LEGENDplex human cytokine panel kits (BioLegend, San Diego, CA) according to the manufacturer's instructions. Plasma samples were diluted with Assay Buffer, and then mixed with Capture beads immobilized with the antibody directed to the analyzed cytokine. After 2 hours incubation at room temperature with shaking, biotinylated Detection antibody to the analyzed cytokine was added and incubated for one more hour at room temperature with shaking. Phycoerythrin (PE) labeled streptavidin was then added to bind with biotin on the Detection antibody, and FACS was used to read the signal of PE on the binding complex (capture antibody-cytokine-detection antibody). The intensity of PE is proportional to the level of analyzed cytokine. A series of cytokine solutions with known concentrations were measured at the same time and used as standards to quantitate the cytokine levels in the analyzed samples.

Figure 44:
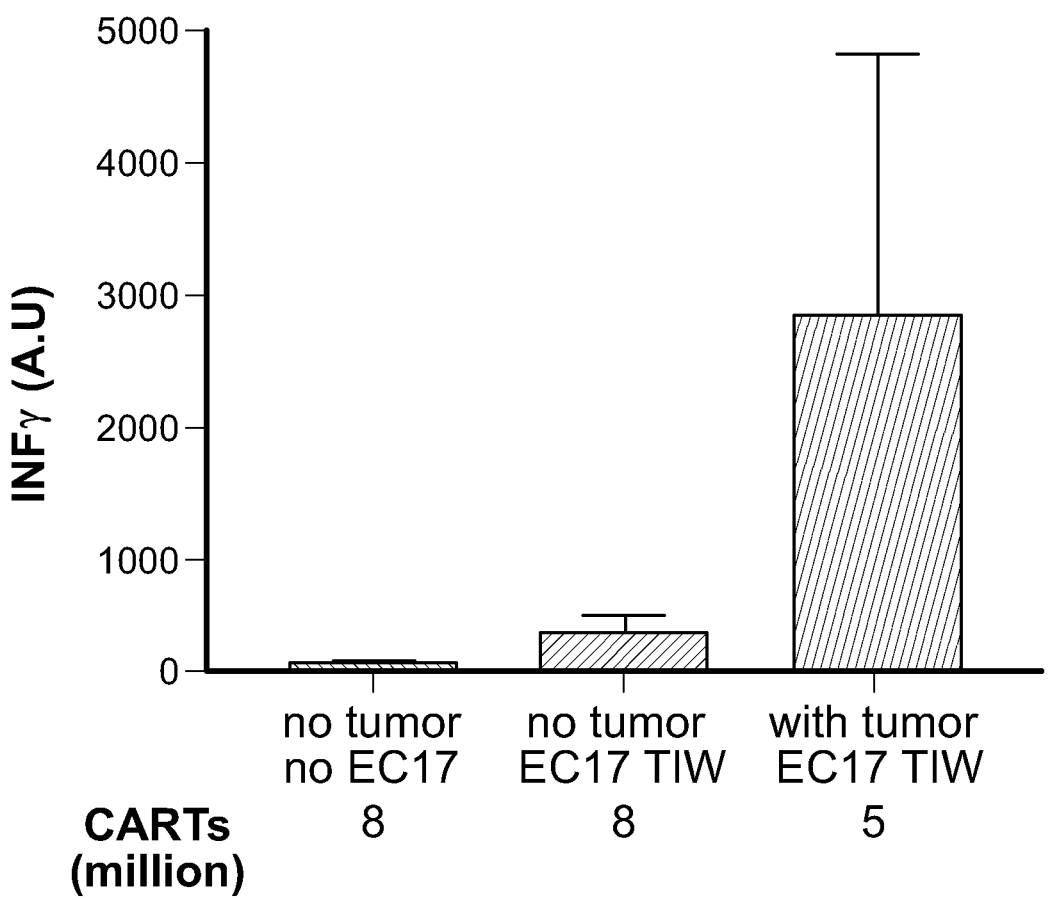
FIG. 44 shows cytokine production following EC17 and CAR-T cell injection in the presence and absence of a tumor.

As shown in FIG. 44, cytokine production (CAR-T activity) is dependent on the presence of the tumor. CAR-T cells are not active in naïve mice even when mice were dosed with 500 nmol/kg EC17 three times per week.

Example 38

Characterization of Bridge Molecules

To examine the ability of bridge molecules to bind anti-fluorescein scFv on CAR T cells, a competitive binding assay was developed. Measurement of the fluorescein signal from CAR T cell bound bridges could not be used due to the overlap of its fluorescence with that of the GFP expressing CAR T cells. For this purpose, FITC-Alexa647 (10 nM) was allowed to bind anti-fluorescein CAR T cells in the absence or presence of excess (1 µM) competing ligand (i.e. FITC-folate, FITC-DUPA, FITC-CA9) for 1 h at room temperature. After incubation, anti-fluorescein CAR T cells were washed 3× with PBS to remove unbounded FITC-Alexa647, and the washed cells were analyzed for Alexa647 fluorescence by flow cytometry.

All of the bridge molecules tested (i.e. FITC-folate, FITC-DUPA, FITC-CA9) were able to bind to the CAR-expressing T cells as established by the ability of the bridges to competitively block FITC-Alexa 647 binding to the engineered T cells (FIG. 45).

Example 39

The Universal CAR T Cell can Eliminate Various Cancer Cells Expressing Orthogonal Antigens Upon Addition of Antigen Matched Bridges In Vitro Each human cancer cell line was seeded at a density of $10^4$ cells/100 µl media into 96 well plates and grown overnight. Anti-fluorescein CAR T cells were added to each well in the absence or presence of bridge molecules. After co-incubation for 6-24 hours, plates were centrifuged at 350×g for 10 min to remove debris and supernatants were analyzed for lactate dehydrogenase release (cell death analysis) using Pierce™ LDH cytotoxicity assay kit (Thermo Fisher Scientific, MA) and interferon γ (IFNγ) levels using a human IFNγ ELISA kit (Biolegend, CA).

Figures 46A, 46B:
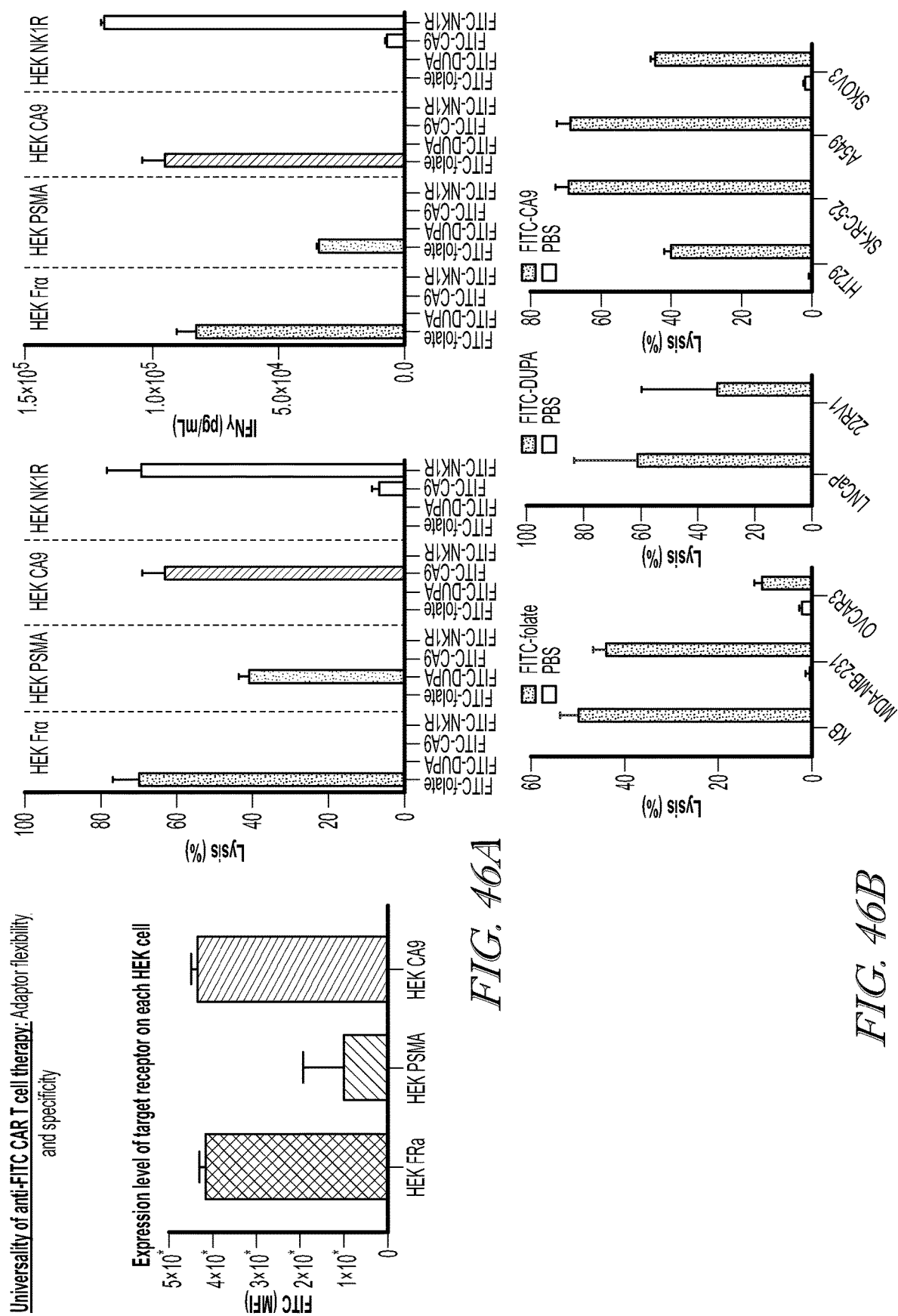
FIG. 46 shows that the universal Car T cell can eliminate various cancer cells expressing orthogonal antigens upon addition of antigen matched bridges in vitro.

In order to evaluate specificity and universality of anti-fluorescein CAR T cells, anti-fluorescein CAR T cells were co-incubated with HEK cells expressing either FR, PSMA, CA9 or NK1R in the presence or absence of bridge molecules respectively. As shown in FIG. 46, panel A, anti-fluorescein CAR T cells can eliminate target HEK cells when antigen matched bridge molecules are present. Universality of anti-fluorescein CAR T cells with multiple bridge molecules was further evaluated with various human cancer cell lines that express either the folate receptor (KB, MDA-MB-231 and OVCAR3), PSMA (LNCaP and 22RV1), or CA9 (HT29, SK-RC-52, A549 and SKOV3) (FIG. 46B). Lysis was specific for the bridge tested and the corresponding tumor expressing the receptor for the bridge tumor ligand.

Example 40

Relationship Between Concentration of Bridge Molecules and the Universal CAR T Cell's Anti-Tumor Activity Each human cancer cell line was seeded at a density of $10^4$ cells/100 µl media into 96 well plates and grown overnight. Anti-fluorescein CAR T cells were added to each well in the absence or presence of bridge molecules. After co-incubation for 6-24 hours, plates were centrifuged at 350×g for 10 min to remove debris and supernatants were analyzed for lactate dehydrogenase release (cell death analysis) using Pierce™ LDH cytotoxicity assay kit (Thermo Fisher Scientific, MA) and interferon γ (IFNγ) levels using human IFNγ ELISA kit (Biolegend, CA).

As shown in FIG. 47, all of the bridge molecules behave similarly. As concentration of bridges was increased, CAR T cell anti-tumor activity was also increased. However, if higher concentrations of bridge molecules were added, CAR T cell anti-tumor activity was then reduced (i.e. a bell-shaped dose response). This result is due to the fact that bridge molecules cannot form a bridge between CAR T cells and cancer cells when higher concentrations of bridge molecules are added since higher concentrations of bridge molecules can saturate both receptors on CAR T cells and cancer cells, respectively.

Example 41

The Universal CAR T Cell can Eliminate Various Cancer Cells Expressing Orthogonal Antigens Upon Addition of Antigen Matched Bridge Molecules In Vivo Multiple clones of MDA-MB-231 expressing orthogonal antigens were generated by using a lentiviral gene delivery system. Immnuodeficient NSG mice (Jackson Laboratory, ME) were implanted subcutaneously with each of MDA-MB-231 cells expressing either the folate receptor, PSMA, or CA9 and were injected intravenously with CAR T cells and then bridge molecules (i.e. either FITC-folate, FITC-DUPA or FITC-CA9) when tumors reached ~100 mm3 in size. Tumors were measured every other day with calipers, and tumor volume was calculated according to the equation: Tumor volume=½(L×W2) where L is the longest axis of the tumor and W is the axis perpendicular to L.

Figure 48:
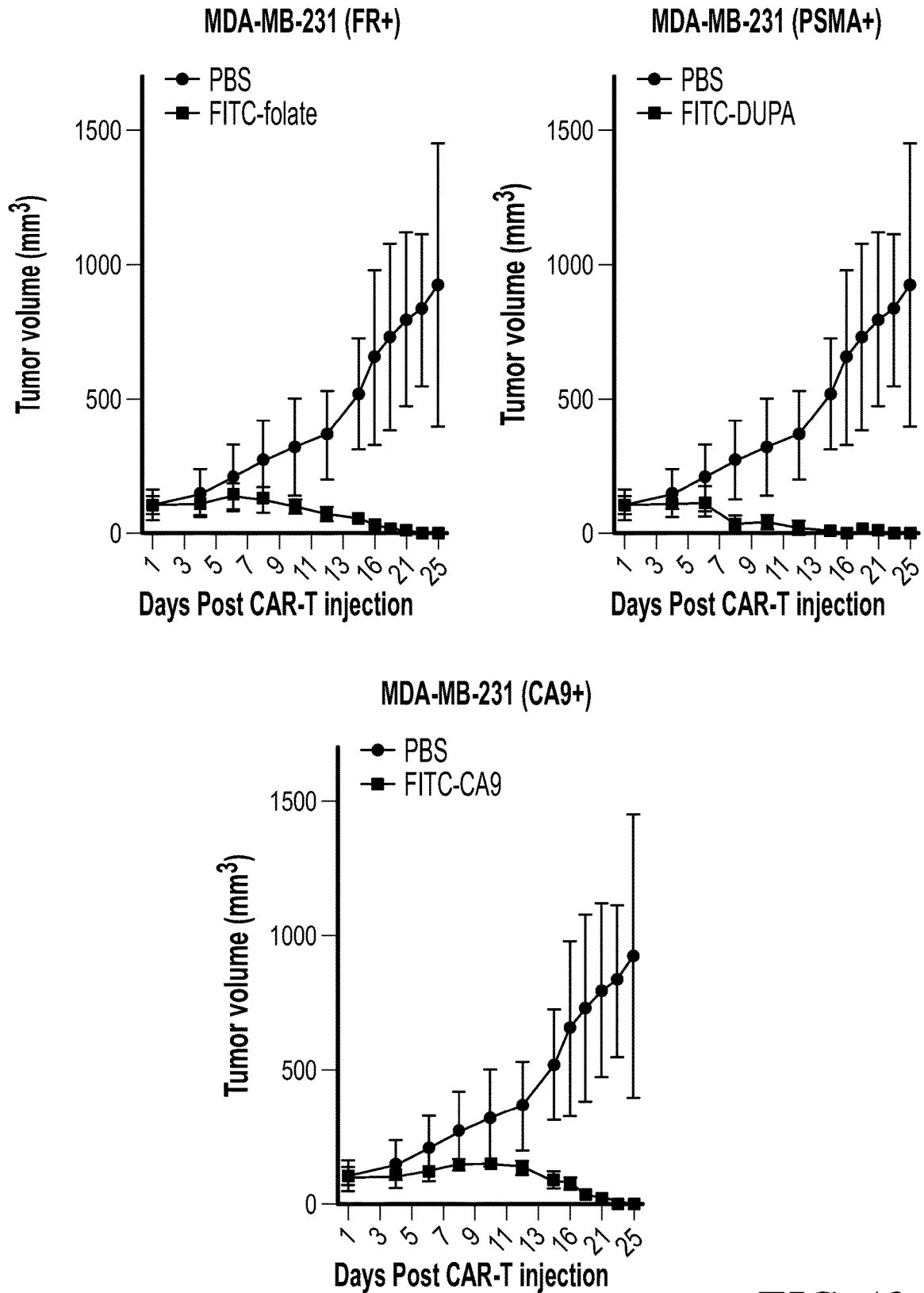
FIG. 48 shows that the universal CAR T cell can eliminate various cancer cells expressing orthogonal antigens upon addition of antigen matched bridges in vivo.

In order to evaluate whether each bridge can induce anti-tumor activity of the anti-fluorescein CAR T cells, multiple clones of MDA-MB-231 expressing either the folate receptor, PSMA or CA9 were generated. As shown in FIG. 48, anti-fluorescein CAR T cells could eliminate tumor cells expressing orthogonal antigens when antigen matched bridges were injected. Taken together, these data demonstrated that a single anti-fluorescein CAR T cell could eliminate multiple tumors by injecting antigen-matched bridges to target antigens.

Example 42

The Universal CAR T Cell can Eliminate Two Tumors Via a Cocktail of Bridge Molecules In Vivo (Two Separated Tumor Model)

In order to evaluate whether a cocktail of bridge molecules can eliminate two tumors expressing orthogonal antigens, we established two different tumor models. As a first tumor model, each of PSMA+ MDA-MB-231 and CA9+ MDA-MB-231 were implanted into NSG mice at two different locations (i.e. right flank: CA9+ MDA-MB-231, left flank: PSMA+ MDA-MB-231). For the second tumor model, PSMA+ MDA-MB-231 and CA9+MDA-MB-231 were pre-mixed at a 1:1 ratio and implanted at one location. As shown in panels A and B of FIG. 49, complete elimination of both tumor cells expressing either PSMA or CA9 can be achieved when both bridges (i.e. cocktail of FITC-PSMA and FITC-CA9) were injected. However, a tumor expressing unmatched antigen (i.e either PSMA or CA9) continuously grew if only one of the bridges (i.e. either FITC-DUPA alone or FITC-CA9 alone) was infused. Taken together, these data demonstrate that anti-fluorescein CAR T cells can overcome tumor heterogeneity by utilizing a cocktail of bridge molecules.

PSMA+ MDA-MB-231 and CA9+ MDA-MB-231 were implanted into NSG mice (Jackson Laboratory, ME) either at two different locations (i.e. right flank: PSMA+ MDA-MB-231, left flank: CA9+ MDA-MB-231) or one location after two tumor cells were pre-mixed (i.e. 50% of PSMA+ MDA-MB-231 and 50% of CA9+ MDA-MB-231). When tumors reached ~100 mm3 in size, anti-fluorescein CAR T cells (8×106) were injected plus FITC-DUPA, FITC-CA9 or both. Tumors were measured every other day with calipers, and tumor volume was calculated according to the equation: Tumor volume=½(L×W2) where L is the longest axis of the tumor and W is the axis perpendicular to L. Results are shown in FIGS. 49A and 49B.

Synthesis of Bridge Molecules

FITC-Folate

Folate-γ-ethylenediamine was coupled to fluorescein isothiocyanate (FITC) isomer I (Sigma-Aldrich) in anhydrous dimethylsulfoxide (DMF) in the presence of tetramethylguanidine and diisopropylamine. The crude product was loaded onto an Xterra RP18 preparative HPLC column (Waters) and eluted with gradient conditions starting with 99% 5 mM sodium phosphate (mobile phase A, pH7.4) and 1% acetonitrile (mobile phase B) and reaching 90% A and 10% B in 10 min at a flow rate of 20 mL/min. Under these conditions, the FITC-folate main peak typically eluted at 27-50 min. The quality of the FITC-folate fraction was monitored by analytical reverse-phase HPLC with a UV detector. Fractions with greater than 98.0% purity (LCMS) were lyophilized to obtain the final FITC-folate product.

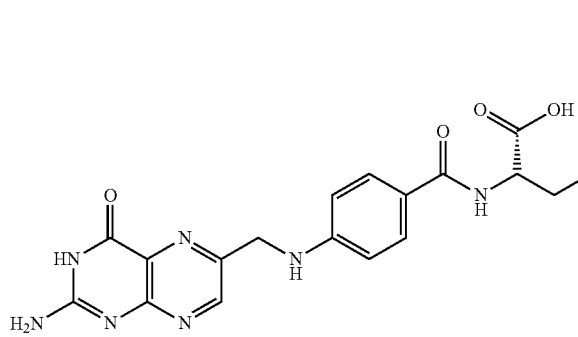
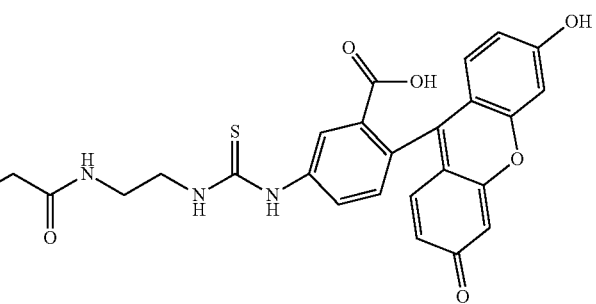

FITC-DUPA

DUPA-FITC was synthesized by solid phase methodology as follows. Universal NovaTag resin (50 mg, 0.53 mM) was swollen with dichloromethane (DCM) (3 mL) followed by dimethylformamide (DMF, 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). After swelling the resin in DMF, a solution of DUPA-(OtBu)—OH (1.5 equiv), HATU (2.5 equiv) and DIPEA (4.0 equiv) in DMF was added. Argon was bubbled for 2 h, and resin was washed with DMF (3×3 mL) and i-PrOH (3×3 mL). After swelling the resin in DCM, a solution of 1 M HOBt in DCM/trifluoroethane (TFE) (1:1) (2×3 mL) was added. Argon was bubbled for 1 h, the solvent was removed and resin was washed with DMF (3×3 mL) and i-PrOH (3×3 mL). After swelling the resin in DMF, a solution of Fmoc-Phe-OH (2.5 equiv), HATU (2.5 equiv) and DIPEA (4.0 equiv) in DMF was added. Argon was bubbled for 2 h, and resin was washed with DMF (3×3 mL) and i-PrOH (3×3 mL). The above sequence was repeated for 2 more coupling steps for addition of 8-aminooctanoic acid and fluorescein isothiocyanate or rhodamine B isothiocyanate. Final compound was cleaved from the resin using a trifluoroacetic acid (TFA):H2O: triisopropylsilane:cocktail (95:2.5:2.5) and concentrated under vacuum. The concentrated product was precipitated in diethyl ether and dried under vacuum. The crude product was purified using preparative RP-HPLC [λ=488 nm; solvent gradient: 1% B to 80% B in 25 min, 80% B wash 30 min run; A=10 mM NH$_4$OAc, pH=7; B=acetonitrile (ACN)]. ACN was removed under vacuum, and pure fractions were freeze-dried to yield DUPA-FITC as a brownish-orange solid. RP-HPLC: tR=8.0 min (A=10 mM NH$_4$OAc, pH=7.0; B=ACN, solvent gradient: 1% B to 50% B in 10 min, 80% B wash 15 min run). 1H NMR (DMSO-d6/D2O): δ 0.98-1.27 (ms, 9H); 1.45 (b, 3H); 1.68-1.85 (ms, 11H); 2.03 (m, 8H); 2.6-3.44 (ms, 12H); 3.82 (b, 2H); 4.35 (m, 1H); 6.53 (d, J=8.1 Hz, 2H), 6.61 (dd, J=5.3, 3.5 Hz, 2H); 6.64 (s, 2H); 7.05 (d, J=8.2 Hz, 2H), 7.19 (m, 5H); 7.76 (d, J=8.0 Hz, 1H); 8.38 (s, 1H). HRMS (ESI) (m/z): (M+H)+ calcd for C51H59N7O15S, 1040.3712, found, 1040.3702. UV/vis: λ max=491 nm.

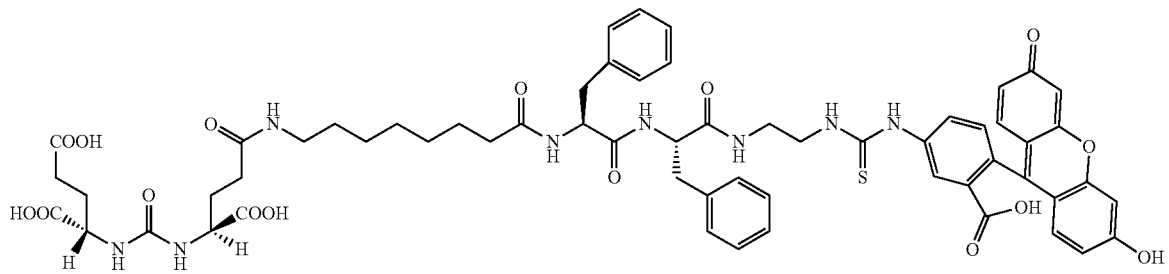 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

FITC-CA9

In a 50 mL round bottom flask CA9 ligand (53.6 mg, synthesized in lab) was dissolved in a desired amount of N,N-Dimethylformamide (DMF) (2-3 mL) using a Teflon magnetic stir bar. Ambient air was removed using vacuum and replaced with nitrogen gas, this was done in three cycles. Then the round bottom was kept under constant nitrogen gas. To the flask, 28.9 mg of N-(3-Dimethylaminopropyl)-N'-ethylcarbodiimide hydrochloride (EDC) was added followed by 21.6 mg 1-Hydroxybenzotriazole hydrate (HOBt) and 18.9 μL of Boc-PEG2-NH$_2$ (purchased from Sigma Aldrich). 5.4 μL of triethylamine (TEA) was added last and the reaction was allowed to stir overnight. The reaction mixture was purified using HPLC and confirm with UHPLC-MS (target m/z of 831). Acetonitrile was removed using high vacuum rotary evaporation and place on lyophilizer for 48 hours. Deprotection of Boc was done with 1:1 TFA:DCM for 30 minutes. TFA/DCM was removed using high vacuum rotary evaporation followed by 30 minutes on high vacuum. The compound was then dissolved in DMF and combined with 5 molar equivalents of N,N-Diisopropylethylamine (DIPEA). 16 mg of fluorescein isothiocyanate (purchased from Life Technologies) was added to the solution and stirred for 1 hour. Reaction mixture was purified by HPLC and target compound was confirmed with UHPLC-MS (target m/z of 1120). The samples was placed on lyophilizer for 48 hours and store compound at −20° C.

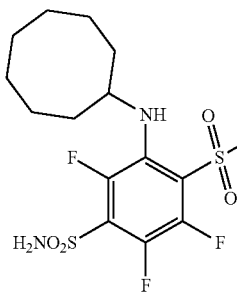
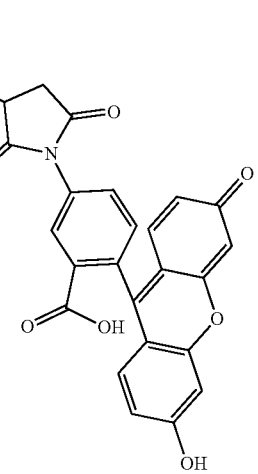

FITC-NK1R

To a stirred solution of NK-1 (0.02 g, 0.0433 mmol, 1.0 eq.), O-(2-Aminoethyl)-O'-[2-(Boc-amino)ethyl]decaethylene glycol (BocNH-PEG11-NH2) (Sigma, 0.0336 g, 0.0521 mmol, 1.2 eq.), Benzotriazol-1-yl-oxytripyrrolidinophosphonium hexafluorophosphate (PYBOP) (0.027 g, 0.0521 mmol, 1.2 eq.) in dry CH2Cl2 was added N,N-Diisopropylethylamine (DIPEA) (0.076 mL, 0.4338 mmol, 10 eq.) under argon at room temperature. The reaction progress was monitored by LCMS and purified by preparative RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, λ=220 nm, 254 nm). The pure fractions were collected, evaporated all organic solvents and lyophilized the sample for 48 h to furnish the NK1-PEG11-NHBoc. Yield: 40.13 mg (97%). To the NK1-PEG11-NHBoc (0.0165 g, 0.015 mmol) in dry $CH_2Cl_2$ was added trifluoroacetic acid (TFA, 20 eq.) and reaction mixture was stirred for 4 h at r.t. The excess of TFA was removed, diluted with water and extracted using CH2Cl2 (3×5 mL). The combined organic layers were washed with brine, dried (Na2SO4) and concentrated. The residue obtained was dried under vacuum and used for next-step without further purification. A stirred solution of NK1-PEG11-NH2 (0.008 g, 0.0081 mmol, 1.0 eq.), Fluorescein isothiocyanate (FITC) (Sigma, 0.0037 g, 0.0097 mmol, 1.2 eq.) in dry dimethylsulfoxide (DMSO, 0.3 mL) was added diisopropylethyl amine (0.0028 mL, 0.0162 mmol, 2.0 eq.) at room temperature under argon. The reaction progress was monitored by LCMS and purified by preparative RP-HPLC (Waters, XBridge™ Prep C18, 5 m; 19×100 mm column, mobile phase A=20 mM ammonium acetate buffer, pH 7, B=acetonitrile, gradient 10-100% B in 30 min, 13 mL/min, λ=280 nm). The pure fractions were collected, evaporated all organic solvents and lyophilized the sample for 48 h to furnish the NK1-PEG11-FITC (5). Yield: 8.54 mg (77%).

The NK-1 compound was synthesized by a two-step procedure starting from base ligand, which was prepared by using a literature procedure. (Ref: DESIGN AND DEVELOPMENT OF NEUROKININ-1 RECEPTOR-BINDING AGENT DELIVERY CONJUGATES, Application Number: PCT/US2015/44229, incorporated herein by reference in its entirety).

Example 43

Control of Cytokine Storm with Bridge Molecules

Regulation of the intensity of a CAR T cell-mediated cytokine release syndrome with the use of low molecular weight bridge molecules is shown. Four novel strategies for eliminating a toxic and sometimes lethal cytokine release syndrome while simultaneously improving CAR T cell therapeutic efficacy are described.

Cell Lines and T Cells

Folate receptor positive cell lines (e.g. KB and MDA-MB-231) were maintained in folic acid free RPMI 1640 (Gibco, Ireland) containing 10% heat-inactivated fetal calf serum and 1% penicillin-streptomycin in 5% $CO_2$ at 37° C. Peripheral blood mononuclear cells (PBMC) were isolated by Ficoll density gradient centrifugation (GE Healthcare Lifesciences, USA) of fresh human blood from healthy volunteers (IRB #: 1702018875). Pure $CD3^+$ T cells were isolated from PBMCs using EasySep™ Human T Cell Isolation Kit (STEM CELL technologies, Canada) and then cultured in TexMACS™ medium (Miltenyi Biotech Inc, CA) containing 1% penicillin and streptomycin sulfate in the presence of human IL-2 (100 IU/ml, Miltenyi Biotech Inc, CA). T cells were divided and the above media was changed every 2-3 days.

Generation of Lentiviral Vector Encoding Anti-Fluorescein CAR Gene

An overlapping PCR method was used to generate the CAR construct containing a single chain fragment variable (scFv) against fluorescein. The coding sequence for the scFv was synthesized (GeneScript, NJ) from an affinity optimized sequence of a human anti-fluorescein antibody, 4M5.3 (Kd=270 fM, 762 bp) [21]. Sequences encoding the human CD8α signal peptide (SP, 63 bp), the hinge and transmembrane regions of CD8α (249 bp), the cytoplasmic domain of 4-1BB (CD137, 141 bp) and the cytoplasmic domain of CD3ζ chain (336 bp) (purchased from GeneScript) were fused with the anti-fluorescein scFv by overlapping PCR. The resulting CAR construct (1551 bp) was inserted into EcoRI/NotI cleaved lentiviral expression vector pCDH-EF1-MCS-(PGK-GFP) (System Biosciences, CA) and expanded/purified using PureLink Hipure plasmid midiprep kit (Invitrogen, CA). The sequence of the CAR construct in lentiviral vector was confirmed by DNA sequencing (Purdue Genomic Core Facility, IN).

Production of Lentivirus and Human T Cell Transduction

To prepare lentivirus containing the anti-fluorescein (scFv) CAR, 293TN packaging cell line was co-transfected with lentiviral vector encoding anti-fluorescein scFv CAR and a $2^{nd}$ generation mixture of packaging plasmids (Cellecta, CA). After 24 and 48 hours transfection, supernatants containing lentivirus encoding the CAR gene were harvested and virus particles were concentrated using a standard polyethylene glycol virus concentration method (Clontech, CA).

Transduction of Human T Cells with CAR-Expressing Lentivirus

Isolated T cells (see above) were activated using Dynabeads coupled to anti-CD3/CD28 antibodies (Life Technologies, CA) for 12-24 hours in the presence of human IL-2 (100 IU/ml) and then transduced with the aforementioned lentivirus encoding both GFP and the anti-fluorescein CAR [50]. After 72 hours transduction, T cells were analyzed for GFP fluorescence by flow cytometry to determine transduction efficiency.

Binding of Bridge to CAR T and Cancer Cell Receptors

Fluorescein-folate (FITC-folate) and fluorescein-PSMA (FITC-DUPA) were synthesized as previously described. To examine the ability of these bridge molecules to bind anti-fluorescein scFv on CAR T cells, a competitive binding assay had to be developed, because measurement of the fluorescein signal from CAR T cell bound bridge could not be used due to the overlap of its fluorescence with that of the GFP expressing CAR T cells. For this purpose, FITC-Alexa647 (10 nM) was allowed to bind anti-fluorescein CAR T cells in the absence or presence of excess (1 µM) competing ligand (i.e. FITC-folate) for 1 h at room temperature. After incubation, anti-fluorescein CAR T cells were washed 3× with PBS to remove unbounded FITC-Alexa647, and the washed cells were analyzed for Alexa647 fluorescence by flow cytometry. For analysis of FITC-folate to binding to folate receptor, FR positive KB cells were incubated with FITC-folate (100 nM) in the absence or presence of excess (10 µM) free folate (i.e. as a competitive ligand). After washing samples with PBS (3 times), samples were analyzed by flow cytometry for fluorescein-folate binding.

Analysis of Anti-Tumor Activity of Anti-Fluorescein CAR T Cells In Vitro

FR positive cancer cell lines (e.g. KB or MDA-MB-231 cells) were seeded at density of $10^4$ cells/100 µl media into 96 well plates and grown overnight. Anti-fluorescein CAR T cells were added to each well in the absence or presence of bridge molecules. After co-incubation for 6-24 hours, plates were centrifuged at 350×g for 10 min to remove debris and supernatants were analyzed for lactate dehydrogenase release (cell death analysis) using Pierce™ LDH cytotoxicity assay kit (Thermo Fisher Scientific, MA) and interferon γ (IFNγ) levels using human IFNγ ELISA kit (Biolegend, CA), while pellets were either evaluated for CAR T cell activation by staining with anti-human CD69 APC (Clone: FN50, Biolegend, CA) or examined for CAR T cell proliferation by culturing for 5 days in TexMACS™ medium (Miltenyi Biotech Inc, CA) containing 1% penicillin and streptomycin sulfate and quantitating by flow cytometry using the intrinsic GFP fluorescence and staining with anti-human CD3 APC antibody (Clone:HIT3a, Biolegend, CA).

Analysis of Anti-Tumor Activity of Anti-Fluorescein CAR T Cells In Vivo

Immnuodeficient NSG mice (Jackson Laboratory) were implanted subcutaneously with MDA-MB-231 cells and injected intravenously with CAR T cells and then fluorescein-folate (as indicated) when tumors reached ~100 mm³ in size. Mice were maintained on folic acid-deficient diet (TD.95247, Envigo) in order to reduce the level of folic acid in mice to a physiological levels found in humans. Tumors were measured every other day with calipers, and tumor volume was calculated according to equation: Tumor volume=½(L×W²) where L is the longest axis of the tumor and W is the axis perpendicular to L. Mouse blood was also collected to measure cytokine levels (e.g. IL-2, IL-6, IFNγ, and TNFα) using LEGENDplex bead-based immunoassay (Biolegend, CA) and systemic toxicity was monitored by measuring body weight loss. All animal care and use followed by National Institutes of Health (NIH) guidelines and all experimental protocols were approved by the Purdue Animal Care and Use Committee.

Statistical Analyses

The GraphPad Prism version 7 software (Graphpad, CA) was used for generation of all graphs and statistical analyses. All figures reported mean±s.e.m values unless otherwise noted. ANOVA was used for multiple comparisons.

Construction and Characterization of an Anti-Fluorescein CAR and it Interaction with a Fluorescein-Folate Bridge Molecules FIG. 63A shows the structure of a fluorescein-folate bridge (FITC-folate). On the structure's left side resides the vitamin, folic acid, which was selected as a representative tumor targeting ligand because its receptor (folate receptor alpha, FRα) is over-expressed on ~40% of human epithelial tumors, but largely absent or inaccessible in normal tissues. On the right side lies fluorescein, which was chosen as a ligand for CAR engagement because a human anti-fluorescein antibody with femtomolar affinity for fluorescein had already been described in the literature. FIG. 63B outlines construction of the CAR (SEQ ID NOS: 1 and 2) that was used to direct the cytotoxic CAR T cell to kill cancer cells. The anti-fluorescein scFv from the aforementioned antibody was fused to the CD3 zeta chain of a T cell receptor that had previously been engineered to contain the intracellular domain of CD137 (4-1BB). Insertion of this CAR construct into a lentiviral vector [pCDH-EF1-MCS-(PGK-GFP)] allowed transduction of pre-activated human T cells with 50-60% efficiency, as shown by the fraction of T cells staining positive for GFP (a fluorescent marker co-transduced with the CAR) (FIG. 63C). FIG. 63D further demonstrates that the CAR-expressing T cells bind fluorescein-folate, as established by the ability of fluorescein-folate to competitively block FITC-Alexa 647 binding to the engineered T cells.

With the ability to generate anti-fluorescein CAR T cells established, the killing potency of the engineered T cells was examined by evaluating the ability of the fluorescein-folate bridge molecule to mediate CAR T cell elimination of tumor cells in culture. As shown in FIG. 64A, fluorescein-folate was found to bind to FR positive KB cells (a cervical cancer cell line) as demonstrated by i) the shift in KB cell fluorescence upon addition of fluorescein-folate, and ii) the blockade of this shift upon competition with excess free folic acid. CAR T cell-mediated KB cell killing was then shown by demonstrating lysis of KB cells in the presence but not in the absence of the bridge. Thus, as shown in FIG. 64B, lysis of the cancer cells was observed when both CAR T cells and fluorescein-folate were present, but not when fluorescein-folate was absent (PBS) or when fluorescein-DUPA (a bridge molecule that bridges to prostate cancer cells but not to KB cells) was present. Moreover, anti-fluorescein CAR T cells were capable of eradicating KB cells at multiple effector to target cell ratios, but again only when fluorescein-folate was present (FIG. 64C). Analysis of concurrent production of IFNγ provided further evidence that the anti-fluorescein CAR T cell's tumoricidal activity was only triggered by addition of the correct fluorescein-folate bridge (FIG. 64D), and related experiments established that both anti-fluorescein CAR T cell proliferation and CAR T cell activation were also dependent on addition of the correct bridge (FIG. 64, panels E and F). Taken together, these data demonstrate that anti-fluorescein CAR T cell functionality is inextricably dependent on the availability of the correct tumor-specific bridge to mediate engagement of the CAR T cell with the desired cancer cell.

Identification of Conditions that Promote a Cytokine Release Syndrome (CRS)

Figure 65C:
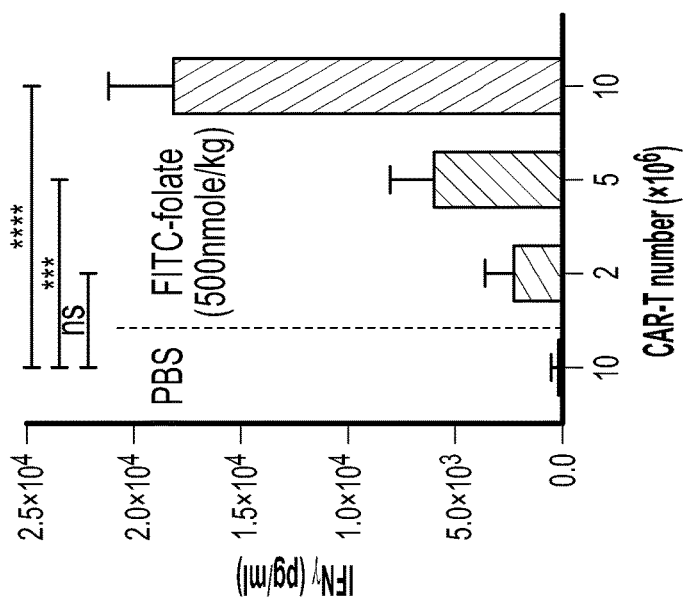
FIG. 65 shows the dependence of CRS on presence of anti-fluorescein CAR T cells, folate receptor positive cancer cells (MDA-MB-231 cells) and FITC-folate in vivo. (A) Bodyweight change (%) determined 4 days after anti-fluorescein CAR T cell (5×106) infusion into either tumor-free or tumor-bearing mice in the presence or absence of FITC-folate (500 nmole/kg administered on days 1 and 2).  P<0.01 by one-way ANOVA test. (B) Effect of CAR T cell number on bodyweight change (%) on day 4 in tumor-bearing mice after administration of either PBS or 500 nmole/kg FITC-folate on days 1 and 2.  P<0.05, ** P<0.0001 by one-way ANOVA test. (C) Effect of CAR T cell number in tumor-bearing mice on plasma IFNγ concentration on day 4. * P<0.001, **** P<0.0001, ns (not significant) by one-way ANOVA test. n=5 mice per group. Bar graphs represent mean±s.e.m.
Figure 65B:
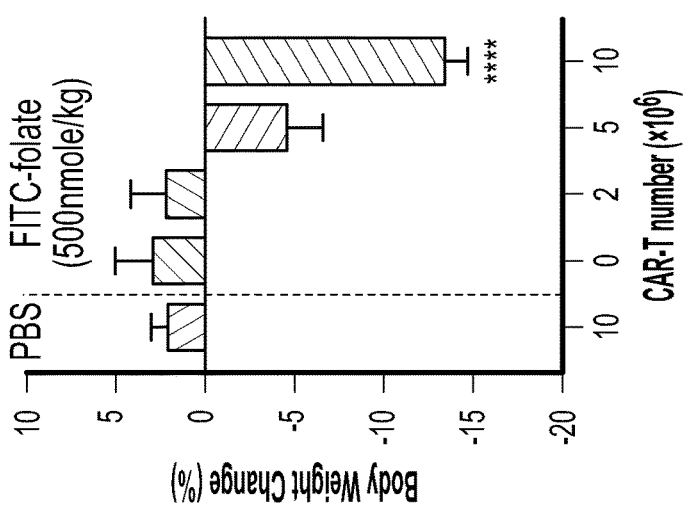
Figure 65A:
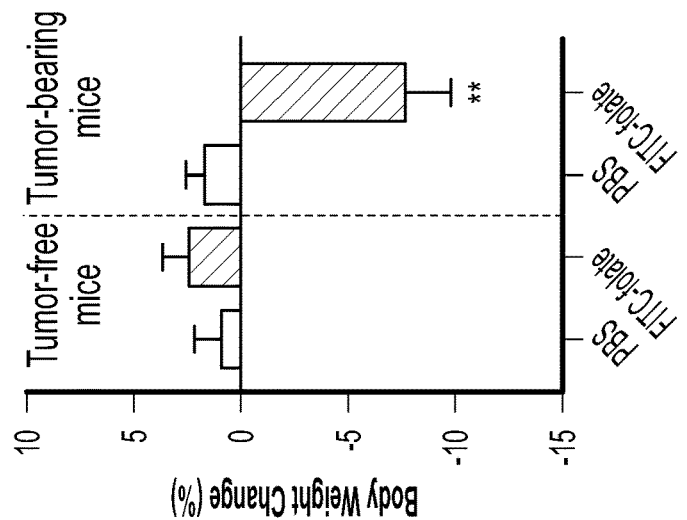

To explore whether manipulation of the duration, concentration or frequency of bridge dosing might be exploited to control a CRS, it was first necessary to identify conditions where an easily measurable CRS would reproducibly occur. After exploration of a number of human tumor xenograft models, it was found that NSG mice implanted with FR positive MDA-MB-231 cells (a human triple negative breast cancer cell line) reliably displayed a potent CRS upon administration of anti-fluorescein CAR T cells plus fluorescein-folate. Thus, as shown in FIG. 65A, body weight loss of ~8% was observed in tumor-bearing mice within 4 days of injection of $5 \times 10^6$ CAR T cells plus 500 nmoles/kg fluorescein-folate; i.e. indicating occurrence of a CRS. In contrast, no weight loss was observed in similar tumor-bearing mice upon injection of CAR T cells in the absence of fluorescein-folate; i.e. consistent with the aforementioned data demonstrating the bridge is required for CAR T cell activation. Significantly, no weight loss was detected in tumor-free mice treated with the same anti-fluorescein CAR T cells, regardless of whether the bridge was present or absent. These latter data confirm that even in the presence of CAR T cells and fluorescein-folate bridge, CAR T cell activation and the consequent body weight loss cannot occur unless a cell with exposed fluorescein (i.e. a fluorescein-decorated MDA-MB-231 cell) can be engaged by the CAR T cell. Because FR expression in healthy tissues is primarily restricted to the apical surface of proximal tubule cells in the kidneys (where FR are inaccessible to immune cells), little or no CAR T cell activation would be expected in tumor-free mice.

To further establish that the intensity of a CRS depends on the number of CAR T cells that successfully form a cytotoxic synapse with a cancer cell, the dependence of body weight loss and IFNγ release was determined as a function of CAR T cell number. As shown in FIG. 65B, administration of the bridger alone promoted no bodyweight loss. Similarly, injection of $10 \times 10^6$ CAR T cells in the absence of the bridge stimulated no decrease in body weight; i.e. confirming that engagement of a cancer cell is required for systemic cytotoxicity. While injection of $2 \times 10^6$ CAR T cells plus 500 nmole/kg bridge also induced no apparent weight loss, infusion of $5 \times 10^6$ or $10 \times 10^6$ CAR T cells plus the same bridge dose promoted increasingly greater losses in body weight. That these decrements in body mass likely arose from CRS is suggested by concurrent analyses of IFNγ release, which also display a sensitive dependence on CAR T cell numbers and the presence of the bridge. Taken together, these data suggest that both CAR T cells and a bridge must be present for induction of CAR T cell activation and the associated CRS.

Strategies to Rapidly Terminate a Pre-Existing Cytokine Release Syndrome

Figure 66A:
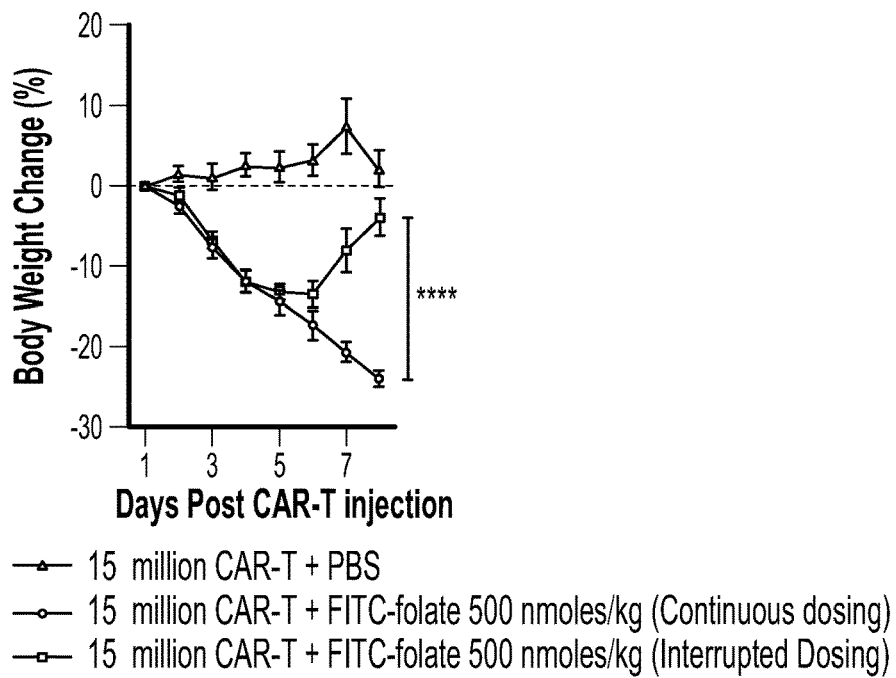
FIG. 66 shows the control of CRS intensity by interruption of bridge administration. (A) Analysis of body weight change (%) as a measure of CRS intensity after administration of a high dose of anti-fluorescein CAR T cells (15×106) in the either absence (PBS) or presence of FITC-folate (500 nmole/kg administered on days 1, and 2, and alternate days thereafter). In the interrupted dosing regimen, the continuous dosing schedule was followed except FITC-folate injections were omitted on days 4 and 6. (B) Analysis of IFNγ levels in mouse plasma on day 6 using the dosing regimens described in part A. (C) Measurement of tumor volumes in mice treated as described in part A. n=5 mice per group. Data represent mean±s.e.m. **** P<0.0001 by one-way ANOVA test.
Figure 66B:
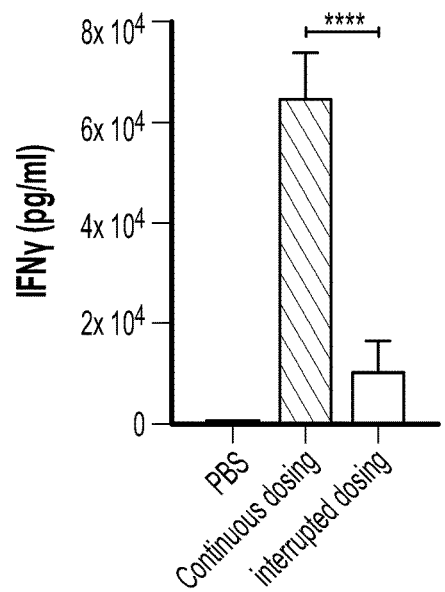
Figure 66C:
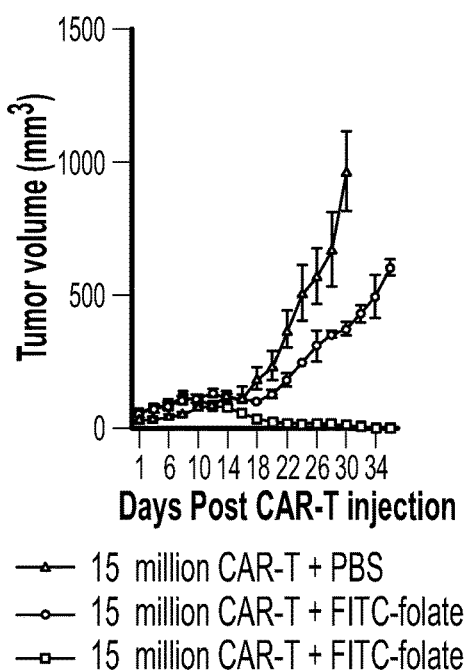

With 92% of all CAR T cell treated ALL patients experiencing a CRS, the question arose whether the ability to control engagement of a CAR T cell with its cancer cell target might be exploited to terminate a CRS after its full activation. To explore this possibility, we first examined whether interruption of fluorescein-folate administration might facilitate cessation of a CRS. As shown in FIG. 66A, a single treatment of MDA-MB-231 tumor-bearing mice with $15 \times 10^6$ anti-fluorescein CAR T cells followed by alternate day administration of 500 nmole/kg of fluorescein-folate promoted a rapid and continuous weight loss, leading to the required euthanasia of three of the mice by day 8 of therapy. In contrast, identically treated mice in which dosing of fluorescein-folate on days 4 and 6 was omitted (but which received continuous alternate day dosing thereafter) showed only a moderate weight loss from which they rapidly recovered. That this weight loss was likely related to the level of cytokine production in the same mice is demonstrated by the related changes in IFNγ levels measured in each mouse's plasma (FIG. 66B). More importantly, the temporary interruption of alternate day dosing not only failed to compromise anti-tumor activity, but instead actually enhanced CAR T cell potency. Thus, as shown in FIG. 66C, whereas untreated or continuously treated mice displayed a rapid increase in tumor growth, mice exposed to interrupted bridge dosing exhibited complete remission of their tumors. These data suggest that a pre-established CRS can be controlled by temporary discontinuation of bridge dosing without subverting CAR T cell cytotoxicity.

Realizing that transient interruption of bridge dosing can lead to a decrease in CRS, we next wondered whether a more potent decrement in CRS might be promoted by addition of ligands that would compete with fluorescein-folate for bridging CAR T cells to cancer cells. For this purpose, we initiated a CRS as described above, and while continuing the usual alternate day dosing of the bridge we simply administered 100-fold excess of free folate on days 4 and 6 to try to terminate the CRS. As shown in FIG. 67A, injection of excess folic acid rapidly prevented the continuous weight loss observed with the uninterrupted bridge dosing. Moreover, as seen in FIG. 66, this competition with adaptor dosing not only reduced the level of IFNγ in the treated mice (FIG. 67B), but also enhanced the therapeutic potency of the CAR T cell therapy (FIG. 67C). These data suggest that transient administration of a benign competing ligand (i.e. the vitamin folic acid) can terminate a CRS without significantly compromising the tumor therapy.

While folic acid can be used to control CRS whenever CAR T cell therapies exploit fluorescein-folate to mediate bridging between the CAR T and cancer cell, it seemed prudent to also examine the ability of fluorescein to block a CRS, since it should prove useful in controlling CRS associated with any fluorescein-linked tumor-specific bridge. Therefore, as described above, a CRS was induced in MDA-MB-231 tumor bearing mice, and its discontinuation was attempted by administration of free fluorescein on day 3 of the CRS. While injection of competing fluorescein induced a decrease in CRS with an increase in therapeutic efficacy, it did so more rapidly than seen with free folate. Thus, as shown in FIG. 67D, all CRS-relevant cytokines declined within 3 hours of fluorescein administration, with IL-2, TNF-α, and IL-6 decreasing >50% over this short timespan. Although IFNγ did not display a decline in plasma concentration at 3 hours, it did demonstrate a decrement by 6 hours post fluorescein injection, suggesting its production is also suppressed by fluorescein addition. Importantly, plasma concentrations of IL-2, TNF-α, and IL-6 had all diminished to nearly background levels by the 6 hour time point.

Strategies to Prevent Emergence of CRS without Compromising Anti-Tumor Activity

Figure 68A:
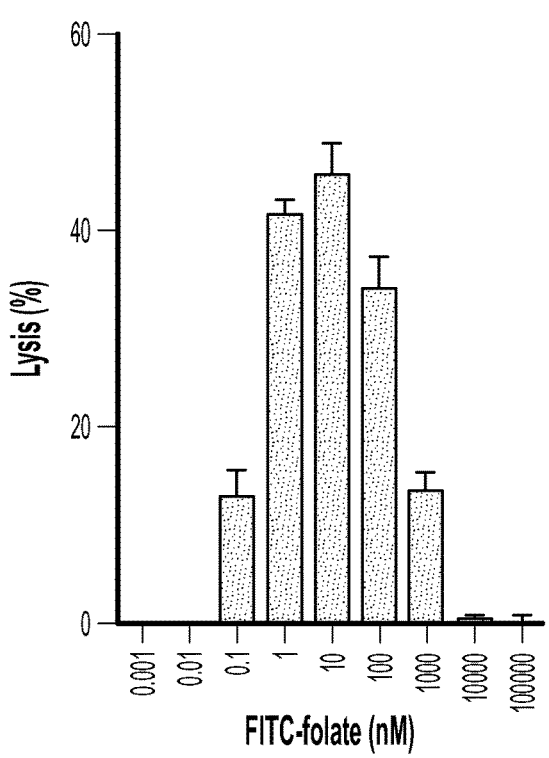
FIG. 68 shows the effect of bridge concentration on the regulation of anti-fluorescein CAR T cell cytokine release and anti-tumor activity in vitro and in vivo. (A) Lysis of MDA-MB-231 cells in culture by anti-fluorescein CAR T cells (5:1=Effector:Tumor cell ratio) in the presence of various concentrations of FITC-folate (0.001 nM to 100000 nM). (B) IFNγ release from cells described in part A. (C) The level of IFNγ in the plasma of MDA-MB-231 tumor bearing mice 6 days after initiation of therapy by injection of 15×106 CAR T cells. Mice were treated with 5, 50, 500, or 2500 nmole/kg FITC-folate on days 1, 2, 8, 10 and alternate days thereafter (treatments on days 4 and 6 were omitted to avoid a CRS). (D) Analysis of tumor growth in treatment groups of panel C. n=5 mice per group. Bar graphs represent mean±s.e.m. **** P<0.0001 by one-way ANOVA test.
Figure 68B:
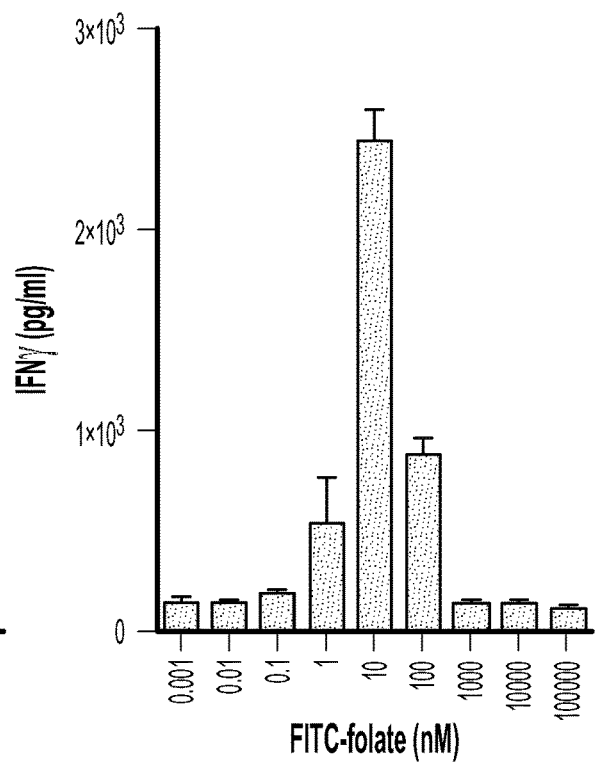
Figure 68C:
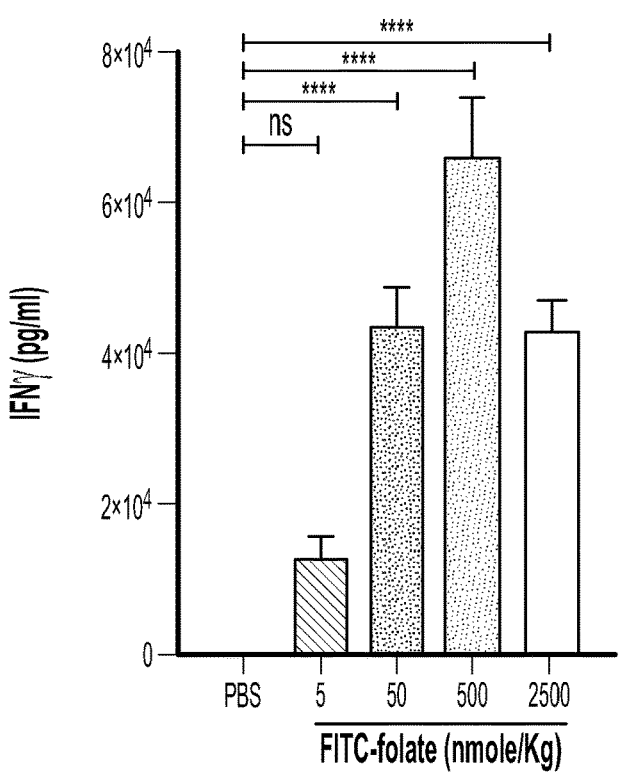
Figure 68D:
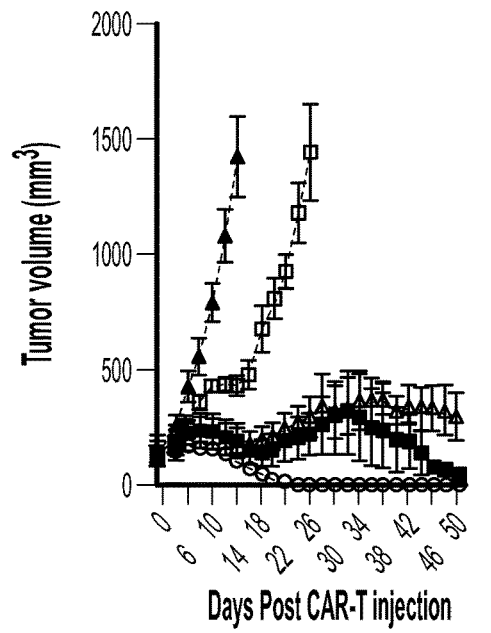

Although a highly elevated and prolonged CRS can often lead to patient death, some level of CRS has been viewed as desirable, since patients displaying no evidence of CRS are not commonly observed to respond to CAR T cell therapies. The question therefore arises whether optimization of either bridge or CAR T cell dosing conditions can result in minimization of a CRS without loss of antitumor activity. To explore this possibility, we first examined the effect of bridge dose on tumor cell lysis and IFNγ release in vitro. For this purpose, anti-fluorescein CAR T cells were added to MDA-MB-231 cell cultures followed by treatment with fluorescein-folate concentrations ranging from 0.001 to 100,000 nM. As shown in FIGS. 68A and B, bridge doses below 0.01 nM exerted little effect on tumor cell lysis and only minimal effect on IFNγ production. In contrast, somewhat higher concentrations of fluorescein-folate wielded a potent impact on both parameters, whereas still higher doses of bridge promoted a reduction in both cytokine release and MDA-MB-231 cell killing. Based on the mechanism of the bridge, it could be predicted that excessive bridge concentrations should saturate all sites on both CAR T cells and cancer cells monovalently, and thereby block bivalent the intercellular bridging function of the bridge.

To evaluate the same bridge concentration dependence in vivo, MDA-MB-231 cells were implanted subcutaneously in NSG mice and the effect of fluorescein-folate dose was again examined by monitoring tumor growth and cytokine release. Unfortunately, as seen previously in FIG. 66, continuous alternate day dosing resulted in the anticipated toxic CRS, regardless of bridge dose, forcing us to omit bridge administration on days 4 and 6. However, even with this modification, analysis of the effect of bridge concentration was possible, revealing a bell-shaped dependence similar to that observed in vitro; i.e. an initial increase in plasma IFNγ was followed by a decrease in its plasma concentration as bridge dose was elevated (FIG. 66C). Importantly, tumor cell shrinkage also displayed a similar bell-shaped dose response, with 500 nmole/kg exhibiting complete tumor eradication and both lower and higher concentrations displaying lower potencies (FIG. 66D). These observations confirm that maximal bridging between CAR T cells and cancer cells will only occur at intermediate bridge concentrations, where sufficient bridge is present to maximize bridge formation, but excess bridge has not been administered to promote autologous competition for the bridging function.

Figure 69A:
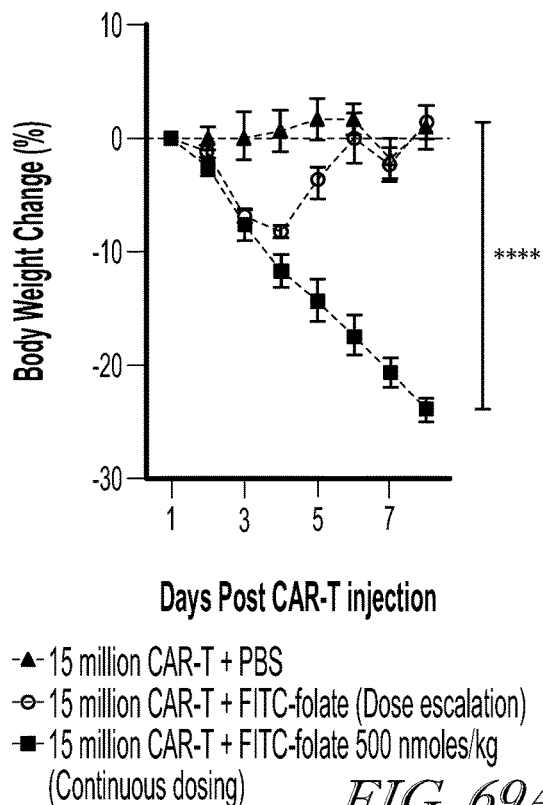
FIG. 69 shows the prevention of CRS by gradual escalation of bridge dose or decrease in bridge dosing frequency. Measurement of body weight change (A) and tumor volume (B) in MDA-MB-231 tumor-bearing mice treated with 15×106 CAR T cells plus either PBS, or a gradual escalation of FITC-folate dose (0.5 nmole/kg on days 1 and 2, 5 nmole/kg on days 4 and 6, 50 nmole/kg on days 8 and 10, and 500 nmole/kg from day 12 onward), or a constant dose of 500 nmole/kg on alternate days. **** P<0.0001 by two-way ANOVA test. Measurement of body weight change (C) and tumor volume (D) in MDA-MB-231 tumor-bearing mice treated with 5×106 CAR T cells plus either PBS or FITC-folate (500 nmole/kg) at different dosing frequencies of 1) one dose/week (on days 1, 8, 15 & etc.), 2), two doses/week (days 1, 4, 8, 11, 15 & etc.), or three doses/week (days 1, 3, 5, 8, 10, 12, 15 & etc.). n=5 mice per group. All data represent mean±s.e.m.
Figure 69B:
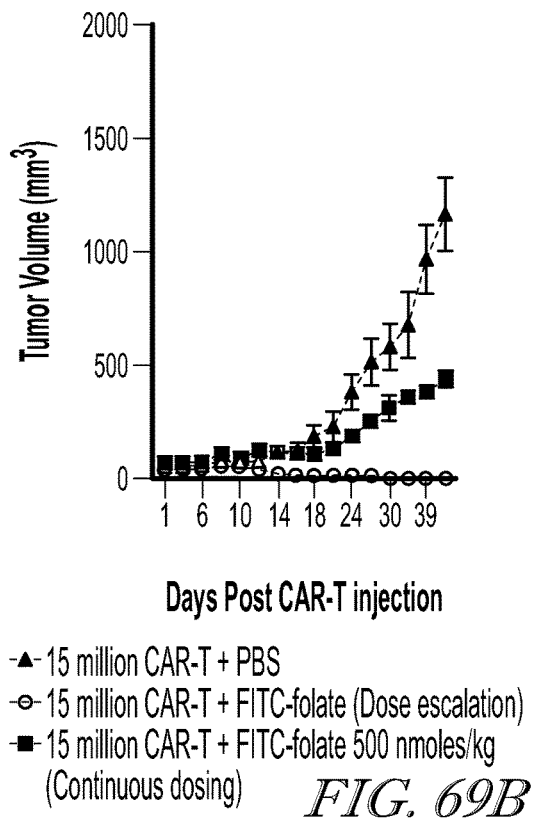

With the ability to exploit bridge dose to control CAR T cell activation now established, we decided to investigate whether a therapeutically active bridge dosing regimen might be identified that could prevent emergence of a toxic CRS without compromising anti-tumor potency. Based on a hypothesis that CRS becomes most severe when CAR T cells are activated too precipitously, we elected to test two less aggressive bridge dosing regimens that might more gradually induce CAR T cell activation. For the first regimen, fluorescein-folate concentration was increased steadily from 0.5 to 500 nmole/kg during each successive administration of the adaptor. As shown in FIG. 69A, this slow escalation of bridge concentration caused only a transient weight loss that resolved within 4 days without any intervention. In contrast, continuous dosing of 500 nmole/kg in the same mice pretreated with 15×10$^6$ CAR T cells caused a dramatic and continuous weight loss that forced eventual euthanasia of the mice. More importantly, the gradual dose escalation regimen resulted in complete cures of the tumor-bearing mice, whereas the continuous toxic dosing schedule provided little therapeutic benefit (FIG. 69B). These data argue strongly that anti-tumor activity can be uncoupled from CRS and that slower CAR T cell activation may in fact enhance tumoricidal activity while reducing CRS.

Figure 69C:
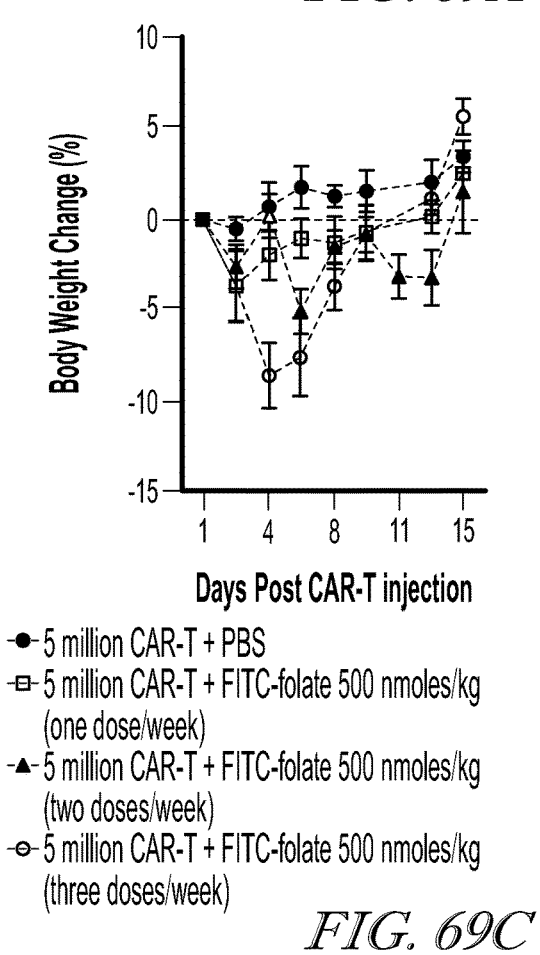
Figure 69D:
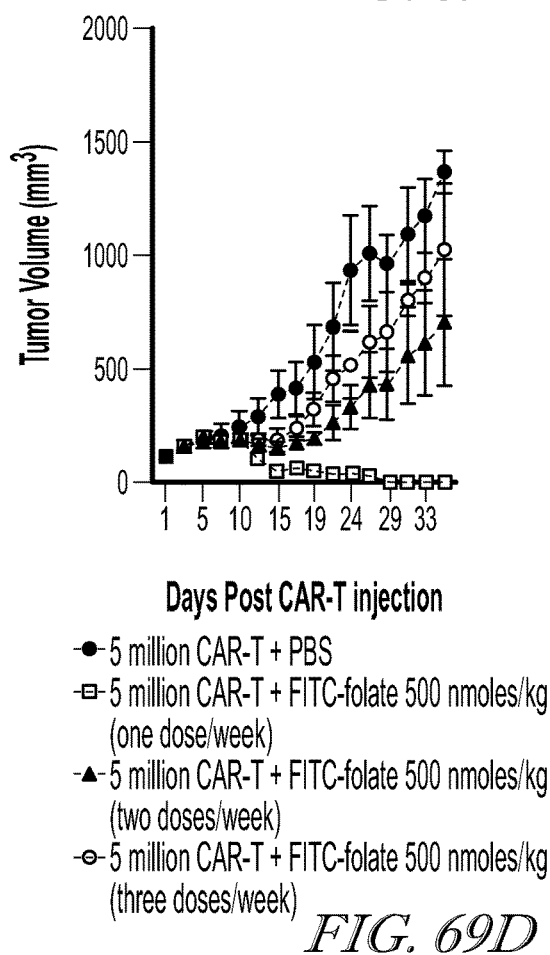

The impact of reducing the frequency of bridge dosing was examined in the hope that introduction of longer intervals between CAR T cell activation might permit some CAR T cell relaxation and thereby reduce any exhaustion that would have normally arisen from chronic antigen exposure. As shown in FIG. 69C, three doses of bridge per week caused significant animal weight loss, while two doses of bridge per week caused less toxicity and a single fluorescein-folate injection per week caused no weight loss. As seen in many of the previous studies, anti-tumor activity increased as CRS decreased; i.e. yielding complete cures when only one dose of bridge was administered per week.

Example 44

Study Using AML Model

EC17/CAR-T therapy in a folate receptor-β positive acute myeloid leukemia model is shown.

Materials:

EC17 (folate-FITC, m.w. 873) was synthesized in house. Sodium fluorescein (AK-FLUOR®, fluorescein injection, USP) was purchased from Purdue Pharmacy.

In-Vivo Methods:

Cell Line

THP-1 is a human monocytic cell line derived from a patient with acute monocytic leukemia, a type of acute myeloid leukemia (AML). THP-1-FRβ is a GFP-positive subclone of THP-1 stably transfected with a human FR. The cells were grown in a folate-free RPMI1640 medium (Gibco BRL) (FFRPMI) containing 10% heat-inactivated fetal calf serum (HIFCS) and antibiotics, and maintained under a 5% CO$_2$ atmosphere using standard cell culture techniques.

Mice

Female NSG™ (NOD.Cg-Prkdc$^{scid}$ Il2rg$^{tm1Wjl}$/SzJ, stock #005557) mice were purchased from The Jackson Laboratory (Bar Harbor, ME) and used when they reached ~4 weeks of age. The mice were fed a folate-deficient diet (TestDiet, St. Louis, MO) on the day of arrival.

Tumor Implantation

THP-1-FRβ tumors were generated by intravenous implantation of cultured cells at 5×10$^6$ per animal in 9 NSG mice.

EC17/CAR-T Therapy of Tumor-Bearing Mice

Starting 11 days post tumor implantation, ~8.3 million of GFP+4M5.3 CAR-T cells were intravenously infused into each mouse. Mice were divided into 3 groups (n=3): (1) CAR-T cell alone, (2) CAR-T cells with weekly EC17 doses at 500 nmol/kg, and (3) CAR-T cells with weekly EC17 doses at 500 nmol/kg plus sodium fluorescein rescue when needed. The first EC17 dose was given two days after CAR-T cell administration. All EC17 doses were given towards the end of day (~3-4 PM) to allow cytokine release syndrome (CRS) to develop overnight. In the following morning after the first EC17 dose, all 6 mice in Groups 2 and 3 showed an onset of CRS with a CRS grade of ~3, sodium fluorescein was then administered at 6 μmol/kg for Group 3 only. All EC17-dosed mice with and without sodium fluorescein rescue completely recovered in the next few days. No additional sodium fluorescein rescue was given for additional EC17 dosing in Group 3. Mice were weighed and monitored for sign of health and disease development. Animals were euthanized when they displayed severe distress/moribund behavior or for comparison purposes. Upon euthanasia, all mice were subject to gross examination for the presence of tumor masses. All visible tumor masses were excised, counted and weighed. Blood, tumor metastases (mets) and normal adjacent tissues were collected for same-day flow cytometry analysis.

Whole Blood Cell Analysis by Flow Cytometry

Plasma was removed from predetermined volumes of whole EDTA treated blood with a 10-minute 4° C. spin at 3000×g and the resulting cell pellets were incubated with a 10-fold volume of room temperature 1×RBC lysis solution (prepared from 10× stock; Biolegend, catalog #420301) for 5 minutes, centrifuged at 400×g for 5 min. The cell pellets were washed in a 10-fold volume of ice-cold phosphate-buffered saline (PBS, pH=7.4 and filtered with a 40 μm nylon filter then pelleted again. The leukocyte cell pellets were then resuspended in a flow cytometry staining solution (1% bovine serum albumin, 50 mg/mL human IgG (Equitech Bio, cat #SLH56-0001), 0.9% sodium azide in PBS, pH=7.4) supplemented with both anti-mouse FcγIII/II receptor (CD16/CD32) block (clone 2.4G2; BD Bioscience, catalog #553142 at 1:100 (v/v) dilution) and anti-human Fc Block (BD Biosciences, catalog #564220 at 1:50 (v/v) dilution). Surface marker staining was performed with the addition of the following fluorochrome conjugated monoclonal antibodies added to each sample for 20 minutes on ice in the dark: anti-human CD45-APCeF780 (clone HI30, eBioscience #47-0459-42 at 1:20 (v/v) dilution), anti-human CD3-BV650 (clone SK7, BD Bioscience, catalog #563999 at 1:20 (v/v) dilution), anti-human CD137-BV650 (clone 4B4-1, BD Bioscience #564092 at 1:20 (v/v) dilution), anti-human CD8α-PECy7 (clone RPA-T8, BD Bioscience, catalog #557746 at 1:20 (v/v) dilution), anti-human CD4-Percpe710 (clone SK3, eBioscience catalog #46-0047-42 at 1:20 (v/v) dilution), anti-human CD25-PE (clone M-A251, BD Bioscience, catalog #555432 at 1:10 (v/v) dilution), anti-human CD33-PE (clone WM53, BD Bioscience, catalog #555450 at 1:5 (v/v) dilution), anti-human CD123-AF647 (clone 9F5, BD Bioscience, catalog #563599 at 1:20 (v/v) dilution). Biotinylated anti-human folate receptor-β (clone m909) was kindly provided by the Low lab at Purdue University (Arthritis Res Ther. 2011; 13(2):R[59]) and detected using streptavidin-eFluor660 (eBioscience, catalog #50-4317 at 1:1000 (v/v) dilution). Folic acid binding was interpreted as a measure of functional folate receptor and was determined by incubation with an Alexa Fluor conjugated folic acid which was synthesized in house. After leukocyte staining, cells were washed with PBS and resuspended in cold PBS containing 3 μM propidium iodide. Flow cytometry data was collected on the Gallios flow cytometer (Beckman Coulter, Brea, CA), where a minimum of 15,000 CountBright™ bead events were collected in an attempt to collect enough leukocyte events for an accurate count of infused CAR T cells in each mouse blood sample. Determination of the concentration of CAR T cells in each blood sample was calculated according to Invitrogen's instructions. Briefly, CAR T cells were identified as human CD45+ GFP+ events and easily distinguished and counted using the Kaluza™ flow cytometry software version 1.5. CountBright™ beads were uniformly labeled with a fluorochrome not utilized in the antibody panel used to identify the CAR T cells and were easily distinguished from the leukocytes and bead events were counted. Because 53,000 CountBright™ beads were added to each sample tube, we calculated the ratio of 53,000 total beads to bead events collected per sample and set the bead ratio equivalent to the unknown number of CAR T cells in each sample divided by the known number of CAR T cell events collected. Solving for the unknown gave us the number of CAR T cells isolated from each blood sample of known volumes. The number of CAR T cells in the circulation of each infused mouse was then represented on the graphs as the total number of CAR T cells per 50 μL of whole blood analyzed. Human peripheral blood mononuclear cells were purchased and used for staining controls for leukocyte surface markers (Human PBMCs, Stem Cell Technologies, catalog #70025.22). Statistical significance was determined by utilizing an unpaired, two-tailed, student's t-test with significance set at p<0.05 for comparisons between each of the three groups of mice.

Preparation of Single Cell Suspension of Tumor and Adjacent Healthy Tissue

Solid tumors and tumor free adjacent tissues were harvested, weighed, and minced into small pieces then transferred into 50 mL tubes containing 20 mL of a tumor digestion cocktail. The enzymatic tumor digestion cocktail consisted of 0.5 mg/mL Collagenase IV (Sigma-Aldrich, Catalog #C5138), 0.5 mg/mL Hyaluronidase (Sigma-Aldrich, Catalog #H3506) and 0.1 mg/mL DNase I (Sigma-Aldrich, Catalog #DN25) in serum-free and folate-deficient RPMI1640 medium supplemented with antibiotics. The tumor fragments were digested for one hour at 37° C. at 300 rpm on a horizontal shaker. Afterwards, the tumor digest was centrifuged at 400×g for 5 minutes and tumor cell pellets were incubated with a 10-fold volume of room temperature 1×RBC lysis solution [prepared from 10× stock; Biolegend, catalog #420301] for 5 minutes, centrifuged at 400 g for 5 min, and the cell pellet was washed in a 10-fold volume of ice cold phosphate buffered saline pH=7.4 and filtered with a 40 μm nylon filter then pelleted again. The tumor cells were analyzed by flow cytometry as previously described above.

Gross Examination of Total Tumor Load

Figure 57A:
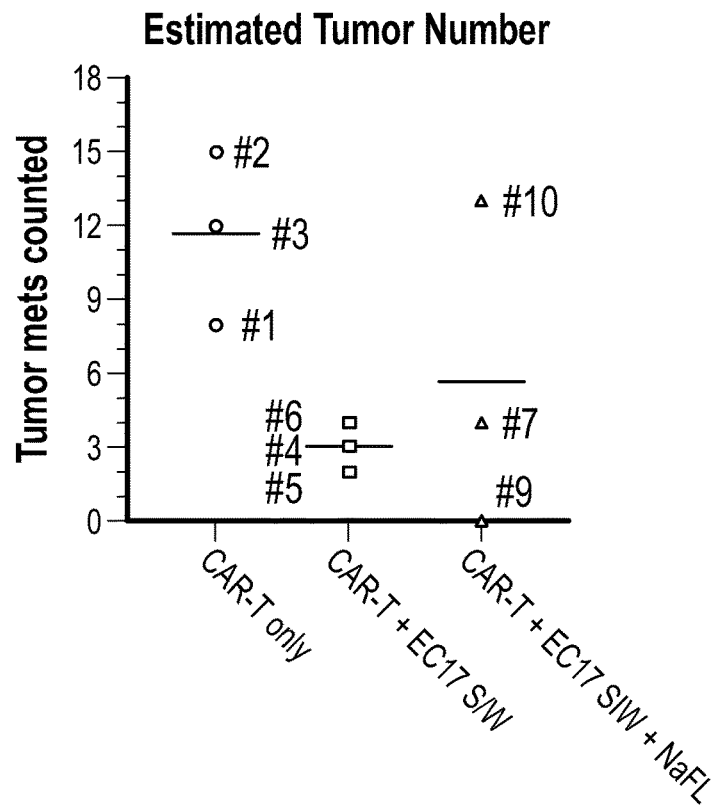
FIG. 57 summarizes the estimated numbers of tumor masses and total tumor weights in all groups examined.
Figure 57B:
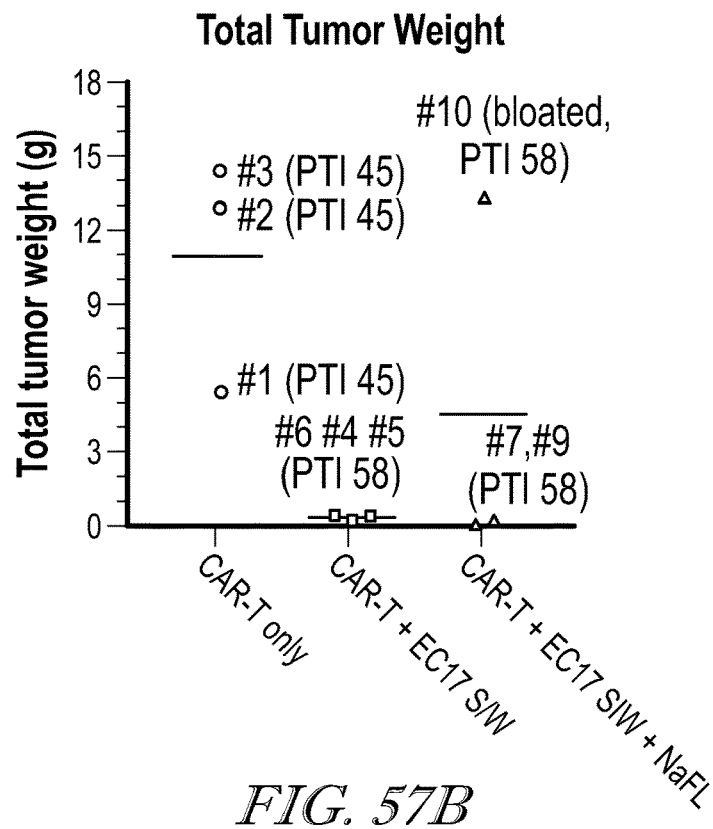

All 3 CAR-T cell control animals in Group 1 (#1, #2, #3) were found bloated on day 45 post tumor implantation (PTI 45) (i.e. 34 days post CAR-T cell administration). Two control animals were euthanized and the third one was dead right before euthanasia. One animal in Group 2 (#5) was euthanized and served as a same-day comparator for Group 1. On day 58 post tumor implantation (PTI 58) (i.e. 46 days post CAR-T administration), the remaining two animals in Group 2 (#4 and #6) were euthanized (#4 was pre-dosed with EC17 the day before). All 3 animals in Group 3 (#7, #9, and #10) were also collected (#7 and #10 were pre-dosed with EC17 the day before). As shown in FIG. 56, metastatic tumor masses of various sizes (large in the ovaries) and locations (except for the lungs) were found in the CAR-T cell only control group. On the same day of collection, only tiny tumor nodules were identified in the EC17 treated animal from Group 2 (#5). FIG. 57 summarizes the estimated numbers of tumor masses and total tumor weights in all groups examined. In general, mice in the CAR-T cell control Group 1 had the most visible tumor masses and a higher total tumor load than the animals in both EC17-treated groups regardless of sodium fluorescein rescue.

Other than one animal in Group 3 (#10), five out of the 6 EC17-treated mice (+/− one-time sodium fluorescein rescue) had minimum tumor load at the time of collection. These preliminary results showed that EC17-controlled CAR-T therapy was highly effective against this AML tumor model.

Characterization of Circulating Tumor Cells

Figure 58A:
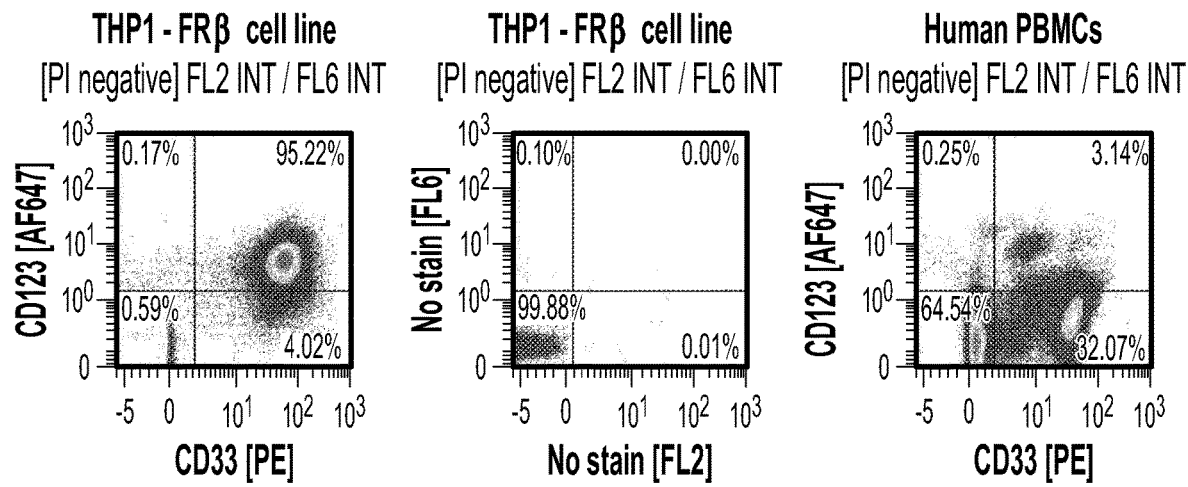
FIGS. 58A and 58B show the characterization of circulating tumor cells.
Figure 58B:
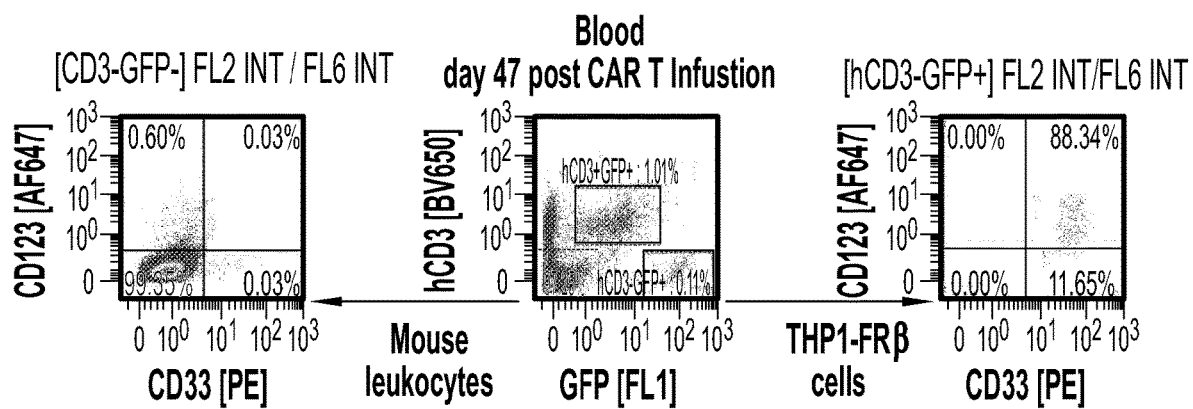

Circulating AML were analyzed and show characteristic surface marker expression, CD33 and CD123, in approximately 90-95% of all patients. To test the anti-leukemia activity of our FITC specific 4M5.3 CAR T cells in this aggressive AML model, we utilized THP-1 cells stably transfected with FRβ and referred to as THP-1-FRβ. We therefore tested our in-vitro THP-1-FRβ cell line and demonstrated these cells also expressed CD33 and CD123 surface expression (FIG. 58A, left dot plot) suggesting an AML phenotype. Unstained THP-1-FRβ cells and fresh human PBMCs served as gating and positive controls, giving us confidence in our assay for these markers (FIG. 58A, middle and right dot plots). When THP-1-FRβ cells were intravenously injected into the NSG mice, the human leukemic cells were easily distinguished from mouse leukocytes in the blood by GFP fluorescence and were observed to retain the surface expression of AML markers, CD33 and CD123 (FIG. 58B). In addition, we confirmed stable FRβ expression on circulating tumor cells in vivo by positive surface staining with Alexa Fluor 647 labeled folic acid (FIG. 59A). The THP-1-FRβ tumor cells also continued to express FRβ in solid tumor metastases isolated from the liver and ovary as seen by flow cytometric staining using an anti-human FRβ antibody (FIG. 59B).

Anti-Leukemia Activity of EC17 Directed CAR T Cells

Figure 60A:
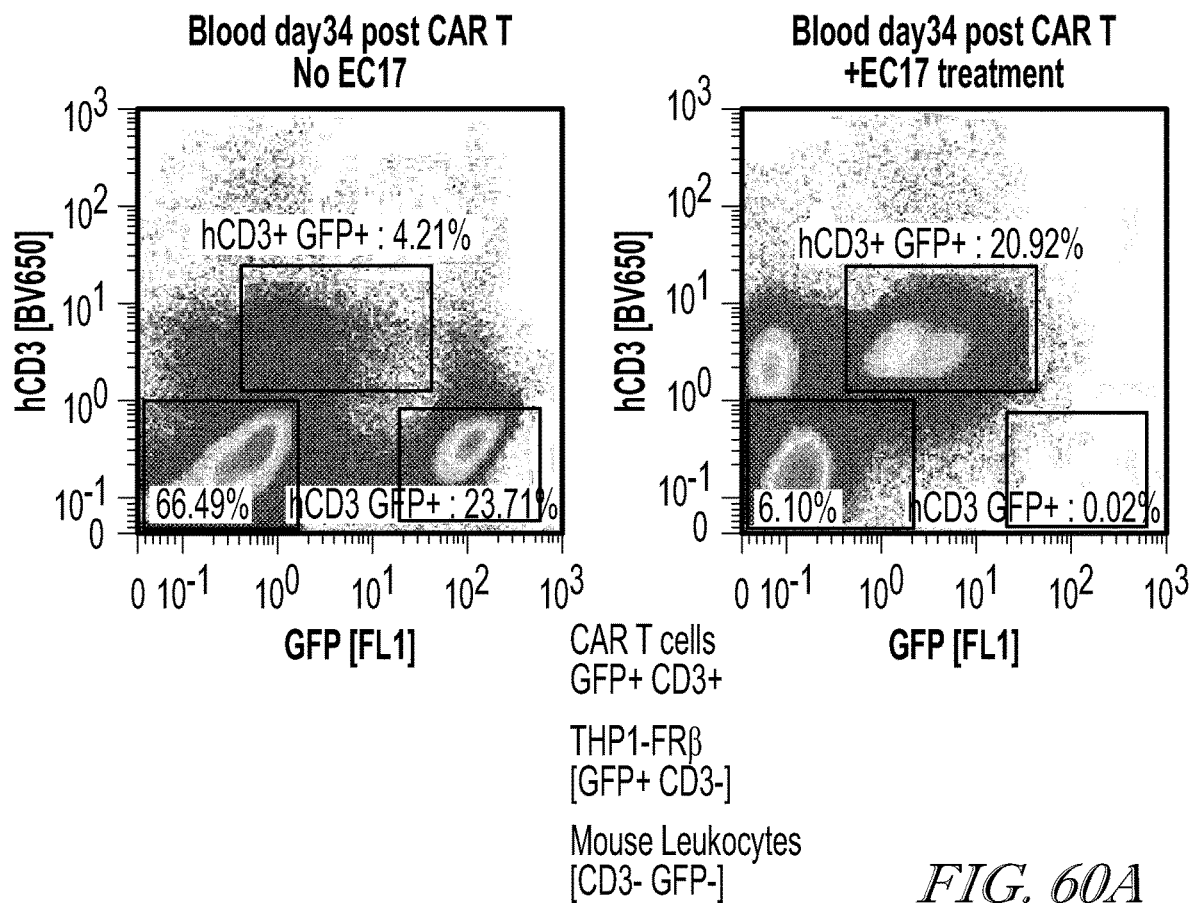
FIGS. 60A and 60B show the percent of whole blood that is CAR T cells upon EC17 injection.
Figure 60B:
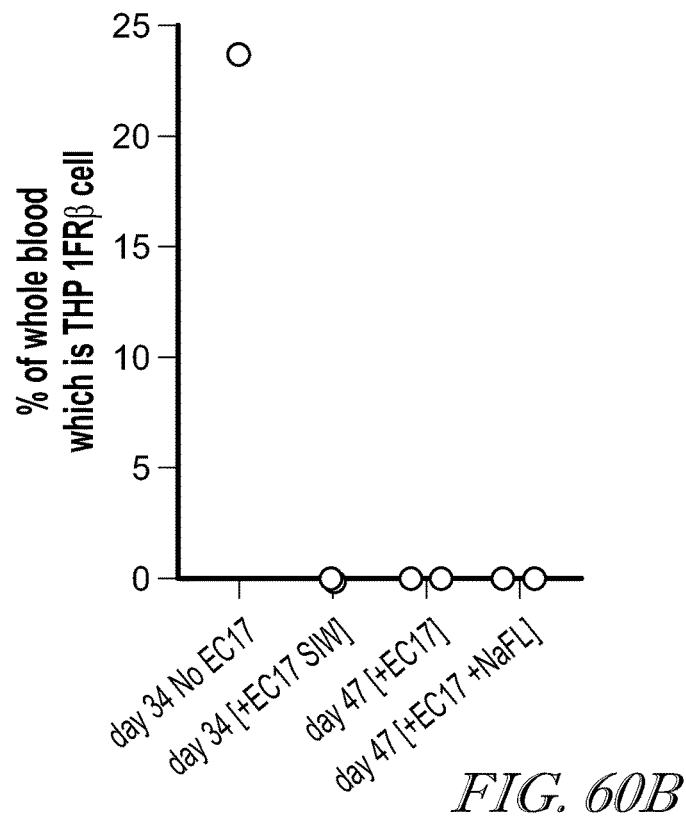

To determine if CAR T cells can be directed to reduce the leukemic load of NSG mice bearing THP-1-FRβ cells, on day 34 post CAR-T infusion, we compared GFP+ tumor cells isolated from the blood of an animal receiving CAR T cells alone in Group 1 that had met euthanasia criteria to that of an animal receiving CAR T cells plus EC17 (500 nmol/kg; SIW) for 4 weeks in Group 2 (FIG. 60). Clearly there was a high leukemia load in the control animal without EC17 treatment as approximately 23% of the total leukocytes are GFP+ leukemia cells (FIG. 60A and FIG. 60B, bar graph). However, in the animal that was infused with CAR T cells and dosed with EC17, significant CAR T cell activity was observed as GFP+ leukemic cells became nearly undetectable in the blood (FIG. 60B). Moreover, the observed anti-leukemia activity of CAR T cells persisted in animals as long as 47 days post CAR T cell infusion as THP1-FRβ cells were still undetectable in the blood (FIG. 60B).

Persistence of Blood-Borne CAR T Cells Post Infusion

Figure 61A:
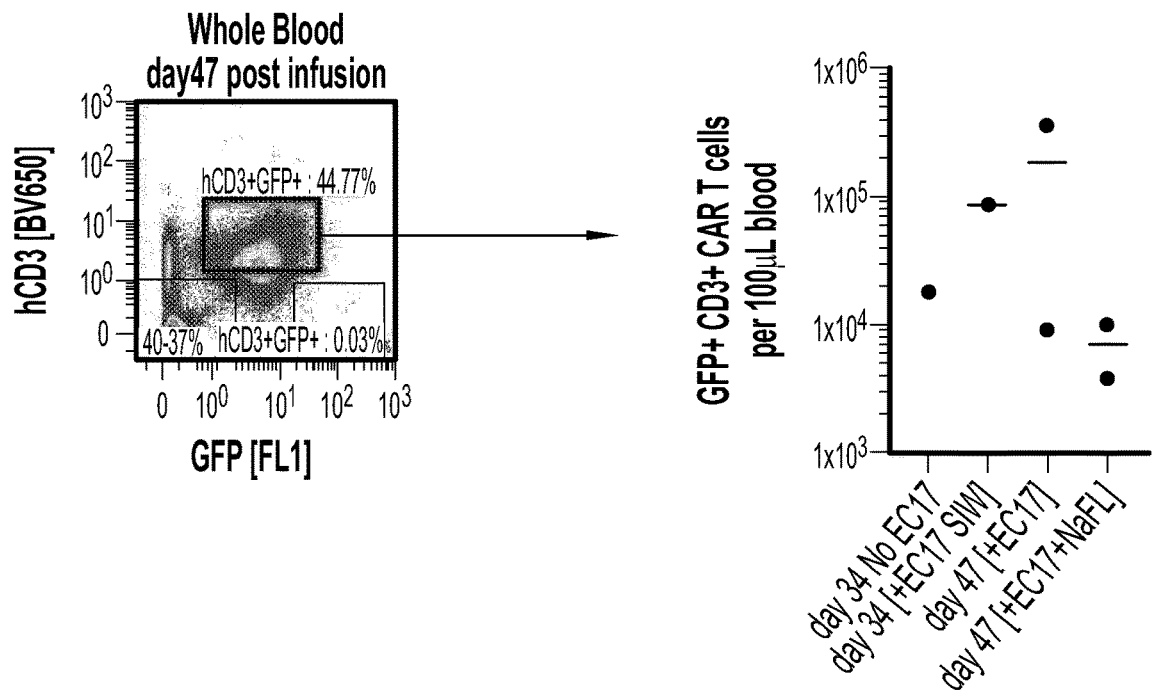
FIGS. 61A and 61B show the persistence of blood-borne CAR T cells post infusion of EC17 with and without rescue and the phenotype post infusion of EC17.
Figure 61B:
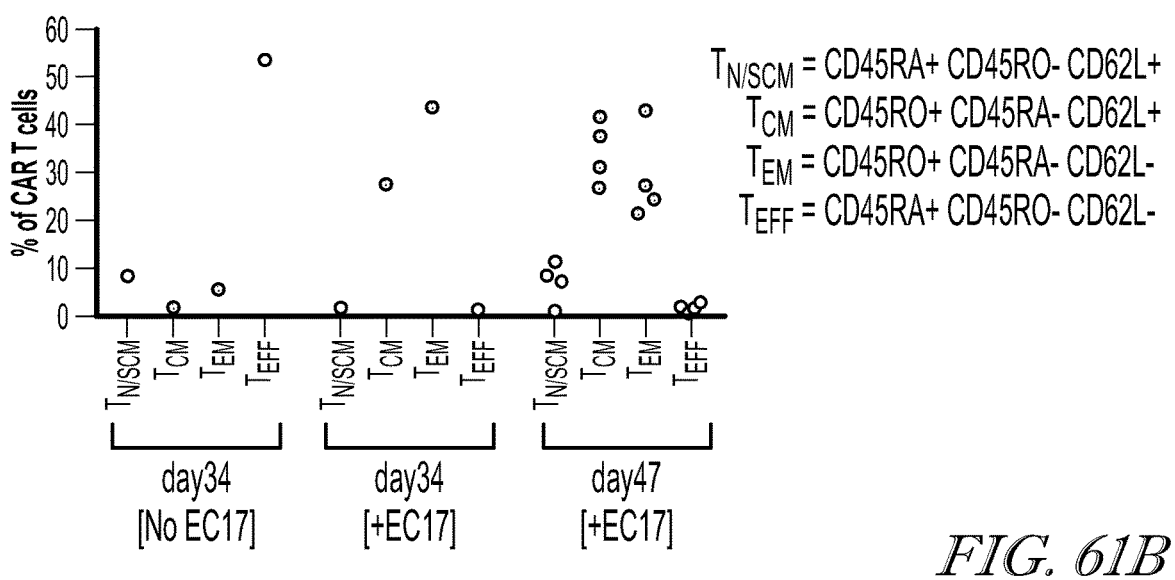

The numbers of FITC-CAR T cells in the circulation were measured by flow cytometric analysis to enumerate the GFP+CD3+ CAR T events in whole blood samples collected from mice at days 34 and 47 (end of study) post CAR T cell infusion (FIG. 61A). Our human CAR T cells transduced with the 4M5.3 construct persisted as long as 34 days post infusion in a control mouse that did not receive any EC17, suggesting that the THP-1-FRP tumor bearing NSG mice were able to sustain the viability of human T cells. In CAR-T cell infused THP1-FRβ bearing mice receiving EC17 on a weekly basis, CAR T cells were noticeably persistent in the blood for as long as 47 days post infusion with number ranging from 3800 to 300,000 CAR T cells per 100 μL of blood (FIG. 61A), with no apparent difference with the control animals. Interestingly, the CAR T cell phenotype isolated from the mice receiving weekly injections of EC17 was primarily that of either central memory/effector memory phenotype (FIG. 61B), whereas the CAR T cells from the mouse which did not receive EC17, still had the effector T cell phenotype (FIG. 61B). CAR T cells with a memory phenotype is a desirable trait for T cell therapy as memory T cells are capable of further cell division to give rise to future effector T cells available for killing cancer cells.

CAR T Cells Localized in Metastatic Tumor Lesions not Adjacent Healthy Tissues

Figure 62A:
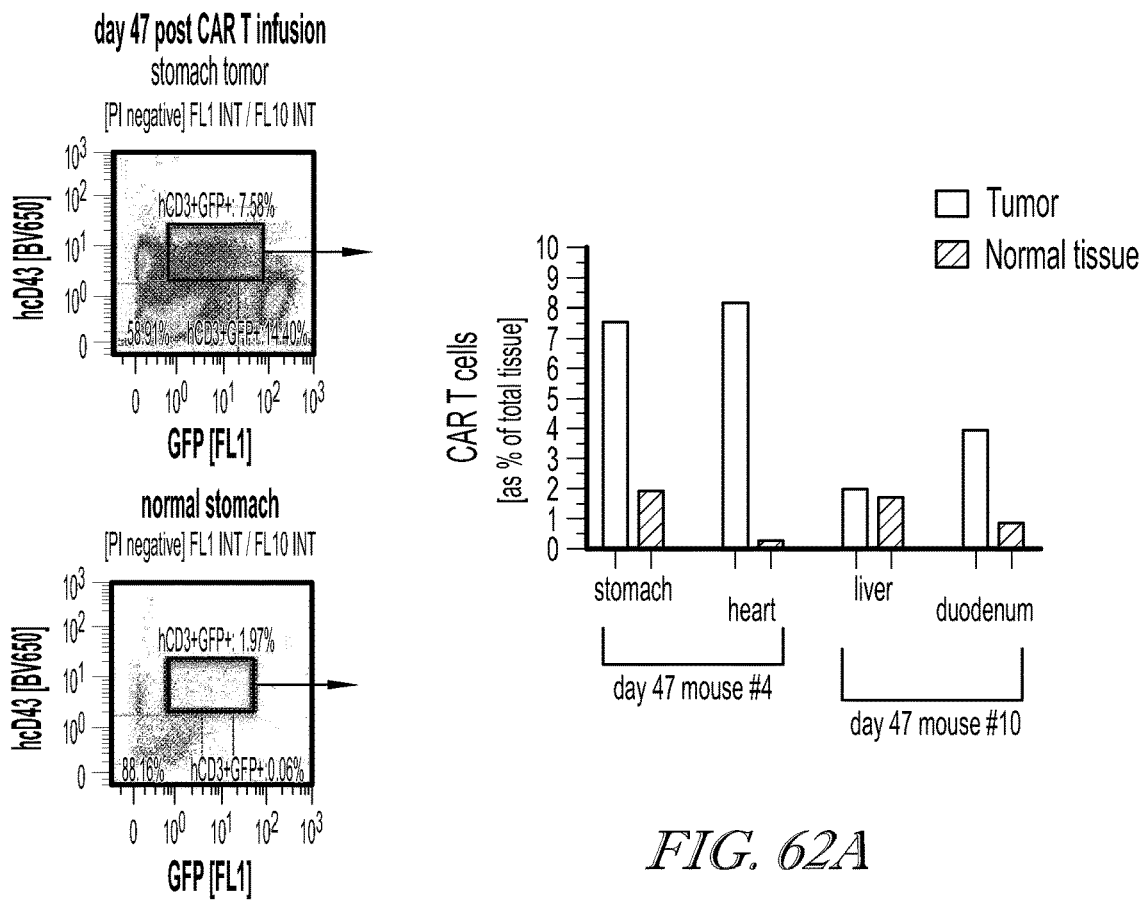
FIGS. 62A and 62B show that CAR T cells localized in metastatic tumor lesions, not adjacent healthy tissues, when EC17 is injected.

Although AML tumor cells are usually found in the blood and bone marrow of patients, occasionally AML cells can form solid tumors anywhere in the body. THP-1-FRβ tumor model in NSG mice resembles that of AML with tumor cells in the blood and metastatic solid tumor lesions in normal tissues such as ovaries, liver, small intestine, brain and stomach. Since EC17/CAR-T treatment significantly reduced total tumor burden (FIG. 56 and FIG. 57), we wanted to assess the presence of CAR T cells within the residual tumors found in EC17 treated animals and study the preference of CAR T cells for the tumors relative to their adjacent normal tissues in the same animal (FIG. 62). Two animals that received CAR-T cell infusion plus 5 weekly doses of EC17 (500 nmol/kg) were euthanized on day 47 post T cell infusion. Residual tumors were found in a few normal organs (e.g. stomach lining, heart, liver, and duodenum). Using flow cytometry on digested samples, we analyzed the presence of CAR T cells in visible solid tumor mets and compared CAR-T cell infiltration to that of adjacent healthy tissue of the same animals where tumors were found. In one animal (mouse #4), CAR T cells were present at higher numbers in tumors found with the stomach and heart (FIG. 62A) but not in healthy adjacent tissues (FIG. 62A). Similar data was also seen in another animal (mouse #10) where tumors were found within the duodenum, however, the difference in CAR T cell numbers between the liver tumor met and healthy liver tissue was not large.

Figure 62B:
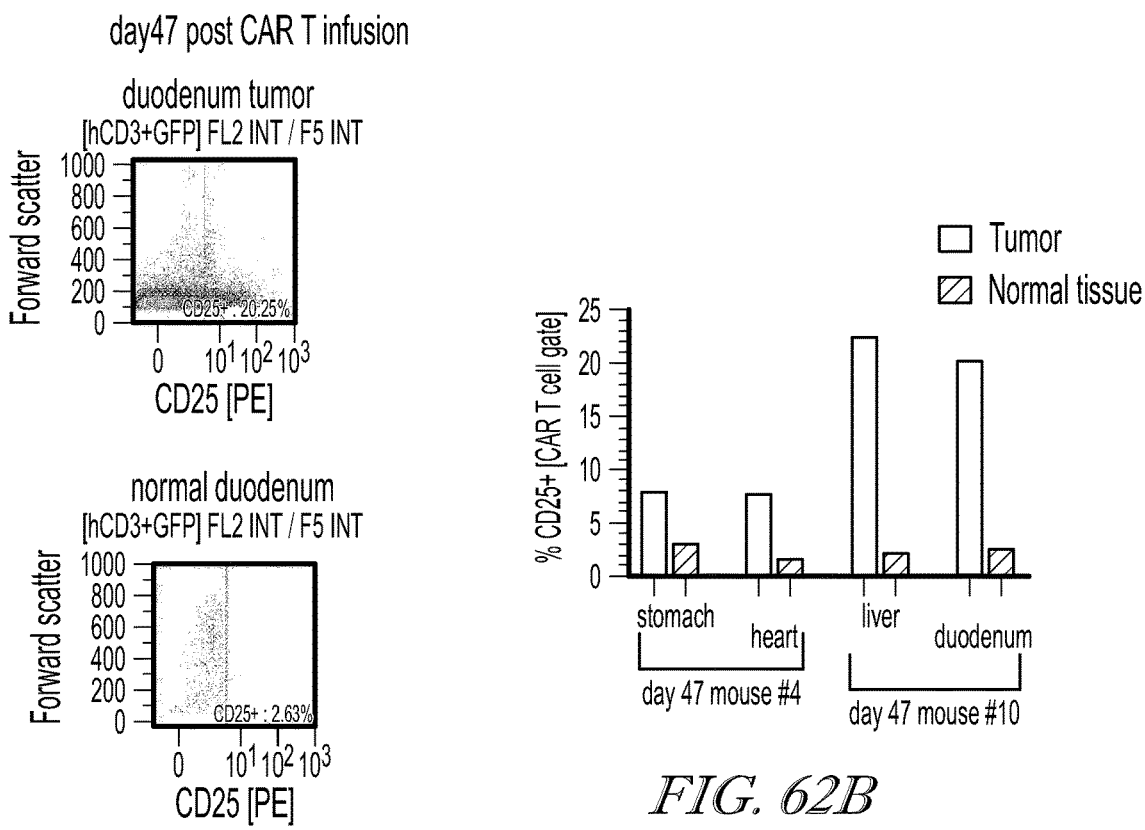

In an effort to measure any activity of the CAR T cells within the tumors, we also stained the surface of CAR T cells for the activity marker, CD25. Interestingly we saw higher levels of CD25 on the CAR T cells in the tumors but not on the CAR T cells isolated from adjacent healthy tissues (FIG. 62B). Taken together (FIGS. 62A and 62B) these data suggest that CAR T cells can follow leukemic cells into healthy tissues and attack them at the metastatic sites of tumor formation and are still active 47 days after infusion. Importantly, mouse #10 was in Group 3 which received sodium fluorescein rescue of sCRS after the first dose of EC17. Although sodium fluorescein was given to this animal, CAR T cells were still persistent in both the blood and the tumors, suggesting that CAR T cell functionality was preserved and these CAR-T cells can be reactivated by EC17 against FR-positive tumor target.

Example 45

EC17 Dose De-Escalation Cycles can Reduce the Toxicity

The effect of EC17 dose de-escalation was investigated on the anti-tumor activity and the toxicity (body weight changes) of CAR-T therapy. 8.5 million frozen anti-FITC CAR-T cells were thawed and i.v. injected into mice bearing s.c. MDA-MB-231 tumors (100-200 mm3). 500 nmol/kg EC17 was administered 2 days after CAR-T injection and caused sCRS in mice. Those mice were successfully rescued with 6 umol/kg NaFL, and then divided into two groups. The first group was dosed with 500 nmol/kg EC17 weekly (SIW), whereas the second group was dosed with two EC17 escalation cycles. Each cycle lasted for 2 weeks (14 days).

Figure 70A:
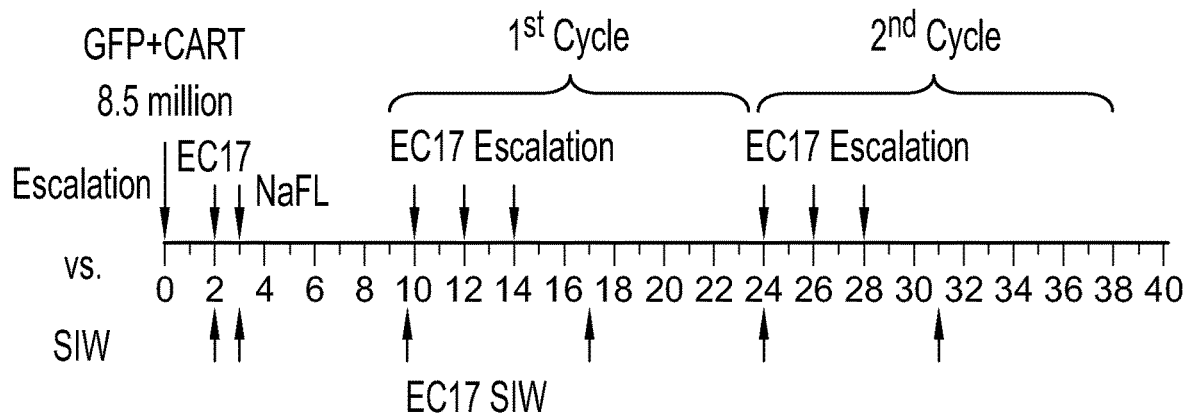
FIG. 70, Panel A shows a dose escalation schema. Panels B-C, show the effect of EC17 dose escalation on the anti-tumor activity and the toxicity (body weight changes) of CAR-T therapy.
Figure 70B:
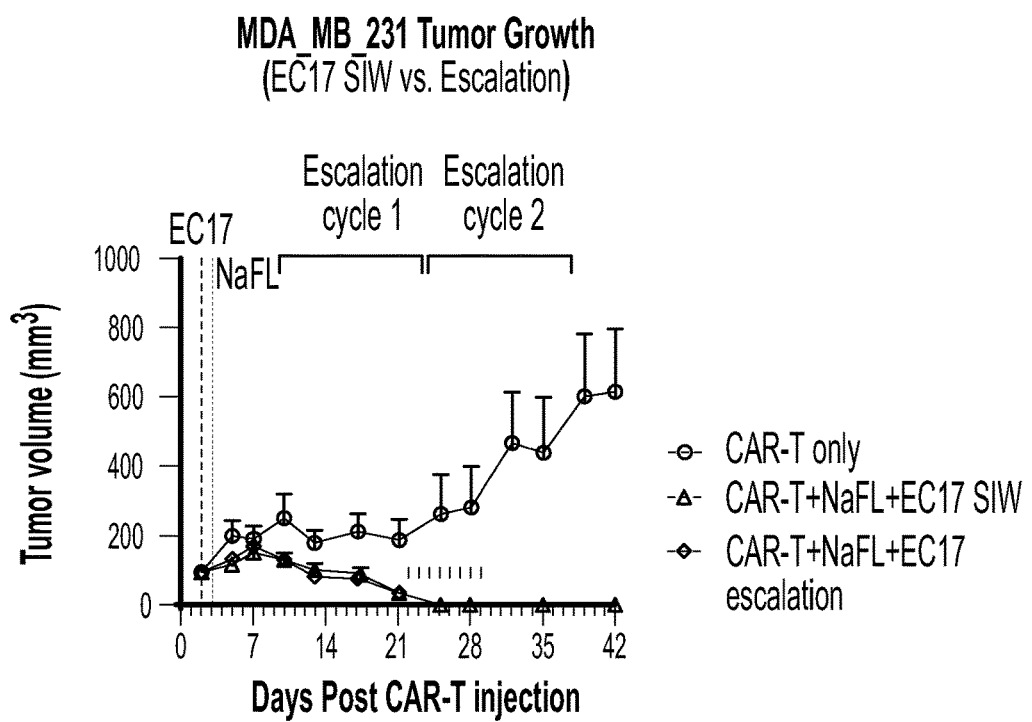
Figure 70C:
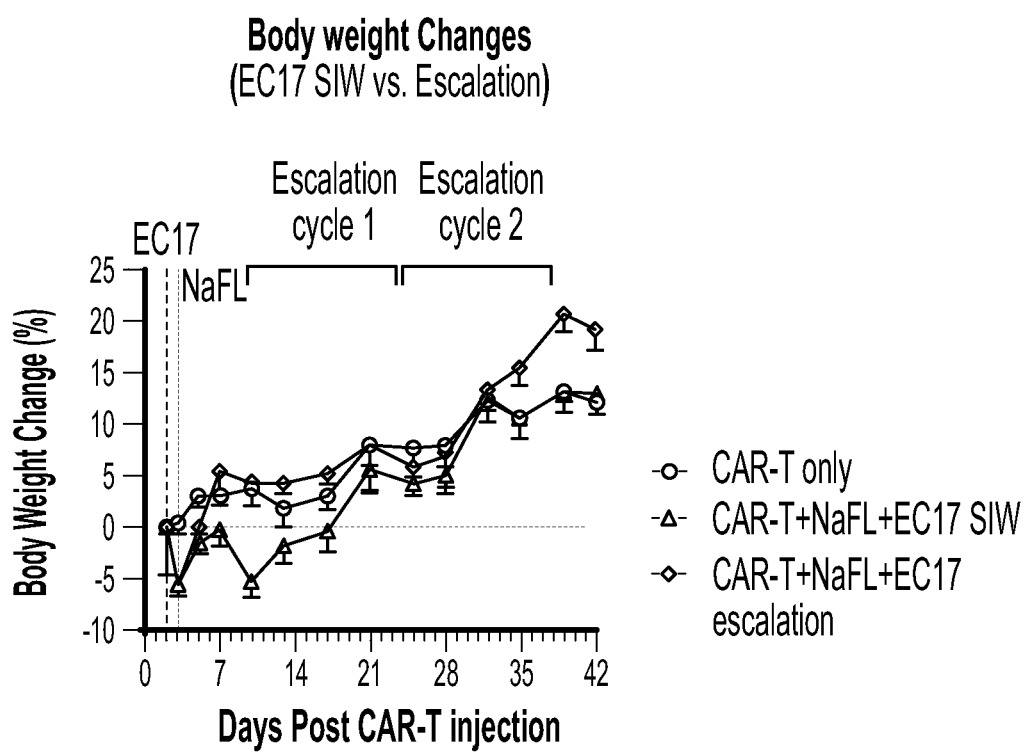

The dosing schedule in each cycle included 5 nmol/kg EC17 at day 1, 50 nmol/kg EC17 at day 3, 500 nmol/kg EC17 on day 5. After 9 days break, the second escalation cycle started. The dosing schedules of both escalation group and SIW group are shown in FIG. 70A. Tumor sizes and body weights were monitored 2-3 times per week. Both groups showed similar response to CAR-T therapy (FIG. 70B), whereas the body weight loss of escalation group was much less than that of the EC17 SIW group (FIG. 70C). The data suggest that EC17 dose de-escalation can reduce toxicity while maintaining the anti-tumor activity of CAR-T cell therapy.

Example 46

CAR-T and EC17 Therapy-Related Toxicity is Correlated with Tumor Size

Figure 71A:
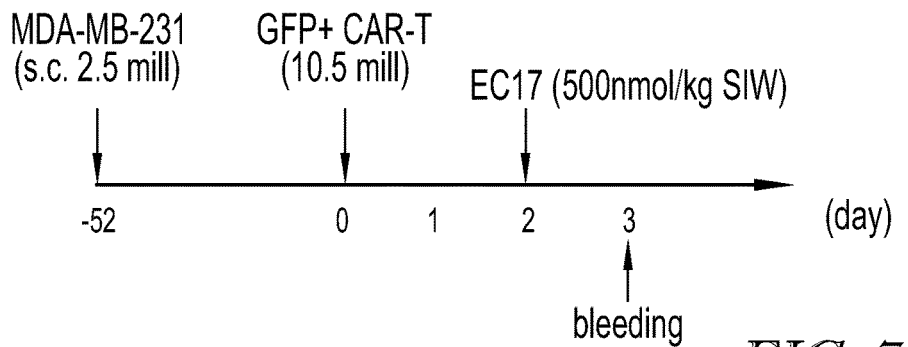
FIG. 71, Panel A shows a scheme for testing whether tumor size correlates with body weight changes and IL-6 release during CAR-T/EC17 therapy. Panels B-C show the results for body weight change and IL-6 levels, respectively.
Figure 71B:
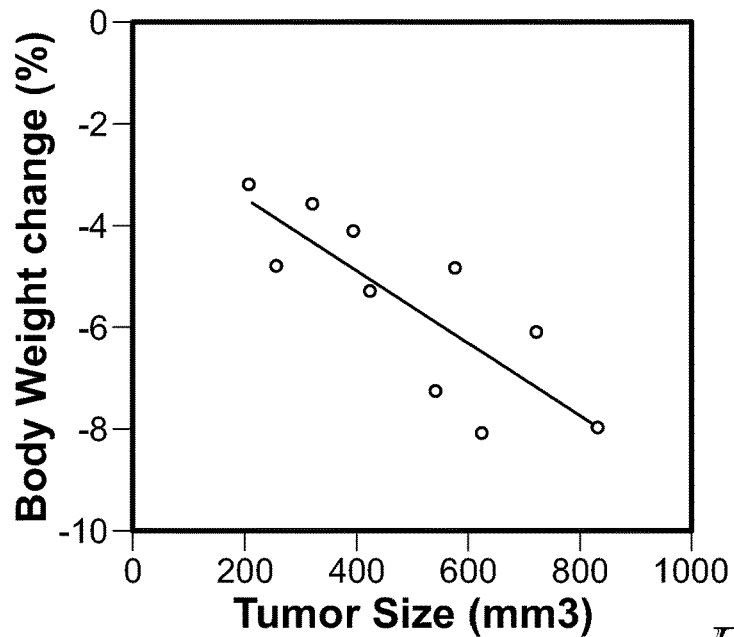
Figure 71C:
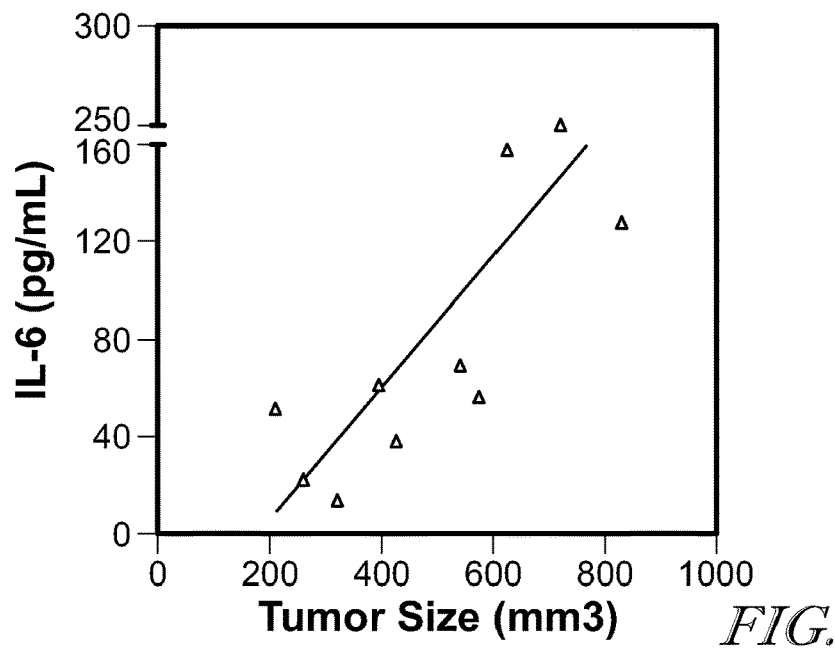

To explore whether CAR-T therapy related toxicity is dependent on tumor load, NSG mice were s.c. implanted with MDA-MB-231. Ten mice with different tumor sizes ranging between 150-900 mm$^3$ were selected for this study. For the CAR-T cells, 10.5 million GFP+FITC-CAR-T cells were i.v. injected followed by 500 nmol/kg EC17 administration 48 hours later (FIG. 71A). Body weights of mice were compared between before CAR-T injection and 18 hours post EC17 administration. As shown in FIG. 71B, body weight changes were shown to be tumor size dependent. With higher tumor burden, mice lost more body weight after CAR-T and EC17 treatment. Eighteen hours after EC17 administration, mice showed grade 2 cytokine release syndrome and their blood samples were collected by cardiopuncture. Plasma samples were separated immediately and stored at −20° C. until the analysis of cytokine levels using a human cytokine detection kit (Biolegend). As shown in FIG. 71C, the production of IL-6 was shown to be tumor size dependent. With higher tumor burden, more IL-6 was produced after CAR-T and EC17 treatment. IL-6 has been widely reported to be the predicting biomarker for severe cytokine release syndrome in human patients with liquid tumors when they are treated with conventional CAR-T therapy. These data suggest that in CAR-T and EC17 therapy, the severity of CRS in solid tumor-bearing mice is also correlated with the tumor burden.

Example 47

Evaluation of EC17-Controlled Anti-FITC CAR T-Cell Therapy in an Aggressive Osteosarcoma Model Materials EC17 (folate-FITC, m.w. 873) was synthesized in house. Sodium fluorescein (AK-FLUOR®, fluorescein injection, USP) was purchased from Purdue Pharmacy.
In-Vivo Methods
Cell Line
HOS-143b is a cell line purchased from ATCC (CRL-8303) that was originated from a 13-year-old Caucasian girl with osteosarcoma. HOS-FRα is subclone of HOS-143b stably transfected with a human FRα. The cells were grown in a folate-free RPMI1640 medium (Gibco BRL) (FFRPMI) containing 5-10% heat-inactivated fetal calf serum (HIFCS) and maintained under a 5% $CO_2$ atmosphere using standard cell culture techniques.

Figure 72A:
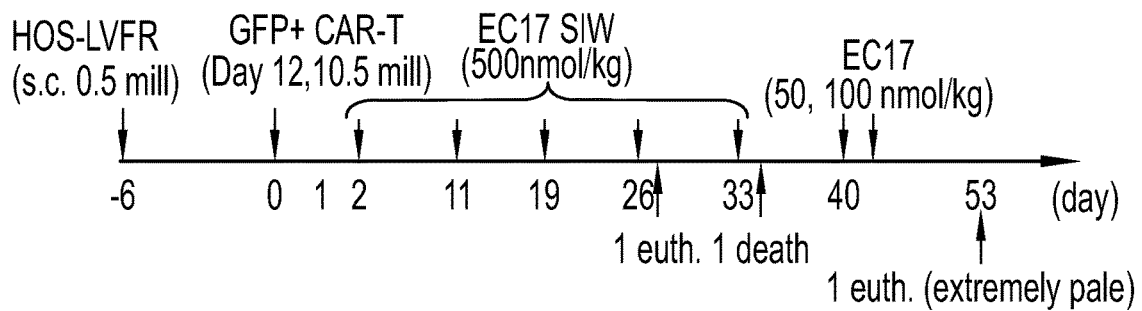
FIG. 72, Panel A shows a scheme for testing whether CAR-T/EC17 therapy is effective in an osteosarcoma model. Panel B shows the tumor size results.

Mice
Female NSG™ (NOD.Cg-Prkdc$^{scid}$ Il2rg$^{tm1Wjl}$/SzJ, stock #005557) mice were purchased from The Jackson Laboratory (Bar Harbor, ME) and used when they reached ~4 weeks of age. The mice were fed a folate-deficient diet (TestDiet, St. Louis, MO) on the day of arrival.
Tumor Implantation
HOS-FRα cells were implanted subcutaneously with 5×10$^5$ per animal in 6 animals.
CAR-T Cell Preparation
GFP+ anti-FITC 4M5.3 scFv-CAR T cells were prepared as described previously. After cultured in-vitro for 12-20 days, they were frozen and stored at −80° C. in a freezing reagent containing 50% heat-inactivated AB+ human serum, 40% T cell culture media, and 10% DMSO. Frozen CAR-T cells were quickly thawed at 37° C., washed twice with PBS, and used for animal injection.
EC17/CAR-T Therapy in Tumor-Bearing Mice
As shown in FIG. 72A, at 6 days after tumor implantation, all animals received 10.5 million CAR T-cells intravenously (Day 0). Two days later, the animals were divided in two groups (n=3 for this study) and received no EC17 treatment or EC17 was dosed intravenously at 500 nmol/kg, once-a-week (SIW) for 4-5 doses. One animal in the EC17-treated group received two more doses of EC17 at 50 and 100 nmol/kg on Days 40 and 42. All EC17 doses were given towards the end of the day (~3-4 PM) to allow cytokine release syndrome (CRS) to develop overnight. Sodium fluorescein rescue was done as needed at 0.6 µmol/kg. Only the last EC17-dosed animal received sodium fluorescein on day 47.
Whole Blood Cell Analysis by Flow Cytometry
Plasma was removed from predetermined volumes of whole EDTA treated blood with a 10-minute 4° C. spin at 3000 g and the resulting cell pellets were incubated with a 10-fold volume of room temperature 1×RBC lysis solution [prepared from 10× stock; Biolegend, catalog #420301] for 5 minutes, centrifuged at 400 g for 5 min, and the cell pellet was washed in a 10-fold volume of ice cold phosphate buffered saline pH=7.4 and filtered with a 40 µm nylon filter and then pelleted again. The leukocyte pellets were then resuspended in flow cytometry staining solution [1% bovine serum albumin, 50 mg/mL human IgG (Equitech Bio, cat #SLH56-0001), 0.9% sodium azide in a phosphate buffered saline, pH=7.4] supplemented with both anti-mouse FcγIII/II receptor (CD16/CD32) block [clone 2.4G2; BD Bioscience, catalog #553142 at 1:100 (v/v) dilution] and anti-human Fc Block [BD Biosciences, catalog #564220 at 1:50 (v/v) dilution]. Leukocyte surface marker staining was performed with the addition of the following fluorochrome conjugated monoclonal antibodies added to each sample for 20 minutes on ice in the dark: anti-human CD45-APCeF780 [clone HI30, eBioscience #47-0459-42 at 1:20 (v/v) dilution], anti-human CD137-BV650 [clone 4B4-1, BD Bioscience #564092 at 1:20 (v/v) dilution], anti-human CD8α-PECy7 [clone RPA-T8, BD Bioscience, catalog #557746 at 1:20 (v/v) dilution], anti-human CD4-Percpe710 [clone SK3, eBioscience catalog #46-0047-42 at 1:20 (v/v) dilution]. After leukocyte staining, the cells were washed with PBS and resuspended in cold PBS containing 53,000 CountBright™ beads [Invitrogen catalog #C36950] and transferred to flow cytometry collection tubes. Flow cytometry data was collected on the Gallios flow cytometer (Beckman Coulter, Brea, CA), where a minimum of 15,000 CountBright™ bead events were collected in an attempt to collect enough leukocyte events for an accurate count of infused CAR T cells in each mouse blood sample. Determination of the concentration of CAR T cells in each blood sample was calculated according to Invitrogen's instructions. Briefly, CAR T cells were identified as human CD45+ GFP+ events and easily distinguished and counted using the Kaluza™ flow cytometry software. CountBright™ beads were uniformly labeled with a fluorochrome not utilized in the antibody panel used to identify the CAR T cells and were easily distinguished from the leukocytes and bead events were counted. Because 53,000 CountBright™ beads were added to each sample tube, the ratio was counted of 53,000 total beads to bead events collected per sample and the bead ratio was set equivalent to the unknown number of CAR T cells in each sample divided by the known number of CAR T cell events collected. Solving for the unknown provided the number of CAR T cells isolated from each blood sample of known volumes. The number of CAR T cells in the circulation of each infused mouse was then represented on the graphs as the total number of CAR T cells per 50 µL of whole blood analyzed.

Preparation of Single Cell Suspension of Tumor and Healthy Tissue

For the animal euthanized on Day 47, blood, normal tissues (liver, spleen, and bone marrow), and a subcutaneous tumor were harvested and minced into small pieces then transferred into 50 mL tubes containing 20 mL of a tumor digestion cocktail. The enzymatic tumor digestion cocktail consisted of 0.5 mg/mL Collagenase IV (Sigma-Aldrich, Catalog #C5138), 0.5 mg/mL Hyaluronidase (Sigma-Aldrich, Catalog #H3506) and 0.1 mg/mL DNase I (Sigma-Aldrich, Catalog #DN25) in serum-free and folate-deficient RPMI1640 medium supplemented with antibiotics. The tumor fragments were digested for one hour at 37° C. at 300 rpm on a horizontal shaker. Afterwards, the tumor digest was centrifuged at 400×g for 5 minutes and tumor cell pellets were incubated with a 10-fold volume of room temperature 1×RBC lysis solution [prepared from 10× stock; Biolegend, catalog #420301] for 5 minutes, centrifuged at 400 g for 5 min, the cell pellet was washed in 10-fold volume of ice cold phosphate buffered saline pH=7.4 and filtered with a 40 µm nylon filter and then pelleted again. Expression of FRα by tumor cells was measured by staining with anti-human FRα [clone LK26, Biolegend catalog #908304 at 1:20 (v/v) dilution. The tumor cells were analyzed by flow cytometry as previously described above.

Data and Results

The study schema is shown in FIG. 72A. The first HOS-FRα tumor-bearing animal in the EC17-treated group received 4 weekly EC17 doses at 500 nmol/kg, but was euthanized on Day 28 due to neurological issues. The second animal in the same group received 5 weekly EC17 doses at 500 nmol/kg, but was found dead on Day 34. The last animal in the same group received 5 weekly EC17 doses at 500 nmol/kg plus two additional EC17 doses at 50 and 100 nmol/kg on Days 40 and 42 respectively. This animal was given sodium fluorescein on Day 47 and was euthanized on Day 53. All animals developed GVHD approximately 5 weeks after CAR-T cell administration.

Figure 72B:
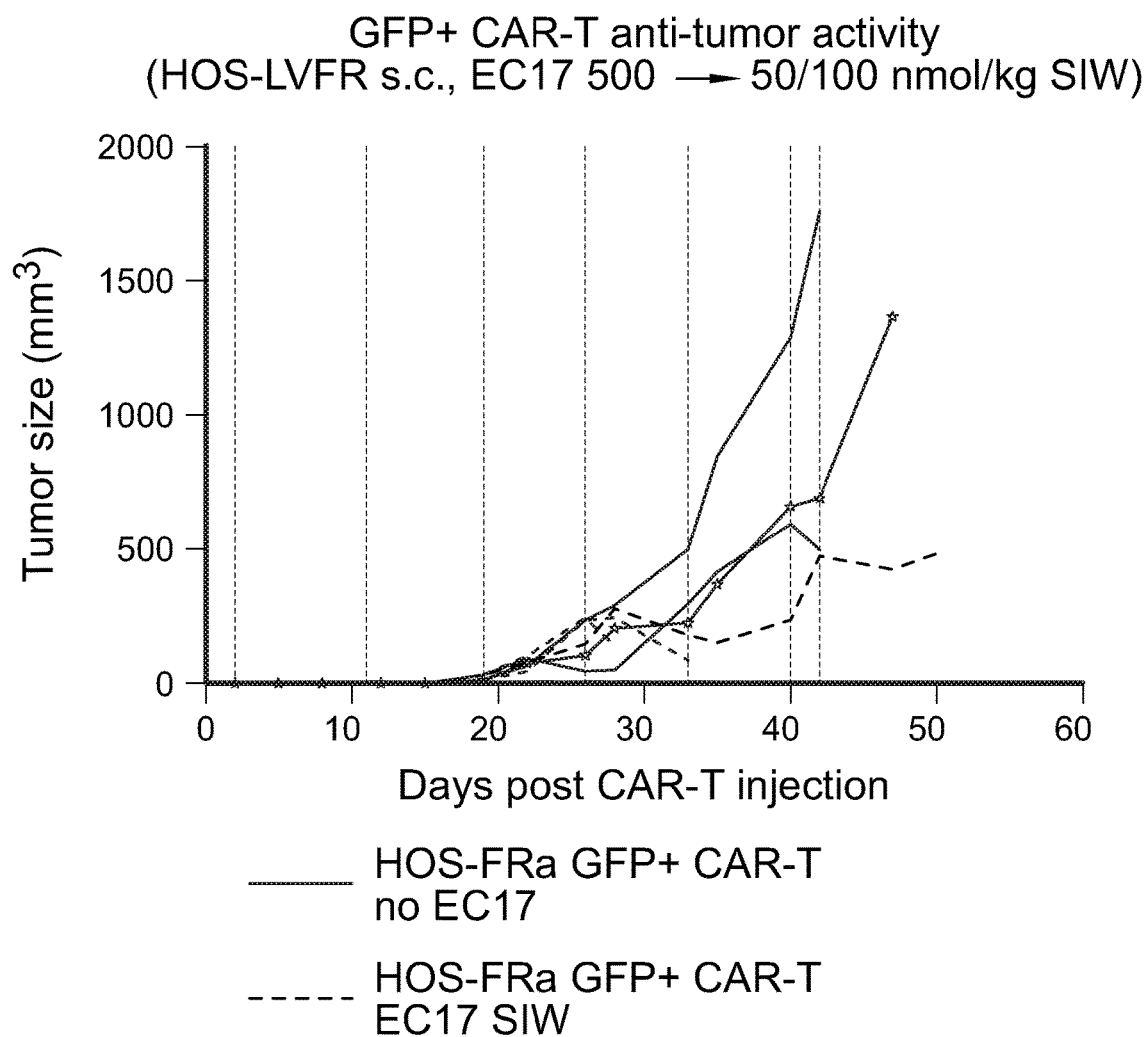
Figure 73:
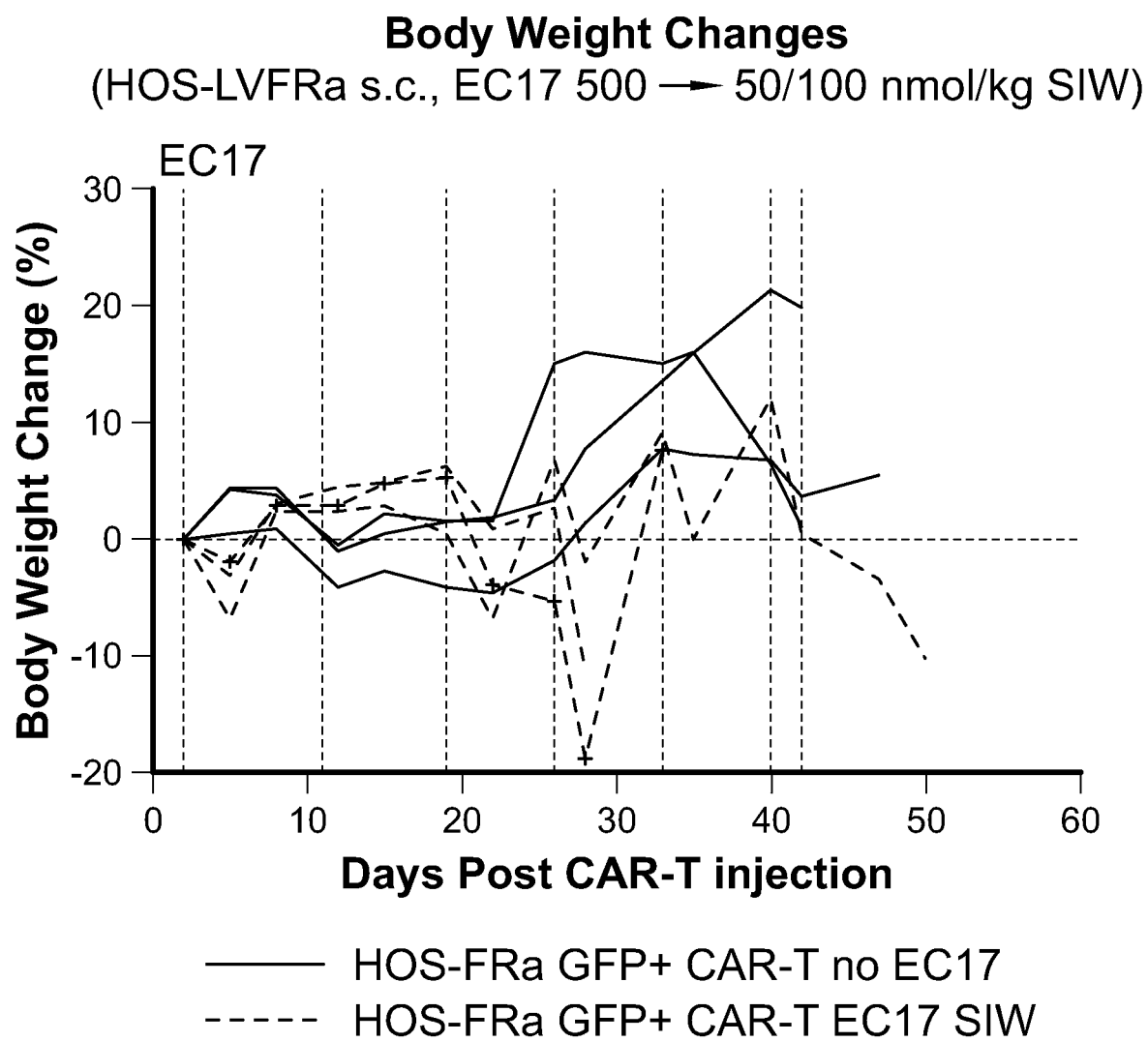
FIG. 73 shows body weight changes for the tests described for FIG. 72.
Figure 74A:
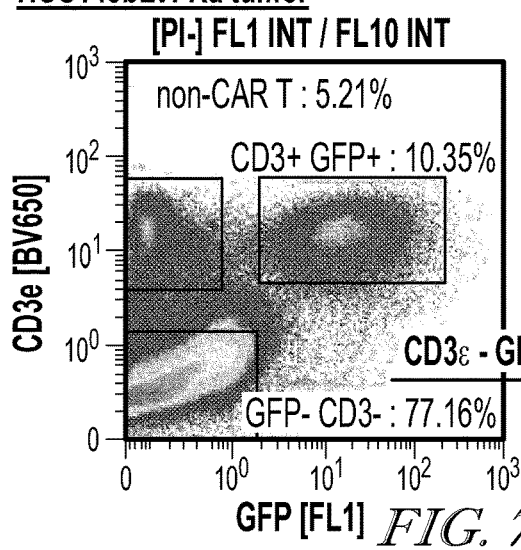
FIG. 74, Panels A-F show that HOS cancer cells express the FR-α.
Figure 74B:
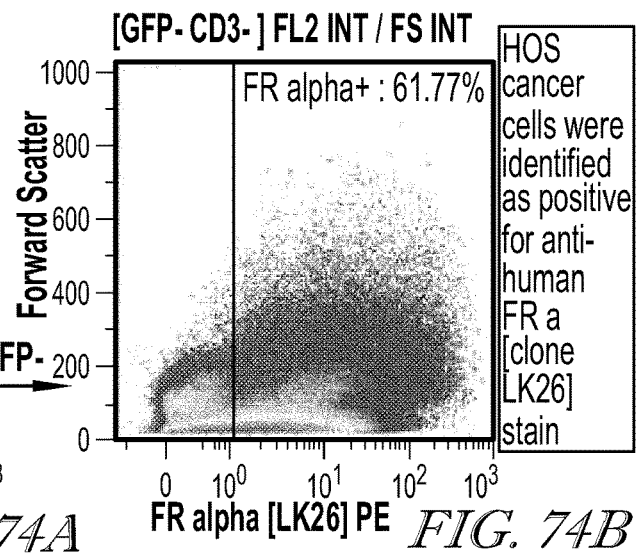
Figure 74C:
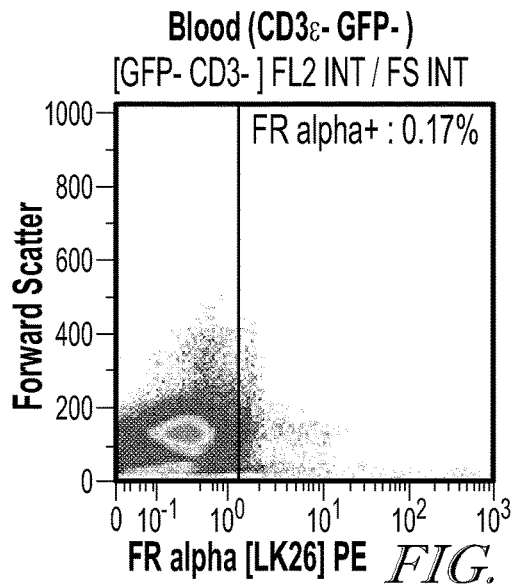
Figure 74D:
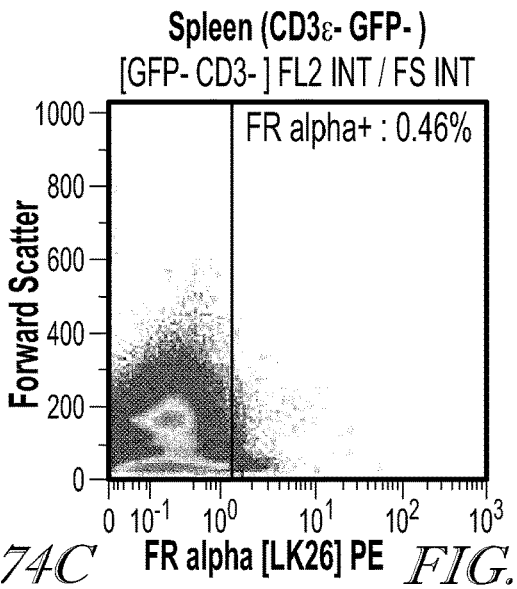
Figure 74E:
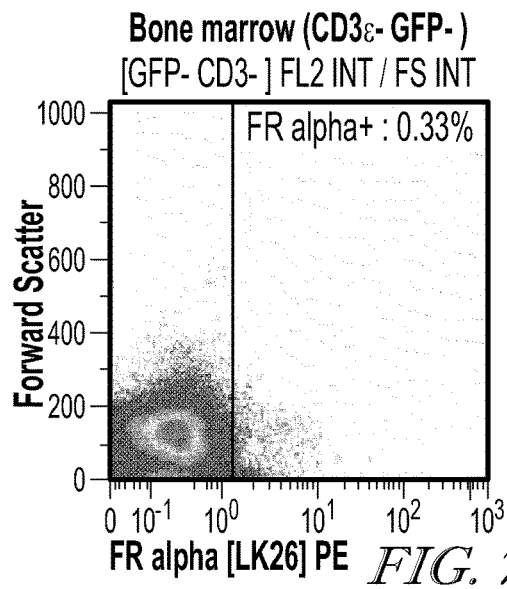
Figure 74F:
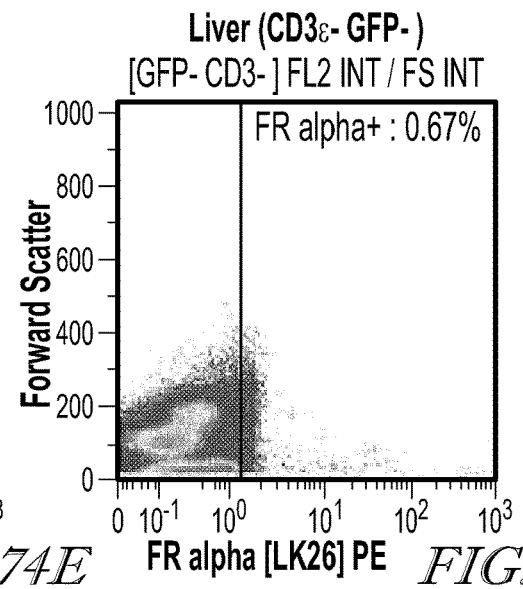

The tumor volume (FIG. 72B) and body weight changes (FIG. 73) were plotted for each individual animal. The solid lines represent HOS-FRα tumor-bearing mice receiving only CAR-T cells. The dashed lines represent HOS-FRα tumor-bearing mice receiving CAR-T cells and EC17 treatment as described above. The EC17 dosing dates were labeled as dotted vertical lines. Tumor volumes and body weight changes were monitored 2-3 times per week. While one CAR-T only group animal was found dead on Day 45 with no apparent reason, all 3 CAR-T-cell control animals had their tumors grow rapidly once established (FIG. 72B, solid lines). In contrast, tumors in all 3 mice dosed with EC17 SIW at 500 nmol/kg started to shrink on Days 28 and 33 (FIG. 72B, dashed lines). Although 2 animals were lost on Days 28 and 34 in the EC17 treated group, the last animal in the same treated group had longer delayed tumor growth and responded to additional low-dose EC17 treatment. The body weight changes in these animals (FIG. 73) suggested that CRS was severe once the tumors reached >200 mm³ in the EC17-treated animals. The CRS coupled with severe GVHD were likely the reasons for observed toxicity and mortality in these animals.

Flow cytometry analysis was conducted in the last animal that was harvested on Day 47. As shown in FIG. 74A-F, HOS cancer cells were identified as positive for anti-human FRα [clone LK26] staining. HOS-FRα cancer cells were not detectable in the normal tissues tested and only detectable in the subcutaneous solid tumor. In addition, these data confirmed the continued surface expression of FRα on HOS-FRα tumor cells in-vivo post EC17/CAR-T treatment.

Example 48

Sodium Fluorescein (NAFL) Rescue can Reduce the Production of Host MCP-1, IL-6 and IL-10 which are Related to the Development of Severe Cytokine Release Syndrome High levels of MCP-1, IL-6 and IL-10 have been reported to be predictive for cytokine release syndrome (CRS) after CAR-T cell therapy for various liquid tumors. Production of these cytokines not only occurs for human CAR-T cells but also for host immune cells including monocytes, macrophages and dentric cells. These cytokines have also been reported to participate in abnormal marcrophage activation and to drive the development of CRS in patients treated with CAR-T cells. Reduction of these cytokines (e.g. IL-6 and MCP-1) has proved to be efficient in managing CRS in CAR-T therapy. Although NSG mice are immune deficient, mouse dentric cells and macrophages are still partially functional. To evaluate whether CAR-T/EC17 therapy can induce the production of these host cytokines in NSG mice, and also to study whether NaFL rescue can reduce the production of these host mouse cytokines, NSG mice bearing MDA-MB-231 tumors were used.

Figure 75:
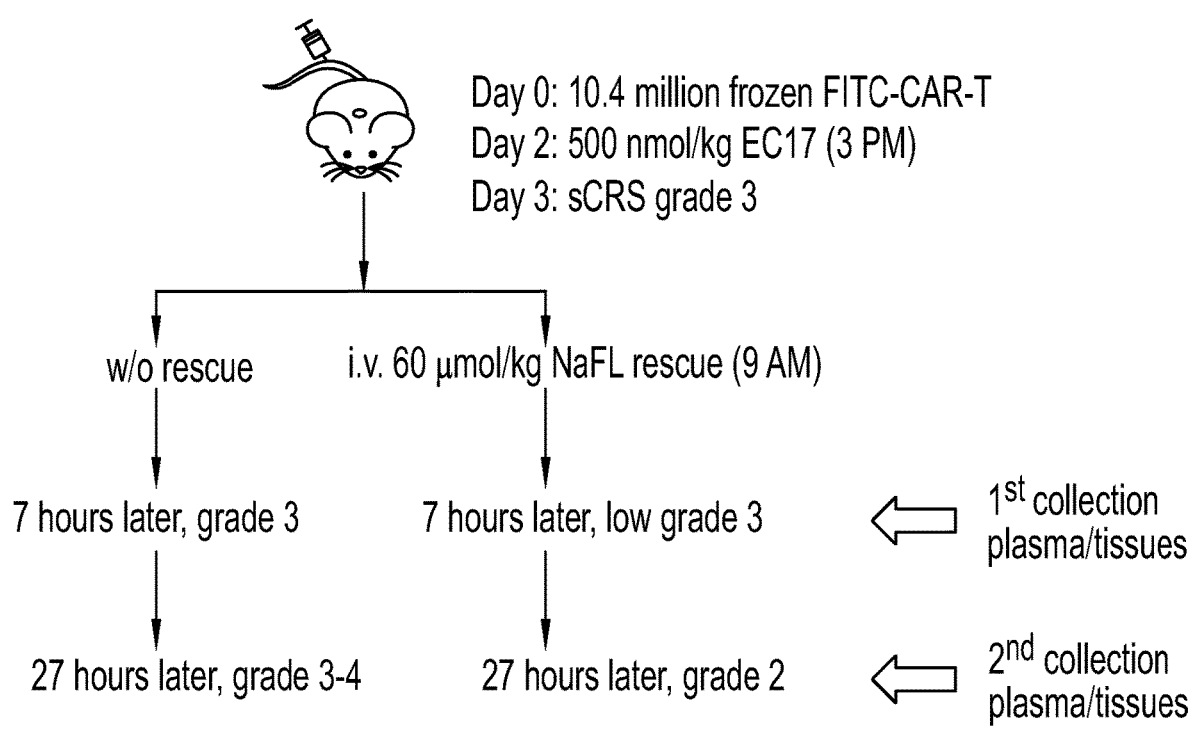
FIG. 75 shows a scheme for testing whether cytokines are produced in response to CAR-T/EC17 therapy and whether NaFL rescues the mice from CRS.
Figure 76A:
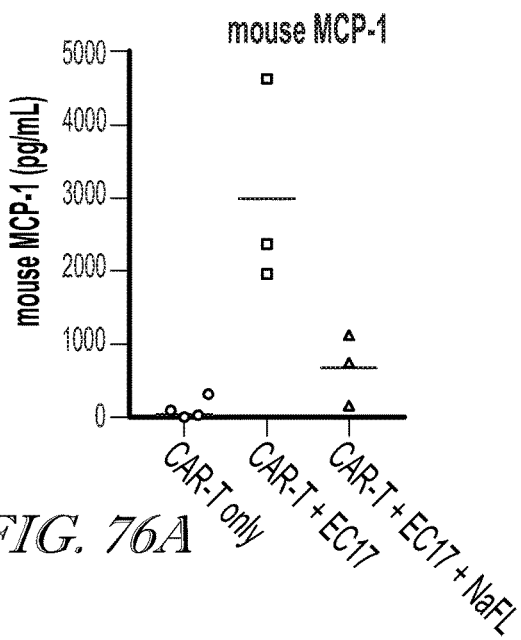
FIG. 76, Panels A-E show reduction of mouse cytokine production by 60 umol/kg NaFL 7 hours post NaFL rescue.
Figure 76B:
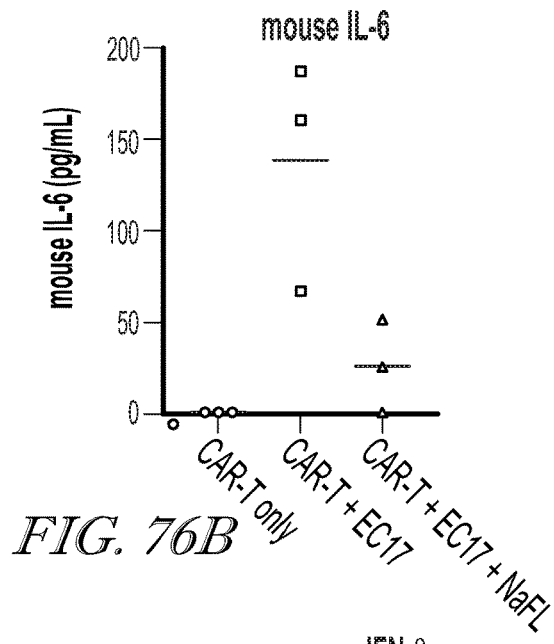
Figure 76C:
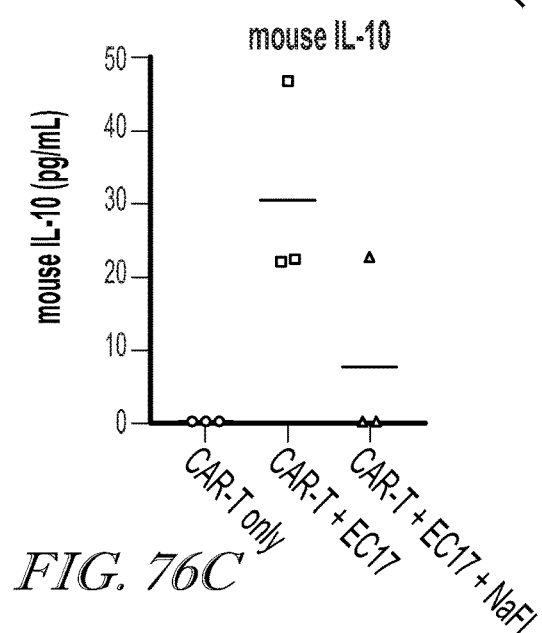
Figure 76D:
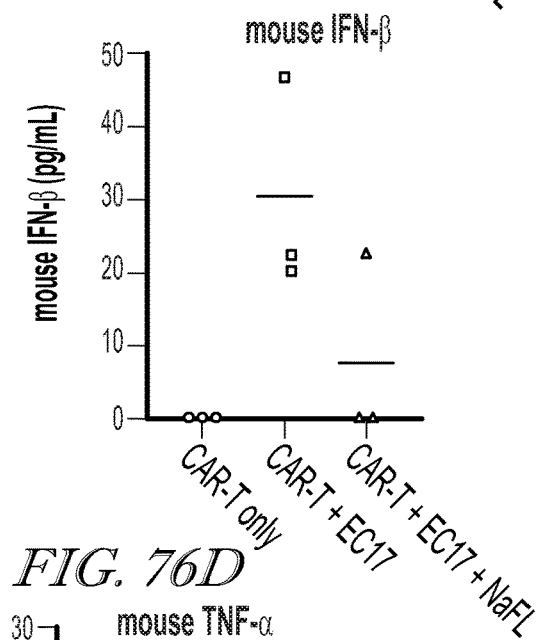
Figure 76E:
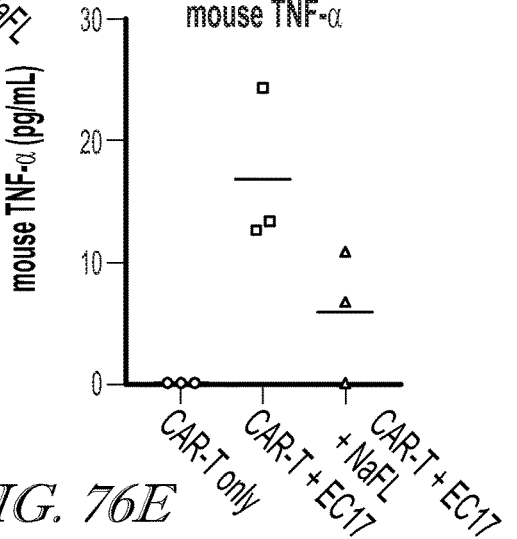
Figure 77A:
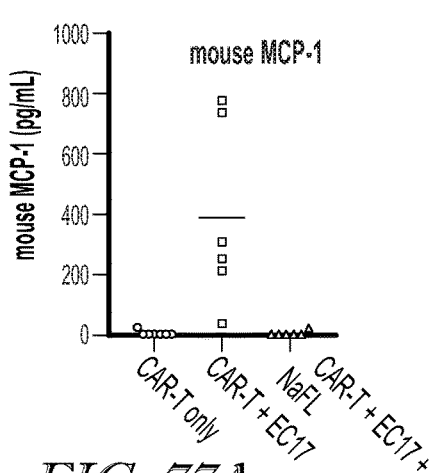
FIG. 77, Panels A-c show reduction of mouse cytokine production by 60 umol/kg NaFL 27 hours post NaFL rescue.
Figure 77B:
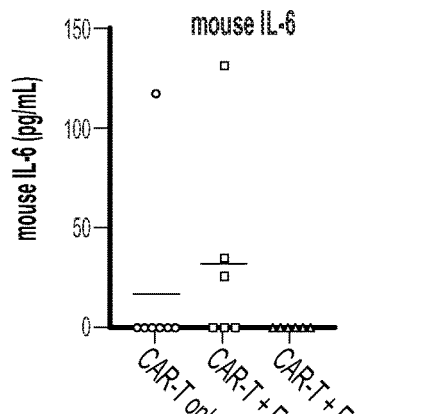
Figure 77C:
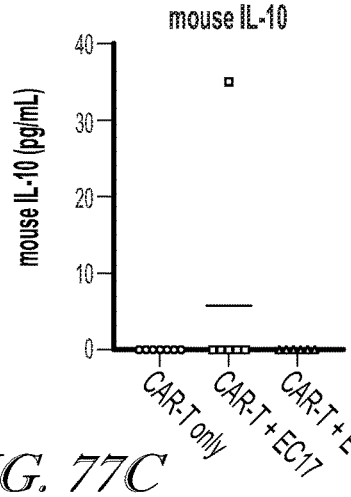

In the first part of the study (FIG. 75), mice were treated with EC17 and FITC-CAR-T cells. When mice started to show sCRS, one dose of 60 umol/kg NaFL was injected for rescue. Mouse blood samples were then collected at both 7 hours and 27 hours post NaFL rescue. Mouse cytokine levels in blood were analyzed using a mouse inflammation panel kit (Cat. No. 740446) from BioLegend by following the manufacturer's instructions. FIGS. 76 A-E show cytokine levels 7 hours post rescue. FIGS. 77A-C show cytokine levels 27 hours post rescue. In summary, mice administered with CAR-T but without EC17 had very low leveld of mouse cytokines in their blood, while mice dosed with EC17 had increased mouse cytokine levels in their blood, including MCP-1, IL-6, IL-10, IFN-β, and TNF-α. More importantly, mouse cytokine levels in the mice rescued with 60 µmol/kg sodium fluorescein were much lower than those in un-rescued mice (both at 7 hours and 27 hours post rescue).

Figure 78:
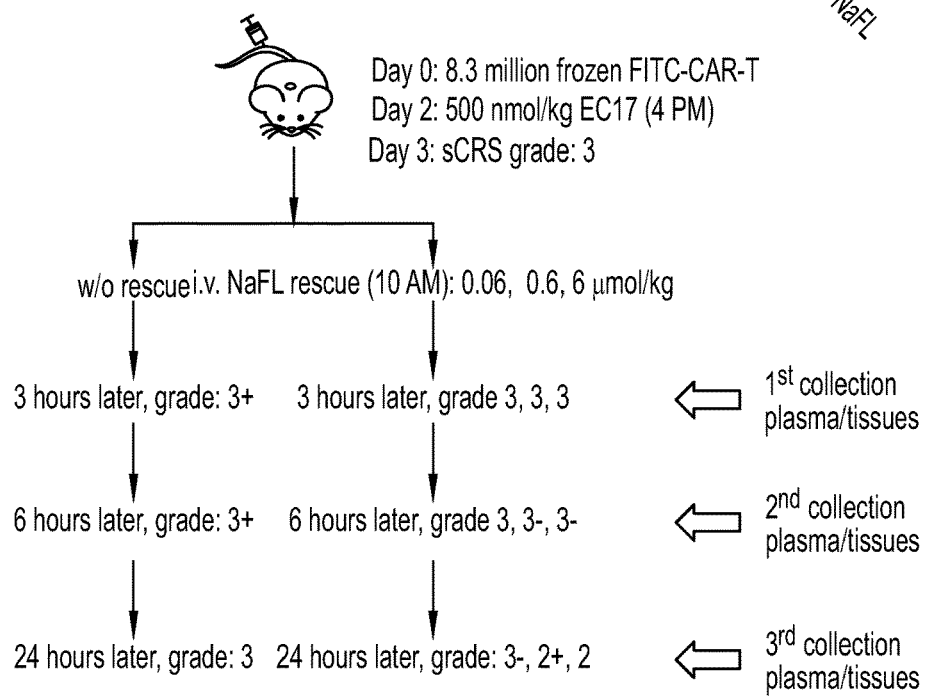
FIG. 78 shows a scheme for testing reduction of mouse cytokine production in response to CAR-T/EC17 therapy by various concentrations of NaFL.
Figure 79:
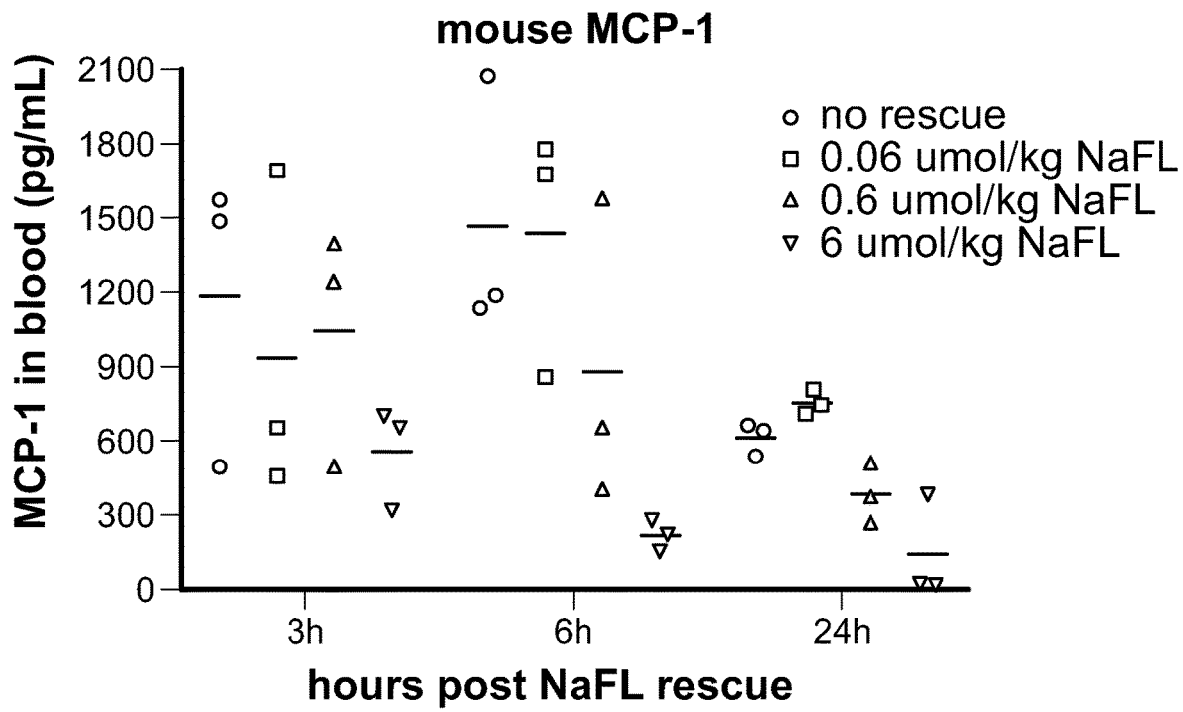
FIG. 79 shows reduction of MCP-1 in response to CAR-T/EC17 therapy by NaFL rescue.
Figure 80:
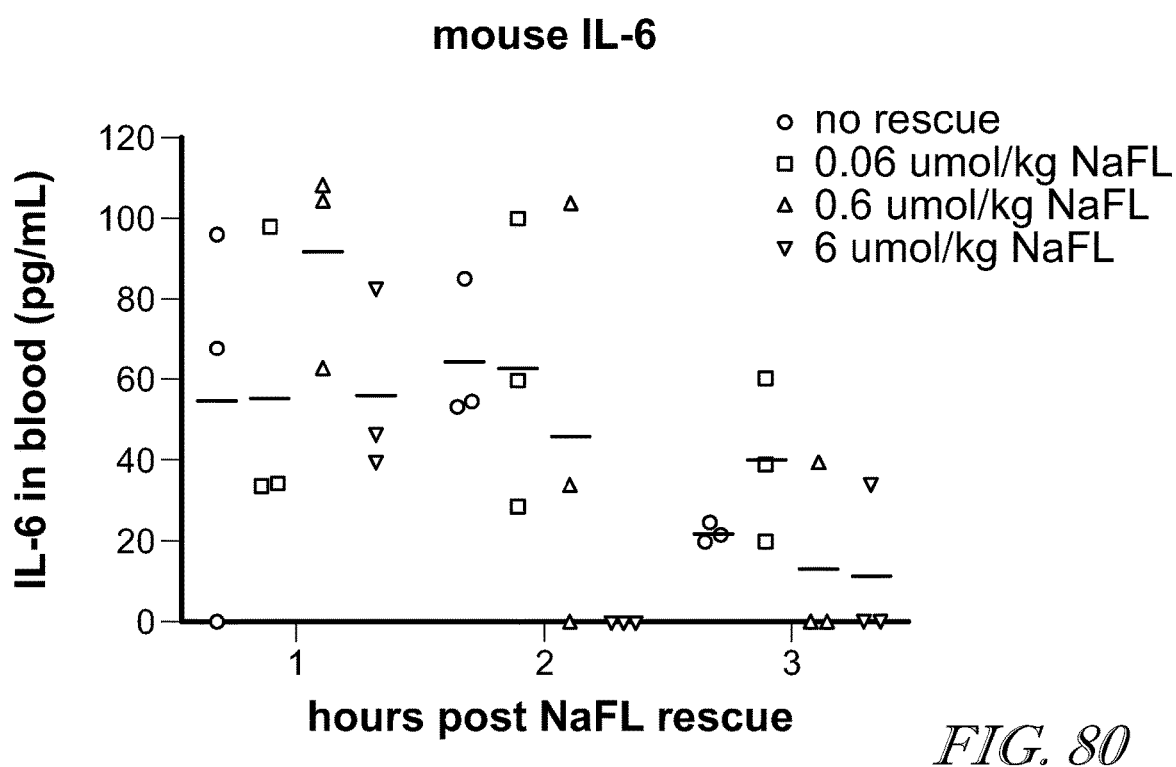
FIG. 80 shows reduction of IL-6 in response to CAR-T/EC17 therapy by NaFL rescue.
Figure 81:
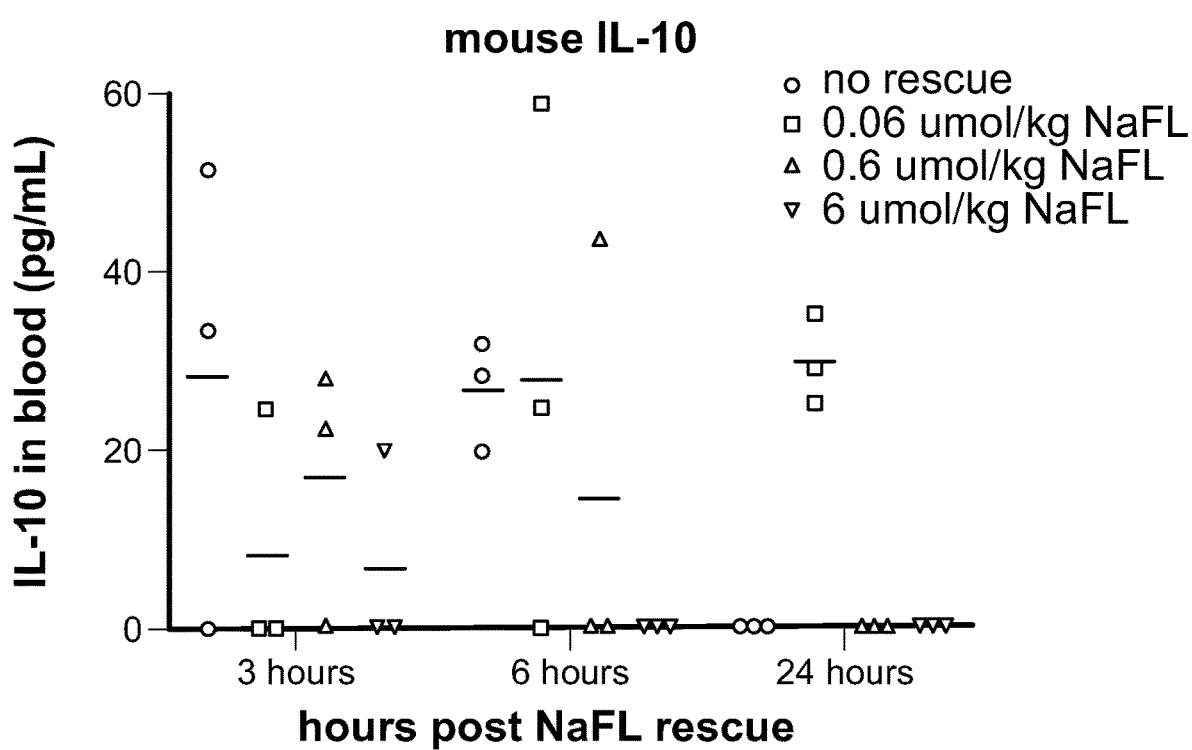
FIG. 81 shows reduction of IL-10 in response to CAR-T/EC17 therapy by NaFL rescue.

In the second part of the study, a series of concentrations of NaFL were tested for their rescue efficiency (FIG. 78). As shown in FIGS. 79-81, mice cytokine levels in blood were also dependent on the concentrations of sodium fluorescein used for rescue, and the median effective dose is about 0.6

µmol/kg with cytokines tested (e.g. MCP-1, IL-6, and IL-10) and the mice started to respond as early as 3 hours post rescue.

In conclusion, CAR-T/EC17 therapy can induce elevated mouse cytokine production, and one dose of NaFL rescue can reduce the production of these CRS related mouse cytokines and improve overall condition of the mice.

Example 49

Mouse MCP-1 Production in Mice is Correlated with CAR-T Cell Number

Figure 82A:
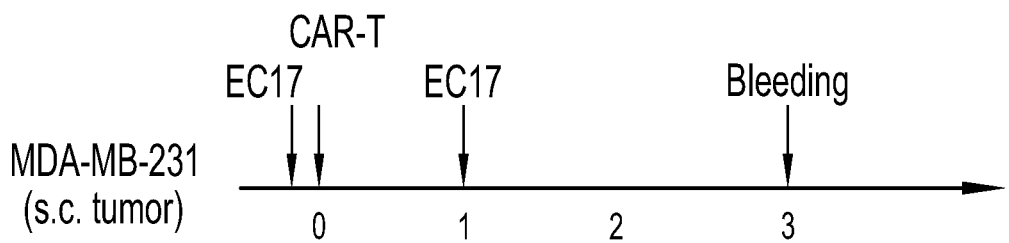
FIG. 82, Panel A shows a scheme for testing whether MCP-1 production in response to CAR-T/EC17 therapy correlates with CAR-T cell number. Panel B shows that MCP-1 production in response to CAR-T/EC17 therapy correlates with CAR-T cell number.
Figure 82B:
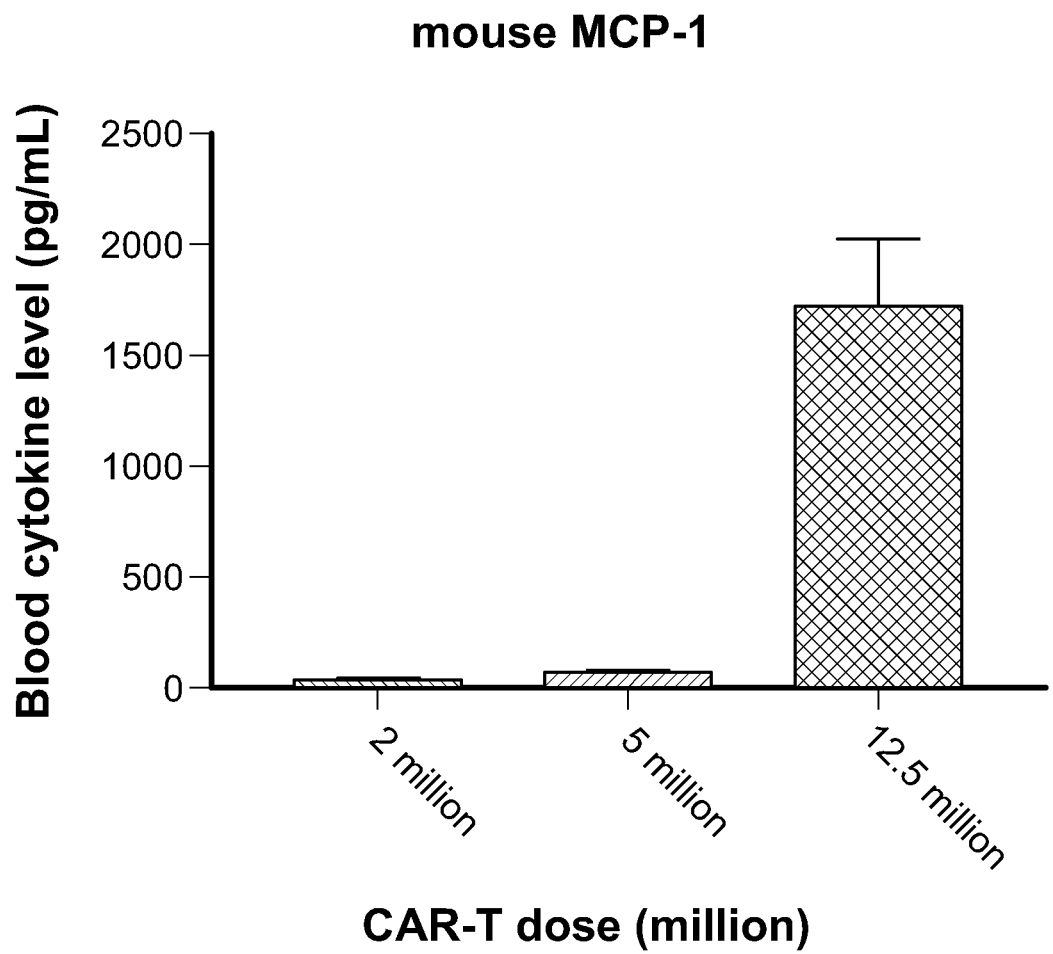

Monocyte chemoattractant protein 1 (MCP-1) is a chemokine molecule that is chemotactic for monocytes/marcrophages. A high level of MCP-1 has been reported to be a predictive biomarker for cytokine release syndrome after CAR-T cell therapy for various liquid tumors including acute lymphoblastic leukemia. Although NSG mice are immune deficient, the functions of dentric cells and macrophages are defective but not totally eliminated. To evaluate whether the CAR-T/EC17 therapy can induce the production of mouse MCP-1 in NSG mouse, and to study whether the production of mouse MCP-1 is correlated with CAR-T number in mice, NSG mice bearing MDA-MB-231 tumors (250-500 mm$^3$) were divided into three groups and administered 500 nmol/kg of body weight of EC17 and different amounts of CAR-T cells (2, 5 or 12.5 million respectively), as shown in FIG. 82A. Two days after the second EC17 dose, mouse blood samples were collected, and the production of mouse MCP-1 in blood was analyzed using a mouse inflammation panel kit (Cat. No. 740446) from BioLegend. As shown in FIG. 82B, mouse MCP-1 is found to correlate with the number of CAR-T cells administered. In conclusion, with the increase in CAR-T cells, the production of mouse MCP-1 also increases, mostly due to the high level of human cytokines released by active human CAR-T cells.

What is claimed is:

1. A method of treating a patient for cancer, the method comprising
   i) administering to the patient a compound, or a pharmaceutically acceptable salt thereof, wherein the compound comprises a folate linked to fluorescein isothiocyanate (FITC) by a linker;
   ii) administering to the patient a chimeric antigen receptor T cell (CAR T cell) composition comprising CAR T cells comprising an anti-FITC antibody or fragment thereof; and
   iii) reducing or preventing cytokine release syndrome (CRS) or cytokine storm by administering to the patient a rescue agent which is a folate,
   wherein step iii) is performed after steps i) and ii), and
   wherein the cancer is a folate receptor-expressing cancer; whereupon the patient is treated for cancer.

2. The method of claim 1, wherein the folate of the rescue agent is folic acid or leucovorin.

3. The method of claim 1, wherein the folate linked to FITC in the compound has the formula

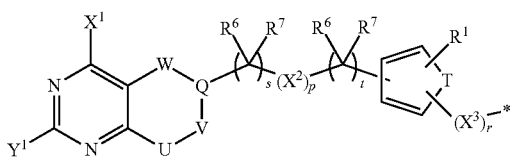

wherein $X^1$ and $Y^1$ are each independently selected from the group consisting of halo, $R^2$, $OR^2$, $SR^3$, and $NR^4R^5$;
wherein U, V, and W represent divalent moieties each independently selected from the group consisting of —($R^{6a}$)C=, —N=, —($R^{6a}$)C($R^{7a}$)—, and —N($R^{4a}$)—;
wherein Q is selected from the group consisting of C and CH and T is selected from the group consisting of S, O, N, and —C=C—;
wherein $X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;
wherein $R^1$ is selected-from the group consisting of hydrogen, halo, $C_1$-$C_{12}$ alkyl, and $C_1$-$C_{12}$ alkoxy;
wherein $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, and $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;
wherein $R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group;
wherein $R^{6a}$ and $R^{7a}$ are each independently selected from the group consisting of hydrogen, halo, $C_1$-$C_{12}$ alkyl, and $C_1$-$C_{12}$ alkoxy; or, $R^{6a}$ and $R^{7a}$ are taken together to form a carbonyl group;
wherein p, r, s, and t are each independently either 0 or 1; and
wherein * represents a covalent bond to the rest of the compound.

4. The method of claim 1, wherein the linker comprises polyethylene glycol (PEG), polyproline, a hydrophilic amino acid, a sugar, an unnatural peptidoglycan, a polyvinylpyrrolidone, pluronic F-127, or a combination thereof.

5. The method of claim 4, wherein the linker comprises PEG.

6. The method of claim 1, wherein the compound, or the pharmaceutically acceptable salt thereof, is not an antibody, and does not comprise a fragment of an antibody.

7. The method of claim 1, wherein the anti-FITC antibody or fragment thereof is a single chain fragment variable (scFv) region, wherein the CAR has a co-stimulation domain and the co-stimulation domain is CD137 (4-1BB), and wherein the CAR has an activation signaling domain and the activation signaling domain is a T cell CD3ζ chain.

8. The method of claim 1, wherein multiple doses of the compound, or the pharmaceutically acceptable salt thereof, and/or the CAR T cell composition are administered.

9. The method of claim 1, wherein the CAR T cells administered to the patient in the CAR T cell composition comprise from about 1 million to about 15 million of the CART cells.

10. The method of claim 1, wherein a CRS grade is determined in the patient, and wherein the CRS grade is 1, 2, 3, or 4.

11. The method of claim 10, wherein the rescue agent is administered after determining the CRS grade.

12. The method of claim 1, wherein the cancer comprises a tumor.

13. The method of claim 12, wherein tumor size is reduced in the patient.

14. The method of claim 1, wherein the CART cell composition is administered simultaneously with the compound or pharmaceutically acceptable salt thereof.

15. The method of claim 1, wherein the CART cell composition is administered after administering the compound or pharmaceutically acceptable salt thereof.

16. The method of claim 1, wherein the CART cell composition is administered before administering the compound or pharmaceutically acceptable salt thereof.

* * * * *